US012121531B2

(12) United States Patent
Anastassiadis et al.

(10) Patent No.: US 12,121,531 B2
(45) Date of Patent: Oct. 22, 2024

(54) TREM COMPOSITIONS AND USES THEREOF

(71) Applicant: Flagship Pioneering Innovations VI, LLC, Cambridge, MA (US)

(72) Inventors: Theonie Anastassiadis, Boston, MA (US); David Charles Donnell Butler, Medford, MA (US); Neil Kubica, Swampscott, MA (US); Qingyi Li, Somerville, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 17/519,120

(22) Filed: Nov. 4, 2021

(65) Prior Publication Data

US 2023/0054178 A1 Feb. 23, 2023

Related U.S. Application Data

(63) Continuation of application No. PCT/US2021/027357, filed on Apr. 14, 2021.

(60) Provisional application No. 63/009,669, filed on Apr. 14, 2020.

(51) Int. Cl.

| | |
|---|---|
| ***A61K 31/7088*** | (2006.01) |
| ***A61K 31/712*** | (2006.01) |
| ***A61K 31/7125*** | (2006.01) |
| ***C12N 15/11*** | (2006.01) |
| ***C12N 15/67*** | (2006.01) |

(52) U.S. Cl.
CPC ........ *A61K 31/7088* (2013.01); *A61K 31/712* (2013.01); *A61K 31/7125* (2013.01); *C12N 15/11* (2013.01); *C12N 15/67* (2013.01); *C12N 2310/313* (2013.01); *C12N 2310/321* (2013.01); *C12N 2310/322* (2013.01)

(58) Field of Classification Search
CPC .............. A61K 31/7088; A61K 31/712; A61K 31/7125; A61K 9/127; A61K 9/5123; A61K 48/0025; C12N 15/11; C12N 15/67; C12N 2310/313; C12N 2310/321; C12N 2310/322; C12N 2310/315; C12N 2310/3341; C12N 15/113; C12N 2310/3521; C12N 2310/3525; C12N 2310/3531; C12N 2310/3533
USPC ....................................... 514/44 R; 536/23.1
See application file for complete search history.

(56) References Cited

U.S. PATENT DOCUMENTS

| | | | | |
|---|---|---|---|---|
| 6,969,763 | B1 | 11/2005 | Ecker et al. | |
| 10,337,065 | B2 * | 7/2019 | Tavazoie | C12Q 1/6809 |
| 2013/0267694 | A1 | 10/2013 | Xu et al. | |
| 2013/0267695 | A1 | 10/2013 | Webb et al. | |

FOREIGN PATENT DOCUMENTS

| | | | | |
|---|---|---|---|---|
| WO | 1999/036519 A1 | | 7/1999 | |
| WO | 2000/027340 A2 | | 5/2000 | |
| WO | 2003/091268 A1 | | 11/2003 | |
| WO | 2007/144508 A2 | | 12/2007 | |
| WO | 2008/014979 A2 | | 2/2008 | |
| WO | 2008/083949 A2 | | 7/2008 | |
| WO | WO-2012006551 A2 | * | 1/2012 | C07H 21/02 |
| WO | 2017/085718 A1 | | 5/2017 | |
| WO | 2017/121988 A1 | | 7/2017 | |
| WO | 2018/161032 A1 | | 9/2018 | |
| WO | 2019/090169 A1 | | 5/2019 | |
| WO | WO-2019090154 A1 | * | 5/2019 | A61K 31/7105 |
| WO | 2019/175316 A1 | | 9/2019 | |
| WO | 2019/204733 A1 | | 10/2019 | |
| WO | 2020/0069194 A1 | | 4/2020 | |
| WO | WO-2020150608 A1 | * | 7/2020 | C12N 15/11 |
| WO | 2020/208169 A1 | | 10/2020 | |
| WO | 2020/247803 A2 | | 12/2020 | |
| WO | 2021/035391 A1 | | 3/2021 | |
| WO | 2021/087401 A1 | | 5/2021 | |
| WO | 2021/113218 A1 | | 6/2021 | |
| WO | 2021/142343 A1 | | 7/2021 | |
| WO | 2021/211762 A2 | | 10/2021 | |

OTHER PUBLICATIONS

Dabrowski et al. The EMBO Journal vol. 14 no. 19 pp. 4872-4882, 1995. (Year: 1995).*
Integrated DNA Technologies, ITDN, https://www.idtdna. com/site/catalog/modifications/category/7. (Year: 2019).*
Modified Bases Modifications. Integrated DNA Technologies, 2019 [online]. [Retrieved on Jul. 9, 2021]. Retrieved from the Internet URL: https://web.archive.org/web/20190904151113/https://www.idtdna.com/site/Catalog/Modifications/Category/7.
Endres et al., " 2'-O-ribose methylation of transfer RNA promotes recovery from oxidative stress in Saccharomyces cerevisiae" PLoS One, 2020, vol. 15, No. 2.
International Search Report and Written Opinion for Application No. PCT/US2021/027357 mailed Oct. 4, 2021.
Sako et al., "A novel therapeutic approach for genetic diseases by introduction of suppressor tRNAs", Nucleic Acid Symp Ser, 2006, No. 50, pp. 239-240.
Pavon-Eternod et al., "Overexpression of initiator methionine tRNA leads to global reprograming of tRNA expression and increased proliferation in human epithelial cells", RNA, 2013, vol. 19, pp. 461-466.
Kirchner et al., "Alteration of protein function by a silent polymorphism linked to tRNA abundance" PLOS Biol, 2017, vol. 15, No. 5.
Lueck et al., "Engineered transfer RNAs for suppression of premature termination codons", Nat Comm , 2019, vol. 10.

(Continued)

*Primary Examiner* — Janet L Epps -Smith
(74) *Attorney, Agent, or Firm* — Lando & Anastasi, LLP

(57) ABSTRACT

The invention relates generally to tRNA-based effector molecules having a non-naturally occurring modification and methods relating thereto.

10 Claims, 1 Drawing Sheet

Specification includes a Sequence Listing.

(56) References Cited

OTHER PUBLICATIONS

Lin et al., "tRNAviz: explore and visualize tRNA sequence features" Nucleic Acids Research, 2019, vol. 47, Webserver Issue, W542-W547.
Pak et al., "tRNA structure and evolution and standardization to the three nucleotide genetic code" Transcription, 2017, vol. 8, No. 4, 205-219.
Sprinzl et al., "Compilation of (RNA Sequences" Nucleic Acids Research, 1978, r15-r27.
Jason S. Feinberg: "Identification of molecular interactions between P-site tRNA and the ribosome essential for translocation" , Proceedings of the National Academy of Sciences, vol. 98, No. 20, Sep. 25, 2001 (Sep. 25, 2001), pp. 11120-11125, XP093156172, ISSN: 0027-8424, DOI: 10.1073/pnas.211184098.
Y.-M. Hou: "An important 2'-OH group for 1-4,7 an RNA-protein interaction", Nucleic Acids Research, vol. 29, No. 4, Feb. 15, 2001 (Feb. 15, 2001), pp. 976-985, XP093156187, GB ISSN: 1362-4962, DOI: 10.1093/nar/29.4.976.
Valerie De Crecy-Lagard: "Matching tRNA 1 modifications in humans to their known and predicted enzymes" , Nucleic Acids Research, vol. 47, No. 5, Jan. 30, 2019 (Jan. 30, 2019), pp. 2143-2159, XP093156180, GB ISSN: 0305-1048, DOI: 10.1093/nar/gkzoll.

* cited by examiner

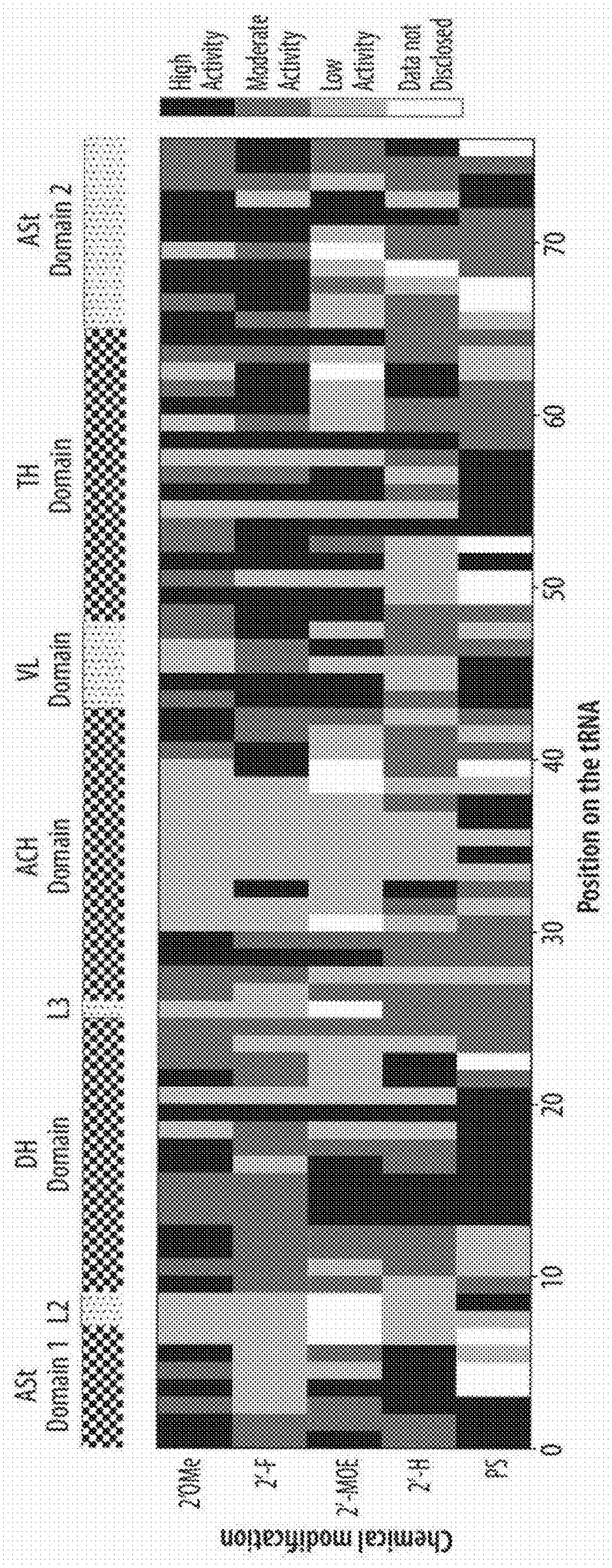
ASt Domain 1
L2
DH Domain
L3
ACH Domain
VL Domain
TH Domain
ASt Domain 2
High Activity
Moderate Activity
Low Activity
Data not Disclosed
2'OMe
2'-F
2'-MOE
2'-H
PS
Chemical modification
0
10
20
30
40
50
60
70
Position on the tRNA

```
                         SEQUENCE LISTING


<160> NUMBER OF SEQ ID NOS: 1293

<210> SEQ ID NO 1
<211> LENGTH: 72
<212> TYPE: DNA
<213> ORGANISM: Homo sapiens

<400> SEQUENCE: 1

gggggtatag ctcagtggta gagcgcgtgc ttagcatgca cgaggtcctg ggttcgatcc      60

ccagtacctc ca                                                          72


<210> SEQ ID NO 2
<211> LENGTH: 73
<212> TYPE: DNA
<213> ORGANISM: Homo sapiens

<400> SEQUENCE: 2

ggggaattag ctcaagtggt agagcgcttg cttagcacgc aagaggtagt gggatcgatg      60

cccacattct cca                                                         73


<210> SEQ ID NO 3
<211> LENGTH: 73
<212> TYPE: DNA
<213> ORGANISM: Homo sapiens

<400> SEQUENCE: 3

ggggaattag ctcaaatggt agagcgctcg cttagcatgc gagaggtagc gggatcgatg      60

cccgcattct cca                                                         73
```

<210> SEQ ID NO 4
<211> LENGTH: 73
<212> TYPE: DNA
<213> ORGANISM: Homo sapiens

<400> SEQUENCE: 4
ggggaattag ctcaagtggt agagcgcttg cttagcatgc aagaggtagt gggatcgatg 60
cccacattct cca 73

<210> SEQ ID NO 5
<211> LENGTH: 73
<212> TYPE: DNA
<213> ORGANISM: Homo sapiens

<400> SEQUENCE: 5
ggggaattag ctcaagcggt agagcgcttg cttagcatgc aagaggtagt gggatcgatg 60
cccacattct cca 73

<210> SEQ ID NO 6
<211> LENGTH: 73
<212> TYPE: DNA
<213> ORGANISM: Homo sapiens

<400> SEQUENCE: 6
ggggaattag ctcaagtggt agagcgcttg cttagcatgc aagaggtagt gggatcaatg 60
cccacattct cca 73

<210> SEQ ID NO 7
<211> LENGTH: 73
<212> TYPE: DNA
<213> ORGANISM: Homo sapiens

<400> SEQUENCE: 7
ggggaattag ctcaagtggt agagcgctcg cttagcatgc gagaggtagt gggatcgatg 60
cccgcattct cca 73

<210> SEQ ID NO 8
<211> LENGTH: 73
<212> TYPE: DNA
<213> ORGANISM: Homo sapiens

<400> SEQUENCE: 8
ggggaattag cccaagtggt agagcgcttg cttagcatgc aagaggtagt gggatcgatg 60
cccacattct cca 73

<210> SEQ ID NO 9
<211> LENGTH: 72
<212> TYPE: DNA
<213> ORGANISM: Homo sapiens

<400> SEQUENCE: 9
gggggtgtag ctcagtggta gagcgcgtgc ttagcatgca cgaggccccg ggttcaatcc 60
ccggcacctc ca 72

<210> SEQ ID NO 10
<211> LENGTH: 72
<212> TYPE: DNA
<213> ORGANISM: Homo sapiens

<400> SEQUENCE: 10
gggggtgtag ctcagtggta gagcgcgtgc ttagcatgta cgaggtcccg ggttcaatcc 60
ccggcacctc ca 72

<210> SEQ ID NO 11
<211> LENGTH: 72
<212> TYPE: DNA
<213> ORGANISM: Homo sapiens

<400> SEQUENCE: 11
ggggatgtag ctcagtggta gagcgcatgc ttagcatgca tgaggtcccg ggttcgatcc 60
ccagcatctc ca 72

<210> SEQ ID NO 12
<211> LENGTH: 72
<212> TYPE: DNA
<213> ORGANISM: Homo sapiens

<400> SEQUENCE: 12
gggggtgtag ctcagtggta gagcgcgtgc ttagcatgca cgaggccctg ggttcaatcc 60
ccagcacctc ca 72

<210> SEQ ID NO 13
<211> LENGTH: 72
<212> TYPE: DNA
<213> ORGANISM: Homo sapiens

<400> SEQUENCE: 13
gggggtatag ctcagcggta gagcgcgtgc ttagcatgca cgaggtcctg ggttcaatcc 60
ccaatacctc ca 72

<210> SEQ ID NO 14
<211> LENGTH: 72
<212> TYPE: DNA
<213> ORGANISM: Homo sapiens

<400> SEQUENCE: 14
gggggtgtag ctcagtggta gagcgcgtgc ttagcatgca cgaggccccg ggttcaatcc 60
ctggcacctc ca 72

<210> SEQ ID NO 15
<211> LENGTH: 73
<212> TYPE: DNA
<213> ORGANISM: Homo sapiens

<400> SEQUENCE: 15
gggggattag ctcaaatggt agagcgctcg cttagcatgc gagaggtagc gggatcgatg 60
cccgcatcct cca 73

<210> SEQ ID NO 16
<211> LENGTH: 73
<212> TYPE: DNA
<213> ORGANISM: Homo sapiens

<400> SEQUENCE: 16
ggggaattag ctcaggcggt agagcgctcg cttagcatgc gagaggtagc gggatcgacg 60
cccgcattct cca 73

<210> SEQ ID NO 17

<211> LENGTH: 72
<212> TYPE: DNA
<213> ORGANISM: Homo sapiens

<400> SEQUENCE: 17
ggggatgtag ctcagtggta gagcgcatgc ttcgcatgta tgaggtcccg ggttcgatcc 60
ccggcatctc ca 72

<210> SEQ ID NO 18
<211> LENGTH: 72
<212> TYPE: DNA
<213> ORGANISM: Homo sapiens

<400> SEQUENCE: 18
ggggatgtag ctcagtggta gagcgcatgc ttcgcatgta tgaggccccg ggttcgatcc 60
ccggcatctc ca 72

<210> SEQ ID NO 19
<211> LENGTH: 72
<212> TYPE: DNA
<213> ORGANISM: Homo sapiens

<400> SEQUENCE: 19
ggggatgtag ctcagtggta gagcgcgcgc ttcgcatgtg tgaggtcccg ggttcaatcc 60
ccggcatctc ca 72

<210> SEQ ID NO 20
<211> LENGTH: 72
<212> TYPE: DNA
<213> ORGANISM: Homo sapiens

<400> SEQUENCE: 20
gggggtgtag ctcagtggta gagcgcgtgc ttcgcatgta cgaggccccg ggttcgaccc 60
ccggctcctc ca 72

<210> SEQ ID NO 21
<211> LENGTH: 72
<212> TYPE: DNA
<213> ORGANISM: Homo sapiens

<400> SEQUENCE: 21
gggggtgtag ctcagtggta gagcgcatgc tttgcatgta tgaggtcccg ggttcgatcc 60
ccggcacctc ca 72

<210> SEQ ID NO 22
<211> LENGTH: 72
<212> TYPE: DNA
<213> ORGANISM: Homo sapiens

<400> SEQUENCE: 22
ggggatgtag ctcagtggta gagcgcatgc tttgcatgta tgaggtcccg ggttcgatcc 60
ccggcatctc ca 72

<210> SEQ ID NO 23
<211> LENGTH: 72
<212> TYPE: DNA
<213> ORGANISM: Homo sapiens

<400> SEQUENCE: 23
ggggatgtag ctcagtggta gagcgcatgc tttgcatgta tgaggccccg ggttcgatcc 60
ccggcatctc ca 72

<210> SEQ ID NO 24
<211> LENGTH: 72
<212> TYPE: DNA
<213> ORGANISM: Homo sapiens

<400> SEQUENCE: 24
ggggatgtag ctcagtggta gagcgcatgc tttgcacgta tgaggccccg ggttcaatcc 60
ccggcatctc ca 72

<210> SEQ ID NO 25
<211> LENGTH: 72
<212> TYPE: DNA
<213> ORGANISM: Homo sapiens

<400> SEQUENCE: 25
gggggtgtag ctcagtggta gagcgcatgc tttgcatgta tgaggcctcg ggttcgatcc 60
ccgacacctc ca 72

<210> SEQ ID NO 26
<211> LENGTH: 72
<212> TYPE: DNA
<213> ORGANISM: Homo sapiens

<400> SEQUENCE: 26
gggggtgtag ctcagtggta gagcacatgc tttgcatgtg tgaggccccg ggttcgatcc 60
ccggcacctc ca 72

<210> SEQ ID NO 27
<211> LENGTH: 71
<212> TYPE: DNA
<213> ORGANISM: Homo sapiens

<400> SEQUENCE: 27
gggggtgtag ctcagtggta gagcgcatgc tttgcatgta tgaggcctcg gttcgatccc 60
cgacacctcc a 71

<210> SEQ ID NO 28
<211> LENGTH: 73
<212> TYPE: DNA
<213> ORGANISM: Homo sapiens

<400> SEQUENCE: 28
gggccagtgg cgcaatggat aacgcgtctg actacggatc agaagattcc aggttcgact 60
cctggctggc tcg 73

<210> SEQ ID NO 29
<211> LENGTH: 73
<212> TYPE: DNA
<213> ORGANISM: Homo sapiens

<400> SEQUENCE: 29
gggccagtgg cgcaatggat aacgcgtctg actacggatc agaagattct aggttcgact 60
cctggctggc tcg 73

<210> SEQ ID NO 30
<211> LENGTH: 73
<212> TYPE: DNA

-continued

<213> ORGANISM: Homo sapiens

<400> SEQUENCE: 30
ggccgcgtgg cctaatggat aaggcgtctg attccggatc agaagattga gggttcgagt 60
cccttcgtgg tcg 73

<210> SEQ ID NO 31
<211> LENGTH: 73
<212> TYPE: DNA
<213> ORGANISM: Homo sapiens

<400> SEQUENCE: 31
gacccagtgg cctaatggat aaggcatcag cctccggagc tggggattgt gggttcgagt 60
cccatctggg tcg 73

<210> SEQ ID NO 32
<211> LENGTH: 73
<212> TYPE: DNA
<213> ORGANISM: Homo sapiens

<400> SEQUENCE: 32
gccccagtgg cctaatggat aaggcactgg cctcctaagc cagggattgt gggttcgagt 60
cccacctggg gta 73

<210> SEQ ID NO 33
<211> LENGTH: 73
<212> TYPE: DNA
<213> ORGANISM: Homo sapiens

<400> SEQUENCE: 33
gccccagtgg cctaatggat aaggcactgg cctcctaagc cagggattgt gggttcgagt 60
cccacctggg gtg 73

<210> SEQ ID NO 34
<211> LENGTH: 73
<212> TYPE: DNA
<213> ORGANISM: Homo sapiens

<400> SEQUENCE: 34
gccccggtgg cctaatggat aaggcattgg cctcctaagc cagggattgt gggttcgagt 60
cccacccggg gta 73

<210> SEQ ID NO 35
<211> LENGTH: 73
<212> TYPE: DNA
<213> ORGANISM: Homo sapiens

<400> SEQUENCE: 35
gccccagtgg cctaatggat aaggcattgg cctcctaagc cagggattgt gggttcgagt 60
cccatctggg gtg 73

<210> SEQ ID NO 36
<211> LENGTH: 73
<212> TYPE: DNA
<213> ORGANISM: Homo sapiens

<400> SEQUENCE: 36
gccccagtgg cctgatggat aaggtactgg cctcctaagc cagggattgt gggttcgagt 60
tccacctggg gta 73

<210> SEQ ID NO 37
<211> LENGTH: 73
<212> TYPE: DNA
<213> ORGANISM: Homo sapiens

<400> SEQUENCE: 37
ggccgcgtgg cctaatggat aaggcgtctg acttcggatc agaagattgc aggttcgagt 60
cctgccgcgg tcg 73

<210> SEQ ID NO 38
<211> LENGTH: 73
<212> TYPE: DNA
<213> ORGANISM: Homo sapiens

<400> SEQUENCE: 38
gaccacgtgg cctaatggat aaggcgtctg acttcggatc agaagattga gggttcgaat 60
ccctccgtgg tta 73

<210> SEQ ID NO 39
<211> LENGTH: 73
<212> TYPE: DNA
<213> ORGANISM: Homo sapiens

<400> SEQUENCE: 39
gaccgcgtgg cctaatggat aaggcgtctg acttcggatc agaagattga gggttcgagt 60
cccttcgtgg tcg 73

<210> SEQ ID NO 40
<211> LENGTH: 73
<212> TYPE: DNA
<213> ORGANISM: Homo sapiens

<400> SEQUENCE: 40
gaccacgtgg cctaatggat aaggcgtctg acttcggatc agaagattga gggttcgaat 60
cccttcgtgg tta 73

<210> SEQ ID NO 41
<211> LENGTH: 73
<212> TYPE: DNA
<213> ORGANISM: Homo sapiens

<400> SEQUENCE: 41
gaccacgtgg cctaatggat aaggcgtctg acttcggatc agaagattga gggttcgaat 60
cccttcgtgg ttg 73

<210> SEQ ID NO 42
<211> LENGTH: 73
<212> TYPE: DNA
<213> ORGANISM: Homo sapiens

<400> SEQUENCE: 42
ggccgtgtgg cctaatggat aaggcgtctg acttcggatc aaaagattgc aggtttgagt 60
tctgccacgg tcg 73

<210> SEQ ID NO 43
<211> LENGTH: 85
<212> TYPE: DNA
<213> ORGANISM: Homo sapiens

<400> SEQUENCE: 43
ggctccgtgg cgcaatggat agcgcattgg acttctagag gctgaaggca ttcaaaggtt 60
ccgggttcga gtcccggcgg agtcg 85

<210> SEQ ID NO 44
<211> LENGTH: 88
<212> TYPE: DNA
<213> ORGANISM: Homo sapiens

<400> SEQUENCE: 44
ggctctgtgg cgcaatggat agcgcattgg acttctagtg acgaatagag caattcaaag 60
gttgtgggtt cgaatcccac cagagtcg 88

<210> SEQ ID NO 45
<211> LENGTH: 91
<212> TYPE: DNA
<213> ORGANISM: Homo sapiens

<400> SEQUENCE: 45
ggctctgtgg cgcaatggat agcgcattgg acttctagct gagcctagtg tggtcattca 60
aaggttgtgg gttcgagtcc caccagagtc g 91

<210> SEQ ID NO 46
<211> LENGTH: 86
<212> TYPE: DNA
<213> ORGANISM: Homo sapiens

<400> SEQUENCE: 46
ggctctgtgg cgcaatggat agcgcattgg acttctagat agttagagaa attcaaaggt 60
tgtgggttcg agtcccacca gagtcg 86

<210> SEQ ID NO 47
<211> LENGTH: 74
<212> TYPE: DNA
<213> ORGANISM: Homo sapiens

<400> SEQUENCE: 47
gtctctgtgg cgcaatggac gagcgcgctg gacttctaat ccagaggttc cgggttcgag 60
tcccggcaga gatg 74

<210> SEQ ID NO 48
<211> LENGTH: 87
<212> TYPE: DNA
<213> ORGANISM: Homo sapiens

<400> SEQUENCE: 48
ggctctgtgg cgcaatggat agcgcattgg acttctagcc taaatcaaga gattcaaagg 60
ttgcgggttc gagtccctcc agagtcg 87

<210> SEQ ID NO 49
<211> LENGTH: 74
<212> TYPE: DNA
<213> ORGANISM: Homo sapiens

<400> SEQUENCE: 49
gtctctgtgg cgcaatcggt tagcgcgttc ggctgttaac cgaaaggttg gtggttcgat 60
cccacccagg gacg 74

-continued

<210> SEQ ID NO 50
<211> LENGTH: 74
<212> TYPE: DNA
<213> ORGANISM: Homo sapiens

<400> SEQUENCE: 50
gtctctgtgg cgcaatcggc tagcgcgttt ggctgttaac taaaaggttg gcggttcgaa 60
cccacccaga ggcg 74

<210> SEQ ID NO 51
<211> LENGTH: 74
<212> TYPE: DNA
<213> ORGANISM: Homo sapiens

<400> SEQUENCE: 51
gtctctgtgg tgcaatcggt tagcgcgttc cgctgttaac cgaaagcttg gtggttcgag 60
cccacccagg gatg 74

<210> SEQ ID NO 52
<211> LENGTH: 74
<212> TYPE: DNA
<213> ORGANISM: Homo sapiens

<400> SEQUENCE: 52
gtctctgtgg cgcaatcggc tagcgcgttt ggctgttaac taaaaagttg gtggttcgaa 60
cacacccaga ggcg 74

<210> SEQ ID NO 53
<211> LENGTH: 74
<212> TYPE: DNA
<213> ORGANISM: Homo sapiens

<400> SEQUENCE: 53
gtctctgtgg cgcaatcggt tagcgcgttc ggctgttaac cgaaaggttg gtggttcgag 60
cccacccagg gacg 74

<210> SEQ ID NO 54
<211> LENGTH: 74
<212> TYPE: DNA
<213> ORGANISM: Homo sapiens

<400> SEQUENCE: 54
gtctctgtgg cgcaatcggt tagcgcattc ggctgttaac cgaaaggttg gtggttcgag 60
cccacccagg gacg 74

<210> SEQ ID NO 55
<211> LENGTH: 74
<212> TYPE: DNA
<213> ORGANISM: Homo sapiens

<400> SEQUENCE: 55
gtctctgtgg cgcaatcggt tagcgcgttc ggctgttaac cgaaagattg gtggttcgag 60
cccacccagg gacg 74

<210> SEQ ID NO 56
<211> LENGTH: 74
<212> TYPE: DNA
<213> ORGANISM: Homo sapiens

<400> SEQUENCE: 56

-continued gtctctgtgg cgcaatcggt tagcgcgttc ggctgttaac tgaaaggttg gtggttcgag 60
cccacccagg gacg 74

<210> SEQ ID NO 57
<211> LENGTH: 74
<212> TYPE: DNA
<213> ORGANISM: Homo sapiens

<400> SEQUENCE: 57
gtctctgtgg cgcaatgggt tagcgcgttc ggctgttaac cgaaaggttg gtggttcgag 60
cccatccagg gacg 74

<210> SEQ ID NO 58
<211> LENGTH: 74
<212> TYPE: DNA
<213> ORGANISM: Homo sapiens

<400> SEQUENCE: 58
gtctctgtgg cgtagtcggt tagcgcgttc ggctgttaac cgaaaagttg gtggttcgag 60
cccacccagg aacg 74

<210> SEQ ID NO 59
<211> LENGTH: 74
<212> TYPE: DNA
<213> ORGANISM: Homo sapiens

<400> SEQUENCE: 59
gtctctgtgg cgcaatcggc tagcgcgttt ggctgttaac taaaaggttg gtggttcgaa 60
cccacccaga ggcg 74

<210> SEQ ID NO 60
<211> LENGTH: 74
<212> TYPE: DNA
<213> ORGANISM: Homo sapiens

<400> SEQUENCE: 60
gtctctgtgg cgcaatcggt tagcgcgttc ggctgttaac tgaaaggtta gtggttcgag 60
cccacccggg gacg 74

<210> SEQ ID NO 61
<211> LENGTH: 72
<212> TYPE: DNA
<213> ORGANISM: Homo sapiens

<400> SEQUENCE: 61
tcctcgttag tatagtggtt agtatccccg cctgtcacgc gggagaccgg ggttcaattc 60
cccgacgggg ag 72

<210> SEQ ID NO 62
<211> LENGTH: 72
<212> TYPE: DNA
<213> ORGANISM: Homo sapiens

<400> SEQUENCE: 62
tcctcgttag tatagtggtg agtatccccg cctgtcacgc gggagaccgg ggttcgattc 60
cccgacgggg ag 72

<210> SEQ ID NO 63
<211> LENGTH: 72

<212> TYPE: DNA
<213> ORGANISM: Homo sapiens

<400> SEQUENCE: 63
tcctcgttag tatagtggtg agtgtccccg tctgtcacgc gggagaccgg ggttcgattc 60
cccgacgggg ag 72

<210> SEQ ID NO 64
<211> LENGTH: 72
<212> TYPE: DNA
<213> ORGANISM: Homo sapiens

<400> SEQUENCE: 64
gggggcatag ctcagtggta gagcatttga ctgcagatca agaggtccct ggttcaaatc 60
caggtgcccc ct 72

<210> SEQ ID NO 65
<211> LENGTH: 72
<212> TYPE: DNA
<213> ORGANISM: Homo sapiens

<400> SEQUENCE: 65
gggggtatag ctcaggggta gagcatttga ctgcagatca agaggtccct ggttcaaatc 60
caggtgcccc cc 72

<210> SEQ ID NO 66
<211> LENGTH: 72
<212> TYPE: DNA
<213> ORGANISM: Homo sapiens

<400> SEQUENCE: 66
gggggtatag cttagcggta gagcatttga ctgcagatca agaggtcccc ggttcaaatc 60
cgggtgcccc ct 72

<210> SEQ ID NO 67
<211> LENGTH: 72
<212> TYPE: DNA
<213> ORGANISM: Homo sapiens

<400> SEQUENCE: 67
gggggtatag cttaggggta gagcatttga ctgcagatca aaaggtccct ggttcaaatc 60
caggtgcccc tt 72

<210> SEQ ID NO 68
<211> LENGTH: 72
<212> TYPE: DNA
<213> ORGANISM: Homo sapiens

<400> SEQUENCE: 68
gggggtatag ctcaggggta gagcatttga ctgcagatca agaggtcccc agttcaaatc 60
tgggtgcccc ct 72

<210> SEQ ID NO 69
<211> LENGTH: 72
<212> TYPE: DNA
<213> ORGANISM: Homo sapiens

<400> SEQUENCE: 69
gggggtatag ctcaggggta gagcatttga ctgcagatca agaagtcccc ggttcaaatc 60

-continued cgggtgcccc ct 72

<210> SEQ ID NO 70
<211> LENGTH: 72
<212> TYPE: DNA
<213> ORGANISM: Homo sapiens

<400> SEQUENCE: 70
gggggtatag ctcaggggta gagcatttga ctgcagatca agaggtctct ggttcaaatc 60
caggtgcccc ct 72

<210> SEQ ID NO 71
<211> LENGTH: 72
<212> TYPE: DNA
<213> ORGANISM: Homo sapiens

<400> SEQUENCE: 71
gggggtatag ctcaggggta gagcacttga ctgcagatca agaagtcctt ggttcaaatc 60
caggtgcccc ct 72

<210> SEQ ID NO 72
<211> LENGTH: 72
<212> TYPE: DNA
<213> ORGANISM: Homo sapiens

<400> SEQUENCE: 72
ggggatatag ctcaggggta gagcatttga ctgcagatca agaggtcccc ggttcaaatc 60
cgggtgcccc cc 72

<210> SEQ ID NO 73
<211> LENGTH: 72
<212> TYPE: DNA
<213> ORGANISM: Homo sapiens

<400> SEQUENCE: 73
gggggtatag ttcaggggta gagcatttga ctgcagatca agaggtccct ggttcaaatc 60
caggtgcccc ct 72

<210> SEQ ID NO 74
<211> LENGTH: 72
<212> TYPE: DNA
<213> ORGANISM: Homo sapiens

<400> SEQUENCE: 74
gggggtatag ctcaggggta gagcatttga ctgcaaatca agaggtccct gattcaaatc 60
caggtgcccc ct 72

<210> SEQ ID NO 75
<211> LENGTH: 72
<212> TYPE: DNA
<213> ORGANISM: Homo sapiens

<400> SEQUENCE: 75
gggggtatag ctcagtggta gagcatttga ctgcagatca agaggtcccc ggttcaaatc 60
cgggtgcccc ct 72

<210> SEQ ID NO 76
<211> LENGTH: 72
<212> TYPE: DNA
<213> ORGANISM: Homo sapiens

<400> SEQUENCE: 76
gggcgtatag ctcaggggta gagcatttga ctgcagatca agaggtcccc agttcaaatc 60
tgggtgcccc ct 72

<210> SEQ ID NO 77
<211> LENGTH: 72
<212> TYPE: DNA
<213> ORGANISM: Homo sapiens

<400> SEQUENCE: 77
gggggtatag ctcacaggta gagcatttga ctgcagatca agaggtcccc ggttcaaatc 60
tgggtgcccc ct 72

<210> SEQ ID NO 78
<211> LENGTH: 70
<212> TYPE: DNA
<213> ORGANISM: Homo sapiens

<400> SEQUENCE: 78
gggcgtatag ctcaggggta gagcatttga ctgcagatca agaggtcccc agttcaaatc 60
tgggtgccca 70

<210> SEQ ID NO 79
<211> LENGTH: 72
<212> TYPE: DNA
<213> ORGANISM: Homo sapiens

<400> SEQUENCE: 79
gggggtatag ctcacaggta gagcatttga ctgcagatca agaggtcccc ggttcaaatc 60
cggttactcc ct 72

<210> SEQ ID NO 80
<211> LENGTH: 72
<212> TYPE: DNA
<213> ORGANISM: Homo sapiens

<400> SEQUENCE: 80
gggggtatag ctcaggggta gagcacttga ctgcagatca agaggtccct ggttcaaatc 60
caggtgcccc ct 72

<210> SEQ ID NO 81
<211> LENGTH: 72
<212> TYPE: DNA
<213> ORGANISM: Homo sapiens

<400> SEQUENCE: 81
gggggtatag ctcagtggta gagcatttga ctgcagatca agaggtccct ggttcaaatc 60
cgggtgcccc ct 72

<210> SEQ ID NO 82
<211> LENGTH: 73
<212> TYPE: DNA
<213> ORGANISM: Homo sapiens

<400> SEQUENCE: 82
gggggtatag ctcagtgggt agagcatttg actgcagatc aagaggtccc cggttcaaat 60
ccgggtgccc cct 73

<210> SEQ ID NO 83
<211> LENGTH: 72
<212> TYPE: DNA
<213> ORGANISM: Homo sapiens

<400> SEQUENCE: 83
gggggtgtag ctcagtggta gagcatttga ctgcagatca agaggtccct ggttcaaatc 60
caggtgcccc ct 72

<210> SEQ ID NO 84
<211> LENGTH: 73
<212> TYPE: DNA
<213> ORGANISM: Homo sapiens

<400> SEQUENCE: 84
gggggtatag ctcaggtggt agagcatttg actgcagatc aagaggtccc cggttcaaat 60
ccgggtgccc cct 73

<210> SEQ ID NO 85
<211> LENGTH: 72
<212> TYPE: DNA
<213> ORGANISM: Homo sapiens

<400> SEQUENCE: 85
gggggtatag ctcaggggta gagcatttga ctgcagatca agaggtcccc ggttcaaatc 60
cgggtgcccc ct 72

<210> SEQ ID NO 86
<211> LENGTH: 72
<212> TYPE: DNA
<213> ORGANISM: Homo sapiens

<400> SEQUENCE: 86
gggggtatag ctcaggggta gagcatttga ctgcagatca agaggtccct ggttcaaatc 60
caggtgcccc ct 72

<210> SEQ ID NO 87
<211> LENGTH: 72
<212> TYPE: DNA
<213> ORGANISM: Homo sapiens

<400> SEQUENCE: 87
ggttccatgg tgtaatggtt agcactctgg actctgaatc cagcgatccg agttcaaatc 60
tcggtggaac ct 72

<210> SEQ ID NO 88
<211> LENGTH: 72
<212> TYPE: DNA
<213> ORGANISM: Homo sapiens

<400> SEQUENCE: 88
ggttccatgg tgtaatggtt agcactctgg actctgaatc cagcgatccg agttcaagtc 60
tcggtggaac ct 72

<210> SEQ ID NO 89
<211> LENGTH: 72
<212> TYPE: DNA
<213> ORGANISM: Homo sapiens

<400> SEQUENCE: 89
ggttccatgg tgtaatggtg agcactctgg actctgaatc cagcgatccg agttcgagtc 60
tcggtggaac ct 72

<210> SEQ ID NO 90
<211> LENGTH: 72
<212> TYPE: DNA
<213> ORGANISM: Homo sapiens

<400> SEQUENCE: 90
ggttccatgg tgtaatggta agcactctgg actctgaatc cagcgatccg agttcgagtc 60
tcggtggaac ct 72

<210> SEQ ID NO 91
<211> LENGTH: 72
<212> TYPE: DNA
<213> ORGANISM: Homo sapiens

<400> SEQUENCE: 91
ggttccatgg tgtaatggtt agcactctgg actctgaatc cggtaatccg agttcaaatc 60
tcggtggaac ct 72

<210> SEQ ID NO 92
<211> LENGTH: 72
<212> TYPE: DNA
<213> ORGANISM: Homo sapiens

<400> SEQUENCE: 92
ggccccatgg tgtaatggtc agcactctgg actctgaatc cagcgatccg agttcaaatc 60
tcggtgggac cc 72

<210> SEQ ID NO 93
<211> LENGTH: 72
<212> TYPE: DNA
<213> ORGANISM: Homo sapiens

<400> SEQUENCE: 93
ggttccatgg tgtaatggta agcactctgg actctgaatc cagccatctg agttcgagtc 60
tctgtggaac ct 72

<210> SEQ ID NO 94
<211> LENGTH: 72
<212> TYPE: DNA
<213> ORGANISM: Homo sapiens

<400> SEQUENCE: 94
ggtcccatgg tgtaatggtt agcactctgg actttgaatc cagcgatccg agttcaaatc 60
tcggtgggac ct 72

<210> SEQ ID NO 95
<211> LENGTH: 72
<212> TYPE: DNA
<213> ORGANISM: Homo sapiens

<400> SEQUENCE: 95
ggtcccatgg tgtaatggtt agcactctgg actttgaatc cagcaatccg agttcgaatc 60
tcggtgggac ct 72

<210> SEQ ID NO 96

<211> LENGTH: 72
<212> TYPE: DNA
<213> ORGANISM: Homo sapiens

<400> SEQUENCE: 96
ggccccatgg tgtaatggtt agcactctgg actttgaatc cagcgatccg agttcaaatc 60
tcggtgggac ct 72

<210> SEQ ID NO 97
<211> LENGTH: 72
<212> TYPE: DNA
<213> ORGANISM: Homo sapiens

<400> SEQUENCE: 97
ggtcccatgg tgtaatggtt agcactctgg gctttgaatc cagcaatccg agttcgaatc 60
ttggtgggac ct 72

<210> SEQ ID NO 98
<211> LENGTH: 72
<212> TYPE: DNA
<213> ORGANISM: Homo sapiens

<400> SEQUENCE: 98
tccctggtgg tctagtggtt aggattcggc gctctcaccg ccgcggcccg ggttcgattc 60
ccggtcaggg aa 72

<210> SEQ ID NO 99
<211> LENGTH: 72
<212> TYPE: DNA
<213> ORGANISM: Homo sapiens

<400> SEQUENCE: 99
tccctggtgg tctagtggtt aggattcggc gctctcaccg ccgcggcccg ggttcgattc 60
ccggtcagga aa 72

<210> SEQ ID NO 100
<211> LENGTH: 72
<212> TYPE: DNA
<213> ORGANISM: Homo sapiens

<400> SEQUENCE: 100
tcccatatgg tctagcggtt aggattcctg gttttcaccc aggtggcccg ggttcgactc 60
ccggtatggg aa 72

<210> SEQ ID NO 101
<211> LENGTH: 72
<212> TYPE: DNA
<213> ORGANISM: Homo sapiens

<400> SEQUENCE: 101
tcccacatgg tctagcggtt aggattcctg gttttcaccc aggcggcccg ggttcgactc 60
ccggtgtggg aa 72

<210> SEQ ID NO 102
<211> LENGTH: 72
<212> TYPE: DNA
<213> ORGANISM: Homo sapiens

<400> SEQUENCE: 102
tccctggtgg tctagtggct aggattcggc gctttcaccg ccgcggcccg ggttcgattc 60
ccggccaggg aa 72

<210> SEQ ID NO 103
<211> LENGTH: 72
<212> TYPE: DNA
<213> ORGANISM: Homo sapiens

<400> SEQUENCE: 103
tccctggtgg tctagtggct aggattcggc gctttcaccg ccgcggcccg ggttcgattc 60
ccggtcaggg aa 72

<210> SEQ ID NO 104
<211> LENGTH: 71
<212> TYPE: DNA
<213> ORGANISM: Homo sapiens

<400> SEQUENCE: 104
gcattggtgg ttcagtggta gaattctcgc ctcccacgcg ggagacccgg gttcaattcc 60
cggccaatgc a 71

<210> SEQ ID NO 105
<211> LENGTH: 71
<212> TYPE: DNA
<213> ORGANISM: Homo sapiens

<400> SEQUENCE: 105
gcgccgctgg tgtagtggta tcatgcaaga ttcccattct tgcgacccgg gttcgattcc 60
cgggcggcgc a 71

<210> SEQ ID NO 106
<211> LENGTH: 71
<212> TYPE: DNA
<213> ORGANISM: Homo sapiens

<400> SEQUENCE: 106
gcattggtgg ttcaatggta gaattctcgc ctcccacgca ggagacccag gttcgattcc 60
tggccaatgc a 71

<210> SEQ ID NO 107
<211> LENGTH: 71
<212> TYPE: DNA
<213> ORGANISM: Homo sapiens

<400> SEQUENCE: 107
gcatgggtgg ttcagtggta gaattctcgc ctgccacgcg ggaggcccgg gttcgattcc 60
cggcccatgc a 71

<210> SEQ ID NO 108
<211> LENGTH: 71
<212> TYPE: DNA
<213> ORGANISM: Homo sapiens

<400> SEQUENCE: 108
gcattggtgg ttcagtggta gaattctcgc ctgccacgcg ggaggcccgg gttcgattcc 60
cggccaatgc a 71

<210> SEQ ID NO 109
<211> LENGTH: 71
<212> TYPE: DNA

<213> ORGANISM: Homo sapiens

<400> SEQUENCE: 109
gcattggtgg ttcagtggta gaattctcgc ctgccacgcg ggaggcccgg gtttgattcc 60
cggccagtgc a 71

<210> SEQ ID NO 110
<211> LENGTH: 71
<212> TYPE: DNA
<213> ORGANISM: Homo sapiens

<400> SEQUENCE: 110
gcataggtgg ttcagtggta gaattcttgc ctgccacgca ggaggcccag gtttgattcc 60
tggcccatgc a 71

<210> SEQ ID NO 111
<211> LENGTH: 71
<212> TYPE: DNA
<213> ORGANISM: Homo sapiens

<400> SEQUENCE: 111
gcattggtgg ttcagtggta gaattctcgc ctgccatgcg ggcggccggg cttcgattcc 60
tggccaatgc a 71

<210> SEQ ID NO 112
<211> LENGTH: 72
<212> TYPE: DNA
<213> ORGANISM: Homo sapiens

<400> SEQUENCE: 112
gcgttggtgg tatagtggtt agcatagctg ccttccaagc agttgacccg ggttcgattc 60
ccggccaacg ca 72

<210> SEQ ID NO 113
<211> LENGTH: 72
<212> TYPE: DNA
<213> ORGANISM: Homo sapiens

<400> SEQUENCE: 113
gcgttggtgg tatagtggtg agcatagctg ccttccaagc agttgacccg ggttcgattc 60
ccggccaacg ca 72

<210> SEQ ID NO 114
<211> LENGTH: 72
<212> TYPE: DNA
<213> ORGANISM: Homo sapiens

<400> SEQUENCE: 114
gcgttggtgg tatagtggta agcatagctg ccttccaagc agttgacccg ggttcgattc 60
ccggccaacg ca 72

<210> SEQ ID NO 115
<211> LENGTH: 72
<212> TYPE: DNA
<213> ORGANISM: Homo sapiens

<400> SEQUENCE: 115
gcgttggtgg tatagtggtg agcatagttg ccttccaagc agttgacccg ggctcgattc 60
ccgcccaacg ca 72

<210> SEQ ID NO 116
<211> LENGTH: 72
<212> TYPE: DNA
<213> ORGANISM: Homo sapiens

<400> SEQUENCE: 116
gccgtgatcg tatagtggtt agtactctgc gttgtggccg cagcaacctc ggttcgaatc 60
cgagtcacgg ca 72

<210> SEQ ID NO 117
<211> LENGTH: 72
<212> TYPE: DNA
<213> ORGANISM: Homo sapiens

<400> SEQUENCE: 117
gccatgatcg tatagtggtt agtactctgc gctgtggccg cagcaacctc ggttcgaatc 60
cgagtcacgg ca 72

<210> SEQ ID NO 118
<211> LENGTH: 74
<212> TYPE: DNA
<213> ORGANISM: Homo sapiens

<400> SEQUENCE: 118
ggccggttag ctcagttggt tagagcgtgg cgctaataac gccaaggtcg cgggttcgat 60
ccccgtacgg gcca 74

<210> SEQ ID NO 119
<211> LENGTH: 74
<212> TYPE: DNA
<213> ORGANISM: Homo sapiens

<400> SEQUENCE: 119
ggccggttag ctcagttggt tagagcgtgg tgctaataac gccaaggtcg cgggttcgat 60
ccccgtactg gcca 74

<210> SEQ ID NO 120
<211> LENGTH: 74
<212> TYPE: DNA
<213> ORGANISM: Homo sapiens

<400> SEQUENCE: 120
ggctggttag ctcagttggt tagagcgtgg tgctaataac gccaaggtcg cgggttcgat 60
ccccgtactg gcca 74

<210> SEQ ID NO 121
<211> LENGTH: 74
<212> TYPE: DNA
<213> ORGANISM: Homo sapiens

<400> SEQUENCE: 121
ggccggttag ctcagttggt tagagcgtgg tgctaataac gccaaggtcg cgggttcgaa 60
ccccgtacgg gcca 74

<210> SEQ ID NO 122
<211> LENGTH: 74
<212> TYPE: DNA
<213> ORGANISM: Homo sapiens

<400> SEQUENCE: 122
ggccggttag ctcagttggt tagagcgtgg tgctaataac gccaaggtcg cgggttcgat 60
ccccgtacgg gcca 74

<210> SEQ ID NO 123
<211> LENGTH: 74
<212> TYPE: DNA
<213> ORGANISM: Homo sapiens

<400> SEQUENCE: 123
ggccggttag ctcagttggt tagagcgtgg tgctaataac gctaaggtcg cgggttcgat 60
ccccgtactg gcca 74

<210> SEQ ID NO 124
<211> LENGTH: 74
<212> TYPE: DNA
<213> ORGANISM: Homo sapiens

<400> SEQUENCE: 124
ggccggttag ctcagttggt cagagcgtgg tgctaataac gccaaggtcg cgggttcgat 60
ccccgtacgg gcca 74

<210> SEQ ID NO 125
<211> LENGTH: 74
<212> TYPE: DNA
<213> ORGANISM: Homo sapiens

<400> SEQUENCE: 125
ggccggttag ctcagtcggc tagagcgtgg tgctaataac gccaaggtcg cgggttcgat 60
ccccgtacgg gcca 74

<210> SEQ ID NO 126
<211> LENGTH: 74
<212> TYPE: DNA
<213> ORGANISM: Homo sapiens

<400> SEQUENCE: 126
ggctggttag ttcagttggt tagagcgtgg tgctaataac gccaaggtcg tgggttcgat 60
ccccatatcg gcca 74

<210> SEQ ID NO 127
<211> LENGTH: 74
<212> TYPE: DNA
<213> ORGANISM: Homo sapiens

<400> SEQUENCE: 127
ggccggttag ctcagttggt aagagcgtgg tgctgataac accaaggtcg cgggctcgac 60
tcccgcaccg gcca 74

<210> SEQ ID NO 128
<211> LENGTH: 93
<212> TYPE: DNA
<213> ORGANISM: Homo sapiens

<400> SEQUENCE: 128
gctccagtgg cgcaatcggt tagcgcgcgg tacttatatg acagtgcgag cggagcaatg 60
ccgaggttgt gagttcgatc ctcacctgga gca 93

-continued

<210> SEQ ID NO 129
<211> LENGTH: 93
<212> TYPE: DNA
<213> ORGANISM: Homo sapiens

<400> SEQUENCE: 129
gctccagtgg cgcaatcggt tagcgcgcgg tacttataca gcagtacatg cagagcaatg 60
ccgaggttgt gagttcgagc ctcacctgga gca 93

<210> SEQ ID NO 130
<211> LENGTH: 94
<212> TYPE: DNA
<213> ORGANISM: Homo sapiens

<400> SEQUENCE: 130
gctccagtgg cgcaatcggt tagcgcgcgg tacttatatg gcagtatgtg tgcgagtgat 60
gccgaggttg tgagttcgag cctcacctgg agca 94

<210> SEQ ID NO 131
<211> LENGTH: 94
<212> TYPE: DNA
<213> ORGANISM: Homo sapiens

<400> SEQUENCE: 131
gctccagtgg cgcaatcggt tagcgcgcgg tacttataca acagtatatg tgcgggtgat 60
gccgaggttg tgagttcgag cctcacctgg agca 94

<210> SEQ ID NO 132
<211> LENGTH: 94
<212> TYPE: DNA
<213> ORGANISM: Homo sapiens

<400> SEQUENCE: 132
gctccagtgg cgcaatcggt tagcgcgcgg tacttataag acagtgcacc tgtgagcaat 60
gccgaggttg tgagttcaag cctcacctgg agca 94

<210> SEQ ID NO 133
<211> LENGTH: 82
<212> TYPE: DNA
<213> ORGANISM: Homo sapiens

<400> SEQUENCE: 133
ggtagcgtgg ccgagcggtc taaggcgctg gattaaggct ccagtctctt cggaggcgtg 60
ggttcgaatc ccaccgctgc ca 82

<210> SEQ ID NO 134
<211> LENGTH: 82
<212> TYPE: DNA
<213> ORGANISM: Homo sapiens

<400> SEQUENCE: 134
ggtagcgtgg ccgagcggtc taaggcgctg gattaaggct ccagtctctt cgggggcgtg 60
ggttcgaatc ccaccgctgc ca 82

<210> SEQ ID NO 135
<211> LENGTH: 82
<212> TYPE: DNA
<213> ORGANISM: Homo sapiens

<400> SEQUENCE: 135
ggtagcgtgg ccgagcggtc taaggcgctg gattaaggct ccagtctctt cgggggcgtg 60
ggttcaaatc ccaccgctgc ca 82

<210> SEQ ID NO 136
<211> LENGTH: 82
<212> TYPE: DNA
<213> ORGANISM: Homo sapiens

<400> SEQUENCE: 136
ggtagcgtgg ccgagtggtc taagacgctg gattaaggct ccagtctctt cgggggcgtg 60
ggtttgaatc ccaccgctgc ca 82

<210> SEQ ID NO 137
<211> LENGTH: 106
<212> TYPE: DNA
<213> ORGANISM: Homo sapiens

<400> SEQUENCE: 137
gtcaggatgg ccgagtggtc taaggcgcca gactcaagct aagcttcctc cgcggtgggg 60
attctggtct ccaatggagg cgtgggttcg aatcccactt ctgaca 106

<210> SEQ ID NO 138
<211> LENGTH: 105
<212> TYPE: DNA
<213> ORGANISM: Homo sapiens

<400> SEQUENCE: 138
gtcaggatgg ccgagtggtc taaggcgcca gactcaagct tggcttcctc gtgttgagga 60
ttctggtctc caatggaggc gtgggttcga atcccacttc tgaca 105

<210> SEQ ID NO 139
<211> LENGTH: 108
<212> TYPE: DNA
<213> ORGANISM: Homo sapiens

<400> SEQUENCE: 139
gtcaggatgg ccgagtggtc taaggcgcca gactcaagct tactgcttcc tgtgttcggg 60
tcttctggtc tccgtatgga ggcgtgggtt cgaatcccac ttctgaca 108

<210> SEQ ID NO 140
<211> LENGTH: 107
<212> TYPE: DNA
<213> ORGANISM: Homo sapiens

<400> SEQUENCE: 140
gtcaggatgg ccgagtggtc taaggcgcca gactcaagtt gctacttccc aggtttgggg 60
cttctggtct ccgcatggag gcgtgggttc gaatcccact tctgaca 107

<210> SEQ ID NO 141
<211> LENGTH: 106
<212> TYPE: DNA
<213> ORGANISM: Homo sapiens

<400> SEQUENCE: 141
gtcaggatgg ccgagtggtc taaggcgcca gactcaaggt aagcaccttg cctgcgggct 60
ttctggtctc cggatggagg cgtgggttcg aatcccactt ctgaca 106

<210> SEQ ID NO 142
<211> LENGTH: 74

-continued

<212> TYPE: DNA
<213> ORGANISM: Homo sapiens

<400> SEQUENCE: 142
gcctccttag tgcagtaggt agcgcatcag tctcaaaatc tgaatggtcc tgagttcaag 60
cctcagaggg ggca 74

<210> SEQ ID NO 143
<211> LENGTH: 84
<212> TYPE: DNA
<213> ORGANISM: Homo sapiens

<400> SEQUENCE: 143
gtcaggatgg ccgagcagtc ttaaggcgct gcgttcaaat cgcaccctcc gctggaggcg 60
tgggttcgaa tcccactttt gaca 84

<210> SEQ ID NO 144
<211> LENGTH: 83
<212> TYPE: DNA
<213> ORGANISM: Homo sapiens

<400> SEQUENCE: 144
gtcaggatgg ccgagcggtc taaggcgctg cgttcaggtc gcagtctccc ctggaggcgt 60
gggttcgaat cccactcctg aca 83

<210> SEQ ID NO 145
<211> LENGTH: 83
<212> TYPE: DNA
<213> ORGANISM: Homo sapiens

<400> SEQUENCE: 145
gtcaggatgg ccgagcggtc taaggcgctg cgttcaggtc gcagtctccc ctggaggcgt 60
gggttcgaat cccacttctg aca 83

<210> SEQ ID NO 146
<211> LENGTH: 83
<212> TYPE: DNA
<213> ORGANISM: Homo sapiens

<400> SEQUENCE: 146
accaggatgg ccgagtggtt aaggcgttgg acttaagatc caatggacat atgtccgcgt 60
gggttcgaac cccactcctg gta 83

<210> SEQ ID NO 147
<211> LENGTH: 83
<212> TYPE: DNA
<213> ORGANISM: Homo sapiens

<400> SEQUENCE: 147
accgggatgg ccgagtggtt aaggcgttgg acttaagatc caatgggctg gtgcccgcgt 60
gggttcgaac cccactctcg gta 83

<210> SEQ ID NO 148
<211> LENGTH: 83
<212> TYPE: DNA
<213> ORGANISM: Homo sapiens

<400> SEQUENCE: 148
accagaatgg ccgagtggtt aaggcgttgg acttaagatc caatggattc atatccgcgt 60
gggttcgaac cccacttctg gta 83

<210> SEQ ID NO 149
<211> LENGTH: 83
<212> TYPE: DNA
<213> ORGANISM: Homo sapiens

<400> SEQUENCE: 149
accgggatgg ctgagtggtt aaggcgttgg acttaagatc caatggacag gtgtccgcgt 60
gggttcgagc cccactcccg gta 83

<210> SEQ ID NO 150
<211> LENGTH: 82
<212> TYPE: DNA
<213> ORGANISM: Homo sapiens

<400> SEQUENCE: 150
ggtagcgtgg ccgagcggtc taaggcgctg gatttaggct ccagtctctt cggaggcgtg 60
ggttcgaatc ccaccgctgc ca 82

<210> SEQ ID NO 151
<211> LENGTH: 82
<212> TYPE: DNA
<213> ORGANISM: Homo sapiens

<400> SEQUENCE: 151
ggtagtgtgg ccgagcggtc taaggcgctg gatttaggct ccagtctctt cgggggcgtg 60
ggttcgaatc ccaccactgc ca 82

<210> SEQ ID NO 152
<211> LENGTH: 82
<212> TYPE: DNA
<213> ORGANISM: Homo sapiens

<400> SEQUENCE: 152
ggtagcgtgg ccgagtggtc taaggcgctg gatttaggct ccagtcattt cgatggcgtg 60
ggttcgaatc ccaccgctgc ca 82

<210> SEQ ID NO 153
<211> LENGTH: 73
<212> TYPE: DNA
<213> ORGANISM: Homo sapiens

<400> SEQUENCE: 153
gcccggctag ctcagtcggt agagcatggg actcttaatc ccagggtcgt gggttcgagc 60
cccacgttgg gcg 73

<210> SEQ ID NO 154
<211> LENGTH: 73
<212> TYPE: DNA
<213> ORGANISM: Homo sapiens

<400> SEQUENCE: 154
gcccagctag ctcagtcggt agagcataag actcttaatc tcagggttgt ggattcgtgc 60
cccatgctgg gtg 73

<210> SEQ ID NO 155
<211> LENGTH: 74
<212> TYPE: DNA
<213> ORGANISM: Homo sapiens

<400> SEQUENCE: 155
gcagctagct cagtcggtag agcatgagac tcttaatctc agggtcatgg gttcgtgccc 60
catgttgggt gcca 74

<210> SEQ ID NO 156
<211> LENGTH: 73
<212> TYPE: DNA
<213> ORGANISM: Homo sapiens

<400> SEQUENCE: 156
gcccggctag ctcagtcggt agagcatgag actcttaatc tcagggtcgt gggttcgagc 60
cccacgttgg gcg 73

<210> SEQ ID NO 157
<211> LENGTH: 73
<212> TYPE: DNA
<213> ORGANISM: Homo sapiens

<400> SEQUENCE: 157
gcccggctag ctcagtcggt agagcatgag acccttaatc tcagggtcgt gggttcgagc 60
cccacgttgg gcg 73

<210> SEQ ID NO 158
<211> LENGTH: 73
<212> TYPE: DNA
<213> ORGANISM: Homo sapiens

<400> SEQUENCE: 158
gcccggctag ctcagtcggt agagcatggg actcttaatc tcagggtcgt gggttcgagc 60
cccacgttgg gcg 73

<210> SEQ ID NO 159
<211> LENGTH: 73
<212> TYPE: DNA
<213> ORGANISM: Homo sapiens

<400> SEQUENCE: 159
gcccggctag ctcagtcgat agagcatgag actcttaatc tcagggtcgt gggttcgagc 60
cgcacgttgg gcg 73

<210> SEQ ID NO 160
<211> LENGTH: 73
<212> TYPE: DNA
<213> ORGANISM: Homo sapiens

<400> SEQUENCE: 160
gcccagctag ctcagtcggt agagcatgag actcttaatc tcagggtcat gggtttgagc 60
cccacgtttg gtg 73

<210> SEQ ID NO 161
<211> LENGTH: 73
<212> TYPE: DNA
<213> ORGANISM: Homo sapiens

<400> SEQUENCE: 161
gcctggctag ctcagtcggc aaagcatgag actcttaatc tcagggtcgt gggctcgagc 60
tccatgttgg gcg 73

-continued

<210> SEQ ID NO 162
<211> LENGTH: 73
<212> TYPE: DNA
<213> ORGANISM: Homo sapiens

<400> SEQUENCE: 162
gcccgactac ctcagtcggt ggagcatggg actcttcatc ccagggttgt gggttcgagc 60
cccacattgg gca 73

<210> SEQ ID NO 163
<211> LENGTH: 73
<212> TYPE: DNA
<213> ORGANISM: Homo sapiens

<400> SEQUENCE: 163
gcctggatag ctcagttggt agagcatcag acttttaatc tgagggtcca gggttcaagt 60
ccctgttcag gca 73

<210> SEQ ID NO 164
<211> LENGTH: 73
<212> TYPE: DNA
<213> ORGANISM: Homo sapiens

<400> SEQUENCE: 164
acccagatag ctcagtcagt agagcatcag acttttaatc tgagggtcca aggttcatgt 60 cccttttttgg gtg 73

<210> SEQ ID NO 165
<211> LENGTH: 73
<212> TYPE: DNA
<213> ORGANISM: Homo sapiens

<400> SEQUENCE: 165
gcctggatag ctcagttggt agagcatcag acttttaatc tgagggtcca gggttcaagt 60
ccctgttcag gcg 73

<210> SEQ ID NO 166
<211> LENGTH: 73
<212> TYPE: DNA
<213> ORGANISM: Homo sapiens

<400> SEQUENCE: 166
gcccggatag ctcagtcggt agagcatcag acttttaatc tgagggtcca gggttcaagt 60
ccctgttcgg gcg 73

<210> SEQ ID NO 167
<211> LENGTH: 73
<212> TYPE: DNA
<213> ORGANISM: Homo sapiens

<400> SEQUENCE: 167
gcctggatag ctcagtcggt agagcatcag acttttaatc tgagggtcca gggttcaagt 60
ccctgttcag gcg 73

<210> SEQ ID NO 168
<211> LENGTH: 73
<212> TYPE: DNA
<213> ORGANISM: Homo sapiens

<400> SEQUENCE: 168
gcccggatag ctcagtcggt agagcatcag acttttaatc tgagggtccg gggttcaagt 60
ccctgttcgg gcg 73

<210> SEQ ID NO 169
<211> LENGTH: 73
<212> TYPE: DNA
<213> ORGANISM: Homo sapiens

<400> SEQUENCE: 169
gcctgggtag ctcagtcggt agagcatcag acttttaatc tgagggtcca gggttcaagt 60
ccctgtccag gcg 73

<210> SEQ ID NO 170
<211> LENGTH: 73
<212> TYPE: DNA
<213> ORGANISM: Homo sapiens

<400> SEQUENCE: 170
gcctggatag ctcagttggt agaacatcag acttttaatc tgacggtgca gggttcaagt 60
ccctgttcag gcg 73

<210> SEQ ID NO 171
<211> LENGTH: 73
<212> TYPE: DNA
<213> ORGANISM: Homo sapiens

<400> SEQUENCE: 171
gcctcgttag cgcagtaggt agcgcgtcag tctcataatc tgaaggtcgt gagttcgatc 60
ctcacacggg gca 73

<210> SEQ ID NO 172
<211> LENGTH: 73
<212> TYPE: DNA
<213> ORGANISM: Homo sapiens

<400> SEQUENCE: 172
gccctcttag cgcagtgggc agcgcgtcag tctcataatc tgaaggtcct gagttcgagc 60
ctcagagagg gca 73

<210> SEQ ID NO 173
<211> LENGTH: 73
<212> TYPE: DNA
<213> ORGANISM: Homo sapiens

<400> SEQUENCE: 173
gcctccttag cgcagtaggc agcgcgtcag tctcataatc tgaaggtcct gagttcgaac 60
ctcagagggg gca 73

<210> SEQ ID NO 174
<211> LENGTH: 73
<212> TYPE: DNA
<213> ORGANISM: Homo sapiens

<400> SEQUENCE: 174
gccctcttag cgcagcgggc agcgcgtcag tctcataatc tgaaggtcct gagttcgagc 60
ctcagagagg gca 73

<210> SEQ ID NO 175

<211> LENGTH: 73
<212> TYPE: DNA
<213> ORGANISM: Homo sapiens

<400> SEQUENCE: 175
gccctcttag cgcagctggc agcgcgtcag tctcataatc tgaaggtcct gagttcaagc 60
ctcagagagg gca 73

<210> SEQ ID NO 176
<211> LENGTH: 73
<212> TYPE: DNA
<213> ORGANISM: Homo sapiens

<400> SEQUENCE: 176
gcctcgttag cgcagtaggc agcgcgtcag tctcataatc tgaaggtcgt gagttcgagc 60
ctcacacggg gca 73

<210> SEQ ID NO 177
<211> LENGTH: 73
<212> TYPE: DNA
<213> ORGANISM: Homo sapiens

<400> SEQUENCE: 177
gccctcttag tgcagctggc agcgcgtcag tttcataatc tgaaagtcct gagttcaagc 60
ctcagagagg gca 73

<210> SEQ ID NO 178
<211> LENGTH: 73
<212> TYPE: DNA
<213> ORGANISM: Homo sapiens

<400> SEQUENCE: 178
gccgaaatag ctcagttggg agagcgttag actgaagatc taaaggtccc tggttcgatc 60
ccgggtttcg gca 73

<210> SEQ ID NO 179
<211> LENGTH: 73
<212> TYPE: DNA
<213> ORGANISM: Homo sapiens

<400> SEQUENCE: 179
gccgaaatag ctcagttggg agagcgttag actgaagatc taaaggtccc tggttcaatc 60
ccgggtttcg gca 73

<210> SEQ ID NO 180
<211> LENGTH: 73
<212> TYPE: DNA
<213> ORGANISM: Homo sapiens

<400> SEQUENCE: 180
gccgagatag ctcagttggg agagcgttag actgaagatc taaaggtccc tggttcaatc 60
ccgggtttcg gca 73

<210> SEQ ID NO 181
<211> LENGTH: 74
<212> TYPE: DNA
<213> ORGANISM: Homo sapiens

<400> SEQUENCE: 181
gccgaaatag ctcagttggg agagcgttag accgaagatc ttaaaggtcc ctggttcaat 60
cccgggtttc ggca 74

<210> SEQ ID NO 182
<211> LENGTH: 74
<212> TYPE: DNA
<213> ORGANISM: Homo sapiens

<400> SEQUENCE: 182
gctgaaatag ctcagttggg agagcgttag actgaagatc ttaaagttcc ctggttcaac 60
cctgggtttc agcc 74

<210> SEQ ID NO 183
<211> LENGTH: 72
<212> TYPE: DNA
<213> ORGANISM: Homo sapiens

<400> SEQUENCE: 183
ggctcgttgg tctaggggta tgattctcgc ttaggatgcg agaggtcccg ggttcaaatc 60
ccggacgagc cc 72

<210> SEQ ID NO 184
<211> LENGTH: 72
<212> TYPE: DNA
<213> ORGANISM: Homo sapiens

<400> SEQUENCE: 184
ggctcgttgg tctaggggta tgattctcgc ttagggtgcg agaggtcccg ggttcaaatc 60
ccggacgagc cc 72

<210> SEQ ID NO 185
<211> LENGTH: 72
<212> TYPE: DNA
<213> ORGANISM: Homo sapiens

<400> SEQUENCE: 185
ggctcgttgg tctaggggta tgattctcgc ttcgggtgcg agaggtcccg ggttcaaatc 60
ccggacgagc cc 72

<210> SEQ ID NO 186
<211> LENGTH: 72
<212> TYPE: DNA
<213> ORGANISM: Homo sapiens

<400> SEQUENCE: 186
ggctcgttgg tctaggggta tgattctcgc ttcgggtgtg agaggtcccg ggttcaaatc 60
ccggacgagc cc 72

<210> SEQ ID NO 187
<211> LENGTH: 72
<212> TYPE: DNA
<213> ORGANISM: Homo sapiens

<400> SEQUENCE: 187
ggctcgttgg tctagtggta tgattctcgc tttgggtgcg agaggtcccg ggttcaaatc 60
ccggacgagc cc 72

<210> SEQ ID NO 188
<211> LENGTH: 72
<212> TYPE: DNA

<213> ORGANISM: Homo sapiens

<400> SEQUENCE: 188
ggctcgttgg tctaggggta tgattctcgg tttgggtccg agaggtcccg ggttcaaatc 60
ccggacgagc cc 72

<210> SEQ ID NO 189
<211> LENGTH: 72
<212> TYPE: DNA
<213> ORGANISM: Homo sapiens

<400> SEQUENCE: 189
ggctcgttgg tctaggggta tgattctcgc tttgggtgcg agaggtcccg ggttcaaatc 60
ccggacgagc cc 72

<210> SEQ ID NO 190
<211> LENGTH: 87
<212> TYPE: DNA
<213> ORGANISM: Homo sapiens

<400> SEQUENCE: 190
gcccggatga tcctcagtgg tctggggtgc aggcttcaaa cctgtagctg tctagcgaca 60
gagtggttca attccacctt tcgggcg 87

<210> SEQ ID NO 191
<211> LENGTH: 84
<212> TYPE: DNA
<213> ORGANISM: Homo sapiens

<400> SEQUENCE: 191
gctcggatga tcctcagtgg tctggggtgc aggcttcaaa cctgtagctg tctagtgaca 60
gagtggttca attccacctt tgta 84

<210> SEQ ID NO 192
<211> LENGTH: 82
<212> TYPE: DNA
<213> ORGANISM: Homo sapiens

<400> SEQUENCE: 192
gtagtcgtgg ccgagtggtt aaggcgatgg actagaaatc cattggggtt tccccgcgca 60
ggttcgaatc ctgccgacta cg 82

<210> SEQ ID NO 193
<211> LENGTH: 82
<212> TYPE: DNA
<213> ORGANISM: Homo sapiens

<400> SEQUENCE: 193
gtagtcgtgg ccgagtggtt aaggcgatgg actagaaatc cattggggtc tccccgcgca 60
ggttcgaatc ctgccgacta cg 82

<210> SEQ ID NO 194
<211> LENGTH: 82
<212> TYPE: DNA
<213> ORGANISM: Homo sapiens

<400> SEQUENCE: 194
gtagtcgtgg ccgagtggtt aaggcgatgg actagaaatc cattggggtt tccccacgca 60
ggttcgaatc ctgccgacta cg 82

<210> SEQ ID NO 195
<211> LENGTH: 82
<212> TYPE: DNA
<213> ORGANISM: Homo sapiens

<400> SEQUENCE: 195
gtagtcgtgg ccgagtggtt aaggtgatgg actagaaacc cattggggtc tccccgcgca 60
ggttcgaatc ctgccgacta cg 82

<210> SEQ ID NO 196
<211> LENGTH: 82
<212> TYPE: DNA
<213> ORGANISM: Homo sapiens

<400> SEQUENCE: 196
gctgtgatgg ccgagtggtt aaggcgttgg actcgaaatc caatggggtc tccccgcgca 60
ggttcgaatc ctgctcacag cg 82

<210> SEQ ID NO 197
<211> LENGTH: 82
<212> TYPE: DNA
<213> ORGANISM: Homo sapiens

<400> SEQUENCE: 197
gctgtgatgg ccgagtggtt aaggcgttgg actcgaaatc caatggggtc tccccgcgca 60
ggttcaaatc ctgctcacag cg 82

<210> SEQ ID NO 198
<211> LENGTH: 82
<212> TYPE: DNA
<213> ORGANISM: Homo sapiens

<400> SEQUENCE: 198
gctgtgatgg ccgagtggtt aaggtgttgg actcgaaatc caatgggggt tccccgcgca 60
ggttcaaatc ctgctcacag cg 82

<210> SEQ ID NO 199
<211> LENGTH: 82
<212> TYPE: DNA
<213> ORGANISM: Homo sapiens

<400> SEQUENCE: 199
gtcacggtgg ccgagtggtt aaggcgttgg actcgaaatc caatggggtt tccccgcaca 60
ggttcgaatc ctgttcgtga cg 82

<210> SEQ ID NO 200
<211> LENGTH: 82
<212> TYPE: DNA
<213> ORGANISM: Homo sapiens

<400> SEQUENCE: 200
gacgaggtgg ccgagtggtt aaggcgatgg actgctaatc cattgtgctc tgcacgcgtg 60
ggttcgaatc ccaccctcgt cg 82

<210> SEQ ID NO 201
<211> LENGTH: 82
<212> TYPE: DNA
<213> ORGANISM: Homo sapiens

<400> SEQUENCE: 201
gacgaggtgg ccgagtggtt aaggcgatgg actgctaatc cattgtgctc tgcacgcgtg 60
ggttcgaatc ccaccttcgt cg 82

<210> SEQ ID NO 202
<211> LENGTH: 82
<212> TYPE: DNA
<213> ORGANISM: Homo sapiens

<400> SEQUENCE: 202
gacgaggtgg ccgagtggtt aaggcgatgg actgctaatc cattgtgctt tgcacgcgtg 60
ggttcgaatc ccatcctcgt cg 82

<210> SEQ ID NO 203
<211> LENGTH: 82
<212> TYPE: DNA
<213> ORGANISM: Homo sapiens

<400> SEQUENCE: 203
gacgaggtgg ccgagtggtt aaggcgatgg actgctaatc cattgtgctc tgcacgcgtg 60
ggttcgaatc ccatcctcgt cg 82

<210> SEQ ID NO 204
<211> LENGTH: 82
<212> TYPE: DNA
<213> ORGANISM: Homo sapiens

<400> SEQUENCE: 204
gacgaggtgg ccgagtggtt aaggcgatgg actgctaatc cattgtgctc tgcacacgtg 60
ggttcgaatc ccatcctcgt cg 82

<210> SEQ ID NO 205
<211> LENGTH: 84
<212> TYPE: DNA
<213> ORGANISM: Homo sapiens

<400> SEQUENCE: 205
ggagaggcct ggccgagtgg ttaaggcgat ggactgctaa tccattgtgc tctgcacgcg 60
tgggttcgaa tcccatcctc gtcg 84

<210> SEQ ID NO 206
<211> LENGTH: 82
<212> TYPE: DNA
<213> ORGANISM: Homo sapiens

<400> SEQUENCE: 206
gcagcgatgg ccgagtggtt aaggcgttgg acttgaaatc caatggggtc tccccgcgca 60
ggttcgaacc ctgctcgctg cg 82

<210> SEQ ID NO 207
<211> LENGTH: 82
<212> TYPE: DNA
<213> ORGANISM: Homo sapiens

<400> SEQUENCE: 207
gtagtcgtgg ccgagtggtt aaggcgatgg acttgaaatc cattggggtt tccccgcgca 60
ggttcgaatc ctgccgacta cg 82

<210> SEQ ID NO 208
<211> LENGTH: 82
<212> TYPE: DNA
<213> ORGANISM: Homo sapiens

<400> SEQUENCE: 208
gtagtcgtgg ccgagtggtt aaggcgatgg acttgaaatc cattggggtc tccccgcgca 60
ggttcgaatc ctgccgacta cg 82

<210> SEQ ID NO 209
<211> LENGTH: 82
<212> TYPE: DNA
<213> ORGANISM: Homo sapiens

<400> SEQUENCE: 209
gtagtcgtgg ccgagtggtt aaggcgatgg acttgaaatc cattggggtt tccccgcgca 60
ggttcgaatc ctgtcggcta cg 82

<210> SEQ ID NO 210
<211> LENGTH: 74
<212> TYPE: DNA
<213> ORGANISM: Homo sapiens

<400> SEQUENCE: 210
ggcgccgtgg cttagttggt taaagcgcct gtctagtaaa caggagatcc tgggttcgaa 60
tcccagcggt gcct 74

<210> SEQ ID NO 211
<211> LENGTH: 74
<212> TYPE: DNA
<213> ORGANISM: Homo sapiens

<400> SEQUENCE: 211
ggctccgtgg cttagctggt taaagcgcct gtctagtaaa caggagatcc tgggttcgaa 60
tcccagcggg gcct 74

<210> SEQ ID NO 212
<211> LENGTH: 74
<212> TYPE: DNA
<213> ORGANISM: Homo sapiens

<400> SEQUENCE: 212
ggctccgtag cttagttggt taaagcgcct gtctagtaaa caggagatcc tgggttcgac 60
tcccagcggg gcct 74

<210> SEQ ID NO 213
<211> LENGTH: 74
<212> TYPE: DNA
<213> ORGANISM: Homo sapiens

<400> SEQUENCE: 213
ggcttcgtgg cttagctggt taaagcgcct gtctagtaaa caggagatcc tgggttcgaa 60
tcccagcgag gcct 74

<210> SEQ ID NO 214
<211> LENGTH: 74
<212> TYPE: DNA
<213> ORGANISM: Homo sapiens

<400> SEQUENCE: 214

-continued ggcgccgtgg cttagctggt taaagcgcct gtctagtaaa caggagatcc tgggttcgaa 60
tcccagcggt gcct 74

<210> SEQ ID NO 215
<211> LENGTH: 74
<212> TYPE: DNA
<213> ORGANISM: Homo sapiens

<400> SEQUENCE: 215
ggccctgtgg cttagctggt caaagcgcct gtctagtaaa caggagatcc tgggttcgaa 60
tcccagcggg gcct 74

<210> SEQ ID NO 216
<211> LENGTH: 74
<212> TYPE: DNA
<213> ORGANISM: Homo sapiens

<400> SEQUENCE: 216
ggctctatgg cttagttggt taaagcgcct gtctcgtaaa caggagatcc tgggttcgac 60
tcccagtggg gcct 74

<210> SEQ ID NO 217
<211> LENGTH: 72
<212> TYPE: DNA
<213> ORGANISM: Homo sapiens

<400> SEQUENCE: 217
ggcgcggtgg ccaagtggta aggcgtcggt ctcgtaaacc gaagatcacg ggttcgaacc 60
ccgtccgtgc ct 72

<210> SEQ ID NO 218
<211> LENGTH: 74
<212> TYPE: DNA
<213> ORGANISM: Homo sapiens

<400> SEQUENCE: 218
ggctctgtgg cttagttggc taaagcgcct gtctcgtaaa caggagatcc tgggttcgaa 60
tcccagcggg gcct 74

<210> SEQ ID NO 219
<211> LENGTH: 72
<212> TYPE: DNA
<213> ORGANISM: Homo sapiens

<400> SEQUENCE: 219
ggcgcggtgg ccaagtggta aggcgtcggt ctcgtaaacc gaagatcgcg ggttcgaacc 60
ccgtccgtgc ct 72

<210> SEQ ID NO 220
<211> LENGTH: 74
<212> TYPE: DNA
<213> ORGANISM: Homo sapiens

<400> SEQUENCE: 220
ggccctgtag ctcagcggtt ggagcgctgg tctcgtaaac ctaggggtcg tgagttcaaa 60
tctcaccagg gcct 74

<210> SEQ ID NO 221
<211> LENGTH: 74

<212> TYPE: DNA
<213> ORGANISM: Homo sapiens

<400> SEQUENCE: 221
ggctctatgg cttagttggt taaagcgcct gtcttgtaaa caggagatcc tgggttcgaa 60
tcccagtaga gcct 74

<210> SEQ ID NO 222
<211> LENGTH: 73
<212> TYPE: DNA
<213> ORGANISM: Homo sapiens

<400> SEQUENCE: 222
ggctccatag ctcagtggtt agagcactgg tcttgtaaac caggggtcgc gagttcgatc 60
ctcgctgggg cct 73

<210> SEQ ID NO 223
<211> LENGTH: 73
<212> TYPE: DNA
<213> ORGANISM: Homo sapiens

<400> SEQUENCE: 223
ggctccatag ctcaggggtt agagcgctgg tcttgtaaac caggggtcgc gagttcaatt 60
ctcgctgggg cct 73

<210> SEQ ID NO 224
<211> LENGTH: 73
<212> TYPE: DNA
<213> ORGANISM: Homo sapiens

<400> SEQUENCE: 224
ggctccatag ctcaggggtt agagcactgg tcttgtaaac caggggtcgc gagttcaaat 60
ctcgctgggg cct 73

<210> SEQ ID NO 225
<211> LENGTH: 73
<212> TYPE: DNA
<213> ORGANISM: Homo sapiens

<400> SEQUENCE: 225
ggccctatag ctcaggggtt agagcactgg tcttgtaaac caggggtcgc gagttcaaat 60
ctcgctgggg cct 73

<210> SEQ ID NO 226
<211> LENGTH: 72
<212> TYPE: DNA
<213> ORGANISM: Homo sapiens

<400> SEQUENCE: 226
ggctccatag ctcaggggtt agagcactgg tcttgtaaac cagggtcgcg agttcaaatc 60
tcgctggggc ct 72

<210> SEQ ID NO 227
<211> LENGTH: 72
<212> TYPE: DNA
<213> ORGANISM: Homo sapiens

<400> SEQUENCE: 227
ggcctcgtgg cgcaacggta gcgcgtctga ctccagatca gaaggttgcg tgttcaaatc 60
acgtcggggt ca 72

<210> SEQ ID NO 228
<211> LENGTH: 72
<212> TYPE: DNA
<213> ORGANISM: Homo sapiens

<400> SEQUENCE: 228
gacctcgtgg cgcaatggta gcgcgtctga ctccagatca gaaggttgcg tgttcaagtc 60
acgtcggggt ca 72

<210> SEQ ID NO 229
<211> LENGTH: 72
<212> TYPE: DNA
<213> ORGANISM: Homo sapiens

<400> SEQUENCE: 229
gacctcgtgg cgcaacggta gcgcgtctga ctccagatca gaaggttgcg tgttcaaatc 60
acgtcggggt ca 72

<210> SEQ ID NO 230
<211> LENGTH: 72
<212> TYPE: DNA
<213> ORGANISM: Homo sapiens

<400> SEQUENCE: 230
gacctcgtgg cgcaacggta gcgcgtctga ctccagatca gaaggctgcg tgttcgaatc 60
acgtcggggt ca 72

<210> SEQ ID NO 231
<211> LENGTH: 72
<212> TYPE: DNA
<213> ORGANISM: Homo sapiens

<400> SEQUENCE: 231
gacctcgtgg cgcaacggca gcgcgtctga ctccagatca gaaggttgcg tgttcaaatc 60
acgtcggggt ca 72

<210> SEQ ID NO 232
<211> LENGTH: 93
<212> TYPE: DNA
<213> ORGANISM: Homo sapiens

<400> SEQUENCE: 232
ccttcaatag ttcagctggt agagcagagg actatagcta cttcctcagt aggagacgtc 60
cttaggttgc tggttcgatt ccagcttgaa gga 93

<210> SEQ ID NO 233
<211> LENGTH: 91
<212> TYPE: DNA
<213> ORGANISM: Homo sapiens

<400> SEQUENCE: 233
ccttcgatag ctcagttggt agagcggagg actgtagttg gctgtgtcct tagacatcct 60
taggtcgctg gttcgaatcc ggctcgaagg a 91

<210> SEQ ID NO 234
<211> LENGTH: 89
<212> TYPE: DNA
<213> ORGANISM: Homo sapiens

<400> SEQUENCE: 234
ccttcgatag ctcagttggt agagcggagg actgtagtgg atagggcgtg gcaatcctta 60
ggtcgctggt tcgattccgg ctcgaagga 89

<210> SEQ ID NO 235
<211> LENGTH: 89
<212> TYPE: DNA
<213> ORGANISM: Homo sapiens

<400> SEQUENCE: 235
ccttcgatag ctcagttggt agagcggagg actgtaggct cattaagcaa ggtatcctta 60
ggtcgctggt tcgaatccgg ctcggagga 89

<210> SEQ ID NO 236
<211> LENGTH: 94
<212> TYPE: DNA
<213> ORGANISM: Homo sapiens

<400> SEQUENCE: 236
ccttcgatag ctcagctggt agagcggagg actgtagatt gtatagacat ttgcggacat 60
ccttaggtcg ctggttcgat tccagctcga agga 94

<210> SEQ ID NO 237
<211> LENGTH: 93
<212> TYPE: DNA
<213> ORGANISM: Homo sapiens

<400> SEQUENCE: 237
ccttcgatag ctcagctggt agagcggagg actgtagcta cttcctcagc aggagacatc 60
cttaggtcgc tggttcgatt ccggctcgaa gga 93

<210> SEQ ID NO 238
<211> LENGTH: 89
<212> TYPE: DNA
<213> ORGANISM: Homo sapiens

<400> SEQUENCE: 238
ccttcgatag ctcagctggt agagcggagg actgtaggcg cgcgcccgtg gccatcctta 60
ggtcgctggt tcgattccgg ctcgaagga 89

<210> SEQ ID NO 239
<211> LENGTH: 94
<212> TYPE: DNA
<213> ORGANISM: Homo sapiens

<400> SEQUENCE: 239
ccttcgatag ctcagctggt agagcggagg actgtagcct gtagaaacat ttgtggacat 60
ccttaggtcg ctggttcgat tccggctcga agga 94

<210> SEQ ID NO 240
<211> LENGTH: 94
<212> TYPE: DNA
<213> ORGANISM: Homo sapiens

<400> SEQUENCE: 240
ccttcgatag ctcagctggt agagcggagg actgtagatt gtacagacat ttgcggacat 60
ccttaggtcg ctggttcgat tccggctcga agga 94

<210> SEQ ID NO 241
<211> LENGTH: 89
<212> TYPE: DNA
<213> ORGANISM: Homo sapiens

<400> SEQUENCE: 241
ccttcgatag ctcagctggt agagcggagg actgtagtac ttaatgtgtg gtcatcctta 60
ggtcgctggt tcgattccgg ctcgaagga 89

<210> SEQ ID NO 242
<211> LENGTH: 89
<212> TYPE: DNA
<213> ORGANISM: Homo sapiens

<400> SEQUENCE: 242
ccttcgatag ctcagctggt agagcggagg actgtagggg tttgaatgtg gtcatcctta 60
ggtcgctggt tcgaatccgg ctcggagga 89

<210> SEQ ID NO 243
<211> LENGTH: 94
<212> TYPE: DNA
<213> ORGANISM: Homo sapiens

<400> SEQUENCE: 243
ccttcgatag ctcagctggt agagcggagg actgtagact gcggaaacgt ttgtggacat 60
ccttaggtcg ctggttcaat tccggctcga agga 94

<210> SEQ ID NO 244
<211> LENGTH: 90
<212> TYPE: DNA
<213> ORGANISM: Homo sapiens

<400> SEQUENCE: 244
ctttcgatag ctcagttggt agagcggagg actgtaggtt cattaaacta aggcatcctt 60
aggtcgctgg ttcgaatccg gctcgaagga 90

<210> SEQ ID NO 245
<211> LENGTH: 88
<212> TYPE: DNA
<213> ORGANISM: Homo sapiens

<400> SEQUENCE: 245
tcttcaatag ctcagctggt agagcggagg actgtaggtg cacgcccgtg gccattctta 60
ggtgctggtt tgattccgac ttggagag 88

<210> SEQ ID NO 246
<211> LENGTH: 73
<212> TYPE: DNA
<213> ORGANISM: Homo sapiens

<400> SEQUENCE: 246
gtttccgtag tgtagtggtt atcacgttcg cctaacacgc gaaaggtccc cggttcgaaa 60
ccgggcggaa aca 73

<210> SEQ ID NO 247
<211> LENGTH: 73
<212> TYPE: DNA
<213> ORGANISM: Homo sapiens

<400> SEQUENCE: 247
gtttccgtag tgtagtggtc atcacgttcg cctaacacgc gaaaggtccc cggttcgaaa 60
ccgggcggaa aca 73

<210> SEQ ID NO 248
<211> LENGTH: 73
<212> TYPE: DNA
<213> ORGANISM: Homo sapiens

<400> SEQUENCE: 248
gtttccgtag tgtagtggtt atcacgttcg cctaacacgc gaaaggtccc tggatcaaaa 60
ccaggcggaa aca 73

<210> SEQ ID NO 249
<211> LENGTH: 73
<212> TYPE: DNA
<213> ORGANISM: Homo sapiens

<400> SEQUENCE: 249
gtttccgtag tgtagtggtt atcacgttcg cctaacacgc gaaaggtccg cggttcgaaa 60
ccgggcggaa aca 73

<210> SEQ ID NO 250
<211> LENGTH: 73
<212> TYPE: DNA
<213> ORGANISM: Homo sapiens

<400> SEQUENCE: 250
gtttccgtag tgtagtggtt atcacgtttg cctaacacgc gaaaggtccc cggttcgaaa 60
ccgggcagaa aca 73

<210> SEQ ID NO 251
<211> LENGTH: 72
<212> TYPE: DNA
<213> ORGANISM: Homo sapiens

<400> SEQUENCE: 251
gggggtgtag ctcagtggta gagcgtatgc ttaacattca tgaggctctg ggttcgatcc 60
ccagcacttc ca 72

<210> SEQ ID NO 252
<211> LENGTH: 73
<212> TYPE: DNA
<213> ORGANISM: Homo sapiens

<400> SEQUENCE: 252
gtttccgtag tgtagtggtt atcacgttcg cctcacacgc gaaaggtccc cggttcgaaa 60
ccgggcggaa aca 73

<210> SEQ ID NO 253
<211> LENGTH: 73
<212> TYPE: DNA
<213> ORGANISM: Homo sapiens

<400> SEQUENCE: 253
gcttctgtag tgtagtggtt atcacgttcg cctcacacgc gaaaggtccc cggttcgaaa 60
ccgggcagaa gca 73

<210> SEQ ID NO 254

<211> LENGTH: 73
<212> TYPE: DNA
<213> ORGANISM: Homo sapiens

<400> SEQUENCE: 254
gtttccgtag tgtagcggtt atcacattcg cctcacacgc gaaaggtccc cggttcgatc 60
ccgggcggaa aca 73

<210> SEQ ID NO 255
<211> LENGTH: 73
<212> TYPE: DNA
<213> ORGANISM: Homo sapiens

<400> SEQUENCE: 255
gtttccgtag tgtagtggtt atcacgttcg cctcacacgc gaaaggtccc cggttcgaaa 60
ctgggcggaa aca 73

<210> SEQ ID NO 256
<211> LENGTH: 74
<212> TYPE: DNA
<213> ORGANISM: Homo sapiens

<400> SEQUENCE: 256
gtttccgtag tgtagtggtt atcacgttcg cctcacacgc gtaaaggtcc ccggttcgaa 60
accgggcgga aaca 74

<210> SEQ ID NO 257
<211> LENGTH: 73
<212> TYPE: DNA
<213> ORGANISM: Homo sapiens

<400> SEQUENCE: 257
gtttccgtag tggagtggtt atcacgttcg cctcacacgc gaaaggtccc cggtttgaaa 60
ccaggcggaa aca 73

<210> SEQ ID NO 258
<211> LENGTH: 73
<212> TYPE: DNA
<213> ORGANISM: Homo sapiens

<400> SEQUENCE: 258
ggttccatag tgtagtggtt atcacgtctg ctttacacgc agaaggtcct gggttcgagc 60
cccagtggaa cca 73

<210> SEQ ID NO 259
<211> LENGTH: 73
<212> TYPE: DNA
<213> ORGANISM: Homo sapiens

<400> SEQUENCE: 259
ggttccatag tgtagcggtt atcacgtctg ctttacacgc agaaggtcct gggttcgagc 60
cccagtggaa cca 73

<210> SEQ ID NO 260
<211> LENGTH: 73
<212> TYPE: DNA
<213> ORGANISM: Homo sapiens

<400> SEQUENCE: 260
ggttccatag tgtagtggtt atcacatctg ctttacacgc agaaggtcct gggttcaagc 60
cccagtggaa cca 73

<210> SEQ ID NO 261
<211> LENGTH: 73
<212> TYPE: DNA
<213> ORGANISM: Homo sapiens

<400> SEQUENCE: 261
gtttccgtgg tgtagtggtt atcacattcg ccttacacgc gaaaggtcct cgggtcgaaa 60
ccgagcggaa aca 73

<210> SEQ ID NO 262
<211> LENGTH: 72
<212> TYPE: DNA
<213> ORGANISM: Homo sapiens

<400> SEQUENCE: 262
agcagagtgg cgcagcggaa gcgtgctggg cccataaccc agaggtcgat ggatcgaaac 60
catcctctgc ta 72

<210> SEQ ID NO 263
<211> LENGTH: 72
<212> TYPE: DNA
<213> ORGANISM: Homo sapiens

<400> SEQUENCE: 263
agcagagtgg cgcagcggaa gcgtgctggg cccataaccc agaggtcgat ggatctaaac 60
catcctctgc ta 72

<210> SEQ ID NO 264
<211> LENGTH: 73
<212> TYPE: DNA
<213> ORGANISM: Homo sapiens

<400> SEQUENCE: 264
tccctggtgg tctagtggct aggattcggc gctttcaccg ccgcggcccg ggttcgattc 60
ccggtcaggg aat 73

<210> SEQ ID NO 265
<211> LENGTH: 72
<212> TYPE: DNA
<213> ORGANISM: Homo sapiens

<400> SEQUENCE: 265
gcgttggtgg tttagtggta gaattctcgc ctcccatgcg ggagacccgg gttcaattcc 60
cggccactgc ac 72

<210> SEQ ID NO 266
<211> LENGTH: 72
<212> TYPE: DNA
<213> ORGANISM: Homo sapiens

<400> SEQUENCE: 266
ggccttggtg gtgcagtggt agaattctcg cctcccacgt gggagacccg ggttcaattc 60
ccggccaatg ca 72

<210> SEQ ID NO 267
<211> LENGTH: 73
<212> TYPE: DNA

<213> ORGANISM: Homo sapiens

<400> SEQUENCE: 267
gtccctggtg gtctagtggc taggattcgg cgctttcacc gccgcggccc gggttcgatt 60
cccggccagg gaa 73

<210> SEQ ID NO 268
<211> LENGTH: 75
<212> TYPE: DNA
<213> ORGANISM: Homo sapiens

<400> SEQUENCE: 268
tgtctctgtg gcgcaatcgg ttagcgcgtt cggctgttaa ccgaaagatt ggtggttcga 60
gcccacccag ggacg 75

<210> SEQ ID NO 269
<211> LENGTH: 86
<212> TYPE: DNA
<213> ORGANISM: Homo sapiens

<400> SEQUENCE: 269
tggctccgtg gcgcaatgga tagcgcattg gacttctaga ggctgaaggc attcaaaggt 60
tccgggttcg agtcccggcg gagtcg 86

<210> SEQ ID NO 270
<211> LENGTH: 74
<212> TYPE: DNA
<213> ORGANISM: Homo sapiens

<400> SEQUENCE: 270
gcccggctag ctcagtcggt agagcatgag actcttaatc tcagggtcgt gggttcgagc 60
cccacgttgg gcgc 74

<210> SEQ ID NO 271
<211> LENGTH: 73
<212> TYPE: DNA
<213> ORGANISM: Homo sapiens

<400> SEQUENCE: 271
gccgtgatcg tatagtggtt agtactctgc gttgtggccg cagcaacctc ggttcgaatc 60
cgagtcacgg cag 73

<210> SEQ ID NO 272
<211> LENGTH: 73
<212> TYPE: DNA
<213> ORGANISM: Homo sapiens

<400> SEQUENCE: 272
gcgttggtgg tatagtggtg agcatagctg ccttccaagc agttgacccg ggttcgattc 60
ccggccaacg cag 73

<210> SEQ ID NO 273
<211> LENGTH: 73
<212> TYPE: DNA
<213> ORGANISM: Homo sapiens

<400> SEQUENCE: 273
tccctggtgg tctagtggtt aggattcggc gctctcaccg ccgcggcccg ggttcgattc 60
ccggtcaggg aaa 73

<210> SEQ ID NO 274
<211> LENGTH: 73
<212> TYPE: DNA
<213> ORGANISM: Homo sapiens

<400> SEQUENCE: 274
aggttccatg gtgtaatggt gagcactctg gactctgaat ccagcgatcc gagttcgagt 60
ctcggtggaa cct 73

<210> SEQ ID NO 275
<211> LENGTH: 75
<212> TYPE: DNA
<213> ORGANISM: Homo sapiens

<400> SEQUENCE: 275
tgtctctgtg gcgtagtcgg ttagcgcgtt cggctgttaa ccgaaaagtt ggtggttcga 60
gcccacccag gaacg 75

<210> SEQ ID NO 276
<211> LENGTH: 75
<212> TYPE: DNA
<213> ORGANISM: Homo sapiens

<400> SEQUENCE: 276
tgtctctgtg gcgcaatcgg ttagcgcgtt cggctgttaa ccgaaaggtt ggtggttcga 60
gcccacccag ggacg 75

<210> SEQ ID NO 277
<211> LENGTH: 75
<212> TYPE: DNA
<213> ORGANISM: Homo sapiens

<400> SEQUENCE: 277
gtctctgtgg cgcaatcggt tagcgcattc ggctgttaac cgaaaggttg gtggttcgag 60
cccacccagg gacgc 75

<210> SEQ ID NO 278
<211> LENGTH: 75
<212> TYPE: DNA
<213> ORGANISM: Homo sapiens

<400> SEQUENCE: 278
gtctctgtgg cgcaatgggt tagcgcgttc ggctgttaac cgaaaggttg gtggttcgag 60
cccatccagg gacgc 75

<210> SEQ ID NO 279
<211> LENGTH: 72
<212> TYPE: DNA
<213> ORGANISM: Homo sapiens

<400> SEQUENCE: 279
gcactggtgg ttcagtggta gaattctcgc ctcacacgcg ggacacccgg gttcaattcc 60
cggtcaaggc aa 72

<210> SEQ ID NO 280
<211> LENGTH: 74
<212> TYPE: DNA
<213> ORGANISM: Homo sapiens

<400> SEQUENCE: 280
gtttccgtag tgtagtggtt atcacgttcg cctcacacgc gaaaggtccc cggttcgaaa 60
ctgggcggaa acag 74

<210> SEQ ID NO 281
<211> LENGTH: 72
<212> TYPE: DNA
<213> ORGANISM: Homo sapiens

<400> SEQUENCE: 281
gcactggtgg ttcagtggta gaattctcgc ctcccacgcg ggagacccgg gtttaattcc 60
cggtcaagat aa 72

<210> SEQ ID NO 282
<211> LENGTH: 75
<212> TYPE: DNA
<213> ORGANISM: Homo sapiens

<400> SEQUENCE: 282
gtttccgtag tgtagtggtt atcacgttcg cctcacacgc gtaaaggtcc ccggttcgaa 60
accgggcgga aacat 75

<210> SEQ ID NO 283
<211> LENGTH: 73
<212> TYPE: DNA
<213> ORGANISM: Homo sapiens

<400> SEQUENCE: 283
tagcagagtg gcgcagcgga agcgtgctgg gcccataacc cagaggtcga tggatcgaaa 60
ccatcctctg cta 73

<210> SEQ ID NO 284
<211> LENGTH: 74
<212> TYPE: DNA
<213> ORGANISM: Homo sapiens

<400> SEQUENCE: 284
gtttccgtag tgtagtggtt atcacgttcg cctcacacgc gaaaggtccc cggttcgaaa 60
ccgggcggaa acaa 74

<210> SEQ ID NO 285
<211> LENGTH: 73
<212> TYPE: DNA
<213> ORGANISM: Homo sapiens

<400> SEQUENCE: 285
tcctcgttag tatagtggtg agtatccccg cctgtcacgc gggagaccgg ggttcgattc 60
cccgacgggg agg 73

<210> SEQ ID NO 286
<211> LENGTH: 72
<212> TYPE: DNA
<213> ORGANISM: Homo sapiens

<400> SEQUENCE: 286
tgcatgggtg gttcagtggt agaattctcg cctgccacgc gggaggcccg ggttcgattc 60
ccggcccatg ca 72

<210> SEQ ID NO 287
<211> LENGTH: 73
<212> TYPE: DNA
<213> ORGANISM: Homo sapiens

<400> SEQUENCE: 287
tccctggtgg tctagtggtt aggattcggc gctctcaccg ccgcggcccg ggttcgattc 60
ccggtcaggg aag 73

<210> SEQ ID NO 288
<211> LENGTH: 73
<212> TYPE: DNA
<213> ORGANISM: Homo sapiens

<400> SEQUENCE: 288
atccttgtta ctatagtggt gagtatctct gcctgtcatg cgtgagagag gggtcgatt 60 ccccgacggg gag 73

<210> SEQ ID NO 289
<211> LENGTH: 72
<212> TYPE: DNA
<213> ORGANISM: Homo sapiens

<400> SEQUENCE: 289
gcattggtgg ttcagtggta gaattctcgc ctgccacgcg ggaggcccgg gttcgattcc 60
cggccaatgc ac 72

<210> SEQ ID NO 290
<211> LENGTH: 84
<212> TYPE: DNA
<213> ORGANISM: Homo sapiens

<400> SEQUENCE: 290
gtcaggatgg ccgagcggtc taaggcgctg cgttcaggtc gcagtctccc ctggaggcgt 60
gggttcgaat cccactcctg acaa 84

<210> SEQ ID NO 291
<211> LENGTH: 73
<212> TYPE: DNA
<213> ORGANISM: Homo sapiens

<400> SEQUENCE: 291
cgcgttggtg gtatagtggt gagcatagct gccttccaag cagttgaccc gggttcgatt 60
cccggccaac gca 73

<210> SEQ ID NO 292
<211> LENGTH: 75
<212> TYPE: DNA
<213> ORGANISM: Homo sapiens

<400> SEQUENCE: 292
cgtctctgtg gcgcaatcgg ttagcgcgtt cggctgttaa ccgaaaggtt ggtggttcga 60
tcccacccag ggacg 75

<210> SEQ ID NO 293
<211> LENGTH: 73
<212> TYPE: DNA
<213> ORGANISM: Homo sapiens

<400> SEQUENCE: 293
cgcgttggtg gtgtagtggt gagcacagct gcctttcaag cagttaacgc gggttcgatt 60
cccgggtaac gaa 73

<210> SEQ ID NO 294
<211> LENGTH: 73
<212> TYPE: DNA
<213> ORGANISM: Homo sapiens

<400> SEQUENCE: 294
cggctcgttg gtctaggggt atgattctcg cttcgggtgc gagaggtccc gggttcaaat 60
cccggacgag ccc 73

<210> SEQ ID NO 295
<211> LENGTH: 73
<212> TYPE: DNA
<213> ORGANISM: Homo sapiens

<400> SEQUENCE: 295
ggctcgttgg tctaggggta tgattctcgc ttagggtgcg agaggtcccg ggttcaaatc 60
ccggacgagc cct 73

<210> SEQ ID NO 296
<211> LENGTH: 74
<212> TYPE: DNA
<213> ORGANISM: Homo sapiens

<400> SEQUENCE: 296
cgcccggata gctcagtcgg tagagcatca gacttttaat ctgagggtcc agggttcaag 60
tccctgttcg ggcg 74

<210> SEQ ID NO 297
<211> LENGTH: 74
<212> TYPE: DNA
<213> ORGANISM: Homo sapiens

<400> SEQUENCE: 297
gcccggatag ctcagtcggt agagcatcag acttttaatc tgagggtcca gggttcaagt 60
ccctgttcgg gcgt 74

<210> SEQ ID NO 298
<211> LENGTH: 107
<212> TYPE: DNA
<213> ORGANISM: Homo sapiens

<400> SEQUENCE: 298
tgtcaggatg gccgagtggt ctaaggcgcc agactcaagg taagcacctt gcctgcgggc 60
tttctggtct ccggatggag gcgtgggttc gaatcccact tctgaca 107

<210> SEQ ID NO 299
<211> LENGTH: 73
<212> TYPE: DNA
<213> ORGANISM: Homo sapiens

<400> SEQUENCE: 299
ttccctggtg gtctagtggt taggattcgg cgctctcacc gccgcggccc gggttcgatt 60
cccggtcagg aaa 73

<210> SEQ ID NO 300
<211> LENGTH: 90

<212> TYPE: DNA
<213> ORGANISM: Homo sapiens

<400> SEQUENCE: 300
gccttcgata gctcagttgg tagagcggag gactgtagtg gatagggcgt ggcaatcctt 60
aggtcgctgg ttcgattccg gctcgaagga 90

<210> SEQ ID NO 301
<211> LENGTH: 74
<212> TYPE: DNA
<213> ORGANISM: Homo sapiens

<400> SEQUENCE: 301
cgggggatta gctcaaatgg tagagcgctc gcttagcatg cgagaggtag cgggatcgat 60
gcccgcatcc tcca 74

<210> SEQ ID NO 302
<211> LENGTH: 94
<212> TYPE: DNA
<213> ORGANISM: Homo sapiens

<400> SEQUENCE: 302
agctccagtg gcgcaatcgg ttagcgcgcg gtacttatac agcagtacat gcagagcaat 60
gccgaggttg tgagttcgag cctcacctgg agca 94

<210> SEQ ID NO 303
<211> LENGTH: 72
<212> TYPE: DNA
<213> ORGANISM: Homo sapiens

<400> SEQUENCE: 303
gcgccgctgg tgtagtggta tcatgcaaga ttcccattct tgcgacccgg gttcgattcc 60
cgggcggcgc at 72

<210> SEQ ID NO 304
<211> LENGTH: 73
<212> TYPE: DNA
<213> ORGANISM: Homo sapiens

<400> SEQUENCE: 304
tcccatatgg tctagcggtt aggattcctg gttttcaccc aggtggcccg ggttcgactc 60
ccggtatggg aac 73

<210> SEQ ID NO 305
<211> LENGTH: 73
<212> TYPE: DNA
<213> ORGANISM: Homo sapiens

<400> SEQUENCE: 305
gggggatgta gctcagtggt agagcgcgcg cttcgcatgt gtgaggtccc gggttcaatc 60
cccggcatct cca 73

<210> SEQ ID NO 306
<211> LENGTH: 72
<212> TYPE: DNA
<213> ORGANISM: Homo sapiens

<400> SEQUENCE: 306
gcattggtgg ttcagtggta gaattctcgc ctgccacgcg ggaggcccgg gttcgattcc 60
cggccaatgc aa 72

<210> SEQ ID NO 307
<211> LENGTH: 74
<212> TYPE: DNA
<213> ORGANISM: Homo sapiens

<400> SEQUENCE: 307
gggccagtgg cgcaatggat aacgcgtctg actacggatc agaagattct aggttcgact 60
cctggctggc tcgc 74

<210> SEQ ID NO 308
<211> LENGTH: 74
<212> TYPE: DNA
<213> ORGANISM: Homo sapiens

<400> SEQUENCE: 308
ggtttccgta gtgtagtggt tatcacgttc gcctaacacg cgaaaggtcc ccggttcgaa 60
accgggcgga aaca 74

<210> SEQ ID NO 309
<211> LENGTH: 74
<212> TYPE: DNA
<213> ORGANISM: Homo sapiens

<400> SEQUENCE: 309
agtttccgta gtgtagtggt tatcacgttc gcctaacacg cgaaaggtcc ccggttcgaa 60
accgggcgga aaca 74

<210> SEQ ID NO 310
<211> LENGTH: 83
<212> TYPE: DNA
<213> ORGANISM: Homo sapiens

<400> SEQUENCE: 310
aggtagcgtg gccgagcggt ctaaggcgct ggattaaggc tccagtctct tcgggggcgt 60
gggttcgaat cccaccgctg cca 83

<210> SEQ ID NO 311
<211> LENGTH: 74
<212> TYPE: DNA
<213> ORGANISM: Homo sapiens

<400> SEQUENCE: 311
gtttccgtag tgtagtggtc atcacgttcg cctaacacgc gaaaggtccc cggttcgaaa 60
ccgggcggaa acat 74

<210> SEQ ID NO 312
<211> LENGTH: 73
<212> TYPE: DNA
<213> ORGANISM: Homo sapiens

<400> SEQUENCE: 312
ggctcgttgg tctaggggta tgattctcgc tttgggtgcg agaggtcccg ggttcaaatc 60
ccggacgagc cca 73

<210> SEQ ID NO 313
<211> LENGTH: 73
<212> TYPE: DNA
<213> ORGANISM: Homo sapiens

<400> SEQUENCE: 313
ggctccatag ctcaggggtt agagcactgg tcttgtaaac cagggtcgcg agttcaaatc 60
tcgctggggc ctg 73

<210> SEQ ID NO 314
<211> LENGTH: 73
<212> TYPE: DNA
<213> ORGANISM: Homo sapiens

<400> SEQUENCE: 314
tggggatgta gctcagtggt agagcgcatg ctttgcatgt atgaggcccc gggttcgatc 60
cccggcatct cca 73

<210> SEQ ID NO 315
<211> LENGTH: 74
<212> TYPE: DNA
<213> ORGANISM: Homo sapiens

<400> SEQUENCE: 315
cgcccggcta gctcagtcgg tagagcatga gactcttaat ctcagggtcg tgggttcgag 60
ccccacgttg ggcg 74

<210> SEQ ID NO 316
<211> LENGTH: 74
<212> TYPE: DNA
<213> ORGANISM: Homo sapiens

<400> SEQUENCE: 316
gtttccgtag tgtagtggtt atcacgttcg cctaacacgc gaaaggtccc cggttcgaaa 60
ccgggcggaa acaa 74

<210> SEQ ID NO 317
<211> LENGTH: 74
<212> TYPE: DNA
<213> ORGANISM: Homo sapiens

<400> SEQUENCE: 317
gcccggctag ctcagtcggt agagcatgag actcttaatc tcagggtcgt gggttcgagc 60
cccacgttgg gcgt 74

<210> SEQ ID NO 318
<211> LENGTH: 74
<212> TYPE: DNA
<213> ORGANISM: Homo sapiens

<400> SEQUENCE: 318
gtttccgtag tgtagtggtt atcacgttcg cctcacacgc gaaaggtccc cggttcgaaa 60
ccgggcggaa acac 74

<210> SEQ ID NO 319
<211> LENGTH: 73
<212> TYPE: DNA
<213> ORGANISM: Homo sapiens

<400> SEQUENCE: 319
cagcagagtg gcgcagcgga agcgtgctgg gcccataacc cagaggtcga tggatcgaaa 60
ccatcctctg cta 73

<210> SEQ ID NO 320
<211> LENGTH: 85
<212> TYPE: DNA
<213> ORGANISM: Homo sapiens

<400> SEQUENCE: 320
ggagaggcct ggccgagtgg ttaaggcgat ggactgctaa tccattgtgc tctgcacgcg 60
tgggttcgaa tcccatcctc gtcgc 85

<210> SEQ ID NO 321
<211> LENGTH: 73
<212> TYPE: DNA
<213> ORGANISM: Homo sapiens

<400> SEQUENCE: 321
ggccccatgg tgtaatggtt agcactctgg actttgaatc cagcgatccg agttcaaatc 60
tcggtgggac ctg 73

<210> SEQ ID NO 322
<211> LENGTH: 73
<212> TYPE: DNA
<213> ORGANISM: Homo sapiens

<400> SEQUENCE: 322
ggccccatgg tgtaatggtt agcactctgg actttgaatc cagcgatccg agttcaaatc 60
tcggtgggac cta 73

<210> SEQ ID NO 323
<211> LENGTH: 83
<212> TYPE: DNA
<213> ORGANISM: Homo sapiens

<400> SEQUENCE: 323
gtagtcgtgg ccgagtggtt aaggcgatgg acttgaaatc cattggggtc tccccgcgca 60
ggttcgaatc ctgccgacta cgg 83

<210> SEQ ID NO 324
<211> LENGTH: 73
<212> TYPE: DNA
<213> ORGANISM: Homo sapiens

<400> SEQUENCE: 324
agcagagtgg cgcagcggaa gcgtgctggg cccataaccc agaggtcgat ggatcgaaac 60
catcctctgc tat 73

<210> SEQ ID NO 325
<211> LENGTH: 74
<212> TYPE: DNA
<213> ORGANISM: Homo sapiens

<400> SEQUENCE: 325
ggaccacgtg gcctaatgga taaggcgtct gacttcggat cagaagattg agggttcgaa 60
tccctccgtg gtta 74

<210> SEQ ID NO 326
<211> LENGTH: 83
<212> TYPE: DNA
<213> ORGANISM: Homo sapiens

<400> SEQUENCE: 326
tgtagtcgtg gccgagtggt taaggcgatg gactagaaat ccattggggt ctccccgcgc 60
aggttcgaat cctgccgact acg 83

<210> SEQ ID NO 327
<211> LENGTH: 73
<212> TYPE: DNA
<213> ORGANISM: Homo sapiens

<400> SEQUENCE: 327
agcagagtgg cgcagcggaa gcgtgctggg cccataaccc agaggtcgat ggatcgaaac 60
catcctctgc tag 73

<210> SEQ ID NO 328
<211> LENGTH: 84
<212> TYPE: DNA
<213> ORGANISM: Homo sapiens

<400> SEQUENCE: 328
cgtcaggatg gccgagcggt ctaaggcgct gcgttcaggt cgcagtctcc cctggaggcg 60
tgggttcgaa tcccactcct gaca 84

<210> SEQ ID NO 329
<211> LENGTH: 75
<212> TYPE: DNA
<213> ORGANISM: Homo sapiens

<400> SEQUENCE: 329
ggctccgtgg cttagctggt taaagcgcct gtctagtaaa caggagatcc tgggttcgaa 60
tcccagcggg gcctg 75

<210> SEQ ID NO 330
<211> LENGTH: 74
<212> TYPE: DNA
<213> ORGANISM: Homo sapiens

<400> SEQUENCE: 330
agggccagtg gcgcaatgga taacgcgtct gactacggat cagaagattc caggttcgac 60
tcctggctgg ctcg 74

<210> SEQ ID NO 331
<211> LENGTH: 74
<212> TYPE: DNA
<213> ORGANISM: Homo sapiens

<400> SEQUENCE: 331
ggtttccgta gtgtagtggt tatcacgttc gcctcacacg cgaaaggtcc ccggttcgaa 60
accgggcgga aaca 74

<210> SEQ ID NO 332
<211> LENGTH: 73
<212> TYPE: DNA
<213> ORGANISM: Homo sapiens

<400> SEQUENCE: 332
aggggatgta gctcagtggt agagcgcatg cttcgcatgt atgaggtccc gggttcgatc 60
cccggcatct cca 73

<210> SEQ ID NO 333

<211> LENGTH: 75
<212> TYPE: DNA
<213> ORGANISM: Homo sapiens

<400> SEQUENCE: 333
tggccggtta gctcagttgg ttagagcgtg gtgctaataa cgccaaggtc gcgggttcga 60
tccccgtacg ggcca 75

<210> SEQ ID NO 334
<211> LENGTH: 73
<212> TYPE: DNA
<213> ORGANISM: Homo sapiens

<400> SEQUENCE: 334
cggctcgttg gtctaggggt atgattctcg cttagggtgc gagaggtccc gggttcaaat 60
cccggacgag ccc 73

<210> SEQ ID NO 335
<211> LENGTH: 74
<212> TYPE: DNA
<213> ORGANISM: Homo sapiens

<400> SEQUENCE: 335
agcccggcta gctcagtcgg tagagcatga gactcttaat ctcagggtcg tgggttcgag 60
ccccacgttg ggcg 74

<210> SEQ ID NO 336
<211> LENGTH: 92
<212> TYPE: DNA
<213> ORGANISM: Homo sapiens

<400> SEQUENCE: 336
tccttcgata gctcagttgg tagagcggag gactgtagtt ggctgtgtcc ttagacatcc 60
ttaggtcgct ggttcgaatc cggctcgaag ga 92

<210> SEQ ID NO 337
<211> LENGTH: 74
<212> TYPE: DNA
<213> ORGANISM: Homo sapiens

<400> SEQUENCE: 337
ggggaattag ctcaaatggt agagcgctcg cttagcatgc gagaggtagc gggatcgatg 60
cccgcattct ccag 74

<210> SEQ ID NO 338
<211> LENGTH: 74
<212> TYPE: DNA
<213> ORGANISM: Homo sapiens

<400> SEQUENCE: 338
cgccctctta gcgcagcggg cagcgcgtca gtctcataat ctgaaggtcc tgagttcgag 60
cctcagagag ggca 74

<210> SEQ ID NO 339
<211> LENGTH: 95
<212> TYPE: DNA
<213> ORGANISM: Homo sapiens

<400> SEQUENCE: 339
tgctccagtg gcgcaatcgg ttagcgcgcg gtacttatat ggcagtatgt gtgcgagtga 60
tgccgaggtt gtgagttcga gcctcacctg gagca 95

<210> SEQ ID NO 340
<211> LENGTH: 73
<212> TYPE: DNA
<213> ORGANISM: Homo sapiens

<400> SEQUENCE: 340
tgccgtgatc gtatagtggt tagtactctg cgttgtggcc gcagcaacct cggttcgaat 60
ccgagtcacg gca 73

<210> SEQ ID NO 341
<211> LENGTH: 75
<212> TYPE: DNA
<213> ORGANISM: Homo sapiens

<400> SEQUENCE: 341
ggccggttag ctcagttggt tagagcgtgg tgctaataac gccaaggtcg cgggttcgat 60
ccccgtacgg gccac 75

<210> SEQ ID NO 342
<211> LENGTH: 74
<212> TYPE: DNA
<213> ORGANISM: Homo sapiens

<400> SEQUENCE: 342
agtttccgta gtgtagtggt tatcacgttt gcctaacacg cgaaaggtcc ccggttcgaa 60
accgggcaga aaca 74

<210> SEQ ID NO 343
<211> LENGTH: 74
<212> TYPE: DNA
<213> ORGANISM: Homo sapiens

<400> SEQUENCE: 343
gcttctgtag tgtagtggtt atcacgttcg cctcacacgc gaaaggtccc cggttcgaaa 60
ccgggcagaa gcaa 74

<210> SEQ ID NO 344
<211> LENGTH: 73
<212> TYPE: DNA
<213> ORGANISM: Homo sapiens

<400> SEQUENCE: 344
ttcctcgtta gtatagtggt gagtatcccc gcctgtcacg cgggagaccg gggttcgatt 60
ccccgacggg gag 73

<210> SEQ ID NO 345
<211> LENGTH: 83
<212> TYPE: DNA
<213> ORGANISM: Homo sapiens

<400> SEQUENCE: 345
gtagtcgtgg ccgagtggtt aaggcgatgg acttgaaatc cattggggtt tccccgcgca 60
ggttcgaatc ctgtcggcta cgg 83

<210> SEQ ID NO 346
<211> LENGTH: 73
<212> TYPE: DNA

<213> ORGANISM: Homo sapiens

<400> SEQUENCE: 346
aggttccatg gtgtaatggt tagcactctg gactctgaat ccagcgatcc gagttcaaat 60
ctcggtggaa cct 73

<210> SEQ ID NO 347
<211> LENGTH: 73
<212> TYPE: DNA
<213> ORGANISM: Homo sapiens

<400> SEQUENCE: 347
tcctcgttag tatagtggtg agtgtccccg tctgtcacgc gggagaccgg ggttcgattc 60
cccgacgggg aga 73

<210> SEQ ID NO 348
<211> LENGTH: 74
<212> TYPE: DNA
<213> ORGANISM: Homo sapiens

<400> SEQUENCE: 348
gtttccgtag tgtagtggtt atcacgttcg cctaacacgc gaaaggtccc tggatcaaaa 60
ccaggcggaa acaa 74

<210> SEQ ID NO 349
<211> LENGTH: 75
<212> TYPE: DNA
<213> ORGANISM: Homo sapiens

<400> SEQUENCE: 349
cggccggtta gctcagttgg ttagagcgtg gtgctaataa cgccaaggtc gcgggttcga 60
tccccgtact ggcca 75

<210> SEQ ID NO 350
<211> LENGTH: 73
<212> TYPE: DNA
<213> ORGANISM: Homo sapiens

<400> SEQUENCE: 350
ggccccatgg tgtaatggtc agcactctgg actctgaatc cagcgatccg agttcaaatc 60
tcggtgggac cca 73

<210> SEQ ID NO 351
<211> LENGTH: 73
<212> TYPE: DNA
<213> ORGANISM: Homo sapiens

<400> SEQUENCE: 351
ggccccatgg tgtaatggtt agcactctgg actttgaatc cagcgatccg agttcaaatc 60
tcggtgggac ctt 73

<210> SEQ ID NO 352
<211> LENGTH: 73
<212> TYPE: DNA
<213> ORGANISM: Homo sapiens

<400> SEQUENCE: 352
tgggggtgta gctcagtggt agagcgcgtg cttagcatgt acgaggtccc gggttcaatc 60
cccggcacct cca 73

<210> SEQ ID NO 353
<211> LENGTH: 73
<212> TYPE: DNA
<213> ORGANISM: Homo sapiens

<400> SEQUENCE: 353
ggggatgtag ctcagtggta gagcgcatgc ttagcatgca tgaggtcccg ggttcgatcc 60
ccagcatctc cag 73

<210> SEQ ID NO 354
<211> LENGTH: 73
<212> TYPE: DNA
<213> ORGANISM: Homo sapiens

<400> SEQUENCE: 354
agggggtgta gctcagtggt agagcgcgtg cttcgcatgt acgaggcccc gggttcgacc 60
cccggctcct cca 73

<210> SEQ ID NO 355
<211> LENGTH: 73
<212> TYPE: DNA
<213> ORGANISM: Homo sapiens

<400> SEQUENCE: 355
gggggtgtag ctcagtggta gagcgcgtgc ttagcatgca cgaggccccg ggttcaatcc 60
ccggcacctc cat 73

<210> SEQ ID NO 356
<211> LENGTH: 73
<212> TYPE: DNA
<213> ORGANISM: Homo sapiens

<400> SEQUENCE: 356
gggggtgtag ctcagtggta gagcgcgtgc ttagcatgca cgaggccccg ggttcaatcc 60
ccggcacctc cag 73

<210> SEQ ID NO 357
<211> LENGTH: 107
<212> TYPE: DNA
<213> ORGANISM: Homo sapiens

<400> SEQUENCE: 357
gtcaggatgg ccgagtggtc taaggcgcca gactcaagct aagcttcctc cgcggtgggg 60
attctggtct ccaatggagg cgtgggttcg aatcccactt ctgacac 107

<210> SEQ ID NO 358
<211> LENGTH: 106
<212> TYPE: DNA
<213> ORGANISM: Homo sapiens

<400> SEQUENCE: 358
tgtcaggatg gccgagtggt ctaaggcgcc agactcaagc ttggcttcct cgtgttgagg 60
attctggtct ccaatggagg cgtgggttcg aatcccactt ctgaca 106

<210> SEQ ID NO 359
<211> LENGTH: 73
<212> TYPE: DNA
<213> ORGANISM: Homo sapiens

<400> SEQUENCE: 359
ggttccatgg tgtaatggtt agcactctgg actctgaatc cagcgatccg agttcaaatc 60
tcggtggaac ctt 73

<210> SEQ ID NO 360
<211> LENGTH: 83
<212> TYPE: DNA
<213> ORGANISM: Homo sapiens

<400> SEQUENCE: 360
ggtagcgtgg ccgagcggtc taaggcgctg gattaaggct ccagtctctt cgggggcgtg 60
ggttcgaatc ccaccgctgc cag 83

<210> SEQ ID NO 361
<211> LENGTH: 74
<212> TYPE: DNA
<213> ORGANISM: Homo sapiens

<400> SEQUENCE: 361
tgcctcctta gcgcagtagg cagcgcgtca gtctcataat ctgaaggtcc tgagttcgaa 60
cctcagaggg ggca 74

<210> SEQ ID NO 362
<211> LENGTH: 74
<212> TYPE: DNA
<213> ORGANISM: Homo sapiens

<400> SEQUENCE: 362
agcccggata gctcagtcgg tagagcatca gacttttaat ctgagggtcc agggttcaag 60
tccctgttcg ggcg 74

<210> SEQ ID NO 363
<211> LENGTH: 74
<212> TYPE: DNA
<213> ORGANISM: Homo sapiens

<400> SEQUENCE: 363
gcctccttag cgcagtaggc agcgcgtcag tctcataatc tgaaggtcct gagttcgaac 60
ctcagagggg gcag 74

<210> SEQ ID NO 364
<211> LENGTH: 73
<212> TYPE: DNA
<213> ORGANISM: Homo sapiens

<400> SEQUENCE: 364
ttccctggtg gtctagtggt taggattcgg cgctctcacc gccgcggccc gggttcgatt 60
cccggtcagg gaa 73

<210> SEQ ID NO 365
<211> LENGTH: 84
<212> TYPE: DNA
<213> ORGANISM: Homo sapiens

<400> SEQUENCE: 365
caccaggatg gccgagtggt taaggcgttg gacttaagat ccaatggaca tatgtccgcg 60
tgggttcgaa ccccactcct ggta 84

<210> SEQ ID NO 366
<211> LENGTH: 73
<212> TYPE: DNA
<213> ORGANISM: Homo sapiens

<400> SEQUENCE: 366
tggctcgttg gtctaggggt atgattctcg cttagggtgc gagaggtccc gggttcaaat 60
cccggacgag ccc 73

<210> SEQ ID NO 367
<211> LENGTH: 74
<212> TYPE: DNA
<213> ORGANISM: Homo sapiens

<400> SEQUENCE: 367
agccccagtg gcctaatgga taaggcattg gcctcctaag ccagggattg tgggttcgag 60
tcccatctgg ggtg 74

<210> SEQ ID NO 368
<211> LENGTH: 73
<212> TYPE: DNA
<213> ORGANISM: Homo sapiens

<400> SEQUENCE: 368
ggggatatag ctcaggggta gagcatttga ctgcagatca agaggtcccc ggttcaaatc 60
cgggtgcccc ccc 73

<210> SEQ ID NO 369
<211> LENGTH: 94
<212> TYPE: DNA
<213> ORGANISM: Homo sapiens

<400> SEQUENCE: 369
cccttcgata gctcagctgg tagagcggag gactgtagct acttcctcag caggagacat 60
ccttaggtcg ctggttcgat tccggctcga agga 94

<210> SEQ ID NO 370
<211> LENGTH: 90
<212> TYPE: DNA
<213> ORGANISM: Homo sapiens

<400> SEQUENCE: 370
cccttcgata gctcagctgg tagagcggag gactgtaggc gcgcgcccgt ggccatcctt 60
aggtcgctgg ttcgattccg gctcgaagga 90

<210> SEQ ID NO 371
<211> LENGTH: 74
<212> TYPE: DNA
<213> ORGANISM: Homo sapiens

<400> SEQUENCE: 371
tgggggatta gctcaaatgg tagagcgctc gcttagcatg cgagaggtag cgggatcgat 60
gcccgcatcc tcca 74

<210> SEQ ID NO 372
<211> LENGTH: 83
<212> TYPE: DNA
<213> ORGANISM: Homo sapiens

<400> SEQUENCE: 372
gtagtcgtgg ccgagtggtt aaggcgatgg actagaaatc cattggggtc tccccgcgca 60
ggttcgaatc ctgccgacta cgg 83

<210> SEQ ID NO 373
<211> LENGTH: 74
<212> TYPE: DNA
<213> ORGANISM: Homo sapiens

<400> SEQUENCE: 373
gcctcgttag cgcagtaggt agcgcgtcag tctcataatc tgaaggtcgt gagttcgatc 60
ctcacacggg gcac 74

<210> SEQ ID NO 374
<211> LENGTH: 92
<212> TYPE: DNA
<213> ORGANISM: Homo sapiens

<400> SEQUENCE: 374
ggctctgtgg cgcaatggat agcgcattgg acttctagct gagcctagtg tggtcattca 60
aaggttgtgg gttcgagtcc caccagagtc ga 92

<210> SEQ ID NO 375
<211> LENGTH: 75
<212> TYPE: DNA
<213> ORGANISM: Homo sapiens

<400> SEQUENCE: 375
gtctctgtgg cgcaatcggt tagcgcgttc ggctgttaac cgaaaggttg gtggttcgag 60
cccacccagg gacgc 75

<210> SEQ ID NO 376
<211> LENGTH: 83
<212> TYPE: DNA
<213> ORGANISM: Homo sapiens

<400> SEQUENCE: 376
ggcagcgatg gccgagtggt taaggcgttg gacttgaaat ccaatggggt ctccccgcgc 60
aggttcgaac cctgctcgct gcg 83

<210> SEQ ID NO 377
<211> LENGTH: 74
<212> TYPE: DNA
<213> ORGANISM: Homo sapiens

<400> SEQUENCE: 377
ggttccatag tgtagtggtt atcacgtctg ctttacacgc agaaggtcct gggttcgagc 60
cccagtggaa ccat 74

<210> SEQ ID NO 378
<211> LENGTH: 74
<212> TYPE: DNA
<213> ORGANISM: Homo sapiens

<400> SEQUENCE: 378
ggttccatag tgtagcggtt atcacgtctg ctttacacgc agaaggtcct gggttcgagc 60
cccagtggaa ccac 74

<210> SEQ ID NO 379
<211> LENGTH: 87

<212> TYPE: DNA
<213> ORGANISM: Homo sapiens

<400> SEQUENCE: 379
tggctctgtg gcgcaatgga tagcgcattg gacttctaga tagttagaga aattcaaagg 60
ttgtgggttc gagtcccacc agagtcg 87

<210> SEQ ID NO 380
<211> LENGTH: 84
<212> TYPE: DNA
<213> ORGANISM: Homo sapiens

<400> SEQUENCE: 380
taccagaatg gccgagtggt taaggcgttg gacttaagat ccaatggatt catatccgcg 60
tgggttcgaa ccccacttct ggta 84

<210> SEQ ID NO 381
<211> LENGTH: 74
<212> TYPE: DNA
<213> ORGANISM: Homo sapiens

<400> SEQUENCE: 381
ggcccggata gctcagtcgg tagagcatca gacttttaat ctgagggtcc ggggttcaag 60
tccctgttcg ggcg 74

<210> SEQ ID NO 382
<211> LENGTH: 74
<212> TYPE: DNA
<213> ORGANISM: Homo sapiens

<400> SEQUENCE: 382
gccgaaatag ctcagttggg agagcgttag actgaagatc taaaggtccc tggttcgatc 60
ccgggtttcg gcag 74

<210> SEQ ID NO 383
<211> LENGTH: 74
<212> TYPE: DNA
<213> ORGANISM: Homo sapiens

<400> SEQUENCE: 383
gcccggatag ctcagtcggt agagcatcag acttttaatc tgagggtcca gggttcaagt 60
ccctgttcgg gcgg 74

<210> SEQ ID NO 384
<211> LENGTH: 74
<212> TYPE: DNA
<213> ORGANISM: Homo sapiens

<400> SEQUENCE: 384
gccgaaatag ctcagttggg agagcgttag actgaagatc taaaggtccc tggttcaatc 60
ccgggtttcg gcag 74

<210> SEQ ID NO 385
<211> LENGTH: 83
<212> TYPE: DNA
<213> ORGANISM: Homo sapiens

<400> SEQUENCE: 385
ggacgaggtg gccgagtggt taaggcgatg gactgctaat ccattgtgct ttgcacgcgt 60

-continued gggttcgaat cccatcctcg tcg 83

<210> SEQ ID NO 386
<211> LENGTH: 73
<212> TYPE: DNA
<213> ORGANISM: Homo sapiens

<400> SEQUENCE: 386
ggctcgttgg tctaggggta tgattctcgg tttgggtccg agaggtcccg ggttcaaatc 60
ccggacgagc ccc 73

<210> SEQ ID NO 387
<211> LENGTH: 83
<212> TYPE: DNA
<213> ORGANISM: Homo sapiens

<400> SEQUENCE: 387
agtcacggtg gccgagtggt taaggcgttg gactcgaaat ccaatggggt ttccccgcac 60
aggttcgaat cctgttcgtg acg 83

<210> SEQ ID NO 388
<211> LENGTH: 73
<212> TYPE: DNA
<213> ORGANISM: Homo sapiens

<400> SEQUENCE: 388
ctcctcgtta gtatagtggt tagtatcccc gcctgtcacg cgggagaccg gggttcaatt 60
ccccgacggg gag 73

<210> SEQ ID NO 389
<211> LENGTH: 73
<212> TYPE: DNA
<213> ORGANISM: Homo sapiens

<400> SEQUENCE: 389
ggacctcgtg gcgcaacggt agcgcgtctg actccagatc agaaggctgc gtgttcgaat 60
cacgtcgggg tca 73

<210> SEQ ID NO 390
<211> LENGTH: 73
<212> TYPE: DNA
<213> ORGANISM: Homo sapiens

<400> SEQUENCE: 390
ggggatgtag ctcagtggta gagcgcatgc tttgcatgta tgaggccccg ggttcgatcc 60
ccggcatctc cat 73

<210> SEQ ID NO 391
<211> LENGTH: 74
<212> TYPE: DNA
<213> ORGANISM: Homo sapiens

<400> SEQUENCE: 391
gccgaaatag ctcagttggg agagcgttag actgaagatc taaaggtccc tggttcgatc 60
ccgggtttcg gcac 74

<210> SEQ ID NO 392
<211> LENGTH: 73
<212> TYPE: DNA
<213> ORGANISM: Homo sapiens

<400> SEQUENCE: 392
aggggatgta gctcagtggt agagcgcatg ctttgcacgt atgaggcccc gggttcaatc 60
cccggcatct cca 73

<210> SEQ ID NO 393
<211> LENGTH: 75
<212> TYPE: DNA
<213> ORGANISM: Homo sapiens

<400> SEQUENCE: 393
gtctctgtgg cgcaatcggt tagcgcgttc ggctgttaac cgaaaggttg gtggttcgag 60
cccacccagg gacgg 75

<210> SEQ ID NO 394
<211> LENGTH: 73
<212> TYPE: DNA
<213> ORGANISM: Homo sapiens

<400> SEQUENCE: 394
tcccacatgg tctagcggtt aggattcctg gttttcaccc aggcggcccg ggttcgactc 60
ccggtgtggg aac 73

<210> SEQ ID NO 395
<211> LENGTH: 74
<212> TYPE: DNA
<213> ORGANISM: Homo sapiens

<400> SEQUENCE: 395
ggctccatag ctcaggggtt agagcgctgg tcttgtaaac caggggtcgc gagttcaatt 60
ctcgctgggg cctg 74

<210> SEQ ID NO 396
<211> LENGTH: 83
<212> TYPE: DNA
<213> ORGANISM: Homo sapiens

<400> SEQUENCE: 396
tggtagtgtg gccgagcggt ctaaggcgct ggatttaggc tccagtctct tcgggggcgt 60
gggttcgaat cccaccactg cca 83

<210> SEQ ID NO 397
<211> LENGTH: 74
<212> TYPE: DNA
<213> ORGANISM: Homo sapiens

<400> SEQUENCE: 397
ggctccatag ctcaggggtt agagcactgg tcttgtaaac caggggtcgc gagttcaaat 60
ctcgctgggg cctc 74

<210> SEQ ID NO 398
<211> LENGTH: 73
<212> TYPE: DNA
<213> ORGANISM: Homo sapiens

<400> SEQUENCE: 398
tggctcgttg gtctagtggt atgattctcg ctttgggtgc gagaggtccc gggttcaaat 60
cccggacgag ccc 73

-continued

<210> SEQ ID NO 399
<211> LENGTH: 95
<212> TYPE: DNA
<213> ORGANISM: Homo sapiens

<400> SEQUENCE: 399
ccttcgatag ctcagctggt agagcggagg actgtagatt gtacagacat ttgcggacat 60
ccttaggtcg ctggttcgat tccggctcga aggaa 95

<210> SEQ ID NO 400
<211> LENGTH: 74
<212> TYPE: DNA
<213> ORGANISM: Homo sapiens

<400> SEQUENCE: 400
aggccctata gctcaggggt tagagcactg gtcttgtaaa ccaggggtcg cgagttcaaa 60
tctcgctggg gcct 74

<210> SEQ ID NO 401
<211> LENGTH: 90
<212> TYPE: DNA
<213> ORGANISM: Homo sapiens

<400> SEQUENCE: 401
tccttcgata gctcagctgg tagagcggag gactgtagta cttaatgtgt ggtcatcctt 60
aggtcgctgg ttcgattccg gctcgaagga 90

<210> SEQ ID NO 402
<211> LENGTH: 73
<212> TYPE: DNA
<213> ORGANISM: Homo sapiens

<400> SEQUENCE: 402
tggctcgttg gtctaggggt atgattctcg ctttgggtgc gagaggtccc gggttcaaat 60
cccggacgag ccc 73

<210> SEQ ID NO 403
<211> LENGTH: 74
<212> TYPE: DNA
<213> ORGANISM: Homo sapiens

<400> SEQUENCE: 403
gcccggctag ctcagtcggt agagcatggg actcttaatc ccagggtcgt gggttcgagc 60
cccacgttgg gcgc 74

<210> SEQ ID NO 404
<211> LENGTH: 75
<212> TYPE: DNA
<213> ORGANISM: Homo sapiens

<400> SEQUENCE: 404
cggccggtta gctcagttgg ttagagcgtg gtgctaataa cgccaaggtc gcgggttcga 60
tccccgtacg ggcca 75

<210> SEQ ID NO 405
<211> LENGTH: 73
<212> TYPE: DNA
<213> ORGANISM: Homo sapiens

<400> SEQUENCE: 405
tcccacatgg tctagcggtt aggattcctg gttttcaccc aggcggcccg ggttcgactc 60
ccggtgtggg aat 73

<210> SEQ ID NO 406
<211> LENGTH: 83
<212> TYPE: DNA
<213> ORGANISM: Homo sapiens

<400> SEQUENCE: 406
gacgaggtgg ccgagtggtt aaggcgatgg actgctaatc cattgtgctc tgcacgcgtg 60
ggttcgaatc ccatcctcgt cga 83

<210> SEQ ID NO 407
<211> LENGTH: 73
<212> TYPE: DNA
<213> ORGANISM: Homo sapiens

<400> SEQUENCE: 407
gccgtgatcg tatagtggtt agtactctgc gttgtggccg cagcaacctc ggttcgaatc 60
cgagtcacgg cat 73

<210> SEQ ID NO 408
<211> LENGTH: 73
<212> TYPE: DNA
<213> ORGANISM: Homo sapiens

<400> SEQUENCE: 408
cgccgtgatc gtatagtggt tagtactctg cgttgtggcc gcagcaacct cggttcgaat 60
ccgagtcacg gca 73

<210> SEQ ID NO 409
<211> LENGTH: 73
<212> TYPE: DNA
<213> ORGANISM: Homo sapiens

<400> SEQUENCE: 409
ggttccatgg tgtaatggtt agcactctgg actctgaatc cagcgatccg agttcaaatc 60
tcggtggaac ctg 73

<210> SEQ ID NO 410
<211> LENGTH: 74
<212> TYPE: DNA
<213> ORGANISM: Homo sapiens

<400> SEQUENCE: 410
tgcccggcta gctcagtcgg tagagcatgg gactcttaat cccagggtcg tgggttcgag 60
ccccacgttg ggcg 74

<210> SEQ ID NO 411
<211> LENGTH: 74
<212> TYPE: DNA
<213> ORGANISM: Homo sapiens

<400> SEQUENCE: 411
gggccgcgtg gcctaatgga taaggcgtct gacttcggat cagaagattg caggttcgag 60
tcctgccgcg gtcg 74

<210> SEQ ID NO 412

<211> LENGTH: 72
<212> TYPE: DNA
<213> ORGANISM: Homo sapiens

<400> SEQUENCE: 412
gcgccgctgg tgtagtggta tcatgcaaga ttcccattct tgcgacccgg gttcgattcc 60
cgggcggcgc ac 72

<210> SEQ ID NO 413
<211> LENGTH: 74
<212> TYPE: DNA
<213> ORGANISM: Homo sapiens

<400> SEQUENCE: 413
gggccgcgtg gcctaatgga taaggcgtct gattccggat cagaagattg agggttcgag 60
tcccttcgtg gtcg 74

<210> SEQ ID NO 414
<211> LENGTH: 74
<212> TYPE: DNA
<213> ORGANISM: Homo sapiens

<400> SEQUENCE: 414
cgccccggtg gcctaatgga taaggcattg gcctcctaag ccagggattg tgggttcgag 60
tcccacccgg ggta 74

<210> SEQ ID NO 415
<211> LENGTH: 74
<212> TYPE: DNA
<213> ORGANISM: Homo sapiens

<400> SEQUENCE: 415
gcccggctag ctcagtcggt agagcatgag acccttaatc tcagggtcgt gggttcgagc 60
cccacgttgg gcgt 74

<210> SEQ ID NO 416
<211> LENGTH: 73
<212> TYPE: DNA
<213> ORGANISM: Homo sapiens

<400> SEQUENCE: 416
aggcgcggtg gccaagtggt aaggcgtcgg tctcgtaaac cgaagatcac gggttcgaac 60
cccgtccgtg cct 73

<210> SEQ ID NO 417
<211> LENGTH: 83
<212> TYPE: DNA
<213> ORGANISM: Homo sapiens

<400> SEQUENCE: 417
ggtagcgtgg ccgagtggtc taaggcgctg gatttaggct ccagtcattt cgatggcgtg 60
ggttcgaatc ccaccgctgc cac 83

<210> SEQ ID NO 418
<211> LENGTH: 83
<212> TYPE: DNA
<213> ORGANISM: Homo sapiens

<400> SEQUENCE: 418
gggtagcgtg gccgagcggt ctaaggcgct ggattaaggc tccagtctct tcgggggcgt 60

-continued gggttcgaat cccaccgctg cca 83

<210> SEQ ID NO 419
<211> LENGTH: 84
<212> TYPE: DNA
<213> ORGANISM: Homo sapiens

<400> SEQUENCE: 419
agtcaggatg gccgagcggt ctaaggcgct gcgttcaggt cgcagtctcc cctggaggcg 60
tgggttcgaa tcccacttct gaca 84

<210> SEQ ID NO 420
<211> LENGTH: 84
<212> TYPE: DNA
<213> ORGANISM: Homo sapiens

<400> SEQUENCE: 420
gtcaggatgg ccgagcggtc taaggcgctg cgttcaggtc gcagtctccc ctggaggcgt 60
gggttcgaat cccacttctg acag 84

<210> SEQ ID NO 421
<211> LENGTH: 74
<212> TYPE: DNA
<213> ORGANISM: Homo sapiens

<400> SEQUENCE: 421
gcctcgttag cgcagtaggc agcgcgtcag tctcataatc tgaaggtcgt gagttcgagc 60
ctcacacggg gcag 74

<210> SEQ ID NO 422
<211> LENGTH: 83
<212> TYPE: DNA
<213> ORGANISM: Homo sapiens

<400> SEQUENCE: 422
ggtagcgtgg ccgagcggtc taaggcgctg gatttaggct ccagtctctt cggaggcgtg 60
ggttcgaatc ccaccgctgc cag 83

<210> SEQ ID NO 423
<211> LENGTH: 89
<212> TYPE: DNA
<213> ORGANISM: Homo sapiens

<400> SEQUENCE: 423
tggctctgtg gcgcaatgga tagcgcattg gacttctagt gacgaataga gcaattcaaa 60
ggttgtgggt tcgaatccca ccagagtcg 89

<210> SEQ ID NO 424
<211> LENGTH: 72
<212> TYPE: DNA
<213> ORGANISM: Homo sapiens

<400> SEQUENCE: 424
cgcattggtg gttcagtggt agaattctcg cctgccacgc gggaggcccg ggttcgattc 60
ccggccaatg ca 72

<210> SEQ ID NO 425
<211> LENGTH: 83
<212> TYPE: DNA

<213> ORGANISM: Homo sapiens

<400> SEQUENCE: 425
gctgtgatgg ccgagtggtt aaggcgttgg actcgaaatc caatggggtc tccccgcgca 60
ggttcgaatc ctgctcacag cgt 83

<210> SEQ ID NO 426
<211> LENGTH: 75
<212> TYPE: DNA
<213> ORGANISM: Homo sapiens

<400> SEQUENCE: 426
ggcgccgtgg cttagctggt taaagcgcct gtctagtaaa caggagatcc tgggttcgaa 60
tcccagcggt gcctg 75

<210> SEQ ID NO 427
<211> LENGTH: 73
<212> TYPE: DNA
<213> ORGANISM: Homo sapiens

<400> SEQUENCE: 427
cgacctcgtg gcgcaacggt agcgcgtctg actccagatc agaaggttgc gtgttcaaat 60
cacgtcgggg tca 73

<210> SEQ ID NO 428
<211> LENGTH: 83
<212> TYPE: DNA
<213> ORGANISM: Homo sapiens

<400> SEQUENCE: 428
agacgaggtg gccgagtggt taaggcgatg gactgctaat ccattgtgct ctgcacgcgt 60
gggttcgaat cccatcctcg tcg 83

<210> SEQ ID NO 429
<211> LENGTH: 75
<212> TYPE: DNA
<213> ORGANISM: Homo sapiens

<400> SEQUENCE: 429
cggcgccgtg gcttagttgg ttaaagcgcc tgtctagtaa acaggagatc ctgggttcga 60
atcccagcgg tgcct 75

<210> SEQ ID NO 430
<211> LENGTH: 73
<212> TYPE: DNA
<213> ORGANISM: Homo sapiens

<400> SEQUENCE: 430
ggcctcgtgg cgcaacggta gcgcgtctga ctccagatca gaaggttgcg tgttcaaatc 60
acgtcggggt caa 73

<210> SEQ ID NO 431
<211> LENGTH: 73
<212> TYPE: DNA
<213> ORGANISM: Homo sapiens

<400> SEQUENCE: 431
agcgttggtg gtatagtggt aagcatagct gccttccaag cagttgaccc gggttcgatt 60
cccggccaac gca 73

<210> SEQ ID NO 432
<211> LENGTH: 73
<212> TYPE: DNA
<213> ORGANISM: Homo sapiens

<400> SEQUENCE: 432
tcctcgttag tatagtggtg agtatccccg cctgtcacgc gggagaccgg ggttcgattc 60
cccgacgggg aga 73

<210> SEQ ID NO 433
<211> LENGTH: 73
<212> TYPE: DNA
<213> ORGANISM: Homo sapiens

<400> SEQUENCE: 433
ggctcgttgg tctaggggta tgattctcgc ttcgggtgcg agaggtcccg ggttcaaatc 60
ccggacgagc cct 73

<210> SEQ ID NO 434
<211> LENGTH: 75
<212> TYPE: DNA
<213> ORGANISM: Homo sapiens

<400> SEQUENCE: 434
ggcgccgtgg cttagttggt taaagcgcct gtctagtaaa caggagatcc tgggttcgaa 60
tcccagcggt gcctt 75

<210> SEQ ID NO 435
<211> LENGTH: 83
<212> TYPE: DNA
<213> ORGANISM: Homo sapiens

<400> SEQUENCE: 435
gtagtcgtgg ccgagtggtt aaggcgatgg actagaaatc cattggggtc tccccgcgca 60
ggttcgaatc ctgccgacta cgt 83

<210> SEQ ID NO 436
<211> LENGTH: 73
<212> TYPE: DNA
<213> ORGANISM: Homo sapiens

<400> SEQUENCE: 436
tgacctcgtg gcgcaatggt agcgcgtctg actccagatc agaaggttgc gtgttcaagt 60
cacgtcgggg tca 73

<210> SEQ ID NO 437
<211> LENGTH: 73
<212> TYPE: DNA
<213> ORGANISM: Homo sapiens

<400> SEQUENCE: 437
aggcgcggtg gccaagtggt aaggcgtcgg tctcgtaaac cgaagatcgc gggttcgaac 60
cccgtccgtg cct 73

<210> SEQ ID NO 438
<211> LENGTH: 73
<212> TYPE: DNA
<213> ORGANISM: Homo sapiens

<400> SEQUENCE: 438
agggggtata gctcagtggt agagcatttg actgcagatc aagaggtccc cggttcaaat 60
ccgggtgccc cct 73

<210> SEQ ID NO 439
<211> LENGTH: 73
<212> TYPE: DNA
<213> ORGANISM: Homo sapiens

<400> SEQUENCE: 439
gggggtatag ctcagtggta gagcatttga ctgcagatca agaggtccct ggttcaaatc 60
cgggtgcccc ctc 73

<210> SEQ ID NO 440
<211> LENGTH: 73
<212> TYPE: DNA
<213> ORGANISM: Homo sapiens

<400> SEQUENCE: 440
gggggtatag ctcagtggta gagcatttga ctgcagatca agaggtcccc ggttcaaatc 60
cgggtgcccc ctc 73

<210> SEQ ID NO 441
<211> LENGTH: 73
<212> TYPE: DNA
<213> ORGANISM: Homo sapiens

<400> SEQUENCE: 441
aggtcccatg gtgtaatggt tagcactctg gactttgaat ccagcgatcc gagttcaaat 60
ctcggtggga cct 73

<210> SEQ ID NO 442
<211> LENGTH: 74
<212> TYPE: DNA
<213> ORGANISM: Homo sapiens

<400> SEQUENCE: 442
gacccagtgg cctaatggat aaggcatcag cctccggagc tggggattgt gggttcgagt 60
cccatctggg tcgc 74

<210> SEQ ID NO 443
<211> LENGTH: 74
<212> TYPE: DNA
<213> ORGANISM: Homo sapiens

<400> SEQUENCE: 443
agccccagtg gcctaatgga taaggcactg gcctcctaag ccagggattg tgggttcgag 60
tcccacctgg ggta 74

<210> SEQ ID NO 444
<211> LENGTH: 74
<212> TYPE: DNA
<213> ORGANISM: Homo sapiens

<400> SEQUENCE: 444
gccccagtgg cctaatggat aaggcactgg cctcctaagc cagggattgt gggttcgagt 60
cccacctggg gtgt 74

<210> SEQ ID NO 445
<211> LENGTH: 74
<212> TYPE: DNA
<213> ORGANISM: Homo sapiens

<400> SEQUENCE: 445
agaccgcgtg gcctaatgga taaggcgtct gacttcggat cagaagattg agggttcgag 60
tcccttcgtg gtcg 74

<210> SEQ ID NO 446
<211> LENGTH: 75
<212> TYPE: DNA
<213> ORGANISM: Homo sapiens

<400> SEQUENCE: 446
cgtctctgtg gcgcaatcgg ttagcgcgtt cggctgttaa ccgaaaggtt ggtggttcga 60
gcccacccag ggacg 75

<210> SEQ ID NO 447
<211> LENGTH: 73
<212> TYPE: DNA
<213> ORGANISM: Homo sapiens

<400> SEQUENCE: 447
ggcgttggtg gtatagtggt tagcatagct gccttccaag cagttgaccc gggttcgatt 60
cccggccaac gca 73

<210> SEQ ID NO 448
<211> LENGTH: 74
<212> TYPE: DNA
<213> ORGANISM: Homo sapiens

<400> SEQUENCE: 448
gtttccgtag tgtagcggtt atcacattcg cctcacacgc gaaaggtccc cggttcgatc 60
ccgggcggaa acag 74

<210> SEQ ID NO 449
<211> LENGTH: 75
<212> TYPE: DNA
<213> ORGANISM: Homo sapiens

<400> SEQUENCE: 449
tggcgccgtg gcttagttgg ttaaagcgcc tgtctagtaa acaggagatc ctgggttcga 60
atcccagcgg tgcct 75

<210> SEQ ID NO 450
<211> LENGTH: 94
<212> TYPE: DNA
<213> ORGANISM: Homo sapiens

<400> SEQUENCE: 450
gctccagtgg cgcaatcggt tagcgcgcgg tacttatatg acagtgcgag cggagcaatg 60
ccgaggttgt gagttcgatc ctcacctgga gcac 94

<210> SEQ ID NO 451
<211> LENGTH: 72
<212> TYPE: DNA
<213> ORGANISM: Homo sapiens

<400> SEQUENCE: 451
gcatgggtgg ttcagtggta gaattctcgc ctgccacgcg ggaggcccgg gttcgattcc 60
cggcccatgc ag 72

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 452
aaaatataaa tatatttc 18

<210> SEQ ID NO 453
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 453 aagct 5

<210> SEQ ID NO 454
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 454 aagtt 5

<210> SEQ ID NO 455
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 455
aattcttcgg aatgt 15

<210> SEQ ID NO 456
<211> LENGTH: 3
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 456 aga 3

<210> SEQ ID NO 457
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 457 agtcc 5

<210> SEQ ID NO 458
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 458 caacc 5

<210> SEQ ID NO 459
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 459 caatc 5

<210> SEQ ID NO 460
<211> LENGTH: 4
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 460 cagc 4

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 461
caggcgggtt ctgcccgcgc 20

<210> SEQ ID NO 462
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 462
catacctgca agggtatc 18

<210> SEQ ID NO 463
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 463

-continued cgaccgcaag gttgt 15

<210> SEQ ID NO 464
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 464
cgaccttgcg gtcat 15

<210> SEQ ID NO 465
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 465
cgatgctaat cacatcgt 18

<210> SEQ ID NO 466
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 466
cgatggtgac atcat 15

<210> SEQ ID NO 467
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 467
cgatggttta catcgt 16

<210> SEQ ID NO 468
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 468
cgccgtaagg tgt 13

<210> SEQ ID NO 469
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 469
cgccttaggt gt 12

<210> SEQ ID NO 470
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 470
cgcctttcga cgcgt 15

<210> SEQ ID NO 471
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 471
cgcttcacgg cgt 13

<210> SEQ ID NO 472
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 472
cggcagcaat gctgt 15

<210> SEQ ID NO 473
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 473
cggctccgcc ttc 13

<210> SEQ ID NO 474
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 474
cgggtatcac agggtc 16

<210> SEQ ID NO 475
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 475
cggtgcgcaa gcgctgt 17

<210> SEQ ID NO 476
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 476
cgtacgggtg accgtacc 18

<210> SEQ ID NO 477
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
cgtcaaagac ttc 13

<210> SEQ ID NO 478
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 478
cgtcgtaaga ctt 13

<210> SEQ ID NO 479
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 479
cgttgaataa acgt 14

<210> SEQ ID NO 480
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 480 ctgtc 5

<210> SEQ ID NO 481
<211> LENGTH: 4
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 481 ggcc 4

<210> SEQ ID NO 482
<211> LENGTH: 7
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 482 ggggatt 7

<210> SEQ ID NO 483
<211> LENGTH: 4
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 483 ggtc 4

<210> SEQ ID NO 484
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 484 ggttt 5

<210> SEQ ID NO 485
<211> LENGTH: 4
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 485 gtag 4

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 486
taactagata ctttcagat 19

<210> SEQ ID NO 487
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 487
tactcgtatg ggtgc 15

<210> SEQ ID NO 488

<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 488
tactttgcgg tgt 13

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 489
taggcgagta acatcgtgc 19

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 490
taggcgtgaa tagcgcctc 19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 491
taggtcgcga gagcggcgc 19

<210> SEQ ID NO 492
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 492
taggtcgcgt aagcggcgc 19

<210> SEQ ID NO 493
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 493
taggtggtta tccacgc 17

<210> SEQ ID NO 494
<211> LENGTH: 5

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 494 tagtc 5

<210> SEQ ID NO 495
<211> LENGTH: 5
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 495 tagtt 5

<210> SEQ ID NO 496
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 496
tatacgtgaa agcgtatc 18

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 497
tatagggtca aaaactctat c 21

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
tatgcagaaa tacctgcatc 20

<210> SEQ ID NO 499
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 499
tccccatacg ggggc 15

<210> SEQ ID NO 500
<211> LENGTH: 14
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 500
tcccgaaggg gttc 14

<210> SEQ ID NO 501
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 501
tctacgtatg tgggc 15

<210> SEQ ID NO 502
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
tctcatagga gttc 14

<210> SEQ ID NO 503
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
tctcctctgg aggc 14

<210> SEQ ID NO 504
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
tcttagcaat aaggt 15

<210> SEQ ID NO 505
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
tcttgtagga gttc 14

<210> SEQ ID NO 506
<211> LENGTH: 15
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 506

tgaacgtaag ttcgc                                                        15


<210> SEQ ID NO 507
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507

tgaactgcga ggttcc                                                       16


<210> SEQ ID NO 508
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508

tgac                                                                     4


<210> SEQ ID NO 509
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509

tgaccgaaag gtcgt                                                        15


<210> SEQ ID NO 510
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510

tgaccgcaag gtcgt                                                        15


<210> SEQ ID NO 511
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511

tgagctctgc tctc                                                         14


<210> SEQ ID NO 512
<211> LENGTH: 18
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 512
tgaggcctca cggcctac 18

<210> SEQ ID NO 513
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 513
tgagggcaac ttcgt 15

<210> SEQ ID NO 514
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 514
tgagggtcat acctcc 16

<210> SEQ ID NO 515
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 515
tgagggtgca aatcctcc 18

<210> SEQ ID NO 516
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 516
tgccgaaagg cgt 13

<210> SEQ ID NO 517
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 517
tgccgtaagg cgt 13

<210> SEQ ID NO 518
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
tgcggtctcc gcgc 14

<210> SEQ ID NO 519
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 519
tgctagagca t 11

<210> SEQ ID NO 520
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 520
tgctcgtata gagctc 16

<210> SEQ ID NO 521
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 521
tggacaattg tctgc 15

<210> SEQ ID NO 522
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 522
tggacagatg tccgt 15

<210> SEQ ID NO 523
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 523
tggacaggtg tccgc 15

<210> SEQ ID NO 524
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 524
tggacggttg tccgc 15

<210> SEQ ID NO 525
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 525
tggacttgtg gtc 13

<210> SEQ ID NO 526
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 526
tggagattct ctccgc 16

<210> SEQ ID NO 527
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 527
tggcataggc ctgc 14

<210> SEQ ID NO 528
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 528
tggcttatgt ctac 14

<210> SEQ ID NO 529
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
tgggagttaa tcccgt 16

<210> SEQ ID NO 530
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
tgggatcttc ccgc 14

<210> SEQ ID NO 531
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 531
tgggcagaaa tgtctc 16

<210> SEQ ID NO 532
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 532
tgggcgttcg cccgc 15

<210> SEQ ID NO 533
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
tgggcttcgc ccgc 14

<210> SEQ ID NO 534
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
tgggggataa ccccgt 16

<210> SEQ ID NO 535
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 535
tgggggtttc cccgt 15

<210> SEQ ID NO 536
<211> LENGTH: 4
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 536 tggt 4

<210> SEQ ID NO 537
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 537
tggtggcaac accgt 15

<210> SEQ ID NO 538
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 538
tggtttatag ccgt 14

<210> SEQ ID NO 539
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 539
tgtacggtaa taccgtacc 19

<210> SEQ ID NO 540
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 540
tgtccgcaag gacgt 15

<210> SEQ ID NO 541
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 541
tgtcctaacg gacgt 15

<210> SEQ ID NO 542
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
tgtcctatta acggacgt 18

<210> SEQ ID NO 543
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 543
tgtccttcac gggcgt 16

<210> SEQ ID NO 544
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 544
tgtcttagga cgt 13

<210> SEQ ID NO 545
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 545
tgtgcgttaa cgcgtacc 18

<210> SEQ ID NO 546
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 546
tgtgtcgcaa ggcacc 16

<210> SEQ ID NO 547
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 547
tgttcgtaag gactt 15

<210> SEQ ID NO 548
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 548
ttcacagaaa tgtgtc 16

<210> SEQ ID NO 549
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 549
ttccctcgtg gagt 14

<210> SEQ ID NO 550
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 550
ttccctctgg gagc 14

<210> SEQ ID NO 551
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 551
ttcccttgtg gatc 14

<210> SEQ ID NO 552
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 552
ttccttcggg agc 13

<210> SEQ ID NO 553
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 553
ttctagcaat agagt 15

<210> SEQ ID NO 554
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 554
ttctccactg gggagc 16

<210> SEQ ID NO 555
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 555
ttctcgagag ggagc 15

<210> SEQ ID NO 556
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
ttctcgtatg agagc 15

<210> SEQ ID NO 557
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 557
tttaaggttt tcccttaac 19

<210> SEQ ID NO 558
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
tttcattgtg gagt 14

<210> SEQ ID NO 559
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 559
tttcgaagga atcc 14

<210> SEQ ID NO 560
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 560
tttcttcgga agc 13

<210> SEQ ID NO 561
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
tttggggcaa ctcaac 16

<210> SEQ ID NO 562
<211> LENGTH: 342
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (5)..(6)
<223> OTHER INFORMATION: a, c, u, or g
<220> FEATURE:
<221> NAME/KEY: modified_base
<222> LOCATION: (15)..(16)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (30)..(32)
<223> OTHER INFORMATION: a, c, u, or g
<220> FEATURE:
<221> NAME/KEY: modified_base
<222> LOCATION: (34)..(34)
<223> OTHER INFORMATION: a, c, u, or g
<220> FEATURE:
<221> NAME/KEY: modified_base
<222> LOCATION: (37)..(37)
<223> OTHER INFORMATION: a, c, u, or g
<220> FEATURE:
<221> NAME/KEY: modified_base
<222> LOCATION: (41)..(45)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (47)..(320)
<223> OTHER INFORMATION: a, c, u, or g
<220> FEATURE:
<221> NAME/KEY: modified_base
<222> LOCATION: (328)..(329)
<223> OTHER INFORMATION: a, c, u, or g
<220> FEATURE:
<221> NAME/KEY: modified_base
<222> LOCATION: (333)..(334)
<223> OTHER INFORMATION: a, c, u, or g
<220> FEATURE:
<221> NAME/KEY: modified_base
<222> LOCATION: (336)..(337)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
      description of substitutions and preferred embodiments

<400> SEQUENCE: 562
rkssnndurg hbyannyugr ndgwdvdydn nnbnhbnryr nnnnndnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn rrduyranny ybnnhnnbwc cd 342

<210> SEQ ID NO 563
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (30)..(30)
<223> OTHER INFORMATION: a, c, u, or g
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 563
rksgrwdkrg hbyavnyggu dgarvrydyn hkywbhryrh dhdhrnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnbhnr gducrayncy ydvhhyywcc d 341

<210> SEQ ID NO 564
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (30)..(30)
<223> OTHER INFORMATION: a, c, u, or g
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
      description of substitutions and preferred embodiments

<400> SEQUENCE: 564

```
ggggrwdurg hbyavnyggu dgarvrydyn hkywkhryrh dhdhrnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnbhnr gducraybcc ydvhhyyucc a                         341
```

<210> SEQ ID NO 565
<211> LENGTH: 343
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(8)
<223> OTHER INFORMATION: a, c, u, or g
<220> FEATURE:
<221> NAME/KEY: modified_base
<222> LOCATION: (12)..(13)
<223> OTHER INFORMATION: a, c, u, or g
<220> FEATURE:
<221> NAME/KEY: modified_base
<222> LOCATION: (17)..(17)
<223> OTHER INFORMATION: a, c, u, or g
<220> FEATURE:
<221> NAME/KEY: modified_base
<222> LOCATION: (22)..(24)
<223> OTHER INFORMATION: a, c, u, or g
<220> FEATURE:
<221> NAME/KEY: modified_base
<222> LOCATION: (26)..(27)
<223> OTHER INFORMATION: a, c, u, or g
<220> FEATURE:
<221> NAME/KEY: modified_base
<222> LOCATION: (30)..(35)
<223> OTHER INFORMATION: a, c, u, or g
<220> FEATURE:
<221> NAME/KEY: modified_base
<222> LOCATION: (38)..(38)
<223> OTHER INFORMATION: a, c, u, or g
<220> FEATURE:
<221> NAME/KEY: modified_base
<222> LOCATION: (43)..(43)
<223> OTHER INFORMATION: a, c, u, or g
<220> FEATURE:
<221> NAME/KEY: modified_base
<222> LOCATION: (45)..(322)

<223> OTHER INFORMATION: a, c, u, or g
<220> FEATURE:
<221> NAME/KEY: misc_feature
<222> LOCATION: (48)..(318)
<223> OTHER INFORMATION: This region may encompass 1-271 nucleotides
<220> FEATURE:
<221> NAME/KEY: modified_base
<222> LOCATION: (329)..(329)
<223> OTHER INFORMATION: a, c, u, or g
<220> FEATURE:
<221> NAME/KEY: modified_base
<222> LOCATION: (333)..(342)
<223> OTHER INFORMATION: a, c, u, or g
<220> FEATURE:
<221> NAME/KEY: misc_feature
<222> LOCATION: (1)..(343)
<223> OTHER INFORMATION: May or may not be present
<220> FEATURE:
<223> OTHER INFORMATION: See specification as filed for detailed
description of substitutions and preferred embodiments

<400> SEQUENCE: 565

```
gnnnnnnnkv gnnhddnhwr rnnnrnnvyn nnnnnbunck rhnbnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnguuyrany ybnnnnnnnn nnd                       343
```

<210> SEQ ID NO 566
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (3)..(3)
<223> OTHER INFORMATION: a, c, u, or g
<220> FEATURE:
<221> NAME/KEY: modified_base
<222> LOCATION: (6)..(7)
<223> OTHER INFORMATION: a, c, u, or g
<220> FEATURE:
<221> NAME/KEY: modified_base
<222> LOCATION: (13)..(13)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (32)..(32)
<223> OTHER INFORMATION: a, c, u, or g
<220> FEATURE:
<221> NAME/KEY: modified_base
<222> LOCATION: (37)..(37)
<223> OTHER INFORMATION: a, c, u, or g
<220> FEATURE:
<221> NAME/KEY: modified_base
<222> LOCATION: (44)..(44)
<223> OTHER INFORMATION: a, c, u, or g
<220> FEATURE:
<221> NAME/KEY: modified_base
<222> LOCATION: (47)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (336)..(338)
<223> OTHER INFORMATION: a, c, u, or g
<220> FEATURE:
<221> NAME/KEY: modified_base
<222> LOCATION: (340)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 566
grnvbnnvkb gbnydrwurg wygarnrydy ynsvyunckr mkbnrrnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnshv gguuyranuy cbdbynnnbn hr 342

<210> SEQ ID NO 567
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (3)..(3)
<223> OTHER INFORMATION: a, c, u, or g
<220> FEATURE:
<221> NAME/KEY: modified_base
<222> LOCATION: (7)..(7)
<223> OTHER INFORMATION: a, c, u, or g
<220> FEATURE:
<221> NAME/KEY: modified_base
<222> LOCATION: (47)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (336)..(336)
<223> OTHER INFORMATION: a, c, u, or g
<220> FEATURE:
<221> NAME/KEY: modified_base
<222> LOCATION: (340)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 567
grnvyvnskk gssydawugg aygarsgyry ykgmyuhckr akymrrnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnshr gguuygavuy cydbynbdbn yg 342

<210> SEQ ID NO 568
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(2)
<223> OTHER INFORMATION: a, c, u, or g
<220> FEATURE:
<221> NAME/KEY: modified_base
<222> LOCATION: (4)..(6)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (17)..(17)
<223> OTHER INFORMATION: a, c, u, or g
<220> FEATURE:
<221> NAME/KEY: modified_base
<222> LOCATION: (25)..(25)
<223> OTHER INFORMATION: a, c, u, or g
<220> FEATURE:
<221> NAME/KEY: modified_base
<222> LOCATION: (28)..(30)
<223> OTHER INFORMATION: a, c, u, or g
<220> FEATURE:
<221> NAME/KEY: modified_base
<222> LOCATION: (43)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (318)..(319)
<223> OTHER INFORMATION: a, c, u, or g
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (331)..(332)
<223> OTHER INFORMATION: a, c, u, or g
<220> FEATURE:
<221> NAME/KEY: modified_base
<222> LOCATION: (334)..(337)
<223> OTHER INFORMATION: a, c, u, or g
<220> FEATURE:
<221> NAME/KEY: modified_base
<222> LOCATION: (339)..(340)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 568
dnynnndurg hnhvrynggb hurdnrynnn bsryyruuwa hbnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnvnnr gukhvwnhcy nnbnnnndnn r 341

<210> SEQ ID NO 569
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (17)..(17)
<223> OTHER INFORMATION: a, c, u, or g
<220> FEATURE:
<221> NAME/KEY: modified_base
<222> LOCATION: (28)..(28)
<223> OTHER INFORMATION: a, c, u, or g
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 569
ruyucygurg hryvrunggb yuarhgcnuu ysryyruuwa hbddannnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnrgur gukhvwdmcy ayysvrrrrb r 341

<210> SEQ ID NO 570
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: misc_feature
<222> LOCATION: (1)..(341)
<223> OTHER INFORMATION: May or may not be present
<220> FEATURE:

<223> OTHER INFORMATION: See specification as filed for detailed
      description of substitutions and preferred embodiments

<400> SEQUENCE: 570
ruyucygurg hryvrubggb yuaghgcbuu ysryyruuaa hyddannnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnrgur gukhvwdmcy ayysvrrrry g 341

<210> SEQ ID NO 571
<211> LENGTH: 342
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(6)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (22)..(22)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (29)..(29)
<223> OTHER INFORMATION: a, c, u, or g
<220> FEATURE:
<221> NAME/KEY: modified_base
<222> LOCATION: (31)..(32)
<223> OTHER INFORMATION: a, c, u, or g
<220> FEATURE:
<221> NAME/KEY: modified_base
<222> LOCATION: (44)..(44)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (47)..(319)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(334)
<223> OTHER INFORMATION: a, c, u, or g
<220> FEATURE:
<221> NAME/KEY: modified_base
<222> LOCATION: (336)..(339)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
      description of substitutions and preferred embodiments

<400> SEQUENCE: 571
knnnnndyrr ynhrrnyygr hnumdnrynb nnvhyurucr hdbnbvnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnns rgyubrhnyy ysnnhnnnnb mr                        342

<210> SEQ ID NO 572
<211> LENGTH: 339
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, u, or g
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: modified_base
<222> LOCATION: (333)..(333)
<223> OTHER INFORMATION: a, c, u, or g
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
      description of substitutions and preferred embodiments

<400> SEQUENCE: 572
knsbbnwyar ywyrgugguk mgwrubysyr yyurucaygb rsrnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnykgrgy ubrhkyycch rwnvvksmr                            339

<210> SEQ ID NO 573
<211> LENGTH: 339
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:

<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 573
umcuyruyag uaurgugguk mguruyycyg ycugucaygy ggrnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnyggrgu uyrmkyyccy rasrrggag 339

<210> SEQ ID NO 574
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (3)..(6)
<223> OTHER INFORMATION: a, c, u, or g
<220> FEATURE:
<221> NAME/KEY: modified_base
<222> LOCATION: (12)..(13)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (24)..(24)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (29)..(32)
<223> OTHER INFORMATION: a, c, u, or g
<220> FEATURE:
<221> NAME/KEY: modified_base
<222> LOCATION: (34)..(34)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (44)..(319)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(334)
<223> OTHER INFORMATION: a, c, u, or g
<220> FEATURE:
<221> NAME/KEY: modified_base
<222> LOCATION: (336)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 574
gsnnnndurv ynnavnkcgd byynrnvbnn nnvnyyrcar mnbnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnb druucranyy yvnnhnnnnn yy 342

<210> SEQ ID NO 575
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 575
gsgsryrkrg yubasnkgdk uaravyahuu grcyrcarau cmarnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnyyydr uucraruyyv gkuryychyy 340

<210> SEQ ID NO 576
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 576
gggsryrkrg yuyasnugrk uagagcayuu gacugcarau cmarnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnyyyrr uucraauyyv gkurcycmyy 340

<210> SEQ ID NO 577
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(2)
<223> OTHER INFORMATION: a, c, u, or g
<220> FEATURE:
<221> NAME/KEY: modified_base
<222> LOCATION: (4)..(6)
<223> OTHER INFORMATION: a, c, u, or g
<220> FEATURE:
<221> NAME/KEY: modified_base
<222> LOCATION: (12)..(13)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (20)..(21)
<223> OTHER INFORMATION: a, c, u, or g
<220> FEATURE:
<221> NAME/KEY: modified_base
<222> LOCATION: (24)..(24)
<223> OTHER INFORMATION: a, c, u, or g
<220> FEATURE:
<221> NAME/KEY: modified_base
<222> LOCATION: (28)..(31)
<223> OTHER INFORMATION: a, c, u, or g
<220> FEATURE:
<221> NAME/KEY: modified_base
<222> LOCATION: (33)..(33)
<223> OTHER INFORMATION: a, c, u, or g
<220> FEATURE:
<221> NAME/KEY: modified_base
<222> LOCATION: (40)..(41)
<223> OTHER INFORMATION: a, c, u, or g
<220> FEATURE:
<221> NAME/KEY: modified_base
<222> LOCATION: (43)..(319)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (331)..(332)
<223> OTHER INFORMATION: a, c, u, or g
<220> FEATURE:
<221> NAME/KEY: modified_base
<222> LOCATION: (335)..(339)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
      description of substitutions and preferred embodiments

<400> SEQUENCE: 577
dnbnnnduvg bnnarnhggn nhanvvynnn nvnyubukrn nhnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnr ruuyvanyby nnbhnnnnnh d 341

<210> SEQ ID NO 578
<211> LENGTH: 340
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(5)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (27)..(28)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (45)..(317)
<223> OTHER INFORMATION: a, c, u, or g
<220> FEATURE:
<221> NAME/KEY: modified_base
<222> LOCATION: (331)..(331)

<223> OTHER INFORMATION: a, c, u, or g
<220> FEATURE:
<221> NAME/KEY: modified_base
<222> LOCATION: (335)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
      description of substitutions and preferred embodiments

<400> SEQUENCE: 578
kdbnnydugg ynbarkmggd navvrynnhb vryubukrrb hvdvnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnndrr uuyvadybyh nbhdnnvhmd 340

<210> SEQ ID NO 579
<211> LENGTH: 340
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (27)..(28)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (45)..(317)
<223> OTHER INFORMATION: a, c, u, or g
<220> FEATURE:
<221> NAME/KEY: modified_base
<222> LOCATION: (331)..(331)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
      description of substitutions and preferred embodiments

<400> SEQUENCE: 579
kdbnvydugg ydbarumggk navvrynnws rryubukrab hsdvnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnndrr uuyvadysyh nbhdbnvhmk 340

<210> SEQ ID NO 580
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(2)
<223> OTHER INFORMATION: a, c, u, or g
<220> FEATURE:
<221> NAME/KEY: modified_base
<222> LOCATION: (5)..(6)
<223> OTHER INFORMATION: a, c, u, or g
<220> FEATURE:
<221> NAME/KEY: modified_base
<222> LOCATION: (9)..(9)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (20)..(21)
<223> OTHER INFORMATION: a, c, u, or g
<220> FEATURE:
<221> NAME/KEY: modified_base
<222> LOCATION: (26)..(27)
<223> OTHER INFORMATION: a, c, u, or g
<220> FEATURE:
<221> NAME/KEY: modified_base
<222> LOCATION: (29)..(33)
<223> OTHER INFORMATION: a, c, u, or g
<220> FEATURE:
<221> NAME/KEY: modified_base
<222> LOCATION: (41)..(41)
<223> OTHER INFORMATION: a, c, u, or g
<220> FEATURE:
<221> NAME/KEY: modified_base
<222> LOCATION: (44)..(318)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (320)..(321)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(336)
<223> OTHER INFORMATION: a, c, u, or g
<220> FEATURE:
<221> NAME/KEY: modified_base
<222> LOCATION: (340)..(341)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:

<223> OTHER INFORMATION: See specification as filed for detailed
description of substitutions and preferred embodiments

<400> SEQUENCE: 580
nnbbnndunr wnhrdnhygn nbhrdnnynn nnnvyuyusr nbvnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnbn nryubrwnyy hbnnnndvvn nd 342

<210> SEQ ID NO 581
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(2)
<223> OTHER INFORMATION: a, c, u, or g
<220> FEATURE:
<221> NAME/KEY: modified_base
<222> LOCATION: (5)..(5)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (20)..(20)
<223> OTHER INFORMATION: a, c, u, or g
<220> FEATURE:
<221> NAME/KEY: modified_base
<222> LOCATION: (29)..(29)
<223> OTHER INFORMATION: a, c, u, or g
<220> FEATURE:
<221> NAME/KEY: modified_base
<222> LOCATION: (31)..(31)
<223> OTHER INFORMATION: a, c, u, or g
<220> FEATURE:
<221> NAME/KEY: modified_base
<222> LOCATION: (39)..(39)
<223> OTHER INFORMATION: a, c, u, or g
<220> FEATURE:
<221> NAME/KEY: modified_base
<222> LOCATION: (43)..(43)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (45)..(316)
<223> OTHER INFORMATION: a, c, u, or g
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (326)..(326)
<223> OTHER INFORMATION: a, c, u, or g
<220> FEATURE:
<221> NAME/KEY: modified_base
<222> LOCATION: (334)..(334)
<223> OTHER INFORMATION: a, c, u, or g
<220> FEATURE:
<221> NAME/KEY: modified_base
<222> LOCATION: (338)..(338)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 581
nnbynbdyrg unurdyagbn krrvvywbnb nvyuyusanb vhndnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnydnr yubrwnychb rkbndvvnvd 340

<210> SEQ ID NO 582
<211> LENGTH: 339
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(1)
<223> OTHER INFORMATION: a, c, u, or g
<220> FEATURE:
<221> NAME/KEY: modified_base
<222> LOCATION: (28)..(28)
<223> OTHER INFORMATION: a, c, u, or g
<220> FEATURE:
<221> NAME/KEY: modified_base
<222> LOCATION: (30)..(30)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: modified_base
<222> LOCATION: (318)..(318)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 582
ncsydbrugg usuakygshk rrsaywbnkn syuyucahbv mndnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnbyrnry uyrwyucyyr gbnwrsraw 339

<210> SEQ ID NO 583
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(7)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (21)..(22)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (29)..(34)
<223> OTHER INFORMATION: a, c, u, or g
<220> FEATURE:
<221> NAME/KEY: modified_base
<222> LOCATION: (41)..(319)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(338)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 583
rbvnnnnuvr ynyrrnyubd nnuadnrynn nnnnyybccv nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnv vsubbrwnhc bbnnnnnnbb yw 342

<210> SEQ ID NO 584

<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (5)..(5)
<223> OTHER INFORMATION: a, c, u, or g
<220> FEATURE:
<221> NAME/KEY: modified_base
<222> LOCATION: (28)..(28)
<223> OTHER INFORMATION: a, c, u, or g
<220> FEATURE:
<221> NAME/KEY: modified_base
<222> LOCATION: (39)..(40)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (317)..(317)
<223> OTHER INFORMATION: a, c, u, or g
<220> FEATURE:
<221> NAME/KEY: modified_base
<222> LOCATION: (335)..(335)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 584
gbvbnsvurr udyrrdcggk dadmaudnhh rhyubccann ynkdnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnbnrgs uubrwuuccy ksbsnvygca 340

<210> SEQ ID NO 585
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (5)..(5)
<223> OTHER INFORMATION: a, c, u, or g
<220> FEATURE:
<221> NAME/KEY: modified_base
<222> LOCATION: (28)..(28)
<223> OTHER INFORMATION: a, c, u, or g
<220> FEATURE:
<221> NAME/KEY: modified_base
<222> LOCATION: (39)..(39)

<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (335)..(335)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 585
gyvynsvurr udyrrwcggk kadmaudnhh rhyubccand ynkdnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnbvrgs uuyrwuuccy ksbsnvygca 340

<210> SEQ ID NO 586
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(7)
<223> OTHER INFORMATION: a, c, u, or g
<220> FEATURE:
<221> NAME/KEY: modified_base
<222> LOCATION: (13)..(13)
<223> OTHER INFORMATION: a, c, u, or g
<220> FEATURE:
<221> NAME/KEY: modified_base
<222> LOCATION: (25)..(26)
<223> OTHER INFORMATION: a, c, u, or g
<220> FEATURE:
<221> NAME/KEY: modified_base
<222> LOCATION: (29)..(31)
<223> OTHER INFORMATION: a, c, u, or g
<220> FEATURE:
<221> NAME/KEY: modified_base
<222> LOCATION: (34)..(34)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (45)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(320)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (332)..(333)
<223> OTHER INFORMATION: a, c, u, or g
<220> FEATURE:
<221> NAME/KEY: modified_base
<222> LOCATION: (336)..(338)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 586
kgynnnnduv gbnhagbyug ghyannvynn ndbnyugugr hnvhnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnn rgyucranyc ynnbhnnnvr ym 342

<210> SEQ ID NO 587
<211> LENGTH: 339
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 587
gchrugaybg uayagkgguu asyacucugy gyuguggccr cagnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnncwyggy ucraaucyga gucaygrca 339

<210> SEQ ID NO 588
<211> LENGTH: 339

```
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
      description of substitutions and preferred embodiments

<400> SEQUENCE: 588

gcmrugayyg uauagugguu agyacucugy gyuguggccr cagnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnncwyggu ucraaucyga gucaygrca                            339

<210> SEQ ID NO 589
<211> LENGTH: 342
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: a, c, u, or g
<220> FEATURE:
<221> NAME/KEY: modified_base
<222> LOCATION: (4)..(5)
<223> OTHER INFORMATION: a, c, u, or g
<220> FEATURE:
<221> NAME/KEY: modified_base
<222> LOCATION: (7)..(7)
<223> OTHER INFORMATION: a, c, u, or g
<220> FEATURE:
<221> NAME/KEY: modified_base
<222> LOCATION: (17)..(17)
<223> OTHER INFORMATION: a, c, u, or g
<220> FEATURE:
<221> NAME/KEY: modified_base
<222> LOCATION: (31)..(32)
<223> OTHER INFORMATION: a, c, u, or g
<220> FEATURE:
<221> NAME/KEY: modified_base
<222> LOCATION: (34)..(34)
<223> OTHER INFORMATION: a, c, u, or g
<220> FEATURE:
<221> NAME/KEY: modified_base
<222> LOCATION: (37)..(37)
<223> OTHER INFORMATION: a, c, u, or g
<220> FEATURE:
<221> NAME/KEY: modified_base
<222> LOCATION: (42)..(320)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
```

<220> FEATURE:
<221> NAME/KEY: modified_base
<222> LOCATION: (328)..(329)
<223> OTHER INFORMATION: a, c, u, or g
<220> FEATURE:
<221> NAME/KEY: modified_base
<222> LOCATION: (332)..(334)
<223> OTHER INFORMATION: a, c, u, or g
<220> FEATURE:
<221> NAME/KEY: modified_base
<222> LOCATION: (336)..(339)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 589
nvsnnbndur gybyrrnywg gbhrdvrydb nnbnyunaur annnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn dsywydannc hnnnhnnnns ba 342

<210> SEQ ID NO 590
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (326)..(327)
<223> OTHER INFORMATION: a, c, u, or g
<220> FEATURE:
<221> NAME/KEY: modified_base
<222> LOCATION: (335)..(335)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 590
gsyybrkurg ykyrruyggy hagmgcrygk urcudauaay ryyrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnryrrs ywydanncyc rymyngrsca 340

<210> SEQ ID NO 591
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 591
gsyysrkurg ykcaruyggy hagmgcgygg urcudauaay rcyrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnngygrg yucrabhcyc rymybgrsca 340

<210> SEQ ID NO 592
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(1)
<223> OTHER INFORMATION: a, c, u, or g
<220> FEATURE:
<221> NAME/KEY: modified_base
<222> LOCATION: (3)..(6)
<223> OTHER INFORMATION: a, c, u, or g
<220> FEATURE:
<221> NAME/KEY: modified_base
<222> LOCATION: (11)..(12)
<223> OTHER INFORMATION: a, c, u, or g
<220> FEATURE:
<221> NAME/KEY: modified_base
<222> LOCATION: (16)..(17)
<223> OTHER INFORMATION: a, c, u, or g
<220> FEATURE:
<221> NAME/KEY: modified_base
<222> LOCATION: (21)..(22)
<223> OTHER INFORMATION: a, c, u, or g
<220> FEATURE:
<221> NAME/KEY: modified_base
<222> LOCATION: (25)..(26)
<223> OTHER INFORMATION: a, c, u, or g
<220> FEATURE:
<221> NAME/KEY: modified_base
<222> LOCATION: (28)..(31)
<223> OTHER INFORMATION: a, c, u, or g
<220> FEATURE:
<221> NAME/KEY: modified_base
<222> LOCATION: (41)..(41)
<223> OTHER INFORMATION: a, c, u, or g
<220> FEATURE:
<221> NAME/KEY: modified_base
<222> LOCATION: (43)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (318)..(319)
<223> OTHER INFORMATION: a, c, u, or g
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (331)..(332)
<223> OTHER INFORMATION: a, c, u, or g
<220> FEATURE:
<221> NAME/KEY: modified_base
<222> LOCATION: (335)..(338)
<223> OTHER INFORMATION: a, c, u, or g
<220> FEATURE:
<221> NAME/KEY: modified_base
<222> LOCATION: (340)..(340)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 592
nbnnnndurs nnbarnnhgg nnddnnbnnn nvdhycauah nbnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnvnnr gdusdanhmy nnbhnnnnvn w 341

<210> SEQ ID NO 593
<211> LENGTH: 339
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(4)
<223> OTHER INFORMATION: a, c, u, or g
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 593
rbcnbvkurg ygcagydggh agyryryyrg kyycauaahy yvrnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnsdkrgd usdadmmymw smbvbgsya 339

<210> SEQ ID NO 594
<211> LENGTH: 339
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 594
rschbvkurg ygcagydggh agcryryyrg kyycauaayc yrrnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnswkrgw usdadmcymw smbvkgsya 339

<210> SEQ ID NO 595
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(7)
<223> OTHER INFORMATION: a, c, u, or g
<220> FEATURE:
<221> NAME/KEY: modified_base
<222> LOCATION: (9)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (23)..(23)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (28)..(34)
<223> OTHER INFORMATION: a, c, u, or g
<220> FEATURE:
<221> NAME/KEY: modified_base
<222> LOCATION: (37)..(37)
<223> OTHER INFORMATION: a, c, u, or g
<220> FEATURE:
<221> NAME/KEY: modified_base
<222> LOCATION: (41)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(320)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (332)..(333)
<223> OTHER INFORMATION: a, c, u, or g
<220> FEATURE:
<221> NAME/KEY: modified_base
<222> LOCATION: (335)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed description of substitutions and preferred embodiments

<400> SEQUENCE: 595
vnnnnnnunn nnvrrnhhgk hhndhnvnnn nnnnhynard nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnn vbyuhvanym bnnbnnnnnn br 342

<210> SEQ ID NO 596
<211> LENGTH: 342
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (33)..(33)
<223> OTHER INFORMATION: a, c, u, or g
<220> FEATURE:
<221> NAME/KEY: modified_base
<222> LOCATION: (41)..(41)
<223> OTHER INFORMATION: a, c, u, or g
<220> FEATURE:
<221> NAME/KEY: modified_base
<222> LOCATION: (43)..(43)
<223> OTHER INFORMATION: a, c, u, or g
<220> FEATURE:

<221> NAME/KEY: modified_base
<222> LOCATION: (46)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: modified_base
<222> LOCATION: (340)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 596
rbbvvndurk hhsrrbhygk hhurwbrhdb hdnryuhard nynhdnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnv gbyuhvanym ybnbbnbbvn ya 342

<210> SEQ ID NO 597
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (33)..(33)
<223> OTHER INFORMATION: a, c, u, or g
<220> FEATURE:
<221> NAME/KEY: modified_base
<222> LOCATION: (43)..(43)
<223> OTHER INFORMATION: a, c, u, or g
<220> FEATURE:
<221> NAME/KEY: modified_base
<222> LOCATION: (46)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: modified_base
<222> LOCATION: (340)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
      description of substitutions and preferred embodiments

<400> SEQUENCE: 597
rbbvvndurk hhsrrbhygk hhurwkrhdb hdnryuhard hynhdnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnv gbyuhvavym ybnbynbbvn ya 342

<210> SEQ ID NO 598
<211> LENGTH: 342
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(7)
<223> OTHER INFORMATION: a, c, u, or g
<220> FEATURE:
<221> NAME/KEY: modified_base
<222> LOCATION: (11)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (26)..(26)
<223> OTHER INFORMATION: a, c, u, or g
<220> FEATURE:
<221> NAME/KEY: modified_base
<222> LOCATION: (30)..(32)
<223> OTHER INFORMATION: a, c, u, or g
<220> FEATURE:
<221> NAME/KEY: modified_base
<222> LOCATION: (44)..(320)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (328)..(328)

<223> OTHER INFORMATION: a, c, u, or g
<220> FEATURE:
<221> NAME/KEY: modified_base
<222> LOCATION: (332)..(333)
<223> OTHER INFORMATION: a, c, u, or g
<220> FEATURE:
<221> NAME/KEY: modified_base
<222> LOCATION: (335)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 598

```
nnnnnnnurs nnharnhwrr nuudrnrydn nnsvyyyuum mbvnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn vryuyrwnhy bnnbnnnnnn hd                        342
```

<210> SEQ ID NO 599
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(1)
<223> OTHER INFORMATION: a, c, u, or g
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (11)..(11)
<223> OTHER INFORMATION: a, c, u, or g
<220> FEATURE:
<221> NAME/KEY: modified_base
<222> LOCATION: (29)..(29)
<223> OTHER INFORMATION: a, c, u, or g
<220> FEATURE:
<221> NAME/KEY: modified_base
<222> LOCATION: (43)..(43)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (45)..(317)
<223> OTHER INFORMATION: a, c, u, or g
<220> FEATURE:
<221> NAME/KEY: modified_base
<222> LOCATION: (331)..(331)
<223> OTHER INFORMATION: a, c, u, or g
<220> FEATURE:
<221> NAME/KEY: modified_base
<222> LOCATION: (333)..(334)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 599
nhvbdnvkrs nhharbhrrb udrdrydbnd gryyyuummy mhndnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnrgr yuyrwbyysy nbnnhndrhr 340

<210> SEQ ID NO 600
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (45)..(316)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 600
vhvbrdvkas cwharuhrrb udrwrcrkvd gacuyuumau chswnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnndrgr yuyrwkyysy hbnhynkryr 340

<210> SEQ ID NO 601
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(6)

<223> OTHER INFORMATION: a, c, u, or g
<220> FEATURE:
<221> NAME/KEY: modified_base
<222> LOCATION: (29)..(31)
<223> OTHER INFORMATION: a, c, u, or g
<220> FEATURE:
<221> NAME/KEY: modified_base
<222> LOCATION: (33)..(33)
<223> OTHER INFORMATION: a, c, u, or g
<220> FEATURE:
<221> NAME/KEY: modified_base
<222> LOCATION: (41)..(41)
<223> OTHER INFORMATION: a, c, u, or g
<220> FEATURE:
<221> NAME/KEY: modified_base
<222> LOCATION: (43)..(318)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (331)..(332)
<223> OTHER INFORMATION: a, c, u, or g
<220> FEATURE:
<221> NAME/KEY: modified_base
<222> LOCATION: (335)..(338)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 601
kbbnnnduag yyyarhyugg bwwgrryrnn nbnyygaarv nbnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnbd guucranych nnbhnnnnvm a 341

<210> SEQ ID NO 602
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 602
kbyvwrruwg yyyaruuggs uagrrydykr brcygaarry syhmnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnyckgg uucrayycys gguywbrvma 340

<210> SEQ ID NO 603
<211> LENGTH: 339
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed description of substitutions and preferred embodiments

<400> SEQUENCE: 603
gcyrarauwg cucaruuggg agagyguuas acygaagauc uwmnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnycuggu ucrayycygg guuucrvca 339

<210> SEQ ID NO 604
<211> LENGTH: 342
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (4)..(6)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (29)..(34)
<223> OTHER INFORMATION: a, c, u, or g
<220> FEATURE:
<221> NAME/KEY: modified_base
<222> LOCATION: (37)..(37)

<223> OTHER INFORMATION: a, c, u, or g
<220> FEATURE:
<221> NAME/KEY: modified_base
<222> LOCATION: (41)..(320)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (331)..(334)
<223> OTHER INFORMATION: a, c, u, or g
<220> FEATURE:
<221> NAME/KEY: modified_base
<222> LOCATION: (336)..(338)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 604
sksnnnduvg bbyagnyygb nyyrdvvynn nnnnhunggr nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn dguucranyc nnnnhnnnbm sm 342

<210> SEQ ID NO 605
<211> LENGTH: 338
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (39)..(39)
<223> OTHER INFORMATION: a, c, u, or g
<220> FEATURE:
<221> NAME/KEY: modified_base
<222> LOCATION: (43)..(313)
<223> OTHER INFORMATION: a, c, u, or g
<220> FEATURE:
<221> NAME/KEY: misc_feature
<222> LOCATION: (43)..(313)
<223> OTHER INFORMATION: This region may encompass 1-271 nucleotides
<220> FEATURE:
<221> NAME/KEY: misc_feature
<222> LOCATION: (1)..(338)
<223> OTHER INFORMATION: May or may not be present
<220> FEATURE:
<223> OTHER INFORMATION: See specification as filed for detailed
description of substitutions and preferred embodiments

<400> SEQUENCE: 605
ggcusguugg kcuagkgbur ugruucucrs yuhggrysnr agnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnncyggguu caaaucvyrg asgagccc 338

<210> SEQ ID NO 606
<211> LENGTH: 338
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (43)..(313)
<223> OTHER INFORMATION: a, c, u, or g
<220> FEATURE:
<221> NAME/KEY: misc_feature
<222> LOCATION: (43)..(313)
<223> OTHER INFORMATION: This region may encompass 1-271 nucleotides
<220> FEATURE:
<221> NAME/KEY: misc_feature
<222> LOCATION: (1)..(338)
<223> OTHER INFORMATION: May or may not be present
<220> FEATURE:
<223> OTHER INFORMATION: See specification as filed for detailed
description of substitutions and preferred embodiments

<400> SEQUENCE: 606
ggcucguugg ucuagkggur ugruucucgs uuhggrysbg agnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnccggguu caaaucccgg acgagccc 338

<210> SEQ ID NO 607
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(7)
<223> OTHER INFORMATION: a, c, u, or g
<220> FEATURE:
<221> NAME/KEY: modified_base
<222> LOCATION: (9)..(13)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (25)..(28)
<223> OTHER INFORMATION: a, c, u, or g
<220> FEATURE:
<221> NAME/KEY: modified_base
<222> LOCATION: (30)..(34)
<223> OTHER INFORMATION: a, c, u, or g
<220> FEATURE:
<221> NAME/KEY: modified_base
<222> LOCATION: (37)..(37)

<223> OTHER INFORMATION: a, c, u, or g
<220> FEATURE:
<221> NAME/KEY: modified_base
<222> LOCATION: (42)..(320)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (332)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 607
dnnnnnnynn nnnarnbhgg nbbannnndn nnnnyynswr mnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn rkuuyradyc ynnnnnnnnn bd 342

<210> SEQ ID NO 608
<211> LENGTH: 341
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(5)
<223> OTHER INFORMATION: a, c, u, or g
<220> FEATURE:
<221> NAME/KEY: modified_base
<222> LOCATION: (36)..(36)
<223> OTHER INFORMATION: a, c, u, or g
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (331)..(331)
<223> OTHER INFORMATION: a, c, u, or g
<220> FEATURE:
<221> NAME/KEY: modified_base
<222> LOCATION: (335)..(336)
<223> OTHER INFORMATION: a, c, u, or g
<220> FEATURE:
<221> NAME/KEY: modified_base
<222> LOCATION: (338)..(339)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed description of substitutions and preferred embodiments

<400> SEQUENCE: 608
knnnnbdurg chsarkbugg uuavdghrdb kdrcynswra ybmvdnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnvyng kuuyradycc nrbhnnbnny d 341

<210> SEQ ID NO 609
<211> LENGTH: 341
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2)..(3)
<223> OTHER INFORMATION: a, c, u, or g
<220> FEATURE:
<221> NAME/KEY: modified_base
<222> LOCATION: (5)..(5)
<223> OTHER INFORMATION: a, c, u, or g
<220> FEATURE:
<221> NAME/KEY: modified_base
<222> LOCATION: (36)..(36)
<223> OTHER INFORMATION: a, c, u, or g
<220> FEATURE:
<221> NAME/KEY: modified_base
<222> LOCATION: (46)..(316)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (335)..(336)
<223> OTHER INFORMATION: a, c, u, or g
<220> FEATURE:
<221> NAME/KEY: modified_base
<222> LOCATION: (338)..(339)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed description of substitutions and preferred embodiments

<400> SEQUENCE: 609
knndnbrurg chsarkcugg uuavdghrwy krrcunswra yymrdnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnvydg guuyraaycc hrbynnynny k 341

<210> SEQ ID NO 610
<211> LENGTH: 341

<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (4)..(7)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (25)..(25)
<223> OTHER INFORMATION: a, c, u, or g
<220> FEATURE:
<221> NAME/KEY: modified_base
<222> LOCATION: (29)..(31)
<223> OTHER INFORMATION: a, c, u, or g
<220> FEATURE:
<221> NAME/KEY: modified_base
<222> LOCATION: (33)..(33)
<223> OTHER INFORMATION: a, c, u, or g
<220> FEATURE:
<221> NAME/KEY: modified_base
<222> LOCATION: (36)..(36)
<223> OTHER INFORMATION: a, c, u, or g
<220> FEATURE:
<221> NAME/KEY: modified_base
<222> LOCATION: (41)..(41)
<223> OTHER INFORMATION: a, c, u, or g
<220> FEATURE:
<221> NAME/KEY: modified_base
<222> LOCATION: (43)..(319)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (331)..(337)
<223> OTHER INFORMATION: a, c, u, or g
<220> FEATURE:
<221> NAME/KEY: modified_base
<222> LOCATION: (341)..(341)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed description of substitutions and preferred embodiments

<400> SEQUENCE: 610
rbbnnnnurg ynhadnhykg hyrdnryrnn nsnhynguwa nsnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnd gwyyvanbyh nnnnnnnrvy n 341

<210> SEQ ID NO 611
<211> LENGTH: 340
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, u, or g
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (24)..(24)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (317)..(317)
<223> OTHER INFORMATION: a, c, u, or g
<220> FEATURE:
<221> NAME/KEY: modified_base
<222> LOCATION: (326)..(326)
<223> OTHER INFORMATION: a, c, u, or g
<220> FEATURE:
<221> NAME/KEY: modified_base
<222> LOCATION: (331)..(332)
<223> OTHER INFORMATION: a, c, u, or g
<220> FEATURE:
<221> NAME/KEY: modified_base
<222> LOCATION: (334)..(334)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
      description of substitutions and preferred embodiments

<400> SEQUENCE: 611
rbbnbnduvg ynharbyggh yrdnryryhb sbcyhguwav svdrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnvndrg wuyvanbyyh nnbndnrvyb 340

<210> SEQ ID NO 612
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(4)
<223> OTHER INFORMATION: a, c, u, or g
<220> FEATURE:
<221> NAME/KEY: modified_base
<222> LOCATION: (6)..(6)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (24)..(24)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (326)..(326)
<223> OTHER INFORMATION: a, c, u, or g
<220> FEATURE:
<221> NAME/KEY: modified_base
<222> LOCATION: (332)..(332)
<223> OTHER INFORMATION: a, c, u, or g
<220> FEATURE:
<221> NAME/KEY: modified_base
<222> LOCATION: (334)..(334)
<223> OTHER INFORMATION: a, c, u, or g
<220> FEATURE:
<221> NAME/KEY: modified_base
<222> LOCATION: (336)..(336)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 612
rsynbnduvg ynharbuggh yrdnryryhk sbcyhguaav smdrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnvhdrg wuyvanbyyh dnbndnrsyu 340

<210> SEQ ID NO 613
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (4)..(6)
<223> OTHER INFORMATION: a, c, u, or g
<220> FEATURE:
<221> NAME/KEY: modified_base
<222> LOCATION: (29)..(32)
<223> OTHER INFORMATION: a, c, u, or g
<220> FEATURE:
<221> NAME/KEY: modified_base
<222> LOCATION: (34)..(34)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (44)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(319)
<223> OTHER INFORMATION: a, c, u, or g
<220> FEATURE:
<221> NAME/KEY: modified_base
<222> LOCATION: (321)..(321)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: modified_base
<222> LOCATION: (336)..(338)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed description of substitutions and preferred embodiments

<400> SEQUENCE: 613
rvvnnndurr ybhhrhyhgg hyuadvvynn nnrnbuccav anbnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnr nguucranyc hynbhnnnbb hd 342

<210> SEQ ID NO 614
<211> LENGTH: 339
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)

<223> OTHER INFORMATION: May or may not be present
<220> FEATURE:
<223> OTHER INFORMATION: See specification as filed for detailed
description of substitutions and preferred embodiments

<400> SEQUENCE: 614
grmmkvrkgg ysmaryuggh arssykkybr rsuccasakb vrwnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnsygkgu ucradycmcr kyksbgyma 339

<210> SEQ ID NO 615
<211> LENGTH: 339
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (44)..(314)
<223> OTHER INFORMATION: a, c, u, or g
<220> FEATURE:
<221> NAME/KEY: misc_feature
<222> LOCATION: (44)..(314)
<223> OTHER INFORMATION: This region may encompass 1-271 nucleotides
<220> FEATURE:
<221> NAME/KEY: misc_feature
<222> LOCATION: (1)..(339)
<223> OTHER INFORMATION: May or may not be present
<220> FEATURE:
<223> OTHER INFORMATION: See specification as filed for detailed
description of substitutions and preferred embodiments

<400> SEQUENCE: 615
grmmkvrkgg ysmaryuggh arssykkybr rsuccasakb vrwnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnsygkgu ucradycmcr kyksbgyma 339

<210> SEQ ID NO 616
<211> LENGTH: 342
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (3)..(6)
<223> OTHER INFORMATION: a, c, u, or g
<220> FEATURE:
<221> NAME/KEY: modified_base
<222> LOCATION: (9)..(10)
<223> OTHER INFORMATION: a, c, u, or g
<220> FEATURE:
<221> NAME/KEY: modified_base
<222> LOCATION: (12)..(13)
<223> OTHER INFORMATION: a, c, u, or g
<220> FEATURE:
<221> NAME/KEY: modified_base
<222> LOCATION: (16)..(16)
<223> OTHER INFORMATION: a, c, u, or g
<220> FEATURE:
<221> NAME/KEY: modified_base
<222> LOCATION: (25)..(26)
<223> OTHER INFORMATION: a, c, u, or g
<220> FEATURE:
<221> NAME/KEY: modified_base
<222> LOCATION: (30)..(32)
<223> OTHER INFORMATION: a, c, u, or g
<220> FEATURE:
<221> NAME/KEY: modified_base
<222> LOCATION: (42)..(42)
<223> OTHER INFORMATION: a, c, u, or g
<220> FEATURE:
<221> NAME/KEY: modified_base
<222> LOCATION: (44)..(317)
<223> OTHER INFORMATION: a, c, u, or g
<220> FEATURE:
<221> NAME/KEY: misc_feature
<222> LOCATION: (47)..(317)
<223> OTHER INFORMATION: This region may encompass 1-271 nucleotides
<220> FEATURE:
<221> NAME/KEY: modified_base
<222> LOCATION: (319)..(320)
<223> OTHER INFORMATION: a, c, u, or g
<220> FEATURE:
<221> NAME/KEY: modified_base
<222> LOCATION: (328)..(328)
<223> OTHER INFORMATION: a, c, u, or g
<220> FEATURE:
<221> NAME/KEY: modified_base
<222> LOCATION: (332)..(333)
<223> OTHER INFORMATION: a, c, u, or g
<220> FEATURE:
<221> NAME/KEY: modified_base
<222> LOCATION: (336)..(340)
<223> OTHER INFORMATION: a, c, u, or g
<220> FEATURE:
<221> NAME/KEY: misc_feature
<222> LOCATION: (1)..(342)
<223> OTHER INFORMATION: May or may not be present
<220> FEATURE:
<223> OTHER INFORMATION: See specification as filed for detailed
description of substitutions and preferred embodiments

<400> SEQUENCE: 616
bbnnnndunn ynnarnyugs yhwrnnrbdn nnrdcuruar vnynnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnvnn vgwuyranuc bnnbhnnnnn vd 342

<210> SEQ ID NO 617
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (336)..(336)

<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed description of substitutions and preferred embodiments

<400> SEQUENCE: 617
bbkkbdauag yucagbugsy uagagydkwk racuruagrk ymwknnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnscugg wuyrahucyr rsubsnmsvd 340

<210> SEQ ID NO 618
<211> LENGTH: 340
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed description of substitutions and preferred embodiments

<400> SEQUENCE: 618
bbkksdauag yucagyuggy uagagcdkwk gacuruagrk ymwknnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnscugg uuyrawuccr rsuysdmsva 340

<210> SEQ ID NO 619
<211> LENGTH: 341
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2)..(2)
<223> OTHER INFORMATION: a, c, u, or g
<220> FEATURE:
<221> NAME/KEY: modified_base
<222> LOCATION: (4)..(7)
<223> OTHER INFORMATION: a, c, u, or g
<220> FEATURE:
<221> NAME/KEY: modified_base
<222> LOCATION: (12)..(12)
<223> OTHER INFORMATION: a, c, u, or g
<220> FEATURE:
<221> NAME/KEY: modified_base
<222> LOCATION: (15)..(16)
<223> OTHER INFORMATION: a, c, u, or g
<220> FEATURE:
<221> NAME/KEY: modified_base
<222> LOCATION: (21)..(21)
<223> OTHER INFORMATION: a, c, u, or g
<220> FEATURE:
<221> NAME/KEY: modified_base
<222> LOCATION: (24)..(25)
<223> OTHER INFORMATION: a, c, u, or g
<220> FEATURE:
<221> NAME/KEY: modified_base
<222> LOCATION: (28)..(28)
<223> OTHER INFORMATION: a, c, u, or g
<220> FEATURE:
<221> NAME/KEY: modified_base
<222> LOCATION: (30)..(33)
<223> OTHER INFORMATION: a, c, u, or g
<220> FEATURE:
<221> NAME/KEY: modified_base
<222> LOCATION: (36)..(36)
<223> OTHER INFORMATION: a, c, u, or g
<220> FEATURE:
<221> NAME/KEY: modified_base
<222> LOCATION: (40)..(319)
<223> OTHER INFORMATION: a, c, u, or g
<220> FEATURE:
<221> NAME/KEY: misc_feature
<222> LOCATION: (46)..(316)
<223> OTHER INFORMATION: This region may encompass 1-271 nucleotides
<220> FEATURE:
<221> NAME/KEY: modified_base
<222> LOCATION: (327)..(327)
<223> OTHER INFORMATION: a, c, u, or g
<220> FEATURE:
<221> NAME/KEY: modified_base
<222> LOCATION: (330)..(339)
<223> OTHER INFORMATION: a, c, u, or g
<220> FEATURE:
<221> NAME/KEY: misc_feature
<222> LOCATION: (1)..(341)
<223> OTHER INFORMATION: May or may not be present
<220> FEATURE:
<223> OTHER INFORMATION: See specification as filed for detailed
description of substitutions and preferred embodiments

<400> SEQUENCE: 619
dndnnnnuvr ynbrnnhugk nyannrynbn nnnhunacrn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnd rdubranhyn nnnnnnnnny v 341

<210> SEQ ID NO 620
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (15)..(16)
<223> OTHER INFORMATION: a, c, u, or g
<220> FEATURE:
<221> NAME/KEY: modified_base
<222> LOCATION: (24)..(24)

<223> OTHER INFORMATION: a, c, u, or g
<220> FEATURE:
<221> NAME/KEY: modified_base
<222> LOCATION: (27)..(27)
<223> OTHER INFORMATION: a, c, u, or g
<220> FEATURE:
<221> NAME/KEY: modified_base
<222> LOCATION: (29)..(30)
<223> OTHER INFORMATION: a, c, u, or g
<220> FEATURE:
<221> NAME/KEY: modified_base
<222> LOCATION: (41)..(43)
<223> OTHER INFORMATION: a, c, u, or g
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (317)..(318)
<223> OTHER INFORMATION: a, c, u, or g
<220> FEATURE:
<221> NAME/KEY: modified_base
<222> LOCATION: (326)..(326)
<223> OTHER INFORMATION: a, c, u, or g
<220> FEATURE:
<221> NAME/KEY: modified_base
<222> LOCATION: (330)..(330)
<223> OTHER INFORMATION: a, c, u, or g
<220> FEATURE:
<221> NAME/KEY: modified_base
<222> LOCATION: (333)..(333)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 620
kbkbshdurr ydbrnnhgku yadnrynynn dhyuhacrhk nnnrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnbnnrr dubranhybn dvndsdwvyv 340

<210> SEQ ID NO 621
<211> LENGTH: 340
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (45)..(315)
<223> OTHER INFORMATION: a, c, u, or g
<220> FEATURE:
<221> NAME/KEY: misc_feature
<222> LOCATION: (45)..(315)
<223> OTHER INFORMATION: This region may encompass 1-271 nucleotides
<220> FEATURE:
<221> NAME/KEY: modified_base
<222> LOCATION: (317)..(318)
<223> OTHER INFORMATION: a, c, u, or g
<220> FEATURE:
<221> NAME/KEY: modified_base
<222> LOCATION: (330)..(330)
<223> OTHER INFORMATION: a, c, u, or g
<220> FEATURE:
<221> NAME/KEY: misc_feature
<222> LOCATION: (1)..(340)
<223> OTHER INFORMATION: May or may not be present
<220> FEATURE:
<223> OTHER INFORMATION: See specification as filed for detailed
description of substitutions and preferred embodiments

<400> SEQUENCE: 621
kbkbsydurg ydbrbhugku yadhryvyhh dyyuhacahk hddrnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnbnngr dubradhyyn dvhrsdwvya 340

<210> SEQ ID NO 622
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 622
ggcuccgugg cgcaauggau agcgcauugg acuucaaauu caaagguucc ggguucgagu 60
cccggcggag ucgcca 76

<210> SEQ ID NO 623
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 623
ggcuccgugg cgcaauggau agcgcauugg acuucaaauu caaagguucc ggguucgagu 60
cccggcggag ucgcca 76

<210> SEQ ID NO 624
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 624
ggcuccgugg cgcaauggau agcgcauugg acuucaaauu caaagguucc ggguucgagu 60
cccggcggag ucgcca 76

<210> SEQ ID NO 625
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 625
ggcuccgugg cgcaauggau agcgcauugg acuucaaauu caaagguucc ggguucgagu 60
cccggcggag ucgcca 76

<210> SEQ ID NO 626
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 626
ggcuccgugg cgcaauggau agcgcauugg acuucaaauu caaagguucc ggguucgagu 60
cccggcggag ucgcca 76

<210> SEQ ID NO 627
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
ggcuccgugg cgcaauggau agcgcauugg acuucaaauu caaagguucc ggguucgagu 60
cccggcggag ucgcca 76

<210> SEQ ID NO 628
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
ggcuccgugg cgcaauggau agcgcauugg acuucaaauu caaagguucc ggguucgagu 60
cccggcggag ucgcca 76

<210> SEQ ID NO 629
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 629
ggcuccgugg cgcaauggau agcgcauugg acuucaaauu caaagguucc ggguucgagu 60
cccggcggag ucgcca 76

<210> SEQ ID NO 630
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 630
ggcuccgugg cgcaauggau agcgcauugg acuucaaauu caaagguucc ggguucgagu 60
cccggcggag ucgcca 76

<210> SEQ ID NO 631
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 631
ggcuccgugg cgcaauggau agcgcauugg acuucaaauu caaagguucc ggguucgagu 60
cccggcggag ucgcca 76

<210> SEQ ID NO 632
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 632
ggcuccgugg cgcaauggau agcgcauugg acuucaaauu caaagguucc ggguucgagu 60
cccggcggag ucgcca 76

<210> SEQ ID NO 633
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 633
ggcuccgugg cgcaauggau agcgcauugg acuucaaauu caaagguucc ggguucgagu 60
cccggcggag ucgcca 76

<210> SEQ ID NO 634
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 634
ggcuccgugg cgcaauggau agcgcauugg acuucaaauu caaagguucc ggguucgagu 60
cccggcggag ucgcca 76

<210> SEQ ID NO 635
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 635
ggcuccgugg cgcaauggau agcgcauugg acuucaaauu caaagguucc ggguucgagu 60
cccggcggag ucgcca 76

<210> SEQ ID NO 636
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 636
ggcuccgugg cgcaauggau agcgcauugg acuucaaauu caaagguucc ggguucgagu 60
cccggcggag ucgcca 76

<210> SEQ ID NO 637
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 637
ggcuccgugg cgcaauggau agcgcauugg acuucaaauu caaagguucc ggguucgagu 60
cccggcggag ucgcca 76

<210> SEQ ID NO 638
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 638
ggcuccgugg cgcaauggau agcgcauugg acuucaaauu caaagguucc ggguucgagu 60
cccggcggag ucgcca 76

<210> SEQ ID NO 639
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 639
ggcuccgugg cgcaauggau agcgcauugg acuucaaauu caaagguucc ggguucgagu 60
cccggcggag ucgcca 76

<210> SEQ ID NO 640
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 640
ggcuccgugg cgcaauggau agcgcauugg acuucaaauu caaagguucc ggguucgagu 60
cccggcggag ucgcca 76

<210> SEQ ID NO 641
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 641
ggcuccgugg cgcaauggau agcgcauugg acuucaaauu caaagguucc ggguucgagu 60
cccggcggag ucgcca 76

<210> SEQ ID NO 642
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 642
ggcuccgugg cgcaauggau agcgcauugg acuucaaauu caaagguucc ggguucgagu 60
cccggcggag ucgcca 76

<210> SEQ ID NO 643
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 643
ggcuccgugg cgcaauggau agcgcauugg acuucaaauu caaagguucc ggguucgagu 60
cccggcggag ucgcca 76

<210> SEQ ID NO 644
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 644
ggcuccgugg cgcaauggau agcgcauugg acuucaaauu caaagguucc ggguucgagu 60
cccggcggag ucgcca 76

<210> SEQ ID NO 645
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 645
ggcuccgugg cgcaauggau agcgcauugg acuucaaauu caaagguucc ggguucgagu 60
cccggcggag ucgcca 76

<210> SEQ ID NO 646
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646
ggcuccgugg cgcaauggau agcgcauugg acuucaaauu caaagguucc ggguucgagu 60
cccggcggag ucgcca 76

<210> SEQ ID NO 647
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 647
ggcuccgugg cgcaauggau agcgcauugg acuucaaauu caaagguucc ggguucgagu 60
cccggcggag ucgcca 76

<210> SEQ ID NO 648
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 648
ggcuccgugg cgcaauggau agcgcauugg acuucaaauu caaagguucc ggguucgagu 60
cccggcggag ucgcca 76

<210> SEQ ID NO 649
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 649
ggcuccgugg cgcaauggau agcgcauugg acuucaaauu caaagguucc ggguucgagu 60
cccggcggag ucgcca 76

<210> SEQ ID NO 650
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 650
ggcuccgugg cgcaauggau agcgcauugg acuucaaauu caaagguucc ggguucgagu 60
cccggcggag ucgcca 76

<210> SEQ ID NO 651
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 651
ggcuccgugg cgcaauggau agcgcauugg acuucaaauu caaagguucc ggguucgagu 60
cccggcggag ucgcca 76

<210> SEQ ID NO 652
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 652
ggcuccgugg cgcaauggau agcgcauugg acuucaaauu caaagguucc ggguucgagu 60
cccggcggag ucgcca 76

<210> SEQ ID NO 653
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 653
ggcuccgugg cgcaauggau agcgcauugg acuucaaauu caaagguucc ggguucgagu 60
cccggcggag ucgcca 76

<210> SEQ ID NO 654
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 654
ggcuccgugg cgcaauggau agcgcauugg acuucaaauu caaagguucc ggguucgagu 60
cccggcggag ucgcca 76

<210> SEQ ID NO 655
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 655
ggcuccgugg cgcaauggau agcgcauugg acuucaaauu caaagguucc ggguucgagu 60
cccggcggag ucgcca 76

<210> SEQ ID NO 656
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 656
ggcuccgugg cgcaauggau agcgcauugg acuucaaauu caaagguucc ggguucgagu 60
cccggcggag ucgcca 76

<210> SEQ ID NO 657

<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 657
ggcuccgugg cgcaauggau agcgcauugg acuucaaauu caaagguucc ggguucgagu 60
cccggcggag ucgcca 76

<210> SEQ ID NO 658
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 658
ggcuccgugg cgcaauggau agcgcauugg acuucaaauu caaagguucc ggguucgagu 60
cccggcggag ucgcca 76

<210> SEQ ID NO 659
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 659
ggcuccgugg cgcaauggau agcgcauugg acuucaaauu caaagguucc ggguucgagu 60
cccggcggag ucgcca 76

<210> SEQ ID NO 660
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 660
ggcuccgugg cgcaauggau agcgcauugg acuucaaauu caaagguucc ggguucgagu 60
cccggcggag ucgcca 76

<210> SEQ ID NO 661
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 661
ggcuccgugg cgcaauggau agcgcauugg acuucaaauu caaagguucc ggguucgagu 60
cccggcggag ucgcca 76

<210> SEQ ID NO 662
<211> LENGTH: 76
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 662
ggcuccgugg cgcaauggau agcgcauugg acuucaaauu caaagguucc ggguucgagu     60
cccggcggag ucgcca                                                     76

<210> SEQ ID NO 663
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
ggcuccgugg cgcaauggau agcgcauugg acuucaaauu caaagguucc ggguucgagu     60
cccggcggag ucgcca                                                     76

<210> SEQ ID NO 664
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
ggcuccgugg cgcaauggau agcgcauugg acuucaaauu caaagguucc ggguucgagu     60
cccggcggag ucgcca                                                     76

<210> SEQ ID NO 665
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
ggcuccgugg cgcaauggau agcgcauugg acuucaaauu caaagguucc ggguucgagu     60
cccggcggag ucgcca                                                     76

<210> SEQ ID NO 666
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
ggcuccgugg cgcaauggau agcgcauugg acuucaaauu caaagguucc ggguucgagu     60
cccggcggag ucgcca                                                     76

<210> SEQ ID NO 667
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
ggcuccgugg cgcaauggau agcgcauugg acuucaaauu caaagguucc ggguucgagu 60
cccggcggag ucgcca 76

<210> SEQ ID NO 668
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 668
ggcuccgugg cgcaauggau agcgcauugg acuucaaauu caaagguucc ggguucgagu 60
cccggcggag ucgcca 76

<210> SEQ ID NO 669
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 669
ggcuccgugg cgcaauggau agcgcauugg acuucaaauu caaagguucc ggguucgagu 60
cccggcggag ucgcca 76

<210> SEQ ID NO 670
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 670
ggcuccgugg cgcaauggau agcgcauugg acuucaaauu caaagguucc ggguucgagu 60
cccggcggag ucgcca 76

<210> SEQ ID NO 671
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 671
ggcuccgugg cgcaauggau agcgcauugg acuucaaauu caaagguucc ggguucgagu 60
cccggcggag ucgcca 76

<210> SEQ ID NO 672
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 672
ggcuccgugg cgcaauggau agcgcauugg acuucaaauu caaagguucc ggguucgagu 60
cccggcggag ucgcca 76

<210> SEQ ID NO 673
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 673
ggcuccgugg cgcaauggau agcgcauugg acuucaaauu caaagguucc ggguucgagu 60
cccggcggag ucgcca 76

<210> SEQ ID NO 674
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 674
ggcuccgugg cgcaauggau agcgcauugg acuucaaauu caaagguucc ggguucgagu 60
cccggcggag ucgcca 76

<210> SEQ ID NO 675
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 675
ggcuccgugg cgcaauggau agcgcauugg acuucaaauu caaagguucc ggguucgagu 60
cccggcggag ucgcca 76

<210> SEQ ID NO 676
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 676
ggcuccgugg cgcaauggau agcgcauugg acuucaaauu caaagguucc ggguucgagu 60
cccggcggag ucgcca 76

<210> SEQ ID NO 677
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 677
ggcuccgugg cgcaauggau agcgcauugg acuucaaauu caaagguucc ggguucgagu 60
cccggcggag ucgcca 76

<210> SEQ ID NO 678
<211> LENGTH: 76

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 678
ggcuccgugg cgcaauggau agcgcauugg acuucaaauu caaagguucc ggguucgagu 60
cccggcggag ucgcca 76

<210> SEQ ID NO 679
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 679
ggcuccgugg cgcaauggau agcgcauugg acuucaaauu caaagguucc ggguucgagu 60
cccggcggag ucgcca 76

<210> SEQ ID NO 680
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 680
ggcuccgugg cgcaauggau agcgcauugg acuucaaauu caaagguucc ggguucgagu 60
cccggcggag ucgcca 76

<210> SEQ ID NO 681
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 681
ggcuccgugg cgcaauggau agcgcauugg acuucaaauu caaagguucc ggguucgagu 60
cccggcggag ucgcca 76

<210> SEQ ID NO 682
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682
ggcuccgugg cgcaauggau agcgcauugg acuucaaauu caaagguucc ggguucgagu 60
cccggcggag ucgcca 76

<210> SEQ ID NO 683
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 683
ggcuccgugg cgcaauggau agcgcauugg acuucaaauu caaagguucc ggguucgagu 60
cccggcggag ucgcca 76

<210> SEQ ID NO 684
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 684
ggcuccgugg cgcaauggau agcgcauugg acuucaaauu caaagguucc ggguucgagu 60
cccggcggag ucgcca 76

<210> SEQ ID NO 685
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 685
ggcuccgugg cgcaauggau agcgcauugg acuucaaauu caaagguucc ggguucgagu 60
cccggcggag ucgcca 76

<210> SEQ ID NO 686
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 686
ggcuccgugg cgcaauggau agcgcauugg acuucaaauu caaagguucc ggguucgagu 60
cccggcggag ucgcca 76

<210> SEQ ID NO 687
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 687
ggcuccgugg cgcaauggau agcgcauugg acuucaaauu caaagguucc ggguucgagu 60
cccggcggag ucgcca 76

<210> SEQ ID NO 688
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 688
ggcuccgugg cgcaauggau agcgcauugg acuucaaauu caaagguucc ggguucgagu 60
cccggcggag ucgcca 76

<210> SEQ ID NO 689
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 689
ggcuccgugg cgcaauggau agcgcauugg acuucaaauu caaagguucc ggguucgagu 60
cccggcggag ucgcca 76

<210> SEQ ID NO 690
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 690
ggcuccgugg cgcaauggau agcgcauugg acuucaaauu caaagguucc ggguucgagu 60
cccggcggag ucgcca 76

<210> SEQ ID NO 691
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 691
ggcuccgugg cgcaauggau agcgcauugg acuucaaauu caaagguucc ggguucgagu 60
cccggcggag ucgcca 76

<210> SEQ ID NO 692
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 692
ggcuccgugg cgcaauggau agcgcauugg acuucaaauu caaagguucc ggguucgagu 60
cccggcggag ucgcca 76

<210> SEQ ID NO 693
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 693
ggcuccgugg cgcaauggau agcgcauugg acuucaaauu caaagguucc ggguucgagu 60
cccggcggag ucgcca 76

<210> SEQ ID NO 694
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 694
ggcuccgugg cgcaauggau agcgcauugg acuucaaauu caaagguucc ggguucgagu 60
cccggcggag ucgcca 76

<210> SEQ ID NO 695
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 695
ggcuccgugg cgcaauggau agcgcauugg acuucaaauu caaagguucc ggguucgagu 60
cccggcggag ucgcca 76

<210> SEQ ID NO 696
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 696
ggcuccgugg cgcaauggau agcgcauugg acuucaaauu caaagguucc ggguucgagu 60
cccggcggag ucgcca 76

<210> SEQ ID NO 697
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 697
ggcuccgugg cgcaauggau agcgcauugg acuucaaauu caaagguucc ggguucgagu 60
cccggcggag ucgcca 76

<210> SEQ ID NO 698
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 698
ggcuccgugg cgcaauggau agcgcauugg acuucaaauu caaagguucc ggguucgagu 60
cccggcggag ucgcca 76

<210> SEQ ID NO 699
<211> LENGTH: 76
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 699
ggcuccgugg cgcaauggau agcgcauugg acuucaaauu caaagguucc ggguucgagu 60
cccggcggag ucgcca 76

<210> SEQ ID NO 700
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 700
ggcuccgugg cgcaauggau agcgcauugg acuucaaauu caaagguucc ggguucgagu 60
cccggcggag ucgcca 76

<210> SEQ ID NO 701
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 701
ggcuccgugg cgcaauggau agcgcauugg acuucaaauu caaagguucc ggguucgagu 60
cccggcggag ucgcca 76

<210> SEQ ID NO 702
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 702
ggcuccgugg cgcaauggau agcgcauugg acuucaaauu caaagguucc ggguucgagu 60
cccggcggag ucgcca 76

<210> SEQ ID NO 703
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 703
ggcuccgugg cgcaauggau agcgcauugg acuucaaauu caaagguucc ggguucgagu 60
cccggcggag ucgcca 76

<210> SEQ ID NO 704
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 704
ggcuccgugg cgcaauggau agcgcauugg acuucaaauu caaagguucc ggguucgagu 60
cccggcggag ucgcca 76

<210> SEQ ID NO 705
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 705
ggcuccgugg cgcaauggau agcgcauugg acuucaaauu caaagguucc ggguucgagu 60
cccggcggag ucgcca 76

<210> SEQ ID NO 706
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 706
ggcuccgugg cgcaauggau agcgcauugg acuucaaauu caaagguucc ggguucgagu 60
cccggcggag ucgcca 76

<210> SEQ ID NO 707
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 707
ggcuccgugg cgcaauggau agcgcauugg acuucaaauu caaagguucc ggguucgagu 60
cccggcggag ucgcca 76

<210> SEQ ID NO 708
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 708
ggcuccgugg cgcaauggau agcgcauugg acuucaaauu caaagguucc ggguucgagu 60
cccggcggag ucgcca 76

<210> SEQ ID NO 709
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 709
ggcuccgugg cgcaauggau agcgcauugg acuucaaauu caaagguucc ggguucgagu 60
cccggcggag ucgcca 76

<210> SEQ ID NO 710
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710
ggcuccgugg cgcaauggau agcgcauugg acuucaaauu caaagguucc ggguucgagu 60
cccggcggag ucgcca 76

<210> SEQ ID NO 711
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 711
ggcuccgugg cgcaauggau agcgcauugg acuucaaauu caaagguucc ggguucgagu 60
cccggcggag ucgcca 76

<210> SEQ ID NO 712
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712
ggcuccgugg cgcaauggau agcgcauugg acuucaaauu caaagguucc ggguucgagu 60
cccggcggag ucgcca 76

<210> SEQ ID NO 713
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 713
ggcuccgugg cgcaauggau agcgcauugg acuucaaauu caaagguucc ggguucgagu 60
cccggcggag ucgcca 76

<210> SEQ ID NO 714
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714
ggcuccgugg cgcaauggau agcgcauugg acuucaaauu caaagguucc ggguucgagu 60
cccggcggag ucgcca 76

<210> SEQ ID NO 715
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 715
ggcuccgugg cgcaauggau agcgcauugg acuucaaauu caaagguucc ggguucgagu 60
cccggcggag ucgcca 76

<210> SEQ ID NO 716
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716
ggcuccgugg cgcaauggau agcgcauugg acuucaaauu caaagguucc ggguucgagu 60
cccggcggag ucgcca 76

<210> SEQ ID NO 717
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717
ggcuccgugg cgcaauggau agcgcauugg acuucaaauu caaagguucc ggguucgagu 60
cccggcggag ucgcca 76

<210> SEQ ID NO 718
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 718
ggcuccgugg cgcaauggau agcgcauugg acuucaaauu caaagguucc ggguucgagu 60
cccggcggag ucgcca 76

<210> SEQ ID NO 719
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719
ggcuccgugg cgcaauggau agcgcauugg acuucaaauu caaagguucc ggguucgagu 60
cccggcggag ucgcca 76

<210> SEQ ID NO 720
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
ggcuccgugg cgcaauggau agcgcauugg acuucaaauu caaagguucc ggguucgagu 60
cccggcggag ucgcca 76

<210> SEQ ID NO 721
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721
ggcuccgugg cgcaauggau agcgcauugg acuucaaauu caaagguucc ggguucgagu 60
cccggcggag ucgcca 76

<210> SEQ ID NO 722
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 722
ggcuccgugg cgcaauggau agcgcauugg acuucaaauu caaagguucc ggguucgagu 60
cccggcggag ucgcca 76

<210> SEQ ID NO 723
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 723
ggcuccgugg cgcaauggau agcgcauugg acuucaaauu caaagguucc ggguucgagu 60
cccggcggag ucgcca 76

<210> SEQ ID NO 724
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 724
ggcuccgugg cgcaauggau agcgcauugg acuucaaauu caaagguucc ggguucgagu 60
cccggcggag ucgcca 76

<210> SEQ ID NO 725
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide -continued

<400> SEQUENCE: 725
ggcuccgugg cgcaauggau agcgcauugg acuucaaauu caaagguucc ggguucgagu 60
cccggcggag ucgcca 76

<210> SEQ ID NO 726
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 726
ggcuccgugg cgcaauggau agcgcauugg acuucaaauu caaagguucc ggguucgagu 60
cccggcggag ucgcca 76

<210> SEQ ID NO 727
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 727
ggcuccgugg cgcaauggau agcgcauugg acuucaaauu caaagguucc ggguucgagu 60
cccggcggag ucgcca 76

<210> SEQ ID NO 728
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 728
ggcuccgugg cgcaauggau agcgcauugg acuucaaauu caaagguucc ggguucgagu 60
cccggcggag ucgcca 76

<210> SEQ ID NO 729
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 729
ggcuccgugg cgcaauggau agcgcauugg acuucaaauu caaagguucc ggguucgagu 60
cccggcggag ucgcca 76

<210> SEQ ID NO 730
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 730
ggcuccgugg cgcaauggau agcgcauugg acuucaaauu caaagguucc ggguucgagu 60
cccggcggag ucgcca 76

<210> SEQ ID NO 731
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 731
ggcuccgugg cgcaauggau agcgcauugg acuucaaauu caaagguucc ggguucgagu 60
cccggcggag ucgcca 76

<210> SEQ ID NO 732
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 732
ggcuccgugg cgcaauggau agcgcauugg acuucaaauu caaagguucc ggguucgagu 60
cccggcggag ucgcca 76

<210> SEQ ID NO 733
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 733
ggcuccgugg cgcaauggau agcgcauugg acuucaaauu caaagguucc ggguucgagu 60
cccggcggag ucgcca 76

<210> SEQ ID NO 734
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 734
ggcuccgugg cgcaauggau agcgcauugg acuucaaauu caaagguucc ggguucgagu 60
cccggcggag ucgcca 76

<210> SEQ ID NO 735
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 735
ggcuccgugg cgcaauggau agcgcauugg acuucaaauu caaagguucc ggguucgagu 60
cccggcggag ucgcca 76

<210> SEQ ID NO 736

<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736
ggcuccgugg cgcaauggau agcgcauugg acuucaaauu caaagguucc ggguucgagu 60
cccggcggag ucgcca 76

<210> SEQ ID NO 737
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 737
ggcuccgugg cgcaauggau agcgcauugg acuucaaauu caaagguucc ggguucgagu 60
cccggcggag ucgcca 76

<210> SEQ ID NO 738
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 738
ggcuccgugg cgcaauggau agcgcauugg acuucaaauu caaagguucc ggguucgagu 60
cccggcggag ucgcca 76

<210> SEQ ID NO 739
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 739
ggcuccgugg cgcaauggau agcgcauugg acuucaaauu caaagguucc ggguucgagu 60
cccggcggag ucgcca 76

<210> SEQ ID NO 740
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
ggcuccgugg cgcaauggau agcgcauugg acuucaaauu caaagguucc ggguucgagu 60
cccggcggag ucgcca 76

<210> SEQ ID NO 741
<211> LENGTH: 76
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 741
ggcuccgugg cgcaauggau agcgcauugg acuucaaauu caaagguucc ggguucgagu 60
cccggcggag ucgcca 76

<210> SEQ ID NO 742
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 742
ggcuccgugg cgcaauggau agcgcauugg acuucaaauu caaagguucc ggguucgagu 60
cccggcggag ucgcca 76

<210> SEQ ID NO 743
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 743
ggcuccgugg cgcaauggau agcgcauugg acuucaaauu caaagguucc ggguucgagu 60
cccggcggag ucgcca 76

<210> SEQ ID NO 744
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 744
ggcuccgugg cgcaauggau agcgcauugg acuucaaauu caaagguucc ggguucgagu 60
cccggcggag ucgcca 76

<210> SEQ ID NO 745
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 745
ggcuccgugg cgcaauggau agcgcauugg acuucaaauu caaagguucc ggguucgagu 60
cccggcggag ucgcca 76

<210> SEQ ID NO 746
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 746
ggcuccgugg cgcaauggau agcgcauugg acuucaaauu caaagguucc ggguucgagu 60
cccggcggag ucgcca 76

<210> SEQ ID NO 747
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 747
ggcuccgugg cgcaauggau agcgcauugg acuucaaauu caaagguucc ggguucgagu 60
cccggcggag ucgcca 76

<210> SEQ ID NO 748
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 748
ggcuccgugg cgcaauggau agcgcauugg acuucaaauu caaagguucc ggguucgagu 60
cccggcggag ucgcca 76

<210> SEQ ID NO 749
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 749
ggcuccgugg cgcaauggau agcgcauugg acuucaaauu caaagguucc ggguucgagu 60
cccggcggag ucgcca 76

<210> SEQ ID NO 750
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 750
ggcuccgugg cgcaauggau agcgcauugg acuucaaauu caaagguucc ggguucgagu 60
cccggcggag ucgcca 76

<210> SEQ ID NO 751
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 751
ggcuccgugg cgcaauggau agcgcauugg acuucaaauu caaagguucc ggguucgagu 60
cccggcggag ucgcca 76

<210> SEQ ID NO 752
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 752
ggcuccgugg cgcaauggau agcgcauugg acuucaaauu caaagguucc ggguucgagu 60
cccggcggag ucgcca 76

<210> SEQ ID NO 753
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 753
ggcuccgugg cgcaauggau agcgcauugg acuucaaauu caaagguucc ggguucgagu 60
cccggcggag ucgcca 76

<210> SEQ ID NO 754
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 754
ggcuccgugg cgcaauggau agcgcauugg acuucaaauu caaagguucc ggguucgagu 60
cccggcggag ucgcca 76

<210> SEQ ID NO 755
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 755
ggcuccgugg cgcaauggau agcgcauugg acuucaaauu caaagguucc ggguucgagu 60
cccggcggag ucgcca 76

<210> SEQ ID NO 756
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 756
ggcuccgugg cgcaauggau agcgcauugg acuucaaauu caaagguucc ggguucgagu 60
cccggcggag ucgcca 76

<210> SEQ ID NO 757
<211> LENGTH: 76

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757
ggcuccgugg cgcaauggau agcgcauugg acuucaaauu caaagguucc ggguucgagu 60
cccggcggag ucgcca 76

<210> SEQ ID NO 758
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
ggcuccgugg cgcaauggau agcgcauugg acuucaaauu caaagguucc ggguucgagu 60
cccggcggag ucgcca 76

<210> SEQ ID NO 759
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
ggcuccgugg cgcaauggau agcgcauugg acuucaaauu caaagguucc ggguucgagu 60
cccggcggag ucgcca 76

<210> SEQ ID NO 760
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
ggcuccgugg cgcaauggau agcgcauugg acuucaaauu caaagguucc ggguucgagu 60
cccggcggag ucgcca 76

<210> SEQ ID NO 761
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761
ggcuccgugg cgcaauggau agcgcauugg acuucaaauu caaagguucc ggguucgagu 60
cccggcggag ucgcca 76

<210> SEQ ID NO 762
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 762
ggcuccgugg cgcaauggau agcgcauugg acuucaaauu caaagguucc ggguucgagu 60
cccggcggag ucgcca 76

<210> SEQ ID NO 763
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 763
ggcuccgugg cgcaauggau agcgcauugg acuucaaauu caaagguucc ggguucgagu 60
cccggcggag ucgcca 76

<210> SEQ ID NO 764
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 764
ggcuccgugg cgcaauggau agcgcauugg acuucaaauu caaagguucc ggguucgagu 60
cccggcggag ucgcca 76

<210> SEQ ID NO 765
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 765
ggcuccgugg cgcaauggau agcgcauugg acuucaaauu caaagguucc ggguucgagu 60
cccggcggag ucgcca 76

<210> SEQ ID NO 766
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 766
ggcuccgugg cgcaauggau agcgcauugg acuucaaauu caaagguucc ggguucgagu 60
cccggcggag ucgcca 76

<210> SEQ ID NO 767
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 767
ggcuccgugg cgcaauggau agcgcauugg acuucaaauu caaagguucc ggguucgagu 60
cccggcggag ucgcca 76

<210> SEQ ID NO 768
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 768
ggcuccgugg cgcaauggau agcgcauugg acuucaaauu caaagguucc ggguucgagu 60
cccggcggag ucgcca 76

<210> SEQ ID NO 769
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 769
ggcuccgugg cgcaauggau agcgcauugg acuucaaauu caaagguucc ggguucgagu 60
cccggcggag ucgcca 76

<210> SEQ ID NO 770
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 770
ggcuccgugg cgcaauggau agcgcauugg acuucaaauu caaagguucc ggguucgagu 60
cccggcggag ucgcca 76

<210> SEQ ID NO 771
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 771
ggcuccgugg cgcaauggau agcgcauugg acuucaaauu caaagguucc ggguucgagu 60
cccggcggag ucgcca 76

<210> SEQ ID NO 772
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 772
ggcuccgugg cgcaauggau agcgcauugg acuucaaauu caaagguucc ggguucgagu 60
cccggcggag ucgcca 76

-continued

<210> SEQ ID NO 773
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 773
ggcuccgugg cgcaauggau agcgcauugg acuucaaauu caaagguucc ggguucgagu 60
cccggcggag ucgcca 76

<210> SEQ ID NO 774
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 774
ggcuccgugg cgcaauggau agcgcauugg acuucaaauu caaagguucc ggguucgagu 60
cccggcggag ucgcca 76

<210> SEQ ID NO 775
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 775
ggcuccgugg cgcaauggau agcgcauugg acuucaaauu caaagguucc ggguucgagu 60
cccggcggag ucgcca 76

<210> SEQ ID NO 776
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 776
ggcuccgugg cgcaauggau agcgcauugg acuucaaauu caaagguucc ggguucgagu 60
cccggcggag ucgcca 76

<210> SEQ ID NO 777
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 777
ggcuccgugg cgcaauggau agcgcauugg acuucaaauu caaagguucc ggguucgagu 60
cccggcggag ucgcca 76

<210> SEQ ID NO 778
<211> LENGTH: 76
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
ggctccgugg cgcaauggau agcgcauugg acuucaaauu caaagguucc ggguucgagu     60
cccggcggag ucgcca                                                     76

<210> SEQ ID NO 779
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
ggcuccgugg cgcaauggau agcgcauugg acuucaaauu caaagguucc ggguucgagu     60
cccggcggag ucgcca                                                     76

<210> SEQ ID NO 780
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
ggcuccgugg cgcaauggau agcgcauugg acuucaaauu caaagguucc ggguucgagu     60
cccggcggag ucgcca                                                     76

<210> SEQ ID NO 781
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
ggcuccgugg cgcaauggau agcgcauugg acuucaaauu caaagguucc ggguucgagu     60
cccggcggag ucgcca                                                     76

<210> SEQ ID NO 782
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
ggcuccgugg cgcaauggau agcgcauugg acuucaaauu caaagguucc ggguucgagu     60
cccggcggag ucgcca                                                     76

<210> SEQ ID NO 783
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 783
ggcuccgugg cgcaauggau agcgcauugg acuucaaauu caaagguucc ggguucgagu 60
cccggcggag ucgcca 76

<210> SEQ ID NO 784
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 784
ggcuccgugg cgcaauggau agcgcauugg acuucaaauu caaagguucc ggguucgagu 60
cccggcggag ucgcca 76

<210> SEQ ID NO 785
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 785
ggcuccgugg cgcaauggau agcgcauugg acuucaaauu caaagguucc ggguucgagu 60
cccggcggag ucgcca 76

<210> SEQ ID NO 786
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 786
ggcuccgugg cgcaauggau agcgcauugg acuucaaauu caaagguucc ggguucgagu 60
cccggcggag ucgcca 76

<210> SEQ ID NO 787
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 787
ggcuccgugg cgcaatggau agcgcauugg acuucaaauu caaagguucc ggguucgagu 60
cccggcggag ucgcca 76

<210> SEQ ID NO 788
<211> LENGTH: 76
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 788
ggcuccgugg cgcaauggau agcgcauugg acuucaaauu caaagguucc ggguucgagu 60
cccggcggag ucgcca 76

<210> SEQ ID NO 789
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 789
ggcuccgugg cgcaauggau agcgcauugg acuucaaauu caaagguucc ggguucgagu 60
cccggcggag ucgcca 76

<210> SEQ ID NO 790
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 790
ggcuccgugg cgcaauggau agcgcauugg acuucaaauu caaagguucc ggguucgagu 60
cccggcggag ucgcca 76

<210> SEQ ID NO 791
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 791
ggcuccgugg cgcaauggat agcgcauugg acuucaaauu caaagguucc ggguucgagu 60
cccggcggag ucgcca 76

<210> SEQ ID NO 792
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 792
ggcuccgugg cgcaauggau agcgcauugg acuucaaauu caaagguucc ggguucgagu 60
cccggcggag ucgcca 76

<210> SEQ ID NO 793
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 793
ggcuccgugg cgcaauggau agcgcauugg acuucaaauu caaagguucc ggguucgagu 60
cccggcggag ucgcca 76

<210> SEQ ID NO 794
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 794
ggcuccgugg cgcaauggau agcgcauugg acuucaaauu caaagguucc ggguucgagu 60
cccggcggag ucgcca 76

<210> SEQ ID NO 795
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 795
ggcuccgugg cgcaauggau agcgcauugg acuucaaauu caaagguucc ggguucgagu 60
cccggcggag ucgcca 76

<210> SEQ ID NO 796
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 796
ggcuccgugg cgcaauggau agcgcauugg acuucaaauu caaagguucc ggguucgagu 60
cccggcggag ucgcca 76

<210> SEQ ID NO 797
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 797
ggcuccgugg cgcaauggau agcgcatugg acuucaaauu caaagguucc ggguucgagu 60
cccggcggag ucgcca 76

<210> SEQ ID NO 798
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 798
ggcuccgugg cgcaauggau agcgcautgg acuucaaauu caaagguucc ggguucgagu 60
cccggcggag ucgcca 76

<210> SEQ ID NO 799
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 799
ggcuccgugg cgcaauggau agcgcauugg acuucaaauu caaagguucc ggguucgagu 60
cccggcggag ucgcca 76

<210> SEQ ID NO 800
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 800
ggcuccgugg cgcaauggau agcgcauugg acuucaaauu caaagguucc ggguucgagu 60
cccggcggag ucgcca 76

<210> SEQ ID NO 801
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 801
ggcuccgugg cgcaauggau agcgcauugg acuucaaauu caaagguucc ggguucgagu 60
cccggcggag ucgcca 76

<210> SEQ ID NO 802
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 802
ggcuccgugg cgcaauggau agcgcauugg actucaaauu caaagguucc ggguucgagu 60
cccggcggag ucgcca 76

<210> SEQ ID NO 803
<211> LENGTH: 76
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 803
ggcuccgugg cgcaauggau agcgcauugg acutcaaauu caaagguucc ggguucgagu     60
cccggcggag ucgcca                                                     76

<210> SEQ ID NO 804
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
ggcuccgugg cgcaauggau agcgcauugg acuucaaauu caaagguucc ggguucgagu     60
cccggcggag ucgcca                                                     76

<210> SEQ ID NO 805
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
ggcuccgugg cgcaauggau agcgcauugg acuucaaauu caaagguucc ggguucgagu     60
cccggcggag ucgcca                                                     76

<210> SEQ ID NO 806
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
ggcuccgugg cgcaauggau agcgcauugg acuucaaauu caaagguucc ggguucgagu     60
cccggcggag ucgcca                                                     76

<210> SEQ ID NO 807
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
ggcuccgugg cgcaauggau agcgcauugg acuucaaauu caaagguucc ggguucgagu     60
cccggcggag ucgcca                                                     76

<210> SEQ ID NO 808
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 808
ggcuccgugg cgcaauggau agcgcauugg acuucaaauu caaagguucc ggguucgagu 60
cccggcggag ucgcca 76

<210> SEQ ID NO 809
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 809
ggcuccgugg cgcaauggau agcgcauugg acuucaaauu caaagguucc ggguucgagu 60
cccggcggag ucgcca 76

<210> SEQ ID NO 810
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 810
ggcuccgugg cgcaauggau agcgcauugg acuucaaauu caaagguucc ggguucgagu 60
cccggcggag ucgcca 76

<210> SEQ ID NO 811
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 811
ggcuccgugg cgcaauggau agcgcauugg acuucaaauu caaagguucc ggguucgagu 60
cccggcggag ucgcca 76

<210> SEQ ID NO 812
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 812
ggcuccgugg cgcaauggau agcgcauugg acuucaaauu caaagguucc ggguucgagu 60
cccggcggag ucgcca 76

<210> SEQ ID NO 813
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 813
ggcuccgugg cgcaauggau agcgcauugg acuucaaauu caaagguucc ggguucgagu 60
cccggcggag ucgcca 76

<210> SEQ ID NO 814
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 814
ggcuccgugg cgcaauggau agcgcauugg acuucaaauu caaaggtucc ggguucgagu 60
cccggcggag ucgcca 76

<210> SEQ ID NO 815
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 815
ggcuccgugg cgcaauggau agcgcauugg acuucaaauu caaaggutcc ggguucgagu 60
cccggcggag ucgcca 76

<210> SEQ ID NO 816
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 816
ggcuccgugg cgcaauggau agcgcauugg acuucaaauu caaagguucc ggguucgagu 60
cccggcggag ucgcca 76

<210> SEQ ID NO 817
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
ggcuccgugg cgcaauggau agcgcauugg acuucaaauu caaagguucc ggguucgagu 60
cccggcggag ucgcca 76

<210> SEQ ID NO 818
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818
ggcuccgugg cgcaauggau agcgcauugg acuucaaauu caaagguucc ggguucgagu 60
cccggcggag ucgcca 76

<210> SEQ ID NO 819
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
ggcuccgugg cgcaauggau agcgcauugg acuucaaauu caaagguucc ggguucgagu 60
cccggcggag ucgcca 76

<210> SEQ ID NO 820
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 820
ggcuccgugg cgcaauggau agcgcauugg acuucaaauu caaagguucc ggguucgagu 60
cccggcggag ucgcca 76

<210> SEQ ID NO 821
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 821
ggcuccgugg cgcaauggau agcgcauugg acuucaaauu caaagguucc gggtucgagu 60
cccggcggag ucgcca 76

<210> SEQ ID NO 822
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 822
ggcuccgugg cgcaauggau agcgcauugg acuucaaauu caaagguucc gggutcgagu 60
cccggcggag ucgcca 76

<210> SEQ ID NO 823
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 823
ggcuccgugg cgcaauggau agcgcauugg acuucaaauu caaagguucc ggguucgagu 60
cccggcggag ucgcca 76

<210> SEQ ID NO 824
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 824
ggcuccgugg cgcaauggau agcgcauugg acuucaaauu caaagguucc ggguucgagu 60
cccggcggag ucgcca 76

<210> SEQ ID NO 825
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 825
ggcuccgugg cgcaauggau agcgcauugg acuucaaauu caaagguucc ggguucgagu 60
cccggcggag ucgcca 76

<210> SEQ ID NO 826
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 826
ggcuccgugg cgcaauggau agcgcauugg acuucaaauu caaagguucc ggguucgagu 60
cccggcggag ucgcca 76

<210> SEQ ID NO 827
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 827
ggcuccgugg cgcaauggau agcgcauugg acuucaaauu caaagguucc ggguucgagt 60
cccggcggag ucgcca 76

<210> SEQ ID NO 828
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 828
ggcuccgugg cgcaauggau agcgcauugg acuucaaauu caaagguucc ggguucgagu 60
cccggcggag ucgcca 76

<210> SEQ ID NO 829
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 829
ggcuccgugg cgcaauggau agcgcauugg acuucaaauu caaagguucc ggguucgagu 60
cccggcggag ucgcca 76

<210> SEQ ID NO 830
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 830
ggcuccgugg cgcaauggau agcgcauugg acuucaaauu caaagguucc ggguucgagu 60
cccggcggag ucgcca 76

<210> SEQ ID NO 831
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 831
ggcuccgugg cgcaauggau agcgcauugg acuucaaauu caaagguucc ggguucgagu 60
cccggcggag ucgcca 76

<210> SEQ ID NO 832
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 832
ggcuccgugg cgcaauggau agcgcauugg acuucaaauu caaagguucc ggguucgagu 60
cccggcggag ucgcca 76

<210> SEQ ID NO 833
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 833
ggcuccgugg cgcaauggau agcgcauugg acuucaaauu caaagguucc ggguucgagu 60
cccggcggag ucgcca 76

<210> SEQ ID NO 834
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 834
ggcuccgugg cgcaauggau agcgcauugg acuucaaauu caaagguucc ggguucgagu 60
cccggcggag ucgcca 76

<210> SEQ ID NO 835
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 835
ggcuccgugg cgcaauggau agcgcauugg acuucaaauu caaagguucc ggguucgagu 60
cccggcggag ucgcca 76

<210> SEQ ID NO 836
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 836
ggcuccgugg cgcaauggau agcgcauugg acuucaaauu caaagguucc ggguucgagu 60
cccggcggag tcgcca 76

<210> SEQ ID NO 837
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 837
ggcuccgugg cgcaauggau agcgcauugg acuucaaauu caaagguucc ggguucgagu 60
cccggcggag ucgcca 76

<210> SEQ ID NO 838
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 838
ggcuccgugg cgcaauggau agcgcauugg acuucaaauu caaagguucc ggguucgagu 60
cccggcggag ucgcca 76

<210> SEQ ID NO 839
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 839
ggcuccgugg cgcaauggau agcgcauugg acuucaaauu caaagguucc ggguucgagu 60
cccggcggag ucgcca 76

<210> SEQ ID NO 840
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 840
ggcuccgugg cgcaauggau agcgcauugg acuucaaauu caaagguucc ggguucgagu 60
cccggcggag ucgcca 76

<210> SEQ ID NO 841
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 841
ggcuccgugg cgcaauggau agcgcauugg acuucaaauu caaagguucc ggguucgagu 60
cccggcggag ucgcca 76

<210> SEQ ID NO 842
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 842
ggcuccgugg cgcaauggau agcgcauugg acuucaaauu caaagguucc ggguucgagu 60
cccggcggag ucgcca 76

<210> SEQ ID NO 843
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 843
ggcuccgugg cgcaauggau agcgcauugg acuucaaauu caaagguucc ggguucgagu 60
cccggcggag ucgcca 76

<210> SEQ ID NO 844
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 844
ggcuccgugg cgcaauggau agcgcauugg acuucaaauu caaagguucc ggguucgagu 60
cccggcggag ucgcca 76

<210> SEQ ID NO 845
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 845
ggcuccgugg cgcaauggau agcgcauugg acuucaaauu caaagguucc ggguucgagu 60
cccggcggag ucgcca 76

<210> SEQ ID NO 846
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 846
ggcuccgugg cgcaauggau agcgcauugg acuucaaauu caaagguucc ggguucgagu 60
cccggcggag ucgcca 76

<210> SEQ ID NO 847
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 847
ggcuccgugg cgcaauggau agcgcauugg acuucaaauu caaagguucc ggguucgagu 60
cccggcggag ucgcca 76

<210> SEQ ID NO 848
<211> LENGTH: 76

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 848
ggcuccgugg cgcaauggau agcgcauugg acuucaaauu caaagguucc ggguucgagu 60
cccggcggag ucgcca 76

<210> SEQ ID NO 849
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 849
ggcuccgugg cgcaauggau agcgcauugg acuucaaauu caaagguucc ggguucgagu 60
cccggcggag ucgcca 76

<210> SEQ ID NO 850
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 850
ggcuccgugg cgcaauggau agcgcauugg acuucaaauu caaagguucc ggguucgagu 60
cccggcggag ucgcca 76

<210> SEQ ID NO 851
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 851
ggcuccgugg cgcaauggau agcgcauugg acuucaaauu caaagguucc ggguucgagu 60
cccggcggag ucgcca 76

<210> SEQ ID NO 852
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 852
ggcuccgugg cgcaauggau agcgcauugg acuucaaauu caaagguucc ggguucgagu 60
cccggcggag ucgcca 76

<210> SEQ ID NO 853
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 853
ggcuccgugg cgcaauggau agcgcauugg acuucaaauu caaagguucc ggguucgagu 60
cccggcggag ucgcca 76

<210> SEQ ID NO 854
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 854
ggcuccgugg cgcaauggau agcgcauugg acuucaaauu caaagguucc ggguucgagu 60
cccggcggag ucgcca 76

<210> SEQ ID NO 855
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 855
ggcuccgugg cgcaauggau agcgcauugg acuucaaauu caaagguucc ggguucgagu 60
cccggcggag ucgcca 76

<210> SEQ ID NO 856
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 856
ggcuccgugg cgcaauggau agcgcauugg acuucaaauu caaagguucc ggguucgagu 60
cccggcggag ucgcca 76

<210> SEQ ID NO 857
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 857
ggcuccgugg cgcaauggau agcgcauugg acuucaaauu caaagguucc ggguucgagu 60
cccggcggag ucgcca 76

<210> SEQ ID NO 858
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 858
ggcuccgugg cgcaauggau agcgcauugg acuucaaauu caaagguucc ggguucgagu 60
cccggcggag ucgcca 76

<210> SEQ ID NO 859
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 859
ggcuccgugg cgcaauggau agcgcauugg acuucaaauu caaagguucc ggguucgagu 60
cccggcggag ucgcca 76

<210> SEQ ID NO 860
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 860
ggcuccgugg cgcaauggau agcgcauugg acuucaaauu caaagguucc ggguucgagu 60
cccggcggag ucgcca 76

<210> SEQ ID NO 861
<211> LENGTH: 76
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
ggcuccgugg cgcaauggau agcgcauugg acuucaaauu caaagguucc ggguucgagu     60
cccggcggag ucgcca                                                     76

<210> SEQ ID NO 862
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
ggcuccgugg cgcaauggau agcgcauugg acuucaaauu caaagguucc ggguucgagu     60
cccggcggag ucgcca                                                     76

<210> SEQ ID NO 863
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
ggcuccgugg cgcaauggau agcgcauugg acuucaaauu caaagguucc ggguucgagu     60
cccggcggag ucgcca                                                     76

<210> SEQ ID NO 864
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
ggcuccgugg cgcaauggau agcgcauugg acuucaaauu caaagguucc ggguucgagu     60
cccggcggag ucgcca                                                     76

<210> SEQ ID NO 865
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 865

-continued ggcuccgugg cgcaauggau agcgcauugg acuucaaauu caaagguucc ggguucgagu 60
cccggcggag ucgcca 76

<210> SEQ ID NO 866
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 866
ggcuccgugg cgcaauggau agcgcauugg acuucaaauu caaagguucc ggguucgagu 60
cccggcggag ucgcca 76

<210> SEQ ID NO 867
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 867
ggcuccgugg cgcaauggau agcgcauugg acuucaaauu caaagguucc ggguucgagu 60
cccggcggag ucgcca 76

<210> SEQ ID NO 868
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 868
ggcuccgugg cgcaauggau agcgcauugg acuucaaauu caaagguucc ggguucgagu 60
cccggcggag ucgcca 76

<210> SEQ ID NO 869
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 869
ggcuccgugg cgcaauggau agcgcauugg acuucaaauu caaagguucc ggguucgagu 60
cccggcggag ucgcca 76

<210> SEQ ID NO 870

<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 870
ggcuccgugg cgcaauggau agcgcauugg acuucaaauu caaagguucc ggguucgagu 60
cccggcggag ucgcca 76

<210> SEQ ID NO 871
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 871
ggcuccgugg cgcaauggau agcgcauugg acuucaaauu caaagguucc ggguucgagu 60
cccggcggag ucgcca 76

<210> SEQ ID NO 872
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 872
ggcuccgugg cgcaauggau agcgcauugg acuucaaauu caaagguucc ggguucgagu 60
cccggcggag ucgcca 76

<210> SEQ ID NO 873
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 873
ggcuccgugg cgcaauggau agcgcauugg acuucaaauu caaagguucc ggguucgagu 60
cccggcggag ucgcca 76

<210> SEQ ID NO 874
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule: Synthetic oligonucleotide

<400> SEQUENCE: 874
ggcuccgugg cgcaauggau agcgcauugg acuucaaauu caaagguucc ggguucgagu 60
cccggcggag ucgcca 76

<210> SEQ ID NO 875
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 875
ggcuccgugg cgcaauggau agcgcauugg acuucaaauu caaagguucc ggguucgagu 60
cccggcggag ucgcca 76

<210> SEQ ID NO 876
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 876
ggcuccgugg cgcaauggau agcgcauugg acuucaaauu caaagguucc ggguucgagu 60
cccggcggag ucgcca 76

<210> SEQ ID NO 877
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 877
ggcuccgugg cgcaauggau agcgcauugg acuucaaauu caaagguucc ggguucgagu 60
cccggcggag ucgcca 76

<210> SEQ ID NO 878
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 878
ggcuccgugg cgcaauggau agcgcauugg acuucaaauu caaagguucc ggguucgagu 60
cccggcggag ucgcca 76

<210> SEQ ID NO 879
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 879
ggcuccgugg cgcaauggau agcgcauugg acuucaaauu caaagguucc ggguucgagu 60
cccggcggag ucgcca 76

<210> SEQ ID NO 880
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 880
ggcuccgugg cgcaauggau agcgcauugg acuucaaauu caaagguucc ggguucgagu 60
cccggcggag ucgcca 76

<210> SEQ ID NO 881
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 881
ggcuccgugg cgcaauggau agcgcauugg acuucaaauu caaagguucc ggguucgagu 60
cccggcggag ucgcca 76

<210> SEQ ID NO 882
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 882
ggcuccgugg cgcaauggau agcgcauugg acuucaaauu caaagguucc ggguucgagu 60
cccggcggag ucgcca 76

<210> SEQ ID NO 883
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
ggcuccgugg cgcaauggau agcgcauugg acuucaaauu caaagguucc ggguucgagu     60
cccggcggag ucgcca                                                     76

<210> SEQ ID NO 884
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
ggcuccgugg cgcaauggau agcgcauugg acuucaaauu caaagguucc ggguucgagu     60
cccggcggag ucgcca                                                     76

<210> SEQ ID NO 885
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
ggcuccgugg cgcaauggau agcgcauugg acuucaaauu caaagguucc ggguucgagu     60
cccggcggag ucgcca                                                     76

<210> SEQ ID NO 886
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
ggcuccgugg cgcaauggau agcgcauugg acuucaaauu caaagguucc ggguucgagu     60
cccggcggag ucgcca                                                     76

<210> SEQ ID NO 887
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 887
ggcuccgugg cgcaauggau agcgcauugg acuucaaauu caaagguucc ggguucgagu 60
cccggcggag ucgcca 76

<210> SEQ ID NO 888
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 888
ggcuccgugg cgcaauggau agcgcauugg acuucaaauu caaagguucc ggguucgagu 60
cccggcggag ucgcca 76

<210> SEQ ID NO 889
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 889
ggcuccgugg cgcaauggau agcgcauugg acuucaaauu caaagguucc ggguucgagu 60
cccggcggag ucgcca 76

<210> SEQ ID NO 890
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 890
ggcuccgugg cgcaauggau agcgcauugg acuucaaauu caaagguucc ggguucgagu 60
cccggcggag ucgcca 76

<210> SEQ ID NO 891
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 891
ggcuccgugg cgcaauggau agcgcauugg acuucaaauu caaagguucc ggguucgagu 60
cccggcggag ucgcca 76

<210> SEQ ID NO 892
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 892
ggcuccgugg cgcaauggau agcgcauugg acuucaaauu caaagguucc ggguucgagu 60
cccggcggag ucgcca 76

<210> SEQ ID NO 893
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 893
ggcuccgugg cgcaauggau agcgcauugg acuucaaauu caaagguucc ggguucgagu 60
cccggcggag ucgcca 76

<210> SEQ ID NO 894
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 894
ggcuccgugg cgcaauggau agcgcauugg acuucaaauu caaagguucc ggguucgagu 60
cccggcggag ucgcca 76

<210> SEQ ID NO 895
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 895
ggcuccgugg cgcaauggau agcgcauugg acuucaaauu caaagguucc ggguucgagu 60
cccggcggag ucgcca 76

<210> SEQ ID NO 896
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule: Synthetic oligonucleotide

<400> SEQUENCE: 896
ggcuccgugg cgcaauggau agcgcauugg acuucaaauu caaagguucc ggguucgagu 60
cccggcggag ucgcca 76

<210> SEQ ID NO 897
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 897
ggcuccgugg cgcaauggau agcgcauugg acuucaaauu caaagguucc ggguucgagu 60
cccggcggag ucgcca 76

<210> SEQ ID NO 898
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 898
ggcuccgugg cgcaauggau agcgcauugg acuucaaauu caaagguucc ggguucgagu 60
cccggcggag ucgcca 76

<210> SEQ ID NO 899
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 899
ggcuccgugg cgcaauggau agcgcauugg acuucaaauu caaagguucc ggguucgagu 60
cccggcggag ucgcca 76

<210> SEQ ID NO 900
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 900
ggcuccgugg cgcaauggau agcgcauugg acuucaaauu caaagguucc ggguucgagu 60
cccggcggag ucgcca 76

<210> SEQ ID NO 901
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 901
ggcuccgugg cgcaauggau agcgcauugg acuucaaauu caaagguucc ggguucgagu 60
cccggcggag ucgcca 76

<210> SEQ ID NO 902
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 902
ggcuccgugg cgcaauggau agcgcauugg acuucaaauu caaagguucc ggguucgagu 60
cccggcggag ucgcca 76

<210> SEQ ID NO 903
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 903
ggcuccgugg cgcaauggau agcgcauugg acuucaaauu caaagguucc ggguucgagu 60
cccggcggag ucgcca 76

<210> SEQ ID NO 904
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 904
ggcuccgugg cgcaauggau agcgcauugg acuucaaauu caaagguucc ggguucgagu 60
cccggcggag ucgcca 76

<210> SEQ ID NO 905
<211> LENGTH: 76
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
ggcuccgugg cgcaauggau agcgcauugg acuucaaauu caaagguucc ggguucgagu     60
cccggcggag ucgcca                                                     76

<210> SEQ ID NO 906
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
ggcuccgugg cgcaauggau agcgcauugg acuucaaauu caaagguucc ggguucgagu     60
cccggcggag ucgcca                                                     76

<210> SEQ ID NO 907
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
ggcuccgugg cgcaauggau agcgcauugg acuucaaauu caaagguucc ggguucgagu     60
cccggcggag ucgcca                                                     76

<210> SEQ ID NO 908
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
ggcuccgugg cgcaauggau agcgcauugg acuucaaauu caaagguucc ggguucgagu     60
cccggcggag ucgcca                                                     76

<210> SEQ ID NO 909
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 909
ggcuccgugg cgcaauggau agcgcauugg acuucaaauu caaagguucc ggguucgagu 60
cccggcggag ucgcca 76

<210> SEQ ID NO 910
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 910
ggcuccgugg cgcaauggau agcgcauugg acuucaaauu caaagguucc ggguucgagu 60
cccggcggag ucgcca 76

<210> SEQ ID NO 911
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 911
ggcuccgugg cgcaauggau agcgcauugg acuucaaauu caaagguucc ggguucgagu 60
cccggcggag ucgcca 76

<210> SEQ ID NO 912
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 912
ggcuccgugg cgcaauggau agcgcauugg acuucaaauu caaagguucc ggguucgagu 60
cccggcggag ucgcca 76

<210> SEQ ID NO 913
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 913
ggcuccgugg cgcaauggau agcgcauugg acuucaaauu caaagguucc ggguucgagu 60
cccggcggag ucgcca 76

<210> SEQ ID NO 914
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
ggcuccgugg cgcaauggau agcgcauugg acuucaaauu caaagguucc ggguucgagu     60
cccggcggag ucgcca                                                     76

<210> SEQ ID NO 915
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
ggcuccgugg cgcaauggau agcgcauugg acuucaaauu caaagguucc ggguucgagu     60
cccggcggag ucgcca                                                     76

<210> SEQ ID NO 916
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
ggcuccgugg cgcaauggau agcgcauugg acuucaaauu caaagguucc ggguucgagu     60
cccggcggag ucgcca                                                     76

<210> SEQ ID NO 917
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
ggcuccgugg cgcaauggau agcgcauugg acuucaaauu caaagguucc ggguucgagu     60
cccggcggag ucgcca                                                     76

<210> SEQ ID NO 918
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918
ggcuccgugg cgcaauggau agcgcauugg acuucaaauu caaagguucc ggguucgagu 60
cccggcggag ucgcca 76

<210> SEQ ID NO 919
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 919
ggcuccgugg cgcaauggau agcgcauugg acuucaaauu caaagguucc ggguucgagu 60
cccggcggag ucgcca 76

<210> SEQ ID NO 920
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 920
ggcuccgugg cgcaauggau agcgcauugg acuucaaauu caaagguucc ggguucgagu 60
cccggcggag ucgcca 76

<210> SEQ ID NO 921
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 921
ggcuccgugg cgcaauggau agcgcauugg acuucaaauu caaagguucc ggguucgagu 60
cccggcggag ucgcca 76

<210> SEQ ID NO 922
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 922
ggcuccgugg cgcaauggau agcgcauugg acuucaaauu caaagguucc ggguucgagu 60
cccggcggag ucgcca 76

<210> SEQ ID NO 923
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 923

-continued ggcuccgugg cgcaauggau agcgcauugg acuucaaauu caaagguucc ggguucgagu 60
cccggcggag ucgcca 76

<210> SEQ ID NO 924
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 924
ggcuccgugg cgcaauggau agcgcauugg acuucaaauu caaagguucc ggguucgagu 60
cccggcggag ucgcca 76

<210> SEQ ID NO 925
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 925
ggcuccgugg cgcaauggau agcgcauugg acuucaaauu caaagguucc ggguucgagu 60
cccggcggag ucgcca 76

<210> SEQ ID NO 926
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 926
ggcuccgugg cgcaauggau agcgcauugg acuucaaauu caaagguucc ggguucgagu 60
cccggcggag ucgcca 76

<210> SEQ ID NO 927
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 927
ggcuccgugg cgcaauggau agcgcauugg acuucaaauu caaagguucc ggguucgagu 60
cccggcggag ucgcca 76

<210> SEQ ID NO 928
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 928
ggcuccgugg cgcaauggau agcgcauugg acuucaaauu caaagguucc ggguucgagu 60
cccggcggag ucgcca 76

<210> SEQ ID NO 929
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 929
ggcuccgugg cgcaauggau agcgcauugg acuucaaauu caaagguucc ggguucgagu 60
cccggcggag ucgcca 76

<210> SEQ ID NO 930
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 930
ggcuccgugg cgcaauggau agcgcauugg acuucaaauu caaagguucc ggguucgagu 60
cccggcggag ucgcca 76

<210> SEQ ID NO 931
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 931
ggcuccgugg cgcaauggau agcgcauugg acuucaaauu caaagguucc ggguucgagu 60
cccggcggag ucgcca 76

<210> SEQ ID NO 932
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 932
ggcuccgugg cgcaauggau agcgcauugg acuucaaauu caaagguucc ggguucgagu 60
cccggcggag ucgcca 76

<210> SEQ ID NO 933
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 933
ggcuccgugg cgcaauggau agcgcauugg acuucaaauu caaagguucc ggguucgagu 60
cccggcggag ucgcca 76

<210> SEQ ID NO 934
<211> LENGTH: 76
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 934
ggcuccgugg cgcaauggau agcgcauugg acuucaaauu caaagguucc ggguucgagu     60
cccggcggag ucgcca                                                     76

<210> SEQ ID NO 935
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
ggcuccgugg cgcaauggau agcgcauugg acuucaaauu caaagguucc ggguucgagu     60
cccggcggag ucgcca                                                     76

<210> SEQ ID NO 936
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
ggcuccgugg cgcaauggau agcgcauugg acuucaaauu caaagguucc ggguucgagu     60
cccggcggag ucgcca                                                     76

<210> SEQ ID NO 937
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 937
ggcuccgugg cgcaauggau agcgcauugg acuucaaauu caaagguucc ggguucgagu     60
cccggcggag ucgcca                                                     76

<210> SEQ ID NO 938
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
ggcuccgugg cgcaauggau agcgcauugg acuucaaauu caaagguucc ggguucgagu     60
cccggcggag ucgcca                                                     76

<210> SEQ ID NO 939
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
ggcuccgugg cgcaauggau agcgcauugg acuucaaauu caaagguucc ggguucgagu 60
cccggcggag ucgcca 76

<210> SEQ ID NO 940
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 940
ggcuccgugg cgcaauggau agcgcauugg acuucaaauu caaagguucc ggguucgagu 60
cccggcggag ucgcca 76

<210> SEQ ID NO 941
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 941
ggcuccgugg cgcaauggau agcgcauugg acuucaaauu caaagguucc ggguucgagu 60
cccggcggag ucgcca 76

<210> SEQ ID NO 942
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 942
ggcuccgugg cgcaauggau agcgcauugg acuucaaauu caaagguucc ggguucgagu 60
cccggcggag ucgcca 76

<210> SEQ ID NO 943
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
ggcuccgugg cgcaauggau agcgcauugg acuucaaauu caaagguucc ggguucgagu 60
cccggcggag ucgcca 76

<210> SEQ ID NO 944
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 944
ggcuccgugg cgcaauggau agcgcauugg acuucaaauu caaagguucc ggguucgagu 60
cccggcggag ucgcca 76

<210> SEQ ID NO 945
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 945
ggcuccgugg cgcaauggau agcgcauugg acuucaaauu caaagguucc ggguucgagu 60
cccggcggag ucgcca 76

<210> SEQ ID NO 946
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 946
ggcuccgugg cgcaauggau agcgcauugg acuucaaauu caaagguucc ggguucgagu 60
cccggcggag ucgcca 76

<210> SEQ ID NO 947
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 947
ggcuccgugg cgcaauggau agcgcauugg acuucaaauu caaagguucc ggguucgagu 60
cccggcggag ucgcca 76

<210> SEQ ID NO 948
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948
ggcuccgugg cgcaauggau agcgcauugg acuucaaauu caaagguucc ggguucgagu 60
cccggcggag ucgcca 76

<210> SEQ ID NO 949
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 949
ggcuccgugg cgcaauggau agcgcauugg acuucaaauu caaagguucc ggguucgagu 60
cccggcggag ucgcca 76

<210> SEQ ID NO 950
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 950
ggcuccgugg cgcaauggau agcgcauugg acuucaaauu caaagguucc ggguucgagu 60
cccggcggag ucgcca 76

<210> SEQ ID NO 951
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 951
ggcuccgugg cgcaauggau agcgcauugg acuucaaauu caaagguucc ggguucgagu 60
cccggcggag ucgcca 76

<210> SEQ ID NO 952
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 952
ggcuccgugg cgcaauggau agcgcauugg acuucaaauu caaagguucc ggguucgagu 60
cccggcggag ucgcca 76

<210> SEQ ID NO 953
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 953
ggcuccgugg cgcaauggau agcgcauugg acuucaaauu caaagguucc ggguucgagu 60
cccggcggag ucgcca 76

<210> SEQ ID NO 954
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 954
ggcuccgugg cgcaauggau agcgcauugg acuucaaauu caaagguucc ggguucgagu 60
cccggcggag ucgcca 76

<210> SEQ ID NO 955
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
ggcuccgugg cgcaauggau agcgcauugg acuucaaauu caaagguucc ggguucgagu     60
cccggcggag ucgcca                                                     76

<210> SEQ ID NO 956
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
ggcuccgugg cgcaauggau agcgcauugg acuucaaauu caaagguucc ggguucgagu     60
cccggcggag ucgcca                                                     76

<210> SEQ ID NO 957
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
ggcuccgugg cgcaauggau agcgcauugg acuucaaauu caaagguucc ggguucgagu     60
cccggcggag ucgcca                                                     76

<210> SEQ ID NO 958
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
ggcuccgugg cgcaauggau agcgcauugg acuucaaauu caaagguucc ggguucgagu     60
cccggcggag ucgcca                                                     76

<210> SEQ ID NO 959
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
ggcuccgugg cgcaauggau agcgcauugg acuucaaauu caaagguucc ggguucgagu     60
cccggcggag ucgcca                                                     76

<210> SEQ ID NO 960
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
ggcuccgugg cgcaauggau agcgcauugg acuucaaauu caaagguucc ggguucgagu 60
cccggcggag ucgcca 76

<210> SEQ ID NO 961
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 961
ggcuccgugg cgcaauggau agcgcauugg acuucaaauu caaagguucc ggguucgagu 60
cccggcggag ucgcca 76

<210> SEQ ID NO 962
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 962
ggcuccgugg cgcaauggau agcgcauugg acuucaaauu caaagguucc ggguucgagu 60
cccggcggag ucgcca 76

<210> SEQ ID NO 963
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 963
ggcuccgugg cgcaauggau agcgcauugg acuucaaauu caaagguucc ggguucgagu 60
cccggcggag ucgcca 76

<210> SEQ ID NO 964
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 964
ggcuccgugg cgcaauggau agcgcauugg acuucaaauu caaagguucc ggguucgagu 60
cccggcggag ucgcca 76

<210> SEQ ID NO 965
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 965
ggcuccgugg cgcaauggau agcgcauugg acuucaaauu caaagguucc ggguucgagu 60
cccggcggag ucgcca 76

<210> SEQ ID NO 966
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 966
ggcuccgugg cgcaauggau agcgcauugg acuucaaauu caaagguucc ggguucgagu 60
cccggcggag ucgcca 76

<210> SEQ ID NO 967
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 967
ggcuccgugg cgcaauggau agcgcauugg acuucaaauu caaagguucc ggguucgagu 60
cccggcggag ucgcca 76

<210> SEQ ID NO 968
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 968
ggcuccgugg cgcaauggau agcgcauugg acuucaaauu caaagguucc ggguucgagu 60
cccggcggag ucgcca 76

<210> SEQ ID NO 969
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 969
ggcuccgugg cgcaauggau agcgcauugg acuucaaauu caaagguucc ggguucgagu 60
cccggcggag ucgcca 76

<210> SEQ ID NO 970
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 970
ggcuccgugg cgcaauggau agcgcauugg acuucaaauu caaagguucc ggguucgagu 60
cccggcggag ucgcca 76

<210> SEQ ID NO 971

<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971
ggcuccgugg cgcaauggau agcgcauugg acuucaaauu caaagguucc ggguucgagu 60
cccggcggag ucgcca 76

<210> SEQ ID NO 972
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 972
ggcuccgugg cgcaauggau agcgcauugg acuucaaauu caaagguucc ggguucgagu 60
cccggcggag ucgcca 76

<210> SEQ ID NO 973
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 973
ggcuccgugg cgcaauggau agcgcauugg acuucaaauu caaagguucc ggguucgagu 60
cccggcggag ucgcca 76

<210> SEQ ID NO 974
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 974
ggcuccgugg cgcaauggau agcgcauugg acuucaaauu caaagguucc ggguucgagu 60
cccggcggag ucgcca 76

<210> SEQ ID NO 975
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 975
ggcuccgugg cgcaauggau agcgcauugg acuucaaauu caaagguucc ggguucgagu 60
cccggcggag ucgcca 76

<210> SEQ ID NO 976
<211> LENGTH: 76
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 976
ggcuccgugg cgcaauggau agcgcauugg acuucaaauu caaagguucc ggguucgagu 60
cccggcggag ucgcca 76

<210> SEQ ID NO 977
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 977
ggcuccgugg cgcaauggau agcgcauugg acuucaaauu caaagguucc ggguucgagu 60
cccggcggag ucgcca 76

<210> SEQ ID NO 978
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 978
ggcuccgugg cgcaauggau agcgcauugg acuucaaauu caaagguucc ggguucgagu 60
cccggcggag ucgcca 76

<210> SEQ ID NO 979
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 979
ggcuccgugg cgcaauggau agcgcauugg acuucaaauu caaagguucc ggguucgagu 60
cccggcggag ucgcca 76

<210> SEQ ID NO 980
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 980
ggcuccgugg cgcaauggau agcgcauugg acuucaaauu caaagguucc ggguucgagu 60
cccggcggag ucgcca 76

<210> SEQ ID NO 981
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 981
ggcuccgugg cgcaauggau agcgcauugg acuucaaauu caaagguucc ggguucgagu 60
cccggcggag ucgcca 76

<210> SEQ ID NO 982
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 982
ggcuccgugg cgcaauggau agcgcauugg acuucaaauu caaagguucc ggguucgagu 60
cccggcggag ucgcca 76

<210> SEQ ID NO 983
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 983
ggcuccgugg cgcaauggau agcgcauugg acuucaaauu caaagguucc ggguucgagu 60
cccggcggag ucgcca 76

<210> SEQ ID NO 984
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 984
ggcuccgugg cgcaauggau agcgcauugg acuucaaauu caaagguucc ggguucgagu 60
cccggcggag ucgcca 76

<210> SEQ ID NO 985
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 985
ggcuccgugg cgcaauggau agcgcauugg acuucaaauu caaagguucc ggguucgagu 60
cccggcggag ucgcca 76

<210> SEQ ID NO 986
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
ggcuccgugg cgcaauggau agcgcauugg acuucaaauu caaagguucc ggguucgagu 60
cccggcggag ucgcca 76

<210> SEQ ID NO 987
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 987
ggcuccgugg cgcaauggau agcgcauugg acuucaaauu caaagguucc ggguucgagu 60
cccggcggag ucgcca 76

<210> SEQ ID NO 988
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 988
ggcuccgugg cgcaauggau agcgcauugg acuucaaauu caaagguucc ggguucgagu 60
cccggcggag ucgcca 76

<210> SEQ ID NO 989
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 989
ggcuccgugg cgcaauggau agcgcauugg acuucaaauu caaagguucc ggguucgagu 60
cccggcggag ucgcca 76

<210> SEQ ID NO 990
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 990
ggcuccgugg cgcaauggau agcgcauugg acuucaaauu caaagguucc ggguucgagu 60
cccggcggag ucgcca 76

<210> SEQ ID NO 991
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 991
ggcuccgugg cgcaauggau agcgcauugg acuucaaauu caaagguucc ggguucgagu 60
cccggcggag ucgcca 76

<210> SEQ ID NO 992
<211> LENGTH: 76

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 992
ggcuccgugg cgcaauggau agcgcauugg acuucaaauu caaagguucc ggguucgagu 60
cccggcggag ucgcca 76

<210> SEQ ID NO 993
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 993
gacgaggugg ccgagugguu aaggcgaugg acucuaaauc cauugugcuc ugcacgcgug 60
gguucgaauc ccauccucgu cgcca 85

<210> SEQ ID NO 994
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 994
gacgaggugg ccgagugguu aaggcgaugg acucuaaauc cauugugcuc ugcacgcgug 60
gguucgaauc ccauccucgu cgcca 85

<210> SEQ ID NO 995
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 995
gacgaggugg ccgagugguu aaggcgaugg acucuaaauc cauugugcuc ugcacgcgug 60
gguucgaauc ccauccucgu cgcca 85

<210> SEQ ID NO 996
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 996
gacgaggugg ccgagugguu aaggcgaugg acucuaaauc cauugugcuc ugcacgcgug 60
gguucgaauc ccauccucgu cgcca 85

<210> SEQ ID NO 997
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 997
gacgaggugg ccgagugguu aaggcgaugg acucuaaauc cauugugcuc ugcacgcgug 60
gguucgaauc ccauccucgu cgcca 85

<210> SEQ ID NO 998
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
gacgaggugg ccgagugguu aaggcgaugg acucuaaauc cauugugcuc ugcacgcgug 60
gguucgaauc ccauccucgu cgcca 85

<210> SEQ ID NO 999
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
gacgaggugg ccgagugguu aaggcgaugg acucuaaauc cauugugcuc ugcacgcgug 60
gguucgaauc ccauccucgu cgcca 85

<210> SEQ ID NO 1000
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000
gacgaggugg ccgagugguu aaggcgaugg acucuaaauc cauugugcuc ugcacgcgug 60
gguucgaauc ccauccucgu cgcca 85

<210> SEQ ID NO 1001
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
gacgaggugg ccgagugguu aaggcgaugg acucuaaauc cauugugcuc ugcacgcgug 60
gguucgaauc ccauccucgu cgcca 85

<210> SEQ ID NO 1002
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002

-continued gacgaggugg ccgagugguu aaggcgaugg acucuaaauc cauugugcuc ugcacgcgug 60
gguucgaauc ccauccucgu cgcca 85

<210> SEQ ID NO 1003
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003
gacgaggugg ccgagugguu aaggcgaugg acucuaaauc cauugugcuc ugcacgcgug 60
gguucgaauc ccauccucgu cgcca 85

<210> SEQ ID NO 1004
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1004
gacgaggugg ccgagugguu aaggcgaugg acucuaaauc cauugugcuc ugcacgcgug 60
gguucgaauc ccauccucgu cgcca 85

<210> SEQ ID NO 1005
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005
gacgaggugg ccgagugguu aaggcgaugg acucuaaauc cauugugcuc ugcacgcgug 60
gguucgaauc ccauccucgu cgcca 85

<210> SEQ ID NO 1006
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006
gacgaggugg ccgagugguu aaggcgaugg acucuaaauc cauugugcuc ugcacgcgug 60
gguucgaauc ccauccucgu cgcca 85

<210> SEQ ID NO 1007
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1007
gacgaggugg ccgagugguu aaggcgaugg acucuaaauc cauugugcuc ugcacgcgug 60
gguucgaauc ccauccucgu cgcca 85

<210> SEQ ID NO 1008
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008
gacgaggugg ccgagugguu aaggcgaugg acucuaaauc cauugugcuc ugcacgcgug 60
gguucgaauc ccauccucgu cgcca 85

<210> SEQ ID NO 1009
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009
gacgaggugg ccgagugguu aaggcgaugg acucuaaauc cauugugcuc ugcacgcgug 60
gguucgaauc ccauccucgu cgcca 85

<210> SEQ ID NO 1010
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1010
gacgaggugg ccgagugguu aaggcgaugg acucuaaauc cauugugcuc ugcacgcgug 60
gguucgaauc ccauccucgu cgcca 85

<210> SEQ ID NO 1011
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1011
gacgaggugg ccgagugguu aaggcgaugg acucuaaauc cauugugcuc ugcacgcgug 60
gguucgaauc ccauccucgu cgcca 85

<210> SEQ ID NO 1012
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1012
gacgaggugg ccgagugguu aaggcgaugg acucuaaauc cauugugcuc ugcacgcgug 60
gguucgaauc ccauccucgu cgcca 85

<210> SEQ ID NO 1013
<211> LENGTH: 85
<212> TYPE: RNA

-continued

<213> ORGANISM: Artificial Sequence
<220> FEATURE:
<223> OTHER INFORMATION: Description of Artificial Sequence: Synthetic
oligonucleotide

<400> SEQUENCE: 1013
gacgaggugg ccgagugguu aaggcgaugg acucuaaauc cauugugcuc ugcacgcgug 60
gguucgaauc ccauccucgu cgcca 85

<210> SEQ ID NO 1014
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1014
gacgaggugg ccgagugguu aaggcgaugg acucuaaauc cauugugcuc ugcacgcgug 60
gguucgaauc ccauccucgu cgcca 85

<210> SEQ ID NO 1015
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1015
gacgaggugg ccgagugguu aaggcgaugg acucuaaauc cauugugcuc ugcacgcgug 60
gguucgaauc ccauccucgu cgcca 85

<210> SEQ ID NO 1016
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1016
gacgaggugg ccgagugguu aaggcgaugg acucuaaauc cauugugcuc ugcacgcgug 60
gguucgaauc ccauccucgu cgcca 85

<210> SEQ ID NO 1017
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1017
gacgaggugg ccgagugguu aaggcgaugg acucuaaauc cauugugcuc ugcacgcgug 60
gguucgaauc ccauccucgu cgcca 85

<210> SEQ ID NO 1018
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide -continued

<400> SEQUENCE: 1018
gacgaggugg ccgagugguu aaggcgaugg acucuaaauc cauugugcuc ugcacgcgug 60
gguucgaauc ccauccucgu cgcca 85

<210> SEQ ID NO 1019
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1019
gacgaggugg ccgagugguu aaggcgaugg acucuaaauc cauugugcuc ugcacgcgug 60
gguucgaauc ccauccucgu cgcca 85

<210> SEQ ID NO 1020
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1020
gacgaggugg ccgagugguu aaggcgaugg acucuaaauc cauugugcuc ugcacgcgug 60
gguucgaauc ccauccucgu cgcca 85

<210> SEQ ID NO 1021
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1021
gacgaggugg ccgagugguu aaggcgaugg acucuaaauc cauugugcuc ugcacgcgug 60
gguucgaauc ccauccucgu cgcca 85

<210> SEQ ID NO 1022
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1022
gacgaggugg ccgagugguu aaggcgaugg acucuaaauc cauugugcuc ugcacgcgug 60
gguucgaauc ccauccucgu cgcca 85

<210> SEQ ID NO 1023
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1023
gacgaggugg ccgagugguu aaggcgaugg acucuaaauc cauugugcuc ugcacgcgug 60
gguucgaauc ccauccucgu cgcca 85

<210> SEQ ID NO 1024
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1024
gacgaggugg ccgagugguu aaggcgaugg acucuaaauc cauugugcuc ugcacgcgug 60
gguucgaauc ccauccucgu cgcca 85

<210> SEQ ID NO 1025
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1025
gacgaggugg ccgagugguu aaggcgaugg acucuaaauc cauugugcuc ugcacgcgug 60
gguucgaauc ccauccucgu cgcca 85

<210> SEQ ID NO 1026
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1026
gacgaggugg ccgagugguu aaggcgaugg acucuaaauc cauugugcuc ugcacgcgug 60
gguucgaauc ccauccucgu cgcca 85

<210> SEQ ID NO 1027
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1027
gacgaggugg ccgagugguu aaggcgaugg acucuaaauc cauugugcuc ugcacgcgug 60
gguucgaauc ccauccucgu cgcca 85

<210> SEQ ID NO 1028
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1028
gacgaggugg ccgagugguu aaggcgaugg acucuaaauc cauugugcuc ugcacgcgug 60
gguucgaauc ccauccucgu cgcca 85

<210> SEQ ID NO 1029
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
gacgaggugg ccgagugguu aaggcgaugg acucuaaauc cauugugcuc ugcacgcgug    60
gguucgaauc ccauccucgu cgcca                                         85

<210> SEQ ID NO 1030
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
gacgaggugg ccgagugguu aaggcgaugg acucuaaauc cauugugcuc ugcacgcgug    60
gguucgaauc ccauccucgu cgcca                                         85

<210> SEQ ID NO 1031
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1031
gacgaggugg ccgagugguu aaggcgaugg acucuaaauc cauugugcuc ugcacgcgug    60
gguucgaauc ccauccucgu cgcca                                         85

<210> SEQ ID NO 1032
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1032
gacgaggugg ccgagugguu aaggcgaugg acucuaaauc cauugugcuc ugcacgcgug    60
gguucgaauc ccauccucgu cgcca                                         85

<210> SEQ ID NO 1033
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033
gacgaggugg ccgagugguu aaggcgaugg acucuaaauc cauugugcuc ugcacgcgug    60
gguucgaauc ccauccucgu cgcca                                         85

<210> SEQ ID NO 1034
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034
gacgaggugg ccgagugguu aaggcgaugg acucuaaauc cauugugcuc ugcacgcgug     60
gguucgaauc ccauccucgu cgcca                                          85

<210> SEQ ID NO 1035
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035
gacgaggugg ccgagugguu aaggcgaugg acucuaaauc cauugugcuc ugcacgcgug     60
gguucgaauc ccauccucgu cgcca                                          85

<210> SEQ ID NO 1036
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
gacgaggugg ccgagugguu aaggcgaugg acucuaaauc cauugugcuc ugcacgcgug     60
gguucgaauc ccauccucgu cgcca                                          85

<210> SEQ ID NO 1037
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1037
gacgaggugg ccgagugguu aaggcgaugg acucuaaauc cauugugcuc ugcacgcgug     60
gguucgaauc ccauccucgu cgcca                                          85

<210> SEQ ID NO 1038
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1038
gacgaggugg ccgagugguu aaggcgaugg acucuaaauc cauugugcuc ugcacgcgug     60
gguucgaauc ccauccucgu cgcca                                          85

<210> SEQ ID NO 1039
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
gacgaggugg ccgagugguu aaggcgaugg acucuaaauc cauugugcuc ugcacgcgug 60
gguucgaauc ccauccucgu cgcca 85

<210> SEQ ID NO 1040
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1040
gacgaggugg ccgagugguu aaggcgaugg acucuaaauc cauugugcuc ugcacgcgug 60
gguucgaauc ccauccucgu cgcca 85

<210> SEQ ID NO 1041
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1041
gacgaggugg ccgagugguu aaggcgaugg acucuaaauc cauugugcuc ugcacgcgug 60
gguucgaauc ccauccucgu cgcca 85

<210> SEQ ID NO 1042
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1042
gacgaggugg ccgagugguu aaggcgaugg acucuaaauc cauugugcuc ugcacgcgug 60
gguucgaauc ccauccucgu cgcca 85

<210> SEQ ID NO 1043
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1043
gacgaggugg ccgagugguu aaggcgaugg acucuaaauc cauugugcuc ugcacgcgug 60
gguucgaauc ccauccucgu cgcca 85

<210> SEQ ID NO 1044
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1044
gacgaggugg ccgagugguu aaggcgaugg acucuaaauc cauugugcuc ugcacgcgug 60
gguucgaauc ccauccucgu cgcca 85

<210> SEQ ID NO 1045
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1045
gacgaggugg ccgagugguu aaggcgaugg acucuaaauc cauugugcuc ugcacgcgug 60
gguucgaauc ccauccucgu cgcca 85

<210> SEQ ID NO 1046
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1046
gacgaggugg ccgagugguu aaggcgaugg acucuaaauc cauugugcuc ugcacgcgug 60
gguucgaauc ccauccucgu cgcca 85

<210> SEQ ID NO 1047
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1047
gacgaggugg ccgagugguu aaggcgaugg acucuaaauc cauugugcuc ugcacgcgug 60
gguucgaauc ccauccucgu cgcca 85

<210> SEQ ID NO 1048
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1048
gacgaggugg ccgagugguu aaggcgaugg acucuaaauc cauugugcuc ugcacgcgug 60
gguucgaauc ccauccucgu cgcca 85

<210> SEQ ID NO 1049
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1049
gacgaggugg ccgagugguu aaggcgaugg acucuaaauc cauugugcuc ugcacgcgug 60
gguucgaauc ccauccucgu cgcca 85

<210> SEQ ID NO 1050

<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1050
gacgaggugg ccgagugguu aaggcgaugg acucuaaauc cauugugcuc ugcacgcgug 60
gguucgaauc ccauccucgu cgcca 85

<210> SEQ ID NO 1051
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1051
gacgaggugg ccgagugguu aaggcgaugg acucuaaauc cauugugcuc ugcacgcgug 60
gguucgaauc ccauccucgu cgcca 85

<210> SEQ ID NO 1052
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1052
gacgaggugg ccgagugguu aaggcgaugg acucuaaauc cauugugcuc ugcacgcgug 60
gguucgaauc ccauccucgu cgcca 85

<210> SEQ ID NO 1053
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1053
gacgaggugg ccgagugguu aaggcgaugg acucuaaauc cauugugcuc ugcacgcgug 60
gguucgaauc ccauccucgu cgcca 85

<210> SEQ ID NO 1054
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054
gacgaggugg ccgagugguu aaggcgaugg acucuaaauc cauugugcuc ugcacgcgug 60
gguucgaauc ccauccucgu cgcca 85

<210> SEQ ID NO 1055
<211> LENGTH: 85
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1055
gacgaggugg ccgagugguu aaggcgaugg acucuaaauc cauugugcuc ugcacgcgug 60
gguucgaauc ccauccucgu cgcca 85

<210> SEQ ID NO 1056
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056
gacgaggugg ccgagugguu aaggcgaugg acucuaaauc cauugugcuc ugcacgcgug 60
gguucgaauc ccauccucgu cgcca 85

<210> SEQ ID NO 1057
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1057
gacgaggugg ccgagugguu aaggcgaugg acucuaaauc cauugugcuc ugcacgcgug 60
gguucgaauc ccauccucgu cgcca 85

<210> SEQ ID NO 1058
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1058
gacgaggugg ccgagugguu aaggcgaugg acucuaaauc cauugugcuc ugcacgcgug 60
gguucgaauc ccauccucgu cgcca 85

<210> SEQ ID NO 1059
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1059
gacgaggugg ccgagugguu aaggcgaugg acucuaaauc cauugugcuc ugcacgcgug 60
gguucgaauc ccauccucgu cgcca 85

<210> SEQ ID NO 1060
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1060
gacgaggugg ccgagugguu aaggcgaugg acucuaaauc cauugugcuc ugcacgcgug 60
gguucgaauc ccauccucgu cgcca 85

<210> SEQ ID NO 1061
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1061
gacgaggugg ccgagugguu aaggcgaugg acucuaaauc cauugugcuc ugcacgcgug 60
gguucgaauc ccauccucgu cgcca 85

<210> SEQ ID NO 1062
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1062
gacgaggugg ccgagugguu aaggcgaugg acucuaaauc cauugugcuc ugcacgcgug 60
gguucgaauc ccauccucgu cgcca 85

<210> SEQ ID NO 1063
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1063
gacgaggugg ccgagugguu aaggcgaugg acucuaaauc cauugugcuc ugcacgcgug 60
gguucgaauc ccauccucgu cgcca 85

<210> SEQ ID NO 1064
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1064
gacgaggugg ccgagugguu aaggcgaugg acucuaaauc cauugugcuc ugcacgcgug 60
gguucgaauc ccauccucgu cgcca 85

<210> SEQ ID NO 1065
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1065
gacgaggugg ccgagugguu aaggcgaugg acucuaaauc cauugugcuc ugcacgcgug 60
gguucgaauc ccauccucgu cgcca 85

<210> SEQ ID NO 1066
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1066
gacgaggugg ccgagugguu aaggcgaugg acucuaaauc cauugugcuc ugcacgcgug 60
gguucgaauc ccauccucgu cgcca 85

<210> SEQ ID NO 1067
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1067
gacgaggugg ccgagugguu aaggcgaugg acucuaaauc cauugugcuc ugcacgcgug 60
gguucgaauc ccauccucgu cgcca 85

<210> SEQ ID NO 1068
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1068
gacgaggugg ccgagugguu aaggcgaugg acucuaaauc cauugugcuc ugcacgcgug 60
gguucgaauc ccauccucgu cgcca 85

<210> SEQ ID NO 1069
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1069
gacgaggugg ccgagugguu aaggcgaugg acucuaaauc cauugugcuc ugcacgcgug 60
gguucgaauc ccauccucgu cgcca 85

<210> SEQ ID NO 1070
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1070
gacgaggugg ccgagugguu aaggcgaugg acucuaaauc cauugugcuc ugcacgcgug 60
gguucgaauc ccauccucgu cgcca 85

<210> SEQ ID NO 1071
<211> LENGTH: 85

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1071
gacgaggugg ccgagugguu aaggcgaugg acucuaaauc cauugugcuc ugcacgcgug     60
gguucgaauc ccauccucgu cgcca                                           85

<210> SEQ ID NO 1072
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1072
gacgaggugg ccgagugguu aaggcgaugg acucuaaauc cauugugcuc ugcacgcgug     60
gguucgaauc ccauccucgu cgcca                                           85

<210> SEQ ID NO 1073
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1073
gacgaggugg ccgagugguu aaggcgaugg acucuaaauc cauugugcuc ugcacgcgug     60
gguucgaauc ccauccucgu cgcca                                           85

<210> SEQ ID NO 1074
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1074
gacgaggugg ccgagugguu aaggcgaugg acucuaaauc cauugugcuc ugcacgcgug     60
gguucgaauc ccauccucgu cgcca                                           85

<210> SEQ ID NO 1075
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
gacgaggugg ccgagugguu aaggcgaugg acucuaaauc cauugugcuc ugcacgcgug     60
gguucgaauc ccauccucgu cgcca                                           85

<210> SEQ ID NO 1076
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1076
gacgaggugg ccgagugguu aaggcgaugg acucuaaauc cauugugcuc ugcacgcgug 60
gguucgaauc ccauccucgu cgcca 85

<210> SEQ ID NO 1077
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
gacgaggugg ccgagugguu aaggcgaugg acucuaaauc cauugugcuc ugcacgcgug 60
gguucgaauc ccauccucgu cgcca 85

<210> SEQ ID NO 1078
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
gacgaggugg ccgagugguu aaggcgaugg acucuaaauc cauugugcuc ugcacgcgug 60
gguucgaauc ccauccucgu cgcca 85

<210> SEQ ID NO 1079
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
gguuccaugg uguaauggua agcacucugg acuuuaaauc cagcgauccg aguucgaguc 60
ucgguggaac cucca 75

<210> SEQ ID NO 1080
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
gguuccaugg uguaauggua agcacucugg acuuuaaauc cagcgauccg aguucgaguc 60
ucgguggaac cucca 75

<210> SEQ ID NO 1081
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
gguuccaugg uguaauggua agcacucugg acuuuaaauc cagcgauccg aguucgaguc 60
ucgguggaac cucca 75

<210> SEQ ID NO 1082
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
gguuccaugg uguaauggua agcacucugg acuuuaaauc cagcgauccg aguucgaguc 60
ucgguggaac cucca 75

<210> SEQ ID NO 1083
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1083
gguuccaugg uguaauggua agcacucugg acuuuaaauc cagcgauccg aguucgaguc 60
ucgguggaac cucca 75

<210> SEQ ID NO 1084
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084
gguuccaugg uguaauggua agcacucugg acuuuaaauc cagcgauccg aguucgaguc 60
ucgguggaac cucca 75

<210> SEQ ID NO 1085
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085
gguuccaugg uguaauggua agcacucugg acuuuaaauc cagcgauccg aguucgaguc 60
ucgguggaac cucca 75

<210> SEQ ID NO 1086
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
gguuccaugg uguaauggua agcacucugg acuuuaaauc cagcgauccg aguucgaguc 60
ucgguggaac cucca 75

<210> SEQ ID NO 1087
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1087
gguuccaugg uguaauggua agcacucugg acuuuaaauc cagcgauccg aguucgaguc 60
ucgguggaac cucca 75

<210> SEQ ID NO 1088
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1088
gguuccaugg uguaauggua agcacucugg acuuuaaauc cagcgauccg aguucgaguc 60
ucgguggaac cucca 75

<210> SEQ ID NO 1089
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1089
gguuccaugg uguaauggua agcacucugg acuuuaaauc cagcgauccg aguucgaguc 60
ucgguggaac cucca 75

<210> SEQ ID NO 1090
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1090
gguuccaugg uguaauggua agcacucugg acuuuaaauc cagcgauccg aguucgaguc 60
ucgguggaac cucca 75

<210> SEQ ID NO 1091
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1091
gguuccaugg uguaauggua agcacucugg acuuuaaauc cagcgauccg aguucgaguc 60
ucgguggaac cucca 75

<210> SEQ ID NO 1092
<211> LENGTH: 75
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 1092
gguuccaugg uguaauggua agcacucugg acuuuaaauc cagcgauccg aguucgaguc 60
ucgguggaac cucca 75

<210> SEQ ID NO 1093
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1093
gguuccaugg uguaauggua agcacucugg acuuuaaauc cagcgauccg aguucgaguc 60
ucgguggaac cucca 75

<210> SEQ ID NO 1094
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1094
gguuccaugg uguaauggua agcacucugg acuuuaaauc cagcgauccg aguucgaguc 60
ucgguggaac cucca 75

<210> SEQ ID NO 1095
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1095
gguuccaugg uguaauggua agcacucugg acuuuaaauc cagcgauccg aguucgaguc 60
ucgguggaac cucca 75

<210> SEQ ID NO 1096
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1096
gguuccaugg uguaauggua agcacucugg acuuuaaauc cagcgauccg aguucgaguc 60
ucgguggaac cucca 75

<210> SEQ ID NO 1097
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1097
gguuccaugg uguaauggua agcacucugg acuuuaaauc cagcgauccg aguucgaguc 60
ucgguggaac cucca 75

<210> SEQ ID NO 1098
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098
gguuccaugg uguaauggua agcacucugg acuuuaaauc cagcgauccg aguucgaguc 60
ucgguggaac cucca 75

<210> SEQ ID NO 1099
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1099
gguuccaugg uguaauggua agcacucugg acuuuaaauc cagcgauccg aguucgaguc 60
ucgguggaac cucca 75

<210> SEQ ID NO 1100
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1100
gguuccaugg uguaauggua agcacucugg acuuuaaauc cagcgauccg aguucgaguc 60
ucgguggaac cucca 75

<210> SEQ ID NO 1101
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1101
gguuccaugg uguaauggua agcacucugg acuuuaaauc cagcgauccg aguucgaguc 60
ucgguggaac cucca 75

<210> SEQ ID NO 1102
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1102
gguuccaugg uguaauggua agcacucugg acuuuaaauc cagcgauccg aguucgaguc 60
ucgguggaac cucca 75

<210> SEQ ID NO 1103
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1103
gguuccaugg uguaauggua agcacucugg acuuuaaauc cagcgauccg aguucgaguc 60
ucgguggaac cucca 75

<210> SEQ ID NO 1104
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1104
gguuccaugg uguaauggua agcacucugg acuuuaaauc cagcgauccg aguucgaguc 60
ucgguggaac cucca 75

<210> SEQ ID NO 1105
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
gguuccaugg uguaauggua agcacucugg acuuuaaauc cagcgauccg aguucgaguc 60
ucgguggaac cucca 75

<210> SEQ ID NO 1106
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
gguuccaugg uguaauggua agcacucugg acuuuaaauc cagcgauccg aguucgaguc 60
ucgguggaac cucca 75

<210> SEQ ID NO 1107
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107
gguuccaugg uguaauggua agcacucugg acuuuaaauc cagcgauccg aguucgaguc 60
ucgguggaac cucca 75

<210> SEQ ID NO 1108
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1108
gguuccaugg uguaauggua agcacucugg acuuuaaauc cagcgauccg aguucgaguc 60
ucgguggaac cucca 75

<210> SEQ ID NO 1109
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1109
gguuccaugg uguaauggua agcacucugg acuuuaaauc cagcgauccg aguucgaguc 60
ucgguggaac cucca 75

<210> SEQ ID NO 1110
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1110
gguuccaugg uguaauggua agcacucugg acuuuaaauc cagcgauccg aguucgaguc 60
ucgguggaac cucca 75

<210> SEQ ID NO 1111
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1111
gguuccaugg uguaauggua agcacucugg acuuuaaauc cagcgauccg aguucgaguc 60
ucgguggaac cucca 75

<210> SEQ ID NO 1112
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1112
gguuccaugg uguaauggua agcacucugg acuuuaaauc cagcgauccg aguucgaguc 60
ucgguggaac cucca 75

<210> SEQ ID NO 1113
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1113
gguuccaugg uguaauggua agcacucugg acuuuaaauc cagcgauccg aguucgaguc 60
ucgguggaac cucca 75

<210> SEQ ID NO 1114
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1114
gguuccaugg uguaauggua agcacucugg acuuuaaauc cagcgauccg aguucgaguc 60
ucgguggaac cucca 75

<210> SEQ ID NO 1115
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1115
gguuccaugg uguaauggua agcacucugg acuuuaaauc cagcgauccg aguucgaguc 60
ucgguggaac cucca 75

<210> SEQ ID NO 1116
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1116
gguuccaugg uguaauggua agcacucugg acuuuaaauc cagcgauccg aguucgaguc 60
ucgguggaac cucca 75

<210> SEQ ID NO 1117
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1117
gguuccaugg uguaauggua agcacucugg acuuuaaauc cagcgauccg aguucgaguc 60
ucgguggaac cucca 75

<210> SEQ ID NO 1118
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1118
gguuccaugg uguaauggua agcacucugg acuuuaaauc cagcgauccg aguucgaguc 60
ucgguggaac cucca 75

<210> SEQ ID NO 1119
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1119
gguuccaugg uguaauggua agcacucugg acuuuaaauc cagcgauccg aguucgaguc 60
ucgguggaac cucca 75

<210> SEQ ID NO 1120
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1120
gguuccaugg uguaauggua agcacucugg acuuuaaauc cagcgauccg aguucgaguc 60
ucgguggaac cucca 75

<210> SEQ ID NO 1121
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1121
gguuccaugg uguaauggua agcacucugg acuuuaaauc cagcgauccg aguucgaguc 60
ucgguggaac cucca 75

<210> SEQ ID NO 1122
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1122
gguuccaugg uguaauggua agcacucugg acuuuaaauc cagcgauccg aguucgaguc 60
ucgguggaac cucca 75

<210> SEQ ID NO 1123
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1123
gguuccaugg uguaauggua agcacucugg acuuuaaauc cagcgauccg aguucgaguc 60
ucgguggaac cucca 75

<210> SEQ ID NO 1124
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1124
gguuccaugg uguaauggua agcacucugg acuuuaaauc cagcgauccg aguucgaguc 60
ucgguggaac cucca 75

<210> SEQ ID NO 1125
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1125
gguuccaugg uguaauggua agcacucugg acuuuaaauc cagcgauccg aguucgaguc 60
ucgguggaac cucca 75

<210> SEQ ID NO 1126
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1126
gguuccaugg uguaauggua agcacucugg acuuuaaauc cagcgauccg aguucgaguc 60
ucgguggaac cucca 75

<210> SEQ ID NO 1127
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1127
gguuccaugg uguaauggua agcacucugg acuuuaaauc cagcgauccg aguucgaguc 60
ucgguggaac cucca 75

<210> SEQ ID NO 1128
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1128
gguuccaugg uguaauggua agcacucugg acuuuaaauc cagcgauccg aguucgaguc 60
ucgguggaac cucca 75

<210> SEQ ID NO 1129

<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
gguuccaugg uguaauggua agcacucugg acuuuaaauc cagcgauccg aguucgaguc 60
ucgguggaac cucca 75

<210> SEQ ID NO 1130
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
gguuccaugg uguaauggua agcacucugg acuuuaaauc cagcgauccg aguucgaguc 60
ucgguggaac cucca 75

<210> SEQ ID NO 1131
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1131
gguuccaugg uguaauggua agcacucugg acuuuaaauc cagcgauccg aguucgaguc 60
ucgguggaac cucca 75

<210> SEQ ID NO 1132
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1132
gguuccaugg uguaauggua agcacucugg acuuuaaauc cagcgauccg aguucgaguc 60
ucgguggaac cucca 75

<210> SEQ ID NO 1133
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1133
gguuccaugg uguaauggua agcacucugg acuuuaaauc cagcgauccg aguucgaguc 60
ucgguggaac cucca 75

<210> SEQ ID NO 1134
<211> LENGTH: 75
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 1134
gguuccaugg uguaauggua agcacucugg acuuuaaauc cagcgauccg aguucgaguc     60
ucgguggaac cucca                                                      75

<210> SEQ ID NO 1135
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1135
gguuccaugg uguaauggua agcacucugg acuuuaaauc cagcgauccg aguucgaguc     60
ucgguggaac cucca                                                      75

<210> SEQ ID NO 1136
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
gguuccaugg uguaauggua agcacucugg acuuuaaauc cagcgauccg aguucgaguc     60
ucgguggaac cucca                                                      75

<210> SEQ ID NO 1137
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
gguuccaugg uguaauggua agcacucugg acuuuaaauc cagcgauccg aguucgaguc     60
ucgguggaac cucca                                                      75

<210> SEQ ID NO 1138
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
gguuccaugg uguaauggua agcacucugg acuuuaaauc cagcgauccg aguucgaguc     60
ucgguggaac cucca                                                      75

<210> SEQ ID NO 1139
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
gguuccaugg uguaauggua agcacucugg acuuuaaauc cagcgauccg aguucgaguc 60
ucgguggaac cucca 75

<210> SEQ ID NO 1140
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
gguuccaugg uguaauggua agcacucugg acuuuaaauc cagcgauccg aguucgaguc 60
ucgguggaac cucca 75

<210> SEQ ID NO 1141
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141
gguuccaugg uguaauggua agcacucugg acuuuaaauc cagcgauccg aguucgaguc 60
ucgguggaac cucca 75

<210> SEQ ID NO 1142
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1142
gguuccaugg uguaauggua agcacucugg acuuuaaauc cagcgauccg aguucgaguc 60
ucgguggaac cucca 75

<210> SEQ ID NO 1143
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1143
gguuccaugg uguaauggua agcacucugg acuuuaaauc cagcgauccg aguucgaguc 60
ucgguggaac cucca 75

<210> SEQ ID NO 1144
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1144
gguuccaugg uguaauggua agcacucugg acuuuaaauc cagcgauccg aguucgaguc 60
ucgguggaac cucca 75

<210> SEQ ID NO 1145
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
gguuccaugg uguaauggua agcacucugg acuuuaaauc cagcgauccg aguucgaguc    60
ucgguggaac cucca                                                    75

<210> SEQ ID NO 1146
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
gguuccaugg uguaauggua agcacucugg acuuuaaauc cagcgauccg aguucgaguc    60
ucgguggaac cucca                                                    75

<210> SEQ ID NO 1147
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
gguuccaugg uguaauggua agcacucugg acuuuaaauc cagcgauccg aguucgaguc    60
ucgguggaac cucca                                                    75

<210> SEQ ID NO 1148
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
gguuccaugg uguaauggua agcacucugg acuuuaaauc cagcgauccg aguucgaguc    60
ucgguggaac cucca                                                    75

<210> SEQ ID NO 1149
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
gguuccaugg uguaauggua agcacucugg acuuuaaauc cagcgauccg aguucgaguc    60
ucgguggaac cucca                                                    75

<210> SEQ ID NO 1150
<211> LENGTH: 75

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1150
gguuccaugg uguaauggua agcacucugg acuuuaaauc cagcgauccg aguucgaguc 60
ucgguggaac cucca 75

<210> SEQ ID NO 1151
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1151
gguuccaugg uguaauggua agcacucugg acuuuaaauc cagcgauccg aguucgaguc 60
ucgguggaac cucca 75

<210> SEQ ID NO 1152
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1152
gguuccaugg uguaauggua agcacucugg acuuuaaauc cagcgauccg aguucgaguc 60
ucgguggaac cucca 75

<210> SEQ ID NO 1153
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1153
gguuccaugg uguaauggua agcacucugg acuuuaaauc cagcgauccg aguucgaguc 60
ucgguggaac cucca 75

<210> SEQ ID NO 1154
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1154
gguuccaugg uguaauggua agcacucugg acuuuaaauc cagcgauccg aguucgaguc 60
ucgguggaac cucca 75

<210> SEQ ID NO 1155
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1155
ggcuccgugg cgcaauggau agcgcauugg acuucaaauu caaagguucc ggguucgagu 60
cccggcggag ucg 73

<210> SEQ ID NO 1156
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1156
ggcuccgugg cgcaauggau agcgcauugg acuucaaauu caaagguucc ggguucgagu 60
cccggcggag ucgcca 76

<210> SEQ ID NO 1157
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1157
ggcuccgugg cgcaauggau agcgcauugg acuucaaauu caaagguucc ggguucgagu 60
cccggcggag ucgcca 76

<210> SEQ ID NO 1158
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1158
ggcuccgugg cgcaauggau agcgcauugg acuucaaauu caaagguucc ggguucgagu 60
cccggcggag ucgcca 76

<210> SEQ ID NO 1159
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1159
ggcuccgugg cgcaauggau agcgcauugg acuucaaauu caaagguucc ggguucgagu 60
cccggcggag ucgcca 76

<210> SEQ ID NO 1160
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1160

-continued ggcuccgugg cgcaauggau agcgcauugg acuucaaauu caaagguucc ggguucgagu 60
cccggcggag ucgcca 76

<210> SEQ ID NO 1161
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1161
ggcuccgugg cgcaauggau agcgcauugg acuucaaauu caaagguucc ggguucgagu 60
cccggcggag ucgcca 76

<210> SEQ ID NO 1162
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1162
ggcuccgugg cgcaauggau agcgcauugg acuucaaauu caaagguucc ggguucgagu 60
cccggcggag ucgcca 76

<210> SEQ ID NO 1163
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1163
ggcuccgugg cgcaauggau agcgcauugg acuucaaauu caaagguucc ggguucgagu 60
cccggcggag ucgcca 76

<210> SEQ ID NO 1164
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1164
ggcuccgugg cgcaauggau agcgcauugg acuucaaauu caaagguucc ggguucgagu 60
cccggcggag ucgcca 76

<210> SEQ ID NO 1165
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1165
ggcuccgugg cgcaauggau agcgcauugg acuucaaauu caaagguucc ggguucgagu 60
cccggcggag ucgcca 76

<210> SEQ ID NO 1166
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1166
ggcuccgugg cgcaauggau agcgcauugg acuucaaauu caaagguucc ggguucgagu 60
cccggcggag ucgcca 76

<210> SEQ ID NO 1167
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1167
ggcuccgugg cgcaauggau agcgcauugg acuucaaauu caaagguucc ggguucgagu 60
cccggcggag ucgcca 76

<210> SEQ ID NO 1168
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1168
ggcuccgugg cgcaauggau agcgcauugg acuucaaauu caaagguucc ggguucgagu 60
cccggcggag ucgcca 76

<210> SEQ ID NO 1169
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1169
ggcuccgugg cgcaauggau agcgcauugg acuucaaauu caaagguucc ggguucgagu 60
cccggcggag ucgcca 76

<210> SEQ ID NO 1170
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1170
ggcuccgugg cgcaauggau agcgcauugg acuucaaauu caaagguucc ggguucgagu 60
cccggcggag ucgcca 76

<210> SEQ ID NO 1171
<211> LENGTH: 76
<212> TYPE: RNA

-continued

<213> ORGANISM: Artificial Sequence
<220> FEATURE:
<223> OTHER INFORMATION: Description of Artificial Sequence: Synthetic
      oligonucleotide

<400> SEQUENCE: 1171
ggcuccgugg cgcaauggau agcgcauugg acuucaaauu caaagguucc ggguucgagu 60
cccggcggag ucgcca 76

<210> SEQ ID NO 1172
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
ggcuccgugg cgcaauggau agcgcauugg acuucaaauu caaagguucc ggguucgagu 60
cccggcggag ucgcca 76

<210> SEQ ID NO 1173
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
ggcuccgugg cgcaauggau agcgcauugg acuucaaauu caaagguucc ggguucgagu 60
cccggcggag ucgcca 76

<210> SEQ ID NO 1174
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
ggcuccgugg cgcaauggau agcgcauugg acuucaaauu caaagguucc ggguucgagu 60
cccggcggag ucgcca 76

<210> SEQ ID NO 1175
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
ggcuccgugg cgcaauggau agcgcauugg acuucaaauu caaagguucc ggguucgagu 60
cccggcggag ucgcc 75

<210> SEQ ID NO 1176
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
ggcuccgugg cgcaauggau agcgcauugg acuucaaauu caaagguucc ggguucgagu 60
cccggcggag ucgc 74

<210> SEQ ID NO 1177
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1177
ggcuccgugg cgcaauggau agcgcauugg acuucaaauu caaagguucc ggguucgagu 60
cccggcggag ucg 73

<210> SEQ ID NO 1178
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1178
ggcuccgugg cgcaauggau agcgcauugg acuucaaauu caaagguucc ggguucgagu 60
cccggcggag ucg 73

<210> SEQ ID NO 1179
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1179
ggcuccgugg cgcaauggau agcgcauugg acuucaaauu caaagguucc ggguucgagu 60
cccggcggag ucgc 74

<210> SEQ ID NO 1180
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1180
ggcuccgugg cgcaauggau agcgcauugg acuucaaauu caaagguucc ggguucgagu 60
cccggcggag ucgcc 75

<210> SEQ ID NO 1181
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1181
ggcuccgugg cgcaauggau agcgcauugg acuucaaauu caaagguucc ggguucgagu 60
cccggcggag ucgcca 76

<210> SEQ ID NO 1182
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1182
ggcuccgugg cgcaauggau agcgcauugg acuucaaauu caaagguucc ggguucgagu 60
cccggcggag ucgcca 76

<210> SEQ ID NO 1183
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1183
ggcuccgugg cgcaauggau agcgcauugg acuucaaauu caaagguucc ggguucgagu 60
cccggcggag ucg 73

<210> SEQ ID NO 1184
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1184
ggcuccgugg cgcaauggau agcgcauugg acuucaaauu caaagguucc ggguucgagu 60
cccggcggag ucg 73

<210> SEQ ID NO 1185
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1185
ggcuccgugg cgcaauggau agcgcauugg acuucaaauu caaagguucc ggguucgagu 60
cccggcggag ucg 73

<210> SEQ ID NO 1186
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1186
ggcuccgugg cgcaauggau agcgcauugg acuucaaauu caaagguucc ggguucgagu 60
cccggcggag ucg 73

-continued

<210> SEQ ID NO 1187
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1187
ggcuccgugg cgcaauggau agcgcauugg acuucaaauu caaagguucc ggguucgagu 60
cccggcggag ucg 73

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1200
ggggaattag ctcaagtggt agagcgcttg cttagcatgc aagaggtagt gggatcgatg 60
cccacattct cca 73

<210> SEQ ID NO 1201
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1201
ggggatgtag ctcagtggta gagcgcatgc ttcgcatgta tgaggtcccg ggttcgatcc 60
ccggcatctc ca 72

<210> SEQ ID NO 1202
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1202
gggggtgtag ctcagtggta gagcgcatgc tttgcatgta tgaggccccg ggttcgatcc 60
ccggcacctc ca 72

<210> SEQ ID NO 1203
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1203
gggccagtgg cgcaatggat aacgcgtctg actacggatc agaagattcc aggttcgact 60
cctggctggc tcg 73

<210> SEQ ID NO 1204
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1204
ggccgcgtgg cctaatggat aaggcgtctg attccggatc agaagattga gggttcgagt 60
cccttcgtgg tcg 73

<210> SEQ ID NO 1205
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1205
gccccagtgg cctaatggat aaggcactgg cctcctaagc cagggattgt gggttcgagt 60
cccacctggg gta 73

<210> SEQ ID NO 1206
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1206
gaccgcgtgg cctaatggat aaggcgtctg acttcggatc agaagattga gggttcgagt 60
ccctccgtgg tcg 73

<210> SEQ ID NO 1207
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other

<400> SEQUENCE: 1207
ggctctgtgg cgcaatggat nagcgcattg gacttctaat tcaaaggttg cgggttcgag 60
tcccnccaga gtcg 74

<210> SEQ ID NO 1208
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (43)..(43)

<223> OTHER INFORMATION: a, c, t, g, unknown or other

<400> SEQUENCE: 1208
gtctctgtgg cgcaatcggt tagcgcgttc ggctgttaac cgnaaaggtt ggtggttcga 60
gcccacccag ggacg 75

<210> SEQ ID NO 1209
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1209
tcctcgttag tatagtggtg agtatccccg cctgtcacgc gggagaccgg ggttcgattc 60
cccgacgggg ag 72

<210> SEQ ID NO 1210
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 1210
gggggtatag ctcagngggt agagcatttg actgcagatc aagaggtccc cggttcaaat 60
ccgggtgccc cct 73

<210> SEQ ID NO 1211
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(20)
<223> OTHER INFORMATION: a, c, t, g, unknown or other

<400> SEQUENCE: 1211
ggttccatgg tgtaatggtn agcactctgg actctgaatc cagcgatccg agttcaagtc 60
tcggtggaac ct 72

<210> SEQ ID NO 1212
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1212
ggtcccatgg tgtaatggtt agcactctgg actttgaatc cagcgatccg agttcaaatc 60
tcggtgggac ct 72

<210> SEQ ID NO 1213
<211> LENGTH: 72

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1213
tccctggtgg tctagtggtt aggattcggc gctctcaccg ccgcggcccg ggttcgattc 60
ccggtcaggg aa 72

<210> SEQ ID NO 1214
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (42)..(42)
<223> OTHER INFORMATION: a, c, t, g, unknown or other

<400> SEQUENCE: 1214
tccctggtgg tctagtggct aggattcggc gctttcaccg cngcggcccg ggttcgattc 60
ccggtcaggg aa 72

<210> SEQ ID NO 1215
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (40)..(40)
<223> OTHER INFORMATION: a, c, t, g, unknown or other

<400> SEQUENCE: 1215
gcattggtgg ttcagtggta gaattctcgc ctcccacgcn ggagacccgg gttcgattcc 60
cggccaatgc a 71

<210> SEQ ID NO 1216
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1216
gcattggtgg ttcagtggta gaattctcgc ctgccacgcg ggaggcccgg gttcgattcc 60
cggccaatgc a 71

<210> SEQ ID NO 1217
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1217
gcgttggtgg tatagtggtg agcatagctg ccttccaagc agttgacccg ggttcgattc 60
ccggccaacg ca 72

<210> SEQ ID NO 1218
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1218
ggccggttag ctcagttggt tagagcgtgg tgctaataac gccaaggtcg cgggttcgat 60
ccccgtacgg gcca 74

<210> SEQ ID NO 1219
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1219
gctccagtgg cgcaatcggt tagcgcgcgg tacttataat gccgaggttg tgagttcgag 60
cctcacctgg agca 74

<210> SEQ ID NO 1220
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1220
ggtagcgtgg ccgagcggtc taaggcgctg gattaaggct ccagtctctt cgggggcgtg 60
ggttcgaatc ccaccgctgc ca 82

<210> SEQ ID NO 1221
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other

<400> SEQUENCE: 1221
gtcaggatgg ccgagtggtc ntaaggcgcc agactcaagt tctggtctcc gnatggaggc 60
gtgggttcga atcccacttc tgaca 85

<210> SEQ ID NO 1222
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1222
gtcaggatgg ccgagcggtc taaggcgctg cgttcaggtc gcagtctccc ctggaggcgt 60
gggttcgaat cccactcctg aca 83

<210> SEQ ID NO 1223
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1223
accaggatgg ccgagtggtt aaggcgttgg acttaagatc caatggacag atgtccgcgt 60
gggttcgaac cccactcctg gta 83

<210> SEQ ID NO 1224
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (54)..(54)
<223> OTHER INFORMATION: a, c, t, g, unknown or other

<400> SEQUENCE: 1224
ggtagcgtgg ccgagcggtc taaggcgctg gatttaggct ccagtctctt cggnggcgtg 60
ggttcgaatc ccaccgctgc ca 82

<210> SEQ ID NO 1225
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1225
gcccggctag ctcagtcggt agagcatgag actcttaatc tcagggtcgt gggttcgagc 60
cccacgttgg gcgnnn 76

<210> SEQ ID NO 1226
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1226
gcctggatag ctcagtcggt agagcatcag acttttaatc tgagggtcca gggttcaagt 60
ccctgttcag gcg 73

<210> SEQ ID NO 1227
<211> LENGTH: 73
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other

<400> SEQUENCE: 1227
gccctcttag cgcagtnggc agcgcgtcag tctcataatc tgaaggtcct gagttcgagc     60
ctcagagagg gca                                                        73

<210> SEQ ID NO 1228
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a, c, t, g, unknown or other

<400> SEQUENCE: 1228
gccgaaatag ctcagttggg agagcgttag actgaagatc ntaaaggtcc ctggttcaat     60
cccgggtttc ggca                                                       74

<210> SEQ ID NO 1229
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
ggctcgttgg tctaggggta tgattctcgc ttaggatgcg agaggtcccg ggttcaaatc     60
ccggacgagc cc                                                         72

<210> SEQ ID NO 1230
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
ggctcgttgg tctaggggta tgattctcgc ttcgggtgcg agaggtcccg ggttcaaatc     60
ccggacgagc cc                                                         72

<210> SEQ ID NO 1231
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
ggctcgttgg tctaggggta tgattctcgc tttgggtgcg agaggtcccg ggttcaaatc     60
ccggacgagc cc                                                         72

<210> SEQ ID NO 1232

<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1232
gtagtcgtgg ccgagtggtt aaggcgatgg actagaaatc cattggggtt tccccgcgca 60
ggttcgaatc ctgccgacta cg 82

<210> SEQ ID NO 1233
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1233
gctgtgatgg ccgagtggtt aaggcgttgg actcgaaatc caatggggtc tccccgcgca 60
ggttcgaatc ctgctcacag cg 82

<210> SEQ ID NO 1234
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 1234
gacgaggnnt ggccgagtgg ttaaggcgat ggactgctaa tccattgtgc tctgcacgcg 60
tgggttcgaa tcccatcctc gtcg 84

<210> SEQ ID NO 1235
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1235
gtagtcgtgg ccgagtggtt aaggcgatgg acttgaaatc cattggggtc tccccgcgca 60
ggttcgaatc ctgccggcta cg 82

<210> SEQ ID NO 1236
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1236
ggctccgtgg cttagctggt taaagcgcct gtctagtaaa caggagatcc tgggttcgaa 60
tcccagcggg gcct 74

<210> SEQ ID NO 1237

<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other

<400> SEQUENCE: 1237
ggcnctgtgg ctnagtnggn taaagcgccg gtctcgtaaa ccnggagatc ntgggttcga 60
atcccancng ggcct 75

<210> SEQ ID NO 1238
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 1238
ggctccatag ctcagngggt tagagcactg gtcttgtaaa ccaggggtcg cgagttcaaa 60
tctcgctggg gcct 74

<210> SEQ ID NO 1239
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1239
gacctcgtgg cgcaacggta gcgcgtctga ctccagatca gaaggttgcg tgttcaaatc 60
acgtcggggt ca 72

<210> SEQ ID NO 1240
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1240
ccttcgatag ctcagctggt agagcggagg actgtagatc cttaggtcgc tggttcgatt 60
ccggctcgaa gga 73

<210> SEQ ID NO 1241
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1241
gtttccgtag tgtagtggtt atcacgttcg cctaacacgc gaaaggtccc cggttcgaaa 60
ccgggcggaa aca 73

<210> SEQ ID NO 1242
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1242
gtttccgtag tgtagtggtt atcacgttcg cctcacacgc gaaaggtccc cggttcgaaa 60
ccgggcggaa aca 73

<210> SEQ ID NO 1243
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1243
ggttccatag tgtagtggtt atcacgtctg ctttacacgc agaaggtcct gggttcgagc 60
cccagtggaa cca 73

<210> SEQ ID NO 1244
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1244
agcagagtgg cgcagcggaa gcgtgctggg cccataaccc agaggtcgat ggatcgaaac 60
catcctctgc ta 72

<210> SEQ ID NO 1245
<211> LENGTH: 76
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1245
ggggaattag ctcaagtggt agagcgcttg cttagcatgc aagaggtagt gggatcgatg     60
cccacattct ccannn                                                     76

<210> SEQ ID NO 1246
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1246
ggggatgtag ctcagtggta gagcgcatgc ttcgcatgta tgaggtcccg ggttcgatcc     60
ccggcatctc cannn                                                      75

<210> SEQ ID NO 1247
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1247
gggggtgtag ctcagtggta gagcgcatgc tttgcatgta tgaggccccg ggttcgatcc     60
ccggcacctc cannn                                                      75

<210> SEQ ID NO 1248
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1248
gggccagtgg cgcaatggat aacgcgtctg actacggatc agaagattcc aggttcgact     60
cctggctggc tcgnnn                                                     76

<210> SEQ ID NO 1249
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1249
ggccgcgtgg cctaatggat aaggcgtctg attccggatc agaagattga gggttcgagt 60
cccttcgtgg tcgnnn 76

<210> SEQ ID NO 1250
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1250
gccccagtgg cctaatggat aaggcactgg cctcctaagc cagggattgt gggttcgagt 60
cccacctggg gtannn 76

<210> SEQ ID NO 1251
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1251
gaccgcgtgg cctaatggat aaggcgtctg acttcggatc agaagattga gggttcgagt 60
ccctccgtgg tcgnnn 76

<210> SEQ ID NO 1252
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (75)..(77)
<223> OTHER INFORMATION: a, c, t, g, unknown or other

<400> SEQUENCE: 1252
ggctctgtgg cgcaatggat nagcgcattg gacttctaat tcaaaggttg cgggttcgag 60
tcccnccaga gtcgnnn 77

<210> SEQ ID NO 1253

<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (76)..(78)
<223> OTHER INFORMATION: a, c, t, g, unknown or other

<400> SEQUENCE: 1253
gtctctgtgg cgcaatcggt tagcgcgttc ggctgttaac cgnaaaggtt ggtggttcga 60
gcccacccag ggacgnnn 78

<210> SEQ ID NO 1254
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1254
tcctcgttag tatagtggtg agtatccccg cctgtcacgc gggagaccgg ggttcgattc 60
cccgacgggg agnnn 75

<210> SEQ ID NO 1255
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (74)..(76)
<223> OTHER INFORMATION: a, c, t, g, unknown or other

<400> SEQUENCE: 1255
gggggtatag ctcagngggt agagcatttg actgcagatc aagaggtccc cggttcaaat 60
ccgggtgccc cctnnn 76

<210> SEQ ID NO 1256
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (73)..(75)
<223> OTHER INFORMATION: a, c, t, g, unknown or other

<400> SEQUENCE: 1256
ggttccatgg tgtaatggtn agcactctgg actctgaatc cagcgatccg agttcaagtc 60
tcggtggaac ctnnn 75

<210> SEQ ID NO 1257
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1257
ggtcccatgg tgtaatggtt agcactctgg actttgaatc cagcgatccg agttcaaatc 60
tcggtgggac ctnnn 75

<210> SEQ ID NO 1258
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1258
tccctggtgg tctagtggtt aggattcggc gctctcaccg ccgcggcccg ggttcgattc 60
ccggtcaggg aannn 75

<210> SEQ ID NO 1259
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (73)..(75)
<223> OTHER INFORMATION: a, c, t, g, unknown or other

<400> SEQUENCE: 1259
tccctggtgg tctagtggct aggattcggc gctttcaccg cngcggcccg ggttcgattc 60
ccggtcaggg aannn 75

<210> SEQ ID NO 1260
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (40)..(40)

<223> OTHER INFORMATION: a, c, t, g, unknown or other
<220> FEATURE:
<221> NAME/KEY: modified_base
<222> LOCATION: (72)..(74)
<223> OTHER INFORMATION: a, c, t, g, unknown or other

<400> SEQUENCE: 1260
gcattggtgg ttcagtggta gaattctcgc ctcccacgcn ggagacccgg gttcgattcc 60
cggccaatgc annn 74

<210> SEQ ID NO 1261
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (72)..(74)
<223> OTHER INFORMATION: a, c, t, g, unknown or other

<400> SEQUENCE: 1261
gcattggtgg ttcagtggta gaattctcgc ctgccacgcg ggaggcccgg gttcgattcc 60
cggccaatgc annn 74

<210> SEQ ID NO 1262
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1262
gcgttggtgg tatagtggtg agcatagctg ccttccaagc agttgacccg ggttcgattc 60
ccggccaacg cannn 75

<210> SEQ ID NO 1263
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (75)..(77)
<223> OTHER INFORMATION: a, c, t, g, unknown or other

<400> SEQUENCE: 1263
ggccggttag ctcagttggt tagagcgtgg tgctaataac gccaaggtcg cgggttcgat 60
ccccgtacgg gccannn 77

<210> SEQ ID NO 1264
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (75)..(77)
<223> OTHER INFORMATION: a, c, t, g, unknown or other

<400> SEQUENCE: 1264
gctccagtgg cgcaatcggt tagcgcgcgg tacttataat gccgaggttg tgagttcgag 60
cctcacctgg agcannn 77

<210> SEQ ID NO 1265
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (83)..(85)
<223> OTHER INFORMATION: a, c, t, g, unknown or other

<400> SEQUENCE: 1265
ggtagcgtgg ccgagcggtc taaggcgctg gattaaggct ccagtctctt cgggggcgtg 60
ggttcgaatc ccaccgctgc cannn 85

<210> SEQ ID NO 1266
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (86)..(88)
<223> OTHER INFORMATION: a, c, t, g, unknown or other

<400> SEQUENCE: 1266
gtcaggatgg ccgagtggtc ntaaggcgcc agactcaagt tctggtctcc gnatggaggc 60
gtgggttcga atcccacttc tgacannn 88

<210> SEQ ID NO 1267
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (84)..(86)
<223> OTHER INFORMATION: a, c, t, g, unknown or other

<400> SEQUENCE: 1267
gtcaggatgg ccgagcggtc taaggcgctg cgttcaggtc gcagtctccc ctggaggcgt 60
gggttcgaat cccactcctg acannn 86

<210> SEQ ID NO 1268
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (84)..(86)
<223> OTHER INFORMATION: a, c, t, g, unknown or other

<400> SEQUENCE: 1268
accaggatgg ccgagtggtt aaggcgttgg acttaagatc caatggacag atgtccgcgt 60
gggttcgaac cccactcctg gtannn 86

<210> SEQ ID NO 1269
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (83)..(85)
<223> OTHER INFORMATION: a, c, t, g, unknown or other

<400> SEQUENCE: 1269
ggtagcgtgg ccgagcggtc taaggcgctg gatttaggct ccagtctctt cggnggcgtg 60
ggttcgaatc ccaccgctgc cannn 85

<210> SEQ ID NO 1270
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(79)
<223> OTHER INFORMATION: a, c, t, g, unknown or other

<400> SEQUENCE: 1270
gcccggctag ctcagtcggt agagcatgag actcttaatc tcagggtcgt gggttcgagc 60
cccacgttgg gcgnnnnnn 79

<210> SEQ ID NO 1271
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1271
gcctggatag ctcagtcggt agagcatcag acttttaatc tgagggtcca gggttcaagt 60
ccctgttcag gcgnnn 76

<210> SEQ ID NO 1272
<211> LENGTH: 76
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (74)..(76)
<223> OTHER INFORMATION: a, c, t, g, unknown or other

<400> SEQUENCE: 1272
gccctcttag cgcagtnggc agcgcgtcag tctcataatc tgaaggtcct gagttcgagc 60
ctcagagagg gcannn 76

<210> SEQ ID NO 1273
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (75)..(77)
<223> OTHER INFORMATION: a, c, t, g, unknown or other

<400> SEQUENCE: 1273
gccgaaatag ctcagttggg agagcgttag actgaagatc ntaaaggtcc ctggttcaat 60
cccgggtttc ggcannn 77

<210> SEQ ID NO 1274
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1274
ggctcgttgg tctaggggta tgattctcgc ttaggatgcg agaggtcccg ggttcaaatc 60
ccggacgagc ccnnn 75

<210> SEQ ID NO 1275
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1275
ggctcgttgg tctaggggta tgattctcgc ttcgggtgcg agaggtcccg ggttcaaatc 60
ccggacgagc ccnnn 75

<210> SEQ ID NO 1276
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1276
ggctcgttgg tctaggggta tgattctcgc tttgggtgcg agaggtcccg ggttcaaatc 60
ccggacgagc ccnnn 75

<210> SEQ ID NO 1277
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (83)..(85)
<223> OTHER INFORMATION: a, c, t, g, unknown or other

<400> SEQUENCE: 1277
gtagtcgtgg ccgagtggtt aaggcgatgg actagaaatc cattggggtt tccccgcgca 60
ggttcgaatc ctgccgacta cgnnn 85

<210> SEQ ID NO 1278
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (83)..(85)
<223> OTHER INFORMATION: a, c, t, g, unknown or other

<400> SEQUENCE: 1278
gctgtgatgg ccgagtggtt aaggcgttgg actcgaaatc caatggggtc tccccgcgca 60
ggttcgaatc ctgctcacag cgnnn 85

<210> SEQ ID NO 1279
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (85)..(87)
<223> OTHER INFORMATION: a, c, t, g, unknown or other

<400> SEQUENCE: 1279
gacgaggnnt ggccgagtgg ttaaggcgat ggactgctaa tccattgtgc tctgcacgcg 60
tgggttcgaa tcccatcctc gtcgnnn						87

<210> SEQ ID NO 1280
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (83)..(85)
<223> OTHER INFORMATION: a, c, t, g, unknown or other

<400> SEQUENCE: 1280
gtagtcgtgg ccgagtggtt aaggcgatgg acttgaaatc cattggggtc tccccgcgca		60 ggttcgaatc ctgccggcta cgnnn						85

<210> SEQ ID NO 1281
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (75)..(77)
<223> OTHER INFORMATION: a, c, t, g, unknown or other

<400> SEQUENCE: 1281
ggctccgtgg cttagctggt taaagcgcct gtctagtaaa caggagatcc tgggttcgaa		60 tcccagcggg gcctnnn						77

<210> SEQ ID NO 1282
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (69)..(69)

<223> OTHER INFORMATION: a, c, t, g, unknown or other
<220> FEATURE:
<221> NAME/KEY: modified_base
<222> LOCATION: (76)..(78)
<223> OTHER INFORMATION: a, c, t, g, unknown or other

<400> SEQUENCE: 1282
ggcnctgtgg ctnagtnggn taaagcgccg gtctcgtaaa ccnggagatc ntgggttcga 60
atcccancng ggcctnnn 78

<210> SEQ ID NO 1283
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (75)..(77)
<223> OTHER INFORMATION: a, c, t, g, unknown or other

<400> SEQUENCE: 1283
ggctccatag ctcagngggt tagagcactg gtcttgtaaa ccaggggtcg cgagttcaaa 60
tctcgctggg gcctnnn 77

<210> SEQ ID NO 1284
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1284
gacctcgtgg cgcaacggta gcgcgtctga ctccagatca gaaggttgcg tgttcaaatc 60
acgtcggggt cannn 75

<210> SEQ ID NO 1285
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1285
ccttcgatag ctcagctggt agagcggagg actgtagatc cttaggtcgc tggttcgatt 60
ccggctcgaa ggannn 76

<210> SEQ ID NO 1286
<211> LENGTH: 76
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1286
gtttccgtag tgtagtggtt atcacgttcg cctaacacgc gaaaggtccc cggttcgaaa 60
ccgggcggaa acannn 76

<210> SEQ ID NO 1287
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1287
gtttccgtag tgtagtggtt atcacgttcg cctcacacgc gaaaggtccc cggttcgaaa 60
ccgggcggaa acannn 76

<210> SEQ ID NO 1288
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (74)..(76)
<223> OTHER INFORMATION: a, c, t, g, unknown or other

<400> SEQUENCE: 1288
ggttccatag tgtagtggtt atcacgtctg ctttacacgc agaaggtcct gggttcgagc 60
cccagtggaa ccannn 76

<210> SEQ ID NO 1289
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (73)..(75)
<223> OTHER INFORMATION: a, c, t, g, unknown or other

<400> SEQUENCE: 1289
agcagagtgg cgcagcggaa gcgtgctggg cccataaccc agaggtcgat ggatcgaaac 60
catcctctgc tannn 75

<210> SEQ ID NO 1290
<211> LENGTH: 73
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 1290

ggcuccgugg cgcaauggau agcgcauugg acuucuaauu caaagguucc ggguucgagu     60

cccggcggag ucg                                                        73


<210> SEQ ID NO 1291
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Pseudouridine

<400> SEQUENCE: 1291

gguuccaugg ugnaauggua agcacucugg acuctgaauc cagcgauccg aguucgaguc     60

ucgguggaac cucca                                                      75


<210> SEQ ID NO 1292
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292

ggcucguugg ucuaggggua ugauucucgc uuagggugcg agaggucccg gguucaaauc     60

ccggacgagc cc                                                         72


<210> SEQ ID NO 1293
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293

ggggauguag cucaguggua gagcgcaugc uuugcaugua ugaggucccg gguucgaucc     60

ccggcaucuc ca                                                         72
```

TREM COMPOSITIONS AND USES THEREOF

CROSS-REFERENCE TO RELATED APPLICATIONS

This application is a continuation of International Application No. PCT/US2021/027357, filed Apr. 14, 2021, which claims priority to U.S. Provisional Application No. 63/009,669, filed on Apr. 14, 2020, the entire contents of which is hereby incorporated by reference.

SEQUENCE LISTING

The instant application contains a Sequence Listing which has been submitted electronically in ASCII format and is hereby incorporated by reference in its entirety. Said ASCII copy, created on May 25, 2021, is named F2099-7004WO (VL63009-W1)_SL.txt and is 435,100 bytes in size.

BACKGROUND

Transfer RNAs (tRNAs) are complex, naturally occurring RNA molecules that possess a number of functions including initiation and elongation of proteins.

SUMMARY

The present disclosure features modified tRNA-based effector molecules (TREMs, e.g., a TREM or TREM fragment), as well as related compositions and uses thereof. As provided herein, TREMs are complex molecules which can mediate a variety of cellular processes. The TREMs disclosed herein comprise at least one modification (e.g., a non-naturally occurring modification), e.g., on a component nucleotide (e.g., a nucleobase or sugar) or within an internucleotide region, e.g., the TREM backbone. In one aspect, provided herein is a TREM comprising a sequence of Formula A: [L1]-[ASt Domain1]-[L2]-[DH Domain]-[L3]-[ACH Domain]-[VL Domain]-[TH Domain]-[L4]-[ASt Domain2], wherein independently, [L1] and [VL Domain], are optional; and one of [L1], [ASt Domain1], [L2]-[DH Domain], [L3], [ACH Domain], [VL Domain], [TH Domain], [L4], and [ASt Domain2] comprises a nucleotide comprising a non-naturally occurring modification.

In an embodiment, the TREM: (a) has the ability to: (i) support protein synthesis, (ii) be charged by a synthetase, (iii) be bound by an elongation factor, (iv) introduce an amino acid into a peptide chain, (v) support elongation, or (vi) support initiation; (b) comprises at least X contiguous nucleotides without a non-naturally occurring modification, wherein X is greater than 3, 4, 5, 6, 7, 8, 9, or 10; (c) comprises at least 3, but less than all of the nucleotides of a type (e.g., A, T, C, G or U) comprise the same non-naturally occurring modification; (d) comprises at least X nucleotides of a type (e.g., A, T, C, G or U) that do not comprise a non-naturally occurring modification, wherein X=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50; (e) comprises no more than 5, 10, or 15 nucleotides of a type (e.g., A, T, C, G or U) that comprise a non-naturally occurring modification; and/or (f) comprises no more than 5, 10, or 15 nucleotides of a type (e.g., A, T, C, G or U) that do not comprise a non-naturally occurring modification.

In an embodiment, the TREM comprises feature (a) (i). In an embodiment, the TREM comprises feature (a) (ii). In an embodiment, the TREM comprises feature (a) (iii). In an embodiment, the TREM comprises feature (a) (iv). In an embodiment, the TREM comprises feature (a) (v). In an embodiment, the TREM comprises feature (a) (vi). In an embodiment, the TREM comprises feature (b). In an embodiment, the TREM comprises feature (c). In an embodiment, the TREM comprises feature (d). In an embodiment, the TREM comprises feature (c). In an embodiment, the TREM comprises feature (f). In an embodiment, the TREM comprises all of features (a)-(f) or a combination thereof.

In an embodiment, the TREM Domain comprising the non-naturally occurring modification has a function, e.g., a domain function described herein.

In an aspect, provided herein is a TREM core fragment comprising a sequence of Formula B:

$$[L1]_y\text{-}[ASt\ \mathrm{Domain1}]_x\text{-}[L2]_y\text{-}[DH\ \mathrm{Domain}]_y\text{-}[L3]_y\text{-}[ACH\ \mathrm{Domain}]_x\text{-}[VL\ \mathrm{Domain}]_y\text{-}[TH\ \mathrm{Domain}]_y\text{-}[L4]_y\text{-}[ASt\ \mathrm{Domain2}]_x,$$

wherein x=1 and y=0 or 1; and one of [ASt Domain1], [ACH Domain], and [ASt Domain2] comprises a nucleotide having a non-naturally occurring modification.

In an embodiment, the TREM has the ability to support protein synthesis. In an embodiment, the TREM has the ability to be able to be charged by a synthetase. In an embodiment, the TREM has the ability to be bound by an elongation factor. In an embodiment, the TREM has the ability to introduce an amino acid into a peptide chain. In an embodiment, the TREM has the ability to support elongation. In an embodiment, the TREM has the ability to support initiation.

In an embodiment, the [ASt Domain1] and/or [ASt Domain2] comprising the non-naturally occurring modification has the ability to initiate or elongate a polypeptide chain.

In an embodiment, the [ACH Domain] comprising the non-naturally occurring modification has the ability to mediate pairing with a codon.

In an embodiment, y=1 for any one, two, three, four, five, six, all or a combination of [L1], [L2], [DH Domain], [L3], [VL Domain], [TH Domain], [L4].

In an embodiment, y=0 for any one, two, three, four, five, six, all or a combination of [L1], [L2], [DH Domain], [L3], [VL Domain], [TH Domain], [L4].

In an embodiment, y=1 for linker [L1], and L1 comprises a nucleotide having a non-naturally occurring modification.

In an embodiment, y=1 for linker [L2], and L2 comprises a nucleotide having a non-naturally occurring modification.

In an embodiment, y=1 for [DH Domain (DHD)], and DHD comprises a nucleotide having a non-naturally occurring modification. In an embodiment, the DHD comprising the non-naturally occurring modification has the ability to mediate recognition of aminoacyl-tRNA synthetase.

In an embodiment, y=1 for linker [L3], and L3 comprises a nucleotide having a non-naturally occurring modification.

In an embodiment, y=1 for [VL Domain (VLD)], and VLD comprises a nucleotide having a non-naturally occurring modification.

In an embodiment, y=1 for [TH Domain (THD)], and THD comprises a nucleotide having a non-naturally occurring modification. In an embodiment, the THD comprising the non-naturally occurring modification has the ability to mediate recognition of the ribosome.

In an embodiment, y=1 for linker [L4], and L4 comprises a nucleotide having a non-naturally occurring modification.

In another aspect, the disclosure provides a TREM fragment comprising a portion of a TREM, wherein the TREM comprises a sequence of Formula A:

[L1]-[ASt Domain1]-[L2]-[DH Domain]-[L3]-[ACH Domain]-[VL Domain]-[TH Domain]-[L4]-[ASt Domain2], and wherein the TREM fragment comprises a non-naturally occurring modification.

In an embodiment, the TREM fragment comprises one, two, three or all or any combination of the following: (a) a TREM half (e.g., from a cleavage in the ACH Domain, e.g., in the anticodon sequence, e.g., a 5' half or a 3' half); (b) a 5' fragment (e.g., a fragment comprising the 5' end, e.g., from a cleavage in a DH Domain or the ACH Domain); (c) a 3' fragment (e.g., a fragment comprising the 3' end, e.g., from a cleavage in the TH Domain); or (d) an internal fragment (e.g., from a cleavage in any one of the ACH Domain, DH Domain or TH Domain).

In an embodiment, the TREM fragment comprise (a) a TREM half which comprises a nucleotide having a non-naturally occurring modification.

In an embodiment, the TREM fragment comprise (b) a 5' fragment which comprises a nucleotide having a non-naturally occurring modification.

In an embodiment, the TREM fragment comprise (c) a 3' fragment which comprises a nucleotide having a non-naturally occurring modification.

In an embodiment, the TREM fragment comprise (d) an internal fragment which comprises a nucleotide having a non-naturally occurring modification.

In an embodiment of any of the TREMs, TREM core fragments, or TREM fragments disclosed herein, the TREM Domain comprises a plurality of nucleotides each having a non-naturally occurring modification. In an embodiment, the non-naturally occurring modification comprises a nucleobase modification, a sugar (e.g., ribose) modification, or a backbone modification. In an embodiment, the non-naturally occurring modification is a sugar (e.g., ribose) modification. In an embodiment, the non-naturally occurring modification is 2'-ribose modification, e.g., a 2'-OMe, 2'-halo (e.g., 2'-F), 2'-MOE, or 2'-deoxy modification. In an embodiment, the non-naturally occurring modification is a backbone modification, e.g., a phosphorothioate modification.

In an embodiment of any of the TREMs, TREM core fragments, or TREM fragments disclosed herein, the TREM sequence comprises a CCA sequence on a terminus, e.g., the 3' terminus. In an embodiment, the TREM sequence does not comprise a CCA sequence on a terminus, e.g., the 3' terminus.

In an embodiment of any of the TREMs, TREM core fragments, or TREM fragments disclosed herein, the non-naturally occurring modification is a modification in a base or a backbone of a nucleotide, e.g., a modification chosen from any one of Tables 5, 6, 7, 8 or or 9.

In an embodiment of any of the TREMs, TREM core fragments, or TREM fragments disclosed herein, the non-naturally occurring modification is a base modification chosen from a modification listed in Table 5.

In an embodiment of any of the TREMs, TREM core fragments, or TREM fragments disclosed herein, the non-naturally occurring modification is a base modification chosen from a modification listed in Table 6.

In an embodiment of any of the TREMs, TREM core fragments, or TREM fragments disclosed herein, the non-naturally occurring modification is a base modification chosen from a modification listed in Table 7.

In an embodiment of any of the TREMs, TREM core fragments, or TREM fragments disclosed herein, the non-naturally occurring modification is a backbone modification chosen from a modification listed in Table 8.

In an embodiment of any of the TREMs, TREM core fragments, or TREM fragments disclosed herein, the non-naturally occurring modification is a backbone modification chosen from a modification listed in Table 9.

In an embodiment of any of the TREMs, TREM core fragments, or TREM fragments disclosed herein, the TREM, TREM core fragment, or TREM fragment is encoded by a sequence provided in Table 1, e.g., any one of SEQ ID NOs 1-451.

In an embodiment of any of the TREMs, TREM core fragments, or TREM fragments disclosed herein, the TREM, TREM core fragment, or TREM fragment is encoded by a consensus sequence chosen from any one of SEQ ID NOs: 562-621.

In an embodiment of any of the TREMs, TREM core fragments, or TREM fragments disclosed herein, the TREM, TREM core fragment, or TREM fragment is encoded by a sequence provided in any one of Tables 15-22, e.g., any one of SEQ ID NOs: 622-1187. In an embodiment, the TREM, TREM core fragment, or TREM fragment is encoded by a sequence provided in Table 15, e.g., any one of SEQ ID NOs: 622-698. In an embodiment, the TREM, TREM core fragment, or TREM fragment is encoded by a sequence provided in Table 16, e.g., any one of SEQ ID NOs: 699-774. In an embodiment, the TREM, TREM core fragment, or TREM fragment is encoded by a sequence provided in Table 17, e.g., any one of SEQ ID NOS: 775-841. In an embodiment, the TREM, TREM core fragment, or TREM fragment is encoded by a sequence provided in Table 18, e.g., any one of SEQ ID NOs: 842-917. In an embodiment, the TREM, TREM core fragment, or TREM fragment is encoded by a sequence provided in Table 19, e.g., any one of SEQ ID NOs: 918-992. In an embodiment, the TREM, TREM core fragment, or TREM fragment is encoded by a sequence provided in Table 20, e.g., any one of SEQ ID NOs: 993-1078. In an embodiment, the TREM, TREM core fragment, or TREM fragment is encoded by a sequence provided in Table 21, e.g., any one of SEQ ID NOs: 1079-1154. In an embodiment, the TREM, TREM core fragment, or TREM fragment is encoded by a sequence provided in Table 22, e.g., any one of SEQ ID NOs: 1155-1187.

In another aspect, the disclosure provides a pharmaceutical composition comprising a TREM, a TREM core fragment, or a TREM fragment disclosed herein.

In another aspect, the disclosure provides a method of making a TREM, a TREM core fragment, or a TREM fragment disclosed herein, comprising linking a first nucleotide to a second nucleotide to form the TREM.

In an embodiment, the TREM, TREM core fragment or TREM fragment is non-naturally occurring (e.g., synthetic).

In an embodiment, the TREM, TREM core fragment or TREM fragment is made by cell-free solid phase synthesis.

In another aspect, the disclosure provides a method of modulating a tRNA pool in a cell comprising: providing a TREM, a TREM core fragment, or a TREM fragment disclosed herein, and contacting the cell with the TREM, TREM core fragment or TREM fragment, thereby modulating the tRNA pool in the cell.

In an aspect, the disclosure provides a method of contacting a cell, tissue, or subject with a TREM, a TREM core fragment, or a TREM fragment disclosed herein, comprising: contacting the cell, tissue or subject with the TREM, TREM core fragment or TREM fragment, thereby contacting the cell, tissue, or subject with the TREM, TREM core fragment or TREM fragment.

In another aspect, the disclosure provides a method of delivering a TREM, TREM core fragment or TREM fragment to a cell, tissue, or subject, comprising: providing a cell, tissue, or subject, and contacting the cell, tissue, or subject, a TREM, a TREM core fragment, or a TREM fragment disclosed herein.

In an aspect, the disclosure provides a method of modulating a tRNA pool in a cell comprising an endogenous open reading frame (ORF), which ORF comprises a codon having a first sequence, comprising:

optionally, acquiring knowledge of the abundance of one or both of (i) and (ii), e.g., acquiring knowledge of the relative amounts of: (i) and (ii) in the cell, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the cell;

contacting the cell with a TREM, a TREM core fragment, or a TREM fragment disclosed herein, wherein the TREM, TREM core fragment or TREM fragment has an anticodon that pairs with: the codon having the first sequence; or the codon other than the codon having the first sequence, in an amount and/or for a time sufficient to modulate the relative amounts of the first tRNA moiety and the second tRNA moiety in the cell, thereby modulating the tRNA pool in the cell.

In another aspect, the disclosure provides a method of modulating a tRNA pool in a subject having an ORF, which ORF comprises a codon having a first sequence, comprising: optionally, acquiring knowledge of the abundance of one or both of (i) and (ii), e.g., acquiring knowledge of the relative amounts of: (i) and (ii) in the subject, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the subject; contacting the subject with a TREM, a TREM core fragment, or a TREM fragment disclosed herein, wherein the TREM, TREM core fragment or TREM fragment has an anticodon that pairs with: the codon having the first sequence; or the codon other than the codon having the first sequence, in an amount and/or for a time sufficient to modulate the relative amounts of the first tRNA moiety and the second tRNA moiety in the subject, thereby modulating the tRNA pool in the subject.

In an aspect, the disclosure provides a method of modulating a tRNA pool in a subject having an endogenous ORF comprising a codon comprising a synonymous mutation (a synonymous mutation codon or SMC), comprising:

providing a composition comprising a TREM, a TREM core fragment, or a TREM fragment disclosed herein, wherein the TREM, TREM core fragment or TREM fragment comprises an isoacceptor tRNA moiety comprising an anticodon sequence that pairs with the SMC (the TREM);

contacting the subject with the composition in an amount and/or for a time sufficient to modulate the tRNA pool in the subject, thereby modulating the tRNA pool in the subject.

In another aspect, the disclosure provides a method of modulating a tRNA pool in a cell comprising an endogenous ORF comprising a codon comprising a SMC, comprising:

providing a composition comprising a TREM, a TREM core fragment, or a TREM fragment disclosed herein, wherein the TREM, TREM core fragment or TREM fragment comprises an isoacceptor tRNA moiety comprising an anticodon sequence that pairs with the SMC (the TREM);

contacting the cell with the composition comprising a TREM in an amount and/or for a time sufficient to modulate the tRNA pool in the cell, thereby modulating the tRNA pool in the cell.

In an aspect, the disclosure provides a method of modulating expression of a protein in a cell, wherein the protein is encoded by a nucleic acid comprising an ORF, which ORF comprises a codon having a mutation, comprising:

contacting the cell with a composition comprising a TREM, a TREM core fragment, or a TREM fragment disclosed herein in an amount and/or for a time sufficient to modulate expression of the encoded protein, wherein the TREM, TREM core fragment or TREM fragment has an anticodon that pairs with the codon having the mutation, thereby modulating expression of the protein in the cell.

In another aspect, the disclosure provides a method of modulating expression of a protein in a subject, wherein the protein is encoded by a nucleic acid comprising an endogenous ORF, which ORF comprises a codon having a mutation, comprising:

contacting the subject with a composition comprising a TREM, a TREM core fragment, or a TREM fragment disclosed herein, in an amount and/or for a time sufficient to modulate expression of the encoded protein, wherein the TREM, TREM core fragment or TREM fragment has an anticodon that pairs with the codon having the mutation, thereby modulating expression of the protein in the subject.

In an embodiment of any of the methods disclosed herein, the mutation in the ORF is a nonsense mutation, e.g., resulting in a premature stop codon chosen from UAA, UGA or UAG. In an embodiment, the stop codon is UAA. In an embodiment, the stop codon is UGA. In an embodiment, the stop codon is UAG.

In an embodiment of any of the methods disclosed herein, the TREM comprises an anticodon that pairs with a stop codon.

TREMs of the disclosure include TREMs, TREM core fragments and TREM fragments. TREMs, TREM core fragments or TREM fragments can be modified with non-naturally occurring modifications to, e.g., increase the level and/or activity (e.g., stability) of the TREM. Pharmaceutical TREM compositions, e.g., comprising TREMs having a non-naturally occurring modification, can be administered to cells, tissues or subjects to modulate these functions, e.g., in vitro or in vivo. Disclosed herein are TREMs, TREM core fragments or TREM fragments comprising non-naturally occurring modifications, TREM compositions, preparations, methods of making TREM compositions and preparations, and methods of using the same.

Additional features of any of the aforesaid TREMs, TREM core fragments, TREM fragments, TREM compositions, preparations, methods of making TREM compositions and preparations, and methods of using TREM compositions and preparations include one or more of the features in the Enumerated Embodiments, Figures, Description, Examples, or Claims.

Those skilled in the art will recognize or be able to ascertain using no more than routine experimentation, many equivalents to the specific embodiments of the invention described herein. Such equivalents are intended to be encompassed by the following Enumerated Embodiments, Figures, Description, Examples, or Claims.

BRIEF DESCRIPTION OF THE DRAWINGS

FIG. 1 is a schematic illustrating the activity (log 2 fold change) of modified TREMs containing a 2'-OMe, 2'-F, 2'-OME, 2'-deoxy, and PS modification at each position along an exemplary TREM sequence (TREM-Arg-TGA) over an unmodified TREM, as outlined in Example 11.

ENUMERATED EMBODIMENTS

Enumerated Embodiments 1

1. A TREM comprising a sequence of Formula A:

[*L*1]-[*ASt*Domain1]-[*L*2]-[*DH*Domain]-[*L*3]-[*ACH*Domain]-[*VL*Domain]-[*TH*Domain]-[*L*4]-[*ASt*Domain2], wherein:

independently, [L1] and [VL Domain], are optional;

one of [L1], [ASt Domain1], [L2]-[DH Domain], [L3], [ACH Domain], [VL Domain], [TH Domain], [L4], and [ASt Domain2] comprises a nucleotide having a non-naturally occurring modification; and wherein:

(a) the TREM has the ability to: support protein synthesis, be charged by a synthetase, be bound by an elongation factor, introduce an amino acid into a peptide chain, support elongation, or support initiation;

(b) the TREM comprises at least X contiguous nucleotides without a non-naturally occurring modification, wherein X is greater than 10;

(c) at least 3, but less than all of the nucleotides of a type (e.g., A, T, C, G or U) comprise the same non-naturally occurring modification;

(d) at least X nucleotides of a type (e.g., A, T, C, G or U) do not comprise a non-naturally occurring modification, wherein X=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50;

(e) no more than 5, 10, or 15 nucleotides of a type (e.g., A, T, C, G or U) comprise a non-naturally occurring modification; and/or (f) no more than 5, 10, or 15 nucleotides of a type (e.g., A, T, C, G or U) do not comprise a non-naturally occurring modification.

2. The TREM of embodiment 1, comprising the feature provided in embodiment 1 (a).

3. The TREM of embodiment 1, comprising the feature provided in embodiment 1 (b).

4. The TREM of embodiment 1, comprising the feature provided in embodiment 1 (c).

5. The TREM of embodiment 1, comprising the feature provided in embodiment 1 (d).

6. The TREM of embodiment 1, comprising the feature provided in embodiment 1 (e).

7. The TREM of embodiment 1, comprising the feature provided in embodiment 1 (f).

8. The TREM of embodiment 1, comprising all of the features provided in embodiments 1 (a)-(f).

9. The TREM of any one of embodiments 1-8, wherein the Domain comprising the non-naturally occurring modification has a function, e.g., a domain function described herein.

10. The TREM of any one of embodiments 1-8, comprising an [L1].

11. The TREM of any one of embodiments 1-8, comprising a [VL Domain].

12. The TREM of any one of embodiments 1-8, wherein: [L1] is a linker comprising a nucleotide having a non-naturally occurring modification.

13. The TREM of any one of embodiments 1-8, wherein [ASt Domain1 (AstD1)] comprises a nucleotide having a non-naturally occurring modification.

14. The TREM of any one of embodiments 1-8, wherein [L2] is a linker comprising a nucleotide having a non-naturally occurring modification.

15. The TREM of any one of embodiments 1-8, wherein [DH Domain (DHD)] comprises a nucleotide having a non-naturally occurring modification.

16. The TREM of any one of embodiments 1-8, wherein [L3] is a linker comprising a nucleotide having a non-naturally occurring modification.

17. The TREM of any one of embodiments 1-8, wherein [ACH Domain (ACHD)] comprises a nucleotide having a non-naturally occurring modification.

18. The TREM of any one of embodiments 1-8, wherein [VL Domain (VLD)] comprises a nucleotide having a non-naturally occurring modification.

19. The TREM of any one of embodiments 1-8, wherein [TH Domain (THD)] comprises a nucleotide having a non-naturally occurring modification.

20. The TREM of any one of embodiments 1-8, wherein [L4] is a linker comprises a nucleotide having a non-naturally occurring modification.

21. The TREM of any one of embodiments 1-8, wherein: [ASt Domain2 (AStD2)] comprises a nucleotide having a non-naturally occurring modification.

22. A TREM core fragment comprising a sequence of Formula B:

$[L1]_y$-$[ASt\ Domain1]_x$-$[L2]_y$-$[DH\ Domain]_y$-$[L3]_y$-$[ACH\ Domain]_x$-$[VL\ Domain]_y$-$[TH\ Domain]_y$-$[L4]_y$-$[ASt\ Domain2]_x$, wherein:

x=1 and y=0 or 1;

one of [ASt Domain1], [ACH Domain], and [ASt Domain2] comprises a nucleotide having a non-naturally occurring modification; and the TREM has the ability to: support protein synthesis; be able to be charged by a synthetase, be bound by an elongation factor, introduce an amino acid into a peptide chain, support elongation, or support initiation.

23. The TREM core fragment of embodiment 22, wherein AStD1 and AStD2 comprise an ASt Domain (AStD).

24. The TREM core fragment of embodiment 22, wherein the [ASt Domain1], and/or [ASt Domain2] comprising the non-naturally occurring modification has the ability to initiate or elongate a polypeptide chain.

25. The TREM core fragment of embodiment 22, wherein the [ACH Domain] comprising the non-naturally occurring modification has the ability to mediate pairing with a codon.

26. The TREM core fragment of embodiment 22, wherein y=1 for any one, two, three, four, five, six, all or a combination of [L1], [L2], [DH Domain], [L3], [VL Domain], [TH Domain], [L4].

27. The TREM core fragment of embodiment 22, wherein y=0 for any one, two, three, four, five, six, all or a combination of [L1], [L2], [DH Domain], [L3], [VL Domain], [TH Domain], [L4].

28. The TREM core fragment of embodiment 22, wherein y=1 for linker [L1], and L1 comprises a nucleotide having a non-naturally occurring modification.
29. The TREM core fragment of embodiment 22, wherein y=1 for linker [L2], and L2 comprises a nucleotide having a non-naturally occurring modification.
30. The TREM core fragment of embodiment 22, wherein y=1 for [DH Domain (DHD)], and DHD comprises a nucleotide having a non-naturally occurring modification.
31. The TREM core fragment of embodiment 30, wherein the DHD comprising the non-naturally occurring modification has the ability to mediate recognition of aminoacyl-tRNA synthetase.
32. The TREM core fragment of embodiment 22, wherein y=1 for linker [L3], and L3 comprises a nucleotide having a non-naturally occurring modification.
33. The TREM core fragment of embodiment 22, wherein y=1 for [VL Domain (VLD)], and VLD comprises a nucleotide having a non-naturally occurring modification.
34. The TREM core fragment of embodiment 22, wherein y=1 for [TH Domain (THD)], and THD comprises a nucleotide having a non-naturally occurring modification.
35. The TREM core fragment of embodiment 34, wherein the THD comprising the non-naturally occurring modification has the ability to mediate recognition of the ribosome.
36. The TREM core fragment of embodiment 22, wherein y=1 for linker [L4], and LA comprises a nucleotide having a non-naturally occurring modification.
37. A TREM fragment comprising a portion of a TREM, wherein the TREM comprises a sequence of Formula A:

[*L*1]-[*ASt* Domain1]-[*L*2]-[*DH* Domain]-[*L*3]-[*ACH* Domain]-[*VL* Domain]-[*TH* Domain]-[*L*4]-[*ASt* Domain2], and wherein:

the TREM fragment comprises:
a non-naturally occurring modification; and
one, two, three or all or any combination of the following:
- (a) a TREM half (e.g., from a cleavage in the ACH Domain, e.g., in the anticodon sequence, e.g., a 5' half or a 3' half);
- (b) a 5' fragment (e.g., a fragment comprising the 5' end, e.g., from a cleavage in a DH Domain or the ACH Domain);
- (c) a 3' fragment (e.g., a fragment comprising the 3' end, e.g., from a cleavage in the TH Domain); or
- (d) an internal fragment (e.g., from a cleavage in any one of the ACH Domain, DH Domain or TH Domain).

38. The TREM of embodiment 37, wherein the TREM fragment comprise (a) a TREM half which comprises a nucleotide having a non-naturally occurring modification.
39. The TREM of embodiment 37, wherein the TREM fragment comprise (b) a 5' fragment which comprises a nucleotide having a non-naturally occurring modification.
40. The TREM of embodiment 37, wherein the TREM fragment comprise (c) a 3' fragment which comprises a nucleotide having a non-naturally occurring modification.
41. The TREM of embodiment 37, wherein the TREM fragment comprise (d) an internal fragment which comprises a nucleotide having a non-naturally occurring modification.
42. The TREM of any one of embodiments 1-8, the TREM core fragment of embodiment 22, or the TREM fragment of embodiment 37, wherein the TREM Domain comprises a plurality of nucleotides each having a non-naturally occurring modification.
43. The TREM of any one of embodiments 1-8, the TREM core fragment of embodiment 22, or the TREM fragment of embodiment 37, wherein at least X of the nucleotides of AStD1 have a non-naturally occurring modification, wherein X is equal to or greater than 1, 2, 3, 4, 5, 6 or 7.
44. The TREM of any one of embodiments 1-8, the TREM core fragment of embodiment 22, or the TREM fragment of embodiment 37, wherein no more than X of the nucleotides of AStD1 have a non-naturally occurring modification, wherein X is equal to or greater than 1, 2, 3, 4, 5, 6 or 7.
45. The TREM of any one of embodiments 1-8, the TREM core fragment of embodiment 22, or the TREM fragment of embodiment 37, wherein at least X of the nucleotides of AStD2 have a non-naturally occurring modification, wherein X is equal to or greater than 1, 2, 3, 4, 5, 6 or 7.
46. The TREM of any one of embodiments 1-8, the TREM core fragment of embodiment 22, or the TREM fragment of embodiment 37, wherein no more than X of the nucleotides of AStD2 have a non-naturally occurring modification, wherein X is equal to or greater than 1, 2, 3, 4, 5, 6 or 7.
47. The TREM of any one of embodiments 1-8, the TREM core fragment of embodiment 22, or the TREM fragment of embodiment 37, wherein at least X of the nucleotides of ACHD have a non-naturally occurring modification, wherein X is equal to or greater than 1, 2, 3, 4, 5, 6, 7, 8, 9, or 10.
48. The TREM of any one of embodiments 1-8, the TREM core fragment of embodiment 22, or the TREM fragment of embodiment 37, wherein at least X of the nucleotides of ACHD have a non-naturally occurring modification, wherein X is equal to or greater than 11, 12, 13, 14, 15, 16, or 17.
49. The TREM of any one of embodiments 1-8, the TREM core fragment of embodiment 22, or the TREM fragment of embodiment 37, wherein no more than X of the nucleotides of ACHD have a non-naturally occurring modification, wherein X is equal to or greater than 1, 2, 3, 4, 5, 6, 7, 8, 9, or 10.
50. The TREM of any one of embodiments 1-8, the TREM core fragment of embodiment 22, or the TREM fragment of embodiment 37, wherein no more than X of the nucleotides of ACHD have a non-naturally occurring modification, wherein X is equal to or greater than 11, 12, 13, 14, 15, or 16.
51. The TREM of any one of embodiments 1-8, the TREM core fragment of embodiment 22, or the TREM fragment of embodiment 37, wherein at least X of the nucleotides of THD have a non-naturally occurring modification, wherein X is equal to or greater than 1, 2, 3, 4, 5, 6, 7, 8, 9, or 10.
52. The TREM of any one of embodiments 1-8, the TREM core fragment of embodiment 22, or the TREM fragment of embodiment 37, wherein at least X of the nucleotides of THD have a non-naturally occurring modification, wherein X is equal to or greater than 11, 12, 13, 14, 15, 16, or 17.
53. The TREM of any one of embodiments 1-8, the TREM core fragment of embodiment 22, or the TREM fragment of embodiment 37, wherein no more than X of the nucleotides of THD have a non-naturally occurring modification, wherein X is equal to or greater than 1, 2, 3, 4, 5, 6, 7, 8, 9, or 10.
54. The TREM of any one of embodiments 1-8, the TREM core fragment of embodiment 22, or the TREM fragment of embodiment 37, wherein no more than X of the nucleotides of THD have a non-naturally occurring modification, wherein X is equal to or greater than 11, 12, 13, 14, 15, or 16.
55. The TREM of any one of embodiments 1-8, the TREM core fragment of embodiment 22, or the TREM fragment of embodiment 37, wherein at least X of the nucleotides of DHD have a non-naturally occurring modification, wherein X is equal to or greater than 2, 3, 4, 5, 6, 7, 8, 9 or 10.

56. The TREM of any one of embodiments 1-8, the TREM core fragment of embodiment 22, or the TREM fragment of embodiment 37, wherein at least X of the nucleotides of DHD have a non-naturally occurring modification, wherein X is equal to or greater than 11, 12, 13, 14, 15, 16, 17, 18 or 19.

57. The TREM of any one of embodiments 1-8, the TREM core fragment of embodiment 22, or the TREM fragment of embodiment 37, wherein no more than X of the nucleotides of DHD have a non-naturally occurring modification, wherein X is equal to or greater than 1, 2, 3, 4, 5, 6, 7, 8, 9, or 10.

58. The TREM of any one of embodiments 1-8, the TREM core fragment of embodiment 22, or the TREM fragment of embodiment 37, wherein no more than X of the nucleotides of DHD have a non-naturally occurring modification, wherein X is equal to or greater than 11, 12, 13, 14, 15, 16, 17, or 18.

59. The TREM of any one of embodiments 1-8, the TREM core fragment of embodiment 22, or the TREM fragment of embodiment 37, wherein at least X of the nucleotides of the VLD have a non-naturally occurring modification, wherein X is equal to or greater than 2, 3, 4, 5, 6, 7, 8, 9, 10, 11, 12, 13, 14, 15, 16, 17, 18, 19, 20, 50, 100, 150, 200 or 271.

60. The TREM of any one of embodiments 1-8, the TREM core fragment of embodiment 22, or the TREM fragment of embodiment 37, wherein all of the nucleotides of the AStD1, AStD2, ACHD, DHD, and/or THD have a non-naturally occurring modification.

61. The TREM of any one of embodiments 1-8, the TREM core fragment of embodiment 22, or the TREM fragment of embodiment 37, wherein at least X of the nucleotides of AStD1 and/or AStD2 do not have a non-naturally occurring modification, wherein X is equal to or greater than 1, 2, 3, 4, 5, 6 or 7.

62. The TREM of any one of embodiments 1-8, the TREM core fragment of embodiment 22, or the TREM fragment of embodiment 37, wherein at least X of the nucleotides of ACHD do not have a non-naturally occurring modification, wherein X is equal to or greater than 1, 2, 3, 4, 5, 6, 7, 8, 9, 10, 11, 12, 13, 14, 15, 16, or 17.

63. The TREM of any one of embodiments 1-8, the TREM core fragment of embodiment 22, or the TREM fragment of embodiment 37, wherein at least X of the nucleotides of THD do not have a non-naturally occurring modification, wherein X is equal to or greater than 1, 2, 3, 4, 5, 6, 7, 8, 9, 10, 11, 12, 13, 14, 15, 16, or 17.

64. The TREM of any one of embodiments 1-8, the TREM core fragment of embodiment 22, or the TREM fragment of embodiment 37, wherein at least X of the nucleotides of DHD do not have a non-naturally occurring modification, wherein X is equal to or greater than 1, 2, 3, 4, 5, 6, 7, 8, 9, 10, 11, 12, 13, 14, 15, 16, 17, 18 or 19.

65. The TREM of any one of embodiments 1-8, the TREM core fragment of embodiment 22, or the TREM fragment of embodiment 37, wherein at least X of the nucleotides of VLD do not have a non-naturally occurring modification, wherein X is equal to or greater than 1, 2, 3, 4, 5, 6, 7, 8, 9, 10, 11, 12, 13, 14, 15, 16, 17, 18, 19, 20, 50, 100, 150, 200 or 271.

66. The TREM of any one of embodiments 1-8, the TREM core fragment of embodiment 22, or the TREM fragment of embodiment 37, wherein the TREM Linker L2 comprises two nucleotides each having a non-naturally occurring modification.

67. The TREM of any one of embodiments 1-8, the TREM core fragment of embodiment 22, or the TREM fragment of embodiment 37, wherein at least X of the nucleotides of the TREM Linker do not have a non-naturally occurring modification, wherein X is equal to 1 or 2.

68. The TREM of any one of embodiments 1-8, the TREM core fragment of embodiment 22, or the TREM fragment of embodiment 37, wherein:

each of a plurality of TREM Domains and Linkers comprises a nucleotide having a non-naturally occurring modification.

69. The TREM, TREM core fragment or TREM fragment of embodiment 68, wherein one of the TREM Domains and Linkers of the plurality comprises a plurality of nucleotides each having a non-naturally occurring modification.

70. The TREM, TREM core fragment or TREM fragment of any of the preceding embodiments, wherein the non-naturally occurring modification is a modification in a base or a backbone of a nucleotide, e.g., a modification chosen from any one of Tables 5-9.

71. The TREM, TREM core fragment or TREM fragment of any of the preceding embodiments, wherein the non-naturally occurring modification is a base modification chosen from a modification listed in Table 5.

72. The TREM, TREM core fragment or TREM fragment of any of the preceding embodiments, wherein the non-naturally occurring modification is a base modification chosen from a modification listed in Table 6.

73. The TREM, TREM core fragment or TREM fragment of any of the preceding embodiments, wherein the non-naturally occurring modification is a base modification chosen from a modification listed in Table 7.

74. The TREM, TREM core fragment or TREM fragment of any of the preceding embodiments, wherein the non-naturally occurring modification is a backbone base modification chosen from a modification listed in Table 8.

75. The TREM, TREM core fragment or TREM fragment of any of the preceding embodiments, wherein the non-naturally occurring modification is a backbone modification chosen from a modification listed in Table 9.

76. The TREM of any one of embodiments 1-8, the TREM core fragment of embodiment 22, or the TREM fragment of embodiment 37, comprising a nucleotide of a first type comprising a non-naturally occurring modification.

77. The TREM of any one of embodiments 1-8, the TREM core fragment of embodiment 22, or the TREM fragment of embodiment 37, comprising a nucleotide of a first type and a nucleotide of a second type comprising a non-naturally occurring modification.

78. The TREM, TREM core fragment or TREM fragment of embodiment 77, wherein the non-naturally occurring modification on the nucleotide of the first type and the non-naturally occurring modification on the nucleotide of the second type are the same non-naturally occurring modification.

79. The TREM, TREM core fragment or TREM fragment of embodiment 77, wherein the non-naturally occurring modification on the nucleotide of the first type and the non-naturally occurring modification on the nucleotide of the second type are different non-naturally occurring modifications.

80. The TREM, TREM core fragment or TREM fragment of embodiments 76 or 77, wherein the nucleotide of the first type is chosen from: A, T, C, G or U.

81. The TREM, TREM core fragment or TREM fragment of embodiments 76 or 77, wherein the nucleotide of the second type is chosen from: A, T, C, G or U.

82. The TREM, TREM core fragment or TREM fragment of embodiments 76 or 77, wherein the nucleotide of the first type is an A.

83. The TREM, TREM core fragment or TREM fragment of embodiments 76 or 77, wherein the nucleotide of the first type is a G.

84. The TREM, TREM core fragment or TREM fragment of embodiments 76 or 77, wherein the nucleotide of the first type is a C.

85. The TREM core fragment or TREM fragment of embodiments 76 or 77, wherein the nucleotide of the first type is a T.

86. The TREM, TREM core fragment or TREM fragment of embodiments 76 or 77, wherein the nucleotide of the first type is a U.

87. The TREM, TREM core fragment or TREM fragment of embodiment 77, wherein when the nucleotide of the first type is an A, the nucleotide of the second type is chosen from: T, C, G or U.

88. The TREM, TREM core fragment or TREM fragment of embodiment 77, wherein when the nucleotide of the first type is a G, the nucleotide of the second type is chosen from: T, C, A or U.

89. The TREM, TREM core fragment or TREM fragment of embodiment 77, wherein when the nucleotide of the first type is a C, the nucleotide of the second type is chosen from: T, A, G or U.

90. The TREM, TREM core fragment or TREM fragment of embodiment 77, wherein when the nucleotide of the first type is a T, the nucleotide of the second type is chosen from: A, C, G or U.

91. The TREM, TREM core fragment or TREM fragment of embodiment 77, wherein when the nucleotide of the first type is a U, the nucleotide of the second type is chosen from: T, C, G or A.

92. The TREM of any one of embodiments 1-8, the TREM core fragment of embodiment 22, or the TREM fragment of embodiment 37, wherein the non-naturally modification is in a purine (A or G).

93. The TREM of any one of embodiments 1-8, the TREM core fragment of embodiment 22, or the TREM fragment of embodiment 37, wherein the non-naturally modification is not in a purine (A or G).

94. The TREM of any one of embodiments 1-8, the TREM core fragment of embodiment 22, or the TREM fragment of embodiment 37, wherein the non-naturally modification is in a pyrimidine (U, T or C).

95. The TREM of any one of embodiments 1-8, the TREM core fragment of embodiment 22, or the TREM fragment of embodiment 37, wherein the non-naturally modification is not in a pyrimidine (U, T or C).

96. The TREM of any one of embodiments 1-8, the TREM core fragment of embodiment 22, or the TREM fragment of embodiment 37, wherein the DHD has a first sequence, a second sequence and a third sequence, optionally wherein the first sequence and the third sequence form a stem and the second sequence forms a loop, e.g., under physiological conditions.

97. The TREM, TREM core fragment or TREM fragment of embodiment 96, wherein the DHD comprises a non-naturally occurring modification in the first sequence or the third sequence, e.g., in the stem.

98. The TREM, TREM core fragment or TREM fragment of embodiment 96, wherein the DHD comprises a non-naturally occurring modification in the second sequence, e.g., in the loop.

100. The TREM of any one of embodiments 1-8, the TREM core fragment of embodiment 22, or the TREM fragment of embodiment 37, wherein the ACHD has a first sequence, a second sequence and a third sequence, optionally wherein the first sequence and the third sequence form a stem and the second sequence forms a loop, e.g., under physiological conditions.

101. The TREM, TREM core fragment or TREM fragment of embodiment 100, wherein the ACHD comprises a non-naturally occurring modification in the first sequence or the third sequence, e.g., in the stem.

102. The TREM, TREM core fragment or TREM fragment of embodiment 100, wherein the ACHD comprises a non-naturally occurring modification in the second sequence, e.g., in the loop.

103. The TREM of any one of embodiments 1-8, the TREM core fragment of embodiment 22, or the TREM fragment of embodiment 37, wherein the THD has a first sequence, a second sequence and a third sequence, optionally wherein the first sequence and the third sequence form a stem and the second sequence forms a loop, e.g., under physiological conditions.

104. The TREM, TREM core fragment or TREM fragment of embodiment 103, wherein the THD comprises a non-naturally occurring modification in the first sequence or the third sequence, e.g., in the stem.

105. The TREM, TREM core fragment or TREM fragment of embodiment 103, wherein the THD comprises a non-naturally occurring modification in the second sequence, e.g., in the loop.

106. The TREM of any one of embodiments 1-8, the TREM core fragment of embodiment 22, or the TREM fragment of embodiment 37, wherein the VLD comprises a variable region having 1-271 nucleotides.

107. The TREM of any one of embodiments 1-8, the TREM core fragment of embodiment 22, or the TREM fragment of embodiment 37, wherein the TREM comprises at least X contiguous nucleotides without a non-naturally occurring modification, wherein X is greater than 10.

108. The TREM of any one of embodiments 1-8, the TREM core fragment of embodiment 22, or the TREM fragment of embodiment 37, wherein at least 3, but less than all of the nucleotides of a type (e.g., A, T, C, G or U) comprise the same non-naturally occurring modification.

109. The TREM of any one of embodiments 1-8, the TREM core fragment of embodiment 22, or the TREM fragment of embodiment 37, wherein at least X nucleotides of a type (e.g., A, T, C, G or U) do not comprise a non-naturally occurring modification, wherein X=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

110. The TREM of any one of embodiments 1-8, the TREM core fragment of embodiment 22, or the TREM fragment of embodiment 37, wherein no more than 5, 10, or 15 of a type (e.g., A, T, C, G or U) comprise a non-naturally occurring modification.

111. The TREM of any one of embodiments 1-8, the TREM core fragment of embodiment 22, or the TREM fragment of embodiment 37, wherein no more than 5, 10, or 15 of a type (e.g., A, T, C, G or U) do not comprise a non-naturally occurring modification.

112. The TREM of any one of embodiments 1-8, the TREM core fragment of embodiment 22, or the TREM fragment of embodiment 37, which specifies X, wherein X is an amino acid selected from alanine, arginine, asparagine, aspartate, cysteine, glutamine, glutamate, glycine, histidine, isoleucine, methionine, leucine, lysine, phenylalanine, proline, serine, threonine, tryptophan, tyrosine, or valine.

113. The TREM of any one of embodiments 1-8, the TREM core fragment of embodiment 22, or the TREM fragment of embodiment 37, which recognizes a codon provided in Table 8 or Table 9.

114. The TREM of any one of embodiments 1-8, the TREM core fragment of embodiment 22, or the TREM fragment of embodiment 37, wherein the TREM is a cognate TREM.

115. The TREM of any one of embodiments 1-8, the TREM core fragment of embodiment 22, or the TREM fragment of embodiment 37, wherein the TREM is a non-cognate TREM.

116. The TREM of any one of embodiments 1-8, the TREM core fragment of embodiment 22, or the TREM fragment of embodiment 37, wherein the TREM, TREM core fragment, or TREM fragment is encoded by a sequence provided in Table 1, e.g., any one of SEQ ID NOs 1-451.

117. The TREM of any one of embodiments 1-8, the TREM core fragment of embodiment 22, or the TREM fragment of embodiment 37, wherein the TREM, TREM core fragment, or TREM fragment is encoded by a consensus sequence chosen from any one of SEQ ID NOs: 562-621.

118. The TREM of any one of embodiments 1-8, the TREM core fragment of embodiment 22, or the TREM fragment of embodiment 37, wherein the TREM, TREM core fragment, or TREM fragment is encoded by a consensus sequence chosen from any one of SEQ ID NOs: 622-1187.

119. A pharmaceutical composition comprising a TREM of any one of embodiments 1-8, the TREM core fragment of embodiment 22, or the TREM fragment of embodiment 37.

120. The pharmaceutical composition of embodiment 119, comprising a pharmaceutically acceptable component, e.g., an excipient.

121. A lipid nanoparticle formulation comprising a TREM of any one of embodiments 1-8, the TREM core fragment of embodiment 22, or the TREM fragment of embodiment 37.

122. A method of making a TREM of any one of embodiments 1-8, the TREM core fragment of embodiment 22, or the TREM fragment of embodiment 37, comprising linking a first nucleotide to a second nucleotide to form the TREM.

123. The method of embodiment 122, wherein the TREM, TREM core fragment or TREM fragment is synthetic (e.g, non-naturally occurring).

124. The method of embodiment 122 or 123, wherein the synthesis is performed in vitro.

125. The method of embodiment 122, wherein the TREM, TREM core fragment or TREM fragment is made by cell-free solid phase synthesis.

126. A cell comprising a TREM of any one of embodiments 1-8, the TREM core fragment of embodiment 22, or the TREM fragment of embodiment 37.

127. A cell comprising a TREM, TREM core fragment or TREM fragment made according to the method of embodiment 122.

128. A method of modulating a tRNA pool in a cell comprising:

providing a TREM of any one of embodiments 1-8, the TREM core fragment of embodiment 22, or the TREM fragment of embodiment 37, and contacting the cell with the TREM, TREM core fragment or TREM fragment, thereby modulating the tRNA pool in the cell.

129. A method of contacting a cell, tissue, or subject with a TREM of any one of embodiments 1-8, the TREM core fragment of embodiment 22, or the TREM fragment of embodiment 37, comprising contacting the cell, tissue or subject with the TREM, TREM core fragment or TREM fragment, thereby contacting the cell, tissue, or subject with the TREM, TREM core fragment or TREM fragment.

130. A method of presenting a TREM, TREM core fragment or TREM fragment to a cell, tissue, or subject with a TREM, TREM core fragment or TREM fragment, comprising contacting the cell, tissue or subject with a TREM of any one of embodiments 1-8, the TREM core fragment of embodiment 22, or the TREM fragment of embodiment 37, thereby presenting the TREM, TREM core fragment or TREM fragment to a cell, tissue, or subject.

131. A method of forming a TREM, TREM core fragment or TREM fragment-contacted cell, tissue, or subject, comprising contacting the cell, tissue or subject with a TREM of any one of embodiments 1-8, the TREM core fragment of embodiment 22, or the TREM fragment of embodiment 37, thereby forming a TREM, TREM core fragment or TREM fragment-contacted cell, tissue, or subject.

132. A method of using a TREM, TREM core fragment or TREM fragment comprising, contacting the cell, tissue or subject with a TREM of any one of embodiments 1-8, the TREM core fragment of embodiment 22, or the TREM fragment of embodiment 37, thereby using the TREM.

133. A method of applying a TREM, TREM core fragment or TREM fragment to a cell, tissue, or subject, comprising contacting the cell, tissue or subject with a TREM of any one of embodiments 1-8, the TREM core fragment of embodiment 22, or the TREM fragment of embodiment 37, thereby applying a TREM, TREM core fragment or TREM fragment to a cell, tissue, or subject.

134. A method of exposing a cell, tissue, or subject to a TREM, comprising contacting the cell, tissue or subject with a TREM of any one of embodiments 1-8, the TREM core fragment of embodiment 22, or the TREM fragment of embodiment 37, thereby exposing a cell, tissue, or subject to a TREM, TREM core fragment or TREM fragment.

135. A method of forming an admixture of a TREM, TREM core fragment or TREM fragment and a cell, tissue, or subject, comprising contacting the cell, tissue or subject with a TREM of any one of embodiments 1-8, the TREM core fragment of embodiment 22, or the TREM fragment of embodiment 37, thereby forming an admixture of a TREM, TREM core fragment or TREM fragment and a cell, tissue, or subject.

136. A method of delivering a TREM, TREM core fragment or TREM fragment to a cell, tissue, or subject, comprising:

providing a cell, tissue, or subject, and contacting the cell, tissue, or subject, a TREM of any one of embodiments 1-8, the TREM core fragment of embodiment 22, or the TREM fragment of embodiment 37.

137. A method, e.g., an ex vivo method, of modulating the metabolism, e.g., the translational capacity of an organelle, comprising:

providing a preparation of an organelle, e.g., mitochondria or chloroplasts, and contacting the organelle with a TREM of any one of embodiments 1-8, the TREM core fragment of embodiment 22, or the TREM fragment of embodiment 37.

138. A method of treating a subject, e.g., modulating the metabolism, e.g., the translational capacity of a cell, in a subject, comprising:

providing, e.g., administering to the subject a TREM of any one of embodiments 1-8, the TREM core fragment of embodiment 22, or the TREM fragment of embodiment 37, thereby treating the subject.

139. A method of modulating a tRNA pool in a cell comprising an endogenous open reading frame (ORF), which ORF comprises a codon having a first sequence, comprising:

optionally, acquiring knowledge of the abundance of one or both of (i) and (ii), e.g., acquiring knowledge of the relative amounts of: (i) and (ii) in the cell, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the cell;

contacting the cell with a TREM of any one of embodiments 1-8, the TREM core fragment of embodiment 22, or the TREM fragment of embodiment 37, wherein the TREM, TREM core fragment or TREM fragment has an anticodon that pairs with: the codon having the first sequence; or the codon other than the codon having the first sequence, in an amount and/or for a time sufficient to modulate the relative amounts of the first tRNA moiety and the second tRNA moiety in the cell, thereby modulating the tRNA pool in the cell.

140. A method of modulating a tRNA pool in a subject having an endogenous open reading frame (ORF), which ORF comprises a codon having a first sequence, comprising:

optionally, acquiring knowledge of the abundance of one or both of (i) and (ii), e.g., acquiring knowledge of the relative amounts of: (i) and (ii) in the subject, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the subject;

contacting the subject with a TREM of any one of embodiments 1-8, the TREM core fragment of embodiment 22, or the TREM fragment of embodiment 37, wherein the TREM, TREM core fragment or TREM fragment has an anticodon that pairs with: the codon having the first sequence; or the codon other than the codon having the first sequence, in an amount and/or for a time sufficient to modulate the relative amounts of the first tRNA moiety and the second tRNA moiety in the subject, thereby modulating the tRNA pool in the subject.

141. A method of modulating a tRNA pool in a subject having an endogenous open reading frame (ORF) comprising a codon comprising a synonymous mutation (a synonymous mutation codon or SMC), comprising:

providing a composition comprising a TREM of any one of embodiments 1-8, the TREM core fragment of embodiment 22, or the TREM fragment of embodiment 37, wherein the TREM, TREM core fragment or TREM fragment comprises an isoacceptor tRNA moiety comprising an anticodon sequence that pairs with the SMC (the TREM);

contacting the subject with the composition in an amount and/or for a time sufficient to modulate the tRNA pool in the subject, thereby modulating the tRNA pool in the subject.

142. A method of modulating a tRNA pool in a cell comprising an endogenous open reading frame (ORF) comprising a codon comprising a synonymous mutation (a synonymous mutation codon or SMC), comprising:

providing a composition comprising a TREM of any one of embodiments 1-8, the TREM core fragment of embodiment 22, or the TREM fragment of embodiment 37, wherein the TREM, TREM core fragment or TREM fragment comprises an isoacceptor tRNA moiety comprising an anticodon sequence that pairs with the SMC (the TREM);

contacting the cell with the composition comprising a TREM in an amount and/or for a time sufficient to modulate the tRNA pool in the cell, thereby modulating the tRNA pool in the cell.

143. A method of modulating expression of a protein in a cell, wherein the protein is encoded by a nucleic acid comprising an endogenous open reading frame (ORF), which ORF comprises a codon having a mutation, comprising:

contacting the cell with a composition comprising a TREM of any one of embodiments 1-8, the TREM core fragment of embodiment 22, or the TREM fragment of embodiment 37 in an amount and/or for a time sufficient to modulate expression of the encoded protein, wherein the TREM, TREM core fragment or TREM fragment has an anticodon that pairs with the codon having the mutation, thereby modulating expression of the protein in the cell.

144. A method of modulating expression of a protein in a subject, wherein the protein is encoded by a nucleic acid comprising an endogenous open reading frame (ORF), which ORF comprises a codon having a mutation, comprising:

contacting the subject with a composition comprising a TREM of any one of embodiments 1-8, the TREM core fragment of embodiment 22, or the TREM fragment of embodiment 37, in an amount and/or for a time sufficient to modulate expression of the encoded protein, wherein the TREM, TREM core fragment or TREM fragment has an anticodon that pairs with the codon having the mutation, thereby modulating expression of the protein in the subject.

145. The method of embodiment 143 or 144, wherein the mutation in the ORF is a nonsense mutation, e.g., resulting in a premature stop codon chosen from UAA, UGA or UAG.

146. The method of embodiment 143 or 144, wherein the TREM comprises an anticodon that pairs with a stop codon.

Enumerated Embodiments II

1000. A TREM Comprising a Nucleotide (at a Position Identified Herein) Comprising a Non-naturally occurring modification or a nucleotide (at a position identified herein) lacking a non-naturally occurring modification.

1001. The TREM of embodiment 1000, comprising the following structure:

[*L*1]-[*ASt* Domain1]-[*L*2]-[*DH* Domain]-[*L*3]-[*ACH* Domain]-[*VL* Domain]-[*TH* Domain]-[*L*4]-[*ASt* Domain2].

1002. A TREM comprising a sequence of Formula A:

[*L*1]-[*ASt* Domain1]-[*L*2]-[*DH* Domain]-[*L*3]-[*ACH* Domain]-[*VL* Domain]-[*TH* Domain]-[*L*4]-[*ASt* Domain2], wherein:

independently, [L1] and [VL Domain], are optional;

one of [L1], [ASt Domain1], [L2]-[DH Domain], [L3], [ACH Domain], [VL Domain], [TH Domain], [L4], and [ASt Domain2] comprises a nucleotide having a non-naturally occurring modification; and wherein:

(a) the TREM has the ability to: (i) support protein synthesis, (ii) be charged by a synthetase, (iii) be bound by an elongation factor, (iv) introduce an amino acid into a peptide chain, (v) support elongation, or (vi) support initiation;

(b) the TREM comprises $X_1$ contiguous nucleotides without a non-naturally occurring modification, wherein $X_1$ is 3, 4, 5, 6, 7, 8, 9, 10 or greater;

(c) the TREM comprises $X_2$ non-naturally occurring modifications, wherein $X_2$ is, 2, 3, 4, or greater;

(d) the TREM comprises $X_3$ different non-naturally occurring modifications, wherein $X_3$ is, 2, 3, 4, or greater;

(e) 3 nucleotides, wherein less than all of the nucleotides of a type (e.g., A, T, C, G or U) comprise the same non-naturally occurring modification;

(f) $X_4$ nucleotides of a type (e.g., A, T, C, G or U) do not comprise a non-naturally occurring modification, wherein $X_4$ is equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50;

(g) no more than 5, 10, or 15 nucleotides of a type (e.g., A, T, C, G or U) comprise a non-naturally occurring modification; and/or (h) no more than 5, 10, or 15 nucleotides of a type (e.g., A, T, C, G or U) do not comprise a non-naturally occurring modification; and/or the ACH Domain comprises a non-extended anticodon.

1003. The TREM of any preceding embodiment, wherein:

(a) the TREM has the ability to: (i) support protein synthesis, (ii) be charged by a synthetase, (iii) be bound by an elongation factor, (iv) introduce an amino acid into a peptide chain, (v) support elongation, or (vi) support initiation.

1004. The TREM of any preceding embodiment, wherein:

(b) the TREM comprises $X_1$ contiguous nucleotides without a non-naturally occurring modification, wherein $X_1$ is 10 or greater.

1005. The TREM of any preceding embodiment, wherein: the TREM comprises at $X_2$ non-naturally occurring modifications, wherein $X_2$ is, 2, 3, 4, or greater.

1006. The TREM of any preceding embodiment, wherein:

(c) the TREM comprises $X_3$ different non-naturally occurring modifications, wherein $X_3$ is, 2, 3, 4, or greater.

1007. The TREM of any preceding embodiment, wherein:

(d) 3 nucleotides, wherein less than all of the nucleotides of a type (e.g., A, T, C, G or U) comprise the same non-naturally occurring modification.

1008. The TREM of any preceding embodiment, wherein:

(e) $X_4$ nucleotides of a type (e.g., A, T, C, G or U) do not comprise a non-naturally occurring modification, wherein $X_4$ is equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

1009. The TREM of any preceding embodiment, wherein:

(f) no more than 5, 10, or 15 nucleotides of a type (e.g., A, T, C, G or U) comprise a non-naturally occurring modification.

1010. The TREM of any preceding embodiment, wherein:

(g) no more than 5, 10, or 15 nucleotides of a type (e.g., A, T, C, G or U) do not comprise a non-naturally occurring modification; and/or the ACH Domain comprises a non-extended anticodon.

1011. The TREM of any preceding embodimentwherein the ACH Domain comprises a non-extended anticodon or does not include an extended anticodon.

1012. A TREM fragment comprising a portion of a TREM, wherein the TREM comprises a sequence of Formula A:

[*L*1]-[*ASt* Domain1]-[*L*2]-[*DH* Domain]-[*L*3]-[*ACH* Domain]-[*VL* Domain]-[*TH* Domain]-[*L*4]-[*ASt* Domain2], and wherein:

the TREM fragment comprises:

a non-naturally occurring modification; and one, two, three or all or any combination of the following:

(a) a TREM half (e.g., from a cleavage in the ACH Domain, e.g., in the anticodon sequence, e.g., a 5' half or a 3' half);

(b) a 5' fragment (e.g., a fragment comprising the 5' end, e.g., from a cleavage in a DH Domain or the ACH Domain);

(c) a 3' fragment (e.g., a fragment comprising the 3' end, e.g., from a cleavage in the TH Domain); or (d) an internal fragment (e.g., from a cleavage in any one of the ACH Domain, DH Domain or TH Domain).

1013. The TREM or TREM fragment of any of the above embodiments, comprising a non-naturally occurring modification on a nucleotide sugar moiety (2'-modification) or in the TREM backbone.

1014. The TREM or TREM fragment of any of the above embodiments, comprising a nucleotide comprising a 2' non-naturally occurring modification on the sugar moiety.

1015. The TREM or TREM fragment of any of the above embodiments, wherein the nucleotide corresponds to any of nucleotides 1-76 of SEQ ID NO: 622, nucleotides 1-85 of SEQ ID NO: 993, or nucleotides 1-75 of SEQ ID NO: 1079 is modified.

1016. The TREM or TREM fragment of embodiments 1000-1015, wherein the nucleotide is in the ASt Domain1.

1017. The TREM or TREM fragment of embodiments 1000-1016, wherein the nucleotide is in the DH Domain.

1018. The TREM or TREM fragment of embodiments 1000-1017, wherein the nucleotide is in the ACH Domain.

1019. The TREM or TREM fragment of embodiments 1000-1018, wherein the nucleotide is in the VL Domain.

1020. The TREM or TREM fragment of embodiments 1000-1019, wherein the nucleotide is in the TH Domain.

1021. The TREM or TREM fragment of embodiments 1000-1020, wherein the nucleotide is in the ASt Domain2.

1022. The TREM or TREM fragment of embodiments 1000-10021, wherein the nucleotide is in a linker domain (e.g., [L1], [L2], [L3], or [L4]).

1023. The TREM or TREM fragment of embodiments 1000-1022, wherein the nucleotide corresponding to any one of nucleotides 1, 2, 4, 6, 10, 12, 13, 17, 18, 20, 22, 29, 30, 42, 43, 45, 50, 52, 56, 59, 61, 65, 66, 68, 69, 71, 72, and 73 of SEQ ID NO: 622 is modified.

1024. The TREM or TREM fragment of embodiments 1000-1022, wherein the nucleotide corresponding to any one of nucleotides 20, 29, 33, 40, 41, 44, 45, 48, 49, 50, 52, 53, 54, 56, 59, 61, 62, 63, 65, 67, 68, 69, 71, 72, 75, and 76 of SEQ ID NO: 622 is modified.

1025. The TREM or TREM fragment of embodiments 1000-1022, wherein the nucleotide corresponding to any one of nucleotides 1, 4, 14, 15, 16, 17, 20, 29, 44, 45, 47, 49, 50, 52, 54, 56, 57, 59, 65, 72, and 73 of SEQ ID NO: 622 is modified.

1026. The TREM or TREM fragment of embodiments 1000-1022, wherein the nucleotide corresponding to any one of nucleotides 3, 4, 5, 6, 14, 15, 16, 20, 22, 23, 33, 54, 59, 62, 63, 72, and 76 of SEQ ID NO: 622 is modified.

1027. The TREM or TREM fragment of embodiments 1000-1022, wherein the nucleotide corresponding to any one of nucleotides 1, 2, 3, 9, 14, 15, 16, 17, 18, 19, 20, 21, 35, 37, 38, 44, 45, 46, 52, 54, 55, 56, 57, 58, 73, and 74 of SEQ ID NO: 622 is modified.

1028. The TREM or TREM fragment of embodiments 1000-1022, wherein the nucleotide corresponding to any one of nucleotides 1, 17, 18, 20, 29, 30, 50, 52, and 73 of SEQ ID NO: 622 is modified.

1029. The TREM or TREM fragment of embodiments 1000-1022, wherein the nucleotide corresponding to any one of nucleotides 1, 4, 5, 34, 38, 39, 61, 79, 80, and 82 of SEQ ID NO: 993 is modified.

1030. The TREM or TREM fragment of embodiments 1000-1022, wherein the nucleotide corresponding to any one of nucleotides 1, 4, 12, 13, 17, 18, 23, 28, 29, 30, 38, 39, 41, 44, 48, 49, 51, 52, 53, 58, 60, 61, 63, 64, 65, 66, 68, 69, 71, 72, 73, 74, and 75 of SEQ ID NO: 1079 is modified.

1031. The TREM or TREM fragment of embodiments 1000-1014, wherein the 2' non-naturally occurring modification comprises an ester, halo, hydrogen, alkyl group.

1032. The TREM or TREM fragment of embodiments 1000-1014, wherein the 2' non-naturally occurring modification comprises a 2'-OMe moiety.

1033. The TREM or TREM fragment of embodiments 1000-1024, wherein the 2' non-naturally occurring modification comprises a 2'-MOE moiety.

1034. The TREM or TREM fragment of embodiments 1000-1014, wherein the 2' non-naturally occurring modification comprises a 2'-halo (e.g., 2'-F or 2'C1).

1035. The TREM or TREM fragment of embodiments 1000-1014, wherein the 2' non-naturally occurring modification comprises a 2'-deoxy group (e.g., a 2'-H).

1036. The TREM or TREM fragment of any of embodiments 1000-1035, comprising a nucleotide that lacks a non-naturally occurring modification, e.g., lacks a 2' non-naturally occurring modification on a sugar moiety.

1037. The TREM or TREM fragment of any of embodiment 1036, wherein the nucleotide corresponds to any of nucleotides 1-76 of SEQ ID NO:622 and lacks a non-naturally occurring modification.

1038. The TREM or TREM fragment of embodiment 1036, wherein the nucleotide is in the ASt Domain1.

1039. The TREM or TREM fragment of embodiment 1036, wherein the nucleotide is in the DH Domain.

1040. The TREM or TREM fragment of embodiment 1036, wherein the nucleotide is in the ACH Domain.

1041. The TREM or TREM fragment of embodiment 1036, wherein the nucleotide is in the VL Domain.

1042. The TREM or TREM fragment of embodiment 1036, wherein the nucleotide is in the TH Domain.

1043. The TREM or TREM fragment of embodiment 1036, wherein the nucleotide is in the ASt Domain2.

1044. The TREM or TREM fragment of embodiment 1036, wherein the nucleotide is in a linker domain (e.g., [L1], [L2], [L3], or [L4]).

1045. The TREM or TREM fragment of embodiment 1036, wherein the nucleotide corresponds to any one of nucleotides 1-76 of SEQ ID NO: 622 and lacks a non-naturally occurring modification, e.g., 2' non-naturally occurring modification on a sugar.

1046. The TREM or TREM fragment of embodiment 1036, wherein the nucleotide corresponding to any one of nucleotides 1-85 of SEQ ID NO: 993 lacks a non-naturally occurring modification, e.g., a 2' non-naturally occurring modification on a sugar.

1047. The TREM or TREM fragment of embodiment 1036, wherein the nucleotide corresponding to any one of nucleotides 1-75 of SEQ ID NO: 1079 lacks a non-naturally occurring modification, e.g., a 2' non-naturally occurring modification on a sugar.

1048. The TREM or TREM fragment of any one of embodiments 1000-1047, comprising a nucleotide comprising a 2' OMe non-naturally occurring modification.

1049. The TREM or TREM fragment of embodiment 1000-1048, wherein the nucleotide corresponds to any of nucleotides 1-76 of SEQ ID NO: 622 is modified.

1050. The TREM or TREM fragment of any of embodiment 1048-1049, wherein the nucleotide is in the ASt Domain1.

1051. The TREM or TREM fragment of any of embodiment 1048-1049, wherein the nucleotide is in the DH Domain.

1052. The TREM or TREM fragment of any of embodiment 1048-1049, wherein the nucleotide is in the ACH Domain.

1053. The TREM or TREM fragment of any of embodiment 1048-1049, wherein the nucleotide is in the VL Domain.

1054. The TREM or TREM fragment of any of embodiment 1048-1049, wherein the nucleotide is in the TH Domain.

1055. The TREM or TREM fragment of any of embodiment 1048-1049, wherein the nucleotide is in the ASt Domain2.

1056. The TREM or TREM fragment of any of embodiment 1048-1049, wherein the nucleotide is in a linker domain (e.g., [L1], [L2], [L3], or [L4]).

1057. The TREM or TREM fragment of any of embodiment 1048-1056, wherein the nucleotide corresponding to any one of nucleotides 1, 2, 4, 6, 10, 12, 13, 17, 18, 20, 22, 29, 30, 42, 43, 45, 50, 52, 56, 59, 61, 65, 66, 68, 69, 71, 72, and 73 of SEQ ID NO: 622 is modified (e.g., a sequence in Table 15).

1058. The TREM or TREM fragment of any of embodiment 1000-1047, comprising a nucleotide comprising a nucleotide that lacks a non-naturally occurring modification, e.g., lacks a 2' OMe modification on a sugar moiety.

1059. The TREM or TREM fragment of embodiment 1058, wherein the nucleotide corresponds to any of nucleotides 1-76 of SEQ ID NO: 622 lacks a non-naturally occurring modification, e.g., lacks a 2' OMe modification on a sugar moiety.

1060. The TREM or TREM fragment of any of embodiment 1058-1059, wherein the nucleotide is in the ASt Domain1.

1061. The TREM or TREM fragment of any of embodiment 1058-1059, wherein the nucleotide is in the DH Domain.

1062. The TREM or TREM fragment of any of embodiment 1058-1059, wherein the nucleotide is in the ACH Domain.

1063 The TREM or TREM fragment of any of embodiment 1058-1059, wherein the nucleotide is in the VL Domain.

1064. The TREM or TREM fragment of any of embodiment 1058-1059, wherein the nucleotide is in the TH Domain.

1065. The TREM or TREM fragment of any of embodiment 1058-1059, wherein the nucleotide is in the ASt Domain2.

1066. The TREM or TREM fragment of any of embodiment 1058-1059, wherein the nucleotide is in a linker domain (e.g., [L1], [L2], [L3], or [L4]).

1067. The TREM or TREM fragment of any of embodiment 1000-1066, comprising a nucleotide comprising a 2' halo, e.g., a 2' fluoro, non-naturally occurring modification on a sugar moiety.

1068. The TREM or TREM fragment of embodiment 1067, wherein the 2' halo is 2' fluoro.

1069. The TREM or TREM fragment of embodiment 1067-1068, wherein the nucleotide corresponding to any of nucleotides 1-76 of SEQ ID NO: 622 is modified.

1070. The TREM or TREM fragment of embodiment 1067-1068, wherein the nucleotide is in the ASt Domain1.

1071. The TREM or TREM fragment of embodiment 1067-1068, wherein the nucleotide is in the DH Domain.

1072. The TREM or TREM fragment of embodiment 1067-1068, wherein the nucleotide is in the ACH Domain.

1073. The TREM or TREM fragment of embodiment 1067-1068, wherein the nucleotide is in the VL Domain.

1074. The TREM or TREM fragment of embodiment 1067-1068, wherein the nucleotide is in the TH Domain.

1075. The TREM or TREM fragment of embodiment 1067-1068, wherein the nucleotide is in the ASt Domain2.

1076. The TREM or TREM fragment of any of embodiment 1067-1068, wherein the nucleotide is in a linker domain (e.g., [L1], [L2], [L3], or [L4]).

1077. The TREM or TREM fragment of any of embodiment 1067-1076, wherein the nucleotide corresponding to any one of nucleotides 20, 29, 33, 40, 41, 44, 45, 48, 49, 50, 52, 53, 54, 56, 59, 61, 62, 63, 65, 67, 68, 69, 71, 72, 75, and 76 of SEQ ID NO: 622 is modified.

1078. The TREM or TREM fragment of any of embodiment 1000-1035, comprising a nucleotide that lacks a non-naturally occurring modification, e.g., lacks a 2' halo, e.g., a 2' fluoro, non-naturally occurring modification on a sugar moiety.

1079. The TREM or TREM fragment of embodiment 1078, wherein 2' halo is 2' fluoro.

1080. The TREM or TREM fragment of any of embodiments 1078-1079, wherein the nucleotide corresponds to any of nucleotides 1-76 of SEQ ID NO: 622 and lacks a non-naturally occurring modification.

1081. The TREM or TREM fragment of any of embodiments 1078-1079, wherein the nucleotide is in the ASt Domain1.

1082. The TREM or TREM fragment of any of embodiments 1078-1079, wherein the nucleotide is in the DH Domain.

1083. The TREM or TREM fragment of any of embodiments 1078-1079, wherein the nucleotide is in the ACH Domain.

1084. The TREM or TREM fragment of any of embodiments 1078-1079, wherein the nucleotide is in the VL Domain.

1085. The TREM or TREM fragment of any of embodiments 1078-1079, wherein the nucleotide is in the TH Domain.

1086. The TREM or TREM fragment of any of embodiments 1078-1079, wherein the nucleotide is in the ASt Domain2.

1087. The TREM or TREM fragment of any of embodiments 1078-1079, wherein the nucleotide is in a linker domain (e.g., [L1], [L2], [L3], or [L4]).

1088. The TREM or TREM fragment of any of embodiment 1000-1013, wherein the nucleotide corresponding to any one of nucleotides 20, 29, 33, 40, 41, 44, 45, 48, 49, 50, 52, 53, 54, 56, 59, 61, 62, 63, 67, 68, 69, 71, 72, 75, and 76 of SEQ ID NO: 622 lacks a non-naturally occurring modification, e.g., a 2' fluoro non-naturally occurring modification on the sugar.

1089. The TREM or TREM fragment of any of embodiments 1000-1088, wherein the non-naturally occurring modification comprises a 2' deoxy nucleotide.

1090. The TREM or TREM fragment of embodiment 1084, wherein the 2' deoxy nucleotide corresponds to any of nucleotides 1-76 of SEQ ID NO: 622 is modified.

1091. The TREM or TREM fragment of any of embodiments 1089-1090, wherein the 2' deoxy nucleotide is in the ASt Domain1.

1092. The TREM or TREM fragment of any of embodiments 1089-1090, wherein the 2' deoxy nucleotide is in the DH Domain.

1093. The TREM or TREM fragment of any of embodiments 1089-1090, wherein the 2' deoxy nucleotide is in the ACH Domain.

1094. The TREM or TREM fragment of any of embodiments 1089-1090, wherein the 2' deoxy nucleotide is in the VL Domain.

1095. The TREM or TREM fragment of any of embodiments 1089-1090, wherein the 2' deoxy nucleotide is in the TH Domain.

1096. The TREM or TREM fragment of any of embodiments 1089-1090, wherein the 2' deoxy nucleotide is in the ASt Domain2.

1097. The TREM or TREM fragment of any of embodiments 1089-1090, wherein the nucleotide is in a linker domain (e.g., [L1], [L2], [L3], or [L4]).

1098. The TREM or TREM fragment of any of embodiments 1089-1090, wherein the nucleotide corresponding to any one of nucleotides 3, 4, 5, 6, 14, 15, 16, 20, 22, 23, 33, 54, 59, 62, 63, 72, and 76 of SEQ ID NO: 622 is a 2' deoxy nucleotide.

1099. The TREM or TREM fragment of any of embodiments 1000-1092, comprising an 2'-OH nucleotide.

1100. The TREM or TREM fragment of embodiment 1099, wherein the 2'-OH nucleotide corresponds to any of nucleotides 1-76 of SEQ ID NO:622.

1101. The TREM or TREM fragment of any of embodiments 1099-1100, wherein the nucleotide is in the ASt Domain1.

1102. The TREM or TREM fragment of any of embodiments 1099-1100, wherein the nucleotide is in the DH Domain.

1103. The TREM or TREM fragment of any of embodiments 1099-1100, wherein the nucleotide is in the ACH Domain.

1104. The TREM or TREM fragment of any of embodiments 1099-1100, wherein the nucleotide is in the VL Domain.

1105. The TREM or TREM fragment of any of embodiments 1099-1100, wherein the nucleotide is in the TH Domain.

1106. The TREM or TREM fragment of any of embodiments 1099-1100, wherein the nucleotide is in the ASt Domain2.

1107. The TREM or TREM fragment of any of embodiments 1099-1100, wherein the nucleotide is in a linker domain (e.g., [L1], [L2], [L3], or [L4]).

1109. The TREM or TREM fragment of any of embodiment 1000-1100, wherein the nucleotide corresponding to any one of nucleotides 3, 4, 5, 6, 14, 15, 16, 20, 22, 23, 33, 54, 59, 62, 63, 72, and 76 of SEQ ID NO: 622 is a 2'-OH nucleotide.

1110. The TREM or TREM fragment of any of embodiments 1000-1109, wherein the non-naturally occurring modification comprises a 2' methoxyethyl (MOE) nucleotide.

1111. The TREM or TREM fragment of embodiment 1110, wherein the nucleotide corresponds to any of nucleotides 1-76 of SEQ ID NO: 622.

1112. The TREM or TREM fragment of any of embodiments 1110-1111, wherein the 2'-MOE nucleotide is in the ASt Domain1.

1113. The TREM or TREM fragment of any of embodiments 1110-1111, wherein the 2'-MOE nucleotide is in the DH Domain.

1114. The TREM or TREM fragment of any of embodiments 1110-1111, wherein the 2'-MOE nucleotide is in the ACH Domain.

1115. The TREM or TREM fragment of any of embodiments 1110-1111, wherein the 2'-MOE nucleotide is in the VL Domain.

1116. The TREM or TREM fragment of any of embodiments 1110-1111, wherein the 2'-MOE nucleotide is in the TH Domain.

1117. The TREM or TREM fragment of any of embodiments 1110-1111, wherein the 2'-MOE nucleotide is in the ASt Domain2.

1118. The TREM or TREM fragment of any of embodiments 1110-1111, wherein the 2'-MOE nucleotide is in a linker domain (e.g., [L1], [L2], [L3], or [L4]).

1119. The TREM or TREM fragment of any of embodiments 1110-1118, wherein the nucleotide corresponding to any one of nucleotides 1, 4, 14, 15, 16, 17, 20, 29, 44, 45, 47, 49, 50, 52, 54, 56, 57, 59, 65, 72, and 73 of SEQ ID NO: 622 is a 2'-MOE nucleotide.

1120. The TREM or TREM fragment of any of embodiments 1000-1109, comprising a nucleotide that lacks a non-naturally occurring modification, e.g., lacks a 2-MOE, e.g., a non-naturally occurring modification on a sugar moiety.

1121. The TREM or TREM fragment of embodiment 1120, wherein the nucleotide corresponds to any of nucleotides 1-76 of SEQ ID NO: 622 and lacks a non-naturally occurring modification.

1122. The TREM or TREM fragment of any of embodiments 1120-1121, wherein the nucleotide is in the ASt Domain1.

1123. The TREM or TREM fragment of any of embodiments 1120-1121, wherein the nucleotide is in the DH Domain.

1124. The TREM or TREM fragment of any of embodiments 1120-1121, wherein the nucleotide is in the ACH Domain.

1125. The TREM or TREM fragment of any of embodiments 1120-1121, wherein the nucleotide is in the VL Domain.

1126. The TREM or TREM fragment of any of embodiments 1120-1121, wherein the nucleotide is in the TH Domain.

1127. The TREM or TREM fragment of any of embodiments 1120-1121, wherein the nucleotide is in the ASt Domain2.

1128. The TREM or TREM fragment of any of embodiments 1120-1121, wherein the nucleotide is in a linker domain (e.g., [L1], [L2], [L3], or [L4]).

1129. The TREM or TREM fragment of any of embodiments 1120-1128, wherein the nucleotide corresponding to any one of nucleotides 1, 4, 14, 15, 16, 17, 20, 29, 44, 45, 47, 49, 50, 52, 54, 56, 57, 59, 65, 72, and 73 of SEQ ID NO: 622 and lacks a 2'-MOE nucleotide.

1130. The TREM or TREM fragment of any of embodiment 1000-1129, comprising a modified backbone, e.g., a modification of the phosphate moiety attached to the 5' or 3' carbon of the sugar moiety of a nucleotide.

1131. The TREM or TREM fragment of embodiment 1130, wherein the phosphate moiety attached to the 5' carbon is modified.

1132. The TREM or TREM fragment of embodiment 1130, wherein the phosphapte moiety attached to the 3' carbon is modified.

1133. The TREM or TREM fragment of embodiment 1130, wherein the modification comprises a phosphothioate moiety.

1134. The TREM or TREM fragment of embodiments 1130-1133, wherein the nucleotide corresponds to any of nucleotides 1-76 of SEQ ID NO: 622 is modified.

1135. The TREM or TREM fragment of embodiments 1130-1133, wherein the modified nucleotide is in the ASt Domain1.

1136. The TREM or TREM fragment of embodiments 1130-1133, wherein the modified nucleotide is in the DH Domain.

1137. The TREM or TREM fragment of embodiments 1130-1133, wherein the modified nucleotide is in the ACH Domain.

1138. The TREM or TREM fragment of embodiments 1130-1133, wherein the modified nucleotide is in the VL Domain.

1139. The TREM or TREM fragment of embodiments 1130-1133, wherein the modified nucleotide is in the TH Domain.

1140. The TREM or TREM fragment of embodiments 1130-1133, wherein the modified nucleotide is in the ASt Domain2.

1141. The TREM or TREM fragment of any of embodiments 1130-1133, wherein the nucleotide is in a linker domain (e.g., [L1], [L2], [L3], or [L4]).

1142. The TREM or TREM fragment of embodiments 1130-1133, wherein the nucleotide corresponding to any one of nucleotides 1, 2, 3, 9, 14, 15, 16, 17, 18, 19, 20, 21, 35, 37, 38, 44, 45, 46, 52, 54, 55, 56, 57, 58, 73, and 74 of SEQ ID NO: 622 is backbone modified, e.g., with a phosphorothioate moiety.

1142. The TREM or TREM fragment of embodiments 1130-1141, wherein the nucleotide corresponding to any one of nucleotides 14, 15, 16, 17, 18, 20, 44, 45, 47, 54, 56, 57, and 59 of SEQ ID NO: 622 is backbone modified, e.g., with a phosphorothioate moiety.

1143. The TREM or TREM fragment of embodiments 1000-1142, lacking a backbone modification, e.g., a phosphorothioate moiety.

1144. The TREM or TREM fragment of embodiment 1143, wherein the nucleotide which is not backbone modified corresponds to any of nucleotides 1-76 of SEQ ID NO: 622.

1145. The TREM or TREM fragment of embodiment 1143, wherein the nucleotide which is not backbone modified is in the ASt Domain1.

1146. The TREM or TREM fragment of embodiment 1143, wherein the nucleotide which is not backbone modified is in the DH Domain.

1147. The TREM or TREM fragment of embodiment 1143, wherein the nucleotide which is not backbone modified is in the ACH Domain.

1148. The TREM or TREM fragment of embodiment 1143, wherein the nucleotide which is not backbone modified is in the VL Domain.

1149. The TREM or TREM fragment of embodiment 1143, wherein the nucleotide which is not backbone modified is in the TH Domain.

1150. The TREM or TREM fragment of embodiment 1143, wherein the nucleotide which is not backbone modified is in the ASt Domain2.

1151. The TREM or TREM fragment of embodiment 1143, wherein the nucleotide which is not backbone modified is in a linker domain (e.g., [L1], [L2], [L3], or [L4]).

1152. The TREM or TREM fragment of any of embodiments 1000-1151, wherein the nucleotide corresponding to any one of nucleotides 1, 2, 3, 9, 14, 15, 16, 17, 18, 19, 20, 21, 35, 37, 38, 44, 45, 46, 52, 54, 55, 56, 57, 58, 73, and 74 of SEQ ID NO: 622 is not backbone modified.

1153. The TREM or TREM fragment of any of embodiments 1000-1152, wherein a position corresponding to a modified position having a value of 3 for the 100 nm for the sequence in Table 15 is modified with a 2'-O Me.

1154. The TREM or TREM fragment of any of embodiments 1000-1152, wherein a position corresponding to a modified position having a value of 2 for the 100 nm for the sequence in Table 15 is modified with a 2'-O Me.

1155. The TREM or TREM fragment of any of embodiments 1000-1152, wherein a position corresponding to a modified position having a value of 1 for the 100 nm for the sequence in Table 15 is modified with a 2'-O Me.

1156. The TREM or TREM fragment of any of embodiments 1000-1152, wherein a position corresponding to a modified position having a value of 3 for the 100 nm for the sequence in Table 15 is not modified.

1157. The TREM or TREM fragment of any of embodiments 1000-1152, wherein a position corresponding to a modified position having a value of 2 for the 100 nm for the sequence in Table 15 is not modified.

1158. The TREM or TREM fragment of any of embodiments 1000-1152, wherein a position corresponding to a modified position having a value of 1 for the 100 nm for the sequence in Table 15 is not modified.

1159. The TREM or TREM fragment of any of embodiments 1000-1152, wherein a position corresponding to a modified position having a value of 3 for the 100 nm for the sequence in Table 21 is modified with a 2'-O Me.

1160. The TREM or TREM fragment of any of embodiments 1000-1152, wherein a position corresponding to a modified position having a value of 2 for the 100 nm for the sequence in Table 21 is modified with a 2'-O Me.

1161. The TREM or TREM fragment of any of embodiments 1000-1152, wherein a position corresponding to a modified position having a value of 1 for the 100 nm for the sequence in Table 21 is modified with a 2'-O Me.

1162. The TREM or TREM fragment of any of embodiments 1000-1152, wherein a position corresponding to a modified position having a value of 3 for the 100 nm for the sequence in Table 21 is not modified.

1163. The TREM or TREM fragment of any of embodiments 1000-1152, wherein a position corresponding to a modified position having a value of 2 for the 100 nm for the sequence in Table 21 is not modified.

1164. The TREM or TREM fragment of any of embodiments 1000-1152, wherein a position corresponding to a modified position having a value of 1 for the 100 nm for the sequence in Table 21 is not modified.

1165. The TREM or TREM fragment of any of embodiments 1000-1152, wherein a position corresponding to a modified position having a value of 3 for the 100 nm for the sequence in Table 22 is modified with a 2'-O Me.

1166. The TREM or TREM fragment of any of embodiments 1000-1152, wherein a position corresponding to a modified position having a value of 2 for the 100 nm for the sequence in Table 22 is modified with a 2'-O Me.

1167. The TREM or TREM fragment of any of embodiments 1000-1152, wherein a position corresponding to a modified position having a value of 1 for the 100 nm for the sequence in Table 22 is modified with a 2'-O Me.

1168. The TREM or TREM fragment of any of embodiments 1000-1152, wherein a position corresponding to a modified position having a value of 3 for the 100 nm for the sequence in Table 22 is not modified.

1169. The TREM or TREM fragment of any of embodiments 1000-1152, wherein a position corresponding to a modified position having a value of 2 for the 100 nm for the sequence in Table 22 is not modified.

1170. The TREM or TREM fragment of any of embodiments 1000-1152, wherein a position corresponding to a modified position having a value of 1 for the 100 nm for the sequence in Table 22 is not modified.

1171 The TREM or TREM fragment of any of embodiments 1000-1152, wherein a position corresponding to a modified position having a value of 3 for the 100 nm for the sequence in Table 17 is modified with a 2'-MOE.

1172. The TREM or TREM fragment of any of embodiments 1000-1152, wherein a position corresponding to a modified position having a value of 2 for the 100 nm for the sequence in Table 17 is modified with a 2'-MOE.

1173. The TREM or TREM fragment of any of embodiments 1000-1152, wherein a position corresponding to a modified position having a value of 1 for the 100 nm for the sequence in Table 17 is modified with a 2'-MOE.

1174. The TREM or TREM fragment of any of embodiments 1000-1152, wherein a position corresponding to a modified position having a value of 3 for the 100 nm for the sequence in Table 17 is not modified.

1175. The TREM or TREM fragment of any of embodiments 1000-1152, wherein a position corresponding to a modified position having a value of 2 for the 100 nm for the sequence in Table 17 is not modified.

1176. The TREM or TREM fragment of any of embodiments 1000-1152, wherein a position corresponding to a modified position having a value of 1 for the 100 nm for the sequence in Table 17 is not modified.

1177. The TREM or TREM fragment of any of embodiments 1000-1152, wherein a position corresponding to a modified position having a value of 3 for the 100 nm for the sequence in Table 16 is modified with a 2'-fluoro.

1178. The TREM or TREM fragment of any of embodiments 1000-1152, wherein a position corresponding to a modified position having a value of 2 for the 100 nm for the sequence in Table 16 is modified with a 2'-fluoro.

1179. The TREM or TREM fragment of any of embodiments 1000-1152, wherein a position corresponding to a modified position having a value of 1 for the 100 nm for the sequence in Table 16 is modified with a 2'-fluoro.

1180. The TREM or TREM fragment of any of embodiments 1000-1152, wherein a position corresponding to a modified position having a value of 3 for the 100 nm for the sequence in Table 16 is not modified.

1181. The TREM or TREM fragment of any of embodiments 1000-1152, wherein a position corresponding to a modified position having a value of 2 for the 100 nm for the sequence in Table 16 is not modified.

1182. The TREM or TREM fragment of any of embodiments 1000-1152, wherein a position corresponding to a modified position having a value of 1 for the 100 nm for the sequence in Table 16 is not modified.

1183. The TREM or TREM fragment of any of embodiments 1000-1152, wherein a position corresponding to a modified position having a value of 3 for the 100 nm for the sequence in Table 18 is modified to be a 2'-deoxy.

1184. The TREM or TREM fragment of any of embodiments 1000-1152, wherein a position corresponding to a modified position having a value of 2 for the 100 nm for the sequence in Table 18 is modified to be a 2'-deoxy.

1185. The TREM or TREM fragment of any of embodiments 1000-1152, wherein a position corresponding to a modified position having a value of 1 for the 100 nm for the sequence in Table 18 is modified to be a 2'-deoxy.

1186. The TREM or TREM fragment of any of embodiments 1000-1152, wherein a position corresponding to a modified position having a value of 3 for the 100 nm for the sequence in Table 18 is not modified.

1187. The TREM or TREM fragment of any of embodiments 1000-1152, wherein a position corresponding to a modified position having a value of 2 for the 100 nm for the sequence in Table 18 is not modified.

1188. The TREM or TREM fragment of any of embodiments 1000-1152, wherein a position corresponding to a modified position having a value of 1 for the 100 nm for the sequence in Table 18 is not modified.

1189. The TREM or TREM fragment of any of embodiments 1000-1152, wherein a position corresponding to a modified position having a value of 3 for the 100 nm for the sequence in Table 19 comprises a phosphorothate.

1190. The TREM or TREM fragment of any of embodiments 1000-1152, wherein a position corresponding to a modified position having a value of 2 for the 100 nm for the sequence in Table 19 comprises a phosphorothate.

1191. The TREM or TREM fragment of any of embodiments 1000-1152, wherein a position corresponding to a modified position having a value of 1 for the 100 nm for the sequence in Table 19 comprises a phosphorothate.

1192. The TREM or TREM fragment of any of embodiments 1000-1152, wherein a position corresponding to a modified position having a value of 3 for the 100 nm for the sequence in Table 19 is not modified.

1193. The TREM or TREM fragment of any of embodiments 1000-1152, wherein a position corresponding to a modified position having a value of 2 for the 100 nm for the sequence in Table 19 is not modified.

1194. The TREM or TREM fragment of any of embodiments 1000-1152, wherein a position corresponding to a modified position having a value of 1 for the 100 nm for the sequence in Table 19 is not modified.

1195. The TREM or TREM fragment of any of embodiments 1000-1152, wherein the TREM comprises an anticodon specific for an amino acid from Table 1.

1196. The TREM or TREM fragment of any of embodiments 1000-1152, wherein the TREM comprises an anticodon of Table 1.

1197. The TREM or TREM fragment of any of embodiments 1000-1196, comprising a first and a second non-naturally occurring modification.

1198. The TREM or TREM fragment of embodiment 1197, comprising comprising a third non-naturally occurring modification.

1199. The or TREM fragment of any of embodiments 1197-1198, comprising, wherein the first and second non-naturally occurring modifications are the same non-naturally occurring modification.

1200. The TREM or TREM fragment of any of embodiments 1197-1198, comprising wherein the first and second non-naturally occurring modifications are different non-naturally occurring modifications.

1201. The TREM or TREM fragment of any of embodiments 1197-1198, comprising wherein the first and second non-naturally occurring modification are on the same nucleotide.

1202. The TREM or TREM fragment of any of embodiments 1197-1198, wherein the first and second non-naturally occurring modification are on the different nucleotides.

1203. The TREM or TREM fragment of any of embodiments 1197-1198, wherein the first and second non-naturally occurring modifications are in the same domain.

1204. The TREM or TREM fragment of any of embodiments 1197-1198, wherein the first and second non-naturally occurring modifications are in different domains.

1205. The TREM or TREM fragment of any one the preceding embodiments, wherein the domain comprising the non-naturally occurring modification has a function, e.g., a domain function described herein.

1206. The TREM or TREM fragment of any of the preceding embodiments, wherein the TREM has at least X % sequence sequence identity with a sequence described herein, e.g., with SEQ ID NO: 622, SEQ ID NO: 993, or SEQ ID NO: 1079, or a consensus sequence disclosed herein, e.g., from Table 9 or 10, wherein X-60, 70, 75, 80, 85, 90, or 95.

1207. The TREM or TREM fragment of embodiment 1206, wherein X=60.

1208. The TREM or TREM fragment of embodiment 1206, wherein X=70.

1209. The TREM or TREM fragment of embodiment 1206, wherein X=75.

1210. The TREM or TREM fragment of embodiment 1206, wherein X=80.

1211. The TREM or TREM fragment of embodiment 1206, wherein X=85.

1212. The TREM or TREM fragment of embodiment 1206, wherein X=90.

1213. The TREM or TREM fragment of embodiment 1206, wherein X=95.

1214. The TREM or TREM fragment of any of embodiments 1001-1213, having a modified nucleotide at a position corresponding to a position that is modified in a row of any of Tables 15-22.

1215. The TREM or TREM fragment of any of embodiments 1001-1213, having a modified nucleotide at a position corresponding to a position that is modified in a row of Table 15.

1216. The TREM or TREM fragment of any of embodiments 1001-1213, having a modified nucleotide at a position corresponding to a position that is modified in a row of Table 16.

1217. The TREM or TREM fragment of any of embodiments 1001-1213, having a modified nucleotide at a position corresponding to a position that is modified in a row of Table 17.

1218. The TREM or TREM fragment of any of embodiments 1001-1213, having a modified nucleotide at a position corresponding to a position that is modified in a row of Table 18.

1219. The TREM or TREM fragment of any of embodiments 1001-1213, having a modified nucleotide at a position corresponding to a position that is modified in a row of Table 19.

1220. The TREM or TREM fragment of any of embodiments 1001-1213, having a modified nucleotide at a position corresponding to a position that is modified in a row of Table 20.

1221. The TREM or TREM fragment of any of embodiments 1001-1213, having a modified nucleotide at a position corresponding to a position that is modified in a row of Table 21.

1222. The TREM or TREM fragment of any of embodiments 1001-1213, having a modified nucleotide at a position corresponding to a position that is modified in a row of Table 22.

1223. The TREM or TREM fragment of any of embodiments 1001-1213, having a modified nucleotide at a first and a modified nucleotide at a second position, wherein the first and second positions correspond to positions that are modified in any one row of Table 22.

1224. A pharmaceutical composition comprising a TREM or TREM fragment of any of the preceding embodiments.

1225. The pharmaceutical composition of embodiment 1224, comprising a pharmaceutically acceptable component, e.g., an excipient.

1226. A lipid nanoparticle formulation comprising a TREM or TREM fragment of any one of embodiments 1000-1213, or a pharmaceutical composition of any one of claims 1224-1225.

1227. A method of making a TREM or TREM fragment of any of embodiments 1000-1213, comprising linking a first nucleotide to a second nucleotide to form the TREM or TREM fragment.

1228. The method of embodiment 1227, wherein the TREM or TREM fragment is non-naturally occurring (e.g., synthetic).

1229. The method of embodiment 1227, wherein the synthesis is performed in vitro.

1230. The method of embodiment 1227, wherein the TREM or TREM fragment is made by cell-free solid phase synthesis.

1231. A cell comprising a TREM or TREM fragment of any of embodiments 1000-1213.

1232. A method of modulating a tRNA pool in a cell comprising:

providing a TREM or TREM fragment of any of embodiments 1000-1213, and contacting the cell with the TREM, thereby modulating the tRNA pool in the cell.

1233. A method of contacting a cell, tissue, or subject with a TREM or TREM fragment of any of embodiments 1000-1213, comprising contacting the cell, tissue or subject with the TREM, thereby contacting the cell, tissue, or subject with the TREM.

1234. A method of presenting a TREM or TREM fragment, to a cell, tissue, or subject, comprising contacting the cell, tissue or subject with a TREM or TREM fragment of any of embodiments 1000-1213, thereby presenting the TREM, TREM core fragment or TREM fragment to a cell, tissue, or subject.

1235. A method of forming a TREM-contacted cell, tissue, or subject, comprising:

contacting the cell, tissue or subject with a TREM or TREM fragment of any of embodiments 1000-1213, thereby forming a TREM-contacted cell, tissue, or subject.

1236. A method of using a TREM comprising, contacting a cell, tissue or subject with a TREM or TREM fragment of any of embodiments 1000-1213, thereby using the TREM.

1237. A method of applying a TREM to a cell, tissue, or subject, comprising contacting the cell, tissue or subject with a TREM or TREM fragment of any of embodiments 1000-1213, thereby applying a TREM to a cell, tissue, or subject.

1238. A method of exposing a cell, tissue, or subject to a TREM, comprising contacting the cell, tissue or subject with a TREM or TREM fragment of any of embodiments 1000-1213, thereby exposing a cell, tissue, or subject to a TREM.

1239. A method of forming an admixture of a TREM, and a cell, tissue, or subject, comprising contacting the cell, tissue or subject with a TREM or TREM fragment of any of embodiments 1000-1213, thereby forming an admixture of a TREM and a cell, tissue, or subject.

1240. A method of delivering a TREM to a cell, tissue, or subject, comprising:

providing a cell, tissue, or subject, and contacting the cell, tissue, or subject, a TREM or TREM fragment of any of embodiments 1000-1213.

1241. A method, e.g., an ex vivo method, of modulating the metabolism, e.g., the translational capacity of an organelle, comprising:

providing a preparation of an organelle, e.g., mitochondria or chloroplasts, and contacting the organelle with a TREM or TREM fragment of any of embodiments 1000-1213.

1242. A method of treating a subject, e.g., modulating the metabolism, e.g., the translational capacity of a cell, in a subject, comprising:

providing, e.g., administering to the subject a TREM or TREM fragment of any of embodiments 1000-1213, thereby treating the subject.

1243. A method of modulating a tRNA pool in a cell comprising an endogenous open reading frame (ORF), which ORF comprises a codon having a first sequence, comprising:

optionally, acquiring knowledge of the abundance of one or both of (i) and (ii), e.g., acquiring knowledge of the relative amounts of: (i) and (ii) in the cell, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the cell;

contacting the cell with a TREM or TREM fragment of any of embodiments 1000-1213, wherein the TREM has an anticodon that pairs with: the codon having the first sequence; or the codon other than the codon having the first sequence, in an amount and/or for a time sufficient to modulate the relative amounts of the first tRNA moiety and the second tRNA moiety in the cell, thereby modulating the tRNA pool in the cell.

1244. A method of modulating a tRNA pool in a subject having an endogenous open reading frame (ORF), which ORF comprises a codon having a first sequence, comprising:

optionally, acquiring knowledge of the abundance of one or both of (i) and (ii), e.g., acquiring knowledge of the relative amounts of: (i) and (ii) in the subject, wherein (i) is a tRNA moiety having an anticodon that pairs with the codon of the ORF having a first sequence (the first tRNA moiety) and (ii) is an isoacceptor tRNA moiety having an anticodon that pairs with a codon other than the codon having the first sequence (the second tRNA moiety) in the subject;

contacting the subject with a TREM or TREM fragment of any of embodiments 1000-1213, wherein the TREM has an anticodon that pairs with: the codon having the first sequence; or the codon other than the codon having the first sequence, in an amount and/or for a time sufficient to modulate the relative amounts of the first tRNA moiety and the second tRNA moiety in the subject, thereby modulating the tRNA pool in the subject.

1245. A method of modulating a tRNA pool in a subject having an endogenous open reading frame (ORF) comprising a codon comprising a synonymous mutation (a synonymous mutation codon or SMC), comprising:

providing a composition comprising a TREM or TREM fragment of any of embodiments 1000-1213, wherein the TREM comprises an isoacceptor tRNA moiety comprising an anticodon sequence that pairs with the SMC (the TREM);

contacting the subject with the composition in an amount and/or for a time sufficient to modulate the tRNA pool in the subject, thereby modulating the tRNA pool in the subject.

1246. A method of modulating a tRNA pool in a cell comprising an endogenous open reading frame (ORF) comprising a codon comprising a synonymous mutation (a synonymous mutation codon or SMC), comprising:

providing a composition comprising a TREM or TREM fragment of any of embodiments 1000-1213, wherein the TREM comprises an isoacceptor tRNA moiety comprising an anticodon sequence that pairs with the SMC (the TREM);

contacting the cell with the composition comprising a TREM in an amount and/or for a time sufficient to modulate the tRNA pool in the cell, thereby modulating the tRNA pool in the cell.

1247. A method of modulating expression of a protein in a cell, wherein the protein is encoded by a nucleic acid comprising an endogenous open reading frame (ORF), which ORF comprises a codon having a mutation, comprising:

contacting the cell with a composition comprising a TREM or TREM fragment of any of embodiments 1000-1213, in an amount and/or for a time sufficient to modulate expression of the encoded protein, wherein the TREM has an anticodon that pairs with the codon having the mutation, thereby modulating expression of the protein in the cell.

1248. A method of modulating expression of a protein in a subject, wherein the protein is encoded by a nucleic acid comprising an endogenous open reading frame (ORF), which ORF comprises a codon having a mutation, comprising:

contacting the subject with a composition comprising a TREM or TREM fragment of any of embodiments 1000-1213, in an amount and/or for a time sufficient to modulate expression of the encoded protein, wherein the TREM has an anticodon that pairs with the codon having the mutation, thereby modulating expression of the protein in the subject.

1249. The method of embodiment 1247 or 1248, wherein the mutation in the ORF is a nonsense mutation, e.g., resulting in a premature stop codon chosen from UAA, UGA or UAG.

1250. The method of embodiment 1247 or 1248, wherein the TREM comprises an anticodon that pairs with a stop codon.

Other features, objects, and advantages of the invention will be apparent from the description and from the claims.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

DETAILED DESCRIPTION OF CERTAIN EMBODIMENTS

The present disclosure features tRNA-based effector molecules (TREMs) comprising a non-naturally occurring modification and methods relating thereto. As disclosed herein, TREMs are complex molecules which can mediate a variety of cellular processes. Pharmaceutical TREM compositions, e.g., TREMs comprising a non-naturally occurring modification, can be administered to a cell, a tissue, or to a subject to modulate these functions.

Definitions

A "nucleotide," as that term is used herein, refers to an entity comprising a sugar, typically a pentameric sugar; a nucleobase; and a phosphate linking group. In an embodiment, a nucleotide comprises a naturally occurring, e.g., naturally occurring in a human cell, nucleotide, e.g., an adenine, thymine, guanine, cytosine, or uracil nucleotide.

A "modification," as that term is used herein with reference to a nucleotide, refers to a modification of the chemical structure, e.g., a covalent modification, of the subject nucleotide. The modification can be naturally occurring or non-naturally occurring. In an embodiment, the modification is non-naturally occurring. In an embodiment, the modification is naturally occurring. In an embodiment, the modification is a synthetic modification. In an embodiment, the modification is a modification provided in Tables 5, 6, 7, 8 or 9.

A "non-naturally occurring modification," as that term is used herein with reference to a nucleotide, refers to a modification that: (a) a cell, e.g., a human cell, does not make on an endogenous tRNA; or (b) a cell, e.g., a human cell, can make on an endogenous tRNA but wherein such modification is in a location in which it does not occur on a native tRNA, e.g., the modification is in a domain, linker or arm, or on a nucleotide and/or at a position within a domain, linker or arm, which does not have such modification in nature. In either case, the modification is added synthetically, e.g., in a cell free reaction, e.g., in a solid state or liquid phase synthetic reaction. In an embodiment, the non-naturally occurring modification is a modification that is not present (in identity, location or position) if a sequence of the TREM is expressed in a mammalian cell, e.g., a HEK293 cell line. Exemplary non-naturally occurring modifications are found in Tables 5, 6, 7, 8 or 9.

A "non-naturally modified nucleotide," as that term is used herein, refers a nucleotide comprising a non-naturally occurring modification on or of a sugar, nucleobase, or phosphate moiety.

A "naturally occurring nucleotide," as that term is used herein, refers to a nucleotide that does not comprise a non-naturally occurring modification. In an embodiment, it includes a naturally occurring modification.

A "tRNA-based effector molecule" or "TREM," as that term is used herein, refers to an RNA molecule comprising a structure or property from (a)-(v) below, and which is a recombinant TREM, a synthetic TREM, or a TREM expressed from a heterologous cell. The TREMs described in the present invention are synthetic molecules and are made, e.g., in a cell free reaction, e.g., in a solid state or liquid phase synthetic reaction. TREMs are chemically distinct, e.g., in terms of primary sequence, type or location of modifications from the endogenous tRNA molecules made in cells, e.g., in mammalian cells, e.g., in human cells. A TREM can have a plurality (e.g., 2, 3, 4, 5, 6, 7, 8, 9) of the structures and functions of (a)-(v).

In an embodiment, a TREM is non-native, as evaluated by structure or the way in which it was made.

In an embodiment, a TREM comprises one or more of the following structures or properties:

(a') an optional linker region of a consensus sequence provided in the "Consensus Sequence" section, e.g., a Linker 1 region;

(a) an amino acid attachment domain that binds an amino acid, e.g., an acceptor stem domain (AStD), wherein an AStD comprises sufficient RNA sequence to mediate, e.g., when present in an otherwise wildtype tRNA, acceptance of an amino acid, e.g., its cognate amino acid or a non-cognate amino acid, and transfer of the amino acid (AA) in the initiation or elongation of a polypeptide chain. Typically, the AStD comprises a 3'-end adenosine (CCA) for acceptor stem charging which is part of synthetase recognition. In an embodiment the AStD has at least 75, 80, 85, 85, 90, 95, or 100% identity with a naturally occurring AStD, e.g., an AStD encoded by a nucleic acid in Table 1. In an embodiment, the TREM can comprise a fragment or analog of an AStD, e.g., an AStD encoded by a nucleic acid in Table 1, which fragment in embodiments has AStD activity and in other embodiments does not have AStD activity. (One of ordinary skill can determine the relevant corresponding sequence for any of the domains, stems, loops, or other sequence features mentioned herein from a sequence encoded by a nucleic acid in Table 1. E.g., one of ordinary skill can determine the sequence which corresponds to an AStD from a tRNA sequence encoded by a nucleic acid in Table 1.)

In an embodiment the AStD falls under the corresponding sequence of a consensus sequence provided in the "Consensus Sequence" section, or differs from the consensus sequence by no more than 1, 2, 5, or 10 positions;

In an embodiment, the AStD comprises residues $R_1$-$R_2$-$R_3$-$R_4$-$R_5$-$R_6$-$R_7$ and residues $R_{65}$-$R_{66}$-$R_{67}$-$R_{68}$-$R_{69}$-$R_{70}$-$R_{71}$ of Formula $I_{ZZZ}$, wherein ZZZ indicates any of the twenty amino acids;

In an embodiment, the AStD comprises residues $R_1$-$R_2$-$R_3$-$R_4$-$R_5$-$R_6$-$R_7$ and residues $R_{65}$-$R_{66}$-$R_{67}$-$R_{68}$-$R_{69}$-$R_{70}$-$R_{71}$ of Formula $II_{ZZZ}$, wherein ZZZ indicates any of the twenty amino acids;

In an embodiment, the AStD comprises residues $R_1$-$R_2$-$R_3$-$R_4$-$R_5$-$R_6$-$R_7$ and residues $R_{65}$-$R_{66}$-$R_{67}$-$R_{68}$-$R_{69}$-$R_{70}$-$R_{71}$ of Formula $III_{ZZZ}$, wherein ZZZ indicates any of the twenty amino acids;

(a'-1) a linker comprising residues $R_8$-$R_9$ of a consensus sequence provided in the "Consensus Sequence" section, e.g., a Linker 2 region;

(b) a dihydrouridine hairpin domain (DHD), wherein a DHD comprises sufficient RNA sequence to mediate, e.g., when present in an otherwise wildtype tRNA, recognition of aminoacyl-tRNA synthetase, e.g., acts as a recognition site for aminoacyl-tRNA synthetase for amino acid charging of the TREM. In embodiments, a DHD mediates the stabilization of the TREM's tertiary structure. In an embodiment the DHD has at least 75, 80, 85, 85, 90, 95, or 100% identity with a naturally occurring DHD, e.g., a DHD encoded by a nucleic acid in Table 1. In an embodiment, the TREM can comprise a fragment or analog of a DHD, e.g., a DHD encoded by a nucleic acid in Table 1, which fragment in embodiments has DHD activity and in other embodiments does not have DHD activity.

In an embodiment the DHD falls under the corresponding sequence of a consensus sequence provided in the "Consensus Sequence" section, or differs from the consensus sequence by no more than 1, 2, 5, or 10 positions;

In an embodiment, the DHD comprises residues $R_{10}$-$R_{11}$-$R_{12}$-$R_{13}$-$R_{14}$ $R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$ of Formula $I_{ZZZ}$, wherein ZZZ indicates any of the twenty amino acids;

In an embodiment, the DHD comprises residues $R_{10}$-$R_{11}$-$R_{12}$-$R_{13}$-$R_{14}$ $R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$ of Formula $II_{ZZZ}$, wherein ZZZ indicates any of the twenty amino acids;

In an embodiment, the DHD comprises residues $R_{10}$-$R_{11}$-$R_{12}$-$R_{13}$-$R_{14}$ $R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$ of Formula $III_{ZZZ}$, wherein ZZZ indicates any of the twenty amino acids;

(b'-1) a linker comprising residue $R_{29}$ of a consensus sequence provided in the "Consensus Sequence" section, e.g., a Linker 3 region;

(c) an anticodon that binds a respective codon in an mRNA, e.g., an anticodon hairpin domain (ACHD), wherein an ACHD comprises sufficient sequence, e.g., an anticodon triplet, to mediate, e.g., when present in an otherwise wildtype tRNA, pairing (with or without wobble) with a codon; In an embodiment the ACHD has at least 75, 80, 85, 85, 90, 95, or 100% identity with a naturally occurring ACHD, e.g., an ACHD encoded by a nucleic acid in Table 1. In an embodiment, the TREM can comprise a fragment or analog of an ACHD, e.g., an ACHD encoded by a nucleic acid in Table 1, which fragment in embodiments has ACHD activity and in other embodiments does not have ACHD activity.

In an embodiment the ACHD falls under the corresponding sequence of a consensus sequence provided in the "Consensus Sequence" section, or differs from the consensus sequence by no more than 1, 2, 5, or 10 positions;

In an embodiment, the ACHD comprises residues-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$ of Formula $I_{ZZZ}$, wherein ZZZ indicates any of the twenty amino acids;

In an embodiment, the ACHD comprises residues-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$ of Formula $II_{ZZZ}$, wherein ZZZ indicates any of the twenty amino acids;

In an embodiment, the ACHD comprises residues-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$ of Formula $III_{ZZZ}$, wherein ZZZ indicates any of the twenty amino acids;

(d) a variable loop domain (VLD), wherein a VLD comprises sufficient RNA sequence to mediate, e.g., when present in an otherwise wildtype tRNA, recognition of aminoacyl-tRNA synthetase, e.g., acts as a recognition site for aminoacyl-tRNA synthetase for amino acid charging of the TREM. In embodiments, a VLD mediates the stabilization of the TREM's tertiary structure. In an embodiment, a VLD modulates, e.g., increases, the specificity of the TREM, e.g., for its cognate amino acid, e.g., the VLD modulates the TREM's cognate adaptor function. In an embodiment the VLD has at least 75, 80, 85, 85, 90, 95, or 100% identity with a naturally occurring VLD, e.g., a VLD encoded by a nucleic acid in Table 1. In an embodiment, the TREM can comprise a fragment or analog of a VLD, e.g., a VLD encoded by a nucleic acid in Table 1, which fragment in embodiments has VLD activity and in other embodiments does not have VLD activity.

In an embodiment the VLD falls under the corresponding sequence of a consensus sequence provided in the "Consensus Sequence" section.

In an embodiment, the VLD comprises residue-$[R_{47}]_x$ of a consensus sequence provided in the "Consensus Sequence" section, wherein x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271);

(e) a thymine hairpin domain (THD), wherein a THD comprises sufficient RNA sequence, to mediate, e.g., when present in an otherwise wildtype tRNA, recognition of the ribosome, e.g., acts as a recognition site for the ribosome to form a TREM-ribosome complex during translation. In an embodiment the THD has at least 75, 80, 85, 85, 90, 95, or 100% identity with a naturally occurring THD, e.g., a THD encoded by a nucleic acid in Table 1. In an embodiment, the TREM can comprise a fragment or analog of a THD, e.g., a THD encoded by a nucleic acid in Table 1, which fragment in embodiments has THD activity and in other embodiments does not have THD activity.

In an embodiment the THD falls under the corresponding sequence of a consensus sequence provided in the "Consensus Sequence" section, or differs from the consensus sequence by no more than 1, 2, 5, or 10 positions;

In an embodiment, the THD comprises residues-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$ of Formula $I_{ZZZ}$, wherein ZZZ indicates any of the twenty amino acids;

In an embodiment, the THD comprises residues-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$ of Formula $II_{ZZZ}$, wherein ZZZ indicates any of the twenty amino acids;

In an embodiment, the THD comprises residues-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$ of Formula $III_{ZZZ}$, wherein ZZZ indicates any of the twenty amino acids;

(e'1) a linker comprising residue $R_{72}$ of a consensus sequence provided in the "Consensus Sequence" section, e.g., a Linker 4 region;

(f) under physiological conditions, it comprises a stem structure and one or a plurality of loop structures, e.g., 1, 2, or 3 loops. A loop can comprise a domain described herein, e.g., a domain selected from (a)-(e). A loop can comprise one or a plurality of domains. In an embodiment, a stem or loop structure has at least 75, 80, 85, 85, 90, 95, or 100% identity with a naturally occurring stem or loop structure, e.g., a stem or loop structure encoded by a nucleic acid in Table 1. In an embodiment, the TREM can comprise a fragment or analog of a stem or loop structure, e.g., a stem or loop structure encoded by a nucleic acid in Table 1, which fragment in embodiments has activity of a stem or loop structure, and in other embodiments does not have activity of a stem or loop structure;

(g) a tertiary structure, e.g., an L-shaped tertiary structure;

(h) adaptor function, i.e., the TREM mediates acceptance of an amino acid, e.g., its cognate amino acid and transfer of the AA in the initiation or elongation of a polypeptide chain;

(i) cognate adaptor function wherein the TREM mediates acceptance and incorporation of an amino acid (e.g., cognate amino acid) associated in nature with the anti-codon of the TREM to initiate or elongate a polypeptide chain;

(j) non-cognate adaptor function, wherein the TREM mediates acceptance and incorporation of an amino acid (e.g., non-cognate amino acid) other than the amino acid associated in nature with the anti-codon of the TREM in the initiation or elongation of a polypeptide chain;

(k) a regulatory function, e.g., an epigenetic function (e.g., gene silencing function or signaling pathway modulation function), cell fate modulation function, mRNA stability modulation function, protein stability modulation function, protein transduction modulation function, or protein compartmentalization function;

(l) a structure which allows for ribosome binding;

(m) a post-transcriptional modification, e.g., a naturally occurring post-trasncriptional modification;

(n) the ability to inhibit a functional property of a tRNA, e.g., any of properties (h)-(k) possessed by a tRNA;

(o) the ability to modulate cell fate;

(p) the ability to modulate ribosome occupancy;

(q) the ability to modulate protein translation;

(r) the ability to modulate mRNA stability;

(s) the ability to modulate protein folding and structure;

(t) the ability to modulate protein transduction or compartmentalization;

(u) the ability to modulate protein stability; or (v) the ability to modulate a signaling pathway, e.g., a cellular signaling pathway.

In an embodiment, a TREM comprises a full-length tRNA molecule or a fragment thereof.

In an embodiment, a TREM comprises the following properties: (a)-(e).

In an embodiment, a TREM comprises the following properties: (a) and (c).

In an embodiment, a TREM comprises the following properties: (a), (c) and (h).

In an embodiment, a TREM comprises the following properties: (a), (c), (h) and (b).

In an embodiment, a TREM comprises the following properties: (a), (c), (h) and (e).

In an embodiment, a TREM comprises the following properties: (a), (c), (h), (b) and (e).

In an embodiment, a TREM comprises the following properties: (a), (c), (h), (b), (e) and (g).

In an embodiment, a TREM comprises the following properties: (a), (c), (h) and (m).

In an embodiment, a TREM comprises the following properties: (a), (c), (h), (m), and (g).

In an embodiment, a TREM comprises the following properties: (a), (c), (h), (m) and (b).

In an embodiment, a TREM comprises the following properties: (a), (c), (h), (m) and (e).

In an embodiment, a TREM comprises the following properties: (a), (c), (h), (m), (g), (b) and (e).

In an embodiment, a TREM comprises the following properties: (a), (c), (h), (m), (g), (b), (e) and (q).

In an embodiment, a TREM comprises:

(i) an amino acid attachment domain that binds an amino acid (e.g., an AStD, as described in (a) herein; and (ii) an anticodon that binds a respective codon in an mRNA (e.g., an ACHD, as described in (c) herein).

In an embodiment the TREM comprises a flexible RNA linker which provides for covalent linkage of (i) to (ii).

In an embodiment, the TREM mediates protein translation.

In an embodiment a TREM comprises a linker, e.g., an RNA linker, e.g., a flexible RNA linker, which provides for covalent linkage between a first and a second structure or domain. In an embodiment, an RNA linker comprises at least 1, 2, 3, 4, 5, 6, 7, 8, 9, 10, 11, 12, 13, 14 or 15 ribonucleotides. A TREM can comprise one or a plurality of linkers, e.g., in embodiments a TREM comprising (a), (b), (c), (d) and (c) can have a first linker between a first and second domain, and a second linker between a third domain and another domain.

In an embodiment, the TREM comprises a sequence of Formula A: [L1]-[ASt Domain1]-[L2]-[DH Domain]-[L3]-[ACH Domain]-[VL Domain]-[TH Domain]-[L4]-[ASt Domain2].

In an embodiment, a TREM comprises an RNA sequence at least 60, 65, 70, 75, 80, 85, 90, 95, 96, 97, 98 or 99% identical with, or which differs by no more than 1, 2, 3, 4, 5, 10, 15, 20, 25, or 30 ribonucleotides from, an RNA sequence encoded by a DNA sequence listed in Table 1, or a fragment or functional fragment thereof. In an embodiment, a TREM comprises an RNA sequence encoded by a DNA sequence listed in Table 1, or a fragment or functional fragment thereof. In an embodiment, a TREM comprises an RNA sequence encoded by a DNA sequence at least 60, 65, 70, 75, 80, 85, 90, 95, 96, 97, 98 or 99% identical with a DNA sequence listed in Table 1, or a fragment or functional fragment thereof. In an embodiment, a TREM comprises a TREM domain, e.g., a domain described herein, comprising at least 60, 65, 70, 75, 80, 85, 90, 95, 96, 97, 98, or 99% identical with, or which differs by no more than 1, 2, 3, 4, 5, 10, or 15, ribonucleotides from, an RNA encoded by a DNA sequence listed in Table 1, or a fragment or a functional fragment thereof. In an embodiment, a TREM comprises a TREM domain, e.g., a domain described herein, comprising an RNA sequence encoded by DNA sequence listed in Table 1, or a fragment or functional fragment thereof. In an embodiment, a TREM comprises a TREM domain, e.g., a domain described herein, comprising an RNA sequence encoded by DNA sequence at least 60, 65, 70, 75, 80, 85, 90, 95, 96, 97, 98 or 99% identical with a DNA sequence listed in Table 1, or a fragment or functional fragment thereof.

In an embodiment, a TREM is 76-90 nucleotides in length. In embodiments, a TREM or a fragment or functional fragment thereof is between 10-90 nucleotides, between 10-80 nucleotides, between 10-70 nucleotides, between 10-60 nucleotides, between 10-50 nucleotides, between 10-40 nucleotides, between 10-30 nucleotides, between 10-20 nucleotides, between 20-90 nucleotides, between 20-80 nucleotides, 20-70 nucleotides, between 20-60 nucleotides, between 20-50 nucleotides, between 20-40 nucleotides, between 30-90 nucleotides, between 30-80 nucleotides, between 30-70 nucleotides, between 30-60 nucleotides, or between 30-50 nucleotides.

In an embodiment, a TREM is aminoacylated, e.g., charged, with an amino acid by an aminoacyl tRNA synthetase.

In an embodiment, a TREM is not charged with an amino acid, e.g., an uncharged TREM (uTREM).

In an embodiment, a TREM comprises less than a full length tRNA. In embodiments, a TREM can correspond to a naturally occurring fragment of a tRNA, or to a non-naturally occurring fragment. Exemplary fragments include: TREM halves (e.g., from a cleavage in the ACHD, e.g., in the anticodon sequence, e.g., 5' halves or 3' halves); a 5' fragment (e.g., a fragment comprising the 5' end, e.g., from a cleavage in a DHD or the ACHD); a 3' fragment (e.g., a fragment comprising the 3' end, e.g., from a cleavage in the THD); or an internal fragment (e.g., from a cleavage in one or more of the ACHD, DHD or THD).

A "TREM core fragment," as that term is used herein, refers to a portion of the sequence of Formula B: $[L1]_y$-[ASt $Domain1]_x$-$[L2]_y$-[DH $Domain]_y$-$[L3]_y$-[ACH $Domain]_x$-[VL $Domain]_y$-[TH $Domain]_y$-$[L4]_y$-[ASt $Domain2]_x$, wherein: x=1 and y=0 or 1.

A "TREM fragment," as used herein, refers to a portion of a TREM, wherein the TREM comprises a sequence of Formula A: [L1]-[ASt Domain1]-[L2]-[DH Domain]-[L3]-[ACH Domain]-[VL Domain]-[TH Domain]-[L4]-[ASt Domain2].

A "cognate adaptor function TREM," as that term is used herein, refers to a TREM which mediates initiation or elongation with the AA (the cognate AA) associated in nature with the anti-codon of the TREM.

"Decreased expression," as that term is used herein, refers to a decrease in comparison to a reference, e.g., in the case where altered control region, or addition of an agent, results in a decreased expression of the subject product, it is decreased relative to an otherwise similar cell without the alteration or addition.

An "exogenous nucleic acid," as that term is used herein, refers to a nucleic acid sequence that is not present in or differs by at least one nucleotide from the closest sequence in a reference cell, e.g., a cell into which the exogenous nucleic acid is introduced. In an embodiment, an exogenous nucleic acid comprises a nucleic acid that encodes a TREM.

An "exogenous TREM," as that term is used herein, refers to a TREM that:

(a) differs by at least one nucleotide or one post transcriptional modification from the closest sequence tRNA in a reference cell, e.g., a cell into which the exogenous nucleic acid is introduced;

(b) has been introduced into a cell other than the cell in which it was transcribed;

(c) is present in a cell other than one in which it naturally occurs; or (d) has an expression profile, e.g., level or distribution, that is non-wildtype, e.g., it is expressed at a higher level than wildtype. In an embodiment, the expression profile can be mediated by a change introduced into a nucleic acid that modulates expression or by addition of an agent that modulates expression of the RNA molecule. In an embodiment an exogenous TREM comprises 1, 2, 3 or 4 of properties (a)-(d).

A "GMP-grade composition," as that term is used herein, refers to a composition in compliance with current good manufacturing practice (cGMP) guidelines, or other similar requirements. In an embodiment, a GMP-grade composition can be used as a pharmaceutical product.

As used herein, the terms "increasing" and "decreasing" refer to modulating that results in, respectively, greater or lesser amounts of function, expression, or activity of a particular metric relative to a reference. For example, subsequent to administration to a cell, tissue or subject of a TREM described herein, the amount of a marker of a metric (e.g., protein translation, mRNA stability, protein folding) as described herein may be increased or decreased by at least 5%, 10%, 15%, 20%, 25%, 30%, 35%, 40%, 45%, 50%, 55%, 60%, 65%, 70%, 75%, 80%, 85%, 90%, 95% or 98%, 2×, 3×, 5×, 10× or more relative to the amount of the marker prior to administration or relative to the effect of a negative control agent. The metric may be measured subsequent to administration at a time that the administration has had the recited effect, e.g., at least 12 hours, 24 hours, one week, one month, 3 months, or 6 months, after a treatment has begun.

"Increased expression," as that term is used herein, refers to an increase in comparison to a reference, e.g., in the case where altered control region, or addition of an agent, results in an increased expression of the subject product, it is increased relative to an otherwise similar cell without the alteration or addition.

A "non-cognate adaptor function TREM," as that term is used herein, refers to a TREM which mediates initiation or elongation with an AA (a non-cognate AA) other than the AA associated in nature with the anti-codon of the TREM. In an embodiment, a non-cognate adaptor function TREM is also referred to as a mischarged TREM (mTREM).

A "non-naturally occurring sequence," as that term is used herein, refers to a sequence wherein an Adenine is replaced by a residue other than an analog of Adenine, a Cytosine is replaced by a residue other than an analog of Cytosine, a Guanine is replaced by a residue other than an analog of Guanine, and a Uracil is replaced by a residue other than an analog of Uracil. An analog refers to any possible derivative of the ribonucleotides, A, G, C or U. In an embodiment, a sequence having a derivative of any one of ribonucleotides A, G, C or U is a non-naturally occurring sequence.

A "pharmaceutical TREM composition," as that term is used herein, refers to a TREM composition that is suitable for pharmaceutical use. Typically, a pharmaceutical TREM composition comprises a pharmaceutical excipient. In an embodiment the TREM will be the only active ingredient in the pharmaceutical TREM composition. In embodiments the pharmaceutical TREM composition is free, substantially free, or has less than a pharmaceutically acceptable amount, of host cell proteins, DNA, e.g., host cell DNA, endotoxins, and bacteria.

A "post-transcriptional processing," as that term is used herein, with respect to a subject molecule, e.g., a TREM, RNA or tRNAs, refers to a covalent modification of the subject molecule. In an embodiment, the covalent modification occurs post-transcriptionally. In an embodiment, the covalent modification occurs co-transcriptionally. In an embodiment the modification is made in vivo, e.g., in a cell used to produce a TREM. In an embodiment the modification is made ex vivo, e.g., it is made on a TREM isolated or obtained from the cell which produced the TREM. In an embodiment, the post-transcriptional modification is selected from a post-transcriptional modification listed in Table 2.

A "synthetic TREM," as that term is used herein, refers to a TREM which was synthesized other than in or by a cell having an endogenous nucleic acid encoding the TREM, e.g., a synthetic TREM is synthetized by cell-free solid phase synthesis. A synthetic TREM can have the same, or a different, sequence, or tertiary structure, as a native tRNA.

A "recombinant TREM," as that term is used herein, refers to a TREM that was expressed in a cell modified by human intervention, having a modification that mediates the production of the TREM, e.g., the cell comprises an exogenous sequence encoding the TREM, or a modification that mediates expression, e.g., transcriptional expression or post-transcriptional modification, of the TREM. A recombinant TREM can have the same, or a different, sequence, set of post-transcriptional modifications, or tertiary structure, as a reference tRNA, e.g., a native tRNA.

A "tRNA", as that term is used herein, refers to a naturally occurring transfer ribonucleic acid in its native state.

A "TREM composition," as that term is used herein, refers to a composition comprising a plurality of TREMs, a plurality of TREM core fragments and/or a plurality of TREM fragments. A TREM composition can comprise one or more species of TREMs, TREM core fragments or TREM fragments. In an embodiment, the composition comprises only a single species of TREM, TREM core fragment or TREM fragment. In an embodiment, the TREM composition comprises a first TREM, TREM core fragment or TREM fragment species; and a second TREM, TREM core fragment or TREM fragment species. In an embodiment, the TREM composition comprises X TREM, TREM core fragment or TREM fragment species, wherein X=2, 3, 4, 5, 6, 7, 8, 9, or 10. In an embodiment, the TREM, TREM core fragment or TREM fragment has at least 70, 75, 80, 85, 90, or 95, or has 100%, identity with a sequence encoded by a nucleic acid in Table 1. A TREM composition can comprise one or more species of TREMs, TREM core fragments or TREM fragments. In an embodiment, the TREM composition is at least 10, 20, 30, 40, 50, 60, 70, 80, 90, 95 or 99% dry weight TREMs (for a liquid composition dry weight refers to the weight after removal of substantially all liquid, e.g., after lyophilization). In an embodiment, the composition is a liquid. In an embodiment, the composition is dry, e.g., a lyophilized material. In an embodiment, the composition is a frozen composition. In an embodiment, the composition is sterile. In an embodiment, the composition comprises at least 0.5 g, 1.0 g, 5.0 g, 10 g, 15 g, 25 g, 50 g, 100 g, 200 g, 400 g, or 500 g (e.g., as determined by dry weight) of TREM.

In an embodiment, at least X % of the TREMs in a TREM composition has a non-naturally occurring modification at a selected position, and X is 80, 90, 95, 96, 97, 98, 99, or 99.5.

In an embodiment, at least X % of the TREMs in a TREM composition has a non-naturally occurring modification at a first position and a non-naturally occurring modification at a second position, and X, independently, is 80, 90, 95, 96, 97, 98, 99, or 99.5. In embodiments, the modification at the first and second position is the same. In embodiments, the modification at the first and second position are different. In embodiments, the nucleiotide at the first and second position is the same, e.g., both are adenine. In embodiments, the nucleiotide at the first and second position are different, e.g., one is adenine and one is thymine.

In an embodiment, at least X % of the TREMs in a TREM composition has a non-naturally occurring modification at a first position and less than Y % have a non-naturally occurring modification at a second position, wherein X is 80, 90, 95, 96, 97, 98, 99, or 99.5 and Y is 20, 20, 5, 2, 1, 0.1, or 0.01. In embodiments, the nucleotide at the first and second position is the same, e.g., both are adenine. In embodiments the nucleotide at the first and second position are different, e.g., one is adenine and one is thymine.

TREM, TREM Core Fragment and TREM Fragment

A "tRNA-based effector molecule" or "TREM" refers to an RNA molecule comprising one or more of the properties described herein. A TREM can comprise a non-naturally occurring modification, e.g., as provided in Tables 4, 5, 6 or 7.

In an embodiment, a TREM includes a TREM comprising a sequence of Formula A; a TREM core fragment comprising a sequence of Formula B; or a TREM fragment comprising a portion of a TREM which TREM comprises a sequence of Formula A.

In an embodiment, a TREM comprises a sequence of Formula A: [L1]-[ASt Domain1]-[L2]-[DH Domain]-[L3]-[ACH Domain]-[VL Domain]-[TH Domain]-[L4]-[ASt Domain2]. In an embodiment, [VL Domain] is optional. In an embodiment, [L1] is optional.

In an embodiment, a TREM core fragment comprises a sequence of Formula B: $[L1]_y$-$[ASt Domain1]_x$-$[L2]_y$-$[DH Domain]_y$-$[L3]_y$-$[ACH Domain]_x$-$[VL Domain]_y$-$[TH Domain]_y$-$[L4]_y$-$[ASt Domain2]_x$, wherein: x=1 and y=0 or 1. In an embodiment, y=0. In an embodiment, y=1;

In an embodiment, a TREM fragment comprises a portion of a TREM, wherein the TREM comprises a sequence of Formula A: [L1]-[ASt Domain1]-[L2]-[DH Domain]-[L3]-[ACH Domain]-[VL Domain]-[TH Domain]-[L4]-[ASt Domain2], and wherein the TREM fragment comprises: one, two, three or all or any combination of the following: a TREM half (e.g., from a cleavage in the ACH Domain, e.g., in the anticodon sequence, e.g., a 5' half or a 3' half); a 5' fragment (e.g., a fragment comprising the 5' end, e.g., from a cleavage in a DH Domain or the ACH Domain); a 3' fragment (e.g., a fragment comprising the 3' end, e.g., from a cleavage in the TH Domain); or an internal fragment (e.g., from a cleavage in any one of the ACH Domain, DH Domain or TH Domain). Exemplary TREM fragments include TREM halves (e.g., from a cleavage in the ACHD, e.g., 5'TREM halves or 3' TREM halves), a 5' fragment (e.g., a fragment comprising the 5' end, e.g., from a cleavage in a DHD or the ACHD), a 3' fragment (e.g., a fragment comprising the 3' end of a TREM, e.g., from a cleavage in the THD), or an internal fragment (e.g., from a cleavage in one or more of the ACHD, DHD or THD).

In an embodiment, a TREM, a TREM core fragment or a TREM fragment can be charged with an amino acid (e.g., a cognate amino acid); charged with a non-cognate amino acid (e.g., a mischarged TREM (mTREM)); or not charged with an amino acid (e.g., an uncharged TREM (uTREM)). In an embodiment, a TREM, a TREM core fragment or a TREM fragment can be charged with an amino acid selected from alanine, arginine, asparagine, aspartate, cysteine, glutamine, glutamate, glycine, histidine, isoleucine, methionine, leucine, lysine, phenylalanine, proline, serine, threonine, tryptophan, tyrosine, or valine.

In some embodiments, a non-extended anticodon is an anticodon of no more than three nucleotides. In an embodiment, a non-extended codon pairs with no more than three codon nucleotides on a nucleic acid being translated.

In an embodiment, the TREM, TREM core fragment or TREM fragment is a cognate TREM. In an embodiment, the TREM, TREM core fragment or TREM fragment is a non-cognate TREM. In an embodiment, the TREM, TREM core fragment or TREM fragment recognizes a codon provided in Table 2 or Table 3.

TABLE 2

| List of codons |
|---|
| AAA |
| AAC |
| AAG |
| AAU |
| ACA |
| ACC |
| ACG |
| ACU |
| AGA |
| AGC |
| AGG |
| AGU |
| AUA |
| AUC |
| AUG |
| AUU |
| CAA |
| CAC |
| CAG |
| CAU |
| CCA |
| CCC |
| CCG |
| CCU |
| CGA |
| CGC |
| CGG |
| CGU |
| CUA |
| CUC |
| CUG |
| CUU |
| GAA |
| GAC |
| GAG |
| GAU |
| GCA |
| GCC |
| GCG |
| GCU |
| GGA |
| GGC |
| GGG |
| GGU |
| GUA |
| GUC |
| GUG |
| GUU |
| UAA |
| UAC |
| UAG |
| UAU |
| UCA |
| UCC |
| UCG |
| UCU |
| UGA |
| UGC |
| UGG |
| UGU |
| UUA |
| UUC |
| UUG |
| UUU |

TABLE 3

Amino acids and corresponding codons

| Amino Acid | mRNA codons |
|---|---|
| Alanine | GCU, GCC, GCA, GCG |
| Arginine | CGU, CGC, CGA, CGG, AGA, AGG |
| Asparagine | AAU, AAC |
| Aspartate | GAU, GAC |
| Cysteine | UGU, UGC |
| Glutamate | GAA, GAG |

TABLE 3-continued

| Amino acids and corresponding codons | |
|---|---|
| Amino Acid | mRNA codons |
| Glutamine | CAA, CAG |
| Glycine | GGU, GGC, GGA, GGG |
| Histidine | CAU, CAC |
| Isoleucine | AUU, AUC, AUA |
| Leucine | UUA, UUG, CUU, CUC, CUA, CUG |
| Lysine | AAA, AAG |
| Methionine | AUG |
| Phenylalanine | UUU, UUC |
| Proline | CCU, CCC, CCA, CCG |
| Serine | UCU, UCC, UCA, UCG, AGU, AGC |
| Stop | UAA, UAG, UGA |
| Threonine | ACU, ACC, ACA, ACG |
| Tryptophan | UGG |
| Tyrosine | UAU, UAC |
| Valine | GUU, GUC, GUA, GUG |

In an embodiment, a TREM comprises a ribonucleic acid (RNA) sequence encoded by a deoxyribonucleic acid (DNA) sequence disclosed in Table 1, e.g., any one of SEQ ID NOs: 1-451 disclosed in Table 1. In an embodiment, a TREM comprises an RNA sequence at least 60%, 65%, 70%, 75%, 80%, 82%, 85%, 87%, 88%, 90%, 92%, 95%, 96%, 97%, 98%, or 99% identical to an RNA sequence encoded by a DNA sequence provided in Table 1, e.g., any one of SEQ ID NOs: 1-451 disclosed in Table 1. In an embodiment, a TREM comprises an RNA sequence encoded by a DNA sequence at least 60%, 65%, 70%, 75%, 80%, 82%, 85%, 87%, 88%, 90%, 92%, 95%, 96%, 97%, 98%, or 99% identical to a DNA sequence provided in Table 1, e.g., any one of SEQ ID NOs: 1-451 disclosed in Table 1.

In an embodiment, a TREM, a TREM core fragment, or TREM fragment comprises at least 5, 10, 15, 20, 25, or 30 consecutive nucleotides of an RNA sequence encoded by a DNA sequence disclosed in Table 1, e.g., at least 5, 10, 15, 20, 25, or 30 consecutive nucleotides of an RNA sequence encoded by any one of SEQ ID NOs: 1-451 disclosed in Table 1. In an embodiment, a TREM, a TREM core fragment, or TREM fragment comprises at least 5, 10, 15, 20, 25, or 30 consecutive nucleotides of an RNA sequence at least 60%, 65%, 70%, 75%, 80%, 82%, 85%, 87%, 88%, 90%, 92%, 95%, 96%, 97%, 98%, or 99% identical to an RNA sequence encoded by a DNA sequence provided in Table 1, e.g., any one of SEQ ID NOs: 1-451 disclosed in Table 1. In an embodiment, a TREM, a TREM core fragment, or TREM fragment comprises at least 5, 10, 15, 20, 25, or 30 consecutive nucleotides of an RNA sequence encoded by a DNA sequence at least 60%, 65%, 70%, 75%, 80%, 82%, 85%, 87%, 88%, 90%, 92%, 95%, 96%, 97%, 98%, or 99% identical to a DNA sequence provided in Table 1, e.g., any one of SEQ ID NOs: 1-451 disclosed in Table 1.

In an embodiment, a TREM core fragment or a TREM fragment comprises at least 5%, 10%, 15%, 20%, 25%, 30%, 35%, 40%, 50%, 55%, 60%, 65%, 70%, 75%, 80%, 85%, 90%, 95%, 96%, 97%, 98% or 99% of an RNA sequence encoded by a DNA sequence provided in Table 1, e.g., any one of SEQ ID NOs: 1-451 disclosed in Table 1. In an embodiment, a TREM core fragment or a TREM fragment comprises at least 5%, 10%, 15%, 20%, 25%, 30%, 35%, 40%, 50%, 55%, 60%, 65%, 70%, 75%, 80%, 85%, 90%, 95%, 96%, 97%, 98% or 99% of an RNA sequence at least 80%, 85%, 90%, 95%, 96%, 97%, 98%, or 99% identical to an RNA sequence encoded by a DNA sequence provided in Table 1, e.g., any one of SEQ ID NOs: 1-451 disclosed in Table 1. In an embodiment, a TREM core fragment or a TREM fragment comprises at least 5%, 10%, 15%, 20%, 25%, 30%, 35%, 40%, 50%, 55%, 60%, 65%, 70%, 75%, 80%, 85%, 90%, 95%, 96%, 97%, 98% or 99% of an RNA sequence encoded by a DNA sequence at least 80%, 85%, 90%, 95%, 96%, 97%, 98%, or 99% identical to a DNA sequence provided in Table 1, e.g., any one of SEQ ID NOs: 1-451 disclosed in Table 1.

In an embodiment, a TREM core fragment or a TREM fragment comprises at least 5 ribonucleotides (nt), 10 nt, 15 nt, 20 nt, 25 nt, 30 nt, 35 nt, 40 nt, 45 nt, 50 nt, 55 nt or 60 nt (but less than the full length) of an RNA sequence encoded by a DNA sequence disclosed in Table 1, e.g., any one of SEQ ID NOs: 1-451 disclosed in Table 1. In an embodiment, a TREM core fragment or a TREM fragment comprises at least 5 ribonucleotides (nt), 10 nt, 15 nt, 20 nt, 25 nt, nt, 35 nt, 40 nt, 45 nt, 50 nt, 55 nt or 60 nt (but less than the full length) of an RNA sequence which is at least 80%, 85%, 90%, 95%, 96%, 97%, 98%, 99% or 100% identical to an RNA sequence encoded by a DNA sequence provided in Table 1, e.g., any one of SEQ ID NOs: 1-451 disclosed in Table 1. In an embodiment, a TREM core fragment or a TREM fragment comprises at least 5 ribonucleotides (nt), 10 nt, 15 nt, 20 nt, 25 nt, 30 nt, 35 nt, 40 nt, 45 nt, 50 nt, 55 nt or 60 nt (but less than the full length) of an RNA sequence encoded by a DNA sequence with at least 80%, 82%, 85%, 87%, 88%, 90%, 92%, 95%, 96%, 97%, 98%, 99% or 100% identity to a DNA sequence provided in Table 1, e.g., any one of SEQ ID NOs: 1-451 disclosed in Table 1.

In an embodiment, a TREM core fragment or a TREM fragment comprises a sequence of a length of between 10-90 ribonucleotides (rnt), between 10-80 rnt, between 10-70 rnt, between 10-60 rnt, between 10-50 rnt, between 10-40 rnt, between 10-30 rnt, between 10-20 rnt, between 20-90 rnt, between 20-80 rnt, 20-70 rnt, between 20-60 rnt, between 20-50 rnt, between 20-40 rnt, between 30-90 rnt, between 30-80 rnt, between 30-70 rnt, between 30-60 rnt, or between 30-50 rnt

TABLE 1

| List of tRNA Sequences | | |
|---|---|---|
| SEQ ID NO | tRNA name | tRNA sequence |
| 1 | Ala_AGC_chr6:28763 741-28763812 (-) | GGGGGTATAGCTCAGTGGTAGAGCGCGTGCT TAGCATGCACGAGGTCCTGGGTTCGATCCCC |
| 2 | Ala_AGC_chr6:26687 485-26687557 (+) | GGGGAATTAGCTCAAGTGGTAGAGCGCTTGC TTAGCACGCAAGAGGTAGTGGGATCGATGCC |
| 3 | Ala_AGC_chr6:26572 092-26572164 (-) | GGGGAATTAGCTCAAATGGTAGAGCGCTCGC TTAGCATGCGAGAGGTAGCGGGATCGATGCC |

TABLE 1-continued

List of tRNA Sequences

| SEQ ID NO | tRNA name | tRNA sequence |
|---|---|---|
| 4 | Ala_AGC_chr6:26682 715-26682787 (+) | GGGGAATTAGCTCAAGTGGTAGAGCGCTTGC TTAGCATGCAAGAGGTAGTGGGATCGATGCC |
| 5 | Ala_AGC_chr6:26705 606-26705678 (+) | GGGGAATTAGCTCAAGCGGTAGAGCGCTTGC TTAGCATGCAAGAGGTAGTGGGATCGATGCC |
| 6 | Ala_AGC_chr6:26673 590-26673662 (+) | GGGGAATTAGCTCAAGTGGTAGAGCGCTTGC TTAGCATGCAAGAGGTAGTGGGATCAATGCC |
| 7 | Ala_AGC_chr14:8944 5442-89445514 (+) | GGGGAATTAGCTCAAGTGGTAGAGCGCTCGC TTAGCATGCGAGAGGTAGTGGGATCGATGCC |
| 8 | Ala_AGC_chr6:58196 623-58196695 (-) | GGGGAATTAGCCCAAGTGGTAGAGCGCTTGC TTAGCATGCAAGAGGTAGTGGGATCGATGCC |
| 9 | Ala_AGC_chr6:28806 221-28806292 (-) | GGGGGTGTAGCTCAGTGGTAGAGCGCGTGCT TAGCATGCACGAGGCCCCGGGTTCAATCCCC |
| 10 | Ala_AGC_chr6:28574 933-28575004 (+) | GGGGGTGTAGCTCAGTGGTAGAGCGCGTGCT TAGCATGTACGAGGTCCCGGGTTCAATCCCC |
| 11 | Ala_AGC_chr6:28626 014-28626085 (-) | GGGGATGTAGCTCAGTGGTAGAGCGCATGCT TAGCATGCATGAGGTCCCGGGTTCGATCCCC |
| 12 | Ala_AGC_chr6:28678 366-28678437 (+) | GGGGGTGTAGCTCAGTGGTAGAGCGCGTGCT TAGCATGCACGAGGCCCTGGGTTCAATCCCC |
| 13 | Ala_AGC_chr6:28779 849-28779920 (-) | GGGGGTATAGCTCAGCGGTAGAGCGCGTGCT TAGCATGCACGAGGTCCTGGGTTCAATCCCC |
| 14 | Ala_AGC_chr6:28687 481-28687552 (+) | GGGGGTGTAGCTCAGTGGTAGAGCGCGTGCT TAGCATGCACGAGGCCCCGGGTTCAATCCCT |
| 15 | Ala_AGC_chr2:27274 082-27274154 (+) | GGGGGATTAGCTCAAATGGTAGAGCGCTCGC TTAGCATGCGAGAGGTAGCGGGATCGATGCC |
| 16 | Ala_AGC_chr6:26730 737-26730809 (+) | GGGGAATTAGCTCAGGCGGTAGAGCGCTCGC TTAGCATGCGAGAGGTAGCGGGATCGACGCC |
| 17 | Ala_CGC_chr6:26553 731-26553802 (+) | GGGGATGTAGCTCAGTGGTAGAGCGCATGCT TCGCATGTATGAGGTCCCGGGTTCGATCCCC |
| 18 | Ala_CGC_chr6:28641 613-28641684 (-) | GGGGATGTAGCTCAGTGGTAGAGCGCATGCT TCGCATGTATGAGGCCCCGGGTTCGATCCCC |
| 19 | Ala_CGC_chr2:15725 7281-157257352 (+) | GGGGATGTAGCTCAGTGGTAGAGCGCGCGCT TCGCATGTGTGAGGTCCCGGGTTCAATCCCC |
| 20 | Ala_CGC_chr6:28697 092-28697163 (+) | GGGGGTGTAGCTCAGTGGTAGAGCGCGTGCT TCGCATGTACGAGGCCCCGGGTTCGACCCCC |
| 21 | Ala_TGC_chr6:28757 547-28757618 (-) | GGGGGTGTAGCTCAGTGGTAGAGCGCATGCT TTGCATGTATGAGGTCCCGGGTTCGATCCCC |
| 22 | Ala_TGC_chr6:28611 222-28611293 (+) | GGGGATGTAGCTCAGTGGTAGAGCGCATGCT TTGCATGTATGAGGTCCCGGGTTCGATCCCC |
| 23 | Ala_TGC_chr5:18063 3868-180633939 (+) | GGGGATGTAGCTCAGTGGTAGAGCGCATGCT TTGCATGTATGAGGCCCCGGGTTCGATCCCC |
| 24 | Ala_TGC_chr12:1254 24512-125424583 (+) | GGGGATGTAGCTCAGTGGTAGAGCGCATGCT TTGCACGTATGAGGCCCCGGGTTCAATCCCC |
| 25 | Ala_TGC_chr6:28785 012-28785083 (-) | GGGGGTGTAGCTCAGTGGTAGAGCGCATGCT TTGCATGTATGAGGCCTCGGGTTCGATCCCC |
| 26 | Ala_TGC_chr6:28726 141-28726212 (-) | GGGGGTGTAGCTCAGTGGTAGAGCACATGCT TTGCATGTGTGAGGCCCCGGGTTCGATCCCC |
| 27 | Ala_TGC_chr6:28770 577-28770647 (-) | GGGGGTGTAGCTCAGTGGTAGAGCGCATGCT TTGCATGTATGAGGCCTCGGTTCGATCCCCG |
| 28 | Arg_ACG_chr6:26328 368-26328440 (+) | GGGCCAGTGGCGCAATGGATAACGCGTCTGA CTACGGATCAGAAGATTCCAGGTTCGACTCC |

TABLE 1-continued

List of tRNA Sequences

| SEQ ID NO | tRNA name | tRNA sequence |
|---|---|---|
| 29 | Arg_ACG_chr3:45730 491-45730563 (-) | GGGCCAGTGGCGCAATGGATAACGCGTCTGA CTACGGATCAGAAGATTCTAGGTTCGACTCC |
| 30 | Arg_CCG_chr6:28710 729-28710801 (-) | GGCCGCGTGGCCTAATGGATAAGGCGTCTGA TTCCGGATCAGAAGATTGAGGGTTCGAGTCC |
| 31 | Arg_CCG_chr17:6601 6013-66016085 (-) | GACCCAGTGGCCTAATGGATAAGGCATCAGC CTCCGGAGCTGGGGATTGTGGGTTCGAGTCC |
| 32 | Arg_CCT_chr17:7303 0001-73030073 (+) | GCCCCAGTGGCCTAATGGATAAGGCACTGGC CTCCTAAGCCAGGGATTGTGGGTTCGAGTCC |
| 33 | Arg_CCT_chr17:7303 0526-73030598 (-) | GCCCCAGTGGCCTAATGGATAAGGCACTGGC CTCCTAAGCCAGGGATTGTGGGTTCGAGTCC |
| 34 | Arg_CCT_chr16:3202 901-3202973 (+) | GCCCCGGTGGCCTAATGGATAAGGCATTGGC CTCCTAAGCCAGGGATTGTGGGTTCGAGTCC |
| 35 | Arg_CCT_chr7:13902 5446-139025518 (+) | GCCCCAGTGGCCTAATGGATAAGGCATTGGC CTCCTAAGCCAGGGATTGTGGGTTCGAGTCC |
| 36 | Arg_CCT_chr16:3243 918-3243990 (+) | GCCCCAGTGGCCTGATGGATAAGGTACTGGC CTCCTAAGCCAGGGATTGTGGGTTCGAGTTC |
| 37 | Arg_TCG_chr15:8987 8304-89878376 (+) | GGCCGCGTGGCCTAATGGATAAGGCGTCTGA CTTCGGATCAGAAGATTGCAGGTTCGAGTCC |
| 38 | Arg_TCG_chr6:26323 046-26323118 (+) | GACCACGTGGCCTAATGGATAAGGCGTCTGA CTTCGGATCAGAAGATTGAGGGTTCGAATCC |
| 39 | Arg_TCG_chr17:7303 1208-73031280 (+) | GACCGCGTGGCCTAATGGATAAGGCGTCTGA CTTCGGATCAGAAGATTGAGGGTTCGAGTCC |
| 40 | Arg_TCG_chr6:26299 905-26299977 (+) | GACCACGTGGCCTAATGGATAAGGCGTCTGA CTTCGGATCAGAAGATTGAGGGTTCGAATCC |
| 41 | Arg_TCG_chr6:28510 891-28510963 (-) | GACCACGTGGCCTAATGGATAAGGCGTCTGA CTTCGGATCAGAAGATTGAGGGTTCGAATCC |
| 42 | Arg_TCG_chr9:11296 0803-112960875 (+) | GGCCGTGTGGCCTAATGGATAAGGCGTCTGA CTTCGGATCAAAAGATTGCAGGTTTGAGTTC |
| 43 | Arg_TCT_chr1:94313 129-94313213 (+) | GGCTCCGTGGCGCAATGGATAGCGCATTGGA CTTCTAGAGGCTGAAGGCATTCAAAGGTTCC |
| 44 | Arg_TCT_chr17:8024 243-8024330 (+) | GGCTCTGTGGCGCAATGGATAGCGCATTGGA CTTCTAGTGACGAATAGAGCAATTCAAAGGT |
| 45 | Arg_TCT_chr9:13110 2355-131102445 (-) | GGCTCTGTGGCGCAATGGATAGCGCATTGGA CTTCTAGCTGAGCCTAGTGTGGTCATTCAAA |
| 46 | Arg_TCT_chr11:5931 8767-59318852 (+) | GGCTCTGTGGCGCAATGGATAGCGCATTGGA CTTCTAGATAGTTAGAGAAATTCAAAGGTTG |
| 47 | Arg_TCT_chr1:15911 1401-159111474 (-) | GTCTCTGTGGCGCAATGGACGAGCGCGCTGG ACTTCTAATCCAGAGGTTCCGGGTTCGAGTC |
| 48 | Arg_TCT_chr6:27529 963-27530049 (+) | GGCTCTGTGGCGCAATGGATAGCGCATTGGA CTTCTAGCCTAAATCAAGAGATTCAAAGGTT |
| 49 | Asn_GTT_chr1:16151 0031-161510104 (+) | GTCTCTGTGGCGCAATCGGTTAGCGCGTTCG GCTGTTAACCGAAAGGTTGGTGGTTCGATCC |
| 50 | Asn_GTT_chr1:14387 9832-143879905 (-) | GTCTCTGTGGCGCAATCGGCTAGCGCGTTTG GCTGTTAACTAAAAGGTTGGCGGTTCGAACC |
| 51 | Asn_GTT_chr1:14430 1611-144301684 (+) | GTCTCTGTGGTGCAATCGGTTAGCGCGTTCCG CTGTTAACCGAAAGCTTGGTGGTTCGAGCCC |
| 52 | Asn_GTT_chr1:14932 6272-149326345 (-) | GTCTCTGTGGCGCAATCGGCTAGCGCGTTTG GCTGTTAACTAAAAAGTTGGTGGTTCGAACA |
| 53 | Asn_GTT_chr1:14824 8115-148248188 (+) | GTCTCTGTGGCGCAATCGGTTAGCGCGTTCG GCTGTTAACCGAAAGGTTGGTGGTTCGAGCC |

TABLE 1-continued

List of tRNA Sequences

| SEQ ID NO | tRNA name | tRNA sequence |
|---|---|---|
| 54 | Asn_GTT_chr1:148598314-148598387 (-) | GTCTCTGTGGCGCAATCGGTTAGCGCATTCGGCTGTTAACCGAAAGGTTGGTGGTTCGAGCC |
| 55 | Asn_GTT_chr1:17216172-17216245 (+) | GTCTCTGTGGCGCAATCGGTTAGCGCGTTCGGCTGTTAACCGAAAGATTGGTGGTTCGAGCC |
| 56 | Asn_GTT_chr1:16847080-16847153 (-) | GTCTCTGTGGCGCAATCGGTTAGCGCGTTCGGCTGTTAACTGAAAGGTTGGTGGTTCGAGCC |
| 57 | Asn_GTT_chr1:149230570-149230643 (-) | GTCTCTGTGGCGCAATGGGTTAGCGCGTTCGGCTGTTAACCGAAAGGTTGGTGGTTCGAGCC |
| 58 | Asn_GTT_chr1:148000805-148000878 (+) | GTCTCTGTGGCGTAGTCGGTTAGCGCGTTCGGCTGTTAACCGAAAAGTTGGTGGTTCGAGCC |
| 59 | Asn_GTT_chr1:149711798-149711871 (-) | GTCTCTGTGGCGCAATCGGCTAGCGCGTTTGGCTGTTAACTAAAAGGTTGGTGGTTCGAACC |
| 60 | Asn_GTT_chr1:145979034-145979107 (-) | GTCTCTGTGGCGCAATCGGTTAGCGCGTTCGGCTGTTAACTGAAAGGTTAGTGGTTCGAGCC |
| 61 | Asp_GTC_chr12:98897281-98897352 (+) | TCCTCGTTAGTATAGTGGTTAGTATCCCCGCCTGTCACGCGGGAGACCGGGGTTCAATTCCCC |
| 62 | Asp_GTC_chr1:161410615-161410686 (-) | TCCTCGTTAGTATAGTGGTGAGTATCCCCGCCTGTCACGCGGGAGACCGGGGTTCGATTCCCC |
| 63 | Asp_GTC_chr6:27551236-27551307 (-) | TCCTCGTTAGTATAGTGGTGAGTGTCCCCGTCTGTCACGCGGGAGACCGGGGTTCGATTCCCC |
| 64 | Cys_GCA_chr7:149007281-149007352 (+) | GGGGGCATAGCTCAGTGGTAGAGCATTTGACTGCAGATCAAGAGGTCCCTGGTTCAAATCCA |
| 65 | Cys_GCA_chr7:149074601-149074672 (-) | GGGGGTATAGCTCAGGGGTAGAGCATTTGACTGCAGATCAAGAGGTCCCTGGTTCAAATCCA |
| 66 | Cys_GCA_chr7:149112229-149112300 (-) | GGGGGTATAGCTTAGCGGTAGAGCATTTGACTGCAGATCAAGAGGTCCCCGGTTCAAATCCG |
| 67 | Cys_GCA_chr7:149344046-149344117 (-) | GGGGGTATAGCTTAGGGGTAGAGCATTTGACTGCAGATCAAAAGGTCCCTGGTTCAAATCCA |
| 68 | Cys_GCA_chr7:149052766-149052837 (-) | GGGGGTATAGCTCAGGGGTAGAGCATTTGACTGCAGATCAAGAGGTCCCCAGTTCAAATCTG |
| 69 | Cys_GCA_chr17:37017937-37018008 (-) | GGGGGTATAGCTCAGGGGTAGAGCATTTGACTGCAGATCAAGAAGTCCCCGGTTCAAATCCG |
| 70 | Cys_GCA_chr7:149281816-149281887 (+) | GGGGGTATAGCTCAGGGGTAGAGCATTTGACTGCAGATCAAGAGGTCTCTGGTTCAAATCCA |
| 71 | Cys_GCA_chr7:149243631-149243702 (+) | GGGGGTATAGCTCAGGGGTAGAGCACTTGACTGCAGATCAAGAAGTCCTTGGTTCAAATCCA |
| 72 | Cys_GCA_chr7:149388272-149388343 (-) | GGGGATATAGCTCAGGGGTAGAGCATTTGACTGCAGATCAAGAGGTCCCCGGTTCAAATCCG |
| 73 | Cys_GCA_chr7:149072850-149072921 (-) | GGGGGTATAGTTCAGGGGTAGAGCATTTGACTGCAGATCAAGAGGTCCCTGGTTCAAATCCA |
| 74 | Cys_GCA_chr7:149310156-149310227 (-) | GGGGGTATAGCTCAGGGGTAGAGCATTTGACTGCAAATCAAGAGGTCCCTGATTCAAATCCA |
| 75 | Cys_GCA_chr4:124430005-124430076 (-) | GGGGGTATAGCTCAGTGGTAGAGCATTTGACTGCAGATCAAGAGGTCCCCGGTTCAAATCCG |
| 76 | Cys_GCA_chr7:149295046-149295117 (+) | GGGCGTATAGCTCAGGGGTAGAGCATTTGACTGCAGATCAAGAGGTCCCCAGTTCAAATCTG |
| 77 | Cys_GCA_chr7:149361915-149361986 (+) | GGGGGTATAGCTCACAGGTAGAGCATTTGACTGCAGATCAAGAGGTCCCCGGTTCAAATCTG |
| 78 | Cys_GCA_chr7:149253802-149253871 (+) | GGGCGTATAGCTCAGGGGTAGAGCATTTGACTGCAGATCAAGAGGTCCCCAGTTCAAATCTG |

TABLE 1-continued

List of tRNA Sequences

| SEQ ID NO | tRNA name | tRNA sequence |
|---|---|---|
| 79 | Cys_GCA_chr7:14929 2305-149292376 (-) | GGGGGTATAGCTCACAGGTAGAGCATTTGAC TGCAGATCAAGAGGTCCCCGGTTCAAATCCG |
| 80 | Cys_GCA_chr7:14928 6164-149286235 (-) | GGGGGTATAGCTCAGGGGTAGAGCACTTGAC TGCAGATCAAGAGGTCCCTGGTTCAAATCCA |
| 81 | Cys_GCA_chr17:3702 5545-37025616 (-) | GGGGGTATAGCTCAGTGGTAGAGCATTTGAC TGCAGATCAAGAGGTCCCTGGTTCAAATCCG |
| 82 | Cys_GCA_chr15:8003 6997-80037069 (+) | GGGGGTATAGCTCAGTGGGTAGAGCATTTGA CTGCAGATCAAGAGGTCCCCGGTTCAAATCC |
| 83 | Cys_GCA_chr3:13194 7944-131948015 (-) | GGGGGTGTAGCTCAGTGGTAGAGCATTTGAC TGCAGATCAAGAGGTCCCTGGTTCAAATCCA |
| 84 | Cys_GCA_chr1:93981 834-93981906 (-) | GGGGGTATAGCTCAGGTGGTAGAGCATTTGA CTGCAGATCAAGAGGTCCCCGGTTCAAATCC |
| 85 | Cys_GCA_chr14:7342 9679-73429750 (+) | GGGGGTATAGCTCAGGGGTAGAGCATTTGAC TGCAGATCAAGAGGTCCCCGGTTCAAATCCG |
| 86 | Cys_GCA_chr3:13195 0642-131950713 (-) | GGGGGTATAGCTCAGGGGTAGAGCATTTGAC TGCAGATCAAGAGGTCCCTGGTTCAAATCCA |
| 87 | Gln_CTG_chr6:18836 402-18836473 (+) | GGTTCCATGGTGTAATGGTTAGCACTCTGGA CTCTGAATCCAGCGATCCGAGTTCAAATCTC |
| 88 | Gln_CTG_chr6:27515 531-27515602 (-) | GGTTCCATGGTGTAATGGTTAGCACTCTGGA CTCTGAATCCAGCGATCCGAGTTCAAGTCTC |
| 89 | Gln_CTG_chr1:14596 3304-145963375 (+) | GGTTCCATGGTGTAATGGTGAGCACTCTGGA CTCTGAATCCAGCGATCCGAGTTCGAGTCTC |
| 90 | Gln_CTG_chr1:14773 7382-147737453 (-) | GGTTCCATGGTGTAATGGTAAGCACTCTGGA CTCTGAATCCAGCGATCCGAGTTCGAGTCTC |
| 91 | Gln_CTG_chr6:27263 212-27263283 (+) | GGTTCCATGGTGTAATGGTTAGCACTCTGGA CTCTGAATCCGGTAATCCGAGTTCAAATCTC |
| 92 | Gln_CTG_chr6:27759 135-27759206 (-) | GGCCCCATGGTGTAATGGTCAGCACTCTGGA CTCTGAATCCAGCGATCCGAGTTCAAATCTC |
| 93 | Gln_CTG_chr1:14780 0937-147801008 (+) | GGTTCCATGGTGTAATGGTAAGCACTCTGGA CTCTGAATCCAGCCATCTGAGTTCGAGTCTCT |
| 94 | Gln_TTG_chr17:4726 9890-47269961 (+) | GGTCCCATGGTGTAATGGTTAGCACTCTGGA CTTTGAATCCAGCGATCCGAGTTCAAATCTC |
| 95 | Gln_TTG_chr6:28557 156-28557227 (+) | GGTCCCATGGTGTAATGGTTAGCACTCTGGA CTTTGAATCCAGCAATCCGAGTTCGAATCTC |
| 96 | Gln_TTG_chr6:26311 424-26311495 (-) | GGCCCCATGGTGTAATGGTTAGCACTCTGGA CTTTGAATCCAGCGATCCGAGTTCAAATCTC |
| 97 | Gln_TTG_chr6:14550 3859-145503930 (+) | GGTCCCATGGTGTAATGGTTAGCACTCTGGG CTTTGAATCCAGCAATCCGAGTTCGAATCTTG |
| 98 | Glu_CTC_chr1:14539 9233-145399304 (-) | TCCCTGGTGGTCTAGTGGTTAGGATTCGGCG CTCTCACCGCCGCGGCCCGGGTTCGATTCCC |
| 99 | Glu_CTC_chr1:24916 8447-249168518 (+) | TCCCTGGTGGTCTAGTGGTTAGGATTCGGCG CTCTCACCGCCGCGGCCCGGGTTCGATTCCC |
| 100 | Glu_TTC_chr2:13109 4701-131094772 (-) | TCCCATATGGTCTAGCGGTTAGGATTCCTGGT TTTCACCCAGGTGGCCCGGGTTCGACTCCCG |
| 101 | Glu_TTC_chr13:4549 2062-45492133 (-) | TCCCACATGGTCTAGCGGTTAGGATTCCTGGT TTTCACCCAGGCGGCCCGGGTTCGACTCCCG |
| 102 | Glu_TTC_chr1:17199 078-17199149 (+) | TCCCTGGTGGTCTAGTGGCTAGGATTCGGCG CTTTCACCGCCGCGGCCCGGGTTCGATTCCCG |
| 103 | Glu_TTC_chr1:16861 774-16861845 (-) | TCCCTGGTGGTCTAGTGGCTAGGATTCGGCG CTTTCACCGCCGCGGCCCGGGTTCGATTCCCG |

TABLE 1-continued

List of tRNA Sequences

| SEQ ID NO | tRNA name | tRNA sequence |
|---|---|---|
| 104 | Gly_CCC_chr1:16872434-16872504 (-) | GCATTGGTGGTTCAGTGGTAGAATTCTCGCCTCCCACGCGGGAGACCCGGGTTCAATTCCCGG |
| 105 | Gly_CCC_chr2:70476123-70476193 (-) | GCGCCGCTGGTGTAGTGGTATCATGCAAGATTCCCATTCTTGCGACCCGGGTTCGATTCCCGG |
| 106 | Gly_CCC_chr17:19764175-19764245 (+) | GCATTGGTGGTTCAATGGTAGAATTCTCGCCTCCCACGCAGGAGACCCAGGTTCGATTCCTGG |
| 107 | Gly_GCC_chr1:161413094-161413164 (+) | GCATGGGTGGTTCAGTGGTAGAATTCTCGCCTGCCACGCGGGAGGCCCGGGTTCGATTCCCG |
| 108 | Gly_GCC_chr1:161493637-161493707 (-) | GCATTGGTGGTTCAGTGGTAGAATTCTCGCCTGCCACGCGGGAGGCCCGGGTTCGATTCCCGG |
| 109 | Gly_GCC_chr16:70812114-70812184 (-) | GCATTGGTGGTTCAGTGGTAGAATTCTCGCCTGCCACGCGGGAGGCCCGGGTTTGATTCCCGG |
| 110 | Gly_GCC_chr1:161450356-161450426 (+) | GCATAGGTGGTTCAGTGGTAGAATTCTTGCCTGCCACGCAGGAGGCCCAGGTTTGATTCCTG |
| 111 | Gly_GCC_chr16:70822597-70822667 (+) | GCATTGGTGGTTCAGTGGTAGAATTCTCGCCTGCCATGCGGGCGGCCGGGCTTCGATTCCTGG |
| 112 | Gly_TCC_chr19:4724082-4724153 (+) | GCGTTGGTGGTATAGTGGTTAGCATAGCTGCCTTCCAAGCAGTTGACCCGGGTTCGATTCCC |
| 113 | Gly_TCC_chr1:145397864-145397935 (-) | GCGTTGGTGGTATAGTGGTGAGCATAGCTGCCTTCCAAGCAGTTGACCCGGGTTCGATTCCC |
| 114 | Gly_TCC_chr17:8124866-8124937 (+) | GCGTTGGTGGTATAGTGGTAAGCATAGCTGCCTTCCAAGCAGTTGACCCGGGTTCGATTCCC |
| 115 | Gly_TCC_chr1:161409961-161410032 (-) | GCGTTGGTGGTATAGTGGTGAGCATAGTTGCCTTCCAAGCAGTTGACCCGGGCTCGATTCCC |
| 116 | His_GTG_chr1:145396881-145396952 (-) | GCCGTGATCGTATAGTGGTTAGTACTCTGCGTTGTGGCCGCAGCAACCTCGGTTCGAATCCGA |
| 117 | His_GTG_chr1:149155828-149155899 (-) | GCCATGATCGTATAGTGGTTAGTACTCTGCGCTGTGGCCGCAGCAACCTCGGTTCGAATCCG |
| 118 | Ile_AAT_chr6:58149254-58149327 (+) | GGCCGGTTAGCTCAGTTGGTTAGAGCGTGGCGCTAATAACGCCAAGGTCGCGGGTTCGATCC |
| 119 | Ile_AAT_chr6:27655967-27656040 (+) | GGCCGGTTAGCTCAGTTGGTTAGAGCGTGGTGCTAATAACGCCAAGGTCGCGGGTTCGATCC |
| 120 | Ile_AAT_chr6:27242990-27243063 (-) | GGCTGGTTAGCTCAGTTGGTTAGAGCGTGGTGCTAATAACGCCAAGGTCGCGGGTTCGATCC |
| 121 | Ile_AAT_chr17:8130309-8130382 (-) | GGCCGGTTAGCTCAGTTGGTTAGAGCGTGGTGCTAATAACGCCAAGGTCGCGGGTTCGAACC |
| 122 | Ile_AAT_chr6:26554350-26554423 (+) | GGCCGGTTAGCTCAGTTGGTTAGAGCGTGGTGCTAATAACGCCAAGGTCGCGGGTTCGATCC |
| 123 | Ile_AAT_chr6:26745255-26745328 (-) | GGCCGGTTAGCTCAGTTGGTTAGAGCGTGGTGCTAATAACGCTAAGGTCGCGGGTTCGATCC |
| 124 | Ile_AAT_chr6:26721221-26721294 (-) | GGCCGGTTAGCTCAGTTGGTCAGAGCGTGGTGCTAATAACGCCAAGGTCGCGGGTTCGATCC |
| 125 | Ile_AAT_chr6:27636362-27636435 (+) | GGCCGGTTAGCTCAGTCGGCTAGAGCGTGGTGCTAATAACGCCAAGGTCGCGGGTTCGATCC |
| 126 | Ile_AAT_chr6:27241739-27241812 (+) | GGCTGGTTAGTTCAGTTGGTTAGAGCGTGGTGCTAATAACGCCAAGGTCGTGGGTTCGATCC |
| 127 | Ile_GAT_chrX:3756418-3756491 (-) | GGCCGGTTAGCTCAGTTGGTAAGAGCGTGGTGCTGATAACACCAAGGTCGCGGGCTCGACTC |
| 128 | Ile_TAT_chr19:39902808-39902900 (-) | GCTCCAGTGGCGCAATCGGTTAGCGCGCGGTACTTATATGACAGTGCGAGCGGAGCAATGCC |

TABLE 1-continued

List of tRNA Sequences

| SEQ ID NO | tRNA name | tRNA sequence |
|---|---|---|
| 129 | Ile_TAT_chr2:430376 76-43037768 (+) | GCTCCAGTGGCGCAATCGGTTAGCGCGCGGT ACTTATACAGCAGTACATGCAGAGCAATGCC |
| 130 | Ile_TAT_chr6:269881 25-26988218 (+) | GCTCCAGTGGCGCAATCGGTTAGCGCGCGGT ACTTATATGGCAGTATGTGTGCGAGTGATGC |
| 131 | Ile_TAT_chr6:275992 00-27599293 (+) | GCTCCAGTGGCGCAATCGGTTAGCGCGCGGT ACTTATACAACAGTATATGTGCGGGTGATGC |
| 132 | Ile_TAT_chr6:285053 67-28505460 (+) | GCTCCAGTGGCGCAATCGGTTAGCGCGCGGT ACTTATAAGACAGTGCACCTGTGAGCAATGC |
| 133 | Leu_AAG_chr5:1805 24474-180524555 (-) | GGTAGCGTGGCCGAGCGGTCTAAGGCGCTGG ATTAAGGCTCCAGTCTCTTCGGAGGCGTGGG |
| 134 | Leu_AAG_chr5:1806 14701-180614782 (+) | GGTAGCGTGGCCGAGCGGTCTAAGGCGCTGG ATTAAGGCTCCAGTCTCTTCGGGGGCGTGGG |
| 135 | Leu_AAG_chr6:2895 6779-28956860 (+) | GGTAGCGTGGCCGAGCGGTCTAAGGCGCTGG ATTAAGGCTCCAGTCTCTTCGGGGGCGTGGG |
| 136 | Leu_AAG_chr6:2844 6400-28446481 (-) | GGTAGCGTGGCCGAGTGGTCTAAGACGCTGG ATTAAGGCTCCAGTCTCTTCGGGGGCGTGGG |
| 137 | Leu_CAA_chr6:28864 000-28864105 (-) | GTCAGGATGGCCGAGTGGTCTAAGGCGCCAG ACTCAAGCTAAGCTTCCTCCGCGGTGGGGAT |
| 138 | Leu_CAA_chr6:28908 830-28908934 (+) | GTCAGGATGGCCGAGTGGTCTAAGGCGCCAG ACTCAAGCTTGGCTTCCTCGTGTTGAGGATTC |
| 139 | Leu_CAA_chr6:27573 417-27573524 (-) | GTCAGGATGGCCGAGTGGTCTAAGGCGCCAG ACTCAAGCTTACTGCTTCCTGTGTTCGGGTCT |
| 140 | Leu_CAA_chr6:27570 348-27570454 (-) | GTCAGGATGGCCGAGTGGTCTAAGGCGCCAG ACTCAAGTTGCTACTTCCCAGGTTTGGGGCTT |
| 141 | Leu_CAA_chr1:24916 8054-249168159 (+) | GTCAGGATGGCCGAGTGGTCTAAGGCGCCAG ACTCAAGGTAAGCACCTTGCCTGCGGGCTTT |
| 142 | Leu_CAA_chr11:9296 790-9296863 (+) | GCCTCCTTAGTGCAGTAGGTAGCGCATCAGT CTCAAAATCTGAATGGTCCTGAGTTCAAGCC |
| 143 | Leu_CAA_chr1:16158 1736-161581819 (-) | GTCAGGATGGCCGAGCAGTCTTAAGGCGCTG CGTTCAAATCGCACCCTCCGCTGGAGGCGTG |
| 144 | Leu_CAG_chr1:16141 1323-161411405 (+) | GTCAGGATGGCCGAGCGGTCTAAGGCGCTGC GTTCAGGTCGCAGTCTCCCCTGGAGGCGTGG |
| 145 | Leu_CAG_chr16:5733 3863-57333945 (+) | GTCAGGATGGCCGAGCGGTCTAAGGCGCTGC GTTCAGGTCGCAGTCTCCCCTGGAGGCGTGG |
| 146 | Leu_TAA_chr6:14453 7684-144537766 (+) | ACCAGGATGGCCGAGTGGTTAAGGCGTTGGA CTTAAGATCCAATGGACATATGTCCGCGTGG |
| 147 | Leu_TAA_chr6:27688 898-27688980 (-) | ACCGGGATGGCCGAGTGGTTAAGGCGTTGGA CTTAAGATCCAATGGGCTGGTGCCCGCGTGG |
| 148 | Leu_TAA_chr11:5931 9228-59319310 (+) | ACCAGAATGGCCGAGTGGTTAAGGCGTTGGA CTTAAGATCCAATGGATTCATATCCGCGTGG |
| 149 | Leu_TAA_chr6:27198 334-27198416 (-) | ACCGGGATGGCTGAGTGGTTAAGGCGTTGGA CTTAAGATCCAATGGACAGGTGTCCGCGTGG |
| 150 | Leu_TAG_chr17:8023 632-8023713 (-) | GGTAGCGTGGCCGAGCGGTCTAAGGCGCTGG ATTTAGGCTCCAGTCTCTTCGGAGGCGTGGG |
| 151 | Leu_TAG_chr14:2109 3529-21093610 (+) | GGTAGTGTGGCCGAGCGGTCTAAGGCGCTGG ATTTAGGCTCCAGTCTCTTCGGGGGCGTGGG |
| 152 | Leu_TAG_chr16:2220 7032-22207113 (-) | GGTAGCGTGGCCGAGTGGTCTAAGGCGCTGG ATTTAGGCTCCAGTCATTTCGATGGCGTGGGT |
| 153 | Lys_CTT_chr14:5870 6613-58706685 (-) | GCCCGGCTAGCTCAGTCGGTAGAGCATGGGA CTCTTAATCCCAGGGTCGTGGGTTCGAGCCC |

TABLE 1-continued

List of tRNA Sequences

| SEQ ID NO | tRNA name | tRNA sequence |
|---|---|---|
| 154 | Lys_CTT_chr19:3606 6750-36066822 (+) | GCCCAGCTAGCTCAGTCGGTAGAGCATAAGA CTCTTAATCTCAGGGTTGTGGATTCGTGCCCC |
| 155 | Lys_CTT_chr19:5242 5393-52425466 (-) | GCAGCTAGCTCAGTCGGTAGAGCATGAGACT CTTAATCTCAGGGTCATGGGTTCGTGCCCCAT |
| 156 | Lys_CTT_chr1:14539 5522-145395594 (-) | GCCCGGCTAGCTCAGTCGGTAGAGCATGAGA CTCTTAATCTCAGGGTCGTGGGTTCGAGCCCC |
| 157 | Lys_CTT_chr16:3207 406-3207478 (-) | GCCCGGCTAGCTCAGTCGGTAGAGCATGAGA CCCTTAATCTCAGGGTCGTGGGTTCGAGCCC |
| 158 | Lys_CTT_chr16:3241 501-3241573 (+) | GCCCGGCTAGCTCAGTCGGTAGAGCATGGGA CTCTTAATCTCAGGGTCGTGGGTTCGAGCCCC |
| 159 | Lys_CTT_chr16:3230 555-3230627 (-) | GCCCGGCTAGCTCAGTCGATAGAGCATGAGA CTCTTAATCTCAGGGTCGTGGGTTCGAGCCG |
| 160 | Lys_CTT_chr1:55423 542-55423614 (-) | GCCCAGCTAGCTCAGTCGGTAGAGCATGAGA CTCTTAATCTCAGGGTCATGGGTTTGAGCCCC |
| 161 | Lys_CTT_chr16:3214 939-3215011 (+) | GCCTGGCTAGCTCAGTCGGCAAAGCATGAGA CTCTTAATCTCAGGGTCGTGGGCTCGAGCTCC |
| 162 | Lys_CTT_chr5:26198 539-26198611 (-) | GCCCGACTACCTCAGTCGGTGGAGCATGGGA CTCTTCATCCCAGGGTTGTGGGTTCGAGCCCC |
| 163 | Lys_TTT_chr16:7351 2216-73512288 (-) | GCCTGGATAGCTCAGTTGGTAGAGCATCAGA CTTTTAATCTGAGGGTCCAGGGTTCAAGTCCC |
| 164 | Lys_TTT_chr12:2784 3306-27843378 (+) | ACCCAGATAGCTCAGTCAGTAGAGCATCAGA CTTTTAATCTGAGGGTCCAAGGTTCATGTCCC |
| 165 | Lys_TTT_chr11:1224 30655-122430727 (+) | GCCTGGATAGCTCAGTTGGTAGAGCATCAGA CTTTTAATCTGAGGGTCCAGGGTTCAAGTCCC |
| 166 | Lys_TTT_chr1:20447 5655-204475727 (+) | GCCCGGATAGCTCAGTCGGTAGAGCATCAGA CTTTTAATCTGAGGGTCCAGGGTTCAAGTCCC |
| 167 | Lys_TTT_chr6:27559 593-27559665 (-) | GCCTGGATAGCTCAGTCGGTAGAGCATCAGA CTTTTAATCTGAGGGTCCAGGGTTCAAGTCCC |
| 168 | Lys_TTT_chr11:5932 3902-59323974 (+) | GCCCGGATAGCTCAGTCGGTAGAGCATCAGA CTTTTAATCTGAGGGTCCGGGGTTCAAGTCCC |
| 169 | Lys_TTT_chr6:27302 769-27302841 (-) | GCCTGGGTAGCTCAGTCGGTAGAGCATCAGA CTTTTAATCTGAGGGTCCAGGGTTCAAGTCCC |
| 170 | Lys_TTT_chr6:28715 521-28715593 (+) | GCCTGGATAGCTCAGTTGGTAGAACATCAGA CTTTTAATCTGACGGTGCAGGGTTCAAGTCCC |
| 171 | Met_CAT_chr8:12416 9470-124169542 (-) | GCCTCGTTAGCGCAGTAGGTAGCGCGTCAGT CTCATAATCTGAAGGTCGTGAGTTCGATCCTC |
| 172 | Met_CAT_chr16:7146 0396-71460468 (+) | GCCCTCTTAGCGCAGTGGGCAGCGCGTCAGT CTCATAATCTGAAGGTCCTGAGTTCGAGCCT |
| 173 | Met_CAT_chr6:28912 352-28912424 (+) | GCCTCCTTAGCGCAGTAGGCAGCGCGTCAGT CTCATAATCTGAAGGTCCTGAGTTCGAACCT |
| 174 | Met_CAT_chr6:26735 574-26735646 (-) | GCCCTCTTAGCGCAGCGGGCAGCGCGTCAGT CTCATAATCTGAAGGTCCTGAGTTCGAGCCT |
| 175 | Met_CAT_chr6:26701 712-26701784 (+) | GCCCTCTTAGCGCAGCTGGCAGCGCGTCAGT CTCATAATCTGAAGGTCCTGAGTTCAAGCCT |
| 176 | Met_CAT_chr16:8741 7628-87417700 (-) | GCCTCGTTAGCGCAGTAGGCAGCGCGTCAGT CTCATAATCTGAAGGTCGTGAGTTCGAGCCT |
| 177 | Met_CAT_chr6:58168 492-58168564 (-) | GCCCTCTTAGTGCAGCTGGCAGCGCGTCAGT TTCATAATCTGAAAGTCCTGAGTTCAAGCCTC |
| 178 | Phe_GAA_chr6:28758 499-28758571 (-) | GCCGAAATAGCTCAGTTGGGAGAGCGTTAGA CTGAAGATCTAAAGGTCCCTGGTTCGATCCC |

TABLE 1-continued

List of tRNA Sequences

| SEQ ID NO | tRNA name | tRNA sequence |
|---|---|---|
| 179 | Phe_GAA_chr11:59333853-59333925 (-) | GCCGAAATAGCTCAGTTGGGAGAGCGTTAGACTGAAGATCTAAAGGTCCCTGGTTCAATCCC |
| 180 | Phe_GAA_chr6:28775610-28775682 (-) | GCCGAGATAGCTCAGTTGGGAGAGCGTTAGACTGAAGATCTAAAGGTCCCTGGTTCAATCCC |
| 181 | Phe_GAA_chr6:28791093-28791166 (-) | GCCGAAATAGCTCAGTTGGGAGAGCGTTAGACCGAAGATCTTAAAGGTCCCTGGTTCAATCC |
| 182 | Phe_GAA_chr6:28731374-28731447 (-) | GCTGAAATAGCTCAGTTGGGAGAGCGTTAGACTGAAGATCTTAAAGTTCCCTGGTTCAACCCT |
| 183 | Pro_AGG_chr16:3241989-3242060 (+) | GGCTCGTTGGTCTAGGGGTATGATTCTCGCTTAGGATGCGAGAGGTCCCGGGTTCAAATCCCG |
| 184 | Pro_AGG_chr1:167684725-167684796 (-) | GGCTCGTTGGTCTAGGGGTATGATTCTCGCTTAGGGTGCGAGAGGTCCCGGGTTCAAATCCCG |
| 185 | Pro_CGG_chr1:167683962-167684033 (+) | GGCTCGTTGGTCTAGGGGTATGATTCTCGCTTCGGGTGCGAGAGGTCCCGGGTTCAAATCCCG |
| 186 | Pro_CGG_chr6:27059521-27059592 (+) | GGCTCGTTGGTCTAGGGGTATGATTCTCGCTTCGGGTGTGAGAGGTCCCGGGTTCAAATCCCG |
| 187 | Pro_TGG_chr14:21101165-21101236 (+) | GGCTCGTTGGTCTAGTGGTATGATTCTCGCTTTGGGTGCGAGAGGTCCCGGGTTCAAATCCCG |
| 188 | Pro_TGG_chr11:75946869-75946940 (-) | GGCTCGTTGGTCTAGGGGTATGATTCTCGGTTTGGGTCCGAGAGGTCCCGGGTTCAAATCCCG |
| 189 | Pro_TGG_chr5:180615854-180615925 (-) | GGCTCGTTGGTCTAGGGGTATGATTCTCGCTTTGGGTGCGAGAGGTCCCGGGTTCAAATCCCG |
| 190 | Ser_TCA_chr19:45981859-45981945 (-) | GCCCGGATGATCCTCAGTGGTCTGGGGTGCAGGCTTCAAACCTGTAGCTGTCTAGCGACAGA |
| 191 | Ser_TCA_chr22:44546537-44546620 (+) | GCTCGGATGATCCTCAGTGGTCTGGGGTGCAGGCTTCAAACCTGTAGCTGTCTAGTGACAGA |
| 192 | Ser_AGA_chr6:27509554-27509635 (-) | GTAGTCGTGGCCGAGTGGTTAAGGCGATGGACTAGAAATCCATTGGGGTTTCCCCGCGCAGG |
| 193 | Ser_AGA_chr6:26327817-26327898 (+) | GTAGTCGTGGCCGAGTGGTTAAGGCGATGGACTAGAAATCCATTGGGGTCTCCCCGCGCAGG |
| 194 | Ser_AGA_chr6:27499987-27500068 (+) | GTAGTCGTGGCCGAGTGGTTAAGGCGATGGACTAGAAATCCATTGGGGTTTCCCCACGCAGG |
| 195 | Ser_AGA_chr6:27521192-27521273 (-) | GTAGTCGTGGCCGAGTGGTTAAGGTGATGGACTAGAAACCCATTGGGGTCTCCCCGCGCAGG |
| 196 | Ser_CGA_chr17:8042199-8042280 (-) | GCTGTGATGGCCGAGTGGTTAAGGCGTTGGACTCGAAATCCAATGGGGTCTCCCCGCGCAGG |
| 197 | Ser_CGA_chr6:27177628-27177709 (+) | GCTGTGATGGCCGAGTGGTTAAGGCGTTGGACTCGAAATCCAATGGGGTCTCCCCGCGCAGG |
| 198 | Ser_CGA_chr6:27640229-27640310 (-) | GCTGTGATGGCCGAGTGGTTAAGGTGTTGGACTCGAAATCCAATGGGGGTTCCCCGCGCAGG |
| 199 | Ser_CGA_chr12:56584148-56584229 (+) | GTCACGGTGGCCGAGTGGTTAAGGCGTTGGACTCGAAATCCAATGGGGTTTCCCCGCACAGG |
| 200 | Ser_GCT_chr6:27065085-27065166 (+) | GACGAGGTGGCCGAGTGGTTAAGGCGATGGACTGCTAATCCATTGTGCTCTGCACGCGTGG |
| 201 | Ser_GCT_chr6:27265775-27265856 (+) | GACGAGGTGGCCGAGTGGTTAAGGCGATGGACTGCTAATCCATTGTGCTCTGCACGCGTGG |
| 202 | Ser_GCT_chr11:66115591-66115672 (+) | GACGAGGTGGCCGAGTGGTTAAGGCGATGGACTGCTAATCCATTGTGCTTTGCACGCGTGGG |
| 203 | Ser_GCT_chr6:28565117-28565198 (-) | GACGAGGTGGCCGAGTGGTTAAGGCGATGGACTGCTAATCCATTGTGCTCTGCACGCGTGG |

TABLE 1-continued

List of tRNA Sequences

| SEQ ID NO | tRNA name | tRNA sequence |
|---|---|---|
| 204 | Ser_GCT_chr6:28180815-28180896 (+) | GACGAGGTGGCCGAGTGGTTAAGGCGATGGACTGCTAATCCATTGTGCTCTGCACACGTGG |
| 205 | Ser_GCT_chr6:26305718-26305801 (-) | GGAGAGGCCTGGCCGAGTGGTTAAGGCGATGGACTGCTAATCCATTGTGCTCTGCACGCGTG |
| 206 | Ser_TGA_chr10:69524261-69524342 (+) | GCAGCGATGGCCGAGTGGTTAAGGCGTTGGACTTGAAATCCAATGGGGTCTCCCCGCGCAGG |
| 207 | Ser_TGA_chr6:27513468-27513549 (+) | GTAGTCGTGGCCGAGTGGTTAAGGCGATGGACTTGAAATCCATTGGGGTTTCCCCGCGCAGG |
| 208 | Ser_TGA_chr6:26312824-26312905 (-) | GTAGTCGTGGCCGAGTGGTTAAGGCGATGGACTTGAAATCCATTGGGGTCTCCCCGCGCAGG |
| 209 | Ser_TGA_chr6:27473607-27473688 (-) | GTAGTCGTGGCCGAGTGGTTAAGGCGATGGACTTGAAATCCATTGGGGTTTCCCCGCGCAGG |
| 210 | Thr_AGT_chr17:8090478-8090551 (+) | GGCGCCGTGGCTTAGTTGGTTAAAGCGCCTGTCTAGTAAACAGGAGATCCTGGGTTCGAATC |
| 211 | Thr_AGT_chr6:26533145-26533218 (-) | GGCTCCGTGGCTTAGCTGGTTAAAGCGCCTGTCTAGTAAACAGGAGATCCTGGGTTCGAATC |
| 212 | Thr_AGT_chr6:28693795-28693868 (+) | GGCTCCGTAGCTTAGTTGGTTAAAGCGCCTGTCTAGTAAACAGGAGATCCTGGGTTCGACTC |
| 213 | Thr_AGT_chr6:27694473-27694546 (+) | GGCTTCGTGGCTTAGCTGGTTAAAGCGCCTGTCTAGTAAACAGGAGATCCTGGGTTCGAATC |
| 214 | Thr_AGT_chr17:8042770-8042843 (-) | GGCGCCGTGGCTTAGCTGGTTAAAGCGCCTGTCTAGTAAACAGGAGATCCTGGGTTCGAATC |
| 215 | Thr_AGT_chr6:27130050-27130123 (+) | GGCCCTGTGGCTTAGCTGGTCAAAGCGCCTGTCTAGTAAACAGGAGATCCTGGGTTCGAATC |
| 216 | Thr_CGT_chr6:28456770-28456843 (-) | GGCTCTATGGCTTAGTTGGTTAAAGCGCCTGTCTCGTAAACAGGAGATCCTGGGTTCGACTCC |
| 217 | Thr_CGT_chr16:14379750-14379821 (+) | GGCGCGGTGGCCAAGTGGTAAGGCGTCGGTCTCGTAAACCGAAGATCACGGGTTCGAACCCC |
| 218 | Thr_CGT_chr6:28615984-28616057 (-) | GGCTCTGTGGCTTAGTTGGCTAAAGCGCCTGTCTCGTAAACAGGAGATCCTGGGTTCGAATC |
| 219 | Thr_CGT_chr17:29877093-29877164 (+) | GGCGCGGTGGCCAAGTGGTAAGGCGTCGGTCTCGTAAACCGAAGATCGCGGGTTCGAACCCC |
| 220 | Thr_CGT_chr6:27586135-27586208 (+) | GGCCCTGTAGCTCAGCGGTTGGAGCGCTGGTCTCGTAAACCTAGGGGTCGTGAGTTCAAATC |
| 221 | Thr_TGT_chr6:28442329-28442402 (-) | GGCTCTATGGCTTAGTTGGTTAAAGCGCCTGTCTTGTAAACAGGAGATCCTGGGTTCGAATCC |
| 222 | Thr_TGT_chr1:222638347-222638419 (+) | GGCTCCATAGCTCAGTGGTTAGAGCACTGGTCTTGTAAACCAGGGGTCGCGAGTTCGATCCT |
| 223 | Thr_TGT_chr14:21081949-21082021 (-) | GGCTCCATAGCTCAGGGGTTAGAGCGCTGGTCTTGTAAACCAGGGGTCGCGAGTTCAATTCT |
| 224 | Thr_TGT_chr14:21099319-21099391 (-) | GGCTCCATAGCTCAGGGGTTAGAGCACTGGTCTTGTAAACCAGGGGTCGCGAGTTCAAATCT |
| 225 | Thr_TGT_chr14:21149849-21149921 (+) | GGCCCTATAGCTCAGGGGTTAGAGCACTGGTCTTGTAAACCAGGGGTCGCGAGTTCAAATCT |
| 226 | Thr_TGT_chr5:180618687-180618758 (-) | GGCTCCATAGCTCAGGGGTTAGAGCACTGGTCTTGTAAACCAGGGTCGCGAGTTCAAATCTC |
| 227 | Trp_CCA_chr17:8124187-8124258 (-) | GGCCTCGTGGCGCAACGGTAGCGCGTCTGACTCCAGATCAGAAGGTTGCGTGTTCAAATCAC |
| 228 | Trp_CCA_chr17:19411494-19411565 (+) | GACCTCGTGGCGCAATGGTAGCGCGTCTGACTCCAGATCAGAAGGTTGCGTGTTCAAGTCAC |

TABLE 1-continued

List of tRNA Sequences

| SEQ ID NO | tRNA name | tRNA sequence |
|---|---|---|
| 229 | Trp_CCA_chr6:26319330-26319401 (-) | GACCTCGTGGCGCAACGGTAGCGCGTCTGACTCCAGATCAGAAGGTTGCGTGTTCAAATCAC |
| 230 | Trp_CCA_chr12:98898030-98898101 (+) | GACCTCGTGGCGCAACGGTAGCGCGTCTGACTCCAGATCAGAAGGCTGCGTGTTCGAATCAC |
| 231 | Trp_CCA_chr7:99067307-99067378 (+) | GACCTCGTGGCGCAACGGCAGCGCGTCTGACTCCAGATCAGAAGGTTGCGTGTTCAAATCAC |
| 232 | Tyr_ATA_chr2:219110549-219110641 (+) | CCTTCAATAGTTCAGCTGGTAGAGCAGAGGACTATAGCTACTTCCTCAGTAGGAGACGTCCTT |
| 233 | Tyr_GTA_chr6:26569086-26569176 (+) | CCTTCGATAGCTCAGTTGGTAGAGCGGAGGACTGTAGTTGGCTGTGTCCTTAGACATCCTTAG |
| 234 | Tyr_GTA_chr2:27273650-27273738 (+) | CCTTCGATAGCTCAGTTGGTAGAGCGGAGGACTGTAGTGGATAGGGCGTGGCAATCCTTAGG |
| 235 | Tyr_GTA_chr6:26577332-26577420 (+) | CCTTCGATAGCTCAGTTGGTAGAGCGGAGGACTGTAGGCTCATTAAGCAAGGTATCCTTAGG |
| 236 | Tyr_GTA_chr14:21125623-21125716 (-) | CCTTCGATAGCTCAGCTGGTAGAGCGGAGGACTGTAGATTGTATAGACATTTGCGGACATCCT |
| 237 | Tyr_GTA_chr8:67025602-67025694 (+) | CCTTCGATAGCTCAGCTGGTAGAGCGGAGGACTGTAGCTACTTCCTCAGCAGGAGACATCCTT |
| 238 | Tyr_GTA_chr8:67026223-67026311 (+) | CCTTCGATAGCTCAGCTGGTAGAGCGGAGGACTGTAGGCGCGCGCCCGTGGCCATCCTTAGG |
| 239 | Tyr_GTA_chr14:21121258-21121351 (-) | CCTTCGATAGCTCAGCTGGTAGAGCGGAGGACTGTAGCCTGTAGAAACATTTGTGGACATCC |
| 240 | Tyr_GTA_chr14:21131351-21131444 (-) | CCTTCGATAGCTCAGCTGGTAGAGCGGAGGACTGTAGATTGTACAGACATTTGCGGACATCC |
| 241 | Tyr_GTA_chr14:21151432-21151520 (+) | CCTTCGATAGCTCAGCTGGTAGAGCGGAGGACTGTAGTACTTAATGTGTGGTCATCCTTAGGT |
| 242 | Tyr_GTA_chr6:26595102-26595190 (+) | CCTTCGATAGCTCAGCTGGTAGAGCGGAGGACTGTAGGGGTTTGAATGTGGTCATCCTTAGGT |
| 243 | Tyr_GTA_chr14:21128117-21128210 (-) | CCTTCGATAGCTCAGCTGGTAGAGCGGAGGACTGTAGACTGCGGAAACGTTTGTGGACATCC |
| 244 | Tyr_GTA_chr6:26575798-26575887 (+) | CTTTCGATAGCTCAGTTGGTAGAGCGGAGGACTGTAGGTTCATTAAACTAAGGCATCCTTAG |
| 245 | Tyr_GTA_chr8:66609532-66609619 (-) | TCTTCAATAGCTCAGCTGGTAGAGCGGAGGACTGTAGGTGCACGCCCGTGGCCATTCTTAGG |
| 246 | Val_AAC_chr3:169490018-169490090 (+) | GTTTCCGTAGTGTAGTGGTTATCACGTTCGCCTAACACGCGAAAGGTCCCCGGTTCGAAACCG |
| 247 | Val_AAC_chr5:180615416-180615488 (-) | GTTTCCGTAGTGTAGTGGTCATCACGTTCGCCTAACACGCGAAAGGTCCCCGGTTCGAAACCG |
| 248 | Val_AAC_chr6:27618707-27618779 (-) | GTTTCCGTAGTGTAGTGGTTATCACGTTCGCCTAACACGCGAAAGGTCCCTGGATCAAAACCA |
| 249 | Val_AAC_chr6:27648885-27648957 (-) | GTTTCCGTAGTGTAGTGGTTATCACGTTCGCCTAACACGCGAAAGGTCCGCGGTTCGAAACCG |
| 250 | Val_AAC_chr6:27203288-27203360 (+) | GTTTCCGTAGTGTAGTGGTTATCACGTTTGCCTAACACGCGAAAGGTCCCCGGTTCGAAACCG |
| 251 | Val_AAC_chr6:28703206-28703277 (-) | GGGGGTGTAGCTCAGTGGTAGAGCGTATGCTTAACATTCATGAGGCTCTGGGTTCGATCCCC |
| 252 | Val_CAC_chr1:161369490-161369562 (-) | GTTTCCGTAGTGTAGTGGTTATCACGTTCGCCTCACACGCGAAAGGTCCCCGGTTCGAAACCG |
| 253 | Val_CAC_chr6:27248049-27248121 (-) | GCTTCTGTAGTGTAGTGGTTATCACGTTCGCCTCACACGCGAAAGGTCCCCGGTTCGAAACCG |

TABLE 1-continued

List of tRNA Sequences

| SEQ ID NO | tRNA name | tRNA sequence |
|---|---|---|
| 254 | Val_CAC_chr19:4724 647-4724719 (-) | GTTTCCGTAGTGTAGCGGTTATCACATTCGCC TCACACGCGAAAGGTCCCCGGTTCGATCCCG |
| 255 | Val_CAC_chr1:14929 8555-149298627 (-) | GTTTCCGTAGTGTAGTGGTTATCACGTTCGCC TCACACGCGAAAGGTCCCCGGTTCGAAACTG |
| 256 | Val_CAC_chr1:14968 4088-149684161 (-) | GTTTCCGTAGTGTAGTGGTTATCACGTTCGCC TCACACGCGTAAAGGTCCCCGGTTCGAAACC |
| 257 | Val_CAC_chr6:27173 867-27173939 (-) | GTTTCCGTAGTGGAGTGGTTATCACGTTCGCC TCACACGCGAAAGGTCCCCGGTTTGAAACCA |
| 258 | Val_TAC_chr11:5931 8102-59318174 (-) | GGTTCCATAGTGTAGTGGTTATCACGTCTGCT TTACACGCAGAAGGTCCTGGGTTCGAGCCCC |
| 259 | Val_TAC_chr11:5931 8460-59318532 (-) | GGTTCCATAGTGTAGCGGTTATCACGTCTGCT TTACACGCAGAAGGTCCTGGGTTCGAGCCCC |
| 260 | Val_TAC_chr10:5895 674-5895746 (-) | GGTTCCATAGTGTAGTGGTTATCACATCTGCT TTACACGCAGAAGGTCCTGGGTTCAAGCCCC |
| 261 | Val_TAC_chr6:27258 405-27258477 (+) | GTTTCCGTGGTGTAGTGGTTATCACATTCGCC TTACACGCGAAAGGTCCTCGGGTCGAAACCG |
| 262 | iMet_CAT_chr1:1536 43726-153643797 (+) | AGCAGAGTGGCGCAGCGGAAGCGTGCTGGG CCCATAACCCAGAGGTCGATGGATCGAAACC |
| 263 | iMet_CAT_chr6:2774 5664-27745735 (+) | AGCAGAGTGGCGCAGCGGAAGCGTGCTGGG CCCATAACCCAGAGGTCGATGGATCTAAACC |
| 264 | Glu_TTC_chr1:16861 773-16861845 (-) | TCCCTGGTGGTCTAGTGGCTAGGATTCGGCG CTTTCACCGCCGCGGCCCGGGTTCGATTCCCG |
| 265 | Gly_CCC_chr1:17004 765-17004836 (-) | GCGTTGGTGGTTTAGTGGTAGAATTCTCGCCT CCCATGCGGGAGACCCGGGTTCAATTCCCGG |
| 266 | Gly_CCC_chr1:17053 779-17053850 (+) | GGCCTTGGTGGTGCAGTGGTAGAATTCTCGC CTCCCACGTGGGAGACCCGGGTTCAATTCCC |
| 267 | Glu_TTC_chr1:17199 077-17199149 (+) | GTCCCTGGTGGTCTAGTGGCTAGGATTCGGC GCTTTCACCGCCGCGGCCCGGGTTCGATTCCC |
| 268 | Asn_GTT_chr1:17216 171-17216245 (+) | TGTCTCTGTGGCGCAATCGGTTAGCGCGTTCG GCTGTTAACCGAAAGATTGGTGGTTCGAGCC |
| 269 | Arg_TCT_chr1:94313 128-94313213 (+) | TGGCTCCGTGGCGCAATGGATAGCGCATTGG ACTTCTAGAGGCTGAAGGCATTCAAAGGTTC |
| 270 | Lys_CTT_chr1:14539 5521-145395594 (-) | GCCCGGCTAGCTCAGTCGGTAGAGCATGAGA CTCTTAATCTCAGGGTCGTGGGTTCGAGCCCC |
| 271 | His_GTG_chr1:14539 6880-145396952 (-) | GCCGTGATCGTATAGTGGTTAGTACTCTGCGT TGTGGCCGCAGCAACCTCGGTTCGAATCCGA |
| 272 | Gly_TCC_chr1:14539 7863-145397935 (-) | GCGTTGGTGGTATAGTGGTGAGCATAGCTGC CTTCCAAGCAGTTGACCCGGGTTCGATTCCC |
| 273 | Glu_CTC_chr1:14539 9232-145399304 (-) | TCCCTGGTGGTCTAGTGGTTAGGATTCGGCG CTCTCACCGCCGCGGCCCGGGTTCGATTCCC |
| 274 | Gln_CTG_chr1:14596 3303-145963375 (+) | AGGTTCCATGGTGTAATGGTGAGCACTCTGG ACTCTGAATCCAGCGATCCGAGTTCGAGTCT |
| 275 | Asn_GTT_chr1:14800 0804-148000878 (+) | TGTCTCTGTGGCGTAGTCGGTTAGCGCGTTCG GCTGTTAACCGAAAAGTTGGTGGTTCGAGCC |
| 276 | Asn_GTT_chr1:14824 8114-148248188 (+) | TGTCTCTGTGGCGCAATCGGTTAGCGCGTTCG GCTGTTAACCGAAAGGTTGGTGGTTCGAGCC |
| 277 | Asn_GTT_chr1:14859 8313-148598387 (-) | GTCTCTGTGGCGCAATCGGTTAGCGCATTCG GCTGTTAACCGAAAGGTTGGTGGTTCGAGCC |
| 278 | Asn_GTT_chr1:14923 0569-149230643 (-) | GTCTCTGTGGCGCAATGGGTTAGCGCGTTCG GCTGTTAACCGAAAGGTTGGTGGTTCGAGCC |

TABLE 1-continued

List of tRNA Sequences

| SEQ ID NO | tRNA name | tRNA sequence |
|---|---|---|
| 279 | Val_CAC_chr1:14929 4665-149294736 (-) | GCACTGGTGGTTCAGTGGTAGAATTCTCGCC TCACACGCGGGACACCCGGGTTCAATTCCCG |
| 280 | Val_CAC_chr1:14929 8554-149298627 (-) | GTTTCCGTAGTGTAGTGGTTATCACGTTCGCC TCACACGCGAAAGGTCCCCGGTTCGAAACTG |
| 281 | Gly_CCC_chr1:14968 0209-149680280 (-) | GCACTGGTGGTTCAGTGGTAGAATTCTCGCC TCCCACGCGGGAGACCCGGGTTTAATTCCCG |
| 282 | Val_CAC_chr1:14968 4087-149684161 (-) | GTTTCCGTAGTGTAGTGGTTATCACGTTCGCC TCACACGCGTAAAGGTCCCCGGTTCGAAACC |
| 283 | Met_CAT_chr1:15364 3725-153643797 (+) | TAGCAGAGTGGCGCAGCGGAAGCGTGCTGG GCCCATAACCCAGAGGTCGATGGATCGAAAC |
| 284 | Val_CAC_chr1:16136 9489-161369562 (-) | GTTTCCGTAGTGTAGTGGTTATCACGTTCGCC TCACACGCGAAAGGTCCCCGGTTCGAAACCG |
| 285 | Asp_GTC_chr1:16141 0614-161410686 (-) | TCCTCGTTAGTATAGTGGTGAGTATCCCCGCC TGTCACGCGGGAGACCGGGGTTCGATTCCCC |
| 286 | Gly_GCC_chr1:16141 3093-161413164 (+) | TGCATGGGTGGTTCAGTGGTAGAATTCTCGC CTGCCACGCGGGAGGCCCGGGTTCGATTCCC |
| 287 | Glu_CTC_chr1:16141 7017-161417089 (-) | TCCCTGGTGGTCTAGTGGTTAGGATTCGGCG CTCTCACCGCCGCGGCCCGGGTTCGATTCCC |
| 288 | Asp_GTC_chr1:16149 2934-161493006 (+) | ATCCTTGTTACTATAGTGGTGAGTATCTCTGC CTGTCATGCGTGAGAGAGGGGGTCGATTCCC |
| 289 | Gly_GCC_chr1:16149 3636-161493707 (-) | GCATTGGTGGTTCAGTGGTAGAATTCTCGCCT GCCACGCGGGAGGCCCGGGTTCGATTCCCGG |
| 290 | Leu_CAG_chr1:16150 0131-161500214 (-) | GTCAGGATGGCCGAGCGGTCTAAGGCGCTGC GTTCAGGTCGCAGTCTCCCCTGGAGGCGTGG |
| 291 | Gly_TCC_chr1:16150 0902-161500974 (+) | CGCGTTGGTGGTATAGTGGTGAGCATAGCTG CCTTCCAAGCAGTTGACCCGGGTTCGATTCCC |
| 292 | Asn_GTT_chr1:16151 0030-161510104 (+) | CGTCTCTGTGGCGCAATCGGTTAGCGCGTTC GGCTGTTAACCGAAAGGTTGGTGGTTCGATC |
| 293 | Glu_TTC_chr1:16158 2507-161582579 (+) | CGCGTTGGTGGTGTAGTGGTGAGCACAGCTG CCTTTCAAGCAGTTAACGCGGGTTCGATTCCC |
| 294 | Pro_CGG_chr1:16768 3961-167684033 (+) | CGGCTCGTTGGTCTAGGGGTATGATTCTCGCT TCGGGTGCGAGAGGTCCCGGGTTCAAATCCC |
| 295 | Pro_AGG_chr1:16768 4724-167684796 (-) | GGCTCGTTGGTCTAGGGGTATGATTCTCGCTT AGGGTGCGAGAGGTCCCGGGTTCAAATCCCG |
| 296 | Lys_TTT_chr1:20447 5654-204475727 (+) | CGCCCGGATAGCTCAGTCGGTAGAGCATCAG ACTTTTAATCTGAGGGTCCAGGGTTCAAGTC |
| 297 | Lys_TTT_chr1:20447 6157-204476230 (-) | GCCCGGATAGCTCAGTCGGTAGAGCATCAGA CTTTTAATCTGAGGGTCCAGGGTTCAAGTCCC |
| 298 | Leu_CAA_chr1:24916 8053-249168159 (+) | TGTCAGGATGGCCGAGTGGTCTAAGGCGCCA GACTCAAGGTAAGCACCTTGCCTGCGGGCTT |
| 299 | Glu_CTC_chr1:24916 8446-249168518 (+) | TTCCCTGGTGGTCTAGTGGTTAGGATTCGGCG CTCTCACCGCCGCGGCCCGGGTTCGATTCCC |
| 300 | Tyr_GTA_chr2:27273 649-27273738 (+) | GCCTTCGATAGCTCAGTTGGTAGAGCGGAGG ACTGTAGTGGATAGGGCGTGGCAATCCTTAG |
| 301 | Ala_AGC_chr2:27274 081-27274154 (+) | CGGGGGATTAGCTCAAATGGTAGAGCGCTCG CTTAGCATGCGAGAGGTAGCGGGATCGATGC |
| 302 | Ile_TAT_chr2:430376 75-43037768 (+) | AGCTCCAGTGGCGCAATCGGTTAGCGCGCGG TACTTATACAGCAGTACATGCAGAGCAATGC |
| 303 | Gly_CCC_chr2:70476 122-70476193 (-) | GCGCCGCTGGTGTAGTGGTATCATGCAAGAT TCCCATTCTTGCGACCCGGGTTCGATTCCCGG |

TABLE 1-continued

List of tRNA Sequences

| SEQ ID NO | tRNA name | tRNA sequence |
|---|---|---|
| 304 | Glu_TTC_chr2:131094700-131094772 (-) | TCCCATATGGTCTAGCGGTTAGGATTCCTGGTTTTCACCCAGGTGGCCCGGGTTCGACTCCCG |
| 305 | Ala_CGC_chr2:157257280-157257352 (+) | GGGGGATGTAGCTCAGTGGTAGAGCGCGCGCTTCGCATGTGTGAGGTCCCGGGTTCAATCCCC |
| 306 | Gly_GCC_chr2:157257658-157257729 (-) | GCATTGGTGGTTCAGTGGTAGAATTCTCGCCTGCCACGCGGGAGGCCCGGGTTCGATTCCCGG |
| 307 | Arg_ACG_chr3:45730490-45730563 (-) | GGGCCAGTGGCGCAATGGATAACGCGTCTGACTACGGATCAGAAGATTCTAGGTTCGACTCC |
| 308 | Val_AAC_chr3:169490017-169490090 (+) | GGTTTCCGTAGTGTAGTGGTTATCACGTTCGCCTAACACGCGAAAGGTCCCCGGTTCGAAACC |
| 309 | Val_AAC_chr5:180596609-180596682 (+) | AGTTTCCGTAGTGTAGTGGTTATCACGTTCGCCTAACACGCGAAAGGTCCCCGGTTCGAAACC |
| 310 | Leu_AAG_chr5:180614700-180614782 (+) | AGGTAGCGTGGCCGAGCGGTCTAAGGCGCTGGATTAAGGCTCCAGTCTCTTCGGGGGCGTGG |
| 311 | Val_AAC_chr5:180615415-180615488 (-) | GTTTCCGTAGTGTAGTGGTCATCACGTTCGCCTAACACGCGAAAGGTCCCCGGTTCGAAACCG |
| 312 | Pro_TGG_chr5:180615853-180615925 (-) | GGCTCGTTGGTCTAGGGGTATGATTCTCGCTTTGGGTGCGAGAGGTCCCGGGTTCAAATCCCG |
| 313 | Thr_TGT_chr5:180618686-180618758 (-) | GGCTCCATAGCTCAGGGGTTAGAGCACTGGTCTTGTAAACCAGGGTCGCGAGTTCAAATCTC |
| 314 | Ala_TGC_chr5:180633867-180633939 (+) | TGGGGATGTAGCTCAGTGGTAGAGCGCATGCTTTGCATGTATGAGGCCCCGGGTTCGATCCCC |
| 315 | Lys_CTT_chr5:180634754-180634827 (+) | CGCCCGGCTAGCTCAGTCGGTAGAGCATGAGACTCTTAATCTCAGGGTCGTGGGTTCGAGCC |
| 316 | Val_AAC_chr5:180645269-180645342 (-) | GTTTCCGTAGTGTAGTGGTTATCACGTTCGCCTAACACGCGAAAGGTCCCCGGTTCGAAACCG |
| 317 | Lys_CTT_chr5:180648978-180649051 (-) | GCCCGGCTAGCTCAGTCGGTAGAGCATGAGACTCTTAATCTCAGGGTCGTGGGTTCGAGCCCC |
| 318 | Val_CAC_chr5:180649394-180649467 (-) | GTTTCCGTAGTGTAGTGGTTATCACGTTCGCCTCACACGCGAAAGGTCCCCGGTTCGAAACCG |
| 319 | Met_CAT_chr6:26286753-26286825 (+) | CAGCAGAGTGGCGCAGCGGAAGCGTGCTGGGCCCATAACCCAGAGGTCGATGGATCGAAAC |
| 320 | Ser_GCT_chr6:26305717-26305801 (-) | GGAGAGGCCTGGCCGAGTGGTTAAGGCGATGGACTGCTAATCCATTGTGCTCTGCACGCGTG |
| 321 | Gln_TTG_chr6:26311423-26311495 (-) | GGCCCCATGGTGTAATGGTTAGCACTCTGGACTTTGAATCCAGCGATCCGAGTTCAAATCTC |
| 322 | Gln_TTG_chr6:26311974-26312046 (-) | GGCCCCATGGTGTAATGGTTAGCACTCTGGACTTTGAATCCAGCGATCCGAGTTCAAATCTC |
| 323 | Ser_TGA_chr6:26312823-26312905 (-) | GTAGTCGTGGCCGAGTGGTTAAGGCGATGGACTTGAAATCCATTGGGGTCTCCCCGCGCAGG |
| 324 | Met_CAT_chr6:26313351-26313423 (-) | AGCAGAGTGGCGCAGCGGAAGCGTGCTGGGCCCATAACCCAGAGGTCGATGGATCGAAACC |
| 325 | Arg_TCG_chr6:26323045-26323118 (+) | GGACCACGTGGCCTAATGGATAAGGCGTCTGACTTCGGATCAGAAGATTGAGGGTTCGAATC |
| 326 | Ser_AGA_chr6:26327816-26327898 (+) | TGTAGTCGTGGCCGAGTGGTTAAGGCGATGGACTAGAAATCCATTGGGGTCTCCCCGCGCAG |
| 327 | Met_CAT_chr6:26330528-26330600 (-) | AGCAGAGTGGCGCAGCGGAAGCGTGCTGGGCCCATAACCCAGAGGTCGATGGATCGAAACC |
| 328 | Leu_CAG_chr6:26521435-26521518 (+) | CGTCAGGATGGCCGAGCGGTCTAAGGCGCTGCGTTCAGGTCGCAGTCTCCCCTGGAGGCGTG |

TABLE 1-continued

List of tRNA Sequences

| SEQ ID NO | tRNA name | tRNA sequence |
|---|---|---|
| 329 | Thr_AGT_chr6:26533 144-26533218 (-) | GGCTCCGTGGCTTAGCTGGTTAAAGCGCCTG TCTAGTAAACAGGAGATCCTGGGTTCGAATC |
| 330 | Arg_ACG_chr6:26537 725-26537798 (+) | AGGGCCAGTGGCGCAATGGATAACGCGTCTG ACTACGGATCAGAAGATTCCAGGTTCGACTC |
| 331 | Val_CAC_chr6:26538 281-26538354 (+) | GGTTTCCGTAGTGTAGTGGTTATCACGTTCGC CTCACACGCGAAAGGTCCCCGGTTCGAAACC |
| 332 | Ala_CGC_chr6:26553 730-26553802 (+) | AGGGGATGTAGCTCAGTGGTAGAGCGCATGC TTCGCATGTATGAGGTCCCGGGTTCGATCCCC |
| 333 | Ile_AAT_chr6:265543 49-26554423 (+) | TGGCCGGTTAGCTCAGTTGGTTAGAGCGTGG TGCTAATAACGCCAAGGTCGCGGGTTCGATC |
| 334 | Pro_AGG_chr6:26555 497-26555569 (+) | CGGCTCGTTGGTCTAGGGGTATGATTCTCGCT TAGGGTGCGAGAGGTCCCGGGTTCAAATCCC |
| 335 | Lys_CTT_chr6:26556 773-26556846 (+) | AGCCCGGCTAGCTCAGTCGGTAGAGCATGAG ACTCTTAATCTCAGGGTCGTGGGTTCGAGCC |
| 336 | Tyr_GTA_chr6:26569 085-26569176 (+) | TCCTTCGATAGCTCAGTTGGTAGAGCGGAGG ACTGTAGTTGGCTGTGTCCTTAGACATCCTTA |
| 337 | Ala_AGC_chr6:26572 091-26572164 (-) | GGGGAATTAGCTCAAATGGTAGAGCGCTCGC TTAGCATGCGAGAGGTAGCGGGATCGATGCC |
| 338 | Met_CAT_chr6:26766 443-26766516 (+) | CGCCCTCTTAGCGCAGCGGGCAGCGCGTCAG TCTCATAATCTGAAGGTCCTGAGTTCGAGCCT |
| 339 | Ile_TAT_chr6:269881 24-26988218 (+) | TGCTCCAGTGGCGCAATCGGTTAGCGCGCGG TACTTATATGGCAGTATGTGTGCGAGTGATG |
| 340 | His_GTG_chr6:27125 905-27125977 (+) | TGCCGTGATCGTATAGTGGTTAGTACTCTGCG TTGTGGCCGCAGCAACCTCGGTTCGAATCCG |
| 341 | Ile_AAT_chr6:271449 93-27145067 (-) | GGCCGGTTAGCTCAGTTGGTTAGAGCGTGGT GCTAATAACGCCAAGGTCGCGGGTTCGATCC |
| 342 | Val_AAC_chr6:27203 287-27203360 (+) | AGTTTCCGTAGTGTAGTGGTTATCACGTTTGC CTAACACGCGAAAGGTCCCCGGTTCGAAACC |
| 343 | Val_CAC_chr6:27248 048-27248121 (-) | GCTTCTGTAGTGTAGTGGTTATCACGTTCGCC TCACACGCGAAAGGTCCCCGGTTCGAAACCG |
| 344 | Asp_GTC_chr6:27447 452-27447524 (+) | TTCCTCGTTAGTATAGTGGTGAGTATCCCCGC CTGTCACGCGGGAGACCGGGGTTCGATTCCC |
| 345 | Ser_TGA_chr6:27473 606-27473688 (-) | GTAGTCGTGGCCGAGTGGTTAAGGCGATGGA CTTGAAATCCATTGGGGTTTCCCCGCGCAGG |
| 346 | Gln_CTG_chr6:27487 307-27487379 (+) | AGGTTCCATGGTGTAATGGTTAGCACTCTGG ACTCTGAATCCAGCGATCCGAGTTCAAATCT |
| 347 | Asp_GTC_chr6:27551 235-27551307 (-) | TCCTCGTTAGTATAGTGGTGAGTGTCCCCGTC TGTCACGCGGGAGACCGGGGTTCGATTCCCC |
| 348 | Val_AAC_chr6:27618 706-27618779 (-) | GTTTCCGTAGTGTAGTGGTTATCACGTTCGCC TAACACGCGAAAGGTCCCTGGATCAAAACCA |
| 349 | Ile_AAT_chr6:276559 66-27656040 (+) | CGGCCGGTTAGCTCAGTTGGTTAGAGCGTGG TGCTAATAACGCCAAGGTCGCGGGTTCGATC |
| 350 | Gln_CTG_chr6:27759 134-27759206 (-) | GGCCCCATGGTGTAATGGTCAGCACTCTGGA CTCTGAATCCAGCGATCCGAGTTCAAATCTC |
| 351 | Gln_TTG_chr6:27763 639-27763711 (-) | GGCCCCATGGTGTAATGGTTAGCACTCTGGA CTTTGAATCCAGCGATCCGAGTTCAAATCTC |
| 352 | Ala_AGC_chr6:28574 932-28575004 (+) | TGGGGGTGTAGCTCAGTGGTAGAGCGCGTGC TTAGCATGTACGAGGTCCCGGGTTCAATCCC |
| 353 | Ala_AGC_chr6:28626 013-28626085 (-) | GGGGATGTAGCTCAGTGGTAGAGCGCATGCT TAGCATGCATGAGGTCCCGGGTTCGATCCCC |

TABLE 1-continued

| List of tRNA Sequences | | |
|---|---|---|
| SEQ ID NO | tRNA name | tRNA sequence |
| 354 | Ala_CGC_chr6:28697091-28697163 (+) | AGGGGGTGTAGCTCAGTGGTAGAGCGCGTGCTTCGCATGTACGAGGCCCCGGGTTCGACCCC |
| 355 | Ala_AGC_chr6:28806220-28806292 (-) | GGGGGTGTAGCTCAGTGGTAGAGCGCGTGCTTAGCATGCACGAGGCCCCGGGTTCAATCCCC |
| 356 | Ala_AGC_chr6:28831461-28831533 (-) | GGGGGTGTAGCTCAGTGGTAGAGCGCGTGCTTAGCATGCACGAGGCCCCGGGTTCAATCCCC |
| 357 | Leu_CAA_chr6:28863999-28864105 (-) | GTCAGGATGGCCGAGTGGTCTAAGGCGCCAGACTCAAGCTAAGCTTCCTCCGCGGTGGGGAT |
| 358 | Leu_CAA_chr6:28908829-28908934 (+) | TGTCAGGATGGCCGAGTGGTCTAAGGCGCCAGACTCAAGCTTGGCTTCCTCGTGTTGAGGATT |
| 359 | Gln_CTG_chr6:28909377-28909449 (-) | GGTTCCATGGTGTAATGGTTAGCACTCTGGACTCTGAATCCAGCGATCCGAGTTCAAATCTC |
| 360 | Leu_AAG_chr6:28911398-28911480 (-) | GGTAGCGTGGCCGAGCGGTCTAAGGCGCTGGATTAAGGCTCCAGTCTCTTCGGGGGCGTGGG |
| 361 | Met_CAT_chr6:28912351-28912424 (+) | TGCCTCCTTAGCGCAGTAGGCAGCGCGTCAGTCTCATAATCTGAAGGTCCTGAGTTCGAACCT |
| 362 | Lys_TTT_chr6:28918805-28918878 (+) | AGCCCGGATAGCTCAGTCGGTAGAGCATCAGACTTTTAATCTGAGGGTCCAGGGTTCAAGTC |
| 363 | Met_CAT_chr6:28921041-28921114 (-) | GCCTCCTTAGCGCAGTAGGCAGCGCGTCAGTCTCATAATCTGAAGGTCCTGAGTTCGAACCT |
| 364 | Glu_CTC_chr6:28949975-28950047 (+) | TTCCCTGGTGGTCTAGTGGTTAGGATTCGGCGCTCTCACCGCCGCGGCCCGGGTTCGATTCCC |
| 365 | Leu_TAA_chr6:144537683-144537766 (+) | CACCAGGATGGCCGAGTGGTTAAGGCGTTGGACTTAAGATCCAATGGACATATGTCCGCGTG |
| 366 | Pro_AGG_chr7:128423503-128423575 (+) | TGGCTCGTTGGTCTAGGGGTATGATTCTCGCTTAGGGTGCGAGAGGTCCCGGGTTCAAATCCC |
| 367 | Arg_CCT_chr7:139025445-139025518 (+) | AGCCCCAGTGGCCTAATGGATAAGGCATTGGCCTCCTAAGCCAGGGATTGTGGGTTCGAGTC |
| 368 | Cys_GCA_chr7:149388271-149388343 (-) | GGGGATATAGCTCAGGGGTAGAGCATTTGACTGCAGATCAAGAGGTCCCCGGTTCAAATCCG |
| 369 | Tyr_GTA_chr8:67025601-67025694 (+) | CCCTTCGATAGCTCAGCTGGTAGAGCGGAGGACTGTAGCTACTTCCTCAGCAGGAGACATCC |
| 370 | Tyr_GTA_chr8:67026222-67026311 (+) | CCCTTCGATAGCTCAGCTGGTAGAGCGGAGGACTGTAGGCGCGCGCCCGTGGCCATCCTTAG |
| 371 | Ala_AGC_chr8:67026423-67026496 (+) | TGGGGGATTAGCTCAAATGGTAGAGCGCTCGCTTAGCATGCGAGAGGTAGCGGGATCGATGC |
| 372 | Ser_AGA_chr8:96281884-96281966 (-) | GTAGTCGTGGCCGAGTGGTTAAGGCGATGGACTAGAAATCCATTGGGGTCTCCCCGCGCAGG |
| 373 | Met_CAT_chr8:124169469-124169542 (-) | GCCTCGTTAGCGCAGTAGGTAGCGCGTCAGTCTCATAATCTGAAGGTCGTGAGTTCGATCCTC |
| 374 | Arg_TCT_chr9:131102354-131102445 (-) | GGCTCTGTGGCGCAATGGATAGCGCATTGGACTTCTAGCTGAGCCTAGTGTGGTCATTCAAA |
| 375 | Asn_GTT_chr10:22518437-22518511 (-) | GTCTCTGTGGCGCAATCGGTTAGCGCGTTCGGCTGTTAACCGAAAGGTTGGTGGTTCGAGCC |
| 376 | Ser_TGA_chr10:69524260-69524342 (+) | GGCAGCGATGGCCGAGTGGTTAAGGCGTTGGACTTGAAATCCAATGGGGTCTCCCCGCGCAG |
| 377 | Val_TAC_chr11:59318101-59318174 (-) | GGTTCCATAGTGTAGTGGTTATCACGTCTGCTTTACACGCAGAAGGTCCTGGGTTCGAGCCCC |
| 378 | Val_TAC_chr11:59318459-59318532 (-) | GGTTCCATAGTGTAGCGGTTATCACGTCTGCTTTACACGCAGAAGGTCCTGGGTTCGAGCCCC |

TABLE 1-continued

List of tRNA Sequences

| SEQ ID NO | tRNA name | tRNA sequence |
|---|---|---|
| 379 | Arg_TCT_chr11:5931 8766-59318852 (+) | TGGCTCTGTGGCGCAATGGATAGCGCATTGG ACTTCTAGATAGTTAGAGAAATTCAAAGGTT |
| 380 | Leu_TAA_chr11:5931 9227-59319310 (+) | TACCAGAATGGCCGAGTGGTTAAGGCGTTGG ACTTAAGATCCAATGGATTCATATCCGCGTG |
| 381 | Lys_TTT_chr11:5932 3901-59323974 (+) | GGCCCGGATAGCTCAGTCGGTAGAGCATCAG ACTTTTAATCTGAGGGTCCGGGGTTCAAGTC |
| 382 | Phe_GAA_chr11:5932 4969-59325042 (-) | GCCGAAATAGCTCAGTTGGGAGAGCGTTAGA CTGAAGATCTAAAGGTCCCTGGTTCGATCCC |
| 383 | Lys_TTT_chr11:5932 7807-59327880 (-) | GCCCGGATAGCTCAGTCGGTAGAGCATCAGA CTTTTAATCTGAGGGTCCAGGGTTCAAGTCCC |
| 384 | Phe_GAA_chr11:5933 3852-59333925 (-) | GCCGAAATAGCTCAGTTGGGAGAGCGTTAGA CTGAAGATCTAAAGGTCCCTGGTTCAATCCC |
| 385 | Ser_GCT_chr11:6611 5590-66115672 (+) | GGACGAGGTGGCCGAGTGGTTAAGGCGATG GACTGCTAATCCATTGTGCTTTGCACGCGTGG |
| 386 | Pro_TGG_chr11:7594 6868-75946940 (-) | GGCTCGTTGGTCTAGGGGTATGATTCTCGGTT TGGGTCCGAGAGGTCCCGGGTTCAAATCCCG |
| 387 | Ser_CGA_chr12:5658 4147-56584229 (+) | AGTCACGGTGGCCGAGTGGTTAAGGCGTTGG ACTCGAAATCCAATGGGGTTTCCCCGCACAG |
| 388 | Asp_GTC_chr12:9889 7280-98897352 (+) | CTCCTCGTTAGTATAGTGGTTAGTATCCCCGC CTGTCACGCGGGAGACCGGGGTTCAATTCCC |
| 389 | Trp_CCA_chr12:9889 8029-98898101 (+) | GGACCTCGTGGCGCAACGGTAGCGCGTCTGA CTCCAGATCAGAAGGCTGCGTGTTCGAATCA |
| 390 | Ala_TGC_chr12:1254 06300-125406372 (-) | GGGGATGTAGCTCAGTGGTAGAGCGCATGCT TTGCATGTATGAGGCCCCGGGTTCGATCCCC |
| 391 | Phe_GAA_chr12:1254 12388-125412461 (-) | GCCGAAATAGCTCAGTTGGGAGAGCGTTAGA CTGAAGATCTAAAGGTCCCTGGTTCGATCCC |
| 392 | Ala_TGC_chr12:1254 24511-125424583 (+) | AGGGGATGTAGCTCAGTGGTAGAGCGCATGC TTTGCACGTATGAGGCCCCGGGTTCAATCCC |
| 393 | Asn_GTT_chr13:3124 8100-31248174 (-) | GTCTCTGTGGCGCAATCGGTTAGCGCGTTCG GCTGTTAACCGAAAGGTTGGTGGTTCGAGCC |
| 394 | Glu_TTC_chr13:4549 2061-45492133 (-) | TCCCACATGGTCTAGCGGTTAGGATTCCTGGT TTTCACCCAGGCGGCCCGGGTTCGACTCCCG |
| 395 | Thr_TGT_chr14:2108 1948-21082021 (-) | GGCTCCATAGCTCAGGGGTTAGAGCGCTGGT CTTGTAAACCAGGGGTCGCGAGTTCAATTCT |
| 396 | Leu_TAG_chr14:2109 3528-21093610 (+) | TGGTAGTGTGGCCGAGCGGTCTAAGGCGCTG GATTTAGGCTCCAGTCTCTTCGGGGGCGTGG |
| 397 | Thr_TGT_chr14:2109 9318-21099391 (-) | GGCTCCATAGCTCAGGGGTTAGAGCACTGGT CTTGTAAACCAGGGGTCGCGAGTTCAAATCT |
| 398 | Pro_TGG_chr14:2110 1164-21101236 (+) | TGGCTCGTTGGTCTAGTGGTATGATTCTCGCT TTGGGTGCGAGAGGTCCCGGGTTCAAATCCC |
| 399 | Tyr_GTA_chr14:2113 1350-21131444 (-) | CCTTCGATAGCTCAGCTGGTAGAGCGGAGGA CTGTAGATTGTACAGACATTTGCGGACATCC |
| 400 | Thr_TGT_chr14:2114 9848-21149921 (+) | AGGCCCTATAGCTCAGGGGTTAGAGCACTGG TCTTGTAAACCAGGGGTCGCGAGTTCAAATC |
| 401 | Tyr_GTA_chr14:2115 1431-21151520 (+) | TCCTTCGATAGCTCAGCTGGTAGAGCGGAGG ACTGTAGTACTTAATGTGTGGTCATCCTTAGG |
| 402 | Pro_TGG_chr14:2115 2174-21152246 (+) | TGGCTCGTTGGTCTAGGGGTATGATTCTCGCT TTGGGTGCGAGAGGTCCCGGGTTCAAATCCC |
| 403 | Lys_CTT_chr14:5870 6612-58706685 (-) | GCCCGGCTAGCTCAGTCGGTAGAGCATGGGA CTCTTAATCCCAGGGTCGTGGGTTCGAGCCC |

TABLE 1-continued

List of tRNA Sequences

| SEQ ID NO | tRNA name | tRNA sequence |
|---|---|---|
| 404 | Ile_AAT_chr14:10278 3428-102783502 (+) | CGGCCGGTTAGCTCAGTTGGTTAGAGCGTGG TGCTAATAACGCCAAGGTCGCGGGTTCGATC |
| 405 | Glu_TTC_chr15:2632 7380-26327452 (-) | TCCCACATGGTCTAGCGGTTAGGATTCCTGGT TTTCACCCAGGCGGCCCGGGTTCGACTCCCG |
| 406 | Ser_GCT_chr15:4088 6022-40886104 (-) | GACGAGGTGGCCGAGTGGTTAAGGCGATGG ACTGCTAATCCATTGTGCTCTGCACGCGTGG |
| 407 | His_GTG_chr15:4549 0803-45490875 (-) | GCCGTGATCGTATAGTGGTTAGTACTCTGCGT TGTGGCCGCAGCAACCTCGGTTCGAATCCGA |
| 408 | His_GTG_chr15:4549 3348-45493420 (+) | CGCCGTGATCGTATAGTGGTTAGTACTCTGC GTTGTGGCCGCAGCAACCTCGGTTCGAATCC |
| 409 | Gln_CTG_chr15:6616 1399-66161471 (-) | GGTTCCATGGTGTAATGGTTAGCACTCTGGA CTCTGAATCCAGCGATCCGAGTTCAAATCTC |
| 410 | Lys_CTT_chr15:7915 2903-79152976 (+) | TGCCCGGCTAGCTCAGTCGGTAGAGCATGGG ACTCTTAATCCCAGGGTCGTGGGTTCGAGCC |
| 411 | Arg_TCG_chr15:8987 8303-89878376 (+) | GGGCCGCGTGGCCTAATGGATAAGGCGTCTG ACTTCGGATCAGAAGATTGCAGGTTCGAGTC |
| 412 | Gly_CCC_chr16:6867 35-686806 (-) | GCGCCGCTGGTGTAGTGGTATCATGCAAGAT TCCCATTCTTGCGACCCGGGTTCGATTCCCGG |
| 413 | Arg_CCG_chr16:3200 674-3200747 (+) | GGGCCGCGTGGCCTAATGGATAAGGCGTCTG ATTCCGGATCAGAAGATTGAGGGTTCGAGTC |
| 414 | Arg_CCT_chr16:3202 900-3202973 (+) | CGCCCCGGTGGCCTAATGGATAAGGCATTGG CCTCCTAAGCCAGGGATTGTGGGTTCGAGTC |
| 415 | Lys_CTT_chr16:3207 405-3207478 (-) | GCCCGGCTAGCTCAGTCGGTAGAGCATGAGA CCCTTAATCTCAGGGTCGTGGGTTCGAGCCC |
| 416 | Thr_CGT_chr16:1437 9749-14379821 (+) | AGGCGCGGTGGCCAAGTGGTAAGGCGTCGGT CTCGTAAACCGAAGATCACGGGTTCGAACCC |
| 417 | Leu_TAG_chr16:2220 7031-22207113 (-) | GGTAGCGTGGCCGAGTGGTCTAAGGCGCTGG ATTTAGGCTCCAGTCATTTCGATGGCGTGGGT |
| 418 | Leu_AAG_chr16:223 08460-22308542 (+) | GGGTAGCGTGGCCGAGCGGTCTAAGGCGCTG GATTAAGGCTCCAGTCTCTTCGGGGGCGTGG |
| 419 | Leu_CAG_chr16:5733 3862-57333945 (+) | AGTCAGGATGGCCGAGCGGTCTAAGGCGCTG CGTTCAGGTCGCAGTCTCCCCTGGAGGCGTG |
| 420 | Leu_CAG_chr16:5733 4391-57334474 (-) | GTCAGGATGGCCGAGCGGTCTAAGGCGCTGC GTTCAGGTCGCAGTCTCCCCTGGAGGCGTGG |
| 421 | Met_CAT_chr16:8741 7627-87417700 (-) | GCCTCGTTAGCGCAGTAGGCAGCGCGTCAGT CTCATAATCTGAAGGTCGTGAGTTCGAGCCT |
| 422 | Leu_TAG_chr17:8023 631-8023713 (-) | GGTAGCGTGGCCGAGCGGTCTAAGGCGCTGG ATTTAGGCTCCAGTCTCTTCGGAGGCGTGGG |
| 423 | Arg_TCT_chr17:8024 242-8024330 (+) | TGGCTCTGTGGCGCAATGGATAGCGCATTGG ACTTCTAGTGACGAATAGAGCAATTCAAAGG |
| 424 | Gly_GCC_chr17:8029 063-8029134 (+) | CGCATTGGTGGTTCAGTGGTAGAATTCTCGC CTGCCACGCGGGAGGCCCGGGTTCGATTCCC |
| 425 | Ser_CGA_chr17:8042 198-8042280 (-) | GCTGTGATGGCCGAGTGGTTAAGGCGTTGGA CTCGAAATCCAATGGGGTCTCCCCGCGCAGG |
| 426 | Thr_AGT_chr17:8042 769-8042843 (-) | GGCGCCGTGGCTTAGCTGGTTAAAGCGCCTG TCTAGTAAACAGGAGATCCTGGGTTCGAATC |
| 427 | Trp_CCA_chr17:8089 675-8089747 (+) | CGACCTCGTGGCGCAACGGTAGCGCGTCTGA CTCCAGATCAGAAGGTTGCGTGTTCAAATCA |
| 428 | Ser_GCT_chr17:8090 183-8090265 (+) | AGACGAGGTGGCCGAGTGGTTAAGGCGATG GACTGCTAATCCATTGTGCTCTGCACGCGTG |

TABLE 1-continued

List of tRNA Sequences

| SEQ ID NO | tRNA name | tRNA sequence |
|---|---|---|
| 429 | Thr_AGT_chr17:8090477-8090551 (+) | CGGCGCCGTGGCTTAGTTGGTTAAAGCGCCTGTCTAGTAAACAGGAGATCCTGGGTTCGAAT |
| 430 | Trp_CCA_chr17:8124186-8124258 (-) | GGCCTCGTGGCGCAACGGTAGCGCGTCTGACTCCAGATCAGAAGGTTGCGTGTTCAAATCAC |
| 431 | Gly_TCC_chr17:8124865-8124937 (+) | AGCGTTGGTGGTATAGTGGTAAGCATAGCTGCCTTCCAAGCAGTTGACCCGGGTTCGATTCCC |
| 432 | Asp_GTC_chr17:8125555-8125627 (-) | TCCTCGTTAGTATAGTGGTGAGTATCCCCGCCTGTCACGCGGGAGACCGGGGTTCGATTCCCC |
| 433 | Pro_CGG_chr17:8126150-8126222 (-) | GGCTCGTTGGTCTAGGGGTATGATTCTCGCTTCGGGTGCGAGAGGTCCCGGGTTCAAATCCCG |
| 434 | Thr_AGT_chr17:8129552-8129626 (-) | GGCGCCGTGGCTTAGTTGGTTAAAGCGCCTGTCTAGTAAACAGGAGATCCTGGGTTCGAATC |
| 435 | Ser_AGA_chr17:8129927-8130009 (-) | GTAGTCGTGGCCGAGTGGTTAAGGCGATGGACTAGAAATCCATTGGGGTCTCCCCGCGCAGG |
| 436 | Trp_CCA_chr17:19411493-19411565 (+) | TGACCTCGTGGCGCAATGGTAGCGCGTCTGACTCCAGATCAGAAGGTTGCGTGTTCAAGTCA |
| 437 | Thr_CGT_chr17:29877092-29877164 (+) | AGGCGCGGTGGCCAAGTGGTAAGGCGTCGGTCTCGTAAACCGAAGATCGCGGGTTCGAACCC |
| 438 | Cys_GCA_chr17:37023897-37023969 (+) | AGGGGGTATAGCTCAGTGGTAGAGCATTTGACTGCAGATCAAGAGGTCCCCGGTTCAAATCC |
| 439 | Cys_GCA_chr17:37025544-37025616 (-) | GGGGGTATAGCTCAGTGGTAGAGCATTTGACTGCAGATCAAGAGGTCCCTGGTTCAAATCCG |
| 440 | Cys_GCA_chr17:37309986-37310058 (-) | GGGGGTATAGCTCAGTGGTAGAGCATTTGACTGCAGATCAAGAGGTCCCCGGTTCAAATCCG |
| 441 | Gln_TTG_chr17:47269889-47269961 (+) | AGGTCCCATGGTGTAATGGTTAGCACTCTGGACTTTGAATCCAGCGATCCGAGTTCAAATCT |
| 442 | Arg_CCG_chr17:66016012-66016085 (-) | GACCCAGTGGCCTAATGGATAAGGCATCAGCCTCCGGAGCTGGGGATTGTGGGTTCGAGTCC |
| 443 | Arg_CCT_chr17:73030000-73030073 (+) | AGCCCCAGTGGCCTAATGGATAAGGCACTGGCCTCCTAAGCCAGGGATTGTGGGTTCGAGTC |
| 444 | Arg_CCT_chr17:73030525-73030598 (-) | GCCCCAGTGGCCTAATGGATAAGGCACTGGCCTCCTAAGCCAGGGATTGTGGGTTCGAGTCC |
| 445 | Arg_TCG_chr17:73031207-73031280 (+) | AGACCGCGTGGCCTAATGGATAAGGCGTCTGACTTCGGATCAGAAGATTGAGGGTTCGAGTC |
| 446 | Asn_GTT_chr19:1383561-1383635 (+) | CGTCTCTGTGGCGCAATCGGTTAGCGCGTTCGGCTGTTAACCGAAAGGTTGGTGGTTCGAGC |
| 447 | Gly_TCC_chr19:4724081-4724153 (+) | GGCGTTGGTGGTATAGTGGTTAGCATAGCTGCCTTCCAAGCAGTTGACCCGGGTTCGATTCCC |
| 448 | Val_CAC_chr19:4724646-4724719 (-) | GTTTCCGTAGTGTAGCGGTTATCACATTCGCCTCACACGCGAAAGGTCCCCGGTTCGATCCCG |
| 449 | Thr_AGT_chr19:33667962-33668036 (+) | TGGCGCCGTGGCTTAGTTGGTTAAAGCGCCTGTCTAGTAAACAGGAGATCCTGGGTTCGAAT |
| 450 | Ile_TAT_chr19:39902807-39902900 (-) | GCTCCAGTGGCGCAATCGGTTAGCGCGCGGTACTTATATGACAGTGCGAGCGGAGCAATGCC |
| 451 | Gly_GCC_chr21:18827106-18827177 (-) | GCATGGGTGGTTCAGTGGTAGAATTCTCGCCTGCCACGCGGGAGGCCCGGGTTCGATTCCCG |

Non-Naturally Occurring Modification

A TREM, a TREM core fragment or a TREM fragment described herein comprises a non-naturally occurring modification, e.g., a modification described in any one of Tables 5-9. A non-naturally occurring modification can be made according to methods known in the art. Exemplary methods of making non-naturally occurring modifications are provided in Examples 4-7.

In an embodiment, a non-naturally occurring modification is a modification that a cell, e.g., a human cell, does not make on an endogenous tRNA.

In an embodiment, a non-naturally occurring modification is a modification that a cell, e.g., a human cell, can make on an endogenous tRNA, but wherein such modification is in a location in which it does not occur on a native tRNA. In an embodiment, the non-naturally occurring modification is in a domain, linker or arm which does not have such modification in nature. In an embodiment, the non-naturally occurring modification is at a position within a domain, linker or arm, which does not have such modification in nature. In an embodiment, the non-naturally occurring modification is on a nucleotide which does not have such modification in nature. In an embodiment, the non-naturally occurring modification is on a nucleotide at a position within a domain, linker or arm, which does not have such modification in nature.

In an embodiment, a TREM, a TREM core fragment or a TREM fragment described herein comprises a non-naturally occurring modification provided in Table 5, or a combination thereof.

TABLE 5

| Exemplary non-naturally occurring modifications<br>Modification |
|---|
| 7-deaza-adenosine |
| Nl-methyl-adenosine |
| N6,N6 (dimethyl)adenine |
| N6-cis-hydroxy-isopentenyl-adenosine |
| thio-adenosine |
| 2-(amino)adenine |
| 2-(aminopropyl)adenine |
| 2-(methylthio) N6 (isopentenyl)adenine |
| 2-(alkyl)adenine |
| 2-(aminoalkyl)adenine |
| 2-(aminopropyl)adenine |
| 2-(halo)adenine |
| 2-(propyl)adenine |
| 2'-azido-2'-deoxy-adenosine |
| 2'-Deoxy-2'-alpha-aminoadenosine |
| 2'-Deoxy-2'-alpha-azidoadenosine |
| 6-(alkyl)adenine |
| 6-(methyl)adenine |
| 6-(alkyl)adenine |
| 6-(methyl)adenine |
| 7-(deaza)adenine |
| 8-(alkenyl)adenine |
| 8-(alkynyl)adenine |
| 8-(amino)adenine |
| 8-(thioalkyl)adenine |
| 8-(alkenyl)adenine |
| 8-(alkyl)adenine |
| 8-(alkynyl)adenine |
| 8-(amino)adenine |
| 8-(halo)adenine |
| 8-(hydroxyl)adenine |
| 8-(thioalkyl)adenine |
| 8-(thiol)adenine |
| 8-azido-adenosine |
| azaadenine |
| deazaadenine |
| N6-(methyl)adenine |
| N6-(isopentyl)adenine |
| 7-deaza-8-aza-adenosine |
| 7-methyladenine |
| 1-deazaadenosine |
| 2'-Fluoro-N6-Bz-deoxyadenosine |
| 2'-OMe-2-Amino-adenosine |
| 2'O-methyl-N6-Bz-deoxyadenosine |
| 2'-alpha-ethynyladenosine |
| 2-aminoadenine |
| 2-Aminoadenosine |
| 2-Amino-adenosine |

TABLE 5-continued

| Exemplary non-naturally occurring modifications<br>Modification |
|---|
| 2'-alpha-Trifluoromethyladenosine |
| 2-Azidoadenosine |
| 2'-beta-Ethynyladenosine |
| 2-Bromoadenosine |
| 2'-beta-Trifluoromethyladenosine |
| 2-Chloroadenosine |
| 2'-Deoxy-2',2'-difluoroadenosine |
| 2'-Deoxy-2'-alpha-mercaptoadenosine |
| 2'-Deoxy-2'-alpha-thiomethoxyadenosine |
| 2'-Deoxy-2'-beta-aminoadenosine |
| 2'-Deoxy-2'-beta-azidoadenosine |
| 2'-Deoxy-2'-beta-bromoadenosine |
| 2'-Deoxy-2'-beta-chloroadenosine |
| 2'-Deoxy-2'-beta-fluoroadenosine |
| 2'-Deoxy-2'-beta-iodoadenosine |
| 2'-Deoxy-2'-beta-mercaptoadenosine |
| 2'-Deoxy-2'-beta-thiomethoxyadenosine |
| 2-Fluoroadenosine |
| 2-Iodoadenosine |
| 2-Mercaptoadenosine |
| 2-methoxy-adenine |
| 2-methylthio-adenine |
| 2-Trifluoromethyladenosine |
| 3-Deaza-3-bromoadenosine |
| 3-Deaza-3-chloroadenosine |
| 3-Deaza-3-fluoroadenosine |
| 3-Deaza-3-iodoadenosine |
| 3-Deazaadenosine |
| 4'-Azidoadenosine |
| 4'-Carbocyclic adenosine |
| 4'-Ethynyladenosine |
| 5'-Homo-adenosine |
| 8-Aza-adenosine |
| 8-bromo-adenosine |
| 8-Trifluoromethyladenosine |
| 9-Deazaadenosine |
| 2-aminopurine |
| 7-deaza-2,6-diaminopurine |
| 7-deaza-8-aza-2,6-diaminopurine |
| 7-deaza-8-aza-2-aminopurine |
| 2,6-diaminopurine |
| 7-deaza-8-aza-adenine, 7-deaza-2-aminopurine |
| 4-methylcytidine |
| 5-aza-cytidine |
| Pseudo-iso-cytidine |
| pyrrolo-cytidine |
| alpha-thio-cytidine |
| 2-(thio)cytosine |
| 2'-Amino-2'-deoxy-cytosine |
| 2'-Azido-2'-deoxy-cytosine |
| 2'-Deoxy-2'-alpha-aminocytidine |
| 2'-Deoxy-2'-alpha-azidocytidine |
| 3 (deaza) 5 (aza)cytosine |
| 3 (methyl)cytosine |
| 3-(alkyl)cytosine |
| 3-(deaza) 5 (aza)cytosine |
| 3-(methyl)cytidine |
| 4,2'-O-dimethylcytidine |
| 5 (halo)cytosine |
| 5 (methyl)cytosine |
| 5 (propynyl)cytosine |
| 5 (trifluoromethyl)cytosine |
| 5-(alkyl)cytosine |
| 5-(alkynyl)cytosine |
| 5-(halo)cytosine |
| 5-(propynyl)cytosine |
| 5-(trifluoromethyl)cytosine |
| 5-bromo-cytidine |
| 5-iodo-cytidine |
| 5-propynyl cytosine |
| 6-(azo)cytosine |
| 6-aza-cytidine |
| aza cytosine |
| deaza cytosine |
| N4 (acetyl)cytosine |
| l-methyl-1-deaza-pseudoisocytidine |
| 1-methyl-pseudoisocytidine |

TABLE 5-continued

| Exemplary non-naturally occurring modifications Modification |
|---|
| 2-methoxy-5-methyl-cytidine |
| 2-methoxy-cytidine |
| 2-thio-5-methyl-cytidine |
| 4-methoxy-1-methyl-pseudoisocytidine |
| 4-methoxy-pseudoisocytidine |
| 4-thio-l-methyl-1-deaza-pseudoisocytidine |
| 4-thio-1-methyl-pseudoisocytidine |
| 4-thio-pseudoisocytidine |
| 5-aza-zebularine |
| 5-methyl-zebularine |
| pyrrolo-pseudoisocytidine |
| zebularine |
| (E)-5-(2-Bromo-vinyl)cytidine |
| 2,2'-anhydro-cytidine |
| 2'-Fluor-N4-Bz-cytidine |
| 2'-Fluoro-N4-Acetyl-cytidine |
| 2'-O-Methyl-N4-Acetyl-cytidine |
| 2'-O-methyl-N4-Bz-cytidine |
| 2'-a-Ethynylcytidine |
| 2'-a-Trifluoromethylcytidine |
| 2'-b-Ethynylcytidine |
| 2'-b-Trifluoromethylcytidine |
| 2'-Deoxy-2',2'-difluorocytidine |
| 2'-Deoxy-2'-alpha-mercaptocytidine |
| 2'-Deoxy-2'-alpha-thiomethoxycytidine |
| 2'-Deoxy-2'-betab-aminocytidine |
| 2'-Deoxy-2'-beta-azidocytidine |
| 2'-Deoxy-2'-beta-bromocytidine |
| 2'-Deoxy-2'-beta-chlorocytidine |
| 2'-Deoxy-2'-beta-fluorocytidine |
| 2'-Deoxy-2'-beta-iodocytidine |
| 2'-Deoxy-2'-beta-mercaptocytidine |
| 2'-Deoxy-2'-beta-thiomethoxycytidine TP |
| 2'-O-Methyl-5-(1-propynyl)cytidine |
| 3'-Ethynylcytidine |
| 4'-Azidocytidine |
| 4'-Carbocyclic cytidine |
| 4'-Ethynylcytidine |
| 5-(1-Propynyl)ara-cytidine |
| 5-(2-Chloro-phenyl)-2-thiocytidine |
| 5-(4-Amino-phenyl)-2-thiocytidine |
| 5-Aminoallyl-cytosine |
| 5-Cyanocytidine |
| 5-Ethynylara-cytidine |
| 5-Ethynylcytidine |
| 5'-Homo-cytidine |
| 5-Methoxycytidine |
| 5-Trifluoromethyl-Cytidine |
| N4-Amino-cytidine |
| N4-Benzoyl-cytidine |
| pseudoisocytidine |
| 6-thio-guanosine |
| 7-deaza-guanosine |
| 8-oxo-guanosine |
| Nl-methyl-guanosine |
| alpha-thio-guanosine |
| 2-(propyl)guanine |
| 2-(alkyl)guanine |
| 2'-Amino-2'-deoxy-guanosine |
| 2'-Azido-2'-deoxy-guanosine |
| 2'-Deoxy-2'-alpha-aminoguanosine |
| 2'-Deoxy-2'-alpha-azidoguanosine |
| 6-(methyl)guanine |
| 6-(alkyl)guanine |
| 6-(methyl)guanine |
| 6-methyl-guanosine |
| 7-(alkyl)guanine |
| 7-(deaza)guanine |
| 7-(methyl)guanine |
| 7-(alkyl)guanine |
| 7-(deaza)guanine |
| 7-(methyl)guanine |
| 8-(alkyl)guanine |
| 8-(alkynyl)guanine |
| 8-(halo)guanine |
| 8-(thioalkyl)guanine |
| 8-(alkenyl)guanine |

TABLE 5-continued

| Exemplary non-naturally occurring modifications Modification |
|---|
| 8-(alkyl)guanine |
| 8-(alkynyl)guanine |
| 8-(amino)guanine |
| 8-(halo)guanine |
| 8-(hydroxyl)guanine |
| 8-(thioalkyl)guanine |
| 8-(thiol)guanine |
| azaguanine |
| deaza guanine |
| N (methyl)guanine |
| N-(methyl)guanine |
| l-methyl-6-thio-guanosine |
| 6-methoxy-guanosine |
| 6-thio-7-deaza-8-aza-guanosine |
| 6-thio-7-deaza-guanosine |
| 6-thio-7-methyl-guanosine |
| 7-deaza-8-aza-guanosine |
| 7-methyl-8-oxo-guanosine |
| N2,N2-dimethyl-6-thio-guanosine |
| N2-methyl-6-thio-guanosine |
| 1-Me-guanosine |
| 2'Fluoro-N2-isobutyl-guanosine |
| 2'O-methyl-N2-isobutyl-guanosine |
| 2'-alpha-Ethynylguanosine |
| 2'-alpha-Trifluoromethylguanosine |
| 2'-beta-Ethynylguanosine |
| 2'-beta-Trifluoromethylguanosine |
| 2'-Deoxy-2',2'-difluoroguanosine |
| 2'-Deoxy-2'-alpha-mercaptoguanosine |
| 2'-Deoxy-2'-alpha-thiomethoxyguanosine |
| 2'-Deoxy-2'-beta-aminoguanosine |
| 2'-Deoxy-2'-beta-azidoguanosine |
| 2'-Deoxy-2'-beta-bromoguanosine |
| 2'-Deoxy-2'-beta-chloroguanosine |
| 2'-Deoxy-2'-beta-fluoroguanosine |
| 2'-Deoxy-2'-beta-iodoguanosine |
| 2'-Deoxy-2'-beta-mercaptoguanosine |
| 2'-Deoxy-2'-beta-thiomethoxyguanosine |
| 4'-Azidoguanosine |
| 4'-Carbocyclic guanosine |
| 4'-Ethynylguanosine |
| 5'-Homo-guanosine |
| 8-bromo-guanosine |
| 9-Deazaguanosine |
| N2-isobutyl-guanosine |
| 7-methylinosine |
| allyamino-thymidine |
| aza thymidine |
| deaza thymidine |
| deoxy-thymidine |
| 5-propynyl uracil |
| alpha-thio-uridine |
| 1-(aminoalkylamino-carbonylethylenyl)-2(thio)-pseudouracil |
| 1-(aminoalkylaminocarbonylethylenyl)-2,4-(dithio)pseudouracil |
| 1-(aminoalkylaminocarbonylethylenyl)-4(thio)pseudouracil |
| 1-(aminoalkylaminocarbonylethylenyl)-pseudouracil |
| 1-(aminocarbonylethylenyl)-2(thio)-pseudouracil |
| 1-(aminocarbonylethylenyl)-2,4-(dithio)pseudouracil |
| 1-(aminocarbonylethylenyl)-4(thio)pseudouracil |
| 1-(aminocarbonylethylenyl)-pseudouracil |
| 1-substituted 2-(thio)-pseudouracil |
| 1-substituted 2,4-(dithio)pseudouracil |
| 1-substituted 4 (thio)pseudouracil |
| 1-substituted pseudouracil |
| 1-(aminoalkylamino-carbonylethylenyl)-2-(thio)-pseudouracil |
| l-Methyl-3-(3-amino-3-carboxypropyl)pseudouridine |
| l-Methyl-3-(3-amino-3-carboxyproovl)pseudo-Uradine |
| 1-Methyl-pseudo-UTP |
| 2 (thio)pseudouracil |
| 2'deoxy uridine |
| 2'fluorouridine |
| 2-(thio)uracil |
| 2,4-(dithio)psuedouracil |
| 2'-methyl, 2'-amino, 2'azido, 2'fluro-guanosine |
| 2'-Amino-2'-deoxy-uridine |
| 2'-Azido-2'-deoxy-uridine |
| 2'-Azido-deoxyuridine |

TABLE 5-continued

| Exemplary non-naturally occurring modifications Modification |
| --- |
| 2'-O-methylpseudouridine |
| 2'deoxyuridine |
| 2'fluorouridine |
| 2'-Deoxy-2'-alpha-aminouridine TP |
| 2'-Deoxy-2'-alpha-azidouridine TP |
| 2-methylpseudouridine |
| 3-(3 amino-3-carboxypropyl)uracil |
| 4-(thio)pseudouracil |
| 4-(thio)pseudouracil |
| 4-(thio)uracil |
| 4-thiouracil |
| 5-(l,3-diazole-1-alkyl)uracil |
| 5-(2-aminopropyl)uracil |
| 5-(aminoalkyl)uracil |
| 5-(dimethylaminoalkyl)uracil |
| 5-(guanidiniumalkyl)uracil |
| 5-(methoxycarbonylmethyl)-2-(thio)uracil |
| 5-(methoxycarbonyl-methyl)uracil |
| 5-(methyl)-2-(thio)uracil |
| 5-(methyl)-2,4-(dithio)uracil |
| 5 (methyl) 4 (thio)uracil |
| 5 (methylaminomethyl)-2 (thio)uracil |
| 5 (methylaminomethyl)-2,4 (dithio)uracil |
| 5 (methylaminomethyl)-4 (thio)uracil |
| 5 (propynyl)uracil |
| 5 (trifluoromethyl)uracil |
| 5-(2-aminopropyl)uracil |
| 5-(alky1)-2-(thio)pseudouracil |
| 5-(alkyl)-2,4 (dithio)pseudouracil |
| 5-(alky1)-4 (thio)pseudouracil |
| 5-(alkyl)pseudouracil |
| 5-(alkyl)uracil |
| 5-(alkynyl)uracil |
| 5-(allylamino)uracil |
| 5-(cyanoalkyl)uracil |
| 5-(dialkylaminoalkyl)uracil |
| 5-(dimethylaminoalkyl)uracil |
| 5-(guanidiniumalkyl)uracil |
| 5-(halo)uracil |
| 5-(1,3-diazole-l-alkyl)uracil |
| 5-(methoxy)uracil |
| 5-(methoxycarbonylmethyl)-2-(thio)uracil |
| 5-(methoxycarbonyl-methyl)uracil |
| 5-(methyl) 2(thio)uracil |
| 5-(methyl) 2,4 (dithio)uracil |
| 5-(methyl) 4 (thio)uracil |
| 5-(methyl)-2-(thio)pseudouracil |
| 5-(methyl)-2,4 (dithio)pseudouracil |
| 5-(methyl)-4 (thio)pseudouracil |
| 5-(methyl)pseudouracil |
| 5-(methylaminomethyl)-2 (thio)uracil |
| 5-(methylaminomethyl)-2,4(dithio)uracil |
| 5-(methylaminomethyl)-4-(thio)uracil |
| 5-(propyny1)uracil |
| 5-(trifluoromethyl)uracil |
| 5-aminoallyl-uridine |
| 5-bromo-uridine |
| 5-iodo-uridine |
| 5-uracil |
| 6 (azo)uracil |
| 6-(azo)uracil |
| 6-aza-uridine |
| allyamino-uracil |
| aza uracil |
| deaza uracil |
| N3 (methyl)uracil |
| Pseudo-uridine-1-2-ethanoic acid |
| pseudouracil |
| 4-Thio-pseudouridine |
| 1-carboxymethyl-pseudouridine |
| l-methyl-1-deaza-pseudouridine |
| 1-propynyl-uridine |
| l-taurinomethyl-1-methyl-uridine |
| l-taurinomethyl-4-thio-uridine |
| 1-taurinomethyl-pseudouridine |
| 2-methoxy-4-thio-pseudouridine |
| 2-thio-l-methyl-1-deaza-pseudouridine |

TABLE 5-continued

| Exemplary non-naturally occurring modifications Modification |
| --- |
| 2-thio-1-methyl-pseudouridine |
| 2-thio-5-aza-uridine |
| 2-thio-dihydropseudouridine |
| 2-thio-dihydrouridine |
| 2-thio-pseudouridine |
| 4-methoxy-2-thio-pseudouridine |
| 4-methoxy-pseudouridine |
| 4-thio-1-methyl-pseudouridine |
| 4-thio-pseudouridine |
| 5-aza-uridine |
| dihydropseudouridine |
| (±)1-(2-Hydroxypropyl)pseudouridine |
| (2R)-l-(2-Hydroxypropyl)pseudouridine |
| (2S)-l-(2-Hydroxypropyl)pseudouridine |
| (E)-5-(2-Bromo-vinyl)ara-uridine |
| (E)-5-(2-Bromo-vinyl)uridine |
| (Z)-5-(2-Bromo-vinyl)ara-uridine |
| (Z)-5-(2-Bromo-vinyl)uridine |
| 1-(2,2,2-Trifluoroethyl)-pseudouridine |
| 1-(2,2,3,3,3-Pentafluoropropyl)pseudouridine |
| 1-(2,2-Diethoxyethy l)pseudouridine |
| 1-(2,4,6-Trimethylbenzyl)pseudouridine |
| 1-(2,4,6-Trimethyl-benzyl)pseudo-uridine |
| 1-(2,4,6-Trimethyl-phenyl)pseudo-uridine |
| 1-(2-Amino-2-carboxyethyl)pseudo-uridine |
| 1-(2-Amino-ethyl)pseudouridine |
| 1-(2-Hydroxyethyl)pseudouridine |
| 1-(2-Methoxyethyl)pseudouridine |
| 1-(3,4-Bis-trifluoromethoxvbenzvl)pseudouridine |
| 1-(3,4-Dimethoxybenzyl)pseudouridine |
| 1-(3-Amino-3-carboxypropyl)pseudo-uridine |
| 1-(3-Amino-propyl)pseudouridine |
| 1-(3-Cyclopropyl-prop-2-ynyl)pseudouridine TP |
| 1-(4-Amino-4-carboxybutyl)pseudouridine |
| 1-(4-Amino-benzyl)pseudouridine |
| 1-(4-Amino-buty l)pseudouridine |
| 1-(4-Amino-phenyl)pseudouridine |
| 1-(4-Azidobenzyl)pseudouridine |
| 1-(4-Bromobenzyl)pseudouridine |
| 1-(4-Chlorobenzyl)pseudouridine |
| 1-(4-Fluorobenzyl)pseudouridin |
| 1-(4-Iodobenzyl)pseudouridine |
| 1-(4-Methanesulfonvlbenzvl)pseudouridine |
| 1-(4-Methoxybenzy l)pseudouridine |
| 1-(4-Methoxy-benzyl)pseudouridine |
| 1-(4-Methoxy-phenyl)pseudouridine |
| 1-(4-Methylbenzyl)pseudouridine |
| 1-(4-Methyl-benzyl)pseudouridine |
| 1-(4-Nitrobenzyl)pseudouridine |
| 1-(4-Nitro-benzy!)pseudouridine |
| 1(4-Nitro-phenyl)pseudouridine |
| 1-(4-Thiomethoxybenzyl)pseudouridine |
| 1-(4-Trifluoromethoxybenzvl)pseudouridine |
| 1-(4-Trifluoromethylbenzyl)pseudouridine |
| 1-(5-Amino-pentyl)pseudouridine |
| 1-(6-Amino-hexyl)pseudouridine |
| 1,6-Dimethyl-pseudouridine |
| l-[3-(2-{2-[2-(2-Aminoethoxy)-ethoxy]-ethoxy}-ethoxy)-propionyl]pseudouridine |
| 1-{3-[2-(2-Aminoethoxy)-ethoxy]-propionvl} pseudouridine |
| 1-Acetylpseudouridine |
| l-Alkyl-6-(1-propynyl)-pseudo-uridine |
| l-Alkyl-6-(2-propynyl)-pseudo-uridine |
| l-Alkyl-6-allyl-pseudo-uridine |
| l-Alkyl-6-ethynyl-pseudo-uridine |
| l-Alkyl-6-homoallyl-pseudo-uridine |
| l-Alkyl-6-vinyl-pseudo-uridine |
| 1-Allylpseudouridine |
| 1-Aminomethyl-pseudo-uridine |
| 1-Benzoylpseudouridine |
| 1-Benzyloxymethylpseudouridine |
| 1-Benzyl-pseudo-uridine |
| l-Biotinyl-PEG2-pseudouridine |
| 1-Biotinylpseudouridine |
| 1-Butyl-pseudo-uridine |
| 1-Cyanomethylpseudouridine |
| 1-Cyclobutylmethyl-pseudo-uridine |

TABLE 5-continued

| Exemplary non-naturally occurring modifications Modification |
|---|
| 1-Cyclobutyl-pseudo-uridine |
| 1-Cycloheptylmethyl-pseudo-uridine |
| 1-Cycloheptyl-pseudo-uridine |
| 1-Cyclohexylmethyl-pseudo-uridine |
| 1-Cyclohexyl-pseudo-uridine |
| 1-Cyclooctylmethyl-pseudo-uridine |
| 1-Cyclooctyl-pseudo-uridine |
| 1-Cyclopentylmethyl-pseudo-uridine |
| 1-Cyclopentyl-pseudo-uridine |
| 1-Cyclopropylmethyl-pseudo-uridine |
| 1-Cyclopropyl-pseudo-uridine |
| 1-Ethyl-pseudo-uridine |
| 1-Hexyl-pseudo-uridine |
| 1-Homoallylpseudouridine |
| 1-Hydroxymethylpseudouridine |
| 1-iso-propyl-pseudo-uridine |
| 1-Me-2-thio-pseudo-uridine |
| 1-Me-4-thio-pseudo-uridine |
| 1-Me-alpha-thio-pseudo-uridine |
| 1-Methanesulfonylmethylpseudouridine |
| 1-Methoxymethylpseudouridine uridine |
| l-Methyl-6-(2,2,2-Trifluoroethyl)pseudo-uridine |
| l-Methyl-6-(4-morpholino)-pseudo-uridine |
| l-Methyl-6-(4-thiomorpholino)-pseudo-uridine |
| l-Methyl-6-(substituted phenyl)pseudo-uridine |
| 1-Methyl-6-amino-pseudo-uridine |
| l-Methyl-6-azido-pseudo-uridine |
| 1-Methyl-6-bromo-pseudo-uridine |
| l-Methyl-6-butyl-pseudo-uridine |
| l-Methyl-6-chloro-pseudo-uridine |
| 1-Methyl-6-cyano-pseudo-uridine |
| l-Methyl-6-dimethylamino-pseudo-uridine |
| l-Methyl-6-ethoxy-pseudo-uridine |
| l-Methyl-6-ethylcarboxylate-pseudo-uridine |
| l-Methyl-6-ethyl-pseudo-uridine |
| l-Methyl-6-fluoro-pseudo-uridine |
| l-Methyl-6-formyl-pseudo-uridine |
| 1-Methyl-6-hydroxyamino-pseudo-uridine |
| l-Methyl-6-hydroxy-pseudo-uridine |
| l-Methyl-6-iodo-pseudo-uridine |
| l-Methyl-6-iso-propyl-pseudo-uridine |
| l-Methyl-6-methoxy-pseudo-uridine |
| l-Methyl-6-methylamino-pseudo-uridine |
| l-Methyl-6-phenyl-pseudo-uridine |
| l-Methyl-6-propyl-pseudo-uridine |
| l-Methyl-6-tert-butyl-pseudo-uridine |
| 1-Methyl-6-trifluoromethoxy-pseudo-uridine |
| l-Methyl-6-trifluoromethyl-pseudo-uridine |
| 1-Morpholinomethylpseudouridine |
| 1-Pentyl-pseudo-uridineuridine |
| 1-Phenyl-pseudo-uridine |
| 1-Pivaloylpseudouridine |
| 1-Propargylpseudouridine |
| 1-Propyl-pseudo-uridine |
| 1-propynyl-pseudouridine |
| 1-p-tolyl-pseudo-uridine |
| 1-tert-Butyl-pseudo-uridine |
| 1-Thiomethoxymethylpseudouridine |
| 1-Thiomorpholinomethylpseudouridine |
| 1-Trifluoroacetylpseudouridine |
| 1-Trifluoromethyl-pseudouridine |
| 1-Vinylpseudouridine |
| 2,2'-anhydro-uridine |
| 2'-bromo-deoxyuridine |
| 2'-F-5-Methyl-2'-deoxy-uridine |
| 2'-OMe-5-Me-uridine |
| 2'-OMe-pseudouridine |
| 2'-alpha-Ethynyluridine |
| 2'-alpha-Trifluoromethyluridine |
| 2'-beta-Ethynyluridine |
| 2'-beta-Trifluoromethyluridiner |
| 2'-Deoxy-2',2'-difluorouridine |
| 2'-Deoxy-2'-a-mercaptouridin |
| 2'-Deoxy-2'-alpha-thiomethoxyuridine |
| 2'-Deoxy-2'-beta-aminouridine |
| 2'-Deoxy-2'-beta-azidouridine |
| 2'-Deoxy-2'-beta-bromouridine |

TABLE 5-continued

| Exemplary non-naturally occurring modifications Modification |
|---|
| 2'-Deoxy-2'-beta-chlorouridine |
| 2'-Deoxy-2'-beta-fluorouridine |
| 2'-Deoxy-2'-beta-iodouridine |
| 2'-Deoxy-2'-beta-mercaptouridine |
| 2'-Deoxy-2'-beta-thiomethoxyuridine |
| 2-methoxy-4-thio-uridine |
| 2-methoxyuridine |
| 2'-O-Methyl-5-(1-propynyl)uridine |
| 3-Alkyl-pseudo-uridine |
| 4'-Azidouridine |
| 4'-Carbocyclic uridine |
| 4'-Ethynyluridine |
| 5-(1-Propynyl)ara-uridine |
| 5-(2-Furanyl)uridine |
| 5-Cyanouridine |
| 5-Dimethylaminouridine |
| 5'-Homo-uridine |
| 5-iodo-2'-fluoro-deoxyuridine |
| 5-Phenylethynyluridine |
| 5-Trideuteromethyl-6-deuterouridine |
| 5-Trifluoromethyl-Uridine |
| 5-Vinylarauridine |
| 6-(2,2,2-Trifluoroethyl)-pseudo-uridine |
| 6-(4-Morpholino)-pseudo-uridine |
| 6-(4-Thiomorpholino)-pseudo-uridine |
| 6-(Substituted-Phenyl)-pseudo-uridine |
| 6-Amino-pseudo-uridine |
| 6-Azido-pseudo-uridine |
| 6-Bromo-pseudo-uridine |
| 6-Butyl-pseudo-uridine |
| 6-Chloro-pseudo-uridine |
| 6-Cyano-pseudo-uridine |
| 6-Dimethylamino-pseudo-uridine |
| 6-Ethoxy-pseudo-uridine |
| 6-Ethylcarboxylate-pseudo-uridine |
| 6-Ethyl-pseudo-uridine |
| 6-Fluoro-pseudo-uridine |
| 6-Formyl-pseudo-uridine |
| 6-Hydroxyamino-pseudo-uridine |
| 6-Hydroxy-pseudo-uridine |
| 6-Iodo-pseudo-uridine |
| 6-iso-Propyl-pseudo-uridine |
| 6-Methoxy-pseudo-uridine |
| 6-Methylamino-pseudo-uridine |
| 6-Methyl-pseudo-uridine |
| 6-Phenyl-pseudo-uridine |
| 6-Phenyl-pseudo-uridine |
| 6-Propyl-pseudo-uridine |
| 6-tert-Butyl-pseudo-uridine |
| 6-Trifluoromethoxy-pseudo-uridine |
| 6-Trifluoromethyl-pseudo-uridine |
| alpha-thio-pseudo-uridine |
| Pseudouridine 1-(4-methylbenzenesulfonic acid) |
| Pseudouridine 1-(4-methylbenzoic acid) TP |
| Pseudouridine l-[3-(2-ethoxy)]propionic acid |
| Pseudouridine l-[3-{2-(2-[2-(2-ethoxy)-ethoxy]-ethoxy)-ethoxy}]propionic acid |
| Pseudouridine 1-[3-{2-(2-[2-{2(2-ethoxy)-ethoxy}-ethoxy]-ethoxy)-ethoxy}]propionic acid |
| Pseudouridine l-[3-{2-(2-[2-ethoxy]-ethoxy)-ethoxv}]propionic acid |
| Pseudouridine l-[3-{2-(2-ethoxy)-ethoxv}] propionic acid |
| Pseudouridine 1-methylphosphonic acid |
| Pseudouridine TP 1-methylphosphonic acid diethyl ester |
| Pseudo-uridine-N1-3-propionic acid |
| Pseudo-uridine-N1-4-butanoic acid |
| Pseudo-uridine-N 1-5-pentanoic acid |
| Pseudo-uridine-N1-6-hexanoic acid |
| Pseudo-uridine-Nl-7-heptanoic acid |
| Pseudo-uridine-N1-methy1-p-benzoic acid |
| Pseudo-uridine-N1-p-benzoic acid |

In an embodiment, a TREM, a TREM core fragment or a TREM fragment described herein comprises a modification provided in Table 6, or a combination thereof. The modifications provided in Table 6 occur naturally in RNAs, and are used herein on a synthetic TREM, a TREM core fragment or a TREM fragment at a position that does not occur in nature.

TABLE 6

| Additional exemplary modifications Modification |
|---|
| 2-methylthio-N6-(cis-hvdroxvisopentenvl)adenosine |
| 2-methylthio-N6-methyladenosine |
| 2-methylthio-N6-threonyl carbamoyladenosine |
| N6-glycinylcarbamoyladenosine |
| N6-isopentenyladenosine |
| N6-methyladenosine |
| N6-threonylcarbamoyladenosine |
| 1,2'-O-dimethyladenosine |
| 1-methyladenosine |
| 2'-O-methyladenosine |
| 2'-O-ribosyladenosine (phosphate) |
| 2-methyladenosine |
| 2-methylthio-N6 isopentenyladenosine |
| 2-methylthio-N6-hydroxynorvalyl carbamoyladenosine |
| 2'-O-methyladenosine |
| 2'-O-ribosyladenosine (phosphate) |
| isopenteny ladenosine |
| N6-(cis-hydroxyisopentenyl)adenosine |
| N6,2'-O-dimethyladenosine |
| N6,2'-O-dimethyladenosine |
| N6,N6,2'-O-trimethyladenosine |
| N6,N6-dimethyladenosine |
| N6-acetyladenosine |
| N6-hydroxynorvalylcarbamoyladenosine |
| N6-methyl-N6-threonylcarbamoyladenosine |
| 2-methyladenosine |
| 2-methylthio-$N^6$-isopentenyladenosine |
| 2-thiocytidine |
| 3-methylcytidine |
| 5-formylcytidine |
| 5-hydroxymethylcytidine |
| 5-methylcytidine |
| N4-acetylcytidine |
| 2'-O-methylcytidine |
| 2'-O-methylcytidine |
| 5,2'-O-dimethylcytidine |
| 5-formyl-2'-O-methylcytidine |
| lysidine |
| N4,2'-O-dimethy lcytidine |
| N4-acetyl-2'-O-methylcytidine |
| N4-methylcytidine |
| N4,N4-Dimethyl-2'-OMe-Cytidine |
| 7-methylguanosine |
| N2,2'-O-dimethylguanosine |
| N2-methylguanosine |
| wyosme |
| 1,2'-O-dimethylguanosine |
| 1-methylguanosine |
| 2'-O-methylguanosine |
| 2'-O-ribosylguanosine (phosphate) |
| 2'-O-methylguanosine |
| 2'-O-ribosylguanosine (phosphate) |
| 7-aminomethyl-7-deazaguanosine |
| 7-cyano-7-deazaguanosine |
| archaeosine |
| methylwyosine |
| N2,7-dimethylguanosine |
| N2,N2,2'-O-trimethylguanosine |
| N2,N2,7-trimethylguanosine |
| N2,N2-dimethylguanosine |
| N2,7,2'-O-trimethylguanosine |
| 1-methylinosine |
| mosme |
| 1,2'-O-dimethylinosine |
| 2'-O-methylinosine |
| 2'-O-methylinosine |
| epoxyqueuosine |
| galactosyl-queuosine |
| mannosyl-queuosine |
| 2'-O-methyluridine |
| 2-thiouridine |
| 3-methyluridine |
| 5-carboxymethyluridine |

TABLE 6-continued

| Additional exemplary modifications Modification |
|---|
| 5-hydroxyuridine |
| 5-methyluridine |
| 5-taurinomethyl-2-thiouridine |
| 5-taurinomethyluridine |
| dihydrouridine |
| pseudouridine |
| (3-(3-amino-3-carboxypropyl)uridine |
| l-methyl-3-(3-amino-5-carboxypropyl)pseudouridine |
| 1-methylpseduouridine |
| 1-methyl-pseudouridine |
| 2'-O-methyluridine |
| 2'-O-methylpseudouridine |
| 2'-O-methyluridine |
| 2-thio-2'-O-methyluridine |
| 3-(3-amino-3-carboxypropyl)uridine |
| 3,2'-0-dimethyluridine |
| 3-Methyl-pseudo-Uridine |
| 4-thiouridine |
| 5-(carboxyhydroxymethyl)uridine |
| 5-(carboxyhydroxymethyl)uridine methyl ester |
| 5,2'-O-dimethyluridine |
| 5,6-dihydro-uridine |
| 5-aminomethy1-2-thiouridine |
| 5-carbamoylmethyl-2'-0-methyluridine |
| 5-carbamoylmethyluridine |
| 5-carboxyhydroxymethyluridine |
| 5-carboxyhydroxymethyluridine methyl ester |
| 5-carboxymethylaminomethyl-2'-O-methyluridine |
| 5-carboxymethylaminomethyl-2-thiouridine |
| 5-carboxymethylaminomethyl-2-thiouridine |
| 5-carboxymethylaminomethyluridine |
| 5-carboxymethylaminomethyluridine |
| 5-Carbamoylmethyluridine |
| 5-methoxycarbonylmethyl-2'-O-methyluridine |
| 5-methoxycarbonylmethy1-2-thiouridine |
| 5-methoxycarbonylmethyluridine |
| 5-methoxyuridine |
| 5-methyl-2-thiouridine |
| 5-methylaminomethyl-2-selenouridine |
| 5-methylaminomethyl-2-thiouridine |
| 5-methylaminomethyluridine |
| 5-Methyldihydrouridine |
| 5-Oxyacetic acid-Uridine |
| 5-Oxyacetic acid-methyl ester-Uridin Nl-methyl-pseudo-uridine |
| uridine 5-oxyacetic acid |
| uridine 5-oxyacetic acid methyl ester |
| 3-(3-Amino-3-carboxypropyl)-Uridine |
| 5-(iso-Pentenylaminomethyl)-2-thiouridine |
| 5-(iso-Pentenylaminomethyl)-2'-O-methyluridine |
| 5-(iso-Pentenylaminomethyl)uridine |
| wybutosine |
| hydroxywybutosine |
| isowyosme |
| peroxywybutosine |
| undermodified hydroxywybutosine |
| 4-demethylwyosine |
| altriol |

In an embodiment, a TREM, a TREM core fragment or a TREM fragment described herein comprises a non-naturally occurring modification provided in Table 7, or a combination thereof.

TABLE 7

| Additional exemplary non-naturally occurring modifications Modification |
|---|
| 2,6-(diamino)purine |
| 1-(aza)-2-(thio)-3-(aza)-phenoxazin-1-yl |
| 1,3-(diaza)-2-(oxo)-phenthiazin-1-yl |
| 1,3-(diaza)-2-(oxo)-phenoxazin-1-yl |
| 1,3,5-(triaza)-2,6-(dioxa)-naphthalene |
| 2 (amino)purine |
| 2,4,5-(trimethyl)phenyl |

TABLE 7-continued

| Additional exemplary non-naturally occurring modifications Modification |
|---|
| 2'methyl, 2'amino, 2'azido, 2'fluro-cytidine |
| 2'methyl, 2'amino, 2'azido, 2'fluro-adenine |
| 2'methyl, 2'amino, 2'azido, 2'fluro-uridine |
| 2'-amino-2'-deoxyribose |
| 2-amino-6-Chloro-purine |
| 2-aza-inosinyl |
| 2'-azido-2'-deoxyribose |
| 2'fluoro-2'-deoxyribose |
| 2'-fluoro-modified bases |
| 2'-O-methyl-ribose |
| 2-oxo-7-aminopyridopyrimidin-3-yl |
| 2-oxo-pyridopyrimidine-3-yl |
| 2-pyridinone |
| 3 nitropyrrole |
| 3-(methyl)-7-(propynyl)isocarbostyrilyl |
| 3-(methyl)isocarbostyrilyl |
| 4-(fluoro)-6-(methyl)benzimidazole |
| 4-(methyl)benzimidazole |
| 4-(methyl)indolyl |
| 4,6-(dimethyl)indolyl |
| 5 nitroindole |
| 5 substituted pyrimidines |
| 5-(methyl)isocarbostyrilyl |
| 5-nitroindole |
| 6-(aza)pyrimidine |
| 6-(azo)thymine |
| 6-(methyl)-7-(aza)indolyl |
| 6-chloro-purine |
| 6-phenyl-pyrrolo-pyrimidin-2-on-3-yl |
| 7-(aminoalkylhydroxy)-1-(aza)-2-(thio)-3-(aza)-phenthiazin-1-yl |
| 7-(aminoalkylhydroxy)-1-(aza)-2-(thio)-3-(aza)-phenoxazin-1-yl |
| 7-(aminoalkylhydroxy)-1,3-(diaza)-2-(oxo)-phenoxazin-1-yl |
| 7-(aminoalkylhydroxy)-1,3-(diaza)-2-(oxo)-phenthiazin-1-yl |
| 7-(aminoalkylhydroxy)-1,3-(diaza)-2-(oxo)-phenoxazin-l-yl |
| 7-(aza)indolyl |
| 7-(guanidiniumalkylhydroxy)-1-(aza)-2-(thio)-3-(aza)-phenoxazinl-yl |
| 7-(guanidiniumalkylhydroxy)-1-(aza)-2-(thio)-3-(aza)-phenthiazin-1-yl |
| 7-(guanidiniumalkylhydroxy)-1-(aza)-2-(thio)-3-(aza)-phenoxazin-1-yl |
| 7-(guanidiniumalkylhydroxy)-1,3-(diaza)-2-(oxo)-phenoxazin-1-yl |
| 7-(guanidiniumalkyl-hydroxy)-1,3-(diaza)-2-(oxo)-phenthiazin-1-yl |
| 7-(guanidiniumalkylhydroxy)-1,3-(diaza)-2-(oxo)-phenoxazin-1-yl |
| 7-(propynyl)isocarbostyrilyl |
| 7-(propynyl)isocarbostyrilyl, propynyl-7-(aza)indolyl |
| 7-deaza-inosinyl |
| 7-substituted 1-(aza)-2-(thio)-3-(aza)-phenoxazin-1-yl |
| 7-substituted 1,3-(diaza)-2-(oxo)-phenoxazin-1-yl |
| 9-(methyl)-imidizopyridinyl |
| aminoindolyl |
| anthracenyl |
| bis-ortho-(aminoalkylhydroxy)-6-phenyl-pyrrolo-nvrimidin-2-on-3-yl |
| bis-ortho-substituted-6-phenyl-pyrrolo-pyrimidin-2-on-3-yl |
| difluorotolyl |
| hypoxanthine |
| imidizopyridinyl |
| inosinyl |
| isocarbostyrilyl |
| isoguanosine |
| N2-substituted purines |
| N6-methyl-2-amino-purine |
| N6-substituted purines |
| N-alkylated derivative |
| napthalenyl |
| nitrobenzimidazolyl |
| nitroimidazolyl |
| nitroindazolyl |
| nitropyrazolyl |
| nubularine |
| O6-substituted purines |
| O-alkylated derivative |
| ortho-(aminoalkylhydroxy)-6-phenyl-pyrrolo-pyrimidin-2-on-3-yl |
| ortho-substituted-6-phenyl-pyrrolo-pyrimidin-2-on-3-yl |
| Oxoformycin TP |
| para-(aminoalkylhydroxy)-6-phenyl-pyrrolo-pyrimidin-2-on-3-yl |
| para-substituted-6-phenyl-pyrrolo-pyrimidin-2-on-3-yl |
| pentacenyl |
| phenanthracenyl |
| phenyl |

TABLE 7-continued

| Additional exemplary non-naturally occurring modifications Modification |
|---|
| propynyl-7-(aza)indolyl |
| pyrenyl |
| pyridopyrimidin-3-yl |
| pyridopyrimidin-3-yl, 2-oxo-7-amino-pyridopyrimidin-3-yl |
| pyrrolo-pyrimidin-2-on-3-yl |
| pyrrolopyrimidinyl |
| pyrrolopyrizinyl |
| stilbenzyl |
| substituted 1,2,4-triazoles |
| tetracenyl |
| tubercidine |
| xanthine |
| Xanthosine |
| 2-thio-zebularine |
| 5-aza-2-thio-zebularine |
| 7-deaza-2-amino-purine |
| pyridin-4-one ribonucleoside |
| 2-Amino-riboside |
| Formycin A |
| Formycin B |
| Pyrrolosine |
| 2'-OH-ara-adenosine |
| 2'-OH-ara-cytidine |
| 2'-OH-ara-uridine |
| 2'-OH-ara-guanosine |
| 5-(2-carbomethoxyvinyl)uridine |
| N6-(19-Amino-pentaoxanonadecyl)adenosine |

In an embodiment, a TREM, a TREM core fragment or a TREM fragment described herein comprises a non-naturally occurring modification provided in Table 8, or a combination thereof.

TABLE 8

| Exemplary backbone modifications Modification |
|---|
| 3'-alkylene phosphonates |
| 3'-amino phosphoramidate |
| alkene containing backbones |
| aminoalkylphosphoramidates |
| aminoalkylphosphotriesters |
| boranophosphates |
| —CH2-0-N(CH3)—CH2— |
| —CH2—N(CH3)—N(CH3)—CH2— |
| —CH2—NH—CH2— |
| chiral phosphonates |
| chiral phosphorothioates |
| formacetyl and thioformacetyl backbones |
| methylene (methylimino) |
| methylene formacetyl and thioformacetyl backbones |
| methyleneimino and methylenehydrazino backbones |
| morpholino linkages |
| —N(CH3)—CH2—CH2— |
| oligonucleosides with heteroatom intenucleoside linkage |
| phosphinates |
| phosphoramidates |
| phosphorodithioates |
| phosphorothioate intenucleoside linkages |
| phosphorothioates |
| phosphotriesters |
| PNA |
| siloxane backbones |
| sulfamate backbones |
| sulfide sulfoxide and sulfone backbones |
| sulfonate and sulfonamide backbones |
| thionoalkylphosphonates |
| thionoalkylphosphotriesters |
| thionophosphoramidates |
| methylphosphonates |
| phosphonoacetates |
| Phosphorothioate |
| Constrained nucleic acid (CNA) |
| 2'-O-methyl |

TABLE 8-continued

| Exemplary backbone modifications Modification |
|---|
| 2'-O-methoxyethyl (MOE) |
| 2' Fluoro |
| Locked nucleic acid (LNA) |
| (S)-constrained ethyl (cEt) |
| Fluoro hexitol nucleic acid (FHNA) |
| 5'-phosphorothioate |
| Phosphorodiamidate Morpholino Oligomer (PMO) |
| Tricyclo-DNA (tcDNA) |
| (S) 5'-C-methyl |
| (E)-vinylphosphonate |
| Methyl phosphonate |
| (S) 5'-C-methyl with phosphate |
| (R) 5'-C-methyl with phosphate |
| DNA |
| (R) 5'-C-methyl |
| GNA (glycol nucleic acid) |
| alkyl phosphonates |
| Phosphorothioate |
| Constrained nucleic acid (CNA) |
| 2'-O-methyl |
| 2'-O-methoxyethyl (MOE) |
| 2' Fluoro |
| Locked nucleic acid (LNA) |
| (S)-constrained ethyl (cEt) |
| Fluoro hexitol nucleic acid (FHNA) |
| 5'-phosphorothioate |
| Phosphorodiamidate Morpholino Oligomer (PMO) |
| Tricyclo-DNA (tcDNA) |
| (S) 5'-C-methyl |
| (E)-vinylphosphonate |
| Methyl phosphonate |
| (S) 5'-C-methyl with phosphate |
| (R) 5'-C-methyl with phosphate |
| DNA |
| (R) 5'-C-methyl |
| GNA (glycol nucleic acid) |
| alkyl phosphonates |

In an embodiment, a TREM, a TREM core fragment or a TREM fragment described herein comprises a non-naturally occurring modification provided in Table 9, or a combination thereof.

TABLE 9

| Exemplary non-naturally occurring backbone modificiations Name of synthetic backbone modifications |
|---|
| Phosphorothioate |
| Constrained nucleic acid (CNA) |
| 2'-O-methylation |
| 2'-O-methoxyethylribose (MOE) |
| 2' Fluoro |
| Locked nucleic acid (LNA) |
| (S)-constrained ethyl (cEt) |
| Fluoro hexitol nucleic acid (FHNA) |
| 5'phosphorothioate |
| Phosphorodiamidate Morpholino Oligomer (PMO) |
| Tricyclo-DNA (tcDNA) |
| (5) 5'-C-methyl |
| (E)-vinylphosphonate |
| Methyl phosphonate |
| (S) 5'-C-methyl with phosphate |

TREM, TREM Core Fragment and TREM Fragment Fusions

In an embodiment, a TREM, a TREM core fragment or a TREM fragment disclosed herein comprises an additional moiety, e.g., a fusion moiety. In an embodiment, the fusion moiety can be used for purification, to alter folding of the TREM, TREM core fragment or TREM fragment, or as a targeting moiety. In an embodiment, the fusion moiety can comprise a tag, a linker, can be cleavable or can include a binding site for an enzyme. In an embodiment, the fusion moiety can be disposed at the N terminal of the TREM or at the C terminal of the TREM, TREM core fragment or TREM fragment. In an embodiment, the fusion moiety can be encoded by the same or different nucleic acid molecule that encodes the TREM, TREM core fragment or TREM fragment.

TREM Consensus Sequence

In an embodiment, a TREM disclosed herein comprises a consensus sequence provided herein.

In an embodiment, a TREM disclosed herein comprises a consensus sequence of Formula $I_{ZZZ}$, wherein zzz indicates any of the twenty amino acids and Formula I corresponds to all species.

In an embodiment, a TREM disclosed herein comprises a consensus sequence of Formula $II_{ZZZ}$, wherein zzz indicates any of the twenty amino acids and Formula II corresponds to mammals.

In an embodiment, a TREM disclosed herein comprises a consensus sequence of Formula $III_{ZZZ}$, wherein zzz indicates any of the twenty amino acids and Formula III corresponds to humans.

In an embodiment, zzz indicates any of the twenty amino acids: alanine, arginine, asparagine, aspartate, cysteine, glutamine, glutamate, glycine, histidine, isoleucine, methionine, leucine, lysine, phenylalanine, proline, serine, threonine, tryptophan, tyrosine, or valine.

In an embodiment, a TREM disclosed herein comprises a property selected from the following:

a) under physiological conditions residue $R_0$ forms a linker region, e.g., a Linker 1 region;

b) under physiological conditions residues $R_1$-$R_2$-$R_3$-$R_4$-$R_5$-$R_6$-$R_7$ and residues $R_{65}$-$R_{66}$-$R_{67}$-$R_{68}$-$R_{69}$-$R_{70}$-$R_{71}$ form a stem region, e.g., an AStD stem region;

c) under physiological conditions residues $R_8$-$R_9$ forms a linker region, e.g., a Linker 2 region;

d) under physiological conditions residues-$R_{10}$-$R_{11}$-$R_{12}$-$R_{13}$-$R_{14}$ $R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$ form a stem-loop region, e.g., a D arm Region;

e) under physiological conditions residue-$R_{29}$ forms a linker region, e.g., a Linker 3 Region;

f) under physiological conditions residues-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$ form a stem-loop region, e.g., an AC arm region;

g) under physiological conditions residue-$[R_{47}]_x$ comprises a variable region, e.g., as described herein;

h) under physiological conditions residues-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$ form a stem-loop region, e.g., a T arm Region; or i) under physiological conditions residue $R_{72}$ forms a linker region, e.g., a Linker 4 region.

Alanine TREM Consensus Sequence

In an embodiment, a TREM disclosed herein comprises the sequence of Formula $I_{ALA}$ (SEQ ID NO: 562), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$, wherein R is a ribonucleotide residue and the consensus for Ala is: $R_0$=absent; $R_{14}$, $R_{57}$=are independently A or absent; $R_{26}$=A, C, G or absent; $R_5$, $R_6$, $R_{15}$, $R_{16}$, $R_{21}$, $R_{30}$, $R_{31}$, $R_{32}$, $R_{34}$, $R_{37}$, $R_{41}$, $R_{42}$, $R_{43}$, $R_{44}$, $R_{45}$, $R_{48}$, $R_{49}$, $R_{50}$, $R_{58}$, $R_{59}$, $R_{63}$, $R_{64}$, $R_{66}$, $R_{67}$=are independently N or absent; $R_{11}$, $R_{35}$, $R_{65}$=are independently A, C, U or absent; $R_1$, $R_9$, $R_{20}$, $R_{38}$, $R_{40}$, $R_{51}$, $R_{52}$, $R_{56}$=are independently A, G or absent; $R_7$, $R_{22}$, $R_{25}$, $R_{27}$, $R_{29}$, $R_{46}$, $R_{53}$, $R_{72}$=are independently A, G, U or absent; $R_{24}$, $R_{69}$=are independently A, U or absent; $R_{70}$, $R_{71}$=are independently C or absent; $R_3$, $R_4$=are independently C, G or absent; $R_{12}$, $R_{33}$, $R_{36}$, $R_{62}$, $R_{68}$=are independently C, G, U or absent; $R_{13}$, $R_{17}$, $R_{28}$, $R_{39}$, $R_{55}$, $R_{60}$, $R_{61}$=are independently C, U or absent; $R_{10}$, $R_{19}$, $R_{23}$=are independently G or absent; $R_2$=G, U or absent; $R_8$, $R_{18}$, $R_{54}$=are independently U or absent; $[R_{47}]_x$=N or absent; wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula $II_{ALA}$ (SEQ ID NO: 563), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ala is:

$R_0$, $R_{18}$=are absent;

$R_{14}$, $R_{24}$, $R_{57}$=are independently A or absent;

$R_{15}$, $R_{26}$, $R_{64}$=are independently A, C, G or absent;

$R_{16}$, $R_{31}$, $R_{50}$, $R_{59}$=are independently N or absent;

$R_{11}$, $R_{32}$, $R_{37}$, $R_{41}$, $R_{43}$, $R_{45}$, $R_{49}$, $R_{65}$, $R_{66}$=are independently A, C, U or absent;

$R_1$, $R_5$, $R_9$, $R_{25}$, $R_{27}$, $R_{38}$, $R_{40}$, $R_{46}$, $R_{51}$, $R_{56}$=are independently A, G or absent;

$R_7$, $R_{22}$, $R_{29}$, $R_{42}$, $R_{44}$, $R_{53}$, $R_{63}$, $R_{72}$=are independently A, G, U or absent;

$R_6$, $R_{35}$, $R_{69}$=are independently A, U or absent;

$R_{55}$, $R_{60}$, $R_{70}$, $R_{71}$=are independently C or absent;

$R_3$=C, G or absent;

$R_{12}$, $R_{36}$, $R_{48}$=are independently C, G, U or absent;

$R_{13}$, $R_{17}$, $R_{28}$, $R_{30}$, $R_{34}$, $R_{39}$, $R_{55}$, $R_{61}$, $R_{62}$, $R_{67}$, $R_{68}$=are independently C, U or absent;

$R_4$, $R_{10}$, $R_{19}$, $R_{20}$, $R_{23}$, $R_{52}$=are independently G or absent;

$R_2$, $R_8$, $R_{33}$=are independently G, U or absent;

$R_{21}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula $III_{ALA}$ (SEQ ID NO: 564), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ala is:

$R_0$, $R_{18}$=are absent;

$R_{14}$, $R_{24}$, $R_{57}$, $R_{72}$=are independently A or absent;

$R_{15}$, $R_{26}$, $R_{64}$=are independently A, C, G or absent;

$R_{16}$, $R_{31}$, $R_{50}$=are independently N or absent;

$R_{11}$, $R_{32}$, $R_{37}$, $R_{41}$, $R_{43}$, $R_{45}$, $R_{49}$, $R_{65}$, $R_{66}$=are independently A, C, U or absent;

$R_5$, $R_9$, $R_{25}$, $R_{27}$, $R_{38}$, $R_{40}$, $R_{46}$, $R_{51}$, $R_{56}$=are independently A, G or absent;

$R_7$, $R_{22}$, $R_{29}$, $R_{42}$, $R_{44}$, $R_{53}$, $R_{63}$=are independently A, G, U or absent;

$R_6$, $R_{35}$=are independently A, U or absent;

$R_{55}$, $R_{60}$, $R_{61}$, $R_{70}$, $R_{71}$=are independently C or absent;

$R_{12}$, $R_{48}$, $R_{59}$=are independently C, G, U or absent;

$R_{13}$, $R_{17}$, $R_{28}$, $R_{30}$, $R_{34}$, $R_{39}$, $R_{55}$, $R_{62}$, $R_{67}$, $R_{68}$=are independently C, U or absent;

$R_1$, $R_2$, $R_3$, $R_4$, $R_{10}$, $R_{19}$, $R_{20}$, $R_{23}$, $R_{52}$=are independently G or absent;

$R_{33}$, $R_{36}$=are independently G, U or absent;

$R_8$, $R_{21}$, $R_{54}$, $R_{69}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Arginine TREM Consensus Sequence

In an embodiment, a TREM disclosed herein comprises the sequence of Formula I ARG (SEQ ID NO: 565), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-

$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Arg is:

$R_{57}$=A or absent;

$R_9$, $R_{27}$=are independently A, C, G or absent;

$R_1$, $R_2$, $R_3$, $R_4$, $R_5$, $R_6$, $R_7$, $R_{11}$, $R_{12}$, $R_{16}$, $R_{21}$, $R_{22}$, $R_{23}$, $R_{25}$, $R_{26}$, $R_{29}$, $R_{30}$, $R_{31}$, $R_{32}$, $R_{33}$, $R_{34}$, $R_{37}$, $R_{42}$, $R_{44}$, $R_{45}$, $R_{46}$, $R_{48}$, $R_{49}$, $R_{50}$, $R_{51}$, $R_{58}$, $R_{62}$, $R_{63}$, $R_{64}$, $R_{65}$, $R_{66}$, $R_{67}$, $R_{68}$, $R_{69}$, $R_{70}$, $R_{71}$=are independently N or absent;

$R_{13}$, $R_{17}$, $R_{41}$=are independently A, C, U or absent;

$R_{19}$, $R_{20}$, $R_{24}$, $R_{40}$, $R_{56}$=are independently A, G or absent;

$R_{14}$, $R_{15}$, $R_{72}$=are independently A, G, U or absent;

$R_{18}$=A, U or absent;

$R_{38}$=C or absent;

$R_{35}$, $R_{43}$, $R_{61}$=are independently C, G, U or absent;

$R_{28}$, $R_{55}$, $R_{59}$, $R_{60}$=are independently C, U or absent;

$R_9$, $R_{10}$, $R_{52}$=are independently G or absent;

$R_8$, $R_{39}$=are independently G, U or absent;

$R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II ARG (SEQ ID NO: 566), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Arg is:

$R_{18}$=absent;

$R_{24}$, $R_{57}$=are independently A or absent;

$R_{41}$=A, C or absent;

$R_3$, $R_7$, $R_{34}$, $R_{50}$=are independently A, C, G or absent;

$R_2$, $R_5$, $R_6$, $R_{12}$, $R_{26}$, $R_{32}$, $R_{37}$, $R_{44}$, $R_{58}$, $R_{66}$, $R_{67}$, $R_{68}$, $R_{70}$=are independently N or absent; $R_{49}$, $R_{71}$=are independently A, C, U or absent; $R_1$, $R_{15}$, $R_{19}$, $R_{25}$, $R_{27}$, $R_{40}$, $R_{45}$, $R_{46}$, $R_{56}$, $R_{72}$=are independently A, G or absent;

$R_{14}$, $R_{29}$, $R_{63}$=are independently A, G, U or absent;

$R_{16}$, $R_{21}$=are independently A, U or absent;

$R_{38}$, $R_{61}$=are independently C or absent;

$R_{33}$, $R_{48}$=are independently C, G or absent;

$R_4$, $R_9$, $R_{11}$, $R_{43}$, $R_{62}$, $R_{64}$, $R_{69}$=are independently C, G, U or absent;

$R_{13}$, $R_{22}$, $R_{28}$, $R_{30}$, $R_{31}$, $R_{35}$, $R_{55}$, $R_{60}$, $R_{65}$=are independently C, U or absent;

$R_9$, $R_{10}$, $R_{20}$, $R_{23}$, $R_{51}$, $R_{52}$=are independently G or absent;

$R_8$, $R_{39}$, $R_{42}$=are independently G, U or absent;

$R_{17}$, $R_{36}$, $R_{53}$, $R_{54}$, $R_{59}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III ARG (SEQ ID NO: 567), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Arg is:

$R_{18}$=is absent;

$R_{15}$, $R_{21}$, $R_{24}$, $R_{41}$, $R_{57}$=are independently A or absent;

$R_{34}$, $R_{44}$=are independently A, C or absent;

$R_3$, $R_5$, $R_{58}$=are independently A, C, G or absent;

$R_2$, $R_6$, $R_{66}$, $R_{70}$=are independently N or absent;

$R_{37}$, $R_{49}$=are independently A, C, U or absent;

$R_1$, $R_{25}$, $R_{29}$, $R_{40}$, $R_{45}$, $R_{46}$, $R_{50}$=are independently A, G or absent;

$R_{14}$, $R_{63}$, $R_{68}$=are independently A, G, U or absent;

$R_{16}$=A, U or absent;

$R_{38}$, $R_{61}$=are independently C or absent;

$R_7$, $R_{11}$, $R_{12}$, $R_{26}$, $R_{48}$=are independently C, G or absent;

$R_{64}$, $R_{67}$, $R_{69}$=are independently C, G, U or absent;

$R_4$, $R_{13}$, $R_{22}$, $R_{28}$, $R_{30}$, $R_{31}$, $R_{35}$, $R_{43}$, $R_{55}$, $R_{60}$, $R_{62}$, $R_{65}$, $R_{71}$=are independently C, U or absent;

$R_9$, $R_{10}$, $R_{19}$, $R_{20}$, $R_{23}$, $R_{27}$, $R_{33}$, $R_{51}$, $R_{52}$, $R_{56}$, $R_{72}$=are independently G or absent;

$R_8$, $R_9$, $R_{32}$, $R_{39}$, $R_{42}$=are independently G, U or absent;

$R_{17}$, $R_{36}$, $R_{53}$, $R_{54}$, $R_{59}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Asparagine TREM Consensus Sequence

In an embodiment, a TREM disclosed herein comprises the sequence of Formula I ASN (SEQ ID NO: 568), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asn is:

$R_0$, $R_{18}$=are absent;

$R_{41}$=A or absent;

$R_{14}$, $R_{48}$, $R_{56}$=are independently A, C, G or absent;

$R_2$, $R_4$, $R_5$, $R_6$, $R_{12}$, $R_{17}$, $R_{26}$, $R_{29}$, $R_{30}$, $R_{31}$, $R_{44}$, $R_{45}$, $R_{46}$, $R_{49}$, $R_{50}$, $R_{58}$, $R_{62}$, $R_{63}$, $R_{65}$, $R_{66}$, $R_{67}$, $R_{68}$, R 70, $R_{71}$=are independently N or absent;

$R_{11}$, $R_{13}$, $R_{22}$, $R_{42}$, $R_{55}$, $R_{59}$=are independently A, C, U or absent;

$R_9$, $R_{15}$, $R_{24}$, $R_{27}$, $R_{34}$, $R_{37}$, $R_{51}$, $R_{72}$=are independently A, G or absent;

$R_1$, $R_7$, $R_{25}$, $R_{69}$=are independently A, G, U or absent;

$R_{40}$, $R_{57}$=are independently A, U or absent;

$R_{60}$=C or absent;

$R_{33}$=C, G or absent;

$R_{21}$, $R_{32}$, $R_{43}$, $R_{64}$=are independently C, G, U or absent;

$R_3$, $R_{16}$, $R_{28}$, $R_{35}$, $R_{36}$, $R_{61}$=are independently C, U or absent;

$R_{10}$, $R_{19}$, $R_{20}$, $R_{52}$=are independently G or absent;

$R_{54}$=G, U or absent;

$R_8$, $R_{23}$, $R_{38}$, $R_{39}$, $R_{53}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II ASN (SEQ ID NO: 569), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asn is:

$R_0$, $R_{18}$=are absent;

$R_{24}$, $R_{41}$, $R_{46}$, $R_{62}$=are independently A or absent;

$R_{59}$=A, C or absent;

$R_{14}$, $R_{56}$, $R_{66}$=are independently A, C, G or absent;

$R_{17}$, $R_{29}$=are independently N or absent;

$R_{11}$, $R_{26}$, $R_{42}$, $R_{55}$=are independently A, C, U or absent;

$R_1$, $R_9$, $R_{12}$, $R_{15}$, $R_{25}$, $R_{34}$, $R_{37}$, $R_{48}$, $R_{51}$, $R_{67}$, $R_{68}$, $R_{69}$, $R_{70}$, $R_{72}$=are independently A, G or absent;

$R_{44}$, $R_{45}$, $R_{55}$=are independently A, G, U or absent;

$R_{40}$, $R_{57}$=are independently A, U or absent;

$R_5$, $R_{28}$, $R_{60}$=are independently C or absent;

$R_{33}$, $R_{65}$=are independently C, G or absent;

$R_{21}$, $R_{43}$, $R_{71}$=are independently C, G, U or absent;

$R_3$, $R_6$, $R_{13}$, $R_{22}$, $R_{32}$, $R_{35}$, $R_{36}$, $R_{61}$, $R_{63}$, $R_{64}$=are independently C, U or absent;

$R_7$, $R_{10}$, $R_{19}$, $R_{20}$, $R_{27}$, $R_{49}$, $R_{52}$=are independently G or absent;

$R_{54}$=G, U or absent;

$R_2$, $R_4$, $R_8$, $R_{16}$, $R_{23}$, $R_{30}$, $R_{31}$, $R_{38}$, $R_{39}$, $R_{50}$, $R_{53}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III ASN (SEQ ID NO: 570), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asn is:

$R_0$, $R_{18}$=are absent;

$R_{24}$, $R_{40}$, $R_{41}$, $R_{46}$, $R_{62}$=are independently A or absent;

$R_{59}$=A, C or absent;

$R_{14}$, $R_{56}$, $R_{66}$=are independently A, C, G or absent;

$R_{11}$, $R_{26}$, $R_{42}$, $R_{55}$=are independently A, C, U or absent;

$R_1$, $R_9$, $R_{12}$, $R_{15}$, $R_{34}$, $R_{37}$, $R_{48}$, $R_{51}$, $R_{67}$, $R_{68}$, $R_{69}$, $R_{70}$=are independently A, G or absent;

$R_{44}$, $R_{45}$, $R_{55}$=are independently A, G, U or absent;

$R_{57}$=A, U or absent;

$R_5$, $R_{28}$, $R_{60}$=are independently C or absent;

$R_{33}$, $R_{65}$=are independently C, G or absent;

$R_{17}$, $R_{21}$, $R_{29}$=are independently C, G, U or absent;

$R_3$, $R_6$, $R_{13}$, $R_{22}$, $R_{32}$, $R_{35}$, $R_{36}$, $R_{43}$, $R_{61}$, $R_{63}$, $R_{64}$, $R_{71}$=are independently C, U or absent;

$R_7$, $R_{10}$, $R_{19}$, $R_{20}$, $R_{25}$, $R_{27}$, $R_{49}$, $R_{52}$, $R_{72}$=are independently G or absent;

$R_{54}$=G, U or absent;

$R_2$, $R_4$, $R_8$, $R_{16}$, $R_{23}$, $R_{30}$, $R_{31}$, $R_{38}$, $R_{39}$, $R_{50}$, $R_{53}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Aspartate TREM Consensus Sequence

In an embodiment, a TREM disclosed herein comprises the sequence of Formula I ASP (SEQ ID NO: 571), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asp is:

$R_0$=absent;

$R_{24}$, $R_{71}$=are independently A, C or absent;

$R_{33}$, $R_{46}$=are independently A, C, G or absent;

$R_2$, $R_3$, $R_4$, $R_5$, $R_6$, $R_{12}$, $R_{16}$, $R_{22}$, $R_{26}$, $R_{29}$, $R_{31}$, $R_{32}$, $R_{44}$, $R_{48}$, $R_{49}$, $R_{58}$, $R_{63}$, $R_{64}$, $R_{66}$, $R_{67}$, $R_{68}$, $R_{69}$=are independently N or absent;

$R_{13}$, $R_{21}$, $R_{34}$, $R_{41}$, $R_{57}$, $R_{65}$=are independently A, C, U or absent;

$R_9$, $R_{10}$, $R_{14}$, $R_{15}$, $R_{20}$, $R_{27}$, $R_{37}$, $R_{40}$, $R_{51}$, $R_{56}$, $R_{72}$=are independently A, G or absent;

$R_7$, $R_{25}$, $R_{42}$=are independently A, G, U or absent;

$R_{39}$=C or absent;

$R_{50}$, $R_{62}$=are independently C, G or absent;

$R_{30}$, $R_{43}$, $R_{45}$, $R_{55}$, $R_{70}$=are independently C, G, U or absent;

$R_8$, $R_{11}$, $R_{17}$, $R_{18}$, $R_{28}$, $R_{35}$, $R_{53}$, $R_{59}$, $R_{60}$, $R_{61}$=are independently C, U or absent;

$R_{19}$, $R_{52}$=are independently G or absent;

$R_1$=G, U or absent;

$R_{23}$, $R_{36}$, $R_{38}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II ASP (SEQ ID NO: 572), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asp is:

$R_0$, $R_{17}$, $R_{18}$, $R_{23}$=are independently absent;

$R_9$, $R_{40}$=are independently A or absent;

$R_{24}$, $R_{71}$=are independently A, C or absent;

$R_{67}$, $R_{68}$=are independently A, C, G or absent;

$R_2$, $R_6$, $R_{66}$=are independently N or absent;

$R_{57}$, $R_{63}$=are independently A, C, U or absent;

$R_{10}$, $R_{14}$, $R_{27}$, $R_{33}$, $R_{37}$, $R_{44}$, $R_{46}$, $R_{51}$, $R_{56}$, $R_{64}$, $R_{72}$=are independently A, G or absent;

$R_7$, $R_{12}$, $R_{26}$, $R_{65}$=are independently A, U or absent;

$R_{39}$, $R_{61}$, $R_{62}$=are independently C or absent;

$R_3$, $R_{31}$, $R_{45}$, $R_{70}$=are independently C, G or absent;

$R_4$, $R_5$, $R_{29}$, $R_{43}$, $R_{55}$=are independently C, G, U or absent;

$R_8$, $R_{11}$, $R_{13}$, $R_{30}$, $R_{32}$, $R_{34}$, $R_{35}$, $R_{41}$, $R_{48}$, $R_{53}$, $R_{59}$, $R_{60}$=are independently C, U or absent;

$R_{15}$, $R_{19}$, $R_{20}$, $R_{25}$, $R_{42}$, $R_{50}$, $R_{52}$=are independently G or absent;

$R_1$, $R_{22}$, $R_{49}$, $R_{58}$, $R_{69}$=are independently G, U or absent;

$R_{16}$, $R_{21}$, $R_{28}$, $R_{36}$, $R_{38}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III ASP (SEQ ID NO: 573), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Asp is:

$R_0$, $R_{17}$, $R_{18}$, $R_{23}$=are absent;

$R_9$, $R_{12}$, $R_{40}$, $R_{65}$, $R_{71}$=are independently A or absent;

$R_2$, $R_{24}$, $R_{57}$=are independently A, C or absent;

$R_6$, $R_{14}$, $R_{27}$, $R_{46}$, $R_{51}$, $R_{56}$, $R_{64}$, $R_{67}$, $R_{68}$=are independently A, G or absent;

$R_3$, $R_{31}$, $R_{35}$, $R_{39}$, $R_{61}$, $R_{62}$=are independently C or absent;

$R_{66}$=C, G or absent;

$R_5$, $R_8$, $R_{29}$, $R_{30}$, $R_{32}$, $R_{34}$, $R_{41}$, $R_{43}$, $R_{48}$, $R_{55}$, $R_{59}$, $R_{60}$, $R_{63}$=are independently C, U or absent;

$R_{10}$, $R_{15}$, $R_{19}$, $R_{20}$, $R_{25}$, $R_{33}$, $R_{37}$, $R_{42}$, $R_{44}$, $R_{45}$, $R_{49}$, R so, R $2, $R_{69}$, $R_{70}$, $R_{72}$=are independently G or absent;

$R_{22}$, $R_{55}$=are independently G, U or absent;

$R_1$, $R_4$, $R_7$, $R_{11}$, $R_{13}$, $R_{16}$, $R_{21}$, $R_{26}$, $R_{28}$, $R_{36}$, $R_{38}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Cysteine TREM Consensus sequence

In an embodiment, a TREM disclosed herein comprises the sequence of Formula I cys (SEQ ID NO: 574), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Cys is:

$R_0$=absent;

$R_{14}$, $R_{39}$, $R_{57}$=are independently A or absent;

$R_{41}$=A, C or absent;

$R_{10}$, $R_{15}$, $R_{27}$, $R_{33}$, $R_{62}$=are independently A, C, G or absent;

$R_3$, $R_4$, $R_5$, $R_6$, $R_{12}$, $R_{13}$, $R_{16}$, $R_{24}$, $R_{26}$, $R_{29}$, $R_{30}$, $R_{31}$, $R_{32}$, $R_{34}$, $R_{42}$, $R_{44}$, $R_{45}$, $R_{46}$, $R_{48}$, $R_{49}$, $R_{58}$, $R_{63}$, $R_{64}$, $R_{66}$, $R_{67}$, $R_{68}$, $R_{69}$, $R_{70}$=are independently N or absent;

$R_{65}$=A, C, U or absent;

$R_9$, $R_{25}$, $R_{37}$, $R_{40}$, $R_{52}$, $R_{56}$=are independently A, G or absent;

$R_7$, $R_{20}$, $R_{51}$=are independently A, G, U or absent;

$R_{18}$, $R_{38}$, $R_{55}$=are independently C or absent;

$R_2$=C, G or absent;

$R_{21}$, $R_{28}$, $R_{43}$, $R_{50}$=are independently C, G, U or absent;

$R_{11}$, $R_{22}$, $R_{23}$, $R_{35}$, $R_{36}$, $R_{59}$, $R_{60}$, $R_{61}$, $R_{71}$, $R_{72}$=are independently C, U or absent;

$R_1$, $R_{19}$=are independently G or absent;

$R_{17}$=G, U or absent;

$R_5$, $R_{83}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II CYS (SEQ ID NO: 575), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Cys is:

$R_0$, $R_{18}$, $R_{23}$=are absent;

$R_{14}$, $R_{24}$, $R_{26}$, $R_{29}$, $R_{39}$, $R_{41}$, $R_{45}$, $R_{57}$=are independently A or absent;

$R_{44}$=A, C or absent;

$R_{27}$, $R_{62}$=are independently A, C, G or absent;

$R_{16}$=A, C, G, U or absent;

$R_{30}$, $R_{70}$=are independently A, C, U or absent;

$R_5$, $R_7$, $R_9$, $R_{25}$, $R_{34}$, $R_{37}$, $R_{40}$, $R_{46}$, $R_{52}$, $R_{56}$, $R_{55}$, $R_{66}$=are independently A, G or absent;

$R_{20}$, $R_{51}$=are independently A, G, U or absent;

$R_{35}$, $R_{38}$, $R_{43}$, $R_{55}$, $R_{69}$=are independently C or absent;

$R_2$, $R_4$, $R_{15}$=are independently C, G or absent;

$R_{13}$=C, G, U or absent;

$R_6$, $R_{11}$, $R_{28}$, $R_{36}$, $R_{48}$, $R_{49}$, R so, $R_{60}$, $R_{61}$, $R_{67}$, $R_{68}$, $R_{71}$, $R_{72}$=are independently C, U or absent;

$R_1$, $R_3$, $R_{10}$, $R_{19}$, $R_{33}$, $R_{63}$=are independently G or absent;

$R_8$, $R_{17}$, $R_{21}$, $R_{64}$=are independently G, U or absent;

$R_{12}$, $R_{22}$, $R_{31}$, $R_{32}$, $R_{42}$, $R_{53}$, $R_{54}$, $R_{65}$=are independently U or absent;

$R_{59}$=U, or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III CYS (SEQ ID NO: 576), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Cys is:

$R_0$, $R_{18}$, $R_{23}$=are absent;

$R_{14}$, $R_{24}$, $R_{26}$, $R_{29}$, $R_{34}$, $R_{39}$, $R_{41}$, $R_{45}$, $R_{57}$, $R_{55}$=are independently A or absent;

$R_{44}$, $R_{70}$=are independently A, C or absent;

$R_{62}$=A, C, G or absent;

$R_{16}$=N or absent;

$R_5$, $R_7$, $R_9$, $R_{20}$, $R_{40}$, $R_{46}$, $R_{51}$, $R_{52}$, $R_{56}$, $R_{66}$=are independently A, G or absent;

$R_{28}$, $R_{35}$, $R_{38}$, $R_{43}$, $R_{55}$, $R_{67}$, $R_{69}$=are independently C or absent;

$R_4$, $R_{15}$=are independently C, G or absent;

$R_6$, $R_{11}$, $R_{13}$, $R_{30}$, $R_{48}$, $R_{49}$, $R_{50}$, $R_{60}$, $R_{61}$, $R_{68}$, $R_{71}$, $R_{72}$=are independently C, U or absent;

$R_1$, $R_2$, $R_3$, $R_{10}$, $R_{19}$, $R_{25}$, $R_{27}$, $R_{33}$, $R_{37}$, $R_{63}$=are independently G or absent;

$R_8$, $R_{21}$, $R_{64}$=are independently G, U or absent;

$R_{12}$, $R_{17}$, $R_{22}$, $R_{31}$, $R_{32}$, $R_{36}$, $R_{42}$, $R_{53}$, $R_{54}$, $R_{59}$, $R_{65}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Glutamine TREM Consensus Sequence

In an embodiment, a TREM disclosed herein comprises the sequence of Formula I GLN (SEQ ID NO: 577), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gln is:

$R_0$, $R_{18}$=are absent;

$R_{14}$, $R_{24}$, $R_{57}$=are independently A or absent;

$R_9$, $R_{26}$, $R_{27}$, $R_{33}$, $R_{56}$=are independently A, C, G or absent;

$R_2$, $R_4$, $R_5$, $R_6$, $R_{12}$, $R_{13}$, $R_{16}$, $R_{21}$, $R_{22}$, $R_{25}$, $R_{29}$, $R_{30}$, $R_{31}$, $R_{32}$, $R_{34}$, $R_{41}$, $R_{42}$, $R_{44}$, $R_{45}$, $R_{46}$, $R_{48}$, $R_{49}$, R so, $R_{58}$, R 62, $R_{63}$, $R_{66}$, $R_{67}$, $R_{68}$, $R_{69}$, $R_{70}$=are independently N or absent;

$R_{17}$, $R_{23}$, $R_{43}$, $R_{65}$, $R_{71}$=are independently A, C, U or absent;

$R_{15}$, $R_{40}$, $R_{51}$, $R_{52}$=are independently A, G or absent;

$R_1$, $R_7$, $R_{72}$=are independently A, G, U or absent;

$R_3$, $R_{11}$, $R_{37}$, $R_{60}$, $R_{64}$=are independently C, G, U or absent;

$R_{28}$, $R_{35}$, $R_{55}$, $R_{59}$, $R_{61}$=are independently C, U or absent;

$R_{10}$, $R_{19}$, $R_{20}$=are independently G or absent;

$R_{39}$=G, U or absent;

$R_8$, $R_{36}$, $R_{38}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II GLN (SEQ ID NO: 578), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gln is:

$R_0$, $R_{18}$, $R_{23}$=are absent;

$R_{14}$, $R_{24}$, $R_{57}$=are independently A or absent;

$R_{17}$, $R_{71}$=are independently A, C or absent;

$R_{25}$, $R_{26}$, $R_{33}$, $R_{44}$, $R_{46}$, $R_{56}$, $R_{69}$=are independently A, C, G or absent;

$R_4$, $R_5$, $R_{12}$, $R_{22}$, $R_{29}$, $R_{30}$, $R_{48}$, $R_{49}$, $R_{63}$, $R_{67}$, $R_{68}$=are independently N or absent;

$R_{31}$, $R_{43}$, $R_{62}$, $R_{65}$, $R_{70}$=are independently A, C, U or absent;

$R_{15}$, $R_{27}$, $R_{34}$, $R_{40}$, $R_{41}$, $R_{51}$, $R_{52}$=are independently A, G or absent;

$R_2$, $R_7$, $R_{21}$, $R_{45}$, $R_{50}$, $R_{58}$, $R_{66}$, $R_{72}$=are independently A, G, U or absent;

$R_3$, $R_{13}$, $R_{32}$, $R_{37}$, $R_{42}$, $R_{60}$, $R_{64}$=are independently C, G, U or absent;

$R_6$, $R_{11}$, $R_{28}$, $R_{35}$, $R_{55}$, $R_{59}$, $R_{61}$=are independently C, U or absent;

$R_9$, $R_{10}$, $R_{19}$, $R_{20}$=are independently G or absent;

$R_1$, $R_{16}$, $R_{39}$=are independently G, U or absent;

$R_8$, $R_{36}$, $R_{38}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III GLN (SEQ ID NO: 579), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gln is:

$R_0$, $R_{18}$, $R_{23}$=are absent;

$R_{14}$, $R_{24}$, $R_{41}$, $R_{57}$=are independently A or absent;

$R_{17}$, $R_{71}$=are independently A, C or absent;

$R_5$, $R_{25}$, $R_{26}$, $R_{46}$, $R_{56}$, $R_{69}$=are independently A, C, G or absent;

$R_4$, $R_{22}$, $R_{29}$, $R_{30}$, $R_{48}$, $R_{49}$, $R_{63}$, $R_{68}$=are independently N or absent;

$R_{43}$, $R_{62}$, $R_{65}$, $R_{70}$=are independently A, C, U or absent;

$R_{15}$, $R_{27}$, $R_{33}$, $R_{34}$, $R_{40}$, $R_{51}$, $R_{52}$=are independently A, G or absent;

$R_2$, $R_7$, $R_{12}$, $R_{45}$, $R_{50}$, $R_{55}$, $R_{66}$=are independently A, G, U or absent;

$R_{31}$=A, U or absent;

$R_{32}$, $R_{44}$, $R_{60}$=are independently C, G or absent;

$R_3$, $R_{13}$, $R_{37}$, $R_{42}$, $R_{64}$, $R_{67}$=are independently C, G, U or absent;

$R_6$, $R_{11}$, $R_{28}$, $R_{35}$, $R_{55}$, $R_{59}$, $R_{61}$=are independently C, U or absent;

$R_9$, $R_{10}$, $R_{19}$, $R_{20}$=are independently G or absent;

$R_1$, $R_{21}$, $R_{39}$, $R_{72}$=are independently G, U or absent;

$R_8$, $R_{16}$, $R_{36}$, $R_{38}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Glutamate TREM Consensus Sequence

In an embodiment, a TREM disclosed herein comprises the sequence of Formula I GLU (SEQ ID NO: 580), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Glu is:

$R_0$=absent;

$R_{34}$, $R_{43}$, $R_{68}$, $R_{69}$=are independently A, C, G or absent;

$R_1$, $R_2$, $R_5$, $R_6$, $R_0$, $R_{12}$, $R_{16}$, $R_{20}$, $R_{21}$, $R_{26}$, $R_{27}$, $R_{29}$, $R_{30}$, $R_{31}$, $R_{32}$, $R_{33}$, $R_{41}$, $R_{44}$, $R_{45}$, $R_{46}$, $R_{48}$, $R_{50}$, $R_{51}$, $R_{58}$, $R_{63}$, $R_{64}$, $R_{65}$, $R_{66}$, $R_{70}$, $R_{71}$=are independently N or absent;

$R_{13}$, $R_{17}$, $R_{23}$, $R_{61}$=are independently A, C, U or absent;

$R_{10}$, $R_{14}$, $R_{24}$, $R_{40}$, $R_{52}$, $R_{56}$=are independently A, G or absent;

$R_7$, $R_{15}$, $R_{25}$, $R_{67}$, $R_{72}$=are independently A, G, U or absent;

$R_{11}$, $R_{57}$=are independently A, U or absent;

$R_{39}$=C, G or absent;

$R_3$, $R_4$, $R_{22}$, $R_{42}$, $R_{49}$, $R_{55}$, $R_{62}$=are independently C, G, U or absent;

$R_{18}$, $R_{28}$, $R_{35}$, $R_{37}$, $R_{53}$, $R_{59}$, $R_{60}$=are independently C, U or absent;

$R_{19}$=G or absent;

$R_8$, $R_{36}$, $R_{38}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II GLU (SEQ ID NO: 581), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Glu is:

$R_0$, $R_{18}$, $R_{23}$=are absent;

$R_{17}$, $R_{40}$=are independently A or absent;

$R_{26}$, $R_{27}$, $R_{34}$, $R_{43}$, $R_{68}$, $R_{69}$, $R_{71}$=are independently A, C, G or absent;

$R_1$, $R_2$, $R_5$, $R_{12}$, $R_{21}$, $R_{31}$, $R_{33}$, $R_{41}$, $R_{45}$, $R_{48}$, $R_{51}$, $R_{55}$, $R_{66}$, $R_{70}$=are independently N or absent;

$R_{44}$, $R_{61}$=are independently A, C, U or absent;

$R_9$, $R_{14}$, $R_{24}$, $R_{25}$, $R_{52}$, $R_{56}$, $R_{63}$=are independently A, G or absent;

$R_7$, $R_{15}$, $R_{46}$, $R_{65}$, $R_{67}$, $R_{72}$=are independently A, G, U or absent;

$R_{29}$, $R_{57}$=are independently A, U or absent;

$R_{60}$=C or absent;

$R_{39}$=C, G or absent;

$R_3$, $R_6$, $R_{20}$, $R_{30}$, $R_{32}$, $R_{42}$, $R_{55}$, $R_{62}$, $R_{65}$=are independently C, G, U or absent;

$R_4$, $R_8$, $R_{16}$, $R_{28}$, $R_{35}$, $R_{37}$, $R_{49}$, $R_{53}$, $R_{59}$=are independently C, U or absent;

$R_{10}$, $R_{19}$=are independently G or absent;

$R_{22}$, $R_{64}$=are independently G, U or absent;

$R_{11}$, $R_{13}$, $R_{36}$, $R_{38}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III GLU (SEQ ID NO: 582), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Glu is:

$R_0$, $R_{17}$, $R_{18}$, $R_{23}$=are absent;
$R_{14}$, $R_{27}$, $R_{40}$, $R_{71}$=are independently A or absent;
$R_{44}$=A, C or absent;
$R_{43}$=A, C, G or absent;
$R_1$, $R_{31}$, $R_{33}$, $R_{45}$, $R_{51}$, $R_{66}$=are independently N or absent;
$R_{21}$, $R_{41}$=are independently A, C, U or absent;
$R_7$, $R_{24}$, $R_{25}$, $R_{50}$, $R_{52}$, $R_{56}$, $R_{63}$, $R_{68}$, $R_{70}$=are independently A, G or absent;
$R_5$, $R_{46}$=are independently A, G, U or absent;
$R_{29}$, $R_{57}$, $R_{67}$, $R_{72}$=are independently A, U or absent;
$R_2$, $R_{39}$, $R_{60}$=are independently C or absent;
$R_3$, $R_{12}$, $R_{20}$, $R_{26}$, $R_{34}$, $R_{69}$=are independently C, G or absent;
$R_6$, $R_{30}$, $R_{42}$, $R_{48}$, $R_{65}$=are independently C, G, U o rabsent;
$R_4$, $R_{16}$, $R_{28}$, $R_{35}$, $R_{37}$, $R_{49}$, $R_{53}$, $R_{55}$, $R_{58}$, $R_{61}$, $R_{62}$=are independently C, U or absent;
$R_9$, $R_{10}$, $R_{19}$, $R_{64}$=are independently G or absent;
$R_{15}$, $R_{22}$, $R_{32}$=are independently G, U or absent;
$R_8$, $R_{11}$, $R_{13}$, $R_{36}$, $R_{38}$, $R_{54}$, $R_{59}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Glycine TREM Consensus Sequence

In an embodiment, a TREM disclosed herein comprises the sequence of Formula I GLY (SEQ ID NO: 583), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gly is:

$R_0$=absent;
$R_{24}$=A or absent;
$R_3$, $R_9$, $R_{40}$, $R_{50}$, $R_{51}$=are independently A, C, G or absent;
$R_4$, $R_5$, $R_6$, $R_7$, $R_{12}$, $R_{16}$, $R_{21}$, $R_{22}$, $R_{26}$, $R_{29}$, $R_{30}$, $R_{31}$, $R_{32}$, $R_{33}$, $R_{34}$, $R_{41}$, $R_{42}$, $R_{43}$, $R_{44}$, $R_{45}$, $R_{46}$, $R_{48}$, $R_{49}$, $R_{58}$, R 63, $R_{64}$, $R_{65}$, $R_{66}$, $R_{67}$, $R_{68}$=are independently N or absent;
$R_{59}$=A, C, U or absent;
$R_1$, $R_{10}$, $R_{14}$, $R_{15}$, $R_{27}$, $R_{56}$=are independently A, G or absent;
$R_{20}$, $R_{25}$=are independently A, G, U or absent;
$R_{57}$, $R_{72}$=are independently A, U or absent;
$R_{38}$, $R_{39}$, $R_{60}$=are independently C or absent;
$R_{52}$=C, G or absent;
$R_2$, $R_{19}$, $R_{37}$, $R_{54}$, $R_{55}$, $R_{61}$, $R_{62}$, $R_{69}$, $R_{70}$=are independently C, G, U or absent;
$R_{11}$, $R_{13}$, $R_{17}$, $R_{28}$, $R_{35}$, $R_{36}$, $R_{71}$=are independently C, U or absent;
$R_8$, $R_{18}$, $R_{23}$, $R_{53}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II GLY (SEQ ID NO: 584), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gly is:

$R_0$, $R_{18}$, $R_{23}$=are absent;
$R_{24}$, $R_{27}$, $R_{40}$, $R_{72}$=are independently A or absent;
$R_{26}$=A, C or absent;
$R_3$, $R_7$, $R_{68}$=are independently A, C, G or absent;
$R_5$, $R_{30}$, $R_{41}$, $R_{42}$, $R_{44}$, $R_{49}$, $R_{67}$=are independently A, C, G, U or absent;
$R_{31}$, $R_{32}$, $R_{34}$=are independently A, C, U or absent;
$R_9$, $R_{10}$, $R_{14}$, $R_{15}$, $R_{33}$, $R_{50}$, $R_{56}$=are independently A, G or absent;
$R_{12}$, $R_{16}$, $R_{22}$, $R_{25}$, $R_{29}$, $R_{46}$=are independently A, G, U or absent;

$R_{57}$=A, U or absent;
$R_{17}$, $R_{38}$, $R_{39}$, $R_{60}$, $R_{61}$, $R_{71}$=are independently C or absent;
$R_6$, $R_{52}$, $R_{64}$, $R_{66}$=are independently C, G or absent;
$R_2$, $R_4$, $R_{37}$, $R_{48}$, $R_{55}$, $R_{65}$=are independently C, G, U or absent;
$R_{13}$, $R_{35}$, $R_{43}$, $R_{62}$, $R_{69}$=are independently C, U or absent;
$R_1$, $R_{19}$, $R_{20}$, $R_{51}$, $R_{70}$=are independently G or absent;
$R_{21}$, $R_{45}$, $R_{63}$=are independently G, U or absent;
$R_8$, $R_{11}$, $R_{28}$, $R_{36}$, $R_{53}$, $R_{54}$, $R_{55}$, $R_{59}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III GLY (SEQ ID NO: 585), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Gly is:
$R_0$, $R_{18}$, $R_{23}$=are absent;
$R_{24}$, $R_{27}$, $R_{40}$, $R_{72}$=are independently A or absent;
$R_{26}$=A, C or absent;
$R_3$, $R_7$, $R_{49}$, $R_{68}$=are independently A, C, G or absent;
$R_5$, $R_{30}$, $R_{41}$, $R_{44}$, $R_{67}$=are independently N or absent;
$R_{31}$, $R_{32}$, $R_{34}$=are independently A, C, U or absent;
$R_9$, $R_{10}$, $R_{14}$, $R_{15}$, $R_{33}$, $R_{50}$, $R_{56}$=are independently A, G or absent;
$R_{12}$, $R_{25}$, $R_{29}$, $R_{42}$, $R_{46}$=are independently A, G, U or absent;
$R_{16}$, $R_{57}$=are independently A, U or absent;
$R_{17}$, $R_{38}$, $R_{39}$, $R_{60}$, $R_{61}$, $R_{71}$=are independently C or absent;
$R_6$, $R_{52}$, $R_{64}$, $R_{66}$=are independently C, G or absent;
$R_{37}$, $R_{48}$, $R_{65}$=are independently C, G, U or absent;
$R_2$, $R_4$, $R_{13}$, $R_{35}$, $R_{43}$, $R_{55}$, $R_{62}$, $R_{69}$=are independently C, U or absent;
$R_1$, $R_{19}$, $R_{20}$, $R_{51}$, $R_{70}$=are independently G or absent;
$R_{21}$, $R_{22}$, $R_{45}$, $R_{63}$=are independently G, U or absent;
$R_8$, $R_{11}$, $R_{28}$, $R_{36}$, $R_{53}$, $R_{54}$, $R_{55}$, $R_{59}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Histidine TREM Consensus Sequence

In an embodiment, a TREM disclosed herein comprises the sequence of Formula I HIS (SEQ ID NO: 586), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for His is:
$R_{23}$=absent;
$R_{14}$, $R_{24}$, $R_{57}$=are independently A or absent;
$R_{72}$=A, C or absent;
$R_9$, $R_{27}$, $R_{43}$, $R_{48}$, $R_{69}$=are independently A, C, G or absent;
$R_3$, $R_4$, $R_5$, $R_6$, $R_{12}$, $R_{25}$, $R_{26}$, $R_{29}$, $R_{30}$, $R_{31}$, $R_{34}$, $R_{42}$, $R_{45}$, $R_{46}$, $R_{49}$, R so, $R_{58}$, $R_{62}$, $R_{63}$, $R_{66}$, $R_{67}$, $R_{68}$=are independently N or absent;
$R_{13}$, $R_{21}$, $R_{41}$, $R_{44}$, $R_{65}$=are independently A, C, U or absent;
$R_{40}$, $R_{51}$, $R_{56}$, $R_{70}$=are independently A, G or absent;
$R_7$, $R_{32}$=are independently A, G, U or absent;
$R_{55}$, $R_{60}$=are independently C or absent;
$R_{11}$, $R_{16}$, $R_{33}$, $R_{64}$=are independently C, G, U or absent;
$R_2$, $R_{17}$, $R_{22}$, $R_{28}$, $R_{35}$, $R_{53}$, $R_{59}$, $R_{61}$, $R_{71}$=are independently C, U or absent;
$R_1$, $R_{10}$, $R_{15}$, $R_{19}$, $R_{20}$, $R_{37}$, $R_{39}$, $R_{52}$=are independently G or absent;
$R_0$=G, U or absent;
$R_8$, $R_{18}$, $R_{36}$, $R_{38}$, $R_{54}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II HIS (SEQ ID NO: 587), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-

$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for His is:

$R_0$, $R_{17}$, $R_{18}$, $R_{23}$=are absent;

$R_7$, $R_{12}$, $R_{14}$, $R_{24}$, $R_{27}$, $R_{45}$, $R_{57}$, $R_{58}$, $R_{63}$, $R_{67}$, $R_{72}$=are independently A or absent;

$R_3$=A, C, U or absent;

$R_4$, $R_{43}$, $R_{56}$, $R_{70}$=are independently A, G or absent;

$R_{49}$=A, U or absent;

$R_2$, $R_{28}$, $R_{30}$, $R_{41}$, $R_{42}$, $R_{44}$, $R_{48}$, $R_{55}$, $R_{60}$, $R_{66}$, $R_{71}$=are independently C or absent;

$R_{25}$=C, G or absent;

$R_9$=C, G, U or absent;

$R_8$, $R_{13}$, $R_{26}$, $R_{33}$, $R_{35}$, $R_{50}$, $R_{53}$, $R_{61}$, $R_{68}$=are independently C, U or absent;

$R_1$, $R_6$, $R_{10}$, $R_{15}$, $R_{19}$, $R_{20}$, $R_{32}$, $R_{34}$, $R_{37}$, $R_{39}$, $R_{40}$, $R_{46}$, R$1, $R_{52}$, $R_{62}$, $R_{64}$, $R_{69}$=are independently G or absent;

$R_{16}$=G, U or absent;

$R_5$, $R_{11}$, $R_{21}$, $R_{22}$, $R_{29}$, $R_{31}$, $R_{36}$, $R_{38}$, $R_{54}$, $R_{59}$, $R_{65}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III HIS (SEQ ID NO: 588), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for His is:

$R_0$, $R_{17}$, $R_{18}$, $R_{23}$=are absent;

$R_7$, $R_{12}$, $R_{14}$, $R_{24}$, $R_{27}$, $R_{45}$, $R_{57}$, $R_{55}$, $R_{63}$, $R_{67}$, $R_{72}$=are independently A or absent;

$R_3$=A, C or absent;

$R_4$, $R_{43}$, $R_{56}$, $R_{70}$=are independently A, G or absent;

$R_{49}$=A, U or absent;

$R_2$, $R_{28}$, $R_{30}$, $R_{41}$, $R_{42}$, $R_{44}$, $R_{48}$, $R_{55}$, $R_{60}$, $R_{66}$, $R_{71}$=are independently C or absent;

$R_8$, $R_9$, $R_{26}$, $R_{33}$, $R_{35}$, $R_{50}$, $R_{61}$, $R_{68}$=are independently C, U or absent;

$R_1$, $R_6$, $R_{10}$, $R_{15}$, $R_{19}$, $R_{20}$, $R_{25}$, $R_{32}$, $R_{34}$, $R_{37}$, $R_{39}$, $R_{40}$, $R_{46}$, $R_{51}$, $R_{52}$, $R_{62}$, $R_{64}$, $R_{69}$=are independently G or absent;

$R_5$, $R_{11}$, $R_{13}$, $R_{16}$, $R_{21}$, $R_{22}$, $R_{29}$, $R_{31}$, $R_{36}$, $R_{38}$, $R_{53}$, $R_{54}$, $R_{59}$, $R_{65}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Isoleucine TREM Consensus sequence

In an embodiment, a TREM disclosed herein comprises the sequence of Formula I ILE (SEQ ID NO: 589), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ile is:

$R_{23}$=absent;

$R_{38}$, $R_{41}$, $R_{57}$, $R_{72}$=are independently A or absent;

$R_1$, $R_{26}$=are independently A, C, G or absent;

$R_0$, $R_3$, $R_4$, $R_6$, $R_{16}$, $R_{31}$, $R_{32}$, $R_{34}$, $R_{37}$, $R_{42}$, $R_{43}$, $R_{44}$, $R_{45}$, $R_{46}$, $R_{48}$, $R_{49}$, $R_{50}$, $R_{58}$, $R_{59}$, $R_{62}$, $R_{63}$, $R_{64}$, $R_{66}$, $R_{67}$, R 68, $R_{69}$=are independently N or absent;

$R_{22}$, $R_{61}$, $R_{65}$=are independently A, C, U or absent;

$R_9$, $R_{14}$, $R_{15}$, $R_{24}$, $R_{27}$, $R_{40}$=are independently A, G or absent;

$R_7$, $R_{25}$, $R_{29}$, $R_{51}$, $R_{56}$=are independently A, G, U or absent;

$R_{18}$, $R_{54}$=are independently A, U or absent;

$R_{60}$=C or absent;

$R_2$, $R_{52}$, $R_{70}$=are independently C, G or absent;

$R_5$, $R_{12}$, $R_{21}$, $R_{30}$, $R_{33}$, $R_{71}$=are independently C, G, U or absent;

$R_{11}$, $R_{13}$, $R_{17}$, $R_{28}$, $R_{35}$, $R_{53}$, $R_{55}$=are independently C, U or absent;

$R_{10}$, $R_{19}$, $R_{20}$=are independently G or absent;

$R_8$, $R_{36}$, $R_{39}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II ILE (SEQ ID NO: 590), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ile is:

$R_0$, $R_{18}$, $R_{23}$=are absent;

$R_{24}$, $R_{38}$, $R_{40}$, $R_{41}$, $R_{57}$, $R_{72}$=are independently A or absent;

$R_{26}$, $R_{65}$=are independently A, C or absent;

$R_{58}$, $R_{59}$, $R_{67}$=are independently N or absent;

$R_{22}$=A, C, U or absent;

$R_6$, $R_9$, $R_{14}$, $R_{15}$, $R_{29}$, $R_{34}$, $R_{43}$, $R_{46}$, $R_{48}$, $R_{50}$, $R_{51}$, $R_{63}$, $R_{69}$=are independently A, G or absent;

$R_{37}$, $R_{56}$=are independently A, G, U or absent;

$R_{54}$=A, U or absent;

$R_{28}$, $R_{35}$, $R_{60}$, $R_{62}$, $R_{71}$=are independently C or absent;

$R_2$, $R_{52}$, $R_{70}$=are independently C, G or absent;

$R_5$=C, G, U or absent;

$R_3$, $R_4$, $R_{11}$, $R_{13}$, $R_{17}$, $R_{21}$, $R_{30}$, $R_{42}$, $R_{44}$, $R_{45}$, $R_{49}$, $R_{53}$, $R_{55}$, $R_{61}$, $R_{64}$, $R_{66}$=are independently C, U or absent;

$R_1$, $R_{10}$, $R_{19}$, $R_{20}$, $R_{25}$, $R_{27}$, $R_{31}$, $R_{68}$=are independently G or absent;

$R_7$, $R_{12}$, $R_{32}$=are independently G, U or absent;

$R_8$, $R_{16}$, $R_{33}$, $R_{36}$, $R_{39}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III ILE (SEQ ID NO: 591), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ile is:

$R_0$, $R_{18}$, $R_{23}$=are absent;

$R_{14}$, $R_{24}$, $R_{38}$, $R_{40}$, $R_{41}$, $R_{57}$, $R_{72}$=are independently A or absent;

$R_{26}$, $R_{65}$=are independently A, C or absent;

$R_{22}$, $R_{59}$=are independently A, C, U or absent;

$R_6$, $R_0$, $R_{15}$, $R_{34}$, $R_{43}$, $R_{46}$, R$1, $R_{56}$, $R_{63}$, $R_{69}$=are independently A, G or absent;

$R_{37}$=A, G, U or absent;

$R_{13}$, $R_{28}$, $R_{35}$, $R_{44}$, $R_{55}$, $R_{60}$, $R_{62}$, $R_{71}$=are independently C or absent;

$R_2$, $R_5$, $R_{70}$=are independently C, G or absent;

$R_{55}$, $R_{67}$=are independently C, G, U or absent;

$R_3$, $R_4$, $R_{11}$, $R_{17}$, $R_{21}$, $R_{30}$, $R_{42}$, $R_{45}$, $R_{49}$, $R_{53}$, $R_{61}$, $R_{64}$, $R_{66}$=are independently C, U or absent;

$R_1$, $R_{10}$, $R_{19}$, $R_{20}$, $R_{25}$, $R_{27}$, $R_{29}$, $R_{31}$, $R_{32}$, $R_{48}$, $R_{50}$, $R_{52}$, $R_{68}$=are independently G or absent;

$R_7$, $R_{12}$=are independently G, U or absent;

$R_8$, $R_{16}$, $R_{33}$, $R_{36}$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Methionine TREM Consensus Sequence

In an embodiment, a TREM disclosed herein comprises the sequence of Formula I MET (SEQ ID NO: 592), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Met is:

$R_0$, $R_{23}$=are absent;

$R_{14}$, $R_{38}$, $R_{40}$, $R_{57}$=are independently A or absent;

$R_{60}$=A, C or absent;

$R_{33}$, $R_{48}$, $R_{70}$=are independently A, C, G or absent;

$R_1$, $R_3$, $R_4$, $R_5$, $R_6$, $R_{11}$, $R_{12}$, $R_{16}$, $R_{17}$, $R_{21}$, $R_{22}$, $R_{26}$, $R_{27}$, $R_{29}$, $R_{30}$, $R_{31}$, $R_{32}$, $R_{42}$, $R_{44}$, $R_{45}$, $R_{46}$, $R_{49}$, $R_{50}$, $R_{58}$, $R_{62}$, $R_{63}$, $R_{66}$, $R_{67}$, $R_{68}$, $R_{69}$, $R_{71}$=are independently N or absent;

$R_{18}$, $R_{35}$, $R_{41}$, $R_{59}$, $R_{65}$=are independently A, C, U or absent;

$R_9$, $R_{15}$, $R_{51}$=are independently A, G or absent;

$R_7$, $R_{24}$, $R_{25}$, $R_{34}$, $R_{53}$, $R_{56}$=are independently A, G, U or absent;

$R_{72}$=A, U or absent;

$R_{37}$=C or absent;

$R_{10}$, $R_{55}$=are independently C, G or absent;

$R_2$, $R_{13}$, $R_{28}$, $R_{43}$, $R_{64}$=are independently C, G, U or absent;

$R_{36}$, $R_{61}$=are independently C, U or absent;

$R_{19}$, $R_{20}$, $R_{52}$=are independently G or absent;

$R_8$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-

12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II MET (SEQ ID NO: 593), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Met is:

$R_0$, $R_{18}$, $R_{22}$, $R_{23}$=are absent;

$R_{14}$, $R_{24}$, $R_{38}$, $R_{40}$, $R_{41}$, $R_{57}$, $R_{72}$=are independently A or absent;

$R_{59}$, $R_{60}$, $R_{62}$, $R_{65}$=are independently A, C or absent;

$R_6$, $R_{45}$, $R_{67}$=are independently A, C, G or absent;

$R_4$=N or absent;

$R_{21}$, $R_{42}$=are independently A, C, U or absent;

$R_1$, $R_9$, $R_{27}$, $R_{29}$, $R_{32}$, $R_{46}$, $R_{51}$=are independently A, G or absent;

$R_{17}$, $R_{49}$, $R_{53}$, $R_{56}$, $R_{55}$=are independently A, G, U or absent;

$R_{63}$=A, U or absent;

$R_3$, $R_{13}$, $R_{37}$=are independently C or absent;

$R_{48}$, $R_{55}$, $R_{64}$, $R_{70}$=are independently C, G or absent;

$R_2$, $R_5$, $R_{66}$, $R_{68}$=are independently C, G, U or absent;

$R_{11}$, $R_{16}$, $R_{26}$, $R_{28}$, $R_{30}$, $R_{31}$, $R_{35}$, $R_{36}$, $R_{43}$, $R_{44}$, $R_{61}$, $R_{71}$=are independently C, U or absent;

$R_{10}$, $R_{12}$, $R_{15}$, $R_{19}$, $R_{20}$, $R_{25}$, $R_{33}$, $R_{52}$, $R_{69}$=are independently G or absent;

$R_7$, $R_{34}$, $R_{50}$=are independently G, U or absent;

$R_8$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III MET (SEQ ID NO: 594), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Met is:

$R_0$, $R_{18}$, $R_{22}$, $R_{23}$=are absent;

$R_{14}$, $R_{24}$, $R_{38}$, $R_{40}$, $R_{41}$, $R_{57}$, $R_{72}$=are independently A or absent;

$R_{59}$, $R_{62}$, $R_{65}$=are independently A, C or absent;

$R_6$, $R_{67}$=are independently A, C, G or absent;

$R_4$, $R_{21}$=are independently A, C, U or absent;

$R_1$, $R_9$, $R_{27}$, $R_{29}$, $R_{32}$, $R_{45}$, $R_{46}$, $R_{51}$=are independently A, G or absent;

$R_{17}$, $R_{56}$, $R_{55}$=are independently A, G, U or absent;

$R_{49}$, $R_{53}$, $R_{63}$=are independently A, U or absent;

$R_3$, $R_{13}$, $R_{26}$, $R_{37}$, $R_{43}$, $R_{60}$=are independently C or absent;

$R_2$, $R_{48}$, $R_{55}$, $R_{64}$, $R_{70}$=are independently C, G or absent;

$R_5$, $R_{66}$=are independently C, G, U or absent;

$R_{11}$, $R_{16}$, $R_{28}$, $R_{30}$, $R_{31}$, $R_{35}$, $R_{36}$, $R_{42}$, $R_{44}$, $R_{61}$, $R_{71}$=are independently C, U or absent;

$R_{10}$, $R_{12}$, $R_{15}$, $R_{19}$, $R_{20}$, $R_{25}$, $R_{33}$, $R_{52}$, $R_{69}$=are independently G or absent;

$R_7$, $R_{34}$, $R_{50}$, $R_{68}$=are independently G, U or absent;

$R_8$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Leucine TREM Consensus Sequence

In an embodiment, a TREM disclosed herein comprises the sequence of Formula I LEU (SEQ ID NO: 595), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Leu is:

$R_0$=absent;

$R_{38}$, $R_{57}$=are independently A or absent;

$R_{60}$=A, C or absent;

$R_1$, $R_{13}$, $R_{27}$, $R_{48}$, $R_{51}$, $R_{56}$=are independently A, C, G or absent;

$R_2$, $R_3$, $R_4$, $R_5$, $R_6$, $R_7$, $R_9$, $R_{10}$, $R_{11}$, $R_{12}$, $R_{16}$, $R_{23}$, $R_{26}$, $R_{28}$, $R_{29}$, $R_{30}$, $R_{31}$, $R_{32}$, $R_{33}$, $R_{34}$, $R_{37}$, $R_{41}$, $R_{42}$, $R_{43}$, $R_{44}$, $R_{45}$, $R_{46}$, $R_{49}$, $R_{50}$, $R_{58}$, $R_{62}$, $R_{63}$, $R_{65}$, $R_{66}$, $R_{67}$, $R_{68}$, $R_{69}$, $R_{70}$=are independently N or absent;

$R_{17}$, $R_{18}$, $R_{21}$, $R_{22}$, $R_{25}$, $R_{35}$, $R_{55}$=are independently A, C, U or absent;

$R_{14}$, $R_{15}$, $R_{39}$, $R_{72}$=are independently A, G or absent;

$R_{24}$, $R_{40}$=are independently A, G, U or absent;
$R_{52}$, $R_{61}$, $R_{64}$, $R_{71}$=are independently C, G, U or absent;
$R_{36}$, $R_{53}$, $R_{59}$=are independently C, U or absent;
$R_{19}$=G or absent;
$R_{20}$-G, U or absent;
$R_{8}$, $R_{54}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II LEU (SEQ ID NO: 596), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Leu is:

$R_0$=absent;
$R_{38}$, $R_{57}$, $R_{72}$=are independently A or absent;
$R_{60}$=A, C or absent;
$R_4$, $R_5$, $R_{48}$, $R_{50}$, $R_{56}$, $R_{69}$=are independently A, C, G or absent;
$R_6$, $R_{33}$, $R_{41}$, $R_{43}$, $R_{46}$, $R_{49}$, $R_{58}$, $R_{63}$, $R_{66}$, $R_{70}$=are independently N or absent;
$R_{11}$, $R_{12}$, $R_{17}$, $R_{21}$, $R_{22}$, $R_{28}$, $R_{31}$, $R_{37}$, $R_{44}$, $R_{55}$=are independently A, C, U or absent;
$R_1$, $R_9$, $R_{14}$, $R_{15}$, $R_{24}$, $R_{27}$, $R_{34}$, $R_{39}$=are independently A, G or absent;
$R_7$, $R_{29}$, $R_{32}$, $R_{40}$, $R_{45}$=are independently A, G, U or absent;
$R_{25}$=A, U or absent;
$R_{13}$=C, G or absent;
$R_2$, $R_3$, $R_{16}$, $R_{26}$, $R_{30}$, $R_{52}$, $R_{62}$, $R_{64}$, $R_{65}$, $R_{67}$, $R_{68}$=are independently C, G, U or absent;
$R_{18}$, $R_{35}$, $R_{42}$, $R_{53}$, $R_{59}$, $R_{61}$, $R_{71}$=are independently C, U or absent;
$R_{19}$, $R_{51}$=are independently G or absent;
$R_{10}$, $R_{20}$=are independently G, U or absent;
$R_8$, $R_{23}$, $R_{36}$, $R_{54}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III LEU (SEQ ID NO: 597), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Leu is:

$R_0$=absent;
$R_{38}$, $R_{57}$, $R_{72}$=are independently A or absent;
$R_{60}$=A, C or absent;
$R_4$, $R_5$, $R_{48}$, $R_{50}$, $R_{56}$, $R_{55}$, $R_{69}$=are independently A, C, G or absent;
$R_6$, $R_{33}$, $R_{43}$, $R_{46}$, $R_{49}$, $R_{63}$, $R_{66}$, $R_{70}$=are independently N or absent;
$R_{11}$, $R_{12}$, $R_{17}$, $R_{21}$, $R_{22}$, $R_{28}$, $R_{31}$, $R_{37}$, $R_{41}$, $R_{44}$, $R_{55}$=are independently A, C, U or absent;
$R_1$, $R_9$, $R_{14}$, $R_{15}$, $R_{24}$, $R_{27}$, $R_{34}$, $R_{39}$=are independently A, G or absent;
$R_7$, $R_{29}$, $R_{32}$, $R_{40}$, $R_{45}$=are independently A, G, U or absent;
$R_{25}$=A, U or absent;
$R_{13}$=C, G or absent;
$R_2$, $R_3$, $R_{16}$, $R_{30}$, $R_{52}$, $R_{62}$, $R_{64}$, $R_{67}$, $R_{68}$=are independently C, G, U or absent;
$R_{18}$, $R_{35}$, $R_{42}$, $R_{53}$, $R_{59}$, $R_{61}$, $R_{65}$, $R_{71}$=are independently C, U or absent;
$R_{19}$, $R_{51}$=are independently G or absent;
$R_{10}$, $R_{20}$, $R_{26}$=are independently G, U or absent;
$R_8$, $R_{23}$, $R_{36}$, $R_{54}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Lysine TREM Consensus Sequence

In an embodiment, a TREM disclosed herein comprises the sequence of Formula I LYS (SEQ ID NO: 598), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-

$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Lys is:

$R_0$=absent;

$R_{14}$=A or absent;

$R_{40}$, $R_{41}$=are independently A, C or absent;

$R_{34}$, $R_{43}$, $R_{51}$=are independently A, C, G or absent;

$R_1$, $R_2$, $R_3$, $R_4$, $R_5$, $R_6$, $R_7$, $R_{11}$, $R_{12}$, $R_{16}$, $R_{21}$, $R_{26}$, $R_{30}$, $R_{31}$, $R_{32}$, $R_{44}$, $R_{45}$, $R_{46}$, $R_{48}$, $R_{49}$, $R_{50}$, $R_{58}$, $R_{62}$, $R_{63}$, $R_{65}$, $R_{66}$, $R_{67}$, $R_{68}$, $R_{69}$, $R_{70}$=are independently N or absent;

$R_{13}$, $R_{17}$, $R_{59}$, $R_{71}$=are independently A, C, U or absent;

$R_9$, $R_{15}$, $R_{19}$, $R_{20}$, $R_{25}$, $R_{27}$, $R_{52}$, $R_{56}$=are independently A, G or absent;

$R_{24}$, $R_{29}$, $R_{72}$=are independently A, G, U or absent;

$R_{18}$, $R_{57}$=are independently A, U or absent;

$R_{10}$, $R_{33}$=are independently C, G or absent;

$R_{42}$, $R_{61}$, $R_{64}$=are independently C, G, U or absent;

$R_{28}$, $R_{35}$, $R_{36}$, $R_{37}$, $R_{53}$, $R_{55}$, $R_{60}$=are independently C, U or absent;

$R_8$, $R_{22}$, $R_{23}$, $R_{38}$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II LYS (SEQ ID NO: 599), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Lys is:

$R_0$, $R_{18}$, $R_{23}$=are absent;

$R_{14}$=A or absent;

$R_{40}$, $R_{41}$, $R_{43}$=are independently A, C or absent;

$R_3$, $R_7$=are independently A, C, G or absent;

$R_1$, $R_6$, $R_{11}$, $R_{31}$, $R_{45}$, $R_{48}$, $R_{49}$, $R_{63}$, $R_{65}$, $R_{66}$, $R_{68}$=are independently N or absent;

$R_2$, $R_{12}$, $R_{13}$, $R_{17}$, $R_{44}$, $R_{67}$, $R_{71}$=are independently A, C, U or absent;

$R_9$, $R_{15}$, $R_{19}$, $R_{20}$, $R_{25}$, $R_{27}$, $R_{34}$, $R_{50}$, $R_{52}$, $R_{56}$, R 70, $R_{72}$=are independently A, G or absent;

$R_5$, $R_{24}$, $R_{26}$, $R_{29}$, $R_{32}$, $R_{46}$, $R_{69}$=are independently A, G, U or absent;

$R_{57}$=A, U or absent;

$R_{10}$, $R_{61}$=are independently C, G or absent;

$R_4$, $R_{16}$, $R_{21}$, $R_{30}$, $R_{55}$, $R_{64}$=are independently C, G, U or absent;

$R_{28}$, $R_{35}$, $R_{36}$, $R_{37}$, $R_{42}$, $R_{53}$, $R_{55}$, $R_{59}$, $R_{60}$, $R_{62}$=are independently C, U or absent;

$R_{33}$, $R_{51}$=are independently G or absent;

$R_8$=G, U or absent;

$R_{22}$, $R_{38}$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III LYS (SEQ ID NO: 600), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Lys is:

$R_0$, $R_{18}$, $R_{23}$=absent;

$R_9$, $R_{14}$, $R_{34}$, $R_{41}$=are independently A or absent;

$R_{40}$=A, C or absent;

$R_1$, $R_3$, $R_7$, $R_{31}$=are independently A, C, G or absent;

$R_{48}$, $R_{65}$, $R_{68}$=are independently N or absent;

$R_2$, $R_{13}$, $R_{17}$, $R_{44}$, $R_{63}$, $R_{66}$=are independently A, C, U or absent;

$R_5$, $R_{15}$, $R_{19}$, $R_{20}$, $R_{25}$, $R_{27}$, $R_{29}$, $R_{50}$, $R_{52}$, $R_{56}$, $R_{70}$, $R_{72}$=are independently A, G or absent;

$R_6$, $R_{24}$, $R_{32}$, $R_{49}$=are independently A, G, U or absent;

$R_{12}$, $R_{26}$, $R_{46}$, $R_{57}$=are independently A, U or absent;

$R_{11}$, $R_{28}$, $R_{35}$, $R_{43}$=are independently C or absent;

$R_{10}$, $R_{45}$, $R_{61}$=are independently C, G or absent;

$R_4$, $R_{21}$, $R_{64}$=are independently C, G, U or absent;

$R_{37}$, R$3, $R_{55}$, $R_{59}$, $R_{60}$, $R_{62}$, $R_{67}$, $R_{71}$=are independently C, U or absent;

$R_{33}$, $R_{51}$=are independently G or absent;

$R_8$, $R_{30}$, $R_{55}$, $R_{69}$=are independently G, U or absent;

$R_{16}$, $R_{22}$, $R_{36}$, $R_{38}$, $R_{39}$, $R_{42}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Phenylalanine TREM Consensus Sequence

In an embodiment, a TREM disclosed herein comprises the sequence of Formula I PHE (SEQ ID NO: 601), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Phe is:

$R_0$, $R_{23}$=are absent;

$R_9$, $R_{14}$, $R_{38}$, $R_{39}$, $R_{57}$, $R_{72}$=are independently A or absent;

$R_{71}$=A, C or absent;

$R_{41}$, $R_{70}$=are independently A, C, G or absent;

$R_4$, $R_5$, $R_6$, $R_{30}$, $R_{31}$, $R_{32}$, $R_{34}$, $R_{42}$, $R_{44}$, $R_{45}$, $R_{46}$, $R_{48}$, $R_{49}$, $R_{58}$, $R_{62}$, $R_{63}$, $R_{66}$, $R_{67}$, $R_{68}$, $R_{69}$=are independently N or absent;

$R_{16}$, $R_{61}$, $R_{65}$=are independently A, C, U or absent;

$R_{15}$, $R_{26}$, $R_{27}$, $R_{29}$, $R_{40}$, $R_{56}$=are independently A, G or absent;

$R_7$, $R_{51}$=are independently A, G, U or absent;

$R_{22}$, $R_{24}$=are independently A, U or absent;

$R_{55}$, $R_{60}$=are independently C or absent;

$R_2$, $R_3$, $R_{21}$, $R_{33}$, $R_{43}$, $R_{50}$, $R_{64}$=are independently C, G, U or absent;

$R_{11}$, $R_{12}$, $R_{13}$, $R_{17}$, $R_{28}$, $R_{35}$, $R_{36}$, $R_{59}$=are independently C, U or absent;

$R_{10}$, $R_{19}$, $R_{20}$, $R_{25}$, $R_{37}$, $R_{52}$=are independently G or absent;

$R_1$=G, U or absent;

$R_8$, $R_{18}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II PHE (SEQ ID NO: 602), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Phe is:

$R_0$, $R_{18}$, $R_{23}$=absent;

$R_{14}$, $R_{24}$, $R_{38}$, $R_{39}$, $R_{57}$, $R_{72}$=are independently A or absent;

$R_{46}$, $R_{71}$=are independently A, C or absent;

$R_4$, $R_{70}$=are independently A, C, G or absent;

$R_{45}$=A, C, U or absent;

$R_6$, $R_7$, $R_{15}$, $R_{26}$, $R_{27}$, $R_{32}$, $R_{34}$, $R_{40}$, $R_{41}$, $R_{56}$, $R_{69}$=are independently A, G or absent;

$R_{29}$=A, G, U or absent;

$R_5$, $R_0$, $R_{67}$=are independently A, U or absent;

$R_{35}$, $R_{49}$, $R_{55}$, $R_{60}$=are independently C or absent;

$R_{21}$, $R_{43}$, $R_{62}$=are independently C, G or absent;

$R_2$, $R_{33}$, $R_{68}$=are independently C, G, U or absent;

$R_3$, $R_{11}$, $R_{12}$, $R_{13}$, $R_{28}$, $R_{30}$, $R_{36}$, $R_{42}$, $R_{44}$, $R_{48}$, $R_{58}$, $R_{59}$, $R_{61}$, $R_{66}$=are independently C, U or absent;

$R_{10}$, $R_{19}$, $R_{20}$, $R_{25}$, $R_{37}$, $R_{51}$, $R_{52}$, $R_{63}$, $R_{64}$=are independently G or absent;

$R_1$, $R_{31}$, $R_{50}$=are independently G, U or absent;

$R_8$, $R_{16}$, $R_{17}$, $R_{22}$, $R_{53}$, $R_{54}$, $R_{65}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III PHE (SEQ ID NO: 603), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Phe is:

$R_0$, $R_{18}$, $R_{22}$, $R_{23}$=absent;

$R_5$, $R_7$, $R_{14}$, $R_{24}$, $R_{26}$, $R_{32}$, $R_{34}$, $R_{38}$, $R_{39}$, $R_{41}$, $R_{57}$, $R_{72}$=are independently A or absent;

$R_{46}$=A, C or absent;

$R_{70}$=A, C, G or absent;

$R_4$, $R_6$, $R_{15}$, $R_{56}$, $R_{69}$=are independently A, G or absent;

$R_0$, $R_{45}$=are independently A, U or absent;

$R_2$, $R_{11}$, $R_{13}$, $R_{35}$, $R_{43}$, $R_{49}$, $R_{55}$, $R_{60}$, $R_{68}$, $R_{71}$=are independently C or absent;

$R_{33}$=C, G or absent;

$R_3$, $R_{28}$, $R_{36}$, $R_{48}$, $R_{58}$, $R_{59}$, $R_{61}$=are independently C, U or absent;

$R_1$, $R_{10}$, $R_{19}$, $R_{20}$, $R_{21}$, $R_{25}$, $R_{27}$, $R_{29}$, $R_{37}$, $R_{40}$, $R_{51}$, $R_{52}$, $R_{62}$, $R_{63}$, $R_{64}$=are independently G or absent;

$R_8$, $R_{12}$, $R_{16}$, $R_{17}$, $R_{30}$, $R_{31}$, $R_{42}$, $R_{44}$, $R_{50}$, $R_{53}$, $R_{54}$, $R_{65}$, $R_{66}$, $R_{67}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Proline TREM Consensus Sequence

In an embodiment, a TREM disclosed herein comprises the sequence of Formula I PRO (SEQ ID NO: 604), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Pro is:

$R_0$=absent;

$R_{14}$, $R_{57}$=are independently A or absent;

$R_{70}$, $R_{72}$=are independently A, C or absent;

$R_9$, $R_{26}$, $R_{27}$=are independently A, C, G or absent;

$R_4$, $R_5$, $R_6$, $R_{16}$, $R_{21}$, $R_{29}$, $R_{30}$, $R_{31}$, $R_{32}$, $R_{33}$, $R_{34}$, $R_{37}$, $R_{41}$, $R_{42}$, $R_{43}$, $R_{44}$, $R_{45}$, $R_{46}$, $R_{48}$, $R_{49}$, R so, $R_{58}$, $R_{61}$, $R_{62}$, $R_{63}$, $R_{64}$, $R_{66}$, $R_{67}$, $R_{68}$=are independently N or absent;

$R_{35}$, $R_{65}$=are independently A, C, U or absent;

$R_{24}$, $R_{40}$, $R_{56}$=are independently A, G or absent;

$R_7$, $R_{25}$, $R_{51}$=are independently A, G, U or absent;

$R_{55}$, $R_{60}$=are independently C or absent;

$R_1$, $R_3$, $R_{71}$=are independently C, G or absent;

$R_{11}$, $R_{12}$, $R_{20}$, $R_{69}$=are independently C, G, U or absent;

$R_{13}$, $R_{17}$, $R_{18}$, $R_{22}$, $R_{23}$, $R_{28}$, $R_{59}$=are independently C, U or absent;

$R_{10}$, $R_{15}$, $R_{19}$, $R_{38}$, $R_{39}$, $R_{52}$=are independently G or absent;

$R_2$=are independently G, U or absent;

$R_8$, $R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II PRO (SEQ ID NO: 605), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Pro is:

$R_0$, $R_{17}$, $R_{18}$, $R_{22}$, $R_{23}$=absent;

$R_{14}$, $R_{45}$, $R_{56}$, $R_{57}$, $R_{55}$, $R_{65}$, $R_{68}$=are independently A or absent;

$R_{61}$=A, C, G or absent;

$R_{43}$=N or absent;

$R_{37}$=A, C, U or absent;

$R_{24}$, $R_{27}$, $R_{33}$, $R_{40}$, $R_{44}$, $R_{63}$=are independently A, G or absent;

$R_3$, $R_{12}$, $R_{30}$, $R_{32}$, $R_{48}$, $R_{55}$, $R_{60}$, $R_{70}$, $R_{71}$, $R_{72}$=are independently C or absent;

$R_5$, $R_{34}$, $R_{42}$, $R_{66}$=are independently C, G or absent;

$R_{20}$=C, G, U or absent;

$R_{35}$, $R_{41}$, $R_{49}$, $R_{62}$=are independently C, U or absent;

$R_1$, $R_2$, $R_6$, $R_9$, $R_{10}$, $R_{15}$, $R_{19}$, $R_{26}$, $R_{38}$, $R_{39}$, $R_{46}$, $R_{50}$, $R_{51}$, $R_{52}$, $R_{64}$, $R_{67}$, $R_{69}$=are independently G or absent;

$R_{11}$, $R_{16}$=are independently G, U or absent;

$R_4$, $R_7$, $R_8$, $R_{13}$, $R_{21}$, $R_{25}$, $R_{28}$, $R_{29}$, $R_{31}$, $R_{36}$, $R_{53}$, $R_{54}$, $R_{59}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III PRO (SEQ ID NO: 606), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Pro is:

$R_0$, $R_{17}$, $R_{18}$, $R_{22}$, $R_{23}$=absent;

$R_{14}$, $R_{45}$, $R_{56}$, $R_{57}$, $R_{55}$, $R_{65}$, $R_{68}$=are independently A or absent;

$R_{37}$=A, C, U or absent;

$R_{24}$, $R_{27}$, $R_{40}$=are independently A, G or absent;

$R_3$, $R_5$, $R_{12}$, $R_{30}$, $R_{32}$, $R_{48}$, $R_{49}$, $R_{55}$, $R_{60}$, $R_{61}$, $R_{62}$, $R_{66}$, $R_{70}$, $R_{71}$, $R_{72}$=are independently C or absent;

$R_{34}$, $R_{42}$=are independently C, G or absent;

$R_{43}$=C, G, U or absent;

$R_{41}$=C, U or absent;

$R_1$, $R_2$, $R_6$, $R_9$, $R_{10}$, $R_{15}$, $R_{19}$, $R_{20}$, $R_{26}$, $R_{33}$, $R_{38}$, $R_{39}$, $R_{44}$, $R_{46}$, $R_{50}$, $R_{51}$, $R_{52}$, $R_{63}$, $R_{64}$, $R_{67}$, $R_{69}$=are independently G or absent;

$R_{16}$=G, U or absent;

$R_4$, $R_7$, $R_8$, $R_{11}$, $R_{13}$, $R_{21}$, $R_{25}$, $R_{28}$, $R_{29}$, $R_{31}$, $R_{35}$, $R_{36}$, $R_{53}$, $R_{54}$, $R_{59}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Serine TREM Consensus sequence

In an embodiment, a TREM disclosed herein comprises the sequence of Formula I SER (SEQ ID NO: 607), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ser is:

$R_0$=absent;

$R_{14}$, $R_{24}$, $R_{57}$=are independently A or absent;

$R_{41}$=A, C or absent;

$R_2$, $R_3$, $R_4$, $R_5$, $R_6$, $R_7$, $R_9$, $R_{10}$, $R_{11}$, $R_{12}$, $R_{13}$, $R_{16}$, $R_{21}$, $R_{25}$, $R_{26}$, $R_{27}$, $R_{28}$, $R_{30}$, $R_{31}$, $R_{32}$, $R_{33}$, $R_{34}$, $R_{37}$, $R_{42}$, $R_{43}$, $R_{44}$, $R_{45}$, $R_{46}$, $R_{48}$, $R_{49}$, $R_{50}$, $R_{62}$, $R_{63}$, $R_{64}$, $R_{65}$, $R_{66}$, $R_{67}$, $R_{68}$, $R_{69}$, $R_{70}$=are independently N or absent;

$R_{18}$=A, C, U or absent;

$R_{15}$, $R_{40}$, $R_{51}$, $R_{56}$=are independently A, G or absent;

$R_1$, $R_{29}$, $R_{58}$, $R_{72}$=are independently A, G, U or absent;

$R_{39}$=A, U or absent;

$R_{60}$=C or absent;

$R_{38}$=C, G or absent;

$R_{17}$, $R_{22}$, $R_{23}$, $R_{71}$=are independently C, G, U or absent;

$R_8$, $R_{35}$, $R_{36}$, $R_{55}$, $R_{59}$, $R_{61}$=are independently C, U or absent;

$R_{19}$, $R_{20}$=are independently G or absent;

$R_{52}$=G, U or absent;

$R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II SER (SEQ ID NO: 608), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ser is:

$R_0$, $R_{23}$=absent;

$R_{14}$, $R_{24}$, $R_{41}$, $R_{57}$=are independently A or absent;

$R_{44}$=A, C or absent;

$R_{25}$, $R_{45}$, $R_{48}$=are independently A, C, G or absent;

$R_2$, $R_3$, $R_4$, $R_5$, $R_{37}$, $R_{50}$, $R_{62}$, $R_{66}$, $R_{67}$, $R_{69}$, $R_{70}$=are independently N or absent;

$R_{12}$, $R_{28}$, $R_{65}$=are independently A, C, U or absent;

$R_9$, $R_{15}$, $R_{29}$, $R_{34}$, $R_{40}$, $R_{56}$, $R_{63}$=are independently A, G or absent;

$R_7$, $R_{26}$, $R_{30}$, $R_{33}$, $R_{46}$, $R_{58}$, $R_{72}$=are independently A, G, U or absent;

$R_{39}$=A, U or absent;

$R_{11}$, $R_{35}$, $R_{60}$, $R_{61}$=are independently C or absent;

$R_{13}$, $R_{38}$=are independently C, G or absent;

$R_6$, $R_{17}$, $R_{31}$, $R_{43}$, $R_{64}$, $R_{68}$=are independently C, G, U or absent;

$R_{36}$, $R_{42}$, $R_{49}$, $R_{55}$, $R_{59}$, $R_{71}$=are independently C, U or absent;

$R_{10}$, $R_{19}$, $R_{20}$, $R_{27}$, $R_{51}$=are independently G or absent;

$R_1$, $R_{16}$, $R_{32}$, $R_{52}$=are independently G, U or absent;

$R_8$, $R_{18}$, $R_{21}$, $R_{22}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III SER (SEQ ID NO: 609), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Ser is:

$R_0$, $R_{23}$=absent;

$R_{14}$, $R_{24}$, $R_{41}$, $R_{57}$, $R_{55}$=are independently A or absent;

$R_{44}$=A, C or absent;

$R_{25}$, $R_{48}$=are independently A, C, G or absent;

$R_2$, $R_3$, $R_5$, $R_{37}$, $R_{66}$, $R_{67}$, $R_{69}$, $R_{70}$=are independently N or absent;

$R_{12}$, $R_{28}$, $R_{62}$=are independently A, C, U or absent;

$R_7$, $R_9$, $R_{15}$, $R_{29}$, $R_{33}$, $R_{34}$, $R_{40}$, $R_{45}$, $R_{56}$, $R_{63}$=are independently A, G or absent;

$R_4$, $R_{26}$, $R_{46}$, $R_{50}$=are independently A, G, U or absent;

$R_{30}$, $R_{39}$=are independently A, U or absent;

$R_{11}$, $R_{17}$, $R_{35}$, $R_{60}$, $R_{61}$=are independently C or absent;

$R_{13}$, $R_{38}$=are independently C, G or absent;

$R_6$, $R_{64}$=are independently C, G, U or absent;

$R_{31}$, $R_{42}$, $R_{43}$, $R_{49}$, $R_{55}$, $R_{59}$, $R_{65}$, $R_{68}$, $R_{71}$=are independently C, U or absent;

$R_{10}$, $R_{19}$, $R_{20}$, $R_{27}$, $R_{51}$, $R_{52}$=are independently G or absent;

$R_1$, $R_{16}$, $R_{32}$, $R_{72}$=are independently G, U or absent;

$R_8$, $R_{18}$, $R_{21}$, $R_{22}$, $R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Threonine TREM Consensus Sequence

In an embodiment, a TREM disclosed herein comprises the sequence of Formula $I_{THR}$ (SEQ ID NO: 610), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Thr is:

$R_0$, $R_{23}$=absent;

$R_{14}$, $R_{41}$, $R_{57}$=are independently A or absent;

$R_{56}$, $R_{70}$=are independently A, C, G or absent;

$R_4$, $R_5$, $R_6$, $R_7$, $R_{12}$, $R_{16}$, $R_{26}$, $R_{30}$, $R_{31}$, $R_{32}$, $R_{34}$, $R_{37}$, $R_{42}$, $R_{44}$, $R_{45}$, $R_{46}$, $R_{48}$, $R_{49}$, $R_{50}$, $R_{58}$, $R_{62}$, $R_{63}$, $R_{64}$, $R_{65}$, R 66, $R_{67}$, $R_{68}$, $R_{72}$=are independently N or absent;

$R_{13}$, $R_{17}$, $R_{21}$, $R_{35}$, $R_{61}$=are independently A, C, U or absent;

$R_1$, $R_9$, $R_{24}$, $R_{27}$, $R_{29}$, $R_{69}$=are independently A, G or absent;

$R_{15}$, $R_{25}$, $R_{51}$=are independently A, G, U or absent;

$R_{40}$, $R_{53}$=are independently A, U or absent;

$R_{33}$, $R_{43}$=are independently C, G or absent;

$R_2$, $R_3$, $R_{59}$=are independently C, G, U or absent;

$R_{11}$, $R_{18}$, $R_{22}$, $R_{28}$, $R_{36}$, $R_{54}$, $R_{55}$, $R_{60}$, $R_{71}$=are independently C, U or absent;

$R_{10}$, $R_{20}$, $R_{38}$, $R_{52}$=are independently G or absent;

$R_{19}$=G, U or absent;

$R_8$, $R_{39}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II THR (SEQ ID NO: 611), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Thr is:

$R_0$, $R_{18}$, $R_{23}$=absent;

$R_{14}$, $R_{41}$, $R_{57}$=are independently A or absent;

$R_9$, $R_{42}$, $R_{44}$, $R_{48}$, $R_{56}$, $R_{70}$=are independently A, C, G or absent;

$R_4$, $R_6$, $R_{12}$, $R_{26}$, $R_{49}$, $R_{58}$, $R_{63}$, $R_{64}$, $R_{66}$, $R_{68}$=are independently N or absent;

$R_{13}$, $R_{21}$, $R_{31}$, $R_{37}$, $R_{62}$=are independently A, C, U or absent;

$R_1$, $R_{15}$, $R_{24}$, $R_{27}$, $R_{29}$, $R_{46}$, $R_{51}$, $R_{69}$=are independently A, G or absent;

$R_7$, $R_{25}$, $R_{45}$, $R_{50}$, $R_{67}$=are independently A, G, U or absent;

$R_{40}$, $R_{53}$=are independently A, U or absent;

$R_{35}$=C or absent;

$R_{33}$, $R_{43}$=are independently C, G or absent;

$R_2$, $R_3$, $R_5$, $R_{16}$, $R_{32}$, $R_{34}$, $R_{59}$, $R_{65}$, $R_{72}$=are independently C, G, U or absent;

$R_{11}$, $R_{17}$, $R_{22}$, $R_{28}$, $R_{30}$, $R_{36}$, $R_{55}$, $R_{60}$, $R_{61}$, $R_{71}$=are independently C, U or absent;

$R_{10}$, $R_{19}$, $R_{20}$, $R_{38}$, $R_{52}$=are independently G or absent;

$R_8$, $R_{39}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula $III_{THR}$ (SEQ ID NO: 612), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Thr is:

$R_0$, $R_{18}$, $R_{23}$=absent;

$R_{14}$, $R_{40}$, $R_{41}$, $R_{57}$=are independently A or absent;

$R_{44}$=A, C or absent;

$R_9$, $R_{42}$, $R_{48}$, $R_{56}$=are independently A, C, G or absent;

$R_4$, $R_6$, $R_{12}$, $R_{26}$, $R_{55}$, $R_{64}$, $R_{66}$, $R_{68}$=are independently N or absent;

$R_{13}$, $R_{21}$, $R_{31}$, $R_{37}$, $R_{49}$, $R_{62}$=are independently A, C, U or absent;

$R_1$, $R_{15}$, $R_{24}$, $R_{27}$, $R_{29}$, $R_{46}$, $R_{51}$, $R_{69}$=are independently A, G or absent;

$R_7$, $R_{25}$, $R_{45}$, $R_{50}$, $R_{63}$, $R_{67}$=are independently A, G, U or absent;

$R_{53}$=A, U or absent;

$R_{35}$=C or absent;

$R_2$, $R_{33}$, $R_{43}$, $R_{70}$=are independently C, G or absent;

$R_5$, $R_{16}$, $R_{34}$, $R_{59}$, $R_{65}$=are independently C, G, U or absent;

$R_3$, $R_{11}$, $R_{22}$, $R_{28}$, $R_{30}$, $R_{36}$, $R_{55}$, $R_{60}$, $R_{61}$, $R_{71}$=are independently C, U or absent;

$R_{10}$, $R_{19}$, $R_{20}$, $R_{38}$, $R_{52}$=are independently G or absent;

$R_{32}$=G, U or absent;

$R_8$, $R_{17}$, $R_{39}$, $R_{54}$, $R_{72}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Tryptophan TREM Consensus Sequence

In an embodiment, a TREM disclosed herein comprises the sequence of Formula I TRP (SEQ ID NO: 613), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Trp is:

$R_0$=absent;

$R_{24}$, $R_{39}$, $R_{41}$, $R_{57}$=are independently A or absent;

$R_2$, $R_3$, $R_{26}$, $R_{27}$, $R_{40}$, $R_{48}$=are independently A, C, G or absent; —N or absent;

$R_{13}$, $R_{14}$, $R_{16}$, $R_{18}$, $R_{21}$, $R_{61}$, $R_{65}$, $R_{71}$=are independently A, C, U or absent;

$R_1$, $R_9$, $R_{10}$, $R_{15}$, $R_{33}$, $R_{50}$, $R_{56}$=are independently A, G or absent;

$R_7$, $R_{25}$, $R_{72}$=are independently A, G, U or absent;

$R_{37}$, $R_{38}$, $R_{55}$, $R_{60}$=are independently C or absent;

$R_{12}$, $R_{35}$, $R_{43}$, $R_{64}$, $R_{69}$, $R_{70}$=are independently C, G, U or absent;

$R_{11}$, $R_{17}$, $R_{22}$, $R_{28}$, $R_{59}$, $R_{62}$=are independently C, U or absent;

$R_{19}$, $R_{20}$, $R_{52}$=are independently G or absent;

$R_8$, $R_{23}$, $R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II TRP (SEQ ID NO: 614), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Trp is:

$R_0$, $R_{18}$, $R_{22}$, $R_{23}$=absent;

$R_{14}$, $R_{24}$, $R_{39}$, $R_{41}$, $R_{57}$, $R_{72}$=are independently A or absent;

$R_3$, $R_4$, $R_{13}$, $R_{61}$, $R_{71}$=are independently A, C or absent;

$R_6$, $R_{44}$=are independently A, C, G or absent;

$R_{21}$=A, C, U or absent;

$R_2$, $R_7$, $R_{15}$, $R_{25}$, $R_{33}$, $R_{34}$, $R_{45}$, $R_{56}$, $R_{63}$=are independently A, G or absent;

$R_{58}$=A, G, U or absent;

$R_{46}$=A, U or absent;

$R_{37}$, $R_{38}$, $R_{55}$, $R_{60}$, $R_{62}$=are independently C or absent;

$R_{12}$, $R_{26}$, $R_{27}$, $R_{35}$, $R_{40}$, $R_{48}$, $R_{67}$=are independently C, G or absent;

$R_{32}$, $R_{43}$, $R_{68}$=are independently C, G, U or absent;

$R_{11}$, $R_{16}$, $R_{28}$, $R_{31}$, $R_{49}$, $R_{59}$, $R_{65}$, $R_{70}$=are independently C, U or absent;

$R_1$, $R_9$, $R_{10}$, $R_{19}$, $R_{20}$, $R_{50}$, $R_{52}$, $R_{69}$=are independently G or absent;

$R_5$, $R_8$, $R_{29}$, $R_{30}$, $R_{42}$, $R_{51}$, $R_{64}$, $R_{66}$=are independently G, U or absent;

$R_{17}$, $R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III TRP (SEQ ID NO: 615), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Trp is:

$R_0$, $R_{18}$, $R_{22}$, $R_{23}$=absent;

$R_{14}$, $R_{24}$, $R_{39}$, $R_{41}$, $R_{57}$, $R_{72}$=are independently A or absent;

$R_3$, $R_4$, $R_{13}$, $R_{61}$, $R_{71}$=are independently A, C or absent;

$R_6$, $R_{44}$=are independently A, C, G or absent;

$R_{21}$=A, C, U or absent;

$R_2$, $R_7$, $R_{15}$, $R_{25}$, $R_{33}$, $R_{34}$, $R_{45}$, $R_{56}$, $R_{63}$=are independently A, G or absent;

$R_{58}$=A, G, U or absent;

$R_{46}$=A, U or absent;

$R_{37}$, $R_{38}$, $R_{55}$, $R_{60}$, $R_{62}$=are independently C or absent;

$R_{12}$, $R_{26}$, $R_{27}$, $R_{35}$, $R_{40}$, $R_{48}$, $R_{67}$=are independently C, G or absent;

$R_{32}$, $R_{43}$, $R_{68}$=are independently C, G, U or absent;

$R_{11}$, $R_{16}$, $R_{28}$, $R_{31}$, $R_{49}$, $R_{59}$, $R_{65}$, $R_{70}$=are independently C, U or absent;

$R_1$, $R_9$, $R_{10}$, $R_{19}$, $R_{20}$, $R_{50}$, $R_{52}$, $R_{69}$=are independently G or absent;

$R_5$, $R_8$, $R_{29}$, $R_{30}$, $R_{42}$, $R_{51}$, $R_{64}$, $R_{66}$=are independently G, U or absent;

$R_{17}$, $R_{36}$, $R_{53}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Tyrosine TREM Consensus Sequence

In an embodiment, a TREM disclosed herein comprises the sequence of Formula I TYR (SEQ ID NO: 616), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Tyr is:

$R_0$=absent;

$R_{14}$, $R_{39}$, $R_{57}$=are independently A or absent;

$R_{41}$, $R_{48}$, $R_{51}$, $R_{71}$=are independently A, C, G or absent;

$R_3$, $R_4$, $R_5$, $R_6$, $R_9$, $R_{10}$, $R_{12}$, $R_{13}$, $R_{16}$, $R_{25}$, $R_{26}$, $R_{30}$, $R_{31}$, $R_{32}$, $R_{42}$, $R_{44}$, $R_{45}$, $R_{46}$, $R_{49}$, $R_{50}$, $R_{58}$, $R_{62}$, $R_{63}$, $R_{66}$, $R_{67}$, $R_{68}$, $R_{69}$, $R_{70}$=are independently N or absent;

$R_{22}$, $R_{65}$=are independently A, C, U or absent;

$R_{15}$, $R_{24}$, $R_{27}$, $R_{33}$, $R_{37}$, $R_{40}$, $R_{56}$=are independently A, G or absent;

$R_7$, $R_{29}$, $R_{34}$, $R_{72}$=are independently A, G, U or absent;

$R_{23}$, $R_{53}$=are independently A, U or absent;

$R_{35}$, $R_{60}$=are independently C or absent;

$R_{20}$=C, G or absent;

$R_1$, $R_2$, $R_{28}$, $R_{61}$, $R_{64}$=are independently C, G, U or absent;

$R_{11}$, $R_{17}$, $R_{21}$, $R_{43}$, $R_{55}$=are independently C, U or absent;

$R_{19}$, $R_{52}$=are independently G or absent;

$R_8$, $R_{18}$, $R_{36}$, $R_{38}$, $R_{54}$, $R_{59}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II TYR (SEQ ID NO: 617), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Tyr is:

$R_0$, $R_{18}$, $R_{23}$=absent;

$R_7$, $R_9$, $R_{14}$, $R_{24}$, $R_{26}$, $R_{34}$, $R_{39}$, $R_{57}$=are independently A or absent;

$R_{44}$, $R_{69}$=are independently A, C or absent;

$R_{71}$=A, C, G or absent;

$R_{68}$=N or absent;

$R_{58}$=A, C, U or absent;

$R_{33}$, $R_{37}$, $R_{41}$, $R_{56}$, $R_{62}$, $R_{63}$=are independently A, G or absent;

$R_6$, $R_{29}$, $R_{72}$=are independently A, G, U or absent;

$R_{31}$, $R_{45}$, $R_{53}$=are independently A, U or absent;

$R_{13}$, $R_{35}$, $R_{49}$, $R_{60}$=are independently C or absent;

$R_{20}$, $R_{48}$, $R_{64}$, $R_{67}$, $R_{70}$=are independently C, G or absent;
$R_1$, $R_2$, $R_5$, $R_{16}$, $R_{66}$=are independently C, G, U or absent;
$R_{11}$, $R_{21}$, $R_{28}$, $R_{43}$, $R_{55}$, $R_{61}$=are independently C, U or absent;
$R_{10}$, $R_{15}$, $R_{19}$, $R_{25}$, $R_{27}$, $R_{40}$, $R_{51}$, $R_{52}$=are independently G or absent;
$R_3$, $R_4$, $R_{30}$, $R_{32}$, $R_{42}$, $R_{46}$=are independently G, U or absent;
$R_8$, $R_{12}$, $R_{17}$, $R_{22}$, $R_{36}$, $R_{38}$, $R_{50}$, $R_{54}$, $R_{59}$, $R_{65}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III TYR (SEQ ID NO: 618), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Tyr is:

$R_0$, $R_{18}$, $R_{23}$=absent;
$R_7$, $R_9$, $R_{14}$, $R_{24}$, $R_{26}$, $R_{34}$, $R_{39}$, $R_{57}$, $R_{72}$=are independently A or absent;
$R_{44}$, $R_{69}$=are independently A, C or absent;
$R_{71}$=A, C, G or absent;
$R_{37}$, $R_{41}$, $R_{56}$, $R_{62}$, $R_{63}$=are independently A, G or absent;
$R_6$, $R_{29}$, $R_{68}$=are independently A, G, U or absent;
$R_{31}$, $R_{45}$, $R_{55}$=are independently A, U or absent;
$R_{13}$, $R_{28}$, $R_{35}$, $R_{49}$, $R_{60}$, $R_{61}$=are independently C or absent;
$R_5$, $R_{48}$, $R_{64}$, $R_{67}$, $R_{70}$=are independently C, G or absent;
$R_1$, $R_2$=are independently C, G, U or absent;
$R_{11}$, $R_{16}$, $R_{21}$, $R_{43}$, $R_{55}$, $R_{66}$=are independently C, U or absent;
$R_{10}$, $R_{15}$, $R_{19}$, $R_{20}$, $R_{25}$, $R_{27}$, $R_{33}$, $R_{40}$, $R_{51}$, $R_{52}$=are independently G or absent;
$R_3$, $R_4$, $R_{30}$, $R_{32}$, $R_{42}$, $R_{46}$=are independently G, U or absent;
$R_8$, $R_{12}$, $R_{17}$, $R_{22}$, $R_{36}$, $R_{38}$, $R_{50}$, $R_{53}$, $R_{54}$, $R_{59}$, $R_{65}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Valine TREM Consensus Sequence

In an embodiment, a TREM disclosed herein comprises the sequence of Formula I VAL (SEQ ID NO: 619), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Val is:

$R_0$, $R_{23}$=absent;
$R_{24}$, $R_{38}$, $R_{57}$=are independently A or absent;
$R_9$, $R_{72}$=are independently A, C, G or absent;
$R_2$, $R_4$, $R_5$, $R_6$, $R_7$, $R_{12}$, $R_{15}$, $R_{16}$, $R_{21}$, $R_{25}$, $R_{26}$, $R_{29}$, $R_{31}$, $R_{32}$, $R_{33}$, $R_{34}$, $R_{37}$, $R_{41}$, $R_{42}$, $R_{43}$, $R_{44}$, $R_{45}$, $R_{46}$, $R_{48}$, $R_{49}$, $R_{50}$, $R_{58}$, $R_{61}$, $R_{62}$, $R_{63}$, $R_{64}$, $R_{65}$, $R_{66}$, $R_{67}$, $R_{68}$, $R_{69}$, $R_{70}$=are independently N or absent;
$R_{17}$, $R_{35}$, $R_{59}$=are independently A, C, U or absent;
$R_{10}$, $R_{14}$, $R_{27}$, $R_{40}$, $R_{52}$, $R_{56}$=are independently A, G or absent;
$R_1$, $R_3$, $R_{51}$, $R_{53}$=are independently A, G, U or absent;
$R_{39}$=C or absent;
$R_{13}$, $R_{30}$, $R_{55}$=are independently C, G, U or absent;
$R_{11}$, $R_{22}$, $R_{28}$, $R_{60}$, $R_{71}$=are independently C, U or absent;
$R_{19}$=G or absent;
$R_{20}$=G, U or absent;
$R_8$, $R_{18}$, $R_{36}$, $R_{54}$=are independently U or absent;
$[R_{47}]_x$=N or absent;
wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula II VAL (SEQ ID NO: 620), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Val is:

$R_0$, $R_{18}$, $R_{23}$=absent;

$R_{24}$, $R_{38}$, $R_{57}$=are independently A or absent;

$R_{64}$, R 70, $R_{72}$=are independently A, C, G or absent;

$R_{15}$, $R_{16}$, $R_{26}$, $R_{29}$, $R_{31}$, $R_{32}$, $R_{43}$, $R_{44}$, $R_{45}$, $R_{49}$, $R_{50}$, $R_{58}$, $R_{62}$, $R_{65}$=are independently N or absent;

$R_6$, $R_{17}$, $R_{34}$, $R_{37}$, $R_{41}$, $R_{59}$=are independently A, C, U or absent;

$R_9$, $R_{10}$, $R_{14}$, $R_{27}$, $R_{40}$, $R_{46}$, $R_{51}$, $R_{52}$, $R_{56}$=are independently A, G or absent;

$R_7$, $R_{12}$, $R_{25}$, $R_{33}$, $R_{53}$, $R_{63}$, $R_{66}$, $R_{68}$=are independently A, G, U or absent;

$R_{69}$=A, U or absent;

$R_{39}$=C or absent;

$R_5$, $R_{67}$=are independently C, G or absent;

$R_2$, $R_4$, $R_{13}$, $R_{48}$, $R_{55}$, $R_{61}$=are independently C, G, U or absent;

$R_{11}$, $R_{22}$, $R_{28}$, $R_{30}$, $R_{35}$, $R_{60}$, $R_{71}$=are independently C, U or absent;

$R_{19}$=G or absent;

$R_1$, $R_3$, $R_{20}$, $R_{42}$=are independently G, U or absent;

$R_8$, $R_{21}$, $R_{36}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

In an embodiment, a TREM disclosed herein comprises the sequence of Formula III VAL (SEQ ID NO: 621), $R_0$-$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-$R_{45}$-$R_{46}$—$[R_{47}]_x$-$R_{48}$-$R_{49}$-$R_{50}$-$R_{51}$-$R_{52}$-$R_{53}$-$R_{54}$-$R_{55}$-$R_{56}$-$R_{57}$-$R_{58}$-$R_{59}$-$R_{60}$-$R_{61}$-$R_{62}$-$R_{63}$-$R_{64}$- $R_{65}$-$R_{66}$-$R_{67}$-$R_{68}$-$R_{69}$-$R_{70}$-$R_{71}$-$R_{72}$ wherein R is a ribonucleotide residue and the consensus for Val is:

$R_0$, $R_{18}$, $R_{23}$=absent;

$R_{24}$, $R_{38}$, $R_{40}$, $R_{57}$, $R_{72}$=are independently A or absent;

$R_{29}$, $R_{64}$, $R_{70}$=are independently A, C, G or absent;

$R_{49}$, $R_{50}$, $R_{62}$=are independently N or absent;

$R_{16}$, $R_{26}$, $R_{31}$, $R_{32}$, $R_{37}$, $R_{41}$, $R_{43}$, $R_{59}$, $R_{65}$=are independently A, C, U or absent;

$R_9$, $R_{14}$, $R_{27}$, $R_{46}$, $R_{52}$, $R_{56}$, $R_{66}$=are independently A, G or absent;

$R_7$, $R_{12}$, $R_{25}$, $R_{33}$, $R_{44}$, $R_{45}$, $R_{53}$, $R_{58}$, $R_{63}$, $R_{68}$=are independently A, G, U or absent;

$R_{69}$=A, U or absent;

$R_{39}$=C or absent;

$R_5$, $R_{67}$=are independently C, G or absent;

$R_2$, $R_4$, $R_{13}$, $R_{15}$, $R_{48}$, $R_{55}$=are independently C, G, U or absent;

$R_6$, $R_{11}$, $R_{22}$, $R_{28}$, $R_{30}$, $R_{34}$, $R_{35}$, $R_{60}$, $R_{61}$, $R_{71}$=are independently C, U or absent;

$R_{10}$, $R_{19}$, $R_{51}$=are independently G or absent;

$R_1$, $R_3$, $R_{20}$, $R_{42}$=are independently G, U or absent;

$R_8$, $R_{17}$, $R_{21}$, $R_{36}$, $R_{54}$=are independently U or absent;

$[R_{47}]_x$=N or absent;

wherein, e.g., x=1-271 (e.g., x=1-250, x=1-225, x=1-200, x=1-175, x=1-150, x=1-125, x=1-100, x=1-75, x=1-50, x=1-40, x=1-30, x=1-29, x=1-28, x=1-27, x=1-26, x=1-25, x=1-24, x=1-23, x=1-22, x=1-21, x=1-20, x=1-19, x=1-18, x=1-17, x=1-16, x=1-15, x=1-14, x=1-13, x=1-12, x=1-11, x=1-10, x=10-271, x=20-271, x=30-271, x=40-271, x=50-271, x=60-271, x=70-271, x=80-271, x=100-271, x=125-271, x=150-271, x=175-271, x=200-271, x=225-271, x=1, x=2, x=3, x=4, x=5, x=6, x=7, x=8, x=9, x=10, x=11, x=12, x=13, x=14, x=15, x=16, x=17, x=18, x=19, x=20, x=21, x=22, x=23, x=24, x=25, x=26, x=27, x=28, x=29, x=30, x=40, x=50, x=60, x=70, x=80, x=90, x=100, x=110, x=125, x=150, x=175, x=200, x=225, x=250, or x=271), provided that the TREM has one or both of the following properties: no more than 15% of the residues are N; or no more than 20 residues are absent.

Variable Region Consensus Sequence

In an embodiment, a TREM disclosed herein comprises a variable region at position $R_{47}$. In an embodiment, the variable region is 1-271 ribonucleotides in length (e.g. 1-250, 1-225, 1-200, 1-175, 1-150, 1-125, 1-100, 1-75, 1-50, 1-40, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 10-271, 20-271, 30-271, 40-271, 50-271, 60-271, 70-271, 80-271, 100-271, 125-271, 150-271, 175-271, 200-271, 225-271, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 125, 150, 175, 200, 225, 250, or 271 ribonucleotides). In an embodiment, the variable region comprises any one, all or a combination of Adenine, Cytosine, Guanine or Uracil.

In an embodiment, the variable region comprises a ribonucleic acid (RNA) sequence encoded by a deoxyribonucleic acid (DNA) sequence disclosed in Table 4. e.g., any one of SEQ ID NOs: 452-561 disclosed in Table 4.

TABLE 4

Exemplary variable region sequences.

| | SEQ ID NO | SEQUENCE |
|---|---|---|
| 1 | 452 | AAAATATAAATATATTTC |
| 2 | 453 | AAGCT |
| 3 | 454 | AAGTT |
| 4 | 455 | AATTCTTCGGAATGT |
| 5 | 456 | AGA |
| 6 | 457 | AGTCC |
| 7 | 458 | CAACC |
| 8 | 459 | CAATC |
| 9 | 460 | CAGC |
| 10 | 461 | CAGGCGGGTTCTGCCCGCGC |
| 11 | 462 | CATACCTGCAAGGGTATC |
| 12 | 463 | CGACCGCAAGGTTGT |

TABLE 4-continued

| Exemplary variable region sequences. | | |
|---|---|---|
| | SEQ ID NO | SEQUENCE |
| 13 | 464 | CGACCTTGCGGTCAT |
| 14 | 465 | CGATGCTAATCACATCGT |
| 15 | 466 | CGATGGTGACATCAT |
| 16 | 467 | CGATGGTTTACATCGT |
| 17 | 468 | CGCCGTAAGGTGT |
| 18 | 469 | CGCCTTAGGTGT |
| 19 | 470 | CGCCTTTCGACGCGT |
| 20 | 471 | CGCTTCACGGCGT |
| 21 | 472 | CGGCAGCAATGCTGT |
| 22 | 473 | CGGCTCCGCCTTC |
| 23 | 474 | CGGGTATCACAGGGTC |
| 24 | 475 | CGGTGCGCAAGCGCTGT |
| 25 | 476 | CGTACGGGTGACCGTACC |
| 26 | 477 | CGTCAAAGACTTC |
| 27 | 478 | CGTCGTAAGACTT |
| 28 | 479 | CGTTGAATAAACGT |
| 29 | 480 | CTGTC |
| 30 | 481 | GGCC |
| 31 | 482 | GGGGATT |
| 32 | 483 | GGTC |
| 33 | 484 | GGTTT |
| 34 | 485 | GTAG |
| 35 | 486 | TAACTAGATACTTTCAGAT |
| 36 | 487 | TACTCGTATGGGTGC |
| 37 | 488 | TACTTTGCGGTGT |
| 38 | 489 | TAGGCGAGTAACATCGTGC |
| 39 | 490 | TAGGCGTGAATAGCGCCTC |
| 40 | 491 | TAGGTCGCGAGAGCGGCGC |
| 41 | 492 | TAGGTCGCGTAAGCGGCGC |
| 42 | 493 | TAGGTGGTTATCCACGC |
| 43 | 494 | TAGTC |
| 44 | 495 | TAGTT |
| 45 | 496 | TATACGTGAAAGCGTATC |
| 46 | 497 | TATAGGGTCAAAAACTCTATC |
| 47 | 498 | TATGCAGAAATACCTGCATC |
| 48 | 499 | TCCCCATACGGGGGC |
| 49 | 500 | TCCCGAAGGGGTTC |
| 50 | 501 | TCTACGTATGTGGGC |

TABLE 4-continued

| Exemplary variable region sequences. | | |
|---|---|---|
| | SEQ ID NO | SEQUENCE |
| 51 | 502 | TCTCATAGGAGTTC |
| 52 | 503 | TCTCCTCTGGAGGC |
| 53 | 504 | TCTTAGCAATAAGGT |
| 54 | 505 | TCTTGTAGGAGTTC |
| 55 | 506 | TGAACGTAAGTTCGC |
| 56 | 507 | TGAACTGCGAGGTTCC |
| 57 | 508 | TGAC |
| 58 | 509 | TGACCGAAAGGTCGT |
| 59 | 510 | TGACCGCAAGGTCGT |
| 60 | 511 | TGAGCTCTGCTCTC |
| 61 | 512 | TGAGGCCTCACGGCCTAC |
| 62 | 513 | TGAGGGCAACTTCGT |
| 63 | 514 | TGAGGGTCATACCTCC |
| 64 | 515 | TGAGGGTGCAAATCCTCC |
| 65 | 516 | TGCCGAAAGGCGT |
| 66 | 517 | TGCCGTAAGGCGT |
| 67 | 518 | TGCGGTCTCCGCGC |
| 68 | 519 | TGCTAGAGCAT |
| 69 | 520 | TGCTCGTATAGAGCTC |
| 70 | 521 | TGGACAATTGTCTGC |
| 71 | 522 | TGGACAGATGTCCGT |
| 72 | 523 | TGGACAGGTGTCCGC |
| 73 | 524 | TGGACGGTTGTCCGC |
| 74 | 525 | TGGACTTGTGGTC |
| 75 | 526 | TGGAGATTCTCTCCGC |
| 76 | 527 | TGGCATAGGCCTGC |
| 77 | 528 | TGGCTTATGTCTAC |
| 78 | 529 | TGGGAGTTAATCCCGT |
| 79 | 530 | TGGGATCTTCCCGC |
| 80 | 531 | TGGGCAGAAATGTCTC |
| 81 | 532 | TGGGCGTTCGCCCGC |
| 82 | 533 | TGGGCTTCGCCCGC |
| 83 | 534 | TGGGGGATAACCCCGT |
| 84 | 535 | TGGGGGTTTCCCCGT |
| 85 | 536 | TGGT |
| 86 | 537 | TGGTGGCAACACCGT |
| 87 | 538 | TGGTTTATAGCCGT |
| 88 | 539 | TGTACGGTAATACCGTACC |

TABLE 4-continued

Exemplary variable region sequences.

| | SEQ ID NO | SEQUENCE |
|---|---|---|
| 89 | 540 | TGTCCGCAAGGACGT |
| 90 | 541 | TGTCCTAACGGACGT |
| 91 | 542 | TGTCCTATTAACGGACGT |
| 92 | 543 | TGTCCTTCACGGGCGT |
| 93 | 544 | TGTCTTAGGACGT |
| 94 | 545 | TGTGCGTTAACGCGTACC |
| 95 | 546 | TGTGTCGCAAGGCACC |
| 96 | 547 | TGTTCGTAAGGACTT |
| 97 | 548 | TTCACAGAAATGTGTC |
| 98 | 549 | TTCCCTCGTGGAGT |
| 99 | 550 | TTCCCTCTGGGAGC |
| 100 | 551 | TTCCCTTGTGGATC |
| 101 | 552 | TTCCTTCGGGAGC |
| 102 | 553 | TTCTAGCAATAGAGT |
| 103 | 554 | TTCTCCACTGGGGAGC |
| 104 | 555 | TTCTCGAGAGGGAGC |
| 105 | 556 | TTCTCGTATGAGAGC |
| 106 | 557 | TTTAAGGTTTTCCCTTAAC |
| 107 | 558 | TTTCATTGTGGAGT |
| 108 | 559 | TTTCGAAGGAATCC |
| 109 | 560 | TTTCTTCGGAAGC |
| 110 | 561 | TTTGGGGCAACTCAAC |

Corresponding Nucleotide Positions

To determine if a selected nucleotide position in a candidate sequence corresponds to a selected position in a reference sequence (e.g., SEQ ID NO: 622. SEQ ID NO: 993. SEQ ID NO: 1079), one or more of the following Evaluations is performed.

Evaluation A:

1. The candidate sequence is aligned with each of the consensus sequences in Tables 9 and 10. The consensus sequence(s) having the most positions aligned (and which has at least 60% of the positions of the candidate sequence aligned) is selected.

The alignment is performed as is follows. The candidate sequence and an isodecoder consensus sequence from Tables 10A-10B are aligned based on a global pairwise alignment calculated with the Needleman-Wunsch algorithm when run with match scores from Table 11, a mismatch penalty of −1, a gap opening penalty of −1, and a gap extension penalty of −0.5, and no penalty for end gaps. The alignment with the highest overall alignment score is then used to determine the percent similarity between the candidate and the consensus sequence by counting the number of matched positions in the alignment, dividing it by the larger of the number of non-N bases in the candidate sequence or the consensus sequence, and multiplying the result by 100.

In cases where multiple alignments (of the candidate and a single consensus sequence) tie for the same score, the percent similarity is the largest percent similarity calculated from the tied alignments. This process is repeated for the candidate sequence with each of the remaining isodecoder consensus sequences in Tables 10A-10B, and the alignment resulting in the greatest percent similarity is selected. If this alignment has a percent similarity equal to or greater than 60%, it is considered a valid alignment and used to relate positions in the candidate sequence to those in the consensus sequence, otherwise the candidate sequence is considered to have not aligned to any of the isodecoder consensus sequences. If there is a tie at this point, all tied consensus sequences are taken forward to step 2 in the analysis.

2. Using the selected consensus sequence(s) from step 1, one determines the consensus sequence position number that aligns with the selected position (e.g., a modified position) in the candidate sequence. One then assigns the position number of the aligned position in the consensus sequence to the selected position in the candidate sequence, in other words, the selected position in the candidate sequence is numbered according to the numbering of the consensus sequence. If there were tied consensus sequences from step one, and they give different position numbers in this step 2, then all such position numbers are taken forward to step 5.

3. The reference sequence is aligned with the consensus sequence chosen in step 1. The alignment is performed as described in step 1.

4. From the alignment in step 3, one determines the consensus sequence position number that aligns with the selected position (e.g., a modified position) in the reference sequence. One then assigns the position number of the aligned position in the consensus sequence to the selected position in the reference sequence, in other words, the selected position in the reference sequence is numbered according to the numbering of the consensus sequence. If there is a tie at this point, all tied consensus sequences are taken forward to step 5 in the analysis.

5. If a value for a position number determined for the reference sequence in step 2 is the same as the value for the position number determined for the candidate sequence in step 4, the positions are defined as corresponding.

Evaluation B:

The reference sequence (e.g., a TREM sequence described herein) and the candidate sequence are aligned with one another. The alignment is performed as follows.

The reference sequence and the candidate sequence are aligned based on a global pairwise alignment calculated with the Needleman-Wunsch algorithm when run with match scores from Table 11, a mismatch penalty of −1, a gap opening penalty of −1, and a gap extension penalty of −0.5, and no penalty for end gaps. The alignment with the highest overall alignment score is then used to determine the percent similarity between the candidate and reference sequence by counting the number of matched based in the alignment, dividing it by the larger of the number of non-N bases in the candidate or reference sequence, and multiplying the result by 100. In cases where multiple alignments tie for the same score, the percent similarity is the largest percent similarity calculated from the tied alignments. If this alignment has a percent similarity equal to or greater than 60%, it is considered a valid alignment and used to relate positions in the candidate sequence to those in the reference sequence, otherwise the candidate sequence is considered to have not aligned to the reference sequence.

If the selected nucleotide position in the reference sequence (e.g., a modified position) is paired with a selected nucleotide position (e.g., a modified position) in the candidate sequence, the positions are defined as corresponding.

If the selected position in the reference sequence and the candidate sequence are found to be corresponding in at least one of Evaluations A and B, the positions correspond. Thus, e.g., if two positions are found to be corresponding under Evaluation A, but do not correspond under Evaluation B, the positions are defined as corresponding.

The numbering given above is used for case of presentation and does not imply a required sequence. If more than one Evaluation is performed, they can be performed in any order.

TABLE 10A

Consensus sequence computationally generated for each isodecoder by aligning members of the isodecoder family

| SEQ ID NO. | Amino Acid | Anticodon | Consensus sequence |
|---|---|---|---|
| 1200 | Ala | AGC | GGGGAATTAGCTCAAGTGGTAGAGCGCTTG CTTAGCATGCAAGAGGTAGTGGGATCGATG CCCACATTCTCCA |
| 1201 | Ala | CGC | GGGGATGTAGCTCAGTGGTAGAGCGCATGC TTCGCATGTATGAGGTCCCGGGTTCGATCCC CGGCATCTCCA |
| 1202 | Ala | TGC | GGGGGTGTAGCTCAGTGGTAGAGCGCATGC TTTGCATGTATGAGGCCCCGGGTTCGATCCC CGGCACCTCCA |
| 1203 | Arg | ACG | GGGCCAGTGGCGCAATGGATAACGCGTCTG ACTACGGATCAGAAGATTCCAGGTTCGACTC CTGGCTGGCTCG |
| 1204 | Arg | CCG | GGCCGCGTGGCCTAATGGATAAGGCGTCTG ATTCCGGATCAGAAGATTGAGGGTTCGAGTC CCTTCGTGGTCG |
| 1205 | Arg | CCT | GCCCCAGTGGCCTAATGGATAAGGCACTGG CCTCCTAAGCCAGGGATTGTGGGTTCGAGTC CCACCTGGGGTA |
| 1206 | Arg | TCG | GACCGCGTGGCCTAATGGATAAGGCGTCTG ACTTCGGATCAGAAGATTGAGGGTTCGAGTC CCTCCGTGGTCG |
| 1207 | Arg | TCT | GGCTCTGTGGCGCAATGGATNAGCGCATTG GACTTCTAATTCAAAGGTTGCGGGTTCGAGT CCCNCCAGAGTCG |
| 1208 | Asn | GTT | GTCTCTGTGGCGCAATCGGTTAGCGCGTTCG GCTGTTAACCGNAAAGGTTGGTGGTTCGAGC CCACCCAGGGACG |
| 1209 | Asp | GTC | TCCTCGTTAGTATAGTGGTGAGTATCCCCGC CTGTCACGCGGGAGACCGGGGTTCGATTCCC CGACGGGGAG |
| 1210 | Cys | GCA | GGGGGTATAGCTCAGNGGGTAGAGCATTTG ACTGCAGATCAAGAGGTCCCCGGTTCAAATC CGGGTGCCCCCT |
| 1211 | Gln | CTG | GGTTCCATGGTGTAATGGTNAGCACTCTGGA CTCTGAATCCAGCGATCCGAGTTCAAGTCTC GGTGGAACCT |
| 1212 | Gln | TTG | GGTCCCATGGTGTAATGGTTAGCACTCTGGA CTTTGAATCCAGCGATCCGAGTTCAAATCTC GGTGGGACCT |
| 1213 | Glu | CTC | TCCCTGGTGGTCTAGTGGTTAGGATTCGGCG CTCTCACCGCCGCGGCCCGGGTTCGATTCCC GGTCAGGGAA |
| 1214 | Glu | TTC | TCCCTGGTGGTCTAGTGGCTAGGATTCGGCG CTTTCACCGCNGCGGCCCGGGTTCGATTCCC GGTCAGGGAA |
| 1215 | Gly | CCC | GCATTGGTGGTTCAGTGGTAGAATTCTCGCC TCCCACGCNGGAGACCCGGGTTCGATTCCCG GCCAATGCA |

TABLE 10A-continued

Consensus sequence computationally generated for each isodecoder by aligning members of the isodecoder family

| SEQ ID NO. | Amino Acid | Anticodon | Consensus sequence |
|---|---|---|---|
| 1216 | Gly | GCC | GCATTGGTGGTTCAGTGGTAGAATTCTCGCC TGCCACGCGGGAGGCCCGGGTTCGATTCCCG GCCAATGCA |
| 1217 | Gly | TCC | GCGTTGGTGGTATAGTGGTGAGCATAGCTGC CTTCCAAGCAGTTGACCCGGGTTCGATTCCC GGCCAACGCA |
| 1218 | Ile | AAT | GGCCGGTTAGCTCAGTTGGTTAGAGCGTGGT GCTAATAACGCCAAGGTCGCGGGTTCGATCC CCGTACGGGCCA |
| 1219 | Ile | TAT | GCTCCAGTGGCGCAATCGGTTAGCGCGCGGT ACTTATAATGCCGAGGTTGTGAGTTCGAGCC TCACCTGGAGCA |
| 1220 | Leu | AAG | GGTAGCGTGGCCGAGCGGTCTAAGGCGCTG GATTAAGGCTCCAGTCTCTTCGGGGGCGTGG GTTCGAATCCCACCGCTGCCA |
| 1221 | Leu | CAA | GTCAGGATGGCCGAGTGGTCNTAAGGCGCC AGACTCAAGTTCTGGTCTCCGNATGGAGGCG TGGGTTCGAATCCCACTTCTGACA |
| 1222 | Leu | CAG | GTCAGGATGGCCGAGCGGTCTAAGGCGCTG CGTTCAGGTCGCAGTCTCCCCTGGAGGCGTG GGTTCGAATCCCACTCCTGACA |
| 1223 | Leu | TAA | ACCAGGATGGCCGAGTGGTTAAGGCGTTGG ACTTAAGATCCAATGGACAGATGTCCGCGTG GGTTCGAACCCCACTCCTGGTA |
| 1224 | Leu | TAG | GGTAGCGTGGCCGAGCGGTCTAAGGCGCTG GATTTAGGCTCCAGTCTCTTCGGNGGCGTGG GTTCGAATCCCACCGCTGCCA |
| 1225 | Lys | CTT | GCCCGGCTAGCTCAGTCGGTAGAGCATGAG ACTCTTAATCTCAGGGTCGTGGGTTCGAGCC CCACGTTGGGCGNNN |
| 1226 | Lys | TTT | GCCTGGATAGCTCAGTCGGTAGAGCATCAG ACTTTTAATCTGAGGGTCCAGGGTTCAAGTC CCTGTTCAGGCG |
| 1227 | Met | CAT | GCCCTCTTAGCGCAGTNGGCAGCGCGTCAGT CTCATAATCTGAAGGTCCTGAGTTCGAGCCT CAGAGAGGGCA |
| 1228 | Phe | GAA | GCCGAAATAGCTCAGTTGGGAGAGCGTTAG ACTGAAGATCNTAAAGGTCCCTGGTTCAATC CCGGGTTTCGGCA |
| 1229 | Pro | AGG | GGCTCGTTGGTCTAGGGGTATGATTCTCGCT TAGGATGCGAGAGGTCCCGGGTTCAAATCC CGGACGAGCCC |
| 1230 | Pro | CGG | GGCTCGTTGGTCTAGGGGTATGATTCTCGCT TCGGGTGCGAGAGGTCCCGGGTTCAAATCCC GGACGAGCCC |
| 1231 | Pro | TGG | GGCTCGTTGGTCTAGGGGTATGATTCTCGCT TTGGGTGCGAGAGGTCCCGGGTTCAAATCCC GGACGAGCCC |
| 1232 | Ser | AGA | GTAGTCGTGGCCGAGTGGTTAAGGCGATGG ACTAGAAATCCATTGGGGTTTCCCCGCGCAG GTTCGAATCCTGCCGACTACG |
| 1233 | Ser | CGA | GCTGTGATGGCCGAGTGGTTAAGGCGTTGG ACTCGAAATCCAATGGGGTCTCCCCGCGCAG GTTCGAATCCTGCTCACAGCG |

TABLE 10A-continued

Consensus sequence computationally generated for each isodecoder by aligning members of the isodecoder family

| SEQ ID NO. | Amino Acid | Anticodon | Consensus sequence |
|---|---|---|---|
| 1234 | Ser | GCT | GACGAGGNNTGGCCGAGTGGTTAAGGCGATGGACTGCTAATCCATTGTGCTCTGCACGCGTGGGTTCGAATCCCATCCTCGTCG |
| 1235 | Ser | TGA | GTAGTCGTGGCCGAGTGGTTAAGGCGATGGACTTGAAATCCATTGGGGTCTCCCCGCGCAGGTTCGAATCCTGCCGGCTACG |
| 1236 | Thr | AGT | GGCTCCGTGGCTTAGCTGGTTAAAGCGCCTGTCTAGTAAACAGGAGATCCTGGGTTCGAATCCCAGCGGGGCCT |
| 1237 | Thr | CGT | GGCNCTGTGGCTNAGTNGGNTAAAGCGCCGGTCTCGTAAACCNGGAGATCNTGGGTTCGAATCCCANCNGGGCCT |
| 1238 | Thr | TGT | GGCTCCATAGCTCAGNGGGTTAGAGCACTGGTCTTGTAAACCAGGGGTCGCGAGTTCAAATCTCGCTGGGGCCT |
| 1239 | Trp | CCA | GACCTCGTGGCGCAACGGTAGCGCGTCTGACTCCAGATCAGAAGGTTGCGTGTTCAAATCACGTCGGGGTCA |
| 1240 | Tyr | GTA | CCTTCGATAGCTCAGCTGGTAGAGCGGAGGACTGTAGATCCTTAGGTCGCTGGTTCGATTCCGGCTCGAAGGA |
| 1241 | Val | AAC | GTTTCCGTAGTGTAGTGGTTATCACGTTCGCCTAACACGCGAAAGGTCCCCGGTTCGAAACCGGGCGGAAACA |
| 1242 | Val | CAC | GTTTCCGTAGTGTAGTGGTTATCACGTTCGCCTCACACGCGAAAGGTCCCCGGTTCGAAACCGGGCGGAAACA |
| 1243 | Val | TAC | GGTTCCATAGTGTAGTGGTTATCACGTCTGCTTTACACGCAGAAGGTCCTGGGTTCGAGCCCCAGTGGAACCA |
| 1244 | iMet | CAT | AGCAGAGTGGCGCAGCGGAAGCGTGCTGGGCCCATAACCCAGAGGTCGATGGATCGAAACCATCCTCTGCTA |

TABLE 10B

Consensus sequence computationally generated for each isodecoder by aligning members of the isodecoder family

| SEQ ID NO | Amino Acid | Anticodon | Consensus sequence |
|---|---|---|---|
| 1245 | Ala | AGC | GGGGAATTAGCTCAAGTGGTAGAGCGCTTGCTTAGCATGCAAGAGGTAGTGGGATCGATGCCCACATTCTCCANNN |
| 1246 | Ala | CGC | GGGGATGTAGCTCAGTGGTAGAGCGCATGCTTCGCATGTATGAGGTCCCGGGTTCGATCCCCGGCATCTCCANNN |
| 1247 | Ala | TGC | GGGGGTGTAGCTCAGTGGTAGAGCGCATGCTTTGCATGTATGAGGCCCCGGGTTCGATCCCCGGCACCTCCANNN |
| 1248 | Arg | ACG | GGGCCAGTGGCGCAATGGATAACGCGTCTGACTACGGATCAGAAGATTCCAGGTTCGACTCCTGGCTGGCTCGNNN |
| 1249 | Arg | CCG | GGCCGCGTGGCCTAATGGATAAGGCGTCTGATTCCGGATCAGAAGATTGAGGGTTCGAGTCCCTTCGTGGTCGNNN |

TABLE 10B-continued

Consensus sequence computationally generated for each isodecoder by aligning members of the isodecoder family

| SEQ ID NO | Amino Acid | Anticodon | Consensus sequence |
|---|---|---|---|
| 1250 | Arg | CCT | GCCCCAGTGGCCTAATGGATAAGGCACTGGC CTCCTAAGCCAGGGATTGTGGGTTCGAGTCC CACCTGGGGTANNN |
| 1251 | Arg | TCG | GACCGCGTGGCCTAATGGATAAGGCGTCTGA CTTCGGATCAGAAGATTGAGGGTTCGAGTCC CTCCGTGGTCGNNN |
| 1252 | Arg | TCT | GGCTCTGTGGCGCAATGGATNAGCGCATTGG ACTTCTAATTCAAAGGTTGCGGGTTCGAGTC CCNCCAGAGTCGNNN |
| 1253 | Asn | GTT | GTCTCTGTGGCGCAATCGGTTAGCGCGTTCG GCTGTTAACCGNAAAGGTTGGTGGTTCGAGC CCACCCAGGGACGNNN |
| 1254 | Asp | GTC | TCCTCGTTAGTATAGTGGTGAGTATCCCCGCC TGTCACGCGGGAGACCGGGGTTCGATTCCCC GACGGGGAGNNN |
| 1255 | Cys | GCA | GGGGGTATAGCTCAGNGGGTAGAGCATTTGA CTGCAGATCAAGAGGTCCCCGGTTCAAATCC GGGTGCCCCCTNNN |
| 1256 | Gln | CTG | GGTTCCATGGTGTAATGGTNAGCACTCTGGA CTCTGAATCCAGCGATCCGAGTTCAAGTCTC GGTGGAACCTNNN |
| 1257 | Gln | TTG | GGTCCCATGGTGTAATGGTTAGCACTCTGGA CTTTGAATCCAGCGATCCGAGTTCAAATCTC GGTGGGACCTNNN |
| 1258 | Glu | CTC | TCCCTGGTGGTCTAGTGGTTAGGATTCGGCG CTCTCACCGCCGCGGCCCGGGTTCGATTCCC GGTCAGGGAANNN |
| 1259 | Glu | TTC | TCCCTGGTGGTCTAGTGGCTAGGATTCGGCG CTTTCACCGCNGCGGCCCGGGTTCGATTCCC GGTCAGGGAANNN |
| 1260 | Gly | CCC | GCATTGGTGGTTCAGTGGTAGAATTCTCGCCT CCCACGCNGGAGACCCGGGTTCGATTCCCGG CCAATGCANNN |
| 1261 | Gly | GCC | GCATTGGTGGTTCAGTGGTAGAATTCTCGCCT GCCACGCGGGAGGCCCGGGTTCGATTCCCGG CCAATGCANNN |
| 1262 | Gly | TCC | GCGTTGGTGGTATAGTGGTGAGCATAGCTGC CTTCCAAGCAGTTGACCCGGGTTCGATTCCC GGCCAACGCANNN |
| 1263 | Ile | AAT | GGCCGGTTAGCTCAGTTGGTTAGAGCGTGGT GCTAATAACGCCAAGGTCGCGGGTTCGATCC CCGTACGGGCCANNN |
| 1264 | Ile | TAT | GCTCCAGTGGCGCAATCGGTTAGCGCGCGGT ACTTATAATGCCGAGGTTGTGAGTTCGAGCC TCACCTGGAGCANNN |
| 1265 | Leu | AAG | GGTAGCGTGGCCGAGCGGTCTAAGGCGCTGG ATTAAGGCTCCAGTCTCTTCGGGGGCGTGGG TTCGAATCCCACCGCTGCCANNN |
| 1266 | Leu | CAA | GTCAGGATGGCCGAGTGGTCNTAAGGCGCCA GACTCAAGTTCTGGTCTCCGNATGGAGGCGT GGGTTCGAATCCCACTTCTGACANNN |
| 1267 | Leu | CAG | GTCAGGATGGCCGAGCGGTCTAAGGCGCTGC GTTCAGGTCGCAGTCTCCCCTGGAGGCGTGG GTTCGAATCCCACTCCTGACANNN |

TABLE 10B-continued

Consensus sequence computationally generated for each isodecoder by aligning members of the isodecoder family

| SEQ ID NO | Amino Acid | Anticodon | Consensus sequence |
|---|---|---|---|
| 1268 | Leu | TAA | ACCAGGATGGCCGAGTGGTTAAGGCGTTGGA CTTAAGATCCAATGGACAGATGTCCGCGTGG GTTCGAACCCCACTCCTGGTANNN |
| 1269 | Leu | TAG | GGTAGCGTGGCCGAGCGGTCTAAGGCGCTGG ATTTAGGCTCCAGTCTCTTCGGNGGCGTGGG TTCGAATCCCACCGCTGCCANNN |
| 1270 | Lys | CTT | GCCCGGCTAGCTCAGTCGGTAGAGCATGAGA CTCTTAATCTCAGGGTCGTGGGTTCGAGCCCC ACGTTGGGCGNNNNNN |
| 1271 | Lys | TTT | GCCTGGATAGCTCAGTCGGTAGAGCATCAGA CTTTTAATCTGAGGGTCCAGGGTTCAAGTCCC TGTTCAGGCGNNN |
| 1272 | Met | CAT | GCCCTCTTAGCGCAGTNGGCAGCGCGTCAGT CTCATAATCTGAAGGTCCTGAGTTCGAGCCT CAGAGAGGGCANNN |
| 1273 | Phe | GAA | GCCGAAATAGCTCAGTTGGGAGAGCGTTAGA CTGAAGATCNTAAAGGTCCCTGGTTCAATCC CGGGTTTCGGCANNN |
| 1274 | Pro | AGG | GGCTCGTTGGTCTAGGGGTATGATTCTCGCTT AGGATGCGAGAGGTCCCGGGTTCAAATCCCG GACGAGCCCNNN |
| 1275 | Pro | CGG | GGCTCGTTGGTCTAGGGGTATGATTCTCGCTT CGGGTGCGAGAGGTCCCGGGTTCAAATCCCG GACGAGCCCNNN |
| 1276 | Pro | TGG | GGCTCGTTGGTCTAGGGGTATGATTCTCGCTT TGGGTGCGAGAGGTCCCGGGTTCAAATCCCG GACGAGCCCNNN |
| 1277 | Ser | AGA | GTAGTCGTGGCCGAGTGGTTAAGGCGATGGA CTAGAAATCCATTGGGGTTTCCCCGCGCAGG TTCGAATCCTGCCGACTACGNNN |
| 1278 | Ser | CGA | GCTGTGATGGCCGAGTGGTTAAGGCGTTGGA CTCGAAATCCAATGGGGTCTCCCCGCGCAGG TTCGAATCCTGCTCACAGCGNNN |
| 1279 | Ser | GCT | GACGAGGNNTGGCCGAGTGGTTAAGGCGAT GGACTGCTAATCCATTGTGCTCTGCACGCGT GGGTTCGAATCCCATCCTCGTCGNNN |
| 1280 | Ser | TGA | GTAGTCGTGGCCGAGTGGTTAAGGCGATGGA CTTGAAATCCATTGGGGTCTCCCCGCGCAGG TTCGAATCCTGCCGGCTACGNNN |
| 1281 | Thr | AGT | GGCTCCGTGGCTTAGCTGGTTAAAGCGCCTG TCTAGTAAACAGGAGATCCTGGGTTCGAATC CCAGCGGGGCCTNNN |
| 1282 | Thr | CGT | GGCNCTGTGGCTNAGTNGGNTAAAGCGCCGG TCTCGTAAACCNGGAGATCNTGGGTTCGAAT CCCANCNGGGCCTNNN |
| 1283 | Thr | TGT | GGCTCCATAGCTCAGNGGGTTAGAGCACTGG TCTTGTAAACCAGGGGTCGCGAGTTCAAATC TCGCTGGGGCCTNNN |
| 1284 | Trp | CCA | GACCTCGTGGCGCAACGGTAGCGCGTCTGAC TCCAGATCAGAAGGTTGCGTGTTCAAATCAC GTCGGGGTCANNN |
| 1285 | Tyr | GTA | CCTTCGATAGCTCAGCTGGTAGAGCGGAGGA CTGTAGATCCTTAGGTCGCTGGTTCGATTCCG GCTCGAAGGANNN |

TABLE 10B-continued

Consensus sequence computationally generated for each isodecoder by aligning members of the isodecoder family

| SEQ ID NO | Amino Acid | Anticodon | Consensus sequence |
|---|---|---|---|
| 1286 | Val | AAC | GTTTCCGTAGTGTAGTGGTTATCACGTTCGCC TAACACGCGAAAGGTCCCCGGTTCGAAACCG GGCGGAAACANNN |
| 1287 | Val | CAC | GTTTCCGTAGTGTAGTGGTTATCACGTTCGCC TCACACGCGAAAGGTCCCCGGTTCGAAACCG GGCGGAAACANNN |
| 1288 | Val | TAC | GGTTCCATAGTGTAGTGGTTATCACGTCTGCT TTACACGCAGAAGGTCCTGGGTTCGAGCCCC AGTGGAACCANNN |
| 1289 | iMet | CAT | AGCAGAGTGGCGCAGCGGAAGCGTGCTGGG CCCATAACCCAGAGGTCGATGGATCGAAACC ATCCTCTGCTANNN |

TABLE 11

Score values alignment

| Row | Candidate nucleotide | Reference nucleotide | Match score |
|---|---|---|---|
| 1 | A | A | 1 |
| 2 | T | T | 1 |
| 3 | U | T | 1 |
| 4 | C | C | 1 |
| 5 | G | G | 1 |
| 6 | A | N | 0 |
| 7 | T | N | 0 |
| 8 | C | N | 0 |
| 9 | G | N | 0 |
| 10 | N | A | 0 |
| 11 | N | T | 0 |
| 12 | N | C | 0 |
| 13 | N | G | 0 |
| 14 | N | N | 0 |

Method of Making TREMs, TREM Core Fragments, and TREM Fragments

In vitro methods for synthesizing oligonucleotides are known in the art and can be used to make a TREM, a TREM core fragment or a TREM fragment disclosed herein. For example, a TREM, TREM core fragment or TREM fragment can be synthesized using solid state synthesis or liquid phase synthesis.

In an embodiment, a TREM, a TREM core fragment or a TREM fragment made according to an in vitro synthesis method disclosed herein has a different modification profile compared to a TREM expressed and isolated from a cell, or compared to a naturally occurring tRNA.

An exemplary method for making a modified TREM is provided in Example 1. The method provided in Example 1 can also be used to make a synthetic TREM core fragment or synthetic TREM fragment. Additional exemplary methods for making a synthetic TREM via 5'-Silyl-2'-Orthoester (2'-ACE) Chemistry is provided in Example 4. The method provided in Example 4 can also be used to make a synthetic TREM core fragment or synthetic TREM fragment. Additional synthetic methods are disclosed in Hartsel S A et al., (2005) *Oligonucleotide Synthesis,* 033-050, the entire contents of which are hereby incorporated by reference.

TREM Composition

In an embodiment, a TREM composition, e.g., a TREM pharmaceutical composition, comprises a pharmaceutically acceptable excipient. Exemplary excipients include those provided in the FDA Inactive Ingredient Database (https://www.accessdata.fda.gov/scripts/cder/iig/index. Cfm).

In an embodiment, a TREM composition, e.g., a TREM pharmaceutical composition, comprises at least 1, 2, 3, 4, 5, 6, 7, 8, 9, 10, 15, 20, 30, 40, 50, 60, 70, 80, 90, 100 or 150 grams of TREM, TREM core fragment or TREM fragment. In an embodiment, a TREM composition, e.g., a TREM pharmaceutical composition, comprises at least 1, 2, 3, 4, 5, 6, 7, 8, 9, 10, 15, 20, 30, 40, 50 or 100 milligrams of TREM, TREM core fragment or TREM fragment.

In an embodiment, a TREM composition, e.g., a TREM pharmaceutical composition, is at least 10, 20, 30, 40, 50, 60, 70, 80, 90, 95 or 99% dry weight TREMs, TREM core fragments or TREM fragments.

In an embodiment, a TREM composition comprises at least $1\times10^6$ TREM molecules, at least $1\times10^7$ TREM molecules, at least $1\times10^8$ TREM molecules or at least $1\times10^9$ TREM molecules.

In an embodiment, a TREM composition comprises at least $1\times10^6$ TREM core fragment molecules, at least $1\times10^7$ TREM core fragment molecules, at least $1\times10^8$ TREM core fragment molecules or at least $1\times10^9$ TREM core fragment molecules.

In an embodiment, a TREM composition comprises at least $1\times10^6$ TREM fragment molecules, at least $1\times10^7$ TREM fragment molecules, at least $1\times10^8$ TREM fragment molecules or at least $1\times10^9$ TREM fragment molecules.

In an embodiment, a TREM composition produced by any of the methods of making disclosed herein can be charged with an amino acid using an in vitro charging reaction as known in the art.

In an embodiment, a TREM composition comprise one or more species of TREMs, TREM core fragments, or TREM fragments. In an embodiment, a TREM composition comprises a single species of TREM, TREM core fragment, or TREM fragment. In an embodiment, a TREM composition comprises a first TREM, TREM core fragment, or TREM fragment species and a second TREM, TREM core fragment, or TREM fragment species. In an embodiment, the TREM composition comprises X TREM, TREM core fragment, or TREM fragment species, wherein X=2, 3, 4, 5, 6, 7, 8, 9, or 10.

In an embodiment, the TREM, TREM core fragment, or TREM fragment has at least 70, 75, 80, 85, 90, or 95, or has 100%, identity with a sequence encoded by a nucleic acid in Table 1. In an embodiment, the TREM comprises a consensus sequence provided herein.

A TREM composition can be formulated as a liquid composition, as a lyophilized composition or as a frozen composition.

In some embodiments, a TREM composition can be formulated to be suitable for pharmaceutical use, e.g., a pharmaceutical TREM composition. In an embodiment, a pharmaceutical TREM composition is substantially free of materials and/or reagents used to separate and/or purify a TREM, TREM core fragment, or TREM fragment.

In some embodiments, a TREM composition can be formulated with water for injection. In some embodiments, a TREM composition formulated with water for injection is suitable for pharmaceutical use, e.g., comprises a pharmaceutical TREM composition.

TREM Characterization

A TREM, TREM core fragment, or TREM fragment, or a TREM composition, e.g., a pharmaceutical TREM composition, produced by any of the methods disclosed herein can be assessed for a characteristic associated with the TREM, TREM core fragment, or TREM fragment or the TREM composition, such as purity, sterility, concentration, structure, or functional activity of the TREM, TREM core fragment, or TREM fragment. Any of the above-mentioned characteristics can be evaluated by providing a value for the characteristic, e.g., by evaluating or testing the TREM, TREM core fragment, or TREM fragment, or the TREM composition, or an intermediate in the production of the TREM composition. The value can also be compared with a standard or a reference value. Responsive to the evaluation, the TREM composition can be classified, e.g., as ready for release, meets production standard for human trials, complies with ISO standards, complies with cGMP standards, or complies with other pharmaceutical standards. Responsive to the evaluation, the TREM composition can be subjected to further processing, e.g., it can be divided into aliquots, e.g., into single or multi-dosage amounts, disposed in a container, e.g., an end-use vial, packaged, shipped, or put into commerce. In embodiments, in response to the evaluation, one or more of the characteristics can be modulated, processed or re-processed to optimize the TREM composition. For example, the TREM composition can be modulated, processed or re-processed to (i) increase the purity of the TREM composition; (ii) decrease the amount of fragments in the composition; (iii) decrease the amount of endotoxins in the composition; (iv) increase the in vitro translation activity of the composition; (v) increase the TREM concentration of the composition; or (vi) inactivate or remove any viral contaminants present in the composition, e.g., by reducing the pH of the composition or by filtration.

In an embodiment, the TREM, TREM core fragment, or TREM fragment (e.g., TREM composition or an intermediate in the production of the TREM composition) has a purity of at least 30%, 40%, 50%, 60%, 70%, 80%, 85%, 90%, 91%, 92%, 93%, 94%, 95%, 96%, 97%, 98%, or 99%, i.e., by mass.

In an embodiment, the TREM (e.g., TREM composition or an intermediate in the production of the TREM composition) has less than 0.1%, 0.5%, 1%, 2%, 3%, 4%, 5%, 6%, 7%, 8%, 9%, 10%, 15%, 20%, 25% TREM fragments relative to full length TREMs.

In an embodiment, the TREM, TREM core fragment, or TREM fragment (e.g., TREM composition or an intermediate in the production of the TREM composition) has low levels or absence of endotoxins, e.g., a negative result as measured by the Limulus amebocyte lysate (LAL) test.

In an embodiment, the TREM, TREM core fragment, or TREM fragment (e.g., TREM composition or an intermediate in the production of the TREM composition) has in-vitro translation activity, e.g., as measured by an assay described in Examples 12-13.

In an embodiment, the TREM, TREM core fragment, or TREM fragment (e.g., TREM composition or an intermediate in the production of the TREM composition) has a TREM concentration of at least 0.1 ng/mL, 0.5 ng/mL, 1 ng/mL, 5 ng/ml, 10 ng/ml, 50 ng/mL, 0.1 ug/mL, 0.5 ug/mL, 1 ug/mL, 2 ug/mL, 5 ug/mL, 10 ug/mL, 20 ug/mL, 30 ug/mL, 40 ug/mL, 50 ug/mL, 60 ug/mL, 70 ug/mL, 80 ug/mL, 100 ug/mL, 200 ug/mL, 300 ug/mL, 500 ug/mL, 1000 ug/mL, 5000 ug/mL, 10,000 ug/mL, or 100,000 ug/mL.

In an embodiment, the TREM, TREM core fragment, or TREM fragment (e.g., TREM composition or an intermediate in the production of the TREM composition) is sterile, e.g., the composition or preparation supports the growth of fewer than 100 viable microorganisms as tested under aseptic conditions, the composition or preparation meets the standard of USP <71>, and/or the composition or preparation meets the standard of USP <85>.

In an embodiment, the TREM, TREM core fragment, or TREM fragment (e.g., TREM composition or an intermediate in the production of the TREM composition) has an undetectable level of viral contaminants, e.g., no viral contaminants. In an embodiment, any viral contaminant, e.g., residual virus, present in the composition is inactivated or removed. In an embodiment, any viral contaminant, e.g., residual virus, is inactivated, e.g., by reducing the pH of the composition. In an embodiment, any viral contaminant, e.g., residual virus, is removed, e.g., by filtration or other methods known in the field.

TREM Administration

Any TREM composition or pharmaceutical composition described herein can be administered to a cell, tissue or subject, e.g., by direct administration to a cell, tissue and/or an organ in vitro, ex-vivo or in vivo. In-vivo administration may be via, e.g., by local, systemic and/or parenteral routes, for example intravenous, subcutaneous, intraperitoneal, intrathecal, intramuscular, ocular, nasal, urogenital, intradermal, dermal, enteral, intravitreal, intracerebral, intrathecal, or epidural.

Vectors and Carriers

In some embodiments the TREM, TREM core fragment, or TREM fragment or TREM composition described herein, is delivered to cells, e.g. mammalian cells or human cells, using a vector. The vector may be, e.g., a plasmid or a virus. In some embodiments, delivery is in vivo, in vitro, ex vivo, or in situ. In some embodiments, the virus is an adeno associated virus (AAV), a lentivirus, or an adenovirus. In some embodiments, the system or components of the system are delivered to cells with a viral-like particle or a virosome. In some embodiments, the delivery uses more than one virus, viral-like particle or virosome.

Carriers

A TREM, a TREM composition or a pharmaceutical TREM composition described herein may comprise, may be formulated with, or may be delivered in, a carrier.

Viral Vectors

The carrier may be a viral vector (e.g., a viral vector comprising a sequence encoding a TREM, a TREM core fragment or a TREM fragment). The viral vector may be administered to a cell or to a subject (e.g., a human subject or animal model) to deliver a TREM, a TREM core fragment or a TREM fragment, a TREM composition or a pharmaceutical TREM composition.

A viral vector may be systemically or locally administered (e.g., injected). Viral genomes provide a rich source of vectors that can be used for the efficient delivery of exogenous genes into a mammalian cell. Viral genomes are known in the art as useful vectors for delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference. In some embodiments the system or components of the system are delivered to cells with a viral-like particle or a virosome.

Cell and Vesicle-Based Carriers

A TREM, a TREM core fragment or a TREM fragment, a TREM composition or a pharmaceutical TREM composition described herein can be administered to a cell in a vesicle or other membrane-based carrier.

In embodiments, a TREM, a TREM core fragment or a TREM fragment, or TREM composition, or pharmaceutical TREM composition described herein is administered in or via a cell, vesicle or other membrane-based carrier. In one embodiment, the TREM, TREM core fragment, TREM fragment, or TREM composition or pharmaceutical TREM composition can be formulated in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

Lipid nanoparticles are another example of a carrier that provides a biocompatible and biodegradable delivery system for the TREM, TREM core fragment, TREM fragment, or TREM composition or pharmaceutical TREM composition described herein. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid-polymer nanoparticles (PLNs), a new type of carrier that combines liposomes and polymers, may also be employed. These nanoparticles possess the complementary advantages of PNPs and liposomes. A PLN is composed of a core-shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi: 10.3390/nano7060122.

Exemplary lipid nanoparticles are disclosed in International Application PCT/US2014/053907, the entire contents of which are hereby incorporated by reference. For example, an LNP described in paragraphs [403-406] or [410-413] of PCT/US2014/053907 can be used as a carrier for the TREM, TREM core fragment, TREM fragment, or TREM composition or pharmaceutical TREM composition described herein.

Additional exemplary lipid nanoparticles are disclosed in U.S. Pat. No. 10,562,849 the entire contents of which are hereby incorporated by reference. For example, an LNP of formula (I) as described in columns 1-3 of U.S. Pat. No. 10,562,849 can be used as a carrier for the TREM, TREM core fragment, TREM fragment, or TREM composition or pharmaceutical TREM composition described herein.

Lipids that can be used in nanoparticle formations (e.g., lipid nanoparticles) include, for example those described in Table 4 of WO2019217941, which is incorporated by reference, e.g., a lipid-containing nanoparticle can comprise one or more of the lipids in Table 4 of WO2019217941. Lipid nanoparticles can include additional elements, such as polymers, such as the polymers described in Table 5 of WO2019217941, incorporated by reference.

In some embodiments, conjugated lipids, when present, can include one or more of PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-O-(2',3'-di(tetradecanoyloxy) propyl-1-O-(w-methoxy (polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt, and those described in Table 2 of WO2019051289 (incorporated by reference), and combinations of the foregoing.

In some embodiments, sterols that can be incorporated into lipid nanoparticles include one or more of cholesterol or cholesterol derivatives, such as those in WO2009/127060 or US2010/0130588, which are incorporated by reference. Additional exemplary sterols include phytosterols, including those described in Eygeris et al (2020), incorporated herein by reference.

In some embodiments, the lipid particle comprises an ionizable lipid, a non-cationic lipid, a conjugated lipid that inhibits aggregation of particles, and a sterol. The amounts of these components can be varied independently and to achieve desired properties. For example, in some embodiments, the lipid nanoparticle comprises an ionizable lipid is in an amount from about 20 mol % to about 90 mol % of the total lipids (in other embodiments it may be 20-70% (mol), 30-60% (mol) or 40-50% (mol); about 50 mol % to about 90 mol % of the total lipid present in the lipid nanoparticle), a non-cationic lipid in an amount from about 5 mol % to about mol % of the total lipids, a conjugated lipid in an amount from about 0.5 mol % to about 20 mol % of the total lipids, and a sterol in an amount from about 20 mol % to about 50 mol % of the total lipids. The ratio of total lipid to nucleic acid can be varied as desired. For example, the total lipid to nucleic acid (mass or weight) ratio can be from about 10:1 to about 30:1.

In some embodiments, the lipid to nucleic acid ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and nucleic acid can be adjusted to provide a desired N/P ratio, for example, N/P ratio of 3, 4, 5, 6, 7, 8, 9, 10 or higher. Generally, the lipid nanoparticle formulation's overall lipid content can range from about 5 mg/ml to about 30 mg/mL.

Some non-limiting example of lipid compounds that may be used (e.g., in combination with other lipid components) to form lipid nanoparticles for the delivery of compositions described herein, e.g., nucleic acid (e.g., RNA) described herein includes,

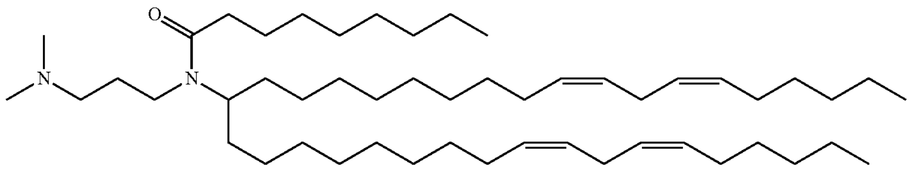
(i)

In some embodiments an LNP comprising Formula (i) is used to deliver a TREM composition described herein to the liver and/or hepatocyte cells.

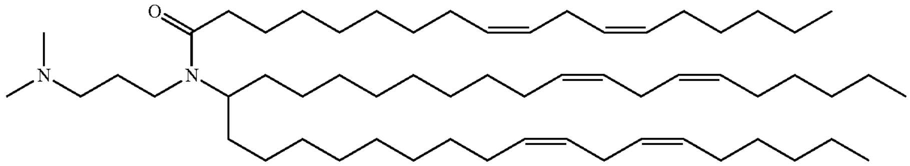
(ii)

In some embodiments an LNP comprising Formula (ii) is used to deliver a TREM composition described herein to the liver and/or hepatocyte cells.

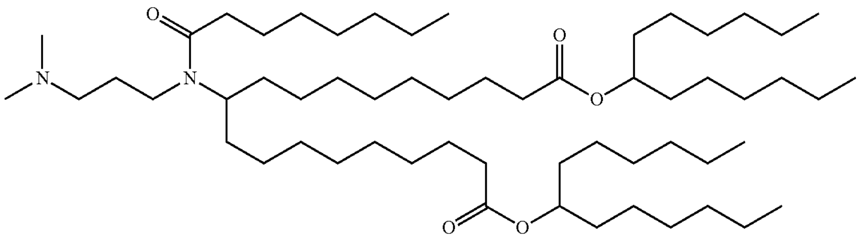
(iii)

In some embodiments an LNP comprising Formula (iii) is used to deliver a TREM composition described herein to the liver and/or hepatocyte cells.

(iv)

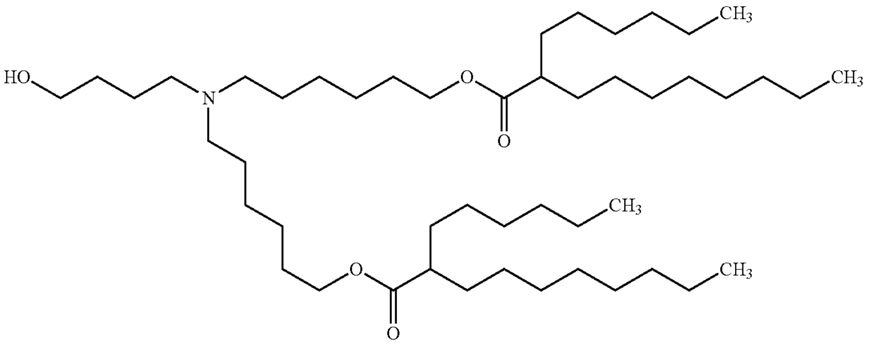

(v)

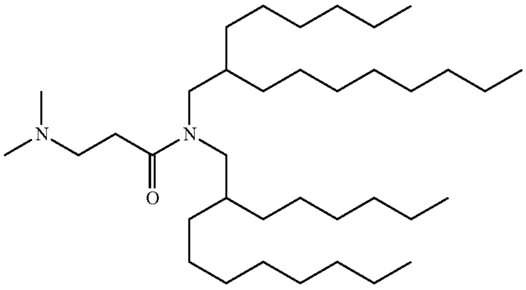

In some embodiments an LNP comprising Formula (v) is used to deliver a TREM composition described herein to the liver and/or hepatocyte cells.

(vi)

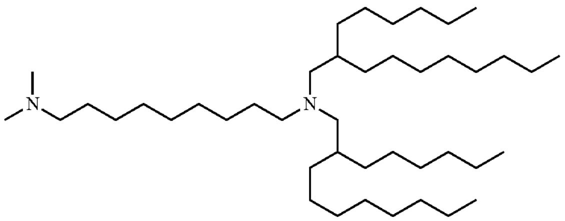

In some embodiments an LNP comprising Formula (vi) is used to deliver a TREM composition described herein to the liver and/or hepatocyte cells.

(vii)

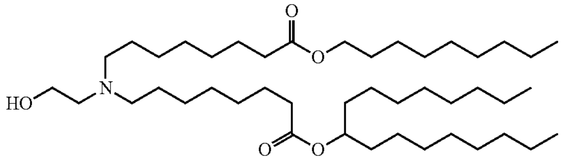

(viii)

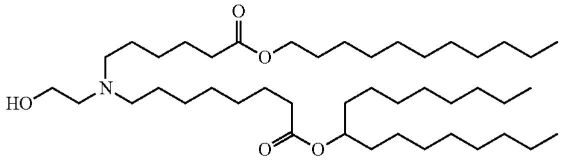

In some embodiments an LNP comprising Formula (viii) is used to deliver a TREM composition described herein to the liver and/or hepatocyte cells.

(ix)

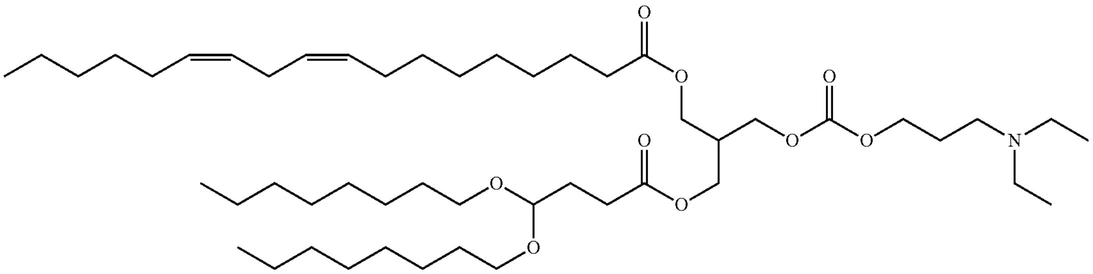

In some embodiments an LNP comprising Formula (ix) is used to deliver a TREM composition described herein to the liver and/or hepatocyte cells.

(x)

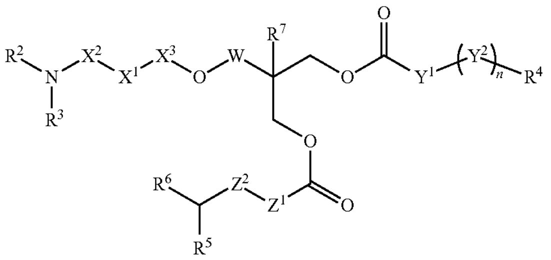

wherein $X^1$ is O. $NR^1$, or a direct bond, $X_2$ is C2-5 alkylene, $X_3$ is C(═O) or a direct bond, R' is H or Me, $R_3$ is Ci-3 alkyl, $R_2$ is Ci-3 alkyl, or $R_2$ taken together with the nitrogen atom to which it is attached and 1-3 carbon atoms of $X_2$ form a 4-, 5-, or 6-membered ring, or X' is $NR^1$, R' and $R_2$ taken together with the nitrogen atoms to which they are attached form a 5- or 6-membered ring, or $R_2$ taken together with $R_3$ and the nitrogen atom to which they are attached form a 5-, 6-, or 7-membered ring, Y' is C2-12 alkylene, $Y^2$ is selected from

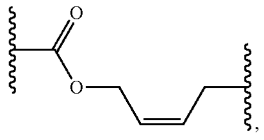

(in either orientation)

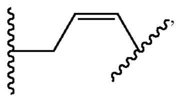

(in either orientation)

-continued

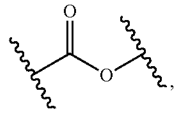

(in either orientation)

n is 0 to 3, $R^4$ is Ci-15 alkyl, $Z^1$ is Ci-6 alkylene or a direct bond, $Z^2$ is

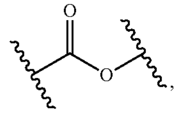 [SMILES: *OC(*)=O]

(in either orientation) or absent, provided that if Z' is a direct bond, $Z^2$ is absent; $R^5$ is C5-9 alkyl or C6-10 alkoxy, $R^6$ is C5-9 alkyl or C6-10 alkoxy, W is methylene or a direct bond, and R' is H or Me, or a salt thereof, provided that if $R_3$ and $R_2$ are C2 alkyls, $X_1$ is O, $X_2$ is linear C3 alkylene, $X_3$ is C(═O), $Y^1$ is linear Ce alkylene, $(Y^2)n-R^4$ is:

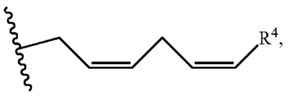

$R_4$ is linear C5 alkyl, $Z^1$ is C2 alkylene, $Z^2$ is absent, W is methylene, and $R^7$ is H, then $R^5$ and $R^6$ are not Cx alkoxy.

In some embodiments an LNP comprising Formula (xii) is used to deliver a TREM composition described herein to the liver and/or hepatocyte cells.

(xi)

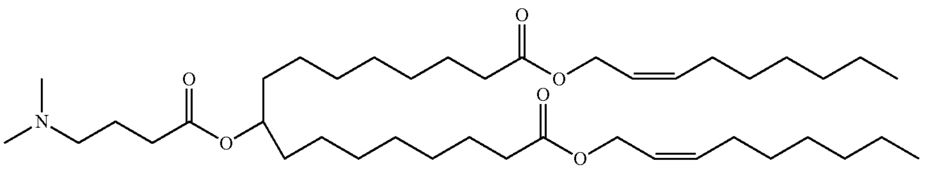

In some embodiments an LNP comprising Formula (xi) is used to deliver a TREM composition described herein to the liver and/or hepatocyte cells.

(xii)

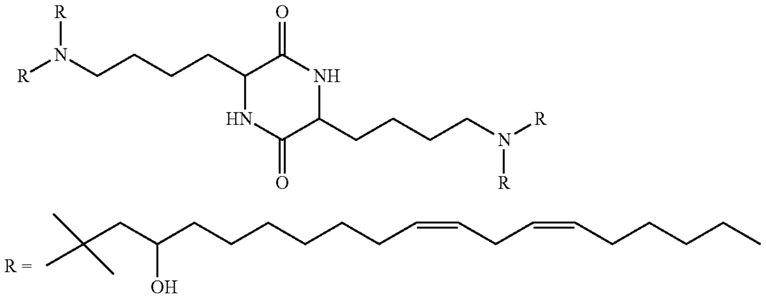

where

-continued

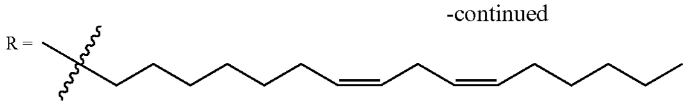

(xiii)

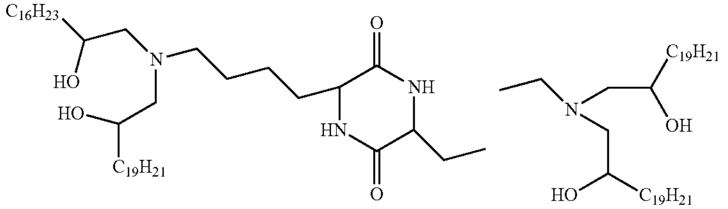

(xiv)

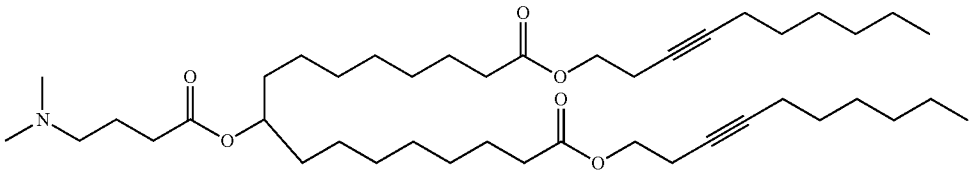

In some embodiments an LNP comprises a compound of Formula (xiii) and a compound of Formula (xiv).

(xv)

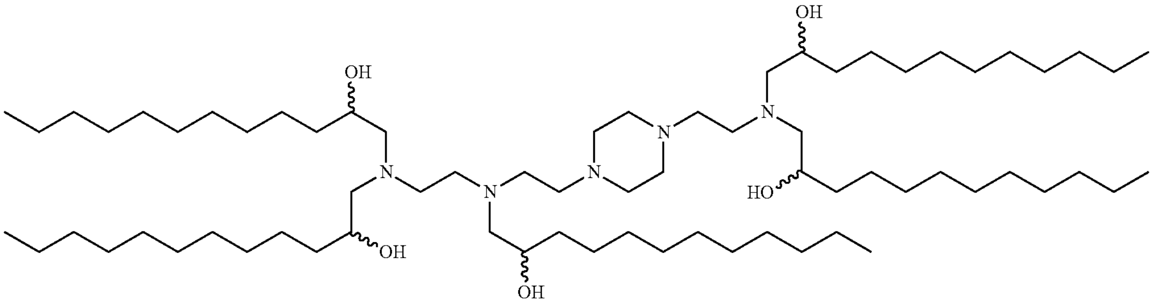

In some embodiments, an LNP comprising Formula (xv) is used to deliver a TREM composition described herein to the liver and/or hepatocyte cells.

(xvi)

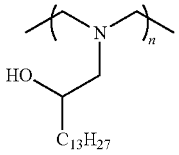

PEI$_{000}$ Core

In some embodiments an LNP comprising a formulation of Formula (xvi) is used to deliver a TREM composition described herein to the lung endothelial cells. 5

(xvii)

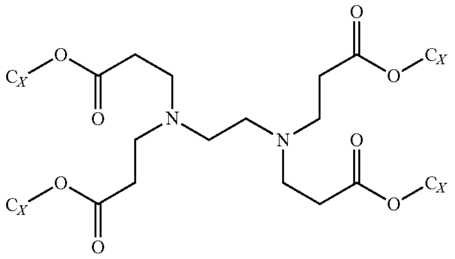

-continued
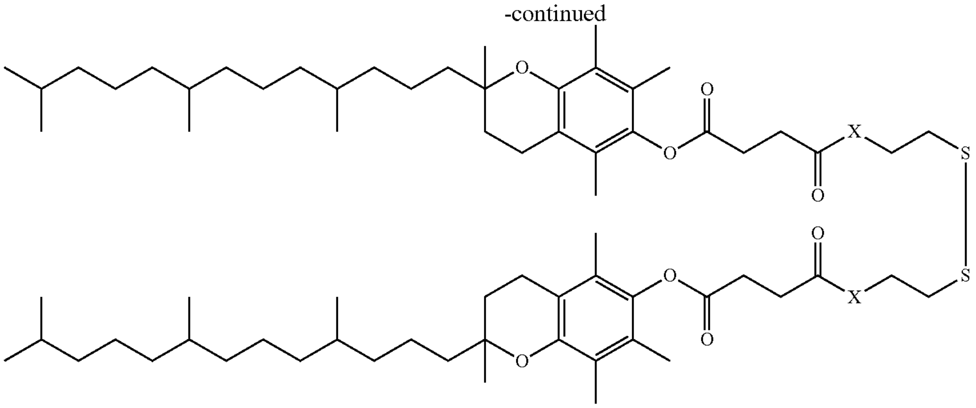
where
X = amino structure
(xviii) (a)
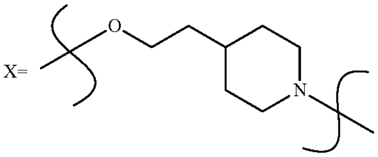
(xviii) (b)
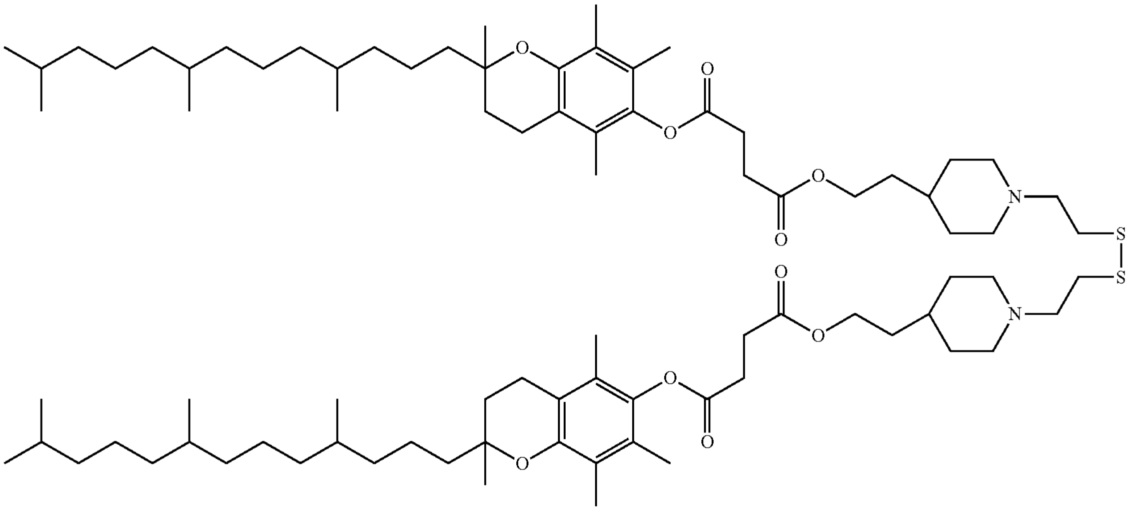
(xix)
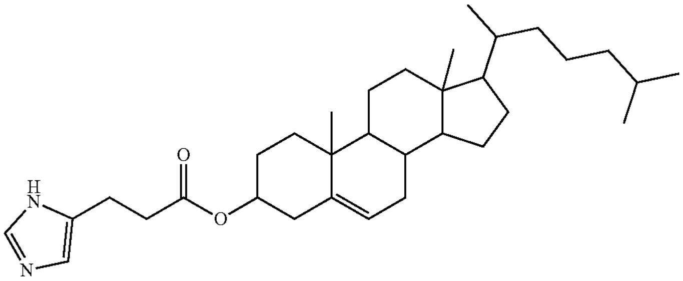

In some embodiments, a lipid compound used to form lipid nanoparticles for the delivery of compositions described herein, e.g., a TREM described herein is made by one of the following reactions:

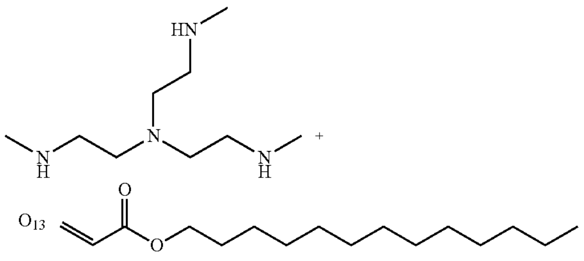

(xx) (a)

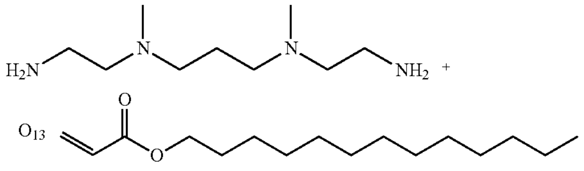

(xx) (b)

In some embodiments, a composition described herein (e.g., TREM composition) is provided in an LNP that comprises an ionizable lipid. In some embodiments, the ionizable lipid is heptadecan-9-yl 8-((2-hydroxyethyl) (6-oxo-6-(undecyloxy) hexyl)amino) octanoate (SM-102); e.g., as described in Example 1 of U.S. Pat. No. 9,867,888 (incorporated by reference herein in its entirety). In some embodiments, the ionizable lipid is 9Z, 12Z)-3-((4,4-bis (octyloxy) butanoyl)oxy)-2-((((3-(diethylamino) propoxy) carbonyl)oxy)methyl) propyl octadeca-9,12-dienoate (LP01), e.g., as synthesized in Example 13 of WO2015/095340 (incorporated by reference herein in its entirety). In some embodiments, the ionizable lipid is Di((Z)-non-2-en-1-yl) 9-((4-dimethylamino)-butanoyl)oxy) heptadecanedioate (L319), e.g. as synthesized in Example 7, 8, or 9 of US2012/0027803 (incorporated by reference herein in its entirety). In some embodiments, the ionizable lipid is 1,1'-((2-(4-(2-((2-(Bis(2-hydroxydodecyl)amino)ethyl) (2-hydroxydodecyl)amino)ethyl) piperazin-1-yl)ethyl) azanediyl) bis(dodecan-2-ol) (C12-200), e.g., as synthesized in Examples 14 and 16 of WO2010/053572 (incorporated by reference herein in its entirety). In some embodiments, the ionizable lipid is Imidazole cholesterol ester (ICE) lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl) propanoate, e.g., Structure (I) from WO2020/106946 (incorporated by reference herein in its entirety).

In some embodiments, an ionizable lipid may be a cationic lipid, an ionizable cationic lipid, e.g., a cationic lipid that can exist in a positively charged or neutral form depending on pH, or an amine-containing lipid that can be readily protonated. In some embodiments, the cationic lipid is a lipid capable of being positively charged, e.g., under physiological conditions. Exemplary cationic lipids include one or more amine group(s) which bear the positive charge. In some embodiments, the lipid particle comprises a cationic lipid in formulation with one or more of neutral lipids, ionizable amine-containing lipids, biodegradable alkyne lipids, steroids, phospholipids including polyunsaturated lipids, structural lipids (e.g., sterols), PEG, cholesterol and polymer conjugated lipids. In some embodiments, the cationic lipid may be an ionizable cationic lipid. An exemplary cationic lipid as disclosed herein may have an effective pKa over 6.0. In embodiments, a lipid nanoparticle may comprise a second cationic lipid having a different effective pKa (e.g., greater than the first effective pKa), than the first cationic lipid. A lipid nanoparticle may comprise between 40 and 60 mol percent of a cationic lipid, a neutral lipid, a steroid, a polymer conjugated lipid, and a therapeutic agent, e.g., a TREM described herein, encapsulated within or associated with the lipid nanoparticle. In some embodiments, the TREM is co-formulated with the cationic lipid. The TREM may be adsorbed to the surface of an LNP, e.g., an LNP comprising a cationic lipid. In some embodiments, the TREM may be encapsulated in an LNP, e.g., an LNP comprising a cationic lipid. In some embodiments, the lipid nanoparticle may comprise a targeting moiety, e.g., coated with a targeting agent. In embodiments, the LNP formulation is biodegradable. In some embodiments, a lipid nanoparticle comprising one or more lipid described herein, e.g., Formula (i), (ii), (ii), (vii) and/or (ix) encapsulates at least 1%, at least 5%, at least 10%, at least 20%, at least 30%, at least 40%, at least 50%, at least 60%, at least 70%, at least 80%, at least 90%, at least 92%, at least 95%, at least 97%, at least 98% or 100% of a TREM.

Exemplary ionizable lipids that can be used in lipid nanoparticle formulations include, without limitation, those listed in Table 1 of WO2019051289, incorporated herein by reference. Additional exemplary lipids include, without limitation, one or more of the following formulae: X of US2016/0311759; I of US20150376115 or in US2016/0376224; I, II or III of US20160151284; I, IA, II, or IIA of US20170210967; I-c of US20150140070; A of US2013/0178541; I of US2013/0303587 or US2013/0123338; I of US2015/0141678; II, III, IV, or V of US2015/0239926; I of US2017/0119904; I or II of WO2017/117528; A of US2012/0149894; A of US2015/0057373; A of WO2013/116126; A of US2013/0090372; A of US2013/0274523; A of US2013/0274504; A of US2013/0053572; A of WO2013/016058; A of WO2012/162210; I of US2008/042973; I, II, III, or IV of US2012/01287670; I or II of US2014/0200257; I, II, or III of US2015/0203446; I or III of US2015/0005363; I, IA, IB, IC, ID, II, IIA, IIB, IIC, IID, or III-XXIV of US2014/0308304; of US2013/0338210; I, II, III, or IV of WO2009/132131; A of US2012/01011478; I or XXXV of US2012/0027796; XIV or XVII of US2012/0058144; of US2013/0323269; I of US2011/0117125; I, II, or III of US2011/0256175; I, II, III, IV, V, VI, VII, VIII, IX, X, XI, XII of US2012/0202871; I, II, III, IV, V, VI, VII, VIII, X, XII, XIII, XIV, XV, or XVI of US2011/0076335; I or II of US2006/008378; I of US2013/0123338; I or X-A-Y-Z of US2015/0064242; XVI, XVII, or XVIII of US2013/0022649; I, II, or III of US2013/0116307; I, II, or III of US2013/0116307; I or II of US2010/0062967; I-X of US2013/0189351; I of US2014/0039032; V of US2018/0028664; I of US2016/0317458; I of US2013/0195920; 5, 6, or 10 of U.S. Pat. No. 10,221,127; III-3 of WO2018/081480; 1-5 or 1-8 of WO2020/081938; 18 or 25 of U.S. Pat. No. 9,867,888; A of US2019/0136231; II of WO2020/219876; 1 of US2012/0027803; OF-02 of US2019/0240349; 23 of U.S. Pat. No. 10,086,013; cKK-E12/A6 of Miao et al (2020); C12-200 of WO2010/053572; 7C1 of Dahlman et al (2017); 304-O13 or 503-013 of Whitehead et al; TS-P4C2 of U.S. Pat. No. 9,708,628; I of WO2020/106946; I of WO2020/106946.

In some embodiments, the ionizable lipid is MC3 (6Z, 9Z,28Z,3 1Z)-heptatriaconta-6,9,28,3 1-tetraen-19-yl-4-(dimethylamino) butanoate (DLin-MC3-DMA or MC3), e.g., as described in Example 9 of WO2019051289A9 (incorporated by reference herein in its entirety). In some embodiments, the ionizable lipid is the lipid ATX-002, e.g., as described in Example 10 of WO2019051289A9 (incorporated by reference herein in its entirety). In some embodiments, the ionizable lipid is (13Z,16Z)-A,A-dimethyl-3-nonyldocosa-13, 16-dien-1-amine (Compound 32), e.g., as described in Example 11 of WO2019051289A9 (incorporated by reference herein in its entirety). In some embodiments, the ionizable lipid is Compound 6 or Compound 22, e.g., as described in Example 12 of WO2019051289A9 (incorporated by reference herein in its entirety).

Exemplary non-cationic lipids include, but are not limited to, distearoyl-sn-glycero-phosphoethanolamine, distcaroylphosphatidylcholine (DSPC), dioleoylphosphatidylcholine (DOPC), dipalmitoylphosphatidylcholine (DPPC), diolcoylphosphatidylglycerol (DOPG), dipalmitoylphosphatidylglycerol (DPPG), dioleoyl-phosphatidylethanolamine (DOPE), palmitoylolcoylphosphatidylcholine (POPC), palmitoyloleoylphosphatidylethanolamine (POPE), diolcoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. It is understood that other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, paimitoyl, stearoyl, or olcoyl. Additional exemplary lipids, in certain embodiments, include, without limitation, those described in Kim et al. (2020) dx.doi.org/10.1021/acs.nanolett.0c01386, incorporated herein by reference. Such lipids include, in some embodiments, plant lipids found to improve liver transfection with mRNA (e.g., DGTS).

Other examples of non-cationic lipids suitable for use in the lipid nanoparticles include, without limitation, nonphosphorous lipids such as, e.g., stearylamine, dodecylamine, hexadecylamine, acetyl palmitate, glycerol ricinoleate, hexadecyl stercate, isopropyl myristate, amphoteric acrylic polymers, triethanolamine-lauryl sulfate, alkyl-aryl sulfate polyethyloxylated fatty acid amides, dioctadecyl dimethyl ammonium bromide, ceramide, sphingomyelin, and the like. Other non-cationic lipids are described in WO2017/099823 or US patent publication US2018/0028664, the contents of which is incorporated herein by reference in their entirety.

In some embodiments, the non-cationic lipid is oleic acid or a compound of Formula I, II, or IV of US2018/0028664, incorporated herein by reference in its entirety. The non-cationic lipid can comprise, for example, 0-30% (mol) of the total lipid present in the lipid nanoparticle. In some embodiments, the non-cationic lipid content is 5-20% (mol) or 10-15% (mol) of the total lipid present in the lipid nanoparticle. In embodiments, the molar ratio of ionizable lipid to the neutral lipid ranges from about 2:1 to about 8:1 (e.g., about 2:1, 3:1, 4:1, 5:1, 6:1, 7:1, or 8:1).

In some embodiments, the lipid nanoparticles do not comprise any phospholipids.

In some aspects, the lipid nanoparticle can further comprise a component, such as a sterol, to provide membrane integrity. One exemplary sterol that can be used in the lipid nanoparticle is cholesterol and derivatives thereof. Non-limiting examples of cholesterol derivatives include polar analogues such as 5a-choiestanol, 53-coprostanol, choiesteryl-(2-hydroxy)-ethyl ether, choiesteryl-(4'-hydroxy)-butyl ether, and 6-ketocholestanol; non-polar analogues such as 5a-cholestane, cholestenone, 5a-cholestanone, 5p-cholestanone, and cholesteryl decanoate; and mixtures thereof. In some embodiments, the cholesterol derivative is a polar analogue, e.g., choiesteryl-(4'-hydroxy)-butyl ether. Exemplary cholesterol derivatives are described in PCT publication WO2009/127060 and US patent publication US2010/0130588, each of which is incorporated herein by reference in its entirety.

In some embodiments, the component providing membrane integrity, such as a sterol, can comprise 0-50% (mol) (e.g., 0-10%, 10-20%, 20-30%, 30-40%, or 40-50%) of the total lipid present in the lipid nanoparticle. In some embodiments, such a component is 20-50% (mol) 30-40% (mol) of the total lipid content of the lipid nanoparticle.

In some embodiments, the lipid nanoparticle can comprise a polyethylene glycol (PEG) or a conjugated lipid molecule. Generally, these are used to inhibit aggregation of lipid nanoparticles and/or provide steric stabilization. Exemplary conjugated lipids include, but are not limited to, PEG-lipid conjugates, polyoxazoline (POZ)-lipid conjugates, polyamide-lipid conjugates (such as *ATTA*-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid.

Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy) propyl-1-0-(w-methoxy (polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, US2017/0119904, and US/099823, the contents of all of which are incorporated herein by reference in their entirety. In some embodiments, a PEG-lipid is a compound of Formula III, III-a-I, III-a-2, III-b-1, III-b-2, or V of US2018/0028664, the content of which is incorporated herein by reference in its entirety. In some embodiments, a PEG-lipid is of Formula II of US20150376115 or US2016/0376224, the content of both of which is incorporated herein by reference in its entirety. In some embodiments, the PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3 [beta]-oxy) carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy (polyethylene glycol)-2000]. In some embodiments, the PEG-lipid comprises PEG-DMG, 1,2-dimyristoyl-sn-glycero-3-phosphoethanolamine-N-[methoxy (polyethylene glycol)-2000]. In some embodiments, the PEG-lipid comprises a structure selected from:

or by total weight of the composition, 0-30% non-cationic-lipid by mole or by total weight of the composition and 1-10% conjugated lipid by mole or by total weight of the composition. Preferably, the composition comprises 30-40% ionizable lipid by mole or by total weight of the composition, 40-50% cholesterol by mole or by total weight of the composition, and 10-20% non-cationic-lipid by mole or by total weight of the composition. In some other embodiments, the composition is 50-75% ionizable lipid by mole or by total weight of the composition, 20-40% cholesterol by mole or by total weight of the composition, and 5 to 10% non-cationic-lipid, by mole or by total weight of the composition and 1-10% conjugated lipid by mole or by total weight of the composition. The composition may contain 60-70% ionizable lipid by mole or by total weight of the composition, 25-35% cholesterol by mole or by total weight of the composition, and 5-10% non-cationic-lipid by mole or by total weight of the composition. The composition may also contain up to 90% ionizable lipid by mole or by total weight of the composition and 2 to 15% non-cationic lipid

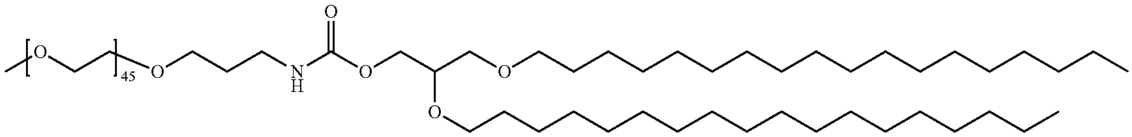
,
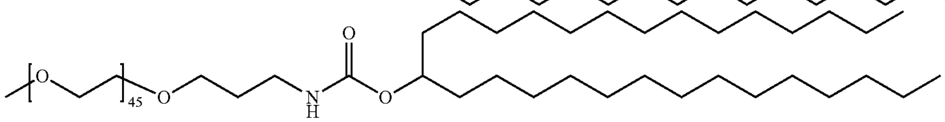
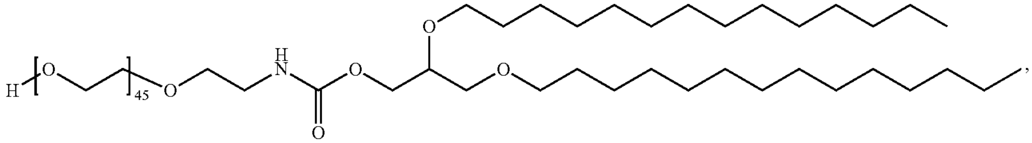
, and
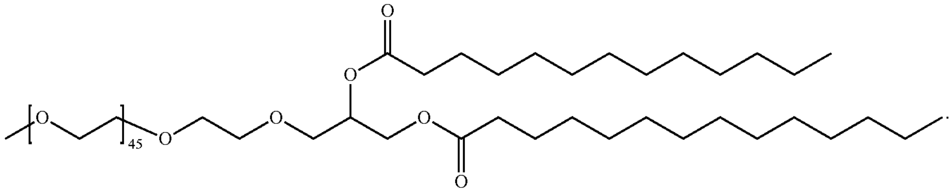
.

In some embodiments, lipids conjugated with a molecule other than a PEG can also be used in place of PEG-lipid. For example, polyoxazoline (POZ)-lipid conjugates, polyamide-lipid conjugates (such as ATTA-lipid conjugates), and cationic-polymer lipid (GPL) conjugates can be used in place of or in addition to the PEG-lipid.

Exemplary conjugated lipids, i.e., PEG-lipids, (POZ)-lipid conjugates, ATTA-lipid conjugates and cationic polymer-lipids are described in the PCT and LIS patent applications listed in Table 2 of WO2019051289A9, the contents of all of which are incorporated herein by reference in their entirety.

In some embodiments, the PEG or the conjugated lipid can comprise 0-20% (mol) of the total lipid present in the lipid nanoparticle. In some embodiments, PEG or the conjugated lipid content is 0.5-10% or 2-5% (mol) of the total lipid present in the lipid nanoparticle. Molar ratios of the ionizable lipid, non-cationic-lipid, sterol, and PEG/conjugated lipid can be varied as needed. For example, the lipid particle can comprise 30-70% ionizable lipid by mole or by total weight of the composition, 0-60% cholesterol by mole by mole or by total weight of the composition. The formulation may also be a lipid nanoparticle formulation, for example comprising 8-30% ionizable lipid by mole or by total weight of the composition, 5-30% non-cationic lipid by mole or by total weight of the composition, and 0-20% cholesterol by mole or by total weight of the composition; 4-25% ionizable lipid by mole or by total weight of the composition, 4-25% non-cationic lipid by mole or by total weight of the composition, 2 to 25% cholesterol by mole or by total weight of the composition, 10 to 35% conjugate lipid by mole or by total weight of the composition, and 5% cholesterol by mole or by total weight of the composition; or 2-30% ionizable lipid by mole or by total weight of the composition, 2-30% non-cationic lipid by mole or by total weight of the composition, 1 to 15% cholesterol by mole or by total weight of the composition, 2 to 35% conjugate lipid by mole or by total weight of the composition, and 1-20% cholesterol by mole or by total weight of the composition; or even up to 90% ionizable lipid by mole or by total weight of the composition and 2-10% non-cationic lipids by mole or by total weight of the composition, or even 100% cationic lipid by mole or by total weight of the composition. In some embodiments, the lipid particle formulation comprises ionizable lipid, phospholipid, cholesterol and a PEG-ylated lipid in a molar ratio of 50:10:38.5:1. 5. In some other embodiments, the lipid particle formulation comprises ionizable lipid, cholesterol and a PEG-ylated lipid in a molar ratio of 60:38.5:1.5.

In some embodiments, the lipid particle comprises ionizable lipid, non-cationic lipid (e.g. phospholipid), a sterol (e.g., cholesterol) and a PEG-ylated lipid, where the molar ratio of lipids ranges from 20 to 70 mole percent for the ionizable lipid, with a target of 40-60, the mole percent of non-cationic lipid ranges from 0 to 30, with a target of 0 to 15, the mole percent of sterol ranges from 20 to 70, with a target of 30 to 50, and the mole percent of PEG-ylated lipid ranges from 1 to 6, with a target of 2 to 5.

In some embodiments, the lipid particle comprises ionizable lipid/non-cationic-lipid/sterol/conjugated lipid at a molar ratio of 50:10:38.5:1.5.

In an aspect, the disclosure provides a lipid nanoparticle formulation comprising phospholipids, lecithin, phosphatidylcholine and phosphatidylethanolamine.

In some embodiments, one or more additional compounds can also be included. Those compounds can be administered separately, or the additional compounds can be included in the lipid nanoparticles of the invention. In other words, the lipid nanoparticles can contain other compounds in addition to the nucleic acid or at least a second nucleic acid, different than the first. Without limitations, other additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

In some embodiments, LNPs are directed to specific tissues by the addition of targeting domains. For example, biological ligands may be displayed on the surface of LNPs to enhance interaction with cells displaying cognate receptors, thus driving association with and cargo delivery to tissues wherein cells express the receptor. In some embodiments, the biological ligand may be a ligand that drives delivery to the liver, e.g., LNPs that display GalNAc result in delivery of nucleic acid cargo to hepatocytes that display asialoglycoprotein receptor (ASGPR). The work of Akinc et al. *Mol Ther* 18 (7): 1357-1364 (2010) teaches the conjugation of a trivalent GalNAc ligand to a PEG-lipid (GalNAc-PEG-DSG) to yield LNPs dependent on ASGPR for observable LNP cargo effect (see, e.g., FIG. 6 of Akinc et al. 2010, supra). Other ligand-displaying LNP formulations, e.g., incorporating folate, transferrin, or antibodies, are discussed in WO2017223135, which is incorporated herein by reference in its entirety, in addition to the references used therein, namely Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; and Peer and Lieberman, Gene Ther. 2011 18:1127-1133.

In some embodiments, LNPs are selected for tissue-specific activity by the addition of a Selective ORgan Targeting (SORT) molecule to a formulation comprising traditional components, such as ionizable cationic lipids, amphipathic phospholipids, cholesterol and poly(ethylene glycol) (PEG) lipids. The teachings of Cheng et al. Nat Nanotechnol 15 (4): 313-320 (2020) demonstrate that the addition of a supplemental "SORT" component precisely alters the in vivo RNA delivery profile and mediates tissue-specific (e.g., lungs, liver, spleen) gene delivery and editing as a function of the percentage and biophysical property of the SORT molecule.

In some embodiments, the LNPs comprise biodegradable, ionizable lipids. In some embodiments, the LNPs comprise (9Z,12Z)-3-((4,4-bis(octyloxy) butanoyl)oxy)-2-((((3-(diethylamino) propoxy) carbonyl)oxy)methyl) propyl octadeca-9,12-dienoate, also called 3-((4,4-bis(octyloxy) butanoyl)oxy)-2-((((3-(diethylamino) propoxy) carbonyl) oxy)methyl) propyl (9Z,12Z)-octadeca-9,12-dienoate) or another ionizable lipid. Sec, e.g, lipids of WO2019/067992, WO/2017/173054, WO2015/095340, and WO2014/136086, as well as references provided therein. In some embodiments, the term cationic and ionizable in the context of LNP lipids is interchangeable, e.g., wherein ionizable lipids are cationic depending on the pH.

In some embodiments, the average LNP diameter of the LNP formulation may be between 10 s of nm and 100 s of nm, e.g., measured by dynamic light scattering (DLS). In some embodiments, the average LNP diameter of the LNP formulation may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the average LNP diameter of the LNP formulation may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In some embodiments, the average LNP diameter of the LNP formulation may be from about 70 nm to about 100 nm. In a particular embodiment, the average LNP diameter of the LNP formulation may be about 80 nm. In some embodiments, the average LNP diameter of the LNP formulation may be about 100 nm. In some embodiments, the average LNP diameter of the LNP formulation ranges from about 1 mm to about 500 mm, from about 5 mm to about 200 mm, from about 10 mm to about 100 mm, from about 20 mm to about 80 mm, from about 25 mm to about 60 mm, from about 30 mm to about 55 mm, from about 35 mm to about 50 mm, or from about 38 mm to about 42 mm.

A LNP may, in some instances, be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. In some embodiments, the zeta potential may describe the surface charge of an LNP. Lipid nanoparticles with relatively low charges, positive or negative, are generally desirable, as more highly charged species may interact undesirably with cells, tissues, and other elements in the body. In some embodiments, the zeta potential of a LNP may be from about-10 mV to about +20 mV, from about-10 mV to about +15 mV, from about-10 mV to about +10 mV, from about-10 mV to about +5 mV, from about-10 mV to about 0 mV, from about-10 mV to about-5 mV, from about-5 mV to about +20 mV, from about-5 mV to about +15 mV, from about-5 mV to about +10 mV, from about-5 mV to about +5 mV, from about-5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a TREM describes the amount of TREM that is encapsulated or otherwise associated with a LNP after preparation, relative to the initial amount provided. The encapsulation efficiency is desirably high (e.g., close to 100%). The encapsulation efficiency may be measured, for example, by comparing the amount of TREM in a solution containing the lipid nanoparticle before and after breaking up the lipid nanoparticle with one or more organic solvents or detergents. An anion exchange resin may be used to measure the amount of free protein or nucleic acid (e.g., RNA) in a solution. Fluorescence may be used to measure the amount of free TREM in a solution. For the lipid nanoparticles described herein, the encapsulation efficiency of a TREM may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In some embodiments, the encapsulation efficiency may be at least 90%. In some embodiments, the encapsulation efficiency may be at least 95%.

A LNP may optionally comprise one or more coatings. In some embodiments, a LNP may be formulated in a capsule, film, or table having a coating. A capsule, film, or tablet including a composition described herein may have any useful size, tensile strength, hardness or density.

Additional exemplary lipids, formulations, methods, and characterization of LNPs are taught by WO2020061457, which is incorporated herein by reference in its entirety.

In some embodiments, in vitro or ex vivo cell lipofections are performed using Lipofectamine MessengerMax (Thermo Fisher) or TransIT-mRNA Transfection Reagent (Mirus Bio). In certain embodiments, LNPs are formulated using the Gen Voy_ILM ionizable lipid mix (Precision NanoSystems). In certain embodiments, LNPs are formulated using 2,2-dilinoleyl-4-dimethylaminoethyl-[1,3]-dioxolane (DLin-KC2-DMA) or dilinoleylmethyl-4-dimethylaminobutyrate (DLin-MC3-DMA or MC3), the formulation and in vivo use of which are taught in Jayaraman et al. Angew Chem Int Ed Engl 51 (34): 8529-8533 (2012), incorporated herein by reference in its entirety.

LNP formulations optimized for the delivery of CRISPR-Cas systems, e.g., Cas9-gRNA RNP, gRNA, Cas9 mRNA, are described in WO2019067992 and WO2019067910, both incorporated by reference.

Additional specific LNP formulations useful for delivery of nucleic acids are described in U.S. Pat. Nos. 8,158,601 and 8,168,775, both incorporated by reference, which include formulations used in patisiran, sold under the name ONPATTRO.

Exosomes can also be used as drug delivery vehicles for the TREM, TREM core fragment, TREM fragment, or TREM compositions or pharmaceutical TREM composition described herein. For a review, see Ha et al. July 2016. Acta Pharmaceutica *Sinica* B. Volume 6, Issue 4, Pages 287-296; https://doi.org/10.1016/j.apsb.2016.02.001.

Ex vivo differentiated red blood cells can also be used as a carrier for a TREM, TREM core fragment, TREM fragment, or TREM composition, or pharmaceutical TREM composition described herein. Sec, e.g., WO2015073587; WO2017123646; WO2017123644; WO2018102740; wO2016183482; WO2015153102; WO2018151829; WO2018009838; Shi et al. 2014. Proc Natl Acad Sci USA. 111 (28): 10131-10136; U.S. Pat. No. 9,644,180; Huang et al. 2017. Nature Communications 8:423; Shi et al. 2014. Proc Natl Acad Sci USA. 111 (28): 10131-10136.

Fusosome compositions, e.g., as described in WO2018208728, can also be used as carriers to deliver the TREM, TREM core fragment, TREM fragment, or TREM composition, or pharmaceutical TREM composition described herein.

Virosomes and virus-like particles (VLPs) can also be used as carriers to deliver a TREM, TREM core fragment, TREM fragment, or TREM composition, or pharmaceutical TREM composition described herein to targeted cells.

Plant nanovesicles, e.g., as described in WO2011097480A1, WO2013070324A1, or WO2017004526A1 can also be used as carriers to deliver the TREM, TREM core fragment, TREM fragment, or TREM composition, or pharmaceutical TREM composition described herein.

Delivery without a Carrier

A TREM, a TREM core fragment or a TREM fragment, a TREM composition or a pharmaceutical TREM composition described herein can be administered to a cell without a carrier, e.g., via naked delivery of the TREM, a TREM core fragment or a TREM fragment, a TREM composition or a pharmaceutical TREM composition.

In some embodiments, naked delivery as used herein refers to delivery without a carrier. In some embodiments, delivery without a carrier, e.g., naked delivery, comprises delivery with a moiety, e.g., a targeting peptide.

In some embodiments, a TREM, a TREM core fragment or a TREM fragment, or TREM composition, or pharmaceutical TREM composition described herein is delivered to a cell without a carrier, e.g., via naked delivery. In some embodiments, the delivery without a carrier, e.g., naked delivery, comprises delivery with a moiety, e.g., a targeting peptide.

Use of TREMs

A TREM composition (e.g., a pharmaceutical TREM composition described herein) can modulate a function in a cell, tissue or subject. In embodiments, a TREM composition (e.g., a pharmaceutical TREM composition) described herein is contacted with a cell or tissue, or administered to a subject in need thereof, in an amount and for a time sufficient to modulate (increase or decrease) one or more of the following parameters: adaptor function (e.g., cognate or non-cognate adaptor function), e.g., the rate, efficiency, robustness, and/or specificity of initiation or elongation of a polypeptide chain; ribosome binding and/or occupancy; regulatory function (e.g., gene silencing or signaling); cell fate; mRNA stability; protein stability; protein transduction; protein compartmentalization. A parameter may be modulated, e.g., by at least 5% (e.g., at least 10%, 15%, 20%, 25%, 30%, 40%, 50%, 60%, 70%, 80%, 90%, 100%, 150%, 200% or more) compared to a reference tissue, cell or subject (e.g., a healthy, wild-type or control cell, tissue or subject).

All references and publications cited herein are hereby incorporated by reference.

The following examples are provided to further illustrate some embodiments of the present invention, but are not intended to limit the scope of the invention; it will be understood by their exemplary nature that other procedures, methodologies, or techniques known to those skilled in the art may alternatively be used.

EXAMPLES

Table of Contents for Examples

| | |
|---|---|
| Example 1 | Synthesis of modified TREMs |
| Example 2 | Synthesis of guanosine 2'-O-MOE phosphoramidite |
| Example 3 | Synthesis of 5,6 dihydrouridine |
| Example 4 | Synthesis of a TREM via 5'-Silyl-2'-Orthoester (2'-ACE) Chemistry |
| Example 5 | Synthesis of an arginine TREM having a 2'-O-MOE modification |
| Example 6 | Method of synthesizing a glutamine TREM having a pseudouridine modification |
| Example 7 | HPLC and MS analysis of modified TREMs |
| Example 8 | Analysis of modified TREMs via anion-exchange HPLC |
| Example 9 | Analysis of TREMs via PAGE Purification and Analysis |
| Example 10 | Deprotection of synthesized TREM |
| Example 11 | Characterization of chemically modified TREMs for readthrough of a premature termination codon (PTC) in a reporter protein |
| Example 12 | Correction of a mis sense mutation in an ORF with administration of a TREM |
| Example 13 | Evaluation of protein expression levels of SMC-containing ORF with administration of a TREM |
| Example 14 | Modulation of translation rate of SMC-containing ORF with TREM administration |

Example 1: Synthesis of a Modified TREM

Generally, TREM molecules (e.g., modified TREMs) may be chemically synthesized and purified by HPLC according to standard solid phase synthesis methods using phosphoramidite chemistry. (see, e.g., Scaringe S. et al. (2004) *Curr Protoc Nucleic Acid Chem,* 2.10.1-2.10.16; Usman N. et al. (1987) *J. Am. Chem. Soc,* 109, 7845-7854). Individually modified TREM molecules containing one or more 2'-methoxy (2'OMe), 2'fluoro (2'F), 2'-methoxyethyl (2'-MOE), or phosphorothioate (PS) modifications were prepared using either TREM-Arg-TGA, TREM-Ser-TAG, or TREM-Gln-TAA sequences as a framework according to phosphoramidite technology on solid phase used in oligonucleotide synthesis. For clarity, the arginine non-cognate TREM molecule named TREM-Arg-TGA contains the sequence of ARG-UCU-TREM body but with the anticodon sequence corresponding to UCA instead of UCU (i.e., SEQ ID NO: 622). Similarly, a serine non-cognate TREM molecule named TREM-Ser-TAG contains the sequence of SER-GCU-TREM body but with the anticodon sequence corresponding to CUA instead of GCU (i.e., SEQ ID NO: 993). A glutamine non-cognate TREM molecule named TREM-Gln-TAA contains the sequence of GLN-CUG-TREM body but with the anticodon sequence corresponding to UUA instead of CUG (i.e., SEQ ID NO: 1079).

To make the 2'OMe modified TREMs, the following 2'-O-methyl phosphoramidites were used: (5'-O-dimethoxytrityl-N6-(benzoyl)-2'-O-methyl-adenosine-3'-O-(2-cyanoethyl-N,N-diisopropy-lamino)phosphoramidite, 5'-O-dimethoxy-trityl-N4-(acetyl)-2'-O-methyl-cytidine-3'-O-(2-cyanoethyl-N,N-diisopropyl-amino)phosphoramidite, (5'-O-dimethoxytrityl-N2-(isobutyryl)-2'-O-methyl-guanosine-3'-O-(2-cyano-ethyl-N,N-diisopropylamino)-phosphoramidite, and 5'-O-dimethoxy-trityl-2'-O-methyluridine-3'-O-(2-cyanoethyl-N,N-diisopropylamino) phosphoramidite. To make the 2'-deoxy and 2'-F modified TREMs, analogous 2'-deoxy and 2'-fluoro-phosphoramidites with the same protecting groups as the 2'-O-methyl RNA amidites were used. To make the 2'-MOE modified TREMs, the following 2'-MOE-phosphoramidites were used: 5'-O-(4,4'-Dimethoxytrityl)-2'-O-methoxyethyl-N6-benzoyl-adenosine-3'-O-[(2-cyanoethyl)-(N,N-diisopropyl)]-phosphoramidite, 5'-O-(4,4'-Dimethoxytrityl)-2'-O-methoxyethyl-5-methyl-N4-benzoyl-cytidine-3'-O-[(2-cyanoethyl)-(N,N-diisopropyl)]-phosphoramidite, 5'-O-(4,4'-Dimethoxytrityl)-2'-O-methoxyethyl-N2-isobutyryl-guanosine-3'-O-[(2-cyanoethyl)-(N,N-diisopropyl)]-phosphoramidite, 5'-O-(4,4'-Dimethoxytrityl)-2'-O-methoxyethyl-5-methyl-uridine-3'-O-[(2-cyanoethyl)-(N,N-diisopropyl)]-phosphoramidite.

During the oligonucleotide synthesis via this phosphoramidites approach, the phosphorothioate was introduced by oxidizing the phosphite triester using a sulfur transfer reagent, such as tetraethylthiuram disulfide (TETD), bis(O,O-diisopropoxy phosphinothioyl) disulfide (Stec's reagent), 3H-1,2-benzodithiol-3-one-1,1,-dioxide (Beaucage reagent), phenylacetyl disulfide (PADS), 3-ethoxy-1,2,4-dithiazoline-5-one (EDITH), 1,2-dithiazole-5-thione (xanthane hydride or ADTT), 3-((dimethylamino-methylidene) amino)-3H-1,2,4-dithiazole-3-thione (DDTT), dimethylthiuram disulfide (DTD), 3-phenyl-1,2,4-dithiazoline-5-one (PolyOrg Sulfa or POS).

Tables 15-22 below describe a series of singly and multiply modified TREMs synthesized according to this procedure. The sequences of each of these TREMs are provided in the table, wherein r: ribonucleotide; m: 2'-OMe; *: PS linkage; f: 2'-fluoro; moc: 2'-moc; d: deoxyribonucleotide; 5MeC: 5-methylcytosine. Thus, for example, mA represents 2'-O-methyl adenosine, moc5MeC represents 2'-MOE nucleotide with 5-methylcytosine nucleobase, and dA represents an adenosine deoxyribonucleotide.

Example 2: Synthesis of Guanosine 2'-O-MOE Phosphoramidite

This example describes the synthesis of guanosine 2'-O-MOE phosphoramidite. Guanosine 2'-O-MOE phosphoramidite is prepared and purified according to previously published procedures (Wen K. et al. (2002) *The Journal of Organic Chemistry,* 67 (22), 7887-7889).

Briefly, guanosine and imidazole are dried by co-evaporation with pyridine, dissolved in dry DMF, and treated with bis(diisopropylchlorosilyl) methane added dropwise at 0° C. The temperature is gradually increased to 25° C. and then held for 5 h. The reaction mixture is poured into ice water, and the precipitated white solid filtered to afford compound 1. To a solution of compound 1, BrCH2CH2OCH3, and TBAI in DMF at −20° C. is added with sodium bis(trimethylsilyl)amide, and the mixture is stirred for 4 hours under argon. After the reaction is quenched with methanol, the THF is evaporated and the residue is precipitated in ice to furnish compound 2. TBAF is added to a solution of compound 2 at 25° C. and then the mixture is stirred at 35° C. for 5 hours. The solvent is then evaporated under reduced pressure, and the residue is filtered in a short pad of silica gel using 10% methanol in dichloromethane to afford guanosine 2'-O-MOE phosphoramidite.

Example 3: Synthesis of 5,6 Dihydrouridine

This example describes the synthesis of 5,6 dihydrouridine. 5,6 dihydrouridine phosphoramidite is prepared and purified according to previously published procedures (Hanze A R et al., (1967) *Journal of the American Chemical Society,* 89 (25), 6720-6725). Briefly, oxygen is bubbled through a solution uridine in the presence of platinum black. The reaction is followed by spotting the reaction mixture on silica gel thin layer chromatographic plates and developing in methanol-chloroform (1:1). After 1 hour, the mixture is cooled and centrifuged and the clear liquid lyophilized to yield the 5,6 dihydrouridine product.

Example 4: Synthesis of a TREM Via 5'-Silyl-2'-Orthoester (2'-ACE) Chemistry

This example describes the synthesis of a TREM via 5'-Silyl-2'-Orthoester (2'-ACE) Chemistry summarized from (Hartsel S A et al., (2005) *Oligonucleotide Synthesis,* 033-050).

Protected Ribonucleoside Monomers

5'-O-silyl-2'-O-ACE protected phosphoramidites are prepared and purified according to previously published procedures (Hartsel S A et al., (2005) *Oligonucleotide Synthesis,* 033-050). Briefly, monomer synthesis begins from standard base-protected ribonucleosides [rA(ibu), rC(acetyl), rG(ibu) and U]. Orthogonal, 5'-silyl-2'-ACE protection and amidite preparation is then accomplished in five general steps:

1. Simultaneous transient protection of the 5'- and 3'-hydroxyl groups with 1,1,3,3tetraispropyldisiloxane (TIPS).
2. Regiospecific conversion of the 2'-hydroxyl to the 2'-O-orthoester using tris(acetoxyethyl) orthoformate (ACE orthoformate).
3. Removal of the 5',3'-TIPS protection.
4. Introduction of the 5'-O-silyl ether protecting group using benzhydryloxybis-(trimethylsilyloxy)-chlorosilane (BzH-C1).
5. Phosphitylation of the 3'-OH with bis(N,N'-diisopropylamino) methoxyphosphine.

The fully protected, phosphitylated monomer is an oil. For ease of handling and dissolution, the phosphoramidite solution is evaporated to dryness in a tared flask to enable quantitation of yields. The phosphoramidite oil is then dissolved in anhydrous acetonitrile, distributed into synthesis vials in 1.0-mmol aliquots, and evaporated to dryness under vacuum in the presence of potassium hydroxide (KOH) and P2O5.

Synthesis of Oligoribonucleosides

TABLE 12

| Synthesis Step | Reagent | Delivery Time | Reaction Time |
|---|---|---|---|
| Deblock | 3% DCA in DCM | 35 | |
| Activator | 0.5M S-ethyl-tetrazole | 6 | |
| Coupling | 0.1M amidite8.0 | 30 | |
| | 0.5M S-ethyl-tetrazole | 8 | 30 |
| Repeat Coupling | | | |
| Oxidation | t-Butyl hydroperoxide | 20 | 10 |
| Repeat Oxidation Delivery | | | |
| Capping | 1-methylimidazole and acetic anhydride | 12 | 10 |
| Desilylation | TEAHF | 35 | |

5'-silyl-2'-ACE oligoribonucleotide synthesis begins with the appropriately modified 3'-terminal nucleoside attached through the 3'-hydroxyl to a polystyrene support. The solid support contained in an appropriate reaction cartridge is then placed on the appropriate column position on the instrument. A synthesis cycle is created using the delivery times and wait steps outlined in Table 12.

1. Initial detritylation: The first step in the synthesis cycle is the removal of the 5' O-DMT from the nucleoside-bound polystyrene support using 3% DCA in DCM.
2. Coupling: The 5-ethylthio-1H-tetrazole solution is delivered to the solid support, followed by simultaneous delivery of an equal quantity of activator and phosphoramidite solution. Depending on the desired sequence and synthesis scale, excess activator and activator plus amidite are alternately delivered repeatedly to increase coupling efficiency, which is typically in excess of 99% per coupling reaction. The 5-ethylthio-1H-tetrazole activates coupling by protonating the diisopropyl amine attached to the trivalent phosphorous. Nucleophilic attack of the 5-ethylthio-1H-tetrazole leads to the formation of the tetrazolide intermediate that reacts with the free 5'-OH of the support-bound nucleoside forming the internucleotide phosphite linkage.
3. Oxidation: In the next step of chain elongation, the phosphorous (III) linkage is oxidized for 10-20 s to the more stable and ultimately desired P(V) linkage using t-butylhydroperoxide.
4. Capping: Although delivery of excess activator and phosphoramidite increases coupling efficiency, a small percentage of unreacted nucleoside may remain support-bound. To prevent the introduction of mixed sequences, the unreacted 5'-OH are "capped" or blocked by acetylating the primary hydroxyl. This acetylation is achieved through simultaneous delivery of 1-methylimidazole and acetic anhydride.
5. 5'-Desilylation: Before the next nucleoside in the sequence can be added to the growing oligonucleotide chain, the 5'-silyl group is removed with fluoride ion. This requires the delivery of triethylamine trihydrogenfluoride for 45 s. The desilylation is rapid and quantitative and no wait step is required.

Steps 2-5 are repeated for each subsequent nucleotide until the desired sequence is constructed.

Oligonucleotide Deprotection

A two-stage rapid deprotection strategy is employed to remove phosphate backbone protection, release the oligonucleotide from the solid support, and remove the exocyclic amine protecting groups on A, G, and C. The treatment also removes the acetyl moiety from the acetoxyethyl orthoester, resulting in the 2'-bis-hydroxyethyl protected intermediate that is now times more labile to final acid deprotection. In the first deprotection step, S2Na2 is used to selectively remove the methyl protection from the internucleotide phosphate, leaving the oligoribonucleotide attached to the polystyrene support. This configuration allows any residual reagent to be thoroughly washed away before proceeding. Alternatively, a multicolumn, manifold approach can also be used.

1. A syringe barrel is attached to one of the two luer fittings on the synthesis column. 2 mL of the S2Na2 reagent is drawn into a second syringe and attached to the opposite side of the synthesis column. The S2Na2 reagent is gently pushed through the column and into the empty syringe barrel continuing back and forth several times. The column, filled with reagent is allowed to sit at room temperature for 10 min.
2. S2Na2 reagent is removed from the column. Using a clean syringe, the column is washed thoroughly with water. In the second deprotection step, 40% 1-methylamine in water is used to free the oligoribonucleotide from the solid support, deprotect the exocyclic base amines, and deacylate the 2'-orthoester leaving the deprotected species.

N-Methylamine Deprotection

1. The solid support resin is transferred from the column into a 4-mL vial
2. 2 mL 40% methylamine is added and heated for 12 min at 60° C.
3. The methylamine is removed and is transferred into a fresh vial.
4. The oligonucleotide solution is evaporated to dryness in a SpeedVac or similar device. Oligonucleotide yields are measured using an ultraviolet (UV) spectrophotometer (absorbance at 260 nm).

Example 5: Synthesis of an Arginine TREM Having a 2'-O-MOE Modification

This example describes the synthesis of an Arg TREM having one 2'-O-MOE modification. The 2'-O-MOE modification can be placed on a nucleotide on any domain or linker of the Arg TREM, or at any position in said domain or linker.

A 2'-ACE RNA oligoribonucleotide synthesis is performed on a modified Applied Biosystems 394 DNA/RNA synthesizer or similar instrument. 2'-O-MOE amidites are synthesized as in Example 2. An oligonucleotide sequence: GGCUCCGUGGCGCAAUGGAUAGCGCAUUGGAC-UUCUAAUUCAAAGGUUCCGGGUU CG (A-MOE) GUCCCGGCGGAGUCG (SEQ ID NO: 1290) is synthesized following the protocol described in example 4. A similar method can be used to add a 2'-O-MOE modification on a TREM specifying any one of the other 19 amino acids.

Example 6: Synthesis of a Glutamine TREM Having a Pseudouridine Modification

This example describes the synthesis of a Gln TREM having a pseudouridine modification. The modification can be placed on a nucleotide on any domain or linker of the Gln TREM, or at any position in said domain or linker.

A 2'-ACE RNA oligoribonucleotide synthesis is performed on a modified Applied Biosystems 394 DNA/RNA synthesizer or similar instrument. Pseudouridine (P) amidites are obtained from Glen Research or similar provider. An oligonucleotide sequence: GGUUCCAUG-GUGPAAUGGUAAGCACUCUGGACUCT-GAAUCCAGCGAUCCGAGUUC GAGUCUCGGUGGAACCUCCA (SEQ ID NO: 1291) is synthesized following the protocol described in example 4.

A similar method can be used to add a pseudouridine modification on a TREM specifying any one of the other 19 amino acids.

Example 7: HPLC and MS Analysis of Modified TREMs

Chemically modified TREM molecules may be analyzed by HPLC, for example, to evaluate the purity and homogeneity of the compositions. A Waters Aquity UPLC system using a Waters BEH C18 column (2.1 mm×50 mm×1.7 μm) may be used for this analysis. Samples may be prepared by dissolving 0.5 nmol of the TREM in 75 μL of water and injecting 2 μL of the solution. The buffers used may be 50 mM dimethylhexylammonium acetate with 10% $CH_3CN$ (acetonitrile) as buffer A and 50 mM dimethylhexylammonium acetate with 75% $CH_3CN$ as buffer B (gradient 25-75% buffer B over 5 mins), with a flow rate of 0.5 mL/min at 60° C. ESI-LCMS data for the chemically modified TREMs may be acquired on a Thermo Ultimate 3000-LTQ-XL mass spectrometer.

Tables 15-22 below describe a series of singly and multiply modified TREMs synthesized according to the protocol outlined in Example 1. The calculated and detected molecular weights for each sequence were determined as outlined herein.

Example 8: Analysis of Modified TREMs Via Anion-Exchange HPLC

This example describes the quality control of a synthesized TREM via anion-exchange HPLC. Using the Dionex DNA-Pac-PA-100 column, a gradient is employed using HPLC buffer A and HPLC buffer B. 0.5 ODUs of a sample that has been dissolved in H2O or Tris buffer, pH 7.5 is injected onto the gradient. The gradient employed is based on oligonucleotide length and can be applied according to Table 13. The parameters provided in Table 14 can be used to program a linear gradient on the HPLC analyzer.

TABLE 13

Oligonucleotide length and gradient percentages

| Length (bases) | Gradient (% B) |
|---|---|
| 0-5 | 0-30 |
| 6-10 | 10-40 |
| 11-16 | 20-50 |
| 17-32 | 30-60 |
| 33-50 | 40-70 |
| >50 | 50-80 |

TABLE 14

Parameters for a linear gradient on HPLC analyzer

| Time (min) | Flow (mL/min) | % Buffer A | % Buffer B |
|---|---|---|---|
| 0 | 1.5 | 100 | 0 |
| 1 | 1.5 | 100 | 0 |
| 3 | 1.5 | 70a | 30a |
| 15 | 1.5 | 40a | 60a |
| 15.5 | 2.5 | 0 | 100 |
| 17 | 2.5 | 0 | 100 |

TABLE 14-continued

| Parameters for a linear gradient on HPLC analyzer | | | |
|---|---|---|---|
| Time (min) | Flow (mL/min) | % Buffer A | % Buffer B |
| 17.25 | 2.5 | 100 | 0 |
| 23 | 2.5 | 100 | 0 |
| s23.1 | 1.5 | 100 | 0 |
| 24 | 1.5 | 100 | 0 |
| 25 | 0.1 | 100 | 0 |

Example 9: Analysis of TREMs Via PAGE Purification and Analysis

This example describes the quality control of a synthesized TREM via PAGE Purification and Analysis. Gel purification and analysis of 2'-ACE protected RNA follows standard protocols for denaturing PAGE (Ellington and Pollard (1998) In *Current Protocols in Molecular Biology*, Chanda, V). Briefly, the 2'-ACE protected oligo is resuspended in 200 mL of gel loading buffer. Invitrogen™ NuPAGE™ 4-12% Bis-Tris Gels or similar gel is prepared in gel apparatus. Samples are loaded and gel ran at 50-120 W, maintaining the apparatus at 40° C. When complete, the gel is exposed to ultraviolet (UV) light at 254 nm to visualize the purity of the RNA using UV shadowing. If necessary, the desired gel band is excised with a clean razor blade. The gel slice is crushed and 0.3M NaOAc elution buffer is added to the gel particles, and soaked overnight. The mixture is decanted and filtered through a Sephadex column such as Nap-10 or Nap-25.

Example 10: Deprotection of Synthesized TREM

This example describes the deprotection of a TREM made according to an in vitro synthesis method. The 2'-protecting groups are removed using 100 mM acetic acid, pH 3.8. The formic acid and ethylene glycol byproducts are removed by incubating at 60° C. for 30 min followed by lyophilization or SpeedVac-ing to dryness. After this final deprotection step, the oligonucleotides are ready for use.

Example 11. Characterization of Chemically Modified TREMs for Readthrough of a Premature Termination Codon (PTC) in a Reporter Protein This example describes an assay to test the ability of a non-cognate chemically modified TREM to readthrough a PTC in a cell line expressing a reporter protein having a PTC. This Example describes analysis of chemically modified arginine, serine, and glutamine non-cognate TREM (i.e., Arg-TGA, Ser-TAG, and Gln-TAA), though a non-cognate TREM specifying any one of the other amino acids can also be used.

A cell line engineered to stably express the NanoLuc reporter construct containing a premature termination codon (PTC) may be generated using the FlpIn system according to the manufacturer's instructions. Delivery of the chemically modified TREMs into the NanoLuc reporter cells is carried out via a reverse transfection reaction using lipofectamine RNAiMAX (ThermoFisher Scientific, USA) according to manufacturer instructions. Briefly, 5 μL of a 2.5 μM solution of chemically modified TREM sample are diluted in a 20 μL RNAiMAX/OptiMEM mixture. After 30 min gentle mixing at room temperature, the 25 μL TREM/transfection mixture is added to a 96-well plate and kept still for 20-30 min before adding the cells. The NanoLuc reporter cells are harvested and diluted to $4\times10^5$ cells/mL in complete growth medium, and 100 μL of the diluted cell suspension is added and mixed to the plate containing the TREM. After 24 h, 100 μL complete growth medium is added to the 96-well plate for cell health.

To monitor the efficacy of the chemically modified TREM to read through the PTC in the reporter construct 48 hours after TREM delivery into cells, a NanoGlo bioluminescent assay (Promega, USA) may be performed according to manufacturer instruction. Briefly, cell media is replaced and allowed to equilibrate to room temperature. NanoGlo reagent is prepared by mixing the buffer with substrate in a 50:1 ratio. 50 μL of mixed NanoGlo reagent is added to the 96-well plate and mixed on the shaker at 600 rpm for 10 min. After 2 min, the plate is centrifuged at 1000 g, followed by a 5 min incubation step at room temperature before measuring sample bioluminescence. As a positive control, a host cell expressing the NanoLuc reporter construct without a PTC is used. As a negative control, a host cell expressing the NanoLuc reporter construct with a PTC is used, but no TREM is transfected. The efficacy of the chemically modified TREMs are measured as a ratio of the NanoLuc luminescence in the experimental sample to the NanoLuc luminescence of the positive control or as a ratio of the NanoLuc luminescence in the experimental sample to the NanoLuc luminescence of the negative control. It is expected that if the sample TREM is functional, it may be able to read-through the stop mutation in the NanoLuc reporter and produce a luminescent reading higher than the luminescent reading measured in the negative control. If the sample TREM is not functional, the stop mutation is not rescued, and luminescence less or equal to the negative control is detected.

The impacts of chemical modification type and position were evaluated in singly and multiply modified TREM sequences as outlined in Table 15-22 below. Tables 15-19 describe the activity of an exemplary chemically modified TREM-Arg-TGA sequence, in which 2'-OMe (Table 15), 2'-F (Table 16), 2'-MOE (Table 17), 2'-deoxy (Table 18), and PS (Table 19) modifications were installed at every position in the TREM sequence. Additional TREM sequences were also modified at every position with a 2'-OMe modification, namely Ser-TAG (Table 20) and Gln-TAA (Table 21). In addition, a selection of multiply modified TREM sequences were prepared according to Examples 1 and 9 and tested as outlined herein; these data are summarized in Table 22. In these tables, the sequences are annotated as follows: r: ribonucleotide; m: 2'-OMe; *: PS linkage; f: 2'-fluoro; moe: 2'-moe; d: deoxyribonucleotide; 5MeC: 5-methylcytosine. Thus, for example, mA represents 2'-O-methyl adenosine, moe5MeC represents 2'-MOE nucleotide with 5-methylcytosine nucleobase, and dA represents an adenosine deoxyribonucleotide.

In addition, in these tables, the results of the activity screen are reported as log 2 fold changes compared with the appropriate unmodified TREM, wherein "1" indicates less than a-0.05 log 2 fold change; "2" indicates greater than or equal to −0.05 and less than 0.55 log 2 fold change; and "3" indicates greater than or equal to 0.55 log 2 fold change. The results for the all the singly modified TREM-Arg-TGA screens is compared in FIG. 1. The results show that certain modifications were tolerated at many positions, but particular sites were sensitive to modification or exhibited improved activity when modified. For example, neither 2'-OMe and 2'-MOE were tolerated at positions 33 in the Arg-TGA sequence, yet 2'-F and 2'-deoxy (DNA) improved the activity at positions 33. 2'OMe was particularly active at positions 1 and 73. 2'-deoxy (DNA) was also well tolerated at position 31. PS modification improved activity when incorporated in-between positions 35 and 36, in-between 37 and 38, in-between 38 and 39, in-between 54 and 55, and in-between positions 55 and 56.

TABLE 15

2'OMe-Modified TREMs (TREM-Arg-TGA) and related data

| SEQ ID NO. | Mod | Sequence | Calculated MW | Detected MW | Results |
|---|---|---|---|---|---|
| 622 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24509.24 | 24508 | 2 |
| 623 | OME 1 | mGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24526.4 | 3 |
| 624 | OME 2 | rGmGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24516.6 | 3 |
| 625 | OME 3 | rGrGmCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24526.6 | 2 |
| 626 | OME 4 | rGrGrCmUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.21 | 24517.6 | 3 |
| 627 | OME 5 | rGrGrCrUmCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24516.5 | 2 |
| 628 | OME 6 | rGrGrCrUrCmCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24511 | 3 |
| 629 | OME 7 | rGrGrCrUrCrCmGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24516.5 | 1 |
| 630 | OME 8 | rGrGrCrUrCrCrGmUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.21 | 24511.6 | 1 |
| 631 | OME 9 | rGrGrCrUrCrCrGrUmGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24514.9 | 1 |

TABLE 15-continued

2'OMe-Modified TREMs (TREM-Arg-TGA) and related data

| SEQ ID NO. | Mod | Sequence | Calculated MW | Detected MW | Results |
|---|---|---|---|---|---|
| 632 | OME 10 | rGrGrCrUrCrCrGrUrGmGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24535.3 | 3 |
| 633 | OME 11 | rGrGrCrUrCrCrGrUrGrGmCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24532.9 | 2 |
| 634 | OME 12 | rGrGrCrUrCrCrGrUrGrGrCmGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24530.5 | 3 |
| 635 | OME 13 | rGrGrCrUrCrCrGrUrGrGrCrGmCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.9 | 3 |
| 636 | OME 14 | rGrGrCrUrCrCrGrUrGrGrCrGrCm ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24530 | 2 |
| 637 | OME 15 | rGrGrCrUrCrCrGrUrGrGrCrGrCr AmArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24531.3 | 2 |
| 638 | OME 16 | rGrGrCrUrCrCrGrUrGrGrCrGrCr ArAmUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.21 | 24530.2 | 2 |
| 639 | OME 17 | rGrGrCrUrCrCrGrUrGrGrCrGrCr ArArUmGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24530 | 3 |
| 640 | OME 18 | rGrGrCrUrCrCrGrUrGrGrCrGrCr ArArUrGmGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24530.3 | 3 |
| 641 | OME 19 | rGrGrCrUrCrCrGrUrGrGrCrGrCr ArArUrGrGmArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24531 | 1 |
| 642 | OME 20 | rGrGrCrUrCrCrGrUrGrGrCrGrCr ArArUrGrGrAmUrArGrCrGrCrAr UrUrGrGrArCrUrUrCrArArArUr | 24523.21 | 24531.5 | 3 |

TABLE 15-continued

2'OMe-Modified TREMs (TREM-Arg-TGA) and related data

| SEQ ID NO. | Mod | Sequence | Calculated MW | Detected MW | Results |
|---|---|---|---|---|---|
| | | UrCrArArArGrGrUrUrCrCrGrGr GrUrUrCrGrArGrUrCrCrCrGrGrC rGrGrArGrUrCrGrCrCrA | | | |
| 643 | OME 21 | rGrGrCrUrCrCrGrUrGrGrCrGrCr ArArUrGrGrArUmArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24521.2 | 1 |
| 644 | OME 22 | rGrGrCrUrCrCrGrUrGrGrCrGrCr ArArUrGrGrArUrAmGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.8 | 3 |
| 645 | OME 23 | rGrGrCrUrCrCrGrUrGrGrCrGrCr ArArUrGrGrArUrArGmCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.9 | 2 |
| 646 | OME 24 | rGrGrCrUrCrCrGrUrGrGrCrGrCr ArArUrGrGrArUrArGrCmGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.7 | 2 |
| 647 | OME 25 | rGrGrCrUrCrCrGrUrGrGrCrGrCr ArArUrGrGrArUrArGrCrGmCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.9 | 2 |
| 648 | OME 26 | rGrGrCrUrCrCrGrUrGrGrCrGrCr ArArUrGrGrArUrArGrCrGrCmAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.3 | 1 |
| 649 | OME 27 | rGrGrCrUrCrCrGrUrGrGrCrGrCr ArArUrGrGrArUrArGrCrGrCrAm UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.21 | 24529.7 | 2 |
| 650 | OME 28 | rGrGrCrUrCrCrGrUrGrGrCrGrCr ArArUrGrGrArUrArGrCrGrCrAr UmUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.21 | 24529.9 | 2 |
| 651 | OME 29 | rGrGrCrUrCrCrGrUrGrGrCrGrCr ArArUrGrGrArUrArGrCrGrCrAr UrUmGrGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.8 | 3 |
| 652 | OME 30 | rGrGrCrUrCrCrGrUrGrGrCrGrCr ArArUrGrGrArUrArGrCrGrCrAr UrUrGmGrArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24530 | 3 |

TABLE 15-continued

2'OMe-Modified TREMs (TREM-Arg-TGA) and related data

| SEQ ID NO. | Mod | Sequence | Calculated MW | Detected MW | Results |
|---|---|---|---|---|---|
| 653 | OME 31 | rGrGrCrUrCrCrGrUrGrGrCrGrCr ArArUrGrGrArUrArGrCrGrCrAr UrUrGrGmArCrUrUrCrArArArUr UrCrArArArGrGrUrUrCrCrGrGr GrUrUrCrGrArGrUrCrCrCrGrGrC rGrGrArGrUrCrGrCrCrA | 24523.24 | 24529.8 | 1 |
| 654 | OME 32 | rGrGrCrUrCrCrGrUrGrGrCrGrCr ArArUrGrGrArUrArGrCrGrCrAr UrUrGrGrAmCrUrUrCrArArArUr UrCrArArArGrGrUrUrCrCrGrGr GrUrUrCrGrArGrUrCrCrCrGrGrC rGrGrArGrUrCrGrCrCrA | 24522.68 | 24524.9 | 1 |
| 655 | OME 33 | rGrGrCrUrCrCrGrUrGrGrCrGrCr ArArUrGrGrArUrArGrCrGrCrAr UrUrGrGrArCmUrUrCrArArArUr UrCrArArArGrGrUrUrCrCrGrGr GrUrUrCrGrArGrUrCrCrCrGrGrC rGrGrArGrUrCrGrCrCrA | 24523.21 | 24529.9 | 1 |
| 656 | OME 34 | rGrGrCrUrCrCrGrUrGrGrCrGrCr ArArUrGrGrArUrArGrCrGrCrAr UrUrGrGrArCrUmUrCrArArArUr UrCrArArArGrGrUrUrCrCrGrGr GrUrUrCrGrArGrUrCrCrCrGrGrC rGrGrArGrUrCrGrCrCrA | 24523.21 | 24529.8 | 1 |
| 657 | OME 35 | rGrGrCrUrCrCrGrUrGrGrCrGrCr ArArUrGrGrArUrArGrCrGrCrAr UrUrGrGrArCrUrUmCrArArArUr UrCrArArArGrGrUrUrCrCrGrGr GrUrUrCrGrArGrUrCrCrCrGrGrC rGrGrArGrUrCrGrCrCrA | 24522.68 | 24530 | 1 |
| 658 | OME 36 | rGrGrCrUrCrCrGrUrGrGrCrGrCr ArArUrGrGrArUrArGrCrGrCrAr UrUrGrGrArCrUrUrCmArArArUr UrCrArArArGrGrUrUrCrCrGrGr GrUrUrCrGrArGrUrCrCrCrGrGrC rGrGrArGrUrCrGrCrCrA | 24523.24 | 24529.8 | 1 |
| 659 | OME 37 | rGrGrCrUrCrCrGrUrGrGrCrGrCr ArArUrGrGrArUrArGrCrGrCrAr UrUrGrGrArCrUrUrCrAmArArUr UrCrArArArGrGrUrUrCrCrGrGr GrUrUrCrGrArGrUrCrCrCrGrGrC rGrGrArGrUrCrGrCrCrA | 24523.24 | 24530 | 1 |
| 660 | OME 38 | rGrGrCrUrCrCrGrUrGrGrCrGrCr ArArUrGrGrArUrArGrCrGrCrAr UrUrGrGrArCrUrUrCrArAmArUr UrCrArArArGrGrUrUrCrCrGrGr GrUrUrCrGrArGrUrCrCrCrGrGrC rGrGrArGrUrCrGrCrCrA | 24523.24 | 24529.7 | 1 |
| 661 | OME 39 | rGrGrCrUrCrCrGrUrGrGrCrGrCr ArArUrGrGrArUrArGrCrGrCrAr UrUrGrGrArCrUrUrCrArArAmUr UrCrArArArGrGrUrUrCrCrGrGr GrUrUrCrGrArGrUrCrCrCrGrGrC rGrGrArGrUrCrGrCrCrA | 24523.21 | 24529.7 | 1 |
| 662 | OME 40 | rGrGrCrUrCrCrGrUrGrGrCrGrCr ArArUrGrGrArUrArGrCrGrCrAr UrUrGrGrArCrUrUrCrArArArUm UrCrArArArGrGrUrUrCrCrGrGr GrUrUrCrGrArGrUrCrCrCrGrGrC rGrGrArGrUrCrGrCrCrA | 24523.21 | 24529.5 | 1 |
| 663 | OME 41 | rGrGrCrUrCrCrGrUrGrGrCrGrCr ArArUrGrGrArUrArGrCrGrCrAr UrUrGrGrArCrUrUrCrArArArUr UmCrArArArGrGrUrUrCrCrGrGr | 24523.24 | 24531.3 | 2 |

TABLE 15-continued

| 2'OMe-Modified TREMs (TREM-Arg-TGA) and related data | | | | | |
|---|---|---|---|---|---|
| SEQ ID NO. | Mod | Sequence | Calculated MW | Detected MW | Results |
| | | GrUrUrCrGrArGrUrCrCrCrGrGrC rGrGrArGrUrCrGrCrCrA | | | |
| 664 | OME 42 | rGrGrCrUrCrCrGrUrGrGrCrGrCr ArArUrGrGrArUrArGrCrGrCrAr UrUrGrGrArCrUrUrCrArArArUr UrCmArArArGrGrUrUrCrCrGrGr GrUrUrCrGrArGrUrCrCrCrGrGrC rGrGrArGrUrCrGrCrCrA | 24523.24 | 24529.9 | 3 |
| 665 | OME 43 | rGrGrCrUrCrCrGrUrGrGrCrGrCr ArArUrGrGrArUrArGrCrGrCrAr UrUrGrGrArCrUrUrCrArArArUr UrCrAmArArGrGrUrUrCrCrGrGr GrUrUrCrGrArGrUrCrCrCrGrGrC rGrGrArGrUrCrGrCrCrA | 24523.24 | 24531.9 | 3 |
| 666 | OME 44 | rGrGrCrUrCrCrGrUrGrGrCrGrCr ArArUrGrGrArUrArGrCrGrCrAr UrUrGrGrArCrUrUrCrArArArUr UrCrArAmArGrGrUrUrCrCrGrGr GrUrUrCrGrArGrUrCrCrCrGrGrC rGrGrArGrUrCrGrCrCrA | 24523.24 | 24529.6 | 2 |
| 667 | OME 45 | rGrGrCrUrCrCrGrUrGrGrCrGrCr ArArUrGrGrArUrArGrCrGrCrAr UrUrGrGrArCrUrUrCrArArArUr UrCrArArAmGrGrUrUrCrCrGrGr GrUrUrCrGrArGrUrCrCrCrGrGrC rGrGrArGrUrCrGrCrCrA | 24523.24 | 24531 | 3 |
| 668 | OME 46 | rGrGrCrUrCrCrGrUrGrGrCrGrCr ArArUrGrGrArUrArGrCrGrCrAr UrUrGrGrArCrUrUrCrArArArUr UrCrArArArGmGrUrUrCrCrGrGr GrUrUrCrGrArGrUrCrCrCrGrGrC rGrGrArGrUrCrGrCrCrA | 24523.24 | 24531.6 | 1 |
| 669 | OME 47 | rGrGrCrUrCrCrGrUrGrGrCrGrCr ArArUrGrGrArUrArGrCrGrCrAr UrUrGrGrArCrUrUrCrArArArUr UrCrArArArGrGmUrUrCrCrGrGr GrUrUrCrGrArGrUrCrCrCrGrGrC rGrGrArGrUrCrGrCrCrA | 24523.21 | 24530.5 | 1 |
| 670 | OME 48 | rGrGrCrUrCrCrGrUrGrGrCrGrCr ArArUrGrGrArUrArGrCrGrCrAr UrUrGrGrArCrUrUrCrArArArUr UrCrArArArGrGrUmUrCrCrGrGr GrUrUrCrGrArGrUrCrCrCrGrGrC rGrGrArGrUrCrGrCrCrA | 24523.21 | 24511.6 | 2 |
| 671 | OME 49 | rGrGrCrUrCrCrGrUrGrGrCrGrCr ArArUrGrGrArUrArGrCrGrCrAr UrUrGrGrArCrUrUrCrArArArUr UrCrArArArGrGrUrUmCrCrGrGr GrUrUrCrGrArGrUrCrCrCrGrGrC rGrGrArGrUrCrGrCrCrA | 24523.24 | 24514.6 | 2 |
| 672 | OME 50 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCmCrGrGr GrUrUrCrGrArGrUrCrCrCrGrGrC rGrGrArGrUrCrGrCrCrA | 24523.24 | 24512.7 | 3 |
| 673 | OME 51 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCmGrGr GrUrUrCrGrArGrUrCrCrCrGrGrC rGrGrArGrUrCrGrCrCrA | 24523.24 | 24519.7 | 2 |
| 674 | OME 52 | rGrGrCrUrCrCrGrUrGrGrCrGrCr ArArUrGrGrArUrArGrCrGrCrAr | 24523.24 | 24517.3 | 3 |

TABLE 15-continued

| 2'OMe-Modified TREMs (TREM-Arg-TGA) and related data | | | | | |
|---|---|---|---|---|---|
| SEQ ID NO. | Mod | Sequence | Calculated MW | Detected MW | Results |
| | | UrUrGrGrArCrUrUrCrArArArUr UrCrArArArGrGrUrUrCrCrGmGr GrUrUrCrGrArGrUrCrCrCrGrGrC rGrGrArGrUrCrGrCrCrA | | | |
| 675 | OME 53 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGm GrUrUrCrGrArGrUrCrCrCrGrGrC rGrGrArGrUrCrGrCrCrA | 24523.24 | 24520.5 | 2 |
| 676 | OME 54 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GmUrUrCrGrArGrUrCrCrCrGrGr CrGrGrArGrUrCrGrCrCrA | 24523.21 | 24516.7 | 2 |
| 677 | OME 55 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUmUrCrGrArGrUrCrCrCrGrGr CrGrGrArGrUrCrGrCrCrA | 24523.21 | 24521.6 | 1 |
| 678 | OME 56 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUmCrGrArGrUrCrCrCrGrGr CrGrGrArGrUrCrGrCrCrA | 24523.24 | 24515.3 | 3 |
| 679 | OME 57 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCmGrArGrUrCrCrCrGrGr CrGrGrArGrUrCrGrCrCrA | 24523.24 | 24523.7 | 2 |
| 680 | OME 58 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGmArGrUrCrCrCrGrGr CrGrGrArGrUrCrGrCrCrA | 24523.24 | 24516.6 | 1 |
| 681 | OME 59 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrAmGrUrCrCrCrGrGr CrGrGrArGrUrCrGrCrCrA | 24523.24 | 24532.2 | 3 |
| 682 | OME 60 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGmUrCrCrCrGrGr CrGrGrArGrUrCrGrCrCrA | 24523.21 | 24516.5 | 1 |
| 683 | OME 61 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUmCrCrCrGrGr CrGrGrArGrUrCrGrCrCrA | 24523.24 | 24520.7 | 3 |
| 684 | OME 62 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCmCrCrGrGr CrGrGrArGrUrCrGrCrCrA | 24523.24 | 24516.8 | 2 |

TABLE 15-continued

| 2'OMe-Modified TREMs (TREM-Arg-TGA) and related data | | | | | |
|---|---|---|---|---|---|
| SEQ ID NO. | Mod | Sequence | Calculated MW | Detected MW | Results |
| 685 | OME 63 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCmCrGrGr CrGrGrArGrUrCrGrCrCrA | 24523.24 | 24523.2 | 1 |
| 686 | OME 64 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCmGrGr CrGrGrArGrUrCrGrCrCrA | 24523.24 | 24529.6 | 2 |
| 687 | OME 65 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGmGr CrGrGrArGrUrCrGrCrCrA | 24523.24 | 24530.9 | 3 |
| 688 | OME 66 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGm CrGrGrArGrUrCrGrCrCrA | 24523.24 | 24523.2 | 3 |
| 689 | OME 67 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC mGrGrArGrUrCrGrCrCrA | 24523.24 | 24530 | 2 |
| 690 | OME 68 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGmGrArGrUrCrGrCrCrA | 24523.24 | 24521.2 | 3 |
| 691 | OME 69 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGmArGrUrCrGrCrCrA | 24523.24 | 24530.4 | 3 |
| 692 | OME 70 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrAmGrUrCrGrCrCrA | 24523.24 | 24521.1 | 1 |
| 693 | OME 71 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGmUrCrGrCrCrA | 24523.21 | 24530.5 | 3 |
| 694 | OME 72 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUmCrGrCrCrA | 24523.24 | 24520.2 | 3 |
| 695 | OME 73 | rGrGrCrUrCrCrGrUrGrGrCrGrCr ArArUrGrGrArUrArGrCrGrCrAr UrUrGrGrArCrUrUrCrArArArUr | 24523.24 | 24530.6 | 3 |

TABLE 15-continued

| 2'OMe-Modified TREMs (TREM-Arg-TGA) and related data | | | | | |
|---|---|---|---|---|---|
| SEQ ID NO. | Mod | Sequence | Calculated MW | Detected MW | Results |
| | | UrCrArArArGrGrUrUrCrCrGrGr GrUrUrCrGrArGrUrCrCrCrGrGrC rGrGrArGrUrCmGrCrCrA | | | |
| 696 | OME 74 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGmCrCrA | 24523.24 | 24519.1 | 2 |
| 697 | OME 75 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCmCrA | 24523.24 | 24531.5 | 2 |
| 698 | OME 76 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCmA | 24523.24 | 24520.2 | 2 |

TABLE 16

| 2'F-Modified TREMs (TREM-Arg-TGA) and related data | | | | | |
|---|---|---|---|---|---|
| SEQ ID NO. | Mod | Sequence | Calculated MW | Detected MW | Results |
| 699 | F 1 | fGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24513.3 | 2 |
| 700 | F 2 | rGfGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.7 | 2 |
| 701 | F 3 | rGrGfCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24509.1 | 1 |
| 702 | F 4 | rGrGrCfUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24514 | 1 |
| 703 | F 5 | rGrGrCrUfCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24515 | 1 |
| 704 | F 6 | rGrGrCrUrCfCrGrUrGrGrCrGrCr ArArUrGrGrArUrArGrCrGrCrAr UrUrGrGrArCrUrUrCrArArArUr | 24510.67 | 24513.8 | 1 |

TABLE 16-continued

2'F-Modified TREMs (TREM-Arg-TGA) and related data

| SEQ ID NO. | Mod | Sequence | Calculated MW | Detected MW | Results |
|---|---|---|---|---|---|
| | | UrCrArArArGrGrUrUrCrCrGrGr GrUrUrCrGrArGrUrCrCrCrGrGrC rGrGrArGrUrCrGrCrCrA | | | |
| 705 | F 7 | rGrGrCrUrCrCfGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24516.7 | 1 |
| 706 | F 8 | rGrGrCrUrCrCrGfUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24517 | 1 |
| 707 | F 9 | rGrGrCrUrCrCrGrUfGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.4 | 1 |
| 708 | F 10 | rGrGrCrUrCrCrGrUrGfGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.2 | 2 |
| 709 | F 11 | rGrGrCrUrCrCrGrUrGrGfCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24517.6 | 2 |
| 710 | F 12 | rGrGrCrUrCrCrGrUrGrGrCfGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.1 | 2 |
| 711 | F 13 | rGrGrCrUrCrCrGrUrGrGrCrGfCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.3 | 2 |
| 712 | F 14 | rGrGrCrUrCrCrGrUrGrGrCrGrCf ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24518.1 | 2 |
| 713 | F 15 | rGrGrCrUrCrCrGrUrGrGrCrGrCr AfArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24519.2 | 2 |
| 714 | F 16 | rGrGrCrUrCrCrGrUrGrGrCrGrCr ArAfUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24518.5 | 2 |

TABLE 16-continued

| 2'F-Modified TREMs (TREM-Arg-TGA) and related data | | | | | |
|---|---|---|---|---|---|
| SEQ ID NO. | Mod | Sequence | Calculated MW | Detected MW | Results |
| 715 | F 17 | rGrGrCrUrCrCrGrUrGrGrCrGrCr ArArUfGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24519.3 | 1 |
| 716 | F 18 | rGrGrCrUrCrCrGrUrGrGrCrGrCr ArArUrGfGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.6 | 2 |
| 717 | F 19 | rGrGrCrUrCrCrGrUrGrGrCrGrCr ArArUrGrGfArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24517.5 | 2 |
| 718 | F 20 | rGrGrCrUrCrCrGrUrGrGrCrGrCr ArArUrGrGrAfUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24518.4 | 3 |
| 719 | F 21 | rGrGrCrUrCrCrGrUrGrGrCrGrCr ArArUrGrGrArUfArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24519 | 1 |
| 720 | F 22 | rGrGrCrUrCrCrGrUrGrGrCrGrCr ArArUrGrGrArUrAfGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24517.5 | 2 |
| 721 | F 23 | rGrGrCrUrCrCrGrUrGrGrCrGrCr ArArUrGrGrArUrArGfCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24517.2 | 2 |
| 722 | F 24 | rGrGrCrUrCrCrGrUrGrGrCrGrCr ArArUrGrGrArUrArGrCfGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24519.3 | 1 |
| 723 | F 25 | rGrGrCrUrCrCrGrUrGrGrCrGrCr ArArUrGrGrArUrArGrCrGfCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.6 | 2 |
| 724 | F 26 | rGrGrCrUrCrCrGrUrGrGrCrGrCr ArArUrGrGrArUrArGrCrGrCfAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24514.8 | 1 |
| 725 | F 27 | rGrGrCrUrCrCrGrUrGrGrCrGrCr ArArUrGrGrArUrArGrCrGrCrAf UrUrGrGrArCrUrUrCrArArArUr UrCrArArArGrGrUrUrCrCrGrGr | 24510.68 | 24519.2 | 1 |

TABLE 16-continued

| 2'F-Modified TREMs (TREM-Arg-TGA) and related data | | | | | |
|---|---|---|---|---|---|
| SEQ ID NO. | Mod | Sequence | Calculated MW | Detected MW | Results |
| | | GrUrUrCrGrArGrUrCrCrCrGrGrC rGrGrArGrUrCrGrCrCrA | | | |
| 726 | F 28 | rGrGrCrUrCrCrGrUrGrGrCrGrCr ArArUrGrGrArUrArGrCrGrCrAr UfUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24518.5 | 2 |
| 727 | F 29 | rGrGrCrUrCrCrGrUrGrGrCrGrCr ArArUrGrGrArUrArGrCrGrCrAr UrUfGrGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.3 | 3 |
| 728 | F 30 | rGrGrCrUrCrCrGrUrGrGrCrGrCr ArArUrGrGrArUrArGrCrGrCrAr UrUrGfGrArCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24517.9 | 2 |
| 729 | F 31 | rGrGrCrUrCrCrGrUrGrGrCrGrCr ArArUrGrGrArUrArGrCrGrCrAr UrUrGrGfArCrUrUrCrArArArUr UrCrArArArGrGrUrUrCrCrGrGr GrUrUrCrGrArGrUrCrCrCrGrGrC rGrGrArGrUrCrGrCrCrA | 24510.68 | 24517.4 | 1 |
| 730 | F 32 | rGrGrCrUrCrCrGrUrGrGrCrGrCr ArArUrGrGrArUrArGrCrGrCrAr UrUrGrGrAfCrUrUrCrArArArUr UrCrArArArGrGrUrUrCrCrGrGr GrUrUrCrGrArGrUrCrCrCrGrGrC rGrGrArGrUrCrGrCrCrA | 24510.67 | 24518.1 | 1 |
| 731 | F 33 | rGrGrCrUrCrCrGrUrGrGrCrGrCr ArArUrGrGrArUrArGrCrGrCrAr UrUrGrGrArCfUrUrCrArArArUr UrCrArArArGrGrUrUrCrCrGrGr GrUrUrCrGrArGrUrCrCrCrGrGrC rGrGrArGrUrCrGrCrCrA | 24510.68 | 24517.7 | 3 |
| 732 | F 34 | rGrGrCrUrCrCrGrUrGrGrCrGrCr ArArUrGrGrArUrArGrCrGrCrAr UrUrGrGrArCrUfUrCrArArArUr UrCrArArArGrGrUrUrCrCrGrGr GrUrUrCrGrArGrUrCrCrCrGrGrC rGrGrArGrUrCrGrCrCrA | 24510.68 | 24518.8 | 1 |
| 733 | F 35 | rGrGrCrUrCrCrGrUrGrGrCrGrCr ArArUrGrGrArUrArGrCrGrCrAr UrUrGrGrArCrUrUfCrArArArUr UrCrArArArGrGrUrUrCrCrGrGr GrUrUrCrGrArGrUrCrCrCrGrGrC rGrGrArGrUrCrGrCrCrA | 24510.67 | 24519 | 1 |
| 734 | F 36 | rGrGrCrUrCrCrGrUrGrGrCrGrCr ArArUrGrGrArUrArGrCrGrCrAr UrUrGrGrArCrUrUrCfArArArUr UrCrArArArGrGrUrUrCrCrGrGr GrUrUrCrGrArGrUrCrCrCrGrGrC rGrGrArGrUrCrGrCrCrA | 24510.68 | 24518.7 | 1 |
| 735 | F 37 | rGrGrCrUrCrCrGrUrGrGrCrGrCr ArArUrGrGrArUrArGrCrGrCrAr UrUrGrGrArCrUrUrCrAfArArUr UrCrArArArGrGrUrUrCrCrGrGr GrUrUrCrGrArGrUrCrCrCrGrGrC rGrGrArGrUrCrGrCrCrA | 24510.68 | 24517.6 | 1 |
| 736 | F 38 | rGrGrCrUrCrCrGrUrGrGrCrGrCr ArArUrGrGrArUrArGrCrGrCrAr | 24510.68 | 24518.4 | 1 |

TABLE 16-continued

2'F-Modified TREMs (TREM-Arg-TGA) and related data

| SEQ ID NO. | Mod | Sequence | Calculated MW | Detected MW | Results |
|---|---|---|---|---|---|
| | | UrUrGrGrArCrUrUrCrArAfArUr UrCrArArArGrGrUrUrCrCrGrGr GrUrUrCrGrArGrUrCrCrCrGrGrC rGrGrArGrUrCrGrCrCrA | | | |
| 737 | F 39 | rGrGrCrUrCrCrGrUrGrGrCrGrCr ArArUrGrGrArUrArGrCrGrCrAr UrUrGrGrArCrUrUrCrArArAfUr UrCrArArArGrGrUrUrCrCrGrGr GrUrUrCrGrArGrUrCrCrCrGrGrC rGrGrArGrUrCrGrCrCrA | 24510.68 | 24519.8 | 1 |
| 738 | F 40 | rGrGrCrUrCrCrGrUrGrGrCrGrCr ArArUrGrGrArUrArGrCrGrCrAr UrUrGrGrArCrUrUrCrArArArUf UrCrArArArGrGrUrUrCrCrGrGr GrUrUrCrGrArGrUrCrCrCrGrGrC rGrGrArGrUrCrGrCrCrA | 24510.68 | 24508.1 | 3 |
| 739 | F 41 | rGrGrCrUrCrCrGrUrGrGrCrGrCr ArArUrGrGrArUrArGrCrGrCrAr UrUrGrGrArCrUrUrCrArArArUr UfCrArArArGrGrUrUrCrCrGrGr GrUrUrCrGrArGrUrCrCrCrGrGrC rGrGrArGrUrCrGrCrCrA | 24510.67 | 24519.7 | 3 |
| 740 | F 42 | rGrGrCrUrCrCrGrUrGrGrCrGrCr ArArUrGrGrArUrArGrCrGrCrAr UrUrGrGrArCrUrUrCrArArArUr UrCfArArArGrGrUrUrCrCrGrGr GrUrUrCrGrArGrUrCrCrCrGrGrC rGrGrArGrUrCrGrCrCrA | 24510.68 | 24519.8 | 2 |
| 741 | F 43 | rGrGrCrUrCrCrGrUrGrGrCrGrCr ArArUrGrGrArUrArGrCrGrCrAr UrUrGrGrArCrUrUrCrArArArUr UrCrAfArArGrGrUrUrCrCrGrGr GrUrUrCrGrArGrUrCrCrCrGrGrC rGrGrArGrUrCrGrCrCrA | 24510.68 | 24518.5 | 2 |
| 742 | F 44 | rGrGrCrUrCrCrGrUrGrGrCrGrCr ArArUrGrGrArUrArGrCrGrCrAr UrUrGrGrArCrUrUrCrArArArUr UrCrArAfArGrGrUrUrCrCrGrGr GrUrUrCrGrArGrUrCrCrCrGrGrC rGrGrArGrUrCrGrCrCrA | 24510.68 | 24519 | 3 |
| 743 | F 45 | rGrGrCrUrCrCrGrUrGrGrCrGrCr ArArUrGrGrArUrArGrCrGrCrAr UrUrGrGrArCrUrUrCrArArArUr UrCrArArAfGrGrUrUrCrCrGrGr GrUrUrCrGrArGrUrCrCrCrGrGrC rGrGrArGrUrCrGrCrCrA | 24510.67 | 24517.7 | 3 |
| 744 | F 46 | rGrGrCrUrCrCrGrUrGrGrCrGrCr ArArUrGrGrArUrArGrCrGrCrAr UrUrGrGrArCrUrUrCrArArArUr UrCrArArArGfGrUrUrCrCrGrGr GrUrUrCrGrArGrUrCrCrCrGrGrC rGrGrArGrUrCrGrCrCrA | 24510.67 | 24518.8 | 2 |
| 745 | F 47 | rGrGrCrUrCrCrGrUrGrGrCrGrCr ArArUrGrGrArUrArGrCrGrCrAr UrUrGrGrArCrUrUrCrArArArUr UrCrArArArGrGfUrUrCrCrGrGr GrUrUrCrGrArGrUrCrCrCrGrGrC rGrGrArGrUrCrGrCrCrA | 24510.68 | 24518.6 | 2 |
| 746 | F 48 | rGrGrCrUrCrCrGrUrGrGrCrGrCr ArArUrGrGrArUrArGrCrGrCrAr UrUrGrGrArCrUrUrCrArArArUr UrCrArArArGrGrUfUrCrCrGrGr GrUrUrCrGrArGrUrCrCrCrGrGrC rGrGrArGrUrCrGrCrCrA | 24510.68 | 24518.5 | 3 |

TABLE 16-continued

2'F-Modified TREMs (TREM-Arg-TGA) and related data

| SEQ ID NO. | Mod | Sequence | Calculated MW | Detected MW | Results |
|---|---|---|---|---|---|
| 747 | F 49 | rGrGrCrUrCrCrGrUrGrGrCrGrCr ArArUrGrGrArUrArGrCrGrCrAr UrUrGrGrArCrUrUrCrArArArUr UrCrArArArGrGrUrUfCrCrGrGr GrUrUrCrGrArGrUrCrCrCrGrGrC rGrGrArGrUrCrGrCrCrA | 24510.67 | 24519.4 | 3 |
| 748 | F 50 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCfCrGrGr GrUrUrCrGrArGrUrCrCrCrGrGrC rGrGrArGrUrCrGrCrCrA | 24510.67 | 24518.6 | 3 |
| 749 | F 51 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCfGrGr GrUrUrCrGrArGrUrCrCrCrGrGrC rGrGrArGrUrCrGrCrCrA | 24510.67 | 24518.2 | 1 |
| 750 | F 52 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGfGr GrUrUrCrGrArGrUrCrCrCrGrGrC rGrGrArGrUrCrGrCrCrA | 24510.67 | 24519.1 | 3 |
| 751 | F 53 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGf GrUrUrCrGrArGrUrCrCrCrGrGrC rGrGrArGrUrCrGrCrCrA | 24510.67 | 24518.7 | 3 |
| 752 | F 54 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GfUrUrCrGrArGrUrCrCrCrGrGrC rGrGrArGrUrCrGrCrCrA | 24510.68 | 24518.9 | 3 |
| 753 | F 55 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUfUrCrGrArGrUrCrCrCrGrGrC rGrGrArGrUrCrGrCrCrA | 24510.68 | 24520.3 | 1 |
| 754 | F 56 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUfCrGrArGrUrCrCrCrGrGrC rGrGrArGrUrCrGrCrCrA | 24510.67 | 24518.6 | 3 |
| 755 | F 57 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCfGrArGrUrCrCrCrGrGrC rGrGrArGrUrCrGrCrCrA | 24510.67 | 24518.2 | 2 |
| 756 | F 58 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGfArGrUrCrCrCrGrGrC rGrGrArGrUrCrGrCrCrA | 24510.68 | 24518 | 1 |
| 757 | F 59 | rGrGrCrUrCrCrGrUrGrGrCrGrCr ArArUrGrGrArUrArGrCrGrCrAr UrUrGrGrArCrUrUrCrArArArUr | 24510.67 | 24518.5 | 3 |

TABLE 16-continued

| 2'F-Modified TREMs (TREM-Arg-TGA) and related data | | | | | |
|---|---|---|---|---|---|
| SEQ ID NO. | Mod | Sequence | Calculated MW | Detected MW | Results |
| | | UrCrArArArGrGrUrUrCrCrGrGr GrUrUrCrGrAfGrUrCrCrCrGrGrC rGrGrArGrUrCrGrCrCrA | | | |
| 758 | F 60 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGfUrCrCrCrGrGrC rGrGrArGrUrCrGrCrCrA | 24510.68 | 24518.2 | 2 |
| 759 | F 61 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUfCrCrCrGrGrC rGrGrArGrUrCrGrCrCrA | 24510.67 | 24517.7 | 3 |
| 760 | F 62 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCfCrCrGrGrC rGrGrArGrUrCrGrCrCrA | 24510.67 | 24519.8 | 3 |
| 761 | F 63 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCfCrGrGrC rGrGrArGrUrCrGrCrCrA | 24510.67 | 24518.4 | 3 |
| 762 | F 64 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCfGrGrC rGrGrArGrUrCrGrCrCrA | 24510.67 | 24519 | 2 |
| 763 | F 65 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGfGrC rGrGrArGrUrCrGrCrCrA | 24510.67 | 24518.2 | 3 |
| 764 | F 66 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGfC rGrGrArGrUrCrGrCrCrA | 24510.67 | 24519.1 | 2 |
| 765 | F 67 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC fGrGrArGrUrCrGrCrCrA | 24510.67 | 24518.5 | 3 |
| 766 | F 68 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGfGrArGrUrCrGrCrCrA | 24510.67 | 24518.2 | 3 |
| 767 | F 69 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGfArGrUrCrGrCrCrA | 24510.68 | 24519.4 | 3 |

TABLE 16-continued

| 2'F-Modified TREMs (TREM-Arg-TGA) and related data | | | | | |
|---|---|---|---|---|---|
| SEQ ID NO. | Mod | Sequence | Calculated MW | Detected MW | Results |
| 768 | F 70 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrAfGrUrCrGrCrCrA | 24510.67 | 24518.4 | 2 |
| 769 | F 71 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGfUrCrGrCrCrA | 24510.68 | 24520.2 | 3 |
| 770 | F 72 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUfCrGrCrCrA | 24510.67 | 24518.4 | 3 |
| 771 | F 73 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCfGrCrCrA | 24510.67 | 24517.9 | 1 |
| 772 | F 74 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGfCrCrA | 24510.67 | 24518.2 | 2 |
| 773 | F 75 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCfCrA | 24510.67 | 24518.2 | 3 |
| 774 | F 76 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCfA | 24510.68 | 24518.3 | 3 |

TABLE 17

| 2'MOE-Modified TREMs (TREM-Arg-TGA) and related data | | | | | |
|---|---|---|---|---|---|
| SEQ ID NO. | Mod | Sequence | Calculated MW | Detected MW | Results |
| 775 | MOE 1 | moeGrGrCrUrCrCrGrUrGrGrCrGr CrArArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24565.5 | 3 |
| 776 | MOE 2 | rGmoeGrCrUrCrCrGrUrGrGrCrGr CrArArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24565.4 | 2 |

TABLE 17-continued

| 2'MOE-Modified TREMs (TREM-Arg-TGA) and related data | | | | | |
|---|---|---|---|---|---|
| SEQ ID NO. | Mod | Sequence | Calculated MW | Detected MW | Results |
| 777 | MOE 3 | rGrGmoe5MeCrUrCrCrGrUrGrGr CrGrCrArArUrGrGrArUrArGrCr GrCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24580.5 | 2 |
| 778 | MOE 4 | rGrGrCmoeTrCrCrGrUrGrGrCrGr CrArArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24580.69 | 24579.3 | 3 |
| 779 | MOE 5 | rGrGrCrUmoe5MeCrCrGrUrGrGr CrGrCrArArUrGrGrArUrArGrCr GrCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24579.6 | 1 |
| 780 | MOE 6 | rGrGrCrUrCmoe5MeCrGrUrGrGr CrGrCrArArUrGrGrArUrArGrCr GrCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24579.6 | 2 |
| 781 | MOE 10 | rGrGrCrUrCrCrGrUrGmoeGrCrGr CrArArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24568.3 | 2 |
| 782 | MOE 11 | rGrGrCrUrCrCrGrUrGrGmoe5Me CrGrCrArArUrGrGrArUrArGrCr GrCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24579 | 1 |
| 783 | MOE 12 | rGrGrCrUrCrCrGrUrGrGrCmoeGr CrArArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24566.6 | 2 |
| 784 | MOE 13 | rGrGrCrUrCrCrGrUrGrGrCrGmoe 5MeCrArArUrGrGrArUrArGrCrG rCrArUrUrGrGrArCrUrUrCrArAr ArUrUrCrArArArGrGrUrUrCrCr GrGrGrUrUrCrGrArGrUrCrCrCrG rGrCrGrGrArGrUrCrGrCrCrA | 24580.68 | 24580 | 2 |
| 785 | MOE 14 | rGrGrCrUrCrCrGrUrGrGrCrGrC moeArArUrGrGrArUrArGrCrGrCrA rUrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24566.69 | 24567.7 | 3 |
| 786 | MOE 15 | rGrGrCrUrCrCrGrUrGrGrCrGrCr AmoeArUrGrGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24561.7 | 3 |
| 787 | MOE 16 | rGrGrCrUrCrCrGrUrGrGrCrGrCr ArAmoeTrGrGrArUrArGrCrGrCr ArUrUrGrGrArCrUrUrCrArArAr UrUrCrArArArGrGrUrUrCrCrGr | 24580.69 | 24581.7 | 3 |

TABLE 17-continued

2'MOE-Modified TREMs (TREM-Arg-TGA) and related data

| SEQ ID NO. | Mod | Sequence | Calculated MW | Detected MW | Results |
|---|---|---|---|---|---|
| | | GrGrUrUrCrGrArGrUrCrCrCrGrG rCrGrGrArGrUrCrGrCrCrA | | | |
| 788 | MOE 17 | rGrGrCrUrCrCrGrUrGrGrCrGrCr ArArUmoeGrGrArUrArGrCrGrCr ArUrUrGrGrArCrUrUrCrArArAr GrGrUrUrCrGrArGrUrCrCrCrGrG rCrGrGrArGrUrCrGrCrCrA | 24566.69 | 24566.4 | 3 |
| 789 | MOE 18 | rGrGrCrUrCrCrGrUrGrGrCrGrCr ArArUrGmoeGrArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24568.6 | 2 |
| 790 | MOE 19 | rGrGrCrUrCrCrGrUrGrGrCrGrCr ArArUrGrGmoeArUrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24563.8 | 1 |
| 791 | MOE 20 | rGrGrCrUrCrCrGrUrGrGrCrGrCr ArArUrGrGrAmoeTrArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24580.69 | 24580.2 | 3 |
| 792 | MOE 21 | rGrGrCrUrCrCrGrUrGrGrCrGrCr ArArUrGrGrArUmoeArGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24565.4 | 1 |
| 793 | MOE 22 | rGrGrCrUrCrCrGrUrGrGrCrGrCr ArArUrGrGrArUrAmoeGrCrGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24566.2 | 1 |
| 794 | MOE 23 | rGrGrCrUrCrCrGrUrGrGrCrGrCr ArArUrGrGrArUrArGmoe5MeCr GrCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24579.5 | 1 |
| 795 | MOE 24 | rGrGrCrUrCrCrGrUrGrGrCrGrCr ArArUrGrGrArUrArGrCmoeGrCr ArUrUrGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24567.3 | 1 |
| 796 | MOE 25 | rGrGrCrUrCrCrGrUrGrGrCrGrCr ArArUrGrGrArUrArGrCrGmoe5 MeCrArUrUrGrGrArCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24578.8 | 2 |
| 797 | MOE 27 | rGrGrCrUrCrCrGrUrGrGrCrGrCr ArArUrGrGrArUrArGrCrGrCrAm oeTrUrGrGrArCrUrUrCrArArArU rUrCrArArArGrGrUrUrCrCrGrGr GrUrUrCrGrArGrUrCrCrCrGrGrC rGrGrArGrUrCrGrCrCrA | 24580.69 | 24580.3 | 2 |
| 798 | MOE 28 | rGrGrCrUrCrCrGrUrGrGrCrGrCr ArArUrGrGrArUrArGrCrGrCrAr UmoeTrGrGrArCrUrUrCrArArAr | 24580.69 | 24582.9 | 1 |

TABLE 17-continued

2'MOE-Modified TREMs (TREM-Arg-TGA) and related data

| SEQ ID NO. | Mod | Sequence | Calculated MW | Detected MW | Results |
|---|---|---|---|---|---|
| | | UrUrCrArArArGrGrUrUrCrCrGr GrGrUrUrCrGrArGrUrCrCrCrGrG rCrGrGrArGrUrCrGrCrCrA | | | |
| 799 | MOE 29 | rGrGrCrUrCrCrGrUrGrGrCrGrCr ArArUrGrGrArUrArGrCrGrCrAr UrUmoeGrGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24568.3 | 3 |
| 800 | MOE 30 | rGrGrCrUrCrCrGrUrGrGrCrGrCr ArArUrGrGrArUrArGrCrGrCrAr UrUrGmoeGrArCrUrUrCrArArAr UrUrCrArArArGrGrUrUrCrCrGr GrGrUrUrCrGrArGrUrCrCrCrGrG rCrGrGrArGrUrCrGrCrCrA | 24566.69 | 24567.7 | 2 |
| 801 | MOE 32 | rGrGrCrUrCrCrGrUrGrGrCrGrCr ArArUrGrGrArUrArGrCrGrCrAr UrUrGrGrAmoe5MeCrUrUrCrAr ArArUrUrCrArArArGrGrUrUrCr CrGrGrGrUrUrCrGrArGrUrCrCrC rGrGrCrGrGrArGrUrCrGrCrCrA | 24580.68 | 24580.4 | 1 |
| 802 | MOE 33 | rGrGrCrUrCrCrGrUrGrGrCrGrCr ArArUrGrGrArUrArGrCrGrCrAr UrUrGrGrArCmoeTrUrCrArArAr UrUrCrArArArGrGrUrUrCrCrGr GrGrUrUrCrGrArGrUrCrCrCrGrG rCrGrGrArGrUrCrGrCrCrA | 24580.69 | 24574.5 | 1 |
| 803 | MOE 34 | rGrGrCrUrCrCrGrUrGrGrCrGrCr ArArUrGrGrArUrArGrCrGrCrAr UrUrGrGrArCrUmoeTrCrArArAr UrUrCrArArArGrGrUrUrCrCrGr GrGrUrUrCrGrArGrUrCrCrCrGrG rCrGrGrArGrUrCrGrCrCrA | 24580.69 | 24581.3 | 1 |
| 804 | MOE 35 | rGrGrCrUrCrCrGrUrGrGrCrGrCr ArArUrGrGrArUrArGrCrGrCrAr UrUrGrGrArCrUrUmoe5MeCrAr ArArUrUrCrArArArGrGrUrUrCr CrGrGrGrUrUrCrGrArGrUrCrCrC rGrGrCrGrGrArGrUrCrGrCrCrA | 24580.68 | 24581 | 1 |
| 805 | MOE 36 | rGrGrCrUrCrCrGrUrGrGrCrGrCr ArArUrGrGrArUrArGrCrGrCrAr UrUrGrGrArCrUrUrCmoeArArAr UrUrCrArArArGrGrUrUrCrCrGr GrGrUrUrCrGrArGrUrCrCrCrGrG rCrGrGrArGrUrCrGrCrCrA | 24566.69 | 24566.6 | 1 |
| 806 | MOE 37 | rGrGrCrUrCrCrGrUrGrGrCrGrCr ArArUrGrGrArUrArGrCrGrCrAr UrUrGrGrArCrUrUrCrAmoeArAr UrUrCrArArArGrGrUrUrCrCrGr GrGrUrUrCrGrArGrUrCrCrCrGrG rCrGrGrArGrUrCrGrCrCrA | 24566.69 | 24572.4 | 1 |
| 807 | MOE 38 | rGrGrCrUrCrCrGrUrGrGrCrGrCr ArArUrGrGrArUrArGrCrGrCrAr UrUrGrGrArCrUrUrCrArAmoeAr UrUrCrArArArGrGrUrUrCrCrGr GrGrUrUrCrGrArGrUrCrCrCrGrG rCrGrGrArGrUrCrGrCrCrA | 24566.69 | 24561.6 | 1 |
| 808 | MOE 41 | rGrGrCrUrCrCrGrUrGrGrCrGrCr ArArUrGrGrArUrArGrCrGrCrAr UrUrGrGrArCrUrUrCrArArArUr Umoe5MeCrArArArGrGrUrUrCr CrGrGrGrUrUrCrGrArGrUrCrCrC rGrGrCrGrGrArGrUrCrGrCrCrA | 24580.68 | 24583.5 | 1 |

TABLE 17-continued

| 2'MOE-Modified TREMs (TREM-Arg-TGA) and related data | | | | | |
|---|---|---|---|---|---|
| SEQ ID NO. | Mod | Sequence | Calculated MW | Detected MW | Results |
| 809 | MOE 42 | rGrGrCrUrCrCrGrUrGrGrCrGrCr ArArUrGrGrArUrArGrCrGrCrAr UrUrGrGrArCrUrUrCrArArArUr UrCmoeArArArGrGrUrUrCrCrGr GrGrUrUrCrGrArGrUrCrCrCrGrG rCrGrGrArGrUrCrGrCrCrA | 24566.69 | 24566.9 | 1 |
| 810 | MOE 43 | rGrGrCrUrCrCrGrUrGrGrCrGrCr ArArUrGrGrArUrArGrCrGrCrAr UrUrGrGrArCrUrUrCrArArArUr UrCrAmoeArArGrGrUrUrCrCrGr GrGrUrUrCrGrArGrUrCrCrCrGrG rCrGrGrArGrUrCrGrCrCrA | 24566.69 | 24566.9 | 2 |
| 811 | MOE 44 | rGrGrCrUrCrCrGrUrGrGrCrGrCr ArArUrGrGrArUrArGrCrGrCrAr UrUrGrGrArCrUrUrCrArArArUr UrCrArAmoeArGrGrUrUrCrCrGr GrGrUrUrCrGrArGrUrCrCrCrGrG rCrGrGrArGrUrCrGrCrCrA | 24566.69 | 24566.9 | 3 |
| 812 | MOE 45 | rGrGrCrUrCrCrGrUrGrGrCrGrCr ArArUrGrGrArUrArGrCrGrCrAr UrUrGrGrArCrUrUrCrArArArUr UrCrArArAmoeGrGrUrUrCrCrGr GrGrUrUrCrGrArGrUrCrCrCrGrG rCrGrGrArGrUrCrGrCrCrA | 24566.69 | 24561 | 3 |
| 813 | MOE 46 | rGrGrCrUrCrCrGrUrGrGrCrGrCr ArArUrGrGrArUrArGrCrGrCrAr UrUrGrGrArCrUrUrCrArArArUr UrCrArArArGmoeGrUrUrCrCrGr GrGrUrUrCrGrArGrUrCrCrCrGrG rCrGrGrArGrUrCrGrCrCrA | 24566.69 | 24560.1 | 1 |
| 814 | MOE 47 | rGrGrCrUrCrCrGrUrGrGrCrGrCr ArArUrGrGrArUrArGrCrGrCrAr UrUrGrGrArCrUrUrCrArArArUr UrCrArArArGrGmoeTrUrCrCrGr GrGrUrUrCrGrArGrUrCrCrCrGrG rCrGrGrArGrUrCrGrCrCrA | 24580.69 | 24575.8 | 3 |
| 815 | MOE 48 | rGrGrCrUrCrCrGrUrGrGrCrGrCr ArArUrGrGrArUrArGrCrGrCrAr UrUrGrGrArCrUrUrCrArArArUr UrCrArArArGrGrUmoeTrCrCrGr GrGrUrUrCrGrArGrUrCrCrCrGrG rCrGrGrArGrUrCrGrCrCrA | 24580.69 | 24580.5 | 1 |
| 816 | MOE 49 | rGrGrCrUrCrCrGrUrGrGrCrGrCr ArArUrGrGrArUrArGrCrGrCrAr UrUrGrGrArCrUrUrCrArArArUr UrCrArArArGrGrUrUmoe5MeCr CrGrGrGrUrUrCrGrArGrUrCrCrC rGrGrCrGrGrArGrUrCrGrCrCrA | 24580.68 | 24578.4 | 3 |
| 817 | MOE 50 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCmoe5Me CrGrGrGrUrUrCrGrArGrUrCrCrC rGrGrCrGrGrArGrUrCrGrCrCrA | 24580.68 | 24578.8 | 3 |
| 818 | MOE 51 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCmoeGr GrGrUrUrCrGrArGrUrCrCrCrGrG rCrGrGrArGrUrCrGrCrCrA | 24566.69 | 24567.5 | 1 |
| 819 | MOE 52 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGmoe | 24566.69 | 24567.2 | 3 |

TABLE 17-continued

2'MOE-Modified TREMs (TREM-Arg-TGA) and related data

| SEQ ID NO. | Mod | Sequence | Calculated MW | Detected MW | Results |
|---|---|---|---|---|---|
| | | GrGrUrUrCrGrArGrUrCrCrCrGrG rCrGrGrArGrUrCrGrCrCrA | | | |
| 820 | MOE 53 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrG moeGrUrUrCrGrArGrUrCrCrCrGrG rCrGrGrArGrUrCrGrCrCrA | 24566.69 | 24566.8 | 2 |
| 821 | MOE 54 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GmoeTrUrCrGrArGrUrCrCrCrGr GrCrGrGrArGrUrCrGrCrCrA | 24580.69 | 24582.3 | 3 |
| 822 | MOE 55 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUmoeTrCrGrArGrUrCrCrCrGr GrCrGrGrArGrUrCrGrCrCrA | 24580.69 | 24575.3 | 1 |
| 823 | MOE 56 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUmoe5MeCrGrArGrUrCrCr CrGrGrCrGrGrArGrUrCrGrCrCrA | 24580.68 | 24581.5 | 3 |
| 824 | MOE 57 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCmoeGrArGrUrCrCrCrGr GrCrGrGrArGrUrCrGrCrCrA | 24566.69 | 24565.3 | 3 |
| 825 | MOE 58 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGmoeArGrUrCrCrCrGr GrCrGrGrArGrUrCrGrCrCrA | 24566.69 | 24570.7 | 1 |
| 826 | MOE 59 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrAmoeGrUrCrCrCrGr GrCrGrGrArGrUrCrGrCrCrA | 24566.69 | 24562.1 | 3 |
| 827 | MOE 60 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGmoeTrCrCrCrGr GrCrGrGrArGrUrCrGrCrCrA | 24580.69 | 24581 | 1 |
| 828 | MOE 61 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUmoe5MeCrCr CrGrGrCrGrGrArGrUrCrGrCrCrA | 24580.68 | 24579.7 | 1 |
| 829 | MOE 62 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCmoe5MeCr CrGrGrCrGrGrArGrUrCrGrCrCrA | 24580.68 | 24579.3 | 1 |
| 830 | MOE 64 | rGrGrCrUrCrCrGrUrGrGrCrGrCr ArArUrGrGrArUrArGrCrGrCrAr | 24566.69 | 24567.3 | 1 |

TABLE 17-continued

| SEQ ID NO. | Mod | Sequence | Calculated MW | Detected MW | Results |
|---|---|---|---|---|---|
| 2'MOE-Modified TREMs (TREM-Arg-TGA) and related data | | | | | |
| | | UrUrGrGrArCrUrUrCrArArArUr UrCrArArArGrGrUrUrCrCrGrGr GrUrUrCrGrArGrUrCrCrCmoeGr GrCrGrGrArGrUrCrGrCrCrA | | | |
| 831 | MOE 65 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGmoe GrCrGrGrArGrUrCrGrCrCrA | 24566.69 | 24563.6 | 3 |
| 832 | MOE 66 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrG moe5MeCrGrGrArGrUrCrGrCrCrA | 24580.68 | 24577.9 | 1 |
| 833 | MOE 67 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC moeGrGrArGrUrCrGrCrCrA | 24566.69 | 24566.7 | 1 |
| 834 | MOE 68 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGmoeGrArGrUrCrGrCrCrA | 24566.69 | 24567.3 | 2 |
| 835 | MOE 69 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGmoeArGrUrCrGrCrCrA | 24566.69 | 24565.9 | 1 |
| 836 | MOE 71 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGmoeTrCrGrCrCrA | 24580.69 | 24579.5 | 1 |
| 837 | MOE 72 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUmoe5MeCrGrCrCrA | 24580.68 | 24583.5 | 3 |
| 838 | MOE 73 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCmoeGrCrCrA | 24566.69 | 24569.6 | 3 |
| 839 | MOE 74 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGmoe5MeCrCrA | 24580.68 | 24580.9 | 1 |
| 840 | MOE 75 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCmoe5MeCrA | 24580.68 | 24579.7 | 2 |

TABLE 17-continued

| 2'MOE-Modified TREMs (TREM-Arg-TGA) and related data | | | | | |
|---|---|---|---|---|---|
| SEQ ID NO. | Mod | Sequence | Calculated MW | Detected MW | Results |
| 841 | MOE 76 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCmoeA | 24566.69 | 24568.2 | 2 |

TABLE 18

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| 842 | DNA 1 | dGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24493.1 | 2 |
| 843 | DNA 2 | rGdGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24493 | 2 |
| 844 | DNA 3 | rGrGdCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.8 | 3 |
| 845 | DNA 4 | rGrGrCdUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24490.9 | 3 |
| 846 | DNA 5 | rGrGrCrUdCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24492.5 | 3 |
| 847 | DNA 6 | rGrGrCrUrCdCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.4 | 3 |
| 848 | DNA 7 | rGrGrCrUrCrCdGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24492.4 | 1 |
| 849 | DNA 8 | rGrGrCrUrCrCrGdUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24493.5 | 1 |
| 850 | DNA 9 | rGrGrCrUrCrCrGrUdGrGrCrGrCr ArArUrGrGrArUrArGrCrGrCrAr | 24492.69 | 24491.2 | 1 |

TABLE 18-continued

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| | | UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | | | |
| 851 | DNA 10 | rGrGrCrUrCrCrGrUrGdGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24491.9 | 1 |
| 852 | DNA 11 | rGrGrCrUrCrCrGrUrGrGdCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.5 | 2 |
| 853 | DNA 12 | rGrGrCrUrCrCrGrUrGrGrCdGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24491.4 | 2 |
| 854 | DNA 13 | rGrGrCrUrCrCrGrUrGrGrCrGdCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.6 | 2 |
| 855 | DNA 14 | rGrGrCrUrCrCrGrUrGrGrCrGrCd ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.4 | 3 |
| 856 | DNA 15 | rGrGrCrUrCrCrGrUrGrGrCrGrCr AdArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.3 | 3 |
| 857 | DNA 16 | rGrGrCrUrCrCrGrUrGrGrCrGrCr ArAdUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.3 | 3 |
| 858 | DNA 17 | rGrGrCrUrCrCrGrUrGrGrCrGrCr ArArUdGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.3 | 2 |
| 859 | DNA 18 | rGrGrCrUrCrCrGrUrGrGrCrGrCr ArArUrGdGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24492.7 | 2 |
| 860 | DNA 19 | rGrGrCrUrCrCrGrUrGrGrCrGrCr ArArUrGrGdArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.3 | 1 |

TABLE 18-continued

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| 861 | DNA 20 | rGrGrCrUrCrCrGrUrGrGrCrGrCr ArArUrGrGrAdUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24497.8 | 3 |
| 862 | DNA 21 | rGrGrCrUrCrCrGrUrGrGrCrGrCr ArArUrGrGrArUdArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24494.8 | 1 |
| 863 | DNA 22 | rGrGrCrUrCrCrGrUrGrGrCrGrCr ArArUrGrGrArUrAdGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24491.2 | 3 |
| 864 | DNA 23 | rGrGrCrUrCrCrGrUrGrGrCrGrCr ArArUrGrGrArUrArGdCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.7 | 3 |
| 865 | DNA 24 | rGrGrCrUrCrCrGrUrGrGrCrGrCr ArArUrGrGrArUrArGrCdGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24490.7 | 1 |
| 866 | DNA 25 | rGrGrCrUrCrCrGrUrGrGrCrGrCr ArArUrGrGrArUrArGrCrGdCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24491.8 | 2 |
| 867 | DNA 26 | rGrGrCrUrCrCrGrUrGrGrCrGrCr ArArUrGrGrArUrArGrCrGrCdAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24494.3 | 2 |
| 868 | DNA 27 | rGrGrCrUrCrCrGrUrGrGrCrGrCr ArArUrGrGrArUrArGrCrGrCrAd UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24504.9 | 2 |
| 869 | DNA 28 | rGrGrCrUrCrCrGrUrGrGrCrGrCr ArArUrGrGrArUrArGrCrGrCrAr UdUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24493.8 | 1 |
| 870 | DNA 29 | rGrGrCrUrCrCrGrUrGrGrCrGrCr ArArUrGrGrArUrArGrCrGrCrAr UrUdGrGrArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24494.2 | 2 |
| 871 | DNA 30 | rGrGrCrUrCrCrGrUrGrGrCrGrCr ArArUrGrGrArUrArGrCrGrCrAr UrUrGdGrArCrUrUrCrArArArUr | 24492.69 | 24492.6 | 2 |

TABLE 18-continued

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| | | UrCrArArArGrGrUrUrCrCrGrGr GrUrUrCrGrArGrUrCrCrCrGrGrC rGrGrArGrUrCrGrCrCrA | | | |
| 872 | DNA 31 | rGrGrCrUrCrCrGrUrGrGrCrGrCr ArArUrGrGrArUrArGrCrGrCrAr UrUrGrGdArCrUrUrCrArArArUr UrCrArArArGrGrUrUrCrCrGrGr GrUrUrCrGrArGrUrCrCrCrGrGrC rGrGrArGrUrCrGrCrCrA | 24492.69 | 24492.2 | 1 |
| 873 | DNA 32 | rGrGrCrUrCrCrGrUrGrGrCrGrCr ArArUrGrGrArUrArGrCrGrCrAr UrUrGrGrAdCrUrUrCrArArArUr UrCrArArArGrGrUrUrCrCrGrGr GrUrUrCrGrArGrUrCrCrCrGrGrC rGrGrArGrUrCrGrCrCrA | 24492.71 | 24490.7 | 2 |
| 874 | DNA 33 | rGrGrCrUrCrCrGrUrGrGrCrGrCr ArArUrGrGrArUrArGrCrGrCrAr UrUrGrGrArCdUrUrCrArArArUr UrCrArArArGrGrUrUrCrCrGrGr GrUrUrCrGrArGrUrCrCrCrGrGrC rGrGrArGrUrCrGrCrCrA | 24492.69 | 24490.5 | 3 |
| 875 | DNA 34 | rGrGrCrUrCrCrGrUrGrGrCrGrCr ArArUrGrGrArUrArGrCrGrCrAr UrUrGrGrArCrUdUrCrArArArUr UrCrArArArGrGrUrUrCrCrGrGr GrUrUrCrGrArGrUrCrCrCrGrGrC rGrGrArGrUrCrGrCrCrA | 24492.69 | 24490.7 | 1 |
| 876 | DNA 35 | rGrGrCrUrCrCrGrUrGrGrCrGrCr ArArUrGrGrArUrArGrCrGrCrAr UrUrGrGrArCrUrUdCrArArArUr UrCrArArArGrGrUrUrCrCrGrGr GrUrUrCrGrArGrUrCrCrCrGrGrC rGrGrArGrUrCrGrCrCrA | 24492.71 | 24494.9 | 1 |
| 877 | DNA 36 | rGrGrCrUrCrCrGrUrGrGrCrGrCr ArArUrGrGrArUrArGrCrGrCrAr UrUrGrGrArCrUrUrCdArArArUr UrCrArArArGrGrUrUrCrCrGrGr GrUrUrCrGrArGrUrCrCrCrGrGrC rGrGrArGrUrCrGrCrCrA | 24492.69 | 24491 | 1 |
| 878 | DNA 37 | rGrGrCrUrCrCrGrUrGrGrCrGrCr ArArUrGrGrArUrArGrCrGrCrAr UrUrGrGrArCrUrUrCrAdArArUr UrCrArArArGrGrUrUrCrCrGrGr GrUrUrCrGrArGrUrCrCrCrGrGrC rGrGrArGrUrCrGrCrCrA | 24492.69 | 24495.2 | 1 |
| 879 | DNA 38 | rGrGrCrUrCrCrGrUrGrGrCrGrCr ArArUrGrGrArUrArGrCrGrCrAr UrUrGrGrArCrUrUrCrArAdArUr UrCrArArArGrGrUrUrCrCrGrGr GrUrUrCrGrArGrUrCrCrCrGrGrC rGrGrArGrUrCrGrCrCrA | 24492.69 | 24494.4 | 2 |
| 880 | DNA 39 | rGrGrCrUrCrCrGrUrGrGrCrGrCr ArArUrGrGrArUrArGrCrGrCrAr UrUrGrGrArCrUrUrCrArArAdUr UrCrArArArGrGrUrUrCrCrGrGr GrUrUrCrGrArGrUrCrCrCrGrGrC rGrGrArGrUrCrGrCrCrA | 24492.69 | 24490.5 | 1 |
| 881 | DNA 40 | rGrGrCrUrCrCrGrUrGrGrCrGrCr ArArUrGrGrArUrArGrCrGrCrAr UrUrGrGrArCrUrUrCrArArArUd UrCrArArArGrGrUrUrCrCrGrGr GrUrUrCrGrArGrUrCrCrCrGrGrC rGrGrArGrUrCrGrCrCrA | 24492.69 | 24490.2 | 2 |

TABLE 18-continued

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| 882 | DNA 41 | rGrGrCrUrCrCrGrUrGrGrCrGrCr ArArUrGrGrArUrArGrCrGrCrAr UrUrGrGrArCrUrUrCrArArArUr UdCrArArArGrGrUrUrCrCrGrGr GrUrUrCrGrArGrUrCrCrCrGrGrC rGrGrArGrUrCrGrCrCrA | 24492.71 | 24494.2 | 2 |
| 883 | DNA 42 | rGrGrCrUrCrCrGrUrGrGrCrGrCr ArArUrGrGrArUrArGrCrGrCrAr UrUrGrGrArCrUrUrCrArArArUr UrCdArArArGrGrUrUrCrCrGrGr GrUrUrCrGrArGrUrCrCrCrGrGrC rGrGrArGrUrCrGrCrCrA | 24492.69 | 24491.6 | 2 |
| 884 | DNA 43 | rGrGrCrUrCrCrGrUrGrGrCrGrCr ArArUrGrGrArUrArGrCrGrCrAr UrUrGrGrArCrUrUrCrArArArUr UrCrAdArArGrGrUrUrCrCrGrGr GrUrUrCrGrArGrUrCrCrCrGrGrC rGrGrArGrUrCrGrCrCrA | 24492.69 | 24493.7 | 1 |
| 885 | DNA 44 | rGrGrCrUrCrCrGrUrGrGrCrGrCr ArArUrGrGrArUrArGrCrGrCrAr UrUrGrGrArCrUrUrCrArArArUr UrCrArAdArGrGrUrUrCrCrGrGr GrUrUrCrGrArGrUrCrCrCrGrGrC rGrGrArGrUrCrGrCrCrA | 24492.69 | 24491.4 | 2 |
| 886 | DNA 45 | rGrGrCrUrCrCrGrUrGrGrCrGrCr ArArUrGrGrArUrArGrCrGrCrAr UrUrGrGrArCrUrUrCrArArArUr UrCrArArAdGrGrUrUrCrCrGrGr GrUrUrCrGrArGrUrCrCrCrGrGrC rGrGrArGrUrCrGrCrCrA | 24492.69 | 24493.1 | 1 |
| 887 | DNA 46 | rGrGrCrUrCrCrGrUrGrGrCrGrCr ArArUrGrGrArUrArGrCrGrCrAr UrUrGrGrArCrUrUrCrArArArUr UrCrArArArGdGrUrUrCrCrGrGr GrUrUrCrGrArGrUrCrCrCrGrGrC rGrGrArGrUrCrGrCrCrA | 24492.69 | 24494 | 1 |
| 888 | DNA 47 | rGrGrCrUrCrCrGrUrGrGrCrGrCr ArArUrGrGrArUrArGrCrGrCrAr UrUrGrGrArCrUrUrCrArArArUr UrCrArArArGrGdUrUrCrCrGrGr GrUrUrCrGrArGrUrCrCrCrGrGrC rGrGrArGrUrCrGrCrCrA | 24492.69 | 24491.1 | 2 |
| 889 | DNA 48 | rGrGrCrUrCrCrGrUrGrGrCrGrCr ArArUrGrGrArUrArGrCrGrCrAr UrUrGrGrArCrUrUrCrArArArUr UrCrArArArGrGrUdUrCrCrGrGr GrUrUrCrGrArGrUrCrCrCrGrGrC rGrGrArGrUrCrGrCrCrA | 24492.69 | 24490 | 2 |
| 890 | DNA 49 | rGrGrCrUrCrCrGrUrGrGrCrGrCr ArArUrGrGrArUrArGrCrGrCrAr UrUrGrGrArCrUrUrCrArArArUr UrCrArArArGrGrUrUdCrCrGrGr GrUrUrCrGrArGrUrCrCrCrGrGrC rGrGrArGrUrCrGrCrCrA | 24492.71 | 24494.4 | 2 |
| 891 | DNA 50 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCdCrGrGr GrUrUrCrGrArGrUrCrCrCrGrGrC rGrGrArGrUrCrGrCrCrA | 24492.71 | 24494 | 1 |
| 892 | DNA 51 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCdGrGr | 24492.69 | 24497.3 | 1 |

TABLE 18-continued

2'-Deoxy-Modified TREMs (TREM-Arg-TGA) and related data

| SEQ ID NO. | Mod | Sequence | Calculated MW | Detected MW | Results |
|---|---|---|---|---|---|
| | | GrUrUrCrGrArGrUrCrCrCrGrGrC rGrGrArGrUrCrGrCrCrA | | | |
| 893 | DNA 52 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGdGr GrUrUrCrGrArGrUrCrCrCrGrGrC rGrGrArGrUrCrGrCrCrA | 24492.69 | 24491.9 | 1 |
| 894 | DNA 53 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGd GrUrUrCrGrArGrUrCrCrCrGrGrC rGrGrArGrUrCrGrCrCrA | 24492.69 | 24491.3 | 1 |
| 895 | DNA 54 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GdUrUrCrGrArGrUrCrCrCrGrGr CrGrGrArGrUrCrGrCrCrA | 24492.69 | 24489.7 | 3 |
| 896 | DNA 55 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUdUrCrGrArGrUrCrCrCrGrGr CrGrGrArGrUrCrGrCrCrA | 24492.69 | 24490.8 | 1 |
| 897 | DNA 56 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUdCrGrArGrUrCrCrCrGrGr CrGrGrArGrUrCrGrCrCrA | 24492.71 | 24493 | 2 |
| 898 | DNA 57 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCdGrArGrUrCrCrCrGrGr CrGrGrArGrUrCrGrCrCrA | 24492.69 | 24494.9 | 1 |
| 899 | DNA 58 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGdArGrUrCrCrCrGrGr CrGrGrArGrUrCrGrCrCrA | 24492.69 | 24493.4 | 2 |
| 900 | DNA 59 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrAdGrUrCrCrCrGrGr CrGrGrArGrUrCrGrCrCrA | 24492.69 | 24491.3 | 3 |
| 901 | DNA 60 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGdUrCrCrCrGrGr CrGrGrArGrUrCrGrCrCrA | 24492.69 | 24490.3 | 2 |
| 902 | DNA 61 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUdCrCrCrGrGr CrGrGrArGrUrCrGrCrCrA | 24492.71 | 24493.3 | 2 |
| 903 | DNA 62 | rGrGrCrUrCrCrGrUrGrGrCrGrCr ArArUrGrGrArUrArGrCrGrCrAr | 24492.71 | 24494.6 | 3 |

TABLE 18-continued

| 2'-Deoxy-Modified TREMs (TREM-Arg-TGA) and related data | | | | | |
|---|---|---|---|---|---|
| SEQ ID NO. | Mod | Sequence | Calculated MW | Detected MW | Results |
| | | UrUrGrGrArCrUrUrCrArArArUr UrCrArArArGrGrUrUrCrCrGrGr GrUrUrCrGrArGrUrCdCrCrGrGr CrGrGrArGrUrCrGrCrCrA | | | |
| 904 | DNA 63 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCdCrGrGr CrGrGrArGrUrCrGrCrCrA | 24492.71 | 24491.7 | 3 |
| 905 | DNA 64 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCdGrGr CrGrGrArGrUrCrGrCrCrA | 24492.69 | 24491.8 | 2 |
| 906 | DNA 65 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGdGr CrGrGrArGrUrCrGrCrCrA | 24492.69 | 24491.9 | 2 |
| 907 | DNA 66 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGd CrGrGrArGrUrCrGrCrCrA | 24492.71 | 24491.5 | 2 |
| 908 | DNA 67 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC dGrGrArGrUrCrGrCrCrA | 24492.69 | 24491.5 | 2 |
| 909 | DNA 68 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGdGrArGrUrCrGrCrCrA | 24492.69 | 24490.5 | 1 |
| 910 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGdArGrUrCrGrCrCrA | 24492.69 | 24494.2 | |
| 911 | DNA 70 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrAdGrUrCrGrCrCrA | 24492.69 | 24500.8 | 2 |
| 912 | DNA 71 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGdUrCrGrCrCrA | 24492.69 | 24491.1 | 2 |
| 913 | DNA 72 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUdCrGrCrCrA | 24492.71 | 24501.2 | 3 |

TABLE 18-continued

2'-Deoxy-Modified TREMs (TREM-Arg-TGA) and related data

| SEQ ID NO. | Mod | Sequence | Calculated MW | Detected MW | Results |
|---|---|---|---|---|---|
| 914 | DNA 73 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCdGrCrCrA | 24492.69 | 24501.4 | 1 |
| 915 | DNA 74 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGdCrCrA | 24492.71 | 24499.8 | 2 |
| 916 | DNA 75 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCdCrA | 24492.71 | 24501.9 | 2 |
| 917 | DNA 76 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCdA | 24492.69 | 24501.9 | 3 |

TABLE 19

Phosphorothioate-Modified TREMs (TREM-Arg-TGA) and related data

| SEQ ID NO. | Mod | Sequence | Calculated MW | Detected MW | Results |
|---|---|---|---|---|---|
| 918 | PS 1 | rG*rGrCrUrCrCrGrUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24525.3 | 24528.7 | 3 |
| 919 | PS 2 | rGrG*rCrUrCrCrGrUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24525.3 | 24532.7 | 3 |
| 920 | PS 3 | rGrGrC*rUrCrCrGrUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24525.3 | 24521.1 | 3 |
| 921 | | rGrGrCrU*rCrCrGrUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24532.3 | |
| 922 | | rGrGrCrUrC*rCrGrUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24532.4 | |
| 923 | PS 6 | rGrGrCrUrCrC*rGrUrGrGrCrGrC rArArUrGrGrArUrArGrCrGrCrAr | 24524.68 | 24529.8 | 1 |

TABLE 19-continued

| Phosphorothioate-Modified TREMs (TREM-Arg-TGA) and related data | | | | | |
|---|---|---|---|---|---|
| SEQ ID NO. | Mod | Sequence | Calculated MW | Detected MW | Results |
| | | UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | | | |
| 924 | | rGrGrCrUrCrCrG*rUrGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530.4 | |
| 925 | PS 8 | rGrGrCrUrCrCrGrU*rGrGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24529.8 | 1 |
| 926 | PS 9 | rGrGrCrUrCrCrGrUrG*rGrCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.1 | 3 |
| 927 | PS 10 | rGrGrCrUrCrCrGrUrGrG*rCrGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24529.8 | 2 |
| 928 | PS 11 | rGrGrCrUrCrCrGrUrGrGrC*rGrC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24532.4 | 1 |
| 929 | PS 12 | rGrGrCrUrCrCrGrUrGrGrCrG*rC rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.2 | 1 |
| 930 | PS 13 | rGrGrCrUrCrCrGrUrGrGrCrGrC* rArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24529.9 | 1 |
| 931 | PS 14 | rGrGrCrUrCrCrGrUrGrGrCrGrCr A*rArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |
| 932 | PS 15 | rGrGrCrUrCrCrGrUrGrGrCrGrCr ArA*rUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.5 | 3 |
| 933 | PS 16 | rGrGrCrUrCrCrGrUrGrGrCrGrCr ArArU*rGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |

TABLE 19-continued

| SEQ ID NO. | Mod | Sequence | Calculated MW | Detected MW | Results |
|---|---|---|---|---|---|
| Phosphorothioate-Modified TREMs (TREM-Arg-TGA) and related data | | | | | |
| 934 | PS 17 | rGrGrCrUrCrCrGrUrGrGrCrGrCr ArArUrG*rGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |
| 935 | PS 18 | rGrGrCrUrCrCrGrUrGrGrCrGrCr ArArUrGrG*rArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |
| 936 | PS 19 | rGrGrCrUrCrCrGrUrGrGrCrGrCr ArArUrGrGrA*rUrArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24525.3 | 24519.6 | 3 |
| 937 | PS 20 | rGrGrCrUrCrCrGrUrGrGrCrGrCr ArArUrGrGrArU*rArGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |
| 938 | PS 21 | rGrGrCrUrCrCrGrUrGrGrCrGrCr ArArUrGrGrArUrA*rGrCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530 | 3 |
| 939 | PS 22 | rGrGrCrUrCrCrGrUrGrGrCrGrCr ArArUrGrGrArUrArG*rCrGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.5 | 2 |
| 940 | | rGrGrCrUrCrCrGrUrGrGrCrGrCr ArArUrGrGrArUrArGrC*rGrCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530.5 | |
| 941 | PS 24 | rGrGrCrUrCrCrGrUrGrGrCrGrCr ArArUrGrGrArUrArGrCrG*rCrAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.9 | 2 |
| 942 | PS 25 | rGrGrCrUrCrCrGrUrGrGrCrGrCr ArArUrGrGrArUrArGrCrGrC*rAr UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24528.8 | 2 |
| 943 | PS 26 | rGrGrCrUrCrCrGrUrGrGrCrGrCr ArArUrGrGrArUrArGrCrGrCrA*r UrUrGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24531.4 | 2 |
| 944 | PS 27 | rGrGrCrUrCrCrGrUrGrGrCrGrCr ArArUrGrGrArUrArGrCrGrCrAr U*rUrGrGrArCrUrUrCrArArArUr | 24524.68 | 24530.8 | 2 |

TABLE 19-continued

| SEQ ID NO. | Mod | Sequence | Calculated MW | Detected MW | Results |
|---|---|---|---|---|---|
| Phosphorothioate-Modified TREMs (TREM-Arg-TGA) and related data | | | | | |
| | | UrCrArArArGrGrUrUrCrCrGrGr GrUrUrCrGrArGrUrCrCrCrGrGrC rGrGrArGrUrCrGrCrCrA | | | |
| 945 | PS 28 | rGrGrCrUrCrCrGrUrGrGrCrGrCr ArArUrGrGrArUrArGrCrGrCrAr UrU*rGrGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530.4 | 1 |
| 946 | PS 29 | rGrGrCrUrCrCrGrUrGrGrCrGrCr ArArUrGrGrArUrArGrCrGrCrAr UrUrG*rGrArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530.6 | 2 |
| 947 | PS 30 | rGrGrCrUrCrCrGrUrGrGrCrGrCr ArArUrGrGrArUrArGrCrGrCrAr UrUrGrG*rArCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24530.6 | 2 |
| 948 | PS 31 | rGrGrCrUrCrCrGrUrGrGrCrGrCr ArArUrGrGrArUrArGrCrGrCrAr UrUrGrGrA*rCrUrUrCrArArArUr UrCrArArArGrGrUrUrCrCrGrGr GrUrUrCrGrArGrUrCrCrCrGrGrC rGrGrArGrUrCrGrCrCrA | 24524.68 | 24529.3 | 2 |
| 949 | PS 32 | rGrGrCrUrCrCrGrUrGrGrCrGrCr ArArUrGrGrArUrArGrCrGrCrAr UrUrGrGrArC*rUrUrCrArArArUr UrCrArArArGrGrUrUrCrCrGrGr GrUrUrCrGrArGrUrCrCrCrGrGrC rGrGrArGrUrCrGrCrCrA | 24524.68 | 24523.9 | 1 |
| 950 | PS 33 | rGrGrCrUrCrCrGrUrGrGrCrGrCr ArArUrGrGrArUrArGrCrGrCrAr UrUrGrGrArCrU*rUrCrArArArUr UrCrArArArGrGrUrUrCrCrGrGr GrUrUrCrGrArGrUrCrCrCrGrGrC rGrGrArGrUrCrGrCrCrA | 24524.68 | 24518.8 | 2 |
| 951 | PS 34 | rGrGrCrUrCrCrGrUrGrGrCrGrCr ArArUrGrGrArUrArGrCrGrCrAr UrUrGrGrArCrUrU*rCrArArArUr UrCrArArArGrGrUrUrCrCrGrGr GrUrUrCrGrArGrUrCrCrCrGrGrC rGrGrArGrUrCrGrCrCrA | 24524.68 | 24524.9 | 1 |
| 952 | PS 35 | rGrGrCrUrCrCrGrUrGrGrCrGrCr ArArUrGrGrArUrArGrCrGrCrAr UrUrGrGrArCrUrUrC*rArArArUr UrCrArArArGrGrUrUrCrCrGrGr GrUrUrCrGrArGrUrCrCrCrGrGrC rGrGrArGrUrCrGrCrCrA | 24524.68 | 24524.8 | 3 |
| 953 | PS 36 | rGrGrCrUrCrCrGrUrGrGrCrGrCr ArArUrGrGrArUrArGrCrGrCrAr UrUrGrGrArCrUrUrCrA*rArArUr UrCrArArArGrGrUrUrCrCrGrGr GrUrUrCrGrArGrUrCrCrCrGrGrC rGrGrArGrUrCrGrCrCrA | 24524.68 | 24518.4 | 1 |
| 954 | PS 37 | rGrGrCrUrCrCrGrUrGrGrCrGrCr ArArUrGrGrArUrArGrCrGrCrAr UrUrGrGrArCrUrUrCrArA*rArUr UrCrArArArGrGrUrUrCrCrGrGr GrUrUrCrGrArGrUrCrCrCrGrGrC rGrGrArGrUrCrGrCrCrA | 24524.68 | 24524.7 | 3 |

TABLE 19-continued

Phosphorothioate-Modified TREMs (TREM-Arg-TGA) and related data

| SEQ ID NO. | Mod | Sequence | Calculated MW | Detected MW | Results |
|---|---|---|---|---|---|
| 955 | PS 38 | rGrGrCrUrCrCrGrUrGrGrCrGrCr ArArUrGrGrArUrArGrCrGrCrAr UrUrGrGrArCrUrUrCrArArA*rUr UrCrArArArGrGrUrUrCrCrGrGr GrUrUrCrGrArGrUrCrCrCrGrGrC rGrGrArGrUrCrGrCrCrA | 24524.68 | 24519.4 | 3 |
| 956 | PS 39 | rGrGrCrUrCrCrGrUrGrGrCrGrCr ArArUrGrGrArUrArGrCrGrCrAr UrUrGrGrArCrUrUrCrArArArU*r UrCrArArArGrGrUrUrCrCrGrGr GrUrUrCrGrArGrUrCrCrCrGrGrC rGrGrArGrUrCrGrCrCrA | 24524.68 | 24529.7 | 1 |
| 957 | | rGrGrCrUrCrCrGrUrGrGrCrGrCr ArArUrGrGrArUrArGrCrGrCrAr UrUrGrGrArCrUrUrCrArArArUr U*rCrArArArGrGrUrUrCrCrGrGr GrUrUrCrGrArGrUrCrCrCrGrGrC rGrGrArGrUrCrGrCrCrA | 24524.68 | 24529.8 | |
| 958 | PS 41 | rGrGrCrUrCrCrGrUrGrGrCrGrCr ArArUrGrGrArUrArGrCrGrCrAr UrUrGrGrArCrUrUrCrArArArUr UrC*rArArArGrGrUrUrCrCrGrGr GrUrUrCrGrArGrUrCrCrCrGrGrC rGrGrArGrUrCrGrCrCrA | 24524.68 | 24529.9 | 2 |
| 959 | | rGrGrCrUrCrCrGrUrGrGrCrGrCr ArArUrGrGrArUrArGrCrGrCrAr UrUrGrGrArCrUrUrCrArArArUr UrCrA*rArArGrGrUrUrCrCrGrGr GrUrUrCrGrArGrUrCrCrCrGrGrC rGrGrArGrUrCrGrCrCrA | 24524.68 | 24530.8 | |
| 960 | PS 43 | rGrGrCrUrCrCrGrUrGrGrCrGrCr ArArUrGrGrArUrArGrCrGrCrAr UrUrGrGrArCrUrUrCrArArArUr UrCrArA*rArGrGrUrUrCrCrGrGr GrUrUrCrGrArGrUrCrCrCrGrGrC rGrGrArGrUrCrGrCrCrA | 24524.68 | 24529.4 | 2 |
| 961 | PS 44 | rGrGrCrUrCrCrGrUrGrGrCrGrCr ArArUrGrGrArUrArGrCrGrCrAr UrUrGrGrArCrUrUrCrArArArUr UrCrArArA*rGrGrUrUrCrCrGrGr GrUrUrCrGrArGrUrCrCrCrGrGrC rGrGrArGrUrCrGrCrCrA | 24524.68 | 24518.4 | 3 |
| 962 | PS 45 | rGrGrCrUrCrCrGrUrGrGrCrGrCr ArArUrGrGrArUrArGrCrGrCrAr UrUrGrGrArCrUrUrCrArArArUr UrCrArArArG*rGrUrUrCrCrGrGr GrUrUrCrGrArGrUrCrCrCrGrGrC rGrGrArGrUrCrGrCrCrA | 24524.68 | 24529.7 | 3 |
| 963 | PS 46 | rGrGrCrUrCrCrGrUrGrGrCrGrCr ArArUrGrGrArUrArGrCrGrCrAr UrUrGrGrArCrUrUrCrArArArUr UrCrArArArGrG*rUrUrCrCrGrGr GrUrUrCrGrArGrUrCrCrCrGrGrC rGrGrArGrUrCrGrCrCrA | 24524.68 | 24520.2 | 3 |
| 964 | PS 47 | rGrGrCrUrCrCrGrUrGrGrCrGrCr ArArUrGrGrArUrArGrCrGrCrAr UrUrGrGrArCrUrUrCrArArArUr UrCrArArArGrGrU*rUrCrCrGrGr GrUrUrCrGrArGrUrCrCrCrGrGrC rGrGrArGrUrCrGrCrCrA | 24524.68 | 24528.3 | 2 |
| 965 | PS 48 | rGrGrCrUrCrCrGrUrGrGrCrGrCr ArArUrGrGrArUrArGrCrGrCrAr UrUrGrGrArCrUrUrCrArArArUr UrCrArArArGrGrUrU*rCrCrGrGr | 24524.68 | 24518.7 | 1 |

TABLE 19-continued

Phosphorothioate-Modified TREMs (TREM-Arg-TGA) and related data

| SEQ ID NO. | Mod | Sequence | Calculated MW | Detected MW | Results |
|---|---|---|---|---|---|
| | | GrUrUrCrGrArGrUrCrCrCrGrGrC rGrGrArGrUrCrGrCrCrA | | | |
| 966 | PS 49 | rGrGrCrUrCrCrGrUrGrGrCrGrCr ArArUrGrGrArUrArGrCrGrCrAr UrUrGrGrArCrUrUrCrArArArUr UrCrArArArGrGrUrUrC*rCrGrGr GrUrUrCrGrArGrUrCrCrCrGrGrC rGrGrArGrUrCrGrCrCrA | 24524.68 | 24529.6 | 2 |
| 967 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrC*rGrGr GrUrUrCrGrArGrUrCrCrCrGrGrC rGrGrArGrUrCrGrCrCrA | 24524.68 | 24530.4 | |
| 968 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrG*rGr GrUrUrCrGrArGrUrCrCrCrGrGrC rGrGrArGrUrCrGrCrCrA | 24524.68 | 24528.8 | |
| 969 | PS 52 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrG*r GrUrUrCrGrArGrUrCrCrCrGrGrC rGrGrArGrUrCrGrCrCrA | 24524.68 | 24526 | 3 |
| 970 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr G*rUrUrCrGrArGrUrCrCrCrGrGr CrGrGrArGrUrCrGrCrCrA | 24524.68 | 24530.7 | |
| 971 | PS 54 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrU*rUrCrGrArGrUrCrCrCrGrGr CrGrGrArGrUrCrGrCrCrA | 24524.68 | 24528.5 | 3 |
| 972 | PS 55 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrU*rCrGrArGrUrCrCrCrGrGr CrGrGrArGrUrCrGrCrCrA | 24524.68 | 24529.7 | 3 |
| 973 | PS 56 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrC*rGrArGrUrCrCrCrGrGr CrGrGrArGrUrCrGrCrCrA | 24524.68 | 24529.4 | 3 |
| 974 | PS 57 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrG*rArGrUrCrCrCrGrGr CrGrGrArGrUrCrGrCrCrA | 24524.68 | 24529.5 | 3 |
| 975 | PS 58 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrA*rGrUrCrCrCrGrGr CrGrGrArGrUrCrGrCrCrA | 24525.3 | 24520.8 | 3 |
| 976 | PS 59 | rGrGrCrUrCrCrGrUrGrGrCrGrCr ArArUrGrGrArUrArGrCrGrCrAr | 24524.68 | 24529.8 | 2 |

TABLE 19-continued

Phosphorothioate-Modified TREMs (TREM-Arg-TGA) and related data

| SEQ ID NO. | Mod | Sequence | Calculated MW | Detected MW | Results |
|---|---|---|---|---|---|
| | | UrUrGrGrArCrUrUrCrArArArUr UrCrArArArGrGrUrUrCrCrGrGr GrUrUrCrGrArG*rUrCrCrCrGrGr CrGrGrArGrUrCrGrCrCrA | | | |
| 977 | PS 60 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrU*rCrCrCrGrGr CrGrGrArGrUrCrGrCrCrA | 24524.68 | 24528.3 | 2 |
| 978 | PS 61 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrC*rCrCrGrGr CrGrGrArGrUrCrGrCrCrA | 24524.68 | 24529.4 | 2 |
| 979 | PS 62 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrC*rCrGrGr CrGrGrArGrUrCrGrCrCrA | 24524.68 | 24530.7 | 2 |
| 980 | PS 63 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrC*rGrGr CrGrGrArGrUrCrGrCrCrA | 24524.68 | 24528.3 | 1 |
| 981 | PS 64 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrG*rGr CrGrGrArGrUrCrGrCrCrA | 24524.68 | 24524.9 | 1 |
| 982 | PS 65 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrG*r CrGrGrArGrUrCrGrCrCrA | 24524.68 | 24523.8 | 2 |
| 983 | PS 66 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC *rGrGrArGrUrCrGrCrCrA | 24524.68 | 24524.4 | 1 |
| 984 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rG*rGrArGrUrCrGrCrCrA | 24524.68 | 24524.7 | |
| 985 | | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrG*rArGrUrCrGrCrCrA | 24524.68 | 24524.3 | |
| 986 | PS 69 | rGrGrCrUrCrCrGrUrGrGrCrGrCr ArArUrGrGrArUrArGrCrGrCrAr UrUrGrGrArCrUrUrCrArArArUr UrCrArArArGrGrUrUrCrCrGrGr GrUrUrCrGrArGrUrCrCrCrGrGrC rGrGrA*rGrUrCrGrCrCrA | 24524.68 | 24522.6 | 2 |

TABLE 19-continued

Phosphorothioate-Modified TREMs (TREM-Arg-TGA) and related data

| SEQ ID NO. | Mod | Sequence | Calculated MW | Detected MW | Results |
|---|---|---|---|---|---|
| 987 | PS 70 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArG*rUrCrGrCrCrA | 24524.68 | 24524.9 | 2 |
| 988 | PS 71 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrU*rCrGrCrCrA | 24524.68 | 24525.1 | 2 |
| 989 | PS 72 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrC*rGrCrCrA | 24524.68 | 24525.3 | 2 |
| 990 | PS 73 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrCrG*rCrCrA | 24525.3 | 24520.4 | 3 |
| 991 | PS 74 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrCrGrC*rCrA | 24525.3 | 24533.1 | 3 |
| 992 | PS 75 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrCrGrCrC*rA | 24525.3 | 24533.2 | 2 |

TABLE 20

2'OMe-Modified TREMs (TREM-Ser-TAG) and related data

| SEQ ID NO. | Mod | Sequence | Calculated MW | Detected MW | Results |
|---|---|---|---|---|---|
| 993 | | rGrArCrGrArGrGrUrGrGrCrCrGrArGrUrGrGrUrUrArArGrGrCrGrArUrGrGrArCrUrCrUrArArArUrCrCrArUrUrGrUrGrGrCrUrCrUrGrCrArCrGrCrGrUrGrGrGrUrUrCrGrArArUrCrCrCrArUrCrCrUrCrGrUrCrGrCrCrA | 27323.32 | 27329.5 | 2 |
| 994 | OME 1 | mGrArCrGrArGrGrUrGrGrCrCrGrArGrUrGrGrUrUrArArGrGrCrGrArUrGrGrArCrUrCrUrArArArUrCrCrArUrUrGrUrGrGrCrUrCrUrGrCrArCrGrCrGrUrGrGrGrUrUrCrGrArArUrCrCrCrArUrCrCrUrCrGrUrCrGrCrCrA | 27337.32 | 27343.3 | 3 |
| 995 | OME 2 | rGmArCrGrArGrGrUrGrGrCrCrGrArGrUrGrGrUrUrArArGrGrCrGrArUrGrGrArCrUrCrUrArArArUrCrCrArUrUrGrUrGrGrCrUrCrUrGrCrArCrGrCrGrUrGrGrGrUrUrCrGrArArUrCrCrCrArUrCrCrUrCrGrUrCrGrCrCrA | 27337.32 | 27342.9 | 2 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| 996 | OME 3 | rGrAmCrGrArGrGrUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27342.3 | 1 |
| 997 | OME 4 | rGrArCmGrArGrGrUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27339.3 | 3 |
| 998 | OME 5 | rGrArCrGmArGrGrUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.7 | 3 |
| 999 | OME 6 | rGrArCrGrAmGrGrUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.8 | 1 |
| 1000 | OME 7 | rGrArCrGrArGmGrUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27341.2 | 1 |
| 1001 | OME 8 | rGrArCrGrArGrGmUrGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27341.4 | 1 |
| 1002 | OME 9 | rGrArCrGrArGrGrUmGrGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.5 | 1 |
| 1003 | OME 10 | rGrArCrGrArGrGrUrGmGrCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.4 | 2 |
| 1004 | OME 11 | rGrArCrGrArGrGrUrGrGmCrCrG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27339.3 | 1 |
| 1005 | OME 12 | rGrArCrGrArGrGrUrGrGrCmCrG rArGrUrGrGrUrUrArArGrGrCrGr | 27337.32 | 27336.2 | 1 |

TABLE 20-continued

| 2'OMe-Modified TREMs (TREM-Ser-TAG) and related data | | | | | |
|---|---|---|---|---|---|
| SEQ ID NO. | Mod | Sequence | Calculated MW | Detected MW | Results |
| | | ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | | | |
| 1006 | OME 13 | rGrArCrGrArGrGrUrGrGrCrCmG rArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27344.3 | 1 |
| 1007 | OME 14 | rGrArCrGrArGrGrUrGrGrCrCrG mArGrUrGrGrUrUrArArGrGrCrG rArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27332.8 | 1 |
| 1008 | OME 15 | rGrArCrGrArGrGrUrGrGrCrCrGr AmGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.7 | 1 |
| 1009 | OME 16 | rGrArCrGrArGrGrUrGrGrCrCrGr ArGmUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.7 | 1 |
| 1010 | OME 17 | rGrArCrGrArGrGrUrGrGrCrCrGr ArGrUmGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338 | 2 |
| 1011 | OME 18 | rGrArCrGrArGrGrUrGrGrCrCrGr ArGrUrGmGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27339 | 2 |
| 1012 | OME 19 | rGrArCrGrArGrGrUrGrGrCrCrGr ArGrUrGrGmUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.1 | 1 |
| 1013 | OME 20 | rGrArCrGrArGrGrUrGrGrCrCrGr ArGrUrGrGrUmUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.2 | 1 |
| 1014 | OME 21 | rGrArCrGrArGrGrUrGrGrCrCrGr ArGrUrGrGrUrUmArArGrGrCrGr ArUrGrGrArCrUrCrUrArArArUr CrCrArUrUrGrUrGrCrUrCrUrGrC rArCrGrCrGrUrGrGrGrUrUrCrGr | 27337.32 | 27337.3 | 1 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| | | ArArUrCrCrCrArUrCrCrUrCrGrU rCrGrCrCrA | | | |
| 1015 | OME 22 | rGrArCrGrArGrGrUrGrGrCrCrGr ArGrUrGrGrUrUrAmArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337 | 1 |
| 1016 | OME 23 | rGrArCrGrArGrGrUrGrGrCrCrGr ArGrUrGrGrUrUrArAmGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.3 | 1 |
| 1017 | OME 24 | rGrArCrGrArGrGrUrGrGrCrCrGr ArGrUrGrGrUrUrArArGmGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27340.9 | 2 |
| 1018 | OME 25 | rGrArCrGrArGrGrUrGrGrCrCrGr ArGrUrGrGrUrUrArArGrGmCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.8 | 1 |
| 1019 | OME 26 | rGrArCrGrArGrGrUrGrGrCrCrGr ArGrUrGrGrUrUrArArGrGrCmGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27336.8 | 1 |
| 1020 | OME 27 | rGrArCrGrArGrGrUrGrGrCrCrGr ArGrUrGrGrUrUrArArGrGrCrGm ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27339.7 | 2 |
| 1021 | OME 28 | rGrArCrGrArGrGrUrGrGrCrCrGr ArGrUrGrGrUrUrArArGrGrCrGr AmUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.9 | 1 |
| 1022 | OME 29 | rGrArCrGrArGrGrUrGrGrCrCrGr ArGrUrGrGrUrUrArArGrGrCrGr ArUmGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.8 | 2 |
| 1023 | OME 30 | rGrArCrGrArGrGrUrGrGrCrCrGr ArGrUrGrGrUrUrArArGrGrCrGr ArUrGmGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.5 | 2 |

TABLE 20-continued

| 2'OMe-Modified TREMs (TREM-Ser-TAG) and related data | | | | | |
|---|---|---|---|---|---|
| SEQ ID NO. | Mod | Sequence | Calculated MW | Detected MW | Results |
| 1024 | OME 31 | rGrArCrGrArGrGrUrGrGrCrCrGr ArGrUrGrGrUrUrArArGrGrCrGr ArUrGrGmArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.7 | 1 |
| 1025 | OME 32 | rGrArCrGrArGrGrUrGrGrCrCrGr ArGrUrGrGrUrUrArArGrGrCrGr ArUrGrGrAmCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27340.4 | 2 |
| 1026 | OME 33 | rGrArCrGrArGrGrUrGrGrCrCrGr ArGrUrGrGrUrUrArArGrGrCrGr ArUrGrGrArCmUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27336.2 | 1 |
| 1027 | OME 34 | rGrArCrGrArGrGrUrGrGrCrCrGr ArGrUrGrGrUrUrArArGrGrCrGr ArUrGrGrArCrUmCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.4 | 3 |
| 1028 | OME 35 | rGrArCrGrArGrGrUrGrGrCrCrGr ArGrUrGrGrUrUrArArGrGrCrGr ArUrGrGrArCrUrCmUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.8 | 1 |
| 1029 | OME 36 | rGrArCrGrArGrGrUrGrGrCrCrGr ArGrUrGrGrUrUrArArGrGrCrGr ArUrGrGrArCrUrCrUmArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338.1 | 1 |
| 1030 | OME 37 | rGrArCrGrArGrGrUrGrGrCrCrGr ArGrUrGrGrUrUrArArGrGrCrGr ArUrGrGrArCrUrCrUrAmArArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27338 | 1 |
| 1031 | OME 38 | rGrArCrGrArGrGrUrGrGrCrCrGr ArGrUrGrGrUrUrArArGrGrCrGr ArUrGrGrArCrUrCrUrArAmArUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27340.8 | 3 |
| 1032 | OME 39 | rGrArCrGrArGrGrUrGrGrCrCrGr ArGrUrGrGrUrUrArArGrGrCrGr ArUrGrGrArCrUrCrUrArArAmUr CrCrArUrUrGrUrGrCrUrCrUrGrC rArCrGrCrGrUrGrGrGrUrUrCrGr ArArUrCrCrCrArUrCrCrUrCrGrU rCrGrCrCrA | 27337.32 | 27337.7 | 3 |
| 1033 | OME 40 | rGrArCrGrArGrGrUrGrGrCrCrGr ArGrUrGrGrUrUrArArGrGrCrGr ArUrGrGrArCrUrCrUrArArArUm | 27337.32 | 27336.6 | 2 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| | | CrCrArUrUrGrUrGrCrUrCrUrGrCrArCrGrCrGrUrGrGrGrUrUrCrGrArArUrCrCrCrArUrCrCrUrCrGrUrCrGrCrCrA | | | |
| 1034 | OME 41 | rGrArCrGrArGrGrUrGrGrCrCrGrArGrUrGrGrUrUrArArGrGrCrGrArUrGrGrArCrUrCrUrArArArUrCmCrArUrUrGrUrGrCrUrCrUrGrCrArCrGrCrGrUrGrGrGrUrUrCrGrArArUrCrCrCrArUrCrCrUrCrGrUrCrGrCrCrA | 27337.32 | 27337 | 2 |
| 1035 | | rGrArCrGrArGrGrUrGrGrCrCrGrArGrUrGrGrUrUrArArGrGrCrGrArUrGrGrArCrUrCrUrArArArUrCrCmArUrUrGrUrGrCrUrCrUrGrCrArCrGrCrGrUrGrGrGrUrUrCrGrArArUrCrCrCrArUrCrCrUrCrGrUrCrGrCrCrA | 27337.32 | 27337.7 | |
| 1036 | OME 43 | rGrArCrGrArGrGrUrGrGrCrCrGrArGrUrGrGrUrUrArArGrGrCrGrArUrGrGrArCrUrCrUrArArArUrCrCrAmUrUrGrUrGrCrUrCrUrGrCrArCrGrCrGrUrGrGrGrUrUrCrGrArArUrCrCrCrArUrCrCrUrCrGrUrCrGrCrCrA | 27337.32 | 27338.3 | 2 |
| 1037 | OME 44 | rGrArCrGrArGrGrUrGrGrCrCrGrArGrUrGrGrUrUrArArGrGrCrGrArUrGrGrArCrUrCrUrArArArUrCrCrArUmUrGrUrGrCrUrCrUrGrCrArCrGrCrGrUrGrGrGrUrUrCrGrArArUrCrCrCrArUrCrCrUrCrGrUrCrGrCrCrA | 27337.32 | 27338.3 | 1 |
| 1038 | OME 45 | rGrArCrGrArGrGrUrGrGrCrCrGrArGrUrGrGrUrUrArArGrGrCrGrArUrGrGrArCrUrCrUrArArArUrCrCrArUrUmGrUrGrCrUrCrUrGrCrArCrGrCrGrUrGrGrGrUrUrCrGrArArUrCrCrCrArUrCrCrUrCrGrUrCrGrCrCrA | 27337.32 | 27338.1 | 1 |
| 1039 | OME 46 | rGrArCrGrArGrGrUrGrGrCrCrGrArGrUrGrGrUrUrArArGrGrCrGrArUrGrGrArCrUrCrUrArArArUrCrCrArUrUrGmUrGrCrUrCrUrGrCrArCrGrCrGrUrGrGrGrUrUrCrGrArArUrCrCrCrArUrCrCrUrCrGrUrCrGrCrCrA | 27337.32 | 27336.3 | 2 |
| 1040 | OME 47 | rGrArCrGrArGrGrUrGrGrCrCrGrArGrUrGrGrUrUrArArGrGrCrGrArUrGrGrArCrUrCrUrArArArUrCrCrArUrUrGrUmGrCrUrCrUrGrCrArCrGrCrGrUrGrGrGrUrUrCrGrArArUrCrCrCrArUrCrCrUrCrGrUrCrGrCrCrA | 27337.32 | 27336.2 | 2 |
| 1041 | OME 48 | rGrArCrGrArGrGrUrGrGrCrCrGrArGrUrGrGrUrUrArArGrGrCrGrArUrGrGrArCrUrCrUrArArArUrCrCrArUrUrGrUrGmCrUrCrUrGrCrArCrGrCrGrUrGrGrGrUrUrCrGrArArUrCrCrCrArUrCrCrUrCrGrUrCrGrCrCrA | 27337.32 | 27338 | 1 |
| 1042 | OME 49 | rGrArCrGrArGrGrUrGrGrCrCrGrArGrUrGrGrUrUrArArGrGrCrGrArUrGrGrArCrUrCrUrArArArUrCrCrArUrUrGrUrGrCmUrCrUrGr | 27337.32 | 27337.6 | 1 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| | | CrArCrGrCrGrUrGrGrGrUrUrCrG rArArUrCrCrCrArUrCrCrUrCrGr UrCrGrCrCrA | | | |
| 1043 | OME 50 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUmCrUrGr CrArCrGrCrGrUrGrGrGrUrUrCrG rArArUrCrCrCrArUrCrCrUrCrGr UrCrGrCrCrA | 27337.32 | 27337.8 | 1 |
| 1044 | OME 51 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCmUrGr CrArCrGrCrGrUrGrGrGrUrUrCrG rArArUrCrCrCrArUrCrCrUrCrGr UrCrGrCrCrA | 27337.32 | 27338.4 | 1 |
| 1045 | OME 52 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUmGr CrArCrGrCrGrUrGrGrGrUrUrCrG rArArUrCrCrCrArUrCrCrUrCrGr UrCrGrCrCrA | 27337.32 | 27336.7 | 1 |
| 1046 | OME 53 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGm CrArCrGrCrGrUrGrGrGrUrUrCrG rArArUrCrCrCrArUrCrCrUrCrGr UrCrGrCrCrA | 27337.32 | 27341.4 | 1 |
| 1047 | OME 54 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC mArCrGrCrGrUrGrGrGrUrUrCrG rArArUrCrCrCrArUrCrCrUrCrGr UrCrGrCrCrA | 27337.32 | 27341.3 | 1 |
| 1048 | OME 55 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rAmCrGrCrGrUrGrGrGrUrUrCrG rArArUrCrCrCrArUrCrCrUrCrGr UrCrGrCrCrA | 27337.32 | 27338.6 | 1 |
| 1049 | OME 56 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCmGrCrGrUrGrGrGrUrUrCrG rArArUrCrCrCrArUrCrCrUrCrGr UrCrGrCrCrA | 27337.32 | 27337.7 | 1 |
| 1050 | OME 57 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGmCrGrUrGrGrGrUrUrCrG rArArUrCrCrCrArUrCrCrUrCrGr UrCrGrCrCrA | 27337.32 | 27336.1 | 1 |
| 1051 | OME 58 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCmGrUrGrGrGrUrUrCrG rArArUrCrCrCrArUrCrCrUrCrGr UrCrGrCrCrA | 27337.32 | 27338.6 | 1 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| 1052 | OME 59 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGmUrGrGrGrUrUrCrG rArArUrCrCrCrArUrCrCrUrCrGr UrCrGrCrCrA | 27337.32 | 27338.6 | 2 |
| 1053 | OME 60 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUmGrGrGrUrUrCrG rArArUrCrCrCrArUrCrCrUrCrGr UrCrGrCrCrA | 27337.32 | 27337.7 | 1 |
| 1054 | OME 61 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGmGrGrUrUrCrG rArArUrCrCrCrArUrCrCrUrCrGr UrCrGrCrCrA | 27337.32 | 27336.4 | 3 |
| 1055 | OME 62 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGmGrUrUrCrG rArArUrCrCrCrArUrCrCrUrCrGr UrCrGrCrCrA | 27337.32 | 27338.2 | 1 |
| 1056 | OME 63 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGmUrUrCrG rArArUrCrCrCrArUrCrCrUrCrGr UrCrGrCrCrA | 27337.32 | 27336.3 | 1 |
| 1057 | OME 64 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUmUrCrG rArArUrCrCrCrArUrCrCrUrCrGr UrCrGrCrCrA | 27337.32 | 27336.9 | 1 |
| 1058 | OME 65 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUmCrG rArArUrCrCrCrArUrCrCrUrCrGr UrCrGrCrCrA | 27337.32 | 27338.2 | 1 |
| 1059 | OME 66 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCmG rArArUrCrCrCrArUrCrCrUrCrGr UrCrGrCrCrA | 27337.32 | 27336 | 1 |
| 1060 | OME 67 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrG mArArUrCrCrCrArUrCrCrUrCrGr UrCrGrCrCrA | 27337.32 | 27337.5 | 1 |
| 1061 | OME 68 | rGrArCrGrArGrGrUrGrGrCrCrGr ArGrUrGrGrUrUrArArGrGrCrGr | 27337.32 | 27336.9 | 1 |

TABLE 20-continued

2'OMe-Modified TREMs (TREM-Ser-TAG) and related data

| SEQ ID NO. | Mod | Sequence | Calculated MW | Detected MW | Results |
|---|---|---|---|---|---|
| | | ArUrGrGrArCrUrCrUrArArArUr CrCrArUrUrGrUrGrCrUrCrUrGrC rArCrGrCrGrUrGrGrGrUrUrCrGr AmArUrCrCrCrArUrCrCrUrCrGr UrCrGrCrCrA | | | |
| 1062 | OME 69 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArAmUrCrCrCrArUrCrCrUrCrGr UrCrGrCrCrA | 27337.32 | 27341.1 | 1 |
| 1063 | OME 70 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUmCrCrCrArUrCrCrUrCrGr UrCrGrCrCrA | 27337.32 | 27337.9 | 1 |
| 1064 | OME 71 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCmCrCrArUrCrCrUrCrGr UrCrGrCrCrA | 27337.32 | 27338.1 | 1 |
| 1065 | OME 72 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCmCrArUrCrCrUrCrGr UrCrGrCrCrA | 27337.32 | 27338.7 | 1 |
| 1066 | OME 73 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCmArUrCrCrUrCrGr UrCrGrCrCrA | 27337.32 | 27336.4 | 2 |
| 1067 | OME 74 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrAmUrCrCrUrCrGr UrCrGrCrCrA | 27337.32 | 27337.8 | 1 |
| 1068 | OME 75 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUmCrCrUrCrGr UrCrGrCrCrA | 27337.32 | 27338 | 1 |
| 1069 | OME 76 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCmCrUrCrGr UrCrGrCrCrA | 27337.32 | 27337.6 | 1 |
| 1070 | OME 77 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr | 27337.32 | 27335.9 | 1 |

TABLE 20-continued

| 2'OMe-Modified TREMs (TREM-Ser-TAG) and related data | | | | | |
|---|---|---|---|---|---|
| SEQ ID NO. | Mod | Sequence | Calculated MW | Detected MW | Results |
| | | ArArUrCrCrCrArUrCrCmUrCrGr UrCrGrCrCrA | | | |
| 1071 | OME 78 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUmCrGr UrCrGrCrCrA | 27337.32 | 27337.9 | 1 |
| 1072 | OME 79 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCmGr UrCrGrCrCrA | 27337.32 | 27336.1 | 3 |
| 1073 | OME 80 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGm UrCrGrCrCrA | 27337.32 | 27337.1 | 3 |
| 1074 | OME 81 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU mCrGrCrCrA | 27337.32 | 27336.5 | 2 |
| 1075 | OME 82 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCmGrCrCrA | 27337.32 | 27336 | 3 |
| 1076 | OME 83 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGmCrCrA | 27337.32 | 27337.4 | 1 |
| 1077 | OME 84 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCmCrA | 27337.32 | 27338.7 | 1 |
| 1078 | OME 85 | rGrArCrGrArGrGrUrGrGrCrCrGr ArGrUrGrGrUrUrArArGrGrCrGr ArUrGrGrArCrUrCrUrArArArUr CrCrArUrUrGrUrGrCrUrCrUrGrC rArCrGrCrGrUrGrGrGrUrUrCrGr ArArUrCrCrCrArUrCrCrUrCrGrU rCrGrCrCmA | 27337.32 | 27337.9 | 1 |

TABLE 21

2' OMe-Modified TREMs (TREM-Gln-TAA) and related data

| SEQ ID NO. | Mod | Sequence | Calculated MW | Detected MW | Results |
|---|---|---|---|---|---|
| 1079 | | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24055.37 | 24059.2 | 2 |
| 1080 | OME 1 | mGrGrUrUrCrCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24071.7 | 3 |
| 1081 | OME 2 | rGmGrUrUrCrCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.8 | 2 |
| 1082 | OME 3 | rGrGmUrUrCrCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24069.7 | 1 |
| 1083 | OME 4 | rGrGrUmUrCrCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073 | 3 |
| 1084 | OME 5 | rGrGrUrUmCrCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24071.3 | 2 |
| 1085 | OME 6 | rGrGrUrUrCmCrArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24074.2 | 1 |
| 1086 | OME 7 | rGrGrUrUrCrCmArUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24074 | 1 |
| 1087 | OME 8 | rGrGrUrUrCrCrAmUrGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24069 | 1 |
| 1088 | OME 9 | rGrGrUrUrCrCrArUmGrGrUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24070.3 | 1 |
| 1089 | OME 10 | rGrGrUrUrCrCrArUrGmGrUrGrU rArArUrGrGrUrArArGrCrArCrUr CrUrGrGrArCrUrUrUrArArArUr | 24069.37 | 24069.2 | 2 |

TABLE 21-continued

| 2' OMe-Modified TREMs (TREM-Gln-TAA) and related data | | | | | |
|---|---|---|---|---|---|
| SEQ ID NO. | Mod | Sequence | Calculated MW | Detected MW | Results |
| | | CrCrArGrCrGrArUrCrCrGrArGrU rUrCrGrArGrUrCrUrCrGrGrUrGr GrArArCrCrUrCrCrA | | | |
| 1090 | OME 11 | rGrGrUrUrCrCrArUrGrGmUrGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24069.4 | 1 |
| 1091 | OME 12 | rGrGrUrUrCrCrArUrGrGrUmGrU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24068.5 | 3 |
| 1092 | OME 13 | rGrGrUrUrCrCrArUrGrGrUrGmU rArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24068.4 | 3 |
| 1093 | OME 14 | rGrGrUrUrCrCrArUrGrGrUrGrU mArArUrGrGrUrArArGrCrArCrU rCrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24070.9 | 2 |
| 1094 | OME 15 | rGrGrUrUrCrCrArUrGrGrUrGrUr AmArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24068.3 | 2 |
| 1095 | OME 16 | rGrGrUrUrCrCrArUrGrGrUrGrUr ArAmUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24067.5 | 2 |
| 1096 | OME 17 | rGrGrUrUrCrCrArUrGrGrUrGrUr ArArUmGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24067.6 | 3 |
| 1097 | OME 18 | rGrGrUrUrCrCrArUrGrGrUrGrUr ArArUrGmGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24067.4 | 3 |
| 1098 | OME 19 | rGrGrUrUrCrCrArUrGrGrUrGrUr ArArUrGrGmUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24067.3 | 1 |
| 1099 | OME 20 | rGrGrUrUrCrCrArUrGrGrUrGrUr ArArUrGrGrUmArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24074 | 1 |

TABLE 21-continued

2' OMe-Modified TREMs (TREM-Gln-TAA) and related data

| SEQ ID NO. | Mod | Sequence | Calculated MW | Detected MW | Results |
|---|---|---|---|---|---|
| 1100 | OME 21 | rGrGrUrUrCrCrArUrGrGrUrGrUr ArArUrGrGrUrAmArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24074.8 | 1 |
| 1101 | | rGrGrUrUrCrCrArUrGrGrUrGrUr ArArUrGrGrUrArAmGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.9 | |
| 1102 | OME 23 | rGrGrUrUrCrCrArUrGrGrUrGrUr ArArUrGrGrUrArArGmCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.8 | 3 |
| 1103 | OME 24 | rGrGrUrUrCrCrArUrGrGrUrGrUr ArArUrGrGrUrArArGrCmArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24075.6 | 1 |
| 1104 | OME 25 | rGrGrUrUrCrCrArUrGrGrUrGrUr ArArUrGrGrUrArArGrCrAmCrUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.4 | 1 |
| 1105 | OME 26 | rGrGrUrUrCrCrArUrGrGrUrGrUr ArArUrGrGrUrArArGrCrArCmUr CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.8 | 1 |
| 1106 | OME 27 | rGrGrUrUrCrCrArUrGrGrUrGrUr ArArUrGrGrUrArArGrCrArCrUm CrUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.8 | 2 |
| 1107 | OME 28 | rGrGrUrUrCrCrArUrGrGrUrGrUr ArArUrGrGrUrArArGrCrArCrUr CmUrGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.8 | 3 |
| 1108 | OME 29 | rGrGrUrUrCrCrArUrGrGrUrGrUr ArArUrGrGrUrArArGrCrArCrUr CrUmGrGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.7 | 3 |
| 1109 | OME 30 | rGrGrUrUrCrCrArUrGrGrUrGrUr ArArUrGrGrUrArArGrCrArCrUr CrUrGmGrArCrUrUrUrArArArUr CrCrArGrCrGrArUrCrCrGrArGrU rUrCrGrArGrUrCrUrCrGrGrUrGr GrArArCrCrUrCrCrA | 24069.37 | 24073.5 | 3 |
| 1110 | OME 31 | rGrGrUrUrCrCrArUrGrGrUrGrUr ArArUrGrGrUrArArGrCrArCrUr CrUrGrGmArCrUrUrUrArArArUr CrCrArGrCrGrArUrCrCrGrArGrU | 24069.37 | 24073.2 | 1 |

TABLE 21-continued

| 2' OMe-Modified TREMs (TREM-Gln-TAA) and related data | | | | | |
|---|---|---|---|---|---|
| SEQ ID NO. | Mod | Sequence | Calculated MW | Detected MW | Results |
| | | rUrCrGrArGrUrCrUrCrGrGrUrGr GrArArCrCrUrCrCrA | | | |
| 1111 | OME 32 | rGrGrUrUrCrCrArUrGrGrUrGrUr ArArUrGrGrUrArArGrCrArCrUr CrUrGrGrAmCrUrUrUrArArArUr CrCrArGrCrGrArUrCrCrGrArGrU rUrCrGrArGrUrCrUrCrGrGrUrGr GrArArCrCrUrCrCrA | 24069.37 | 24074.1 | 1 |
| 1112 | OME 33 | rGrGrUrUrCrCrArUrGrGrUrGrUr ArArUrGrGrUrArArGrCrArCrUr CrUrGrGrArCmUrUrUrArArArUr CrCrArGrCrGrArUrCrCrGrArGrU rUrCrGrArGrUrCrUrCrGrGrUrGr GrArArCrCrUrCrCrA | 24069.37 | 24073.7 | 1 |
| 1113 | OME 34 | rGrGrUrUrCrCrArUrGrGrUrGrUr ArArUrGrGrUrArArGrCrArCrUr CrUrGrGrArCrUmUrUrArArArUr CrCrArGrCrGrArUrCrCrGrArGrU rUrCrGrArGrUrCrUrCrGrGrUrGr GrArArCrCrUrCrCrA | 24069.37 | 24074.4 | 2 |
| 1114 | OME 35 | rGrGrUrUrCrCrArUrGrGrUrGrUr ArArUrGrGrUrArArGrCrArCrUr CrUrGrGrArCrUrUmUrArArArUr CrCrArGrCrGrArUrCrCrGrArGrU rUrCrGrArGrUrCrUrCrGrGrUrGr GrArArCrCrUrCrCrA | 24069.37 | 24073.7 | 1 |
| 1115 | OME 36 | rGrGrUrUrCrCrArUrGrGrUrGrUr ArArUrGrGrUrArArGrCrArCrUr CrUrGrGrArCrUrUrUmArArArUr CrCrArGrCrGrArUrCrCrGrArGrU rUrCrGrArGrUrCrUrCrGrGrUrGr GrArArCrCrUrCrCrA | 24069.37 | 24073.3 | 1 |
| 1116 | OME 37 | rGrGrUrUrCrCrArUrGrGrUrGrUr ArArUrGrGrUrArArGrCrArCrUr CrUrGrGrArCrUrUrUrAmArArUr CrCrArGrCrGrArUrCrCrGrArGrU rUrCrGrArGrUrCrUrCrGrGrUrGr GrArArCrCrUrCrCrA | 24069.37 | 24073.3 | 1 |
| 1117 | OME 38 | rGrGrUrUrCrCrArUrGrGrUrGrUr ArArUrGrGrUrArArGrCrArCrUr CrUrGrGrArCrUrUrUrArAmArUr CrCrArGrCrGrArUrCrCrGrArGrU rUrCrGrArGrUrCrUrCrGrGrUrGr GrArArCrCrUrCrCrA | 24069.37 | 24073.8 | 3 |
| 1118 | OME 39 | rGrGrUrUrCrCrArUrGrGrUrGrUr ArArUrGrGrUrArArGrCrArCrUr CrUrGrGrArCrUrUrUrArArAmUr CrCrArGrCrGrArUrCrCrGrArGrU rUrCrGrArGrUrCrUrCrGrGrUrGr GrArArCrCrUrCrCrA | 24069.37 | 24073.6 | 3 |
| 1119 | OME 40 | rGrGrUrUrCrCrArUrGrGrUrGrUr ArArUrGrGrUrArArGrCrArCrUr CrUrGrGrArCrUrUrUrArArArUm CrCrArGrCrGrArUrCrCrGrArGrU rUrCrGrArGrUrCrUrCrGrGrUrGr GrArArCrCrUrCrCrA | 24069.37 | 24073.3 | 2 |
| 1120 | OME 41 | rGrGrUrUrCrCrArUrGrGrUrGrUr ArArUrGrGrUrArArGrCrArCrUr CrUrGrGrArCrUrUrUrArArArUr CmCrArGrCrGrArUrCrCrGrArGr UrUrCrGrArGrUrCrUrCrGrGrUr GrGrArArCrCrUrCrCrA | 24069.37 | 24074 | 3 |
| 1121 | OME 42 | rGrGrUrUrCrCrArUrGrGrUrGrUr ArArUrGrGrUrArArGrCrArCrUr | 24069.37 | 24073.6 | 2 |

TABLE 21-continued

2' OMe-Modified TREMs (TREM-Gln-TAA) and related data

| SEQ ID NO. | Mod | Sequence | Calculated MW | Detected MW | Results |
|---|---|---|---|---|---|
| | | CrUrGrGrArCrUrUrUrArArArUr CrCmArGrCrGrArUrCrCrGrArGr UrUrCrGrArGrUrCrUrCrGrGrUr GrGrArArCrCrUrCrCrA | | | |
| 1122 | OME 43 | rGrGrUrUrCrCrArUrGrGrUrGrUr ArArUrGrGrUrArArGrCrArCrUr CrUrGrGrArCrUrUrUrArArArUr CrCrAmGrCrGrArUrCrCrGrArGr UrUrCrGrArGrUrCrUrCrGrGrUr GrGrArArCrCrUrCrCrA | 24069.37 | 24074.3 | 1 |
| 1123 | OME 44 | rGrGrUrUrCrCrArUrGrGrUrGrUr ArArUrGrGrUrArArGrCrArCrUr CrUrGrGrArCrUrUrUrArArArUr CrCrArGmCrGrArUrCrCrGrArGr UrUrCrGrArGrUrCrUrCrGrGrUr GrGrArArCrCrUrCrCrA | 24069.37 | 24074.6 | 3 |
| 1124 | OME 45 | rGrGrUrUrCrCrArUrGrGrUrGrUr ArArUrGrGrUrArArGrCrArCrUr CrUrGrGrArCrUrUrUrArArArUr CrCrArGrCmGrArUrCrCrGrArGr UrUrCrGrArGrUrCrUrCrGrGrUr GrGrArArCrCrUrCrCrA | 24069.37 | 24074.5 | 1 |
| 1125 | OME 46 | rGrGrUrUrCrCrArUrGrGrUrGrUr ArArUrGrGrUrArArGrCrArCrUr CrUrGrGrArCrUrUrUrArArArUr CrCrArGrCrGmArUrCrCrGrArGr UrUrCrGrArGrUrCrUrCrGrGrUr GrGrArArCrCrUrCrCrA | 24069.37 | 24073.5 | 1 |
| 1126 | OME 47 | rGrGrUrUrCrCrArUrGrGrUrGrUr ArArUrGrGrUrArArGrCrArCrUr CrUrGrGrArCrUrUrUrArArArUr CrCrArGrCrGrAmUrCrCrGrArGr UrUrCrGrArGrUrCrUrCrGrGrUr GrGrArArCrCrUrCrCrA | 24069.37 | 24073.8 | 1 |
| 1127 | OME 48 | rGrGrUrUrCrCrArUrGrGrUrGrUr ArArUrGrGrUrArArGrCrArCrUr CrUrGrGrArCrUrUrUrArArArUr CrCrArGrCrGrArUmCrCrGrArGr UrUrCrGrArGrUrCrUrCrGrGrUr GrGrArArCrCrUrCrCrA | 24069.37 | 24074.2 | 3 |
| 1128 | OME 49 | rGrGrUrUrCrCrArUrGrGrUrGrUr ArArUrGrGrUrArArGrCrArCrUr CrUrGrGrArCrUrUrUrArArArUr CrCrArGrCrGrArUrCmCrGrArGr UrUrCrGrArGrUrCrUrCrGrGrUr GrGrArArCrCrUrCrCrA | 24069.37 | 24074.5 | 3 |
| 1129 | OME 50 | rGrGrUrUrCrCrArUrGrGrUrGrUr ArArUrGrGrUrArArGrCrArCrUr CrUrGrGrArCrUrUrUrArArArUr CrCrArGrCrGrArUrCrCmGrArGr UrUrCrGrArGrUrCrUrCrGrGrUr GrGrArArCrCrUrCrCrA | 24069.37 | 24073.5 | 2 |
| 1130 | OME 51 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGmArGr UrUrCrGrArGrUrCrUrCrGrGrUr GrGrArArCrCrUrCrCrA | 24069.37 | 24074.5 | 3 |
| 1131 | OME 52 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrAmGr UrUrCrGrArGrUrCrUrCrGrGrUr GrGrArArCrCrUrCrCrA | 24069.37 | 24072.4 | 3 |

TABLE 21-continued

2' OMe-Modified TREMs (TREM-Gln-TAA) and related data

| SEQ ID NO. | Mod | Sequence | Calculated MW | Detected MW | Results |
|---|---|---|---|---|---|
| 1132 | OME 53 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGm UrUrCrGrArGrUrCrUrCrGrGrUr GrGrArArCrCrUrCrCrA | 24069.37 | 24069.5 | 3 |
| 1133 | OME 54 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU mUrCrGrArGrUrCrUrCrGrGrUrG rGrArArCrCrUrCrCrA | 24069.37 | 24068.7 | 1 |
| 1134 | OME 55 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUmCrGrArGrUrCrUrCrGrGrUrG rGrArArCrCrUrCrCrA | 24069.37 | 24068.3 | 2 |
| 1135 | OME 56 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCmGrArGrUrCrUrCrGrGrUrG rGrArArCrCrUrCrCrA | 24069.37 | 24069.5 | 2 |
| 1136 | OME 57 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGmArGrUrCrUrCrGrGrUrG rGrArArCrCrUrCrCrA | 24069.37 | 24068.2 | 1 |
| 1137 | OME 58 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrAmGrUrCrUrCrGrGrUrG rGrArArCrCrUrCrCrA | 24069.37 | 24067.8 | 3 |
| 1138 | OME 59 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGmUrCrUrCrGrGrUrG rGrArArCrCrUrCrCrA | 24069.37 | 24068.2 | 1 |
| 1139 | OME 60 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUmCrUrCrGrGrUrG rGrArArCrCrUrCrCrA | 24069.37 | 24068 | 3 |
| 1140 | OME 61 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCmUrCrGrGrUrG rGrArArCrCrUrCrCrA | 24069.37 | 24068.1 | 3 |
| 1141 | OME 62 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUmCrGrGrUrG rGrArArCrCrUrCrCrA | 24069.37 | 24068.1 | 1 |
| 1142 | OME 63 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU | 24069.37 | 24067.6 | 3 |

TABLE 21-continued

2' OMe-Modified TREMs (TREM-Gln-TAA) and related data

| SEQ ID NO. | Mod | Sequence | Calculated MW | Detected MW | Results |
|---|---|---|---|---|---|
| | | rUrCrGrArGrUrCrUrCmGrGrUrG rGrArArCrCrUrCrCrA | | | |
| 1143 | OME 64 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGmGrUrG rGrArArCrCrUrCrCrA | 24069.37 | 24069.3 | 3 |
| 1144 | OME 65 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGmUrG rGrArArCrCrUrCrCrA | 24069.37 | 24067.3 | 3 |
| 1145 | OME 66 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUmG rGrArArCrCrUrCrCrA | 24069.37 | 24068.7 | 3 |
| 1146 | OME 67 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrG mGrArArCrCrUrCrCrA | 24069.37 | 24067 | 2 |
| 1147 | OME 68 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GmArArCrCrUrCrCrA | 24069.37 | 24068.3 | 3 |
| 1148 | OME 69 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrAmArCrCrUrCrCrA | 24069.37 | 24067.6 | 3 |
| 1149 | OME 70 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArAmCrCrUrCrCrA | 24069.37 | 24067 | 1 |
| 1150 | OME 71 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCmCrUrCrCrA | 24069.37 | 24067.2 | 3 |
| 1151 | OME 72 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCmUrCrCrA | 24069.37 | 24066.9 | 3 |
| 1152 | OME 73 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUmCrCrA | 24069.37 | 24067 | 3 |
| 1153 | OME 74 | rGrGrUrUrCrCrArUrGrGrUrGrUr ArArUrGrGrUrArArGrCrArCrUr | 24069.37 | 24067.6 | 3 |

TABLE 21-continued

2' OMe-Modified TREMs (TREM-Gln-TAA) and related data

| SEQ ID NO. | Mod | Sequence | Calculated MW | Detected MW | Results |
|---|---|---|---|---|---|
| | | CrUrGrGrArCrUrUrUrArArArUr CrCrArGrCrGrArUrCrCrGrArGrU rUrCrGrArGrUrCrUrCrGrGrUrGr GrArArCrCrUrCmCrA | | | |
| 1154 | OME 75 | rGrGrUrUrCrCrArUrGrGrUrGrUr ArArUrGrGrUrArArGrCrArCrUr CrUrGrGrArCrUrUrUrArArArUr CrCrArGrCrGrArUrCrCrGrArGrU rUrCrGrArGrUrCrUrCrGrGrUrGr GrArArCrCrUrCrCmA | 24069.37 | 24067.3 | 3 |

TABLE 22

Additional modified TREMs (TREM-Arg-TGA) and related data

| SEQ ID NO. | Mod | Sequence | Calculated MW | Detected MW | Results |
|---|---|---|---|---|---|
| 1155 | CCA | rGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCr G | 23569.11 | 23574.5 | 3 |
| 1156 | m1 ,m73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm GrCrCrA | 24536.69 | 24536.1 | 3 |
| 1157 | m1, m52, m73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGmGrGrUrUrCrGr ArGrUrCrCrCrGrGrCrGrGrArGrUrC mGrCrCrA | 24550.69 | 24548.1 | 3 |
| 1158 | m1, m50, m52, m73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCmCrGmGrGrUrUrCrGr ArGrUrCrCrCrGrGrCrGrGrArGrUrC mGrCrCrA | 24564.69 | 24564.3 | 3 |
| 1159 | m1, m18, m50, m52, m73 | mGrGrCrUrCrCrGrUrGrGrCrGrCrAr ArUrGmGrArUrArGrCrGrCrArUrUr GrGrArCrUrUrCrArArArUrUrCrArA rArGrGrUrUrCmCrGmGrGrUrUrCrG rArGrUrCrCrCrGrGrCrGrGrArGrUr CmGrCrCrA | 24578.69 | 24585.7 | 3 |
| 1160 | m8, m52 | rGrGrCrUrCrCrGmUrGrGrCrGrCrAr ArUrGrGrArUrArGrCrGrCrArUrUrG rGrArCrUrUrCrArArArUrUrCrArAr ArGrGrUrUrCrCrGmGrGrUrUrCrGr ArGrUrCrCrCrGrGrCrGrGrArGrUrC rGrCrCrA | 24536.69 | 24536.7 | 3 |
| 1161 | m1, m17, m18, m50, m52, m73 | mGrGrCrUrCrCrGrUrGrGrCrGrCrAr ArUmGmGrArUrArGrCrGrCrArUrU rGrGrArCrUrUrCrArArArUrUrCrAr ArArGrGrUrUrCmCrGmGrGrUrUrCr GrArGrUrCrCrCrGrGrCrGrGrArGrU rCmGrCrCrA | 24592.7 | 24591.3 | 3 |
| 1162 | m39, m52 | rGrGrCrUrCrCrGrUrGrGrCrGrCrAr ArUrGrGrArUrArGrCrGrCrArUrUrG rGrArCrUrUrCrArArAmUrUrCrArAr ArGrGrUrUrCrCrGmGrGrUrUrCrGr | 24536.69 | 24539.1 | 2 |

TABLE 22-continued

Additional modified TREMs (TREM-Arg-TGA) and related data

| SEQ ID NO. | Mod | Sequence | Calculated MW | Detected MW | Results |
|---|---|---|---|---|---|
| | | ArGrUrCrCrCrGrGrCrGrGrArGrUrC rGrCrCrA | | | |
| 1163 | m52, m62 | rGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGmGrGrUrUrCrGr ArGrUrCmCrCrGrGrCrGrGrArGrUr CrGrCrCrA | 24536.68 | 24535.5 | 3 |
| 1164 | moe (1); PS (1) | moeG*rGrGrCrUrCrCrGrUrGrGrCrGrC rArArUrGrGrArUrArGrCrGrCrArUr UrGrGrArCrUrUrCrArArArUrUrCrA rArArGrGrUrUrCrCrGrGrGrUrUrCr GrArGrUrCrCrCrGrGrCrGrGrArGrU rCrGrCrCrA | 24582.69 | 24581.7 | 3 |
| 1165 | m (1); PS (1) | mG*rGrGrCrUrCrCrGrUrGrGrCrGrCrA rArUrGrGrArUrArGrCrGrCrArUrUr GrGrArCrUrUrCrArArArUrUrCrArA rArGrGrUrUrCrCrGrGrGrUrUrCrGr ArGrUrCrCrCrGrGrCrGrGrArGrUrC rGrCrCrA | 24538.69 | 24545.5 | 3 |
| 1166 | m (1); PS (1, 2, 74, 75) | mG*rG*rCrUrCrCrGrUrGrGrCrGrCr ArArUrGrGrArUrArGrCrGrCrArUrU rGrGrArCrUrUrCrArArArUrUrCrAr ArArGrGrUrUrCrCrGrGrGrUrUrCrG rArGrUrCrCrCrGrGrCrGrGrArGrUr CrGrC*rC*rA | 24586.69 | 24594.9 | 3 |
| 1167 | m (1, 2); PS (1, 2, 74, 75) | mG*mG*rCrUrCrCrGrUrGrGrCrGrC rArArUrGrGrArUrArGrCrGrCrArUr UrGrGrArCrUrUrCrArArArUrUrCrA rArArGrGrUrUrCrCrGrGrGrUrUrCr GrArGrUrCrCrCrGrGrCrGrGrArGrU rCrGrC*rC*rA | 24600.69 | 24603.5 | 3 |
| 1168 | m (1, 2, 74, 75); PS (1, 2, 74, 75) | mG*mG*rCrUrCrCrGrUrGrGrCrGrC rArArUrGrGrArUrArGrCrGrCrArUr UrGrGrArCrUrUrCrArArArUrUrCrA rArArGrGrUrUrCrCrGrGrGrUrUrCr GrArGrUrCrCrCrGrGrCrGrGrArGrU rCrGmC*mC*rA | 24628.68 | 24632.7 | 3 |
| 1169 | m (1, 2, 74, 75, 76); PS (1, 2, 74, 75) | mG*mG*rCrUrCrCrGrUrGrGrCrGrC rArArUrGrGrArUrArGrCrGrCrArUr UrGrGrArCrUrUrCrArArArUrUrCrA rArArGrGrUrUrCrCrGrGrGrUrUrCr GrArGrUrCrCrCrGrGrCrGrGrArGrU rCrGmC*mC*mA | 24642.69 | 24646.2 | 3 |
| 1170 | | mGrGrCrUrCrCrGrUrGrGrCrGrCrAr ArUrGrGrArUrArGrCrGrCrArUrUm GmGrArCrUrUrCrArArArUrUrCrAr ArArGrGrUrUrCmCrGmGrGrUrUm CrGrArGrUrCrCrCrGmGrCrGrGrAr GmUrCmGrCrCrA | 24634.7 | 24632.6 | 3 |
| 1171 | | mGrGrCmUrCrCrGrUrGrGrCrGrCrA rArUrGrGrAmUrArGrCrGrCrArUrU mGmGrArCrUrUrCrArArArUrUrCrA rArArGrGrUrUrCmCrGmGrGrUrUm CrGrArGrUrCrCrCrGmGrCrGrGrAr GmUrCmGrCrCrA | 24662.7 | 24667.1 | 2 |
| 1172 | | mGrGrCmUrCrCrGrUrGrGrCrGmCr ArArUmGmGrAmUrArGrCrGmCrAr UrUmGmGrArCrUrUrCrArArArUrU rCrArArArGrGrUrUmCmCrGmGrGr UrUmCrGrAmGrUrCrCrCrGmGrCrG rGmArGmUmCmGrCrCrA | 24774.7 | 24779.4 | 3 |
| 1173 | | mGrGrCmUrCrCrGrUrGmGmCmGm CrArArUmGmGrAmUrArGrCrGmCr | 24872.7 | 24881.5 | 1 |

TABLE 22-continued

| Additional modified TREMs (TREM-Arg-TGA) and related data | | | | | |
|---|---|---|---|---|---|
| SEQ ID NO. | Mod | Sequence | Calculated MW | Detected MW | Results |
| | | ArUrUmGmGrArCrUrUrCrArArArU rUrCrArArAmGrGrUrUmCmCrGmG rGrUrUmCrGrAmGrUmCrCrCrGmG mCrGmGmArGmUmCmGrCrCrA | | | |
| 1174 | | mGrGrCmUrCmCrGrUrGmGmCmG mCrArArUmGmGrAmUrAmGrCrG mCrArUrUmGmGrArCrUrUrCrArAr ArUrUmCmAmArAmGrGrUrUmCm CrGmGrGrUrUmCrGrAmGrUmCmC rCrGmGmCmGmGmArGmUmCmGr CrCmA | 24984.71 | 24992.1 | 1 |
| 1175 | N-1; m73 | rGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm GrCrC | 24193.48 | 24197.4 | |
| 1176 | N-2; m73 | rGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm GrC | 23888.3 | 23889.2 | 3 |
| 1177 | N-3; m73 | rGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm G | 23583.11 | 23583.8 | 1 |
| 1178 | N-3, m1, 73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm G | 23597.12 | 23598.2 | 1 |
| 1179 | N-2; m1, 73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm GrC | 23902.3 | 23904.4 | 3 |
| 1180 | N-1; m1, 73 | mGrGrCrUrCrCrGrUrGrGrCrGrCrAr ArUrGrGrArUrArGrCrGrCrArUrUrG rGrArCrUrUrCrArArArUrUrCrArAr ArGrGrUrUrCrCrGrGrGrUrUrCrGrA rGrUrCrCrCrGrGrCrGrGrArGrUrCm GrCrC | 24207.48 | 24208.3 | 3 |
| 1181 | m1-6, DS1, DS2, TS1 | mGmGmCmUmCmCrGrUrGmGmC mGmCrArArUrGrGrArUrAmGmCm GmCrArUrUrGrGrArCrUrUrCrArAr ArUrUrCrArArArGrGrUrUmCmCm GmGmGrUrUrCrGrArGrUrCrCrCrGr GrCrGrGrArGrUrCrGrCrCrA | 24774.69 | 24779.6 | 3 |
| 1182 | m1-6, DS1, DS2, TS1, m73 | mGmGmCmUmCmCrGrUrGmGmC mGmCrArArUrGrGrArUrAmGmCm GmCrArUrUrGrGrArCrUrUrCrArAr ArUrUrCrArArArGrGrUrUmCmCm GmGmGrUrUrCrGrArGrUrCrCrCrGr GrCrGrGrArGrUrCmGrCrCrA | 24788.69 | 24782.3 | 3 |
| 1183 | N-3, m1-6, DS1, DS2, TS1, m73 | mGmGmCmUmCmCrGrUrGmGmC mGmCrArArUrGrGrArUrAmGmCm GmCrArUrUrGrGrArCrUrUrCrArAr ArUrUrCrArArArGrGrUrUmCmCm GmGmGrUrUrCrGrArGrUrCrCrCrGr GrCrGrGrArGrUrCmG | 23849.11 | 23854.6 | 1 |

TABLE 22-continued

Additional modified TREMs (TREM-Arg-TGA) and related data

| SEQ ID NO. | Mod | Sequence | Calculated MW | Detected MW | Results |
|---|---|---|---|---|---|
| 1184 | N-3, m1 | mGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrCrG | 23583.11 | 23587.8 | 3 |
| 1185 | N-3, m1-6 | mGmGmCmUmCmCrGrUrGrGrCrGrCrArArUrGrGrArUrArGrCrGrCrArUrUrGrGrArCrUrUrCrArArArUrUrCrArArArGrGrUrUrCrCrGrGrGrUrUrCrGrArGrUrCrCrCrGrGrCrGrGrArGrUrCrG | 23653.11 | 23646.8 | 3 |
| 1186 | N-3, PS 54 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrU*rUrCrGrArGrUrCrCrCrGrGrCrGrGrArGrUrCrG | 23585.11 | 23589.6 | 3 |
| 1187 | N-3, PS 55 | rGrGrCrUrCrCrGrUrGrGrCrGrCrArArUrGrGrArUrArGrCrGrCrArUrUrGrGrArCrUrUrCrArArArUrUrCrArArArGrGrUrUrCrCrGrGrGrUrU*rCrGrArGrUrCrCrCrGrGrCrGrGrArGrUrCrG | 23585.11 | 23589.9 | |

Example 12: Correction of a Missense Mutation in an ORF with Administration of a TREM This example describes the administration of a TREM to correct a missense mutation. In this example, a TREM translates a reporter with a missense mutation into a wild type (WT) protein by incorporation of the WT amino acid (at the missense position) in the protein.

Host Cell Modification

A cell line stably expressing a GFP reporter construct containing a missense mutation, for example T2031 or E222G, which prevent GFP excitation at the 470 nm and 390 nm wavelengths, is generated using the FlpIn system according to manufacturer's instructions. Briefly, HEK293T (293T ATCC® CRL-3216) cells are co-transfected with an expression vector containing a GFP reporter with a missense mutation, such as pcDNA5/FRT-NanoLuc-TAA and a pOG44 Flp-Recombinase expression vector using Lipofectamine2000 according to manufacturer's instructions. After 24 hours, the media is replaced with fresh media. The next day, the cells are split 1:2 and selected with 100 ug/mL Hygromycin for 5 days. The remaining cells are expanded and tested for reporter construct expression.

Synthesis and Preparation of TREM

The TREM is synthesized as described in Example 1 and quality control methods as described in Examples 7-9 are performed. To ensure proper folding, the TREM is heated at 85° C. for 2 minutes and then snap cooled at 4° C. for 5 minutes.

Transfection of Non-Cognate TREM into Host Cells

To deliver the TREM to mammalian cells, 100 nM of TREM is transfected into cells expressing the ORF having a missense mutation using lipofectamine 2000 reagents according to the manufacturer's instructions. After 6-18 hours, the transfection media is removed and replaced with fresh complete media.

Missense Mutation Correction Assay

To monitor the efficacy of the TREM to correct the missense mutation in the reporter construct, 24-48 hours after TREM transfection, cell media is replaced, and cell fluorescence is measured. As a negative control, no TREM is transfected in the cells and as a positive control, cells expressing WT GFP are used for this assay. If the TREM is functional, it is expected that the GFP protein produced fluoresces when illuminated with a 390 nm excitation wavelength using a fluorimeter, as observed in the positive control. If the TREM is not functional, the GFP protein produced fluoresces only when excited with a 470 nm wavelength, as is observed in the negative control.

Example 13: Evaluation of Protein Expression Levels of SMC-Containing ORF with Administration of a TREM This example describes administration of a TREM to alter expression levels of an SMC-containing ORF.

To create a system in which to study the effects of TREM administration on protein expression levels of an SMC-containing protein, in this example, from the PNPL3A gene coding for adiponutrin, a plasmid containing the PNPL3A rs738408 ORF sequence is transfected in the normal human hepatocyte cell line THLE-3, edited by CRISPR/Cas to contain a frameshift mutation in a coding exon of PNPLA3 to knock out endogenous PNPLA3 (THLE-3_PNPLA3KO cells). As a control, an aliquot of THLE-3_PNPLA3KO cells are transfected with a plasmid containing the wildtype PNPL3A ORF sequence.

Synthesis and Preparation of TREM

An arginine TREM is synthesized as described in Example 1 and quality control methods as described in Examples 7-9 are performed. To ensure proper folding, the TREM is heated at 85° C. for 2 minutes and then snap cooled at 4° C. for 5 minutes.

Evaluation of Protein Level of SMC-Containing ORF

A TREM is delivered to the THLE-3_PNPLA3KO cells containing the rs738408 ORF sequence as well as to the THLE-3_PNPLA3KO cells containing the wildtype PNPL3A ORF sequence. In this example, the TREM contains a proline isoacceptor containing an AGG anticodon, that base pairs to the CCT codon, i.e. with the sequence GGCUCGUUGGUCUAGGGGUAUGAUUCUCGC-UUAGGGUGCGAGAGGUCCCGGGUU CAAAUCCCGGACGAGCCC (SEQ ID NO: 1292). A time course is performed ranging from 30 minutes to 6 hours with hour-long interval time points. At each time point, cells are trypsinized, washed and lysed. Cell lysates are analyzed by Western blotting and blots are probed with antibodies against the adiponutrin protein. A total protein loading control, such as GAPDH, actin or tubulin, is also probed as a loading control.

The methods described in this example can be adopted for use to evaluate the expression levels of the adiponutrin protein in rs738408 ORF containing cells.

Example 14: Modulation of Protein Translation Rate of SMC-Containing ORF with TREM Administration This example describes administration of a TREM to alter the rate of protein translation of an SMC-containing ORF.

To monitor the effects of TREM addition on translation elongation rates, an in vitro translation system, in this example the RRL system from Promega, is used in which the fluorescence change over time of a reporter gene, in this example GFP, is a surrogate for translation rates.

Synthesis and Preparation of TREM

An arginine TREM is synthesized as described in Example 1 and quality control methods as described in Examples 7-9 are performed. To ensure proper folding, the TREM is heated at 85° C. for 2 minutes and then snap cooled at 4° C. for 5 minutes.

Evaluation of Protein Translation Rate of SMC-Containing ORF

First, a rabbit reticulocyte lysate that is depleted of the endogenous tRNA using an antisense oligonucleotide targeting the sequence between the anticodon and variable loop is generated (see, e.g., Cui et al. 2018. *Nucleic Acids Res.* 46 (12): 6387-6400). In this example, a TREM comprising an alanine isoacceptor containing an UGC anticodon, that base pairs to the GCA codon, i.e. with the sequence GGGGAU-GUAGCUCAGUGGUAGAGCGCAUGCUUUGCAU-GUAUGAGGUCCCGGGUU CGAUCCCCGGCAU-CUCCA (SEQ ID NO: 1293) is added to the in vitro translation assay lysate in addition to 0.1-0.5 ug/uL of mRNA coding for the wildtype TERT ORF fused to the GFP ORF by a linker or an mRNA coding for the rs2736098 TERT ORF fused to the GFP ORF by a linker. The progress of GFP mRNA translation is monitored by fluorescence increase on a microplate reader at 37° C. using $\lambda_{ex}485/\lambda_{em}528$ with data points collected every 30 seconds over a period of 1 hour. The amount of fluorescence change over time is plotted to determine the rate of translation elongation of the wildtype ORF compared to the rs2736098 ORF with and without TREM addition. The methods described in this example can be adopted for use to evaluate the translation rate of the rs2736098 ORF and the wildtype ORF in the presence or absence of TREM.

What is claimed is:

1. A method of delivering a tRNA-based effector molecule (TREM) to a cell or a subject, comprising administering to the cell or subject a TREM, wherein the TREM comprises a non-naturally occurring modification at a nucleotide position corresponding to a selected nucleotide position of a reference sequence, wherein the reference sequence is SEQ ID NO: 622, and the selected nucleotide position is selected from nucleotide positions 2, 3, and 73 of SEQ ID NO: 622;

the non-naturally occurring modification is selected from an internucleotide modification and a 2'-modification on a nucleotide sugar moiety;

the TREM comprises at least 73 nucleotides; and the TREM is capable of mediating acceptance of an amino acid or transfer of the amino acid in the initiation or elongation of a polypeptide chain;

thereby delivering the TREM to the cell or subject.

2. The method of claim 1, wherein the selected nucleotide position of the reference sequence is nucleotide position 2.

3. The method of claim 1, wherein the selected nucleotide position of the reference sequence is nucleotide position 3.

4. The method of claim 1, wherein the selected nucleotide position of the reference sequence is nucleotide position 73.

5. The method of claim 1, wherein the non-naturally occurring modification is selected from 2'-OMe, 2'-F, 2'-deoxy, 2'-MOE, and a phosphorothioate internucleotide modification.

6. The method of claim 1, wherein the TREM further comprises a non-naturally occurring modification at nucleotide position 16 or nucleotide position 52 of the reference sequence.

7. The method of claim 1, wherein the TREM further comprises an anticodon domain comprising a non-naturally occurring modification.

8. The method of claim 1, wherein the TREM further comprises an anticodon domain that does not comprise a non-naturally occurring modification.

9. The method of claim 1, wherein the TREM is formulated as a lipid nanoparticle.

10. The method of claim 1, wherein the TREM is delivered to a subject having a premature termination codon (PTC) disorder.

* * * * *